(12) United States Patent
Ridley et al.

(10) Patent No.: US 12,077,799 B2
(45) Date of Patent: Sep. 3, 2024

(54) CHIMERIC TERPENE SYNTHASES

(71) Applicant: Ginkgo Bioworks, Inc., Boston, MA (US)

(72) Inventors: Christian Ridley, Acton, MA (US); Jue Wang, Seattle, WA (US); Scott Marr, Boston, MA (US)

(73) Assignee: Ginkgo Bioworks, Inc., Boston, MA (US)

( * ) Notice: Subject to any disclaimer, the term of this patent is extended or adjusted under 35 U.S.C. 154(b) by 541 days.

(21) Appl. No.: 16/969,965

(22) PCT Filed: Feb. 14, 2019

(86) PCT No.: PCT/US2019/018122
§ 371 (c)(1),
(2) Date: Aug. 13, 2020

(87) PCT Pub. No.: WO2019/161141
PCT Pub. Date: Aug. 22, 2019

(65) Prior Publication Data
US 2021/0147880 A1 May 20, 2021

Related U.S. Application Data

(60) Provisional application No. 62/630,640, filed on Feb. 14, 2018.

(51) Int. Cl.
*C12P 5/00* (2006.01)
*C12N 9/88* (2006.01)
*C12P 7/02* (2006.01)

(52) U.S. Cl.
CPC ............ *C12P 5/007* (2013.01); *C12N 9/88* (2013.01); *C12P 7/02* (2013.01); *C12Y 402/03087* (2013.01)

(58) Field of Classification Search
CPC .... C12P 5/007; C12P 7/02; C12Y 402/03087; C12N 9/88; C12N 15/52; A61K 8/31; A61K 8/34; A61Q 13/00; C11B 9/00
See application file for complete search history.

(56) References Cited

U.S. PATENT DOCUMENTS

| | | |
|---|---|---|
| 6,531,303 B1 | 3/2003 | Millis et al. |
| 6,689,593 B2 | 2/2004 | Millis et al. |
| 7,273,735 B2 | 9/2007 | Schalk et al. |
| 7,622,288 B2 | 11/2009 | Schalk |
| 7,790,413 B2 | 9/2010 | Schalk |
| 7,790,426 B2 | 9/2010 | Schalk et al. |
| 7,888,095 B2 | 2/2011 | Keasling et al. |
| 8,058,046 B2 | 11/2011 | Schalk et al. |
| 8,236,512 B1 | 8/2012 | Zhao et al. |
| 8,765,403 B2 | 7/2014 | Dueber et al. |
| 8,927,238 B2 | 1/2015 | Schalk et al. |
| 9,222,096 B2 | 12/2015 | Spangenberg et al. |
| 9,297,004 B2 | 3/2016 | Schalk |
| 9,303,252 B2 | 4/2016 | Amick et al. |
| 9,714,418 B2 | 7/2017 | Amick et al. |
| 9,714,440 B2 | 7/2017 | Schalk et al. |
| 9,745,602 B2 | 8/2017 | Daviet et al. |
| 9,809,829 B2 | 11/2017 | Keasling et al. |
| 9,856,460 B2 | 1/2018 | Dueber et al. |
| 9,909,145 B2 | 3/2018 | Daviet et al. |
| 9,969,999 B2 | 5/2018 | Schalk |
| 10,400,254 B1 | 9/2019 | Wu et al. |
| 11,485,985 B2 * | 11/2022 | Goeke ................... A23L 27/10 |
| 11,618,908 B2 | 4/2023 | Philippe et al. |
| 2003/0092144 A1 | 5/2003 | Millis et al. |
| 2004/0110257 A1 | 6/2004 | Millis et al. |
| 2004/0234662 A1 | 11/2004 | Ben-Yehoshua |
| 2006/0206957 A1 | 9/2006 | Schalk |
| 2008/0268500 A1 | 10/2008 | Schalk |
| 2009/0025060 A1 | 1/2009 | Mukherjee et al. |
| 2009/0280545 A1 | 11/2009 | Mendez et al. |
| 2012/0196315 A1 | 8/2012 | Zhao et al. |
| 2012/0246767 A1 | 9/2012 | Amick et al. |
| 2015/0099283 A1 | 4/2015 | Schalk et al. |
| 2017/0283841 A1 | 10/2017 | Schalk et al. |
| 2020/0299737 A1 | 9/2020 | Goeke et al. |
| 2021/0254107 A1 | 8/2021 | Philippe et al. |

FOREIGN PATENT DOCUMENTS

| | | | |
|---|---|---|---|
| CN | 103352034 A | 10/2013 | |
| CN | 112921024 A | 6/2021 | |
| JP | 2015-165798 A | 9/2015 | |
| JP | 2016/154502_MT | * 1/2016 | ............... C12N 1/19 |
| JP | 2016-154502 A | 9/2016 | |
| WO | WO 2005/021705 A2 | 3/2005 | |
| WO | WO 2005/052163 A2 | 6/2005 | |

(Continued)

OTHER PUBLICATIONS

Kumeta et al., Characterization of d-Guaiene Synthases from Cultured Cells of Aquilaria, Responsible for the Formation of the Sesquiterpenes in Agarwood1[C][W][OA]. Plant Physiol., 2010, vol. 154: 1998-2007. (Year: 2010).*

Mattivi F., Key enzymes behind black pepper aroma in wines. J. Exptl. Botany., extra Botany: 2016, vol. 67(3): 555-567. (Year: 2016).*

Xu et al., Identification of genes related to agarwood formation: transcriptome analysis of healthy and wounded tissues of Aquilaria sinensis. BMC Genomics, 2013, vol. 14: pp. 1-16. (Year: 2013).*

(Continued)

*Primary Examiner* — Ganapathirama Raghu
(74) *Attorney, Agent, or Firm* — Wolf, Greenfield & Sacks, P.C.

(57) ABSTRACT

Described herein are chimeric terpene synthases, methods for making chimeric terpene synthases, and methods for making terpenes using the same.

20 Claims, 14 Drawing Sheets
Specification includes a Sequence Listing.

(56) References Cited

FOREIGN PATENT DOCUMENTS

| WO | WO 2006/014837 A1 | 2/2006 |
|---|---|---|
| WO | WO 2011/141855 A1 | 11/2011 |
| WO | WO 2012/058636 A1 | 5/2012 |
| WO | WO 2012/159161 A1 | 11/2012 |
| WO | WO 2014/081963 A2 | 5/2014 |
| WO | WO 2014/206412 A1 | 12/2014 |
| WO | WO 2015/181823 A1 | 12/2015 |
| WO | WO 2017/050971 A | 3/2017 |
| WO | WO 2017/075538 A1 | 5/2017 |
| WO | WO 2018/053507 A2 | 3/2018 |
| WO | WO 2019/110299 A1 | 6/2019 |
| WO | WO 2019/175607 A1 | 9/2019 |
| WO | WO 2019/224536 A1 | 11/2019 |
| WO | WO 2020/051488 A1 | 3/2020 |
| WO | WO 2020/081739 | 4/2020 |
| WO | wo 2020/176547 A1 | 9/2020 |
| WO | WO 2020/225820 | 11/2020 |
| WO | WO 2022/240995 | 11/2022 |
| WO | WO 2023/159069 A1 | 8/2023 |

OTHER PUBLICATIONS

[No Author Listed], (+)-delta-cadinene synthase isozyme A. Uniprot Accession No. Q43714. Nov. 22, 2017, entry version 89; Nov. 1, 1996, sequence version 1. Accessible at https://rest.uniprot.org/unisave/Q43714?format=txt&versions=89. 2 pages.
[No Author Listed], (+)-delta-cadinene synthase isozyme XC1. Uniprot Accession No. Q39761. Nov. 22, 2017, entry version 88; Nov. 1, 1996, sequence version 1. Accessible at https://rest.uniprot.org/unisave/Q39761?format=txt&versions=88. 3 pages.
[No Author Listed], (+)-delta-cadinene synthase isozyme XC14. Uniprot Accession No. Q39760. Nov. 22, 2017, entry version 88; Nov. 1, 1996, sequence version 1. Accessible at https://rest.uniprot.org/unisave/Q39760?format=txt&versions=88. 2 pages.
[No Author Listed], (+)-delta-cadinene synthase. Uniprot Accession No. Q9SAN0. Nov. 22, 2017, entry version 66; May 1, 2000, sequence version 1. Accessible at https://rest.uniprot.org/unisave/Q9SAN0?format=txt&versions=66. 2 pages.
[No Author Listed], (R)-limonene synthase. Uniprot Accession No. Q2XSC6. Nov. 22, 2017, entry version 44; Dec. 20, 2005, sequence version 1. Accessible at https://rest.uniprot.org/unisave/Q2XSC6?format=txt&versions=44. 2 pages.
[No Author Listed], (Z)-gamma-bisabolene synthase 1. Uniprot Accession No. Q9T0J9. Dec. 20, 2017, entry version 97; Jan. 11, 2011, sequence version 2. Accessible at https://rest.uniprot.org/unisave/Q9T0J9?format=txt&versions=97. 4 pages.
[No Author Listed], Alpha-zingiberene synthase. Uniprot Accession No. Q5SBP4. Nov. 22, 2017, entry version 48; Dec. 21, 2004, sequence version 1. Accessible at https://rest.uniprot.org/unisave/Q5SBP4?format=txt&versions=48. 2 pages.
[No Author Listed], Beta-eudesmol synthase. Uniprot Accession No. B1B1U4. Nov. 22, 2017, entry version 37; Apr. 29, 2008, sequence version 1. Accessible at https://rest.uniprot.org/unisave/B1B1U4?format=txt&versions=37. 2 pages.
[No Author Listed], Bifunctional abietadiene synthase, chloroplastic. Uniprot Accession No. Q38710. Nov. 22, 2017, entry version 95; Nov. 1, 1996, sequence version 1. Accessible at https://rest.uniprot.org/unisave/Q38710?format=txt&versions=95. 7 pages.
[No Author Listed], Bifunctional cis-abienol synthase, chloroplastic. Uniprot Accession No. H8ZM73. Nov. 22, 2017, entry version 23; May 16, 2012, sequence version 1. Accessible at https://rest.uniprot.org/unisave/H8ZM73?format=txt&versions=23. 2 pages.
[No Author Listed], Delta-elemene synthase. Uniprot Accession No. A0A097ZIE0. Nov. 22, 2017, entry version 12; Jan. 7, 2015, sequence version 1. Accessible at https://rest.uniprot.org/unisave/A0A097ZIE0?format=txt&versions=12. 2 pages.
[No Author Listed], delta-guaiene synthase [Aquilaria crassna]. Genbank Acc. No. ACY38196.1. Accessible at https://www.ncbi.nlm.nih.gov/protein/ACY38196. Dec. 2, 2010. 2 pages.

[No Author Listed], Delta-guaiene synthase 1. Uniprot Accession No. D0VMR6. Nov. 22, 2017, entry version 27; Dec. 15, 2009, sequence version 1. Accessible at https://rest.uniprot.org/unisave/D0VMR6?format=txt&versions=27. 2 pages.
[No Author Listed], Delta-guaiene synthase 2. Uniprot Accession No. D0VMR7. Nov. 22, 2017, entry version 27; Dec. 15, 2009, sequence version 1. Accessible at https://rest.uniprot.org/unisave/D0VMR7?format=txt&versions=27. 2 pages.
[No Author Listed], Delta-guaiene synthase 3. Uniprot Accession No. D0VMR8. Nov. 22, 2017, entry version 27; Dec. 15, 2009, sequence version 1. Accessible at https://rest.uniprot.org/unisave/D0VMR8?format=txt&versions=27. 2 pages.
[No Author Listed], E)-beta-ocimene synthase. Uniprot Accession No. Q5CD81. Nov. 22, 2017, entry version 49; Apr. 12, 2005, sequence version 1. Accessible at https://rest.uniprot.org/unisave/Q5CD81?format=txt&versions=49. 2 pages.
[No Author Listed], Limonene synthase. Uniprot Accession No. Q9FV72. Nov. 22, 2017, entry version 65; Mar. 1, 2001, sequence version 1. Accessible at https://rest.uniprot.org/unisave/Q9FV72?format=txt&versions=65. 2 pages.
[No Author Listed], Myrcene synthase, chloroplastic. Uniprot Accession No. O24474. Nov. 22, 2017, entry version 91; Jan. 1, 1998, sequence version 1. Accessible at https://rest.uniprot.org/unisave/O24474?format=txt&versions=91. 2 pages.
[No Author Listed], Patchoulol synthase. Uniprot Accession No. Q49SP3. Nov. 22, 2017, entry version 54; Sep. 13, 2005, sequence version 1. Accessible at https://rest.uniprot.org/unisave/Q49SP3?format=txt&versions=54. 3 pages.
[No Author Listed], Predicted: Vitis vinifera (−)-germacrene D synthase (LOC100255553), mRNA. NCBI Reference Sequence No. XM_002282452.3. Nov. 23, 2016. Retrieved from https://www.ncbi.nlm.nih.gov/nuccore/XM_002282452.3/#locus_1104681058. 2 pages.
[No Author Listed], Putative delta-guaiene synthase. Uniprot Accession No. A0A0A0QUT9. Nov. 22, 2017, entry version 12; Feb. 4, 2015, sequence version 1. Accessible at https://rest.uniprot.org/unisave/A0A0A0QUT9?format=txt&versions=12. 2 pages.
[No Author Listed], Sclareol synthase, chloroplastic. Primary Uniprot Accession No. G8GJ94. Secondary Uniprot Accession No. K4HYB0. Nov. 22, 2017, entry version 23; Jan. 25, 2012, sequence version 1. Accessible at https://rest.uniprot.org/unisave/G8GJ94?format=txt&versions=23. 1 page.
[No Author Listed], Sesquiterpene synthase 2. Uniprot Accession No. Q9FQ26. Dec. 20, 2017, entry version 71; Mar. 1, 2001, sequence version 1. Accessible at https://rest.uniprot.org/unisave/Q9FQ26?format=txt&versions=71. 2 pages.
[No Author Listed], Terpene synthase. Uniprot Accession No. G5CV47. Nov. 22, 2017, entry version 44; Dec. 14, 2011, sequence version 1. Accessible at https://rest.uniprot.org/unisave/G5CV47?format=txt&versions=44. 2 pages.
[No Author Listed], Uncharacterized protein. Uniprot Accession No. A0A067D5M4. Dec. 20, 2017, entry version 19; Sep. 3, 2014, sequence version 1. Accessible at https://rest.uniprot.org/unisave/A0A067D5M4?format=txt&versions=19. 2 pages.
[No Author Listed], Uncharacterized protein. Uniprot Accession No. A0A067FTE8. Nov. 22, 2017, entry version 17; Sep. 3, 2014, sequence version 1. Accessible at https://rest.uniprot.org/unisave/A0A067FTE8?format=txt&versions=17. 2 pages.
[No Author Listed], Uncharacterized protein. Uniprot Accession No. A0A068UHT0. Nov. 22, 2017, entry version 14; Oct. 1, 2014, entry version 1. Accessible at https://rest.uniprot.org/unisave/A0A068UHT0?format=txt&versions=14. 2 pages.
[No Author Listed], Uncharacterized protein. Uniprot Accession No. A0A068VE40. Nov. 22, 2017, entry version 14; Oct. 1, 2014, sequence version 1. Accessible at https://rest.uniprot.org/unisave/A0A068VE40?format=txt&versions=14. 2 pages.
[No Author Listed], Uncharacterized protein. Uniprot Accession No. A0A068VI46. Nov. 22, 2017, entry version 14; Oct. 1, 2014, sequence version 1. Accessible at https://rest.uniprot.org/unisave/A0A068VI46?format=txt&versions=14. 1 page.
An et al., Characterization of Guaiene Synthases from Stellera chamaejasme L. Flowers and Their Application in De novo Pro-

(56) References Cited

OTHER PUBLICATIONS duction of (−)-Rotundone in Yeast. J Agric Food Chem. Mar. 11, 2020;68(10):3214-3219. doi: 10.1021/acs.jafc.9b08303. Epub Mar. 2, 2020.

Asadollahi et al., Production of plant sesquiterpenes in *Saccharomyces cerevisiae*: effect of ERG9 repression on sesquiterpene biosynthesis. Biotechnol Bioeng. Feb. 15, 2008;99(3):666-77. doi: 10.1002/bit.21581.

Chen et al., Terpene synthase genes in eukaryotes beyond plants and fungi: Occurrence in social amoebae. PNAS 2016;113(43):12132-37. doi: 10.1073/pnas.1610379113.

Christianson, Unearthing the roots of the terpenome. Curr Opin Chem Biol. Apr. 2008;12(2):141-50. doi: 10.1016/j.cbpa.2007.12.008. Epub Feb. 20, 2008.

Degenhardt et al., Monoterpene and sesquiterpene synthases and the origin of terpene skeletal diversity in plants. Phytochemistry. Oct.-Nov. 2009;70(15-16):1621-37. doi: 10.1016/j.phytochem.2009.07.030. Epub Sep. 28, 2009.

Donald et al., Effects of overproduction of the catalytic domain of 3-hydroxy-3-methylglutaryl coenzyme A reductase on squalene synthesis in *Saccharomyces cerevisiae*. Appl Environ Microbiol. Sep. 1997;63(9):3341-4. doi: 10.1128/AEM.63.9.3341-3344.1997.

Drew et al., Two key polymorphisms in a newly discovered allele of the Vitis vinifera TPS24 gene are responsible for the production of the rotundone precursor α-guaiene. J Exp Bot. Feb. 2016;67(3):799-808. doi: 10.1093/jxb/erv491. Epub Nov. 17, 2015.

Entian et al., 25 Yeast Genetic Strain and Plasmid Collections. Meth Microbiol. 2007;36:629-66.

Fisch et al., A strategy of exon shuffling for making large peptide repertoires displayed on filamentous bacteriophage. Proc Natl Acad Sci U S A. Jul. 23, 1996;93(15):7761-6. doi: 10.1073/pnas.93.15.7761.

Gong et al., Diterpene synthases and their responsible cyclic natural products. Nat Prod Bioprospect. Apr. 2014;4(2):59-72. doi: 10.1007/s13659-014-0012-8. Epub Apr. 18, 2014.

Jacobsen, Fragrant Genes of Extinct Flowers Have Been Brought Back to Life. Scientific American. Feb. 1, 2019. Originally published with the title "Ghost Flowers" in Scientific American 320, 2, 30-39 (Feb. 2019) doi:10.1038/scientificamerican0219-30.

Kumeta et al., Characterization of delta-guaiene synthases from cultured cells of Aquilaria, responsible for the formation of the sesquiterpenes in agarwood. Plant Physiol. Dec. 2010;154(4):1998-2007. doi: 10.1104/pp.110.161828. Epub Oct. 19, 2010.

Kumeta et al., Genomic organization of δ-guaiene synthase genes in Aquilaria crassna and its possible use for the identification of Aquilaria species. J Nat Med. Jul. 2011;65(3-4):508-13. doi: 10.1007/s11418-011-0529-7. Epub Apr. 7, 2011.

Nixon et al., Assembly of an active enzyme by the linkage of two protein modules. Proc Natl Acad Sci U S A. Feb. 18, 1997;94(4):1069-73. doi: 10.1073/pnas.94.4.1069.

Özaydin et al., Carotenoid-based phenotypic screen of the yeast deletion collection reveals new genes with roles in isoprenoid production. Metab Eng. Jan. 2013;15:174-83. doi: 10.1016/j.ymben.2012.07.010. Epub Aug. 17, 2012.

Ro et al., Production of the antimalarial drug precursor artemisinic acid in engineered yeast. Nature. Apr. 13, 2006;440(7086):940-3. doi: 10.1038/nature04640.

Starks et al., Structural basis for cyclic terpene biosynthesis by tobacco 5-epi-aristolochene synthase. Science. Sep. 19, 1997;277(5333):1815-20. doi: 10.1126/science.277.5333.1815.

Van Beek et al., The Essential Oil of Patchouli, Pogostemon cablin: A review. Flavour Fragr J. Jan. 2018;33(1):6-51. doi: 10.1002/ffj.3418. First Published Oct. 26, 2017.

Zhang et al., Engineering yeast metabolism for production of terpenoids for use as perfume ingredients, pharmaceuticals and biofuels. FEMS Yeast Res. Dec. 1, 2017;17(8). doi: 10.1093/femsyr/fox080. 11 pages.

Invitation to Pay Additional Fees for Application No. PCT/US2019/018122, mailed May 10, 2019.

International Search Report and Written Opinion for Application No. PCT/US2019/018122, mailed Jul. 3, 2019.

International Preliminary Report on Patentability for Application No. PCT/US2019/018122, mailed Aug. 27, 2020.

[No Author Listed], Geneseq Database Accession No. ADY58798. Jun. 15, 2007. 1 page.

[No Author Listed], Geneseq Database Accession No. AZV95121. Jun. 2, 20121. 2 pages.

[No Author Listed], Geneseq Database Accession No. BCJ75688. Jan. 28, 2016. 1 page.

[No Author Listed], Jpo Proteins Database Accession No. DM615049. Dec. 23, 2015. 1 page.

[No Author Listed], (−)-germacrene d synthase [Quercus suber]. GenBank Acc. No. POF02014.1. Accessible at https://www.ncbi.nlm.nih.gov/protein/1336374868?sat=47&satkey=123431. Jan. 29, 2018. 2 pages.

Back et al., Identifying functional domains within terpene cyclases using a domain-swapping strategy. Proc Natl Acad Sci U S A. Jun. 25, 1996;93(13):6841-5. doi: 10.1073/pnas.93.13.6841.

[No Author Listed], Aquilaria crassna delta-guaiene synthase-like protein (C1) mRNA, complete cds. Genbank Acc. No. GU083696.1. Accessible at https://www.ncbi.nlm.nih.gov/nuccore/GU083696. Dec. 2, 2010. 2 pages.

[No Author Listed], Aquilaria crassna delta-guaiene synthase (C2) mRNA, complete cds. Genbank Acc. No. GU083697.1. Accessible at https://www.ncbi.nlm.nih.gov/nuccore/GU083697. Dec. 2, 2010. 2 pages.

[No Author Listed], Aquilaria crassna delta-guaiene synthase (C3) mRNA, complete cds. Genbank Acc. No. GU083698.1. Accessible at https://www.ncbi.nlm.nih.gov/nuccore/GU083698. Dec. 2, 2010. 2 pages.

[No Author Listed], Aquilaria crassna delta-guaiene synthase (C4) mRNA, complete cds. Genbank Acc. No. GU083699.1. Accessible at https://www.ncbi.nlm.nih.gov/nuccore/GU083699. Dec. 2, 2010. 2 pages.

[No Author Listed], Aquilaria crassna delta-guaiene synthase-like protein-like (L154) mRNA, complete sequence. Genbank Acc. No. GU083700.1. Accessible at https://www.ncbi.nlm.nih.gov/nuccore/GU083700. Dec. 2, 2010. 2 pages.

Amiri et al., Metabolic engineering of Saccharomyces cerevisiae for linalool production. Biotechnol Lett. Mar. 2016;38(3):503-8. doi: 10.1007/s10529-015-2000-4. Epub Nov. 2, 20157.

Asadollahi et al., Enhancement of farnesyl diphosphate pool as direct precursor of sesquiterpenes through metabolic engineering of the mevalonate pathway in *Saccharomyces cerevisiae*. Biotechnol Bioeng. May 1, 2010;106(1):86-96. doi: 10.1002/bit.22668.

Asadollahi et al., Enhancing sesquiterpene production in *Saccharomyces cerevisiae* through in silico driven metabolic engineering. Metab Eng. Nov. 2009;11(6):328-34. doi: 10.1016/j.ymben.2009.07.001. Epub Jul. 18, 2009.

Azzarina et al., Temporal and spatial expression of terpene synthase genes associated with agarwood formation in *Aquilaria malaccensis* Lam. N Z J Forestry Sci. Jun. 20, 2016;46(12):1-13. doi: 10.1186/s40490-016-0068-9.

Chen et al., Enhancement of the catalytic activity of Isopentenyl diphosphate isomerase (IDI) from *Saccharomyces cerevisiae* through random and site-directed mutagenesis. Microb Cell Fact. Apr. 30, 2018;17(1):65. doi: 10.1186/s12934-018-0913-z. Erratum in: Microb Cell Fact. Jan. 13, 2020;19(1):8.

Chung et al., Genome-scale in silico modeling and analysis for designing synthetic terpenoid-producing microbial cell factories. Chem Eng Sci. Nov. 15, 2013;103:100-8. doi: 10.1016/j.ces.2012.09.006. Epub Sep. 19, 2012.

Deng et al., Enhanced (S)-linalool production by fusion expression of farnesyl diphosphate synthase and linalool synthase in *Saccharomyces cerevisiae*. J Appl Microbiol. Jul. 2016;121(1):187-95. doi: 10.1111/jam.13105. Epub May 27, 2016.

Dong et al., Enhance production of diterpenoids in yeast by overexpression of the fused enzyme of ERG20 and its mutant mERG20. J Biotechnol. Jan. 10, 2020;307:29-34. doi: 10.1016/j.jbiotec.2019.10.019. Epub Nov. 3, 2019.

(56) References Cited

OTHER PUBLICATIONS

Dueholm et al., In planta and in silico characterization of five sesquiterpene synthases from *Vitis vinifera* (cv. Shiraz) berries. Planta. Jan. 2019;249(1):59-70. doi: 10.1007/s00425-018-2986-7. Epub Aug. 22, 2018.

Faraldos et al., Doubly deuterium-labeled patchouli alcohol from cyclization of singly labeled [2-$^2$H$_1$]farnesyl diphosphate catalyzed by recombinant patchoulol synthase. J Am Chem Soc. Mar. 10, 2010;132(9):2998-3008. doi: 10.1021/ja909251r. Supporting Information, 37 pages.

Gao et al., Identification and characterization of terpene synthase genes accounting for volatile terpene emissions in flowers of *Freesia x hybrida*. J Exp Bot. Aug. 14, 2018;69(18):4249-4265. doi: 10.1093/jxb/ery224.

Greenhagen et al., Identifying and manipulating structural determinates linking catalytic specificities in terpene synthases. Proc Natl Acad Sci U S A. Jun. 27, 2006;103(26):9826-31. doi: 10.1073/pnas. 0601605103. Epub Jun. 19, 2006.

Gruchattka et al., In silico profiling of *Escherichia coli* and *Saccharomyces cerevisiae* as terpenoid factories. Microb Cell Fact. Sep. 23, 2013;12:84. doi: 10.1186/1475-2859-12-84.

Gruchattka et al., In Vivo Validation of In Silico Predicted Metabolic Engineering Strategies in Yeast: Disruption of α-Ketoglutarate Dehydrogenase and Expression of ATP-Citrate Lyase for Terpenoid Production. PLoS One. Dec. 23, 2015;10(12):e0144981. doi: 10.1371/journal.pone.0144981.

He et al., Building an octaploid genome and transcriptome of the medicinal plant *Pogostemon cablin* from Lamiales. Sci Data. Dec. 11, 2018;5:180274. doi: 10.1038/sdata.2018.274.

He et al., Survey of the genome of *Pogostemon cablin* provides insights into its evolutionary history and sesquiterpenoid biosynthesis. Sci Rep. May 20, 2016;6:26405. doi: 10.1038/srep26405.

Hong et al., Efficient production of lycopene in *Saccharomyces cerevisiae* by enzyme engineering and increasing membrane flexibility and NAPDH production. Appl Microbiol Biotechnol. Jan. 2019;103(1):211-223. doi: 10.1007/s00253-018-9449-8. Epub Oct. 20, 2018.

Huang et al., Production of the pepper aroma compound, (−)-rotundone, by aerial oxidation of α-guaiene. J Agric Food Chem. Nov. 5, 2014;62(44):10809-15. doi: 10.1021/jf504693e. Epub Oct. 21, 2014.

Kampranis et al., Developing a yeast cell factory for the production of terpenoids. Comput Struct Biotechnol J. Oct. 2012;3:e201210006. doi: 10.5936/csbj.201210006. Epub Nov. 5, 2012.

Kennedy et al., Positive and negative regulation of squalene synthase (ERG9), an ergosterol biosynthetic gene, in *Saccharomyces cerevisiae*. Biochim Biophys Acta. Jan. 26, 2001;1517(2):177-89. doi: 10.1016/s0167-4781(00)00246-3.

Kumeta et al., Characterization of α-humulene synthases responsible for the production of sesquiterpenes induced by methyl jasmonate in Aquilaria cell culture. J Nat Med. Jul. 2016;70(3):452-9. doi: 10.1007/s11418-016-0999-8. Epub May 14, 2016.

Kurihara et al., γ-Glutamylputrescine synthetase in the putrescine utilization pathway of *Escherichia coli* K-12. J Biol Chem. Jul. 18, 2008;283(29):19981-90. doi: 10.1074/jbc.M800133200. Epub May 21, 2008.

Kurosaki et al., Cloning and Characterization of δ-Guaiene Synthase Genes Encoding a Sesquiterpene Cyclase from *Aquilaria microcarpa* Cell Cultures. Am J Plant Sci. Oct. 23, 2015;6:2603-11. doi: 10.4236/ajps.2015.616263.

Kurosaki et al., Efficient Production of δ-Guaiene, an Aroma Sesquiterpene Compound Accumulated in Agarwood, by Mevalonate Pathway-Engineered *Escherichia coli* Cells. Adv Biosci Biotechnol. Jan. 2016;7(11):435-45. doi: 10.4236/abb.2016.711042.

Lee et al., Induction, cloning and functional expression of a sesquiterpene biosynthetic enzyme, δ-guaiene synthase, of *Aquilaria microcarpa* cell cultures. Nat Prod Commun. Sep. 2014;9(9):1231-5.

Li et al., Improving lycopene production in *Saccharomyces cerevisiae* through optimizing pathway and chassis metabolism. Chem Eng Sci. Jan. 16, 2019;193:364-9. doi: 10.1016/j.ces.2018.09.030.

Liu et al., The yeast peroxisome: A dynamic storage depot and subcellular factory for squalene overproduction. Metab Eng. Jan. 2020;57:151-161. doi: 10.1016/j.ymben.2019.11.001. Epub Nov. 9, 2019.

Ma et al., Significantly Enhanced Production of Patchoulol in Metabolically Engineered *Saccharomyces cerevisiae*. J Agric Food Chem. Aug. 7, 2019;67(31):8590-8598. doi: 10.1021/acs.jafc. 9b03456. Epub Jul. 26, 2019.

Martin et al., Functional annotation, genome organization and phylogeny of the grapevine (*Vitis vinifera*) terpene synthase gene family based on genome assembly, FLcDNA cloning, and enzyme assays. BMC Plant Biol. Oct. 21, 2010;10:226. doi: 10.1186/1471-2229-10-226.

Meadows et al., Rewriting yeast central carbon metabolism for industrial isoprenoid production. Nature. Sep. 29, 2016;537(7622):694-697. doi: 10.1038/nature19769. Epub Sep. 21, 2016.

O'Maille et al., Quantitative exploration of the catalytic landscape separating divergent plant sesquiterpene synthases. Nat Chem Biol. Oct. 2008;4(10):617-23. doi: 10.1038/nchembio.113. Epub Sep. 7, 2008.

Paramasivan et al., Progress in terpene synthesis strategies through engineering of *Saccharomyces cerevisiae*. Crit Rev Biotechnol. Dec. 2017;37(8):974-989. doi: 10.1080/07388551.2017.1299679. Epub Apr. 20, 2017.

Peng et al., A squalene synthase protein degradation method for improved sesquiterpene production in *Saccharomyces cerevisiae*. Metab Eng. Jan. 2017;39:209-219. doi: 10.1016/j.ymben.2016.12. 003. Epub Dec. 8, 2016.

Shiba et al., Engineering of the pyruvate dehydrogenase bypass in *Saccharomyces cerevisiae* for high-level production of isoprenoids. Metab Eng. Mar. 2007;9(2):160-8. doi: 10.1016/j.ymben.2006.10. 005. Epub Nov. 17, 2006.

Smit et al., Linking Terpene Synthases to Sesquiterpene Metabolism in Grapevine Flowers. Front Plant Sci. Feb. 21, 2019;10:177. doi: 10.3389/fpls.2019.00177.

Steele et al., Sesquiterpene synthases from grand fir (*Abies grandis*). Comparison of constitutive and wound-induced activities, and cDNA isolation, characterization, and bacterial expression of δ-selinene synthase and γ-humulene synthase. J Biol Chem. Jan. 23, 1998;273(4):2078-89. doi: 10.1074/jbc.273.4.2078.

Sun et al., Identification of novel knockout targets for improving terpenoids biosynthesis in *Saccharomyces cerevisiae*. PLoS One. Nov. 11, 2014;9(11):e112615. doi: 10.1371/journal.pone.0112615.

Takahashi et al., Metabolic engineering of sesquiterpene metabolism in yeast. Biotechnol Bioeng. May 1, 2007;97(1):170-81. doi: 10.1002/bit.21216.

Takase et al., Cytochrome P450 CYP71BE5 in grapevine (*Vitis vinifera*) catalyzes the formation of the spicy aroma compound (−)-rotundone. J Exp Bot. Feb. 2016;67(3):787-98. doi: 10.1093/jxb/erv496. Epub Nov. 20, 2015.

Tang et al., Molecular identification and expression of sesquiterpene pathway genes responsible for patchoulol biosynthesis and regulation in *Pogostemon cablin*. Bot Stud. Jul. 2, 2019;60(1):11. doi: 10.1186/s40529-019-0259-9.

Vickers et al., Recent advances in synthetic biology for engineering isoprenoid production in yeast. Curr Opin Chem Biol. Oct. 2017;40:47-56. doi: 10.1016/j.cbpa.2017.05.017. Epub Jun. 14, 2017.

Westfall et al., Production of amorphadiene in yeast, and its conversion to dihydroartemisinic acid, precursor to the antimalarial agent artemisinin. Proc Natl Acad Sci U S A. Jan. 17, 2012;109(3):E111-8. doi: 10.1073/pnas.1110740109. Epub Jan. 12, 2012.

Wu et al., Rapid Discovery and Functional Characterization of Terpene Synthases from Four Endophytic Xylariaceae. PLoS One. Feb. 17, 2016;11(2):e0146983. doi: 10.1371/journal.pone.0146983.

Yanagibashi et al., Beneficial effect of optimizing the expression balance of the mevalonate pathway introduced into the mitochondria on terpenoid production in *Saccharomyces cerevisiae*. J Biosci Bioeng. Jan. 2024;137(1):16-23. doi: 10.1016/j.jbiosc.2023.11.004. Epub Dec. 1, 2023.

Yee et al., Engineered mitochondrial production of monoterpenes in *Saccharomyces cerevisiae*. Metab Eng. Sep. 2019;55:76-84. doi: 10.1016/j.ymben.2019.06.004. Epub Jun. 19, 2019.

(56) References Cited

OTHER PUBLICATIONS

Zhang et al., High-level production of linalool by engineered *Saccharomyces cerevisiae* harboring dual mevalonate pathways in mitochondria and cytoplasm. Enzyme Microb Technol. Mar. 2020;134:109462. doi: 10.1016/j.enzmictec.2019.109462. Epub Nov. 5, 2019. Journal Pre-proof, 21 pages.

Zhang et al., Production of sesquiterpenoid zerumbone from metabolic engineered *Saccharomyces cerevisiae*. Metab Eng. Sep. 2018;49:28-35. doi: 10.1016/j.ymben.2018.07.010. Epub Jul. 19, 2018.

Zhuang et al., Building terpene production platforms in yeast. Biotechnol Bioeng. Sep. 2015;112(9):1854-64. doi: 10.1002/bit.25588. Epub May 12, 2015.

\* cited by examiner

SEQUENCE LISTING

```
<160> NUMBER OF SEQ ID NOS: 357

<210> SEQ ID NO 1
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 1

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
                20                  25                  30

Met Phe Ile Ile Cys Pro Asp Thr Asp Ile Asp Ala Ala Thr Glu Leu
            35                  40                  45

Gln Tyr Glu Glu Leu Lys Ala Gln Val Arg Lys Met Ile Met Glu Pro
        50                  55                  60

Val Asp Asp Ser Asn Gln Lys Leu Pro Phe Ile Asp Ala Val Gln Arg
65                  70                  75                  80

Leu Gly Val Ser Tyr His Phe Glu Lys Glu Ile Glu Asp Glu Leu Glu
                85                  90                  95

Asn Ile Tyr Arg Asp Thr Asn Asn Asp Ala Asp Thr Asp Leu Tyr
            100                 105                 110

Thr Thr Ala Leu Arg Phe Arg Leu Leu Arg Glu His Gly Phe Asp Ile
        115                 120                 125

Ser Cys Asp Ala Phe Asn Lys Leu Lys Asp Glu Glu Gly Asn Phe Lys
130                 135                 140

Ala Ser Leu Thr Ser Asp Val Pro Gly Leu Leu Glu Leu Tyr Glu Ala
145                 150                 155                 160

Ser Tyr Leu Arg Val His Gly Glu Asp Ile Leu Asp Glu Ala Ile Ser
                165                 170                 175

Phe Ala Thr Ala Gln Leu Thr Leu Ala Leu Pro Thr Leu His His Pro
            180                 185                 190

Leu Ser Glu Gln Val Gly His Ala Leu Lys Gln Ser Ile Arg Arg Gly
        195                 200                 205

Leu Pro Arg Val Glu Ala Arg Asn Phe Ile Ser Ile Tyr Gln Asp Leu
    210                 215                 220

Glu Ser His Asn Lys Ala Leu Leu Gln Phe Ala Lys Ile Asp Phe Asn
225                 230                 235                 240

Met Leu Gln Leu Leu His Arg Lys Glu Leu Ser Glu Ile Cys Arg Trp
                245                 250                 255

Trp Lys Asp Leu Asp Phe Thr Arg Lys Leu Pro Phe Ala Arg Asp Arg
```

Val Val Glu Gly Tyr Phe Trp Ile Met Gly Val Tyr Phe Glu Pro Gln
            260                 265                 270
275

Tyr Ser Leu Gly Arg Lys Met Leu Thr Lys Val Ile Ala Met Ala Ser
        290                 295                 300

Ile Val Asp Asp Thr Tyr Asp Ser Phe Ala Thr Tyr Asp Glu Leu Ile
305                 310                 315                 320

Pro Tyr Thr Asp Ala Ile Glu Arg Trp Asp Ile Lys Cys Met Asn Gln
                325                 330                 335

Leu Pro Asn Tyr Met Gln Ile Ser Tyr Lys Ala Leu Leu Asp Val Tyr
            340                 345                 350

Glu Glu Met Glu Gln Leu Leu Ala Asp Lys Gly Arg Gln Tyr Arg Val
        355                 360                 365

Glu Tyr Ala Lys Lys Ala Met Ile Arg Leu Val Gln Ala Tyr Leu Leu
    370                 375                 380

Glu Ala Lys Trp Thr His Leu Asn Tyr Lys Pro Thr Phe Glu Glu Phe
385                 390                 395                 400

Arg Asp Asn Ala Leu Pro Thr Ser Gly Tyr Ala Met Leu Ala Ile Thr
                405                 410                 415

Ala Phe Val Gly Met Gly Glu Val Ile Thr Pro Glu Thr Phe Glu Trp
            420                 425                 430

Ala Ala Ser Asp Pro Lys Ile Ile Lys Ala Ser Thr Ile Ile Cys Arg
        435                 440                 445

Phe Met Asp Asp Ile Ala Glu His Lys Phe Asn His Arg Arg Glu Asp
    450                 455                 460

Asp Cys Ser Ala Ile Glu Cys Tyr Met Glu Gln Tyr Lys Val Thr Ala
465                 470                 475                 480

Gln Glu Ala Tyr Asp Glu Phe Asn Lys His Ile Glu Ser Ser Trp Lys
                485                 490                 495

Asp Val Asn Glu Glu Phe Leu Lys Pro Thr Glu Met Pro Thr Pro Val
            500                 505                 510

Leu Cys Arg Ser Leu Asn Leu Ala Arg Val Met Asp Val Leu Tyr Arg
        515                 520                 525

Glu Gly Asp Gly Tyr Thr His Val Gly Lys Ala Ala Lys Gly Gly Ile
    530                 535                 540

Thr Ser Leu Leu Ile Asp Pro Ile Gln Ile
545                 550

<210> SEQ ID NO 2
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 2

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
            20                  25                  30

Met Phe Ile Ile Cys Pro Asp Thr Ile Asp Ala Ala Thr Glu Leu
        35                  40                  45

Gln Tyr Glu Glu Leu Lys Ala Gln Val Arg Lys Met Ile Met Glu Pro
    50                  55                  60

Val Asp Asp Ser Asn Gln Lys Leu Pro Phe Ile Asp Ala Val Gln Arg

```
            65                  70                  75                  80
Leu Gly Val Ser Tyr His Phe Glu Lys Glu Ile Glu Asp Glu Leu Glu
                    85                  90                  95
Asn Ile Tyr Arg Asp Thr Asn Asn Asp Ala Asp Thr Asp Leu Tyr
                100                 105                 110
Thr Thr Ala Leu Arg Phe Arg Leu Leu Arg Glu His Gly Phe Asp Ile
                115                 120                 125
Ser Cys Glu Ala Phe Asn Lys Leu Lys Asp Glu Gly Asn Phe Lys
    130                 135                 140
Ala Ser Leu Thr Ser Asp Val Arg Gly Leu Leu Glu Leu Tyr Gln Ala
145                 150                 155                 160
Ser Tyr Met Arg Ile His Gly Glu Asp Ile Leu Asp Glu Ala Ile Ser
                165                 170                 175
Phe Thr Thr Ala Gln Leu Thr Leu Ala Leu Pro Thr Leu Asp Pro Pro
                180                 185                 190
Leu Ser Glu Gln Val Gly His Ala Leu Lys Gln Ser Ile Arg Arg Gly
                195                 200                 205
Leu Pro Arg Val Glu Ala Arg Asn Phe Ile Ser Ile Tyr Gln Asp Leu
    210                 215                 220
Glu Ser His Asn Lys Ala Leu Leu Gln Phe Ala Lys Ile Asp Phe Asn
225                 230                 235                 240
Met Leu Gln Leu Leu His Arg Lys Glu Leu Ser Glu Ile Cys Arg Trp
                245                 250                 255
Trp Lys Asp Leu Asp Phe Thr Arg Lys Leu Pro Phe Ala Arg Asp Arg
                260                 265                 270
Val Val Glu Gly Tyr Phe Trp Ile Met Gly Val Tyr Phe Glu Pro Gln
                275                 280                 285
Tyr Ser Leu Gly Arg Lys Met Leu Thr Lys Val Ile Ala Met Ala Ser
    290                 295                 300
Ile Val Asp Asp Thr Tyr Asp Ser Phe Ala Thr Tyr Asp Glu Leu Ile
305                 310                 315                 320
Pro Tyr Thr Asp Ala Ile Glu Arg Trp Asp Ile Lys Cys Met Asn Gln
                325                 330                 335
Leu Pro Asn Tyr Met Gln Ile Ser Tyr Lys Ala Leu Leu Asp Val Tyr
                340                 345                 350
Glu Glu Met Glu Gln Leu Leu Ala Asp Lys Gly Arg Gln Tyr Arg Val
                355                 360                 365
Glu Tyr Ala Lys Lys Ala Met Ile Arg Leu Val Gln Ala Tyr Leu Leu
    370                 375                 380
Glu Ala Lys Trp Thr His Leu Asn Tyr Lys Pro Thr Phe Glu Glu Phe
385                 390                 395                 400
Arg Asp Asn Ala Leu Pro Thr Ser Gly Tyr Ala Met Leu Ala Ile Thr
                405                 410                 415
Ala Phe Val Gly Met Gly Glu Val Ile Thr Pro Glu Thr Phe Glu Trp
                420                 425                 430
Ala Ala Ser Asp Pro Lys Ile Ile Lys Ala Ser Thr Ile Ile Cys Arg
                435                 440                 445
Phe Met Asp Asp Ile Ala Glu His Lys Phe Asn His Arg Arg Glu Asp
    450                 455                 460
Asp Cys Ser Ala Ile Glu Cys Tyr Met Lys Gln Tyr Gly Ala Thr Ala
465                 470                 475                 480
Gln Glu Ala Tyr Asp Glu Phe Asn Lys His Ile Glu Ser Ser Trp Lys
                485                 490                 495
```

-continued

```
Asp Val Asn Glu Glu Phe Leu Lys Pro Thr Glu Met Pro Thr Pro Val
                500                 505                 510

Leu Cys Arg Ser Leu Asn Leu Ala Arg Val Met Asp Val Leu Tyr Arg
            515                 520                 525

Glu Gly Asp Gly Tyr Thr His Val Gly Lys Ala Ala Lys Gly Gly Ile
        530                 535                 540

Thr Ser Leu Leu Ile Asp Pro Ile Gln Ile
545                 550

<210> SEQ ID NO 3
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 3

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
            20                  25                  30

Met Phe Ile Ile Cys Pro Asp Thr Asp Ile Asp Ala Ala Thr Glu Leu
        35                  40                  45

Gln Tyr Glu Glu Leu Lys Ala Gln Val Arg Lys Met Ile Met Glu Pro
    50                  55                  60

Val Asp Asp Ser Asn Gln Lys Leu Pro Phe Ile Asp Ala Val Gln Arg
65                  70                  75                  80

Leu Gly Val Ser Tyr His Phe Glu Lys Glu Ile Glu Asp Glu Leu Glu
                85                  90                  95

Asn Ile Tyr Arg Asp Thr Asn Asn Asp Ala Asp Thr Asp Leu Tyr
            100                 105                 110

Thr Thr Ala Leu Arg Phe Arg Leu Leu Arg Glu His Gly Phe Asp Ile
        115                 120                 125

Ser Cys Asp Ala Phe Asn Lys Leu Lys Asp Glu Glu Gly Asn Phe Lys
    130                 135                 140

Ala Ser Leu Thr Ser Asp Val Pro Gly Leu Leu Glu Leu Tyr Glu Ala
145                 150                 155                 160

Ser Tyr Leu Arg Val His Gly Glu Asp Ile Leu Asp Glu Ala Ile Ser
                165                 170                 175

Phe Ala Thr Ala Gln Leu Thr Leu Ala Leu Pro Thr Leu His His Pro
            180                 185                 190

Leu Ser Glu Gln Val Gly His Ala Leu Lys Gln Ser Ile Arg Arg Gly
        195                 200                 205

Leu Pro Arg Val Glu Ala Arg Asn Phe Ile Ser Ile Tyr Gln Asp Leu
    210                 215                 220

Glu Ser His Asn Lys Ala Leu Leu Gln Phe Ala Lys Ile Asp Phe Asn
225                 230                 235                 240

Met Leu Gln Leu Leu His Arg Lys Glu Leu Ser Glu Ile Cys Arg Trp
                245                 250                 255

Trp Lys Asp Leu Asp Phe Thr Arg Lys Leu Pro Phe Ala Arg Asp Arg
            260                 265                 270

Val Val Glu Gly Tyr Phe Trp Ile Met Gly Val Tyr Phe Glu Pro Gln
        275                 280                 285

Tyr Ser Leu Gly Arg Lys Met Leu Thr Lys Val Ile Ala Met Ala Ser
    290                 295                 300
```

```
Ile Val Asp Asp Thr Tyr Asp Ser Phe Ala Tyr Asp Glu Leu Ile
305                 310                 315                 320

Pro Tyr Thr Asp Ala Ile Glu Arg Trp Asp Ile Lys Cys Met Asn Gln
            325                 330                 335

Leu Pro Asn Tyr Met Gln Ile Ser Tyr Lys Ala Leu Leu Asp Val Tyr
            340                 345                 350

Glu Glu Met Glu Gln Leu Leu Ala Asp Lys Gly Arg Gln Tyr Arg Val
            355                 360                 365

Glu Tyr Ala Lys Lys Ala Met Ile Arg Leu Val Gln Ala Tyr Leu Leu
            370                 375                 380

Glu Ala Lys Trp Thr His Leu Asn Tyr Lys Pro Thr Phe Glu Glu Phe
385                 390                 395                 400

Arg Asp Asn Ala Leu Pro Thr Ser Gly Tyr Ala Met Leu Ala Ile Thr
                405                 410                 415

Ala Phe Val Gly Met Gly Glu Val Ile Thr Pro Glu Thr Phe Glu Trp
            420                 425                 430

Ala Ala Ser Asp Pro Lys Ile Ile Lys Ala Ser Thr Ile Ile Cys Arg
            435                 440                 445

Phe Met Asp Asp Ile Ala Glu His Lys Phe Asn His Arg Arg Glu Asp
            450                 455                 460

Asp Cys Ser Ala Ile Glu Cys Tyr Met Lys Gln Tyr Gly Ala Thr Ala
465                 470                 475                 480

Gln Glu Ala Tyr Asp Glu Phe Asn Lys His Ile Glu Ser Ser Trp Lys
            485                 490                 495

Asp Val Asn Glu Glu Phe Leu Lys Pro Thr Glu Met Pro Thr Pro Val
            500                 505                 510

Leu Cys Arg Ser Leu Asn Leu Ala Arg Val Met Asp Val Leu Tyr Arg
            515                 520                 525

Glu Gly Asp Gly Tyr Thr His Val Gly Lys Ala Ala Lys Gly Gly Ile
            530                 535                 540

Thr Ser Leu Leu Ile Asp Pro Ile Gln Ile
545                 550

<210> SEQ ID NO 4
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 4

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
            20                  25                  30

Met Phe Ile Ile Cys Pro Asp Thr Asp Ile Asp Ala Ala Thr Glu Leu
        35                  40                  45

Gln Tyr Glu Glu Leu Lys Ala Gln Val Arg Lys Met Ile Met Glu Pro
    50                  55                  60

Val Asp Asp Ser Asn Gln Lys Leu Pro Phe Ile Asp Ala Val Gln Arg
65                  70                  75                  80

Leu Gly Val Ser Tyr His Phe Glu Lys Glu Ile Glu Asp Glu Leu Glu
                85                  90                  95

Asn Ile Tyr Arg Asp Thr Asn Asn Asn Asp Ala Asp Thr Asp Leu Tyr
            100                 105                 110
```

```
Thr Thr Ala Leu Arg Phe Arg Leu Leu Arg Glu His Gly Phe Asp Ile
        115                 120                 125

Ser Cys Glu Ala Phe Asn Lys Leu Lys Asp Glu Glu Gly Asn Phe Lys
130                 135                 140

Ala Ser Leu Thr Ser Asp Val Arg Gly Leu Leu Glu Leu Tyr Gln Ala
145                 150                 155                 160

Ser Tyr Met Arg Ile His Gly Glu Asp Ile Leu Asp Glu Ala Ile Ser
                165                 170                 175

Phe Thr Thr Ala Gln Leu Thr Leu Ala Leu Pro Thr Leu Asp Pro Pro
            180                 185                 190

Leu Ser Glu Gln Val Gly His Ala Leu Lys Gln Ser Ile Arg Arg Gly
        195                 200                 205

Leu Pro Arg Val Glu Ala Arg Asn Phe Ile Ser Ile Tyr Gln Asp Leu
    210                 215                 220

Glu Ser His Asn Lys Ser Leu Leu Glu Phe Ala Lys Ile Asp Phe Asn
225                 230                 235                 240

Leu Leu Gln Leu Leu His Arg Lys Glu Leu Ser Glu Ile Cys Arg Trp
                245                 250                 255

Trp Lys Asp Leu Asp Phe Thr Arg Lys Leu Pro Phe Ala Arg Asp Arg
            260                 265                 270

Val Val Glu Gly Tyr Phe Trp Ile Met Gly Val Tyr Phe Glu Pro Gln
        275                 280                 285

Tyr Ser Leu Gly Arg Lys Met Leu Thr Lys Val Ile Ala Met Ala Ser
    290                 295                 300

Ile Val Asp Asp Thr Tyr Asp Ser Phe Ala Thr Tyr Asp Glu Leu Ile
305                 310                 315                 320

Pro Tyr Thr Asp Ala Ile Glu Arg Trp Asp Ile Lys Cys Met Asn Gln
                325                 330                 335

Leu Pro Asn Tyr Met Gln Ile Ser Tyr Lys Ala Leu Leu Asp Val Tyr
            340                 345                 350

Glu Glu Met Glu Gln Leu Leu Ala Asp Lys Gly Arg Gln Tyr Arg Val
        355                 360                 365

Glu Tyr Ala Lys Lys Ala Met Ile Arg Leu Val Gln Ala Tyr Leu Leu
    370                 375                 380

Glu Ala Lys Trp Thr His Leu Asn Tyr Lys Pro Thr Phe Glu Glu Phe
385                 390                 395                 400

Arg Asp Asn Ala Leu Pro Thr Ser Gly Tyr Ala Met Leu Ala Ile Thr
                405                 410                 415

Ala Phe Val Gly Met Gly Glu Val Ile Thr Pro Glu Thr Phe Glu Trp
            420                 425                 430

Ala Ala Ser Asp Pro Lys Ile Ile Lys Ala Ser Thr Ile Ile Cys Arg
        435                 440                 445

Phe Met Asp Asp Ile Ala Glu His Lys Phe Asn His Arg Arg Glu Asp
    450                 455                 460

Asp Cys Ser Ala Ile Glu Cys Tyr Met Glu Gln Tyr Lys Val Thr Ala
465                 470                 475                 480

Gln Glu Ala Tyr Asp Glu Phe Asn Lys His Ile Glu Ser Ser Trp Lys
                485                 490                 495

Asp Val Asn Glu Glu Phe Leu Lys Pro Thr Glu Met Pro Thr Pro Val
            500                 505                 510

Leu Cys Arg Ser Leu Asn Leu Ala Arg Val Met Asp Val Leu Tyr Arg
        515                 520                 525
```

```
Glu Gly Asp Gly Tyr Thr His Val Gly Lys Ala Ala Lys Gly Gly Ile
        530                 535                 540

Thr Ser Leu Leu Ile Asp Pro Ile Gln Ile
545                 550

<210> SEQ ID NO 5
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 5

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
            20                  25                  30

Met Phe Ile Ile Cys Pro Asp Thr Asp Ile Asp Ala Ala Thr Glu Leu
        35                  40                  45

Gln Tyr Glu Glu Leu Lys Ala Gln Val Arg Lys Met Ile Met Glu Pro
    50                  55                  60

Val Asp Asp Ser Asn Gln Lys Leu Pro Phe Ile Asp Ala Val Gln Arg
65                  70                  75                  80

Leu Gly Val Ser Tyr His Phe Glu Lys Glu Ile Glu Asp Glu Leu Glu
                85                  90                  95

Asn Ile Tyr Arg Asp Thr Asn Asn Asn Asp Ala Asp Thr Asp Leu Tyr
            100                 105                 110

Thr Thr Ala Leu Arg Phe Arg Leu Leu Arg Glu His Gly Phe Asp Ile
        115                 120                 125

Ser Cys Asp Ala Phe Asn Lys Leu Lys Asp Glu Glu Gly Asn Phe Lys
    130                 135                 140

Ala Ser Leu Thr Ser Asp Val Pro Gly Leu Leu Glu Leu Tyr Glu Ala
145                 150                 155                 160

Ser Tyr Leu Arg Val His Gly Glu Asp Ile Leu Asp Glu Ala Ile Ser
                165                 170                 175

Phe Ala Thr Ala Gln Leu Thr Leu Ala Leu Pro Thr Leu His His Pro
            180                 185                 190

Leu Ser Glu Gln Val Gly His Ala Leu Lys Gln Ser Ile Arg Arg Gly
        195                 200                 205

Leu Pro Arg Val Glu Ala Arg Asn Phe Ile Ser Ile Tyr Gln Asp Leu
    210                 215                 220

Glu Ser His Asn Lys Ser Leu Leu Glu Phe Ala Lys Ile Asp Phe Asn
225                 230                 235                 240

Leu Leu Gln Leu Leu His Arg Lys Glu Leu Ser Glu Ile Cys Arg Trp
                245                 250                 255

Trp Lys Asp Leu Asp Phe Thr Arg Lys Leu Pro Phe Ala Arg Asp Arg
            260                 265                 270

Val Val Glu Gly Tyr Phe Trp Ile Met Gly Val Tyr Phe Glu Pro Gln
        275                 280                 285

Tyr Ser Leu Gly Arg Lys Met Leu Thr Lys Val Ile Ala Met Ala Ser
    290                 295                 300

Ile Val Asp Asp Thr Tyr Asp Ser Phe Ala Thr Tyr Asp Glu Leu Ile
305                 310                 315                 320

Pro Tyr Thr Asp Ala Ile Glu Arg Trp Asp Ile Lys Cys Met Asn Gln
                325                 330                 335
```

```
Leu Pro Asn Tyr Met Gln Ile Ser Tyr Lys Ala Leu Leu Asp Val Tyr
            340                 345                 350

Glu Glu Met Glu Gln Leu Leu Ala Asp Lys Gly Arg Gln Tyr Arg Val
        355                 360                 365

Glu Tyr Ala Lys Lys Ala Met Ile Arg Leu Val Gln Ala Tyr Leu Leu
    370                 375                 380

Glu Ala Lys Trp Thr His Leu Asn Tyr Lys Pro Thr Phe Glu Glu Phe
385                 390                 395                 400

Arg Asp Asn Ala Leu Pro Thr Ser Gly Tyr Ala Met Leu Ala Ile Thr
                405                 410                 415

Ala Phe Val Gly Met Gly Glu Val Ile Thr Pro Glu Thr Phe Glu Trp
            420                 425                 430

Ala Ala Ser Asp Pro Lys Ile Ile Lys Ala Ser Thr Ile Ile Cys Arg
        435                 440                 445

Phe Met Asp Asp Ile Ala Glu His Lys Phe Asn His Arg Arg Glu Asp
    450                 455                 460

Asp Cys Ser Ala Ile Glu Cys Tyr Met Glu Gln Tyr Lys Val Thr Ala
465                 470                 475                 480

Gln Glu Ala Tyr Asp Glu Phe Asn Lys His Ile Glu Ser Ser Trp Lys
                485                 490                 495

Asp Val Asn Glu Glu Phe Leu Lys Pro Thr Glu Met Pro Thr Pro Val
            500                 505                 510

Leu Cys Arg Ser Leu Asn Leu Ala Arg Val Met Asp Val Leu Tyr Arg
        515                 520                 525

Glu Gly Asp Gly Tyr Thr His Val Gly Lys Ala Ala Lys Gly Gly Ile
    530                 535                 540

Thr Ser Leu Leu Ile Asp Pro Ile Gln Ile
545                 550

<210> SEQ ID NO 6
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 6

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
            20                  25                  30

Met Phe Ile Ile Cys Pro Asp Thr Asp Ile Asp Ala Ala Thr Glu Leu
        35                  40                  45

Gln Tyr Glu Glu Leu Lys Ala Gln Val Arg Lys Met Ile Met Glu Pro
    50                  55                  60

Val Asp Asp Ser Asn Gln Lys Leu Pro Phe Ile Asp Ala Val Gln Arg
65                  70                  75                  80

Leu Gly Val Ser Tyr His Phe Glu Lys Glu Ile Glu Asp Glu Leu Glu
                85                  90                  95

Asn Ile Tyr Arg Asp Thr Asn Asn Asp Ala Asp Thr Asp Leu Tyr
            100                 105                 110

Thr Thr Ala Leu Arg Phe Arg Leu Leu Arg Glu His Gly Phe Asp Ile
        115                 120                 125

Ser Cys Glu Ala Phe Asn Lys Leu Lys Asp Glu Glu Gly Asn Phe Lys
    130                 135                 140
```

```
Ala Ser Leu Thr Ser Asp Val Arg Gly Leu Leu Glu Leu Tyr Gln Ala
145                 150                 155                 160

Ser Tyr Met Arg Ile His Gly Glu Asp Ile Leu Asp Glu Ala Ile Ser
                165                 170                 175

Phe Thr Thr Ala Gln Leu Thr Leu Ala Leu Pro Thr Leu Asp Pro Pro
            180                 185                 190

Leu Ser Glu Gln Val Gly His Ala Leu Lys Gln Ser Ile Arg Arg Gly
        195                 200                 205

Leu Pro Arg Val Glu Ala Arg Asn Phe Ile Ser Ile Tyr Gln Asp Leu
    210                 215                 220

Glu Ser His Asn Lys Ser Leu Leu Glu Phe Ala Lys Ile Asp Phe Asn
225                 230                 235                 240

Leu Leu Gln Leu Leu His Arg Lys Glu Leu Ser Glu Ile Cys Arg Trp
                245                 250                 255

Trp Lys Asp Leu Asp Phe Thr Arg Lys Leu Pro Phe Ala Arg Asp Arg
                260                 265                 270

Val Val Glu Gly Tyr Phe Trp Ile Met Gly Val Tyr Phe Glu Pro Gln
            275                 280                 285

Tyr Ser Leu Gly Arg Lys Met Leu Thr Lys Val Ile Ala Met Ala Ser
        290                 295                 300

Ile Val Asp Asp Thr Tyr Asp Ser Phe Ala Thr Tyr Asp Glu Leu Ile
305                 310                 315                 320

Pro Tyr Thr Asp Ala Ile Glu Arg Trp Asp Ile Lys Cys Met Asn Gln
                325                 330                 335

Leu Pro Asn Tyr Met Gln Ile Ser Tyr Lys Ala Leu Leu Asp Val Tyr
                340                 345                 350

Glu Glu Met Glu Gln Leu Leu Ala Asp Lys Gly Arg Gln Tyr Arg Val
            355                 360                 365

Glu Tyr Ala Lys Lys Ala Met Ile Arg Leu Val Gln Ala Tyr Leu Leu
        370                 375                 380

Glu Ala Lys Trp Thr His Leu Asn Tyr Lys Pro Thr Phe Glu Glu Phe
385                 390                 395                 400

Arg Asp Asn Ala Leu Pro Thr Ser Gly Tyr Ala Met Leu Ala Ile Thr
                405                 410                 415

Ala Phe Val Gly Met Gly Glu Val Ile Thr Pro Glu Thr Phe Glu Trp
                420                 425                 430

Ala Ala Ser Asp Pro Lys Ile Ile Lys Ala Ser Thr Ile Ile Cys Arg
            435                 440                 445

Phe Met Asp Asp Ile Ala Glu His Lys Phe Asn His Arg Arg Glu Asp
    450                 455                 460

Asp Cys Ser Ala Ile Glu Cys Tyr Met Lys Gln Tyr Gly Ala Thr Ala
465                 470                 475                 480

Gln Glu Ala Tyr Asp Glu Phe Asn Lys His Ile Glu Ser Ser Trp Lys
                485                 490                 495

Asp Val Asn Glu Glu Phe Leu Lys Pro Thr Glu Met Pro Thr Pro Val
            500                 505                 510

Leu Cys Arg Ser Leu Asn Leu Ala Arg Val Met Asp Val Leu Tyr Arg
        515                 520                 525

Glu Gly Asp Gly Tyr Thr His Val Gly Lys Ala Ala Lys Gly Gly Ile
    530                 535                 540

Thr Ser Leu Leu Ile Asp Pro Ile Gln Ile
545                 550
```

```
<210> SEQ ID NO 7
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 7

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
            20                  25                  30

Met Phe Ile Ile Cys Pro Asp Thr Asp Ile Asp Ala Ala Thr Glu Leu
        35                  40                  45

Gln Tyr Glu Glu Leu Lys Ala Gln Val Arg Lys Met Ile Met Glu Pro
    50                  55                  60

Val Asp Asp Ser Asn Gln Lys Leu Pro Phe Ile Asp Ala Val Gln Arg
65                  70                  75                  80

Leu Gly Val Ser Tyr His Phe Glu Lys Glu Ile Glu Asp Glu Leu Glu
                85                  90                  95

Asn Ile Tyr Arg Asp Thr Asn Asn Asp Ala Asp Thr Asp Leu Tyr
            100                 105                 110

Thr Thr Ala Leu Arg Phe Arg Leu Leu Arg Glu His Gly Phe Asp Ile
        115                 120                 125

Ser Cys Asp Ala Phe Asn Lys Leu Lys Asp Glu Gly Asn Phe Lys
    130                 135                 140

Ala Ser Leu Thr Ser Asp Val Pro Gly Leu Leu Glu Leu Tyr Glu Ala
145                 150                 155                 160

Ser Tyr Leu Arg Val His Gly Glu Asp Ile Leu Asp Glu Ala Ile Ser
                165                 170                 175

Phe Ala Thr Ala Gln Leu Thr Leu Ala Leu Pro Thr Leu His His Pro
            180                 185                 190

Leu Ser Glu Gln Val Gly His Ala Leu Lys Gln Ser Ile Arg Arg Gly
        195                 200                 205

Leu Pro Arg Val Glu Ala Arg Asn Phe Ile Ser Ile Tyr Gln Asp Leu
    210                 215                 220

Glu Ser His Asn Lys Ser Leu Leu Glu Phe Ala Lys Ile Asp Phe Asn
225                 230                 235                 240

Leu Leu Gln Leu Leu His Arg Lys Glu Leu Ser Glu Ile Cys Arg Trp
                245                 250                 255

Trp Lys Asp Leu Asp Phe Thr Arg Lys Leu Pro Phe Ala Arg Asp Arg
            260                 265                 270

Val Val Glu Gly Tyr Phe Trp Ile Met Gly Val Tyr Phe Glu Pro Gln
        275                 280                 285

Tyr Ser Leu Gly Arg Lys Met Leu Thr Lys Val Ile Ala Met Ala Ser
    290                 295                 300

Ile Val Asp Asp Thr Tyr Asp Ser Phe Ala Thr Tyr Asp Glu Leu Ile
305                 310                 315                 320

Pro Tyr Thr Asp Ala Ile Glu Arg Trp Asp Ile Lys Cys Met Asn Gln
                325                 330                 335

Leu Pro Asn Tyr Met Gln Ile Ser Tyr Lys Ala Leu Leu Asp Val Tyr
            340                 345                 350

Glu Glu Met Glu Gln Leu Leu Ala Asp Lys Gly Arg Gln Tyr Arg Val
        355                 360                 365

Glu Tyr Ala Lys Lys Ala Met Ile Arg Leu Val Gln Ala Tyr Leu Leu
```

```
                370                 375                 380
Glu Ala Lys Trp Thr His Leu Asn Tyr Lys Pro Thr Phe Glu Glu Phe
385                 390                 395                 400

Arg Asp Asn Ala Leu Pro Thr Ser Gly Tyr Ala Met Leu Ala Ile Thr
                405                 410                 415

Ala Phe Val Gly Met Gly Glu Val Ile Thr Pro Glu Thr Phe Glu Trp
                420                 425                 430

Ala Ala Ser Asp Pro Lys Ile Ile Lys Ala Ser Thr Ile Ile Cys Arg
                435                 440                 445

Phe Met Asp Asp Ile Ala Glu His Lys Phe Asn His Arg Arg Glu Asp
                450                 455                 460

Asp Cys Ser Ala Ile Glu Cys Tyr Met Lys Gln Tyr Gly Ala Thr Ala
465                 470                 475                 480

Gln Glu Ala Tyr Asp Glu Phe Asn Lys His Ile Glu Ser Ser Trp Lys
                485                 490                 495

Asp Val Asn Glu Glu Phe Leu Lys Pro Thr Glu Met Pro Thr Pro Val
                500                 505                 510

Leu Cys Arg Ser Leu Asn Leu Ala Arg Val Met Asp Val Leu Tyr Arg
                515                 520                 525

Glu Gly Asp Gly Tyr Thr His Val Gly Lys Ala Ala Lys Gly Gly Ile
                530                 535                 540

Thr Ser Leu Leu Ile Asp Pro Ile Gln Ile
545                 550

<210> SEQ ID NO 8
<211> LENGTH: 556
<212> TYPE: PRT
<213> ORGANISM: Artificial Sequence
<220> FEATURE:
<223> OTHER INFORMATION: Synthetic polypeptide

<400> SEQUENCE: 8

Ser Ile Gln Val Pro Gln Ile Ser Ser Gln Asn Ala Lys Ser Gln Val
1               5                   10                  15

Met Arg Arg Thr Ala Asn Phe His Pro Ser Val Trp Gly Asp Arg Phe
                20                  25                  30

Ala Asn Tyr Thr Ala Glu Asp Lys Met Asn His Ala Arg Asp Leu Lys
                35                  40                  45

Glu Leu Lys Ala Leu Lys Glu Glu Val Gly Arg Lys Leu Leu Ala Thr
            50                  55                  60

Ala Gly Pro Ile Gln Leu Asn Leu Ile Asp Ala Ile Gln Arg Leu Gly
65                  70                  75                  80

Val Gly Tyr His Phe Glu Arg Glu Leu Glu Gln Ala Leu Gln His Leu
                85                  90                  95

Tyr Asn Glu Lys Tyr Ser Asp Asp Thr Glu Asp Asp Leu Tyr Arg
                100                 105                 110

Ile Ser Leu Arg Phe Arg Leu Leu Arg Gln His Gly Tyr Asn Val Ser
            115                 120                 125

Cys Asp Lys Phe Asn Met Phe Lys Asp Lys Gly Asn Phe Lys Glu
                130                 135                 140

Ser Leu Ala Ser Asp Ala Leu Gly Met Leu Ser Leu Tyr Glu Ala Ala
145                 150                 155                 160

His Leu Gly Val His Gly Glu Asp Ile Leu Asp Glu Ala Ile Ala Phe
                165                 170                 175

Thr Thr Thr His Leu Lys Ser Val Ala Thr His Leu Ser Asn Pro Leu
```

180                 185                 190
Lys Ala Gln Val Arg His Ala Leu Arg Gln Pro Leu His Arg Gly Leu
            195                 200                 205

Pro Arg Leu Glu His Arg Arg Tyr Ile Ser Ile Tyr Gln Asp Asp Ala
        210                 215                 220

Ser His Tyr Lys Ala Leu Leu Thr Leu Ala Lys Leu Asp Phe Asn Leu
225                 230                 235                 240

Val Gln Ser Leu His Lys Lys Glu Leu Cys Glu Ile Ser Arg Trp Trp
                245                 250                 255

Lys Asp Leu Asp Phe Ala Arg Lys Leu Pro Phe Ala Arg Asp Arg Met
            260                 265                 270

Val Glu Cys Tyr Phe Trp Ile Leu Gly Val Tyr Phe Glu Pro Asn Tyr
        275                 280                 285

Ser Leu Ala Arg Arg Ile Leu Thr Lys Val Ile Ala Met Thr Ser Ile
    290                 295                 300

Ile Asp Asp Ile Tyr Asp Val Tyr Gly Thr Pro Glu Glu Leu Lys Leu
305                 310                 315                 320

Phe Thr Glu Val Ile Glu Arg Trp Asp Glu Ser Ser Met Asp Gln Leu
                325                 330                 335

Pro Glu Tyr Met Gln Thr Phe Phe Gly Ala Leu Leu Asp Leu Tyr Asn
            340                 345                 350

Glu Ile Glu Lys Glu Ile Ala Asn Glu Gly Trp Ser Tyr Arg Val Gln
        355                 360                 365

Tyr Ala Lys Glu Ala Met Lys Ile Leu Val Glu Gly Tyr Tyr Asp Glu
    370                 375                 380

Ser Lys Trp Phe His Glu Asn Tyr Ile Pro Lys Met Glu Glu Tyr Met
385                 390                 395                 400

Arg Val Ala Leu Val Thr Ser Gly Tyr Thr Met Leu Thr Thr Val Ser
                405                 410                 415

Phe Leu Gly Met Asp Asn Ile Val Thr Lys Glu Thr Phe Asp Trp Val
            420                 425                 430

Phe Ser Arg Pro Lys Ile Ile Arg Ala Ser Glu Ile Ile Gly Arg Phe
        435                 440                 445

Met Asp Asp Ile Lys Ser His Lys Phe Glu Gln Glu Arg Gly His Cys
    450                 455                 460

Ala Ser Ala Val Glu Cys Tyr Met Arg Glu His Gly Val Ser Glu Glu
465                 470                 475                 480

Glu Ala Cys Ser Glu Leu Lys Lys Gln Val Asp Asn Ala Trp Lys Asp
                485                 490                 495

Ile Asn His Glu Met Ile Phe Ser Glu Thr Ser Lys Ala Val Pro Met
            500                 505                 510

Ser Val Leu Thr Arg Val Leu Asn Leu Thr Arg Val Ile Asp Val Val
        515                 520                 525

Tyr Lys Glu Gly Asp Gly Tyr Thr His Val Gly Asn Glu Met Lys Gln
    530                 535                 540

Asn Val Ala Ala Leu Leu Ile Asp Gln Val Pro Ile
545                 550                 555

<210> SEQ ID NO 9
<211> LENGTH: 554
<212> TYPE: PRT
<213> ORGANISM: Artificial Sequence
<220> FEATURE:
<223> OTHER INFORMATION: Synthetic polypeptide

```
<400> SEQUENCE: 9

Glu Lys Gln Ser Leu Thr Phe Asp Gly Asp Glu Ala Lys Ile Asp
1               5                   10                  15

Arg Lys Ser Ser Lys Tyr His Pro Ser Ile Trp Gly Asp Tyr Phe Ile
            20                  25                  30

Gln Asn Ser Ser Leu Thr His Ala Lys Glu Ser Thr Gln Arg Met Ile
            35                  40                  45

Lys Arg Val Glu Glu Leu Lys Val Gln Val Lys Ser Met Phe Lys Asp
        50                  55                  60

Thr Ser Asp Leu Leu Gln Leu Met Asn Leu Ile Asn Ser Ile Gln Met
65                  70                  75                  80

Leu Gly Leu Asp Tyr His Phe Glu Asn Glu Ile Asp Glu Ala Leu Arg
                    85                  90                  95

Leu Ile Tyr Glu Val Asp Asp Lys Ser Tyr Gly Leu Tyr Glu Thr Ser
                100                 105                 110

Leu Arg Phe Gln Leu Leu Arg Gln His Gly Tyr His Val Asp Gly Glu
            115                 120                 125

Glu Ala Phe Asn Met Leu Lys Asp Glu Glu Gly Asn Phe Lys Ala Ser
        130                 135                 140

Leu Thr Ser Asp Val Pro Gly Leu Leu Glu Leu Tyr Gln Ala Ser Tyr
145                 150                 155                 160

Met Arg Ile His Gly Glu Asp Ile Leu Asp Glu Ala Ile Ser Phe Thr
                    165                 170                 175

Thr Ala Gln Leu Thr Leu Ala Leu Pro Thr Leu Asp Pro Pro Leu Ser
                180                 185                 190

Ala Gln Val Ser Leu Phe Leu Glu Leu Pro Leu Cys Arg Arg Asn Lys
            195                 200                 205

Ile Leu Leu Ala Arg Lys Tyr Ile Leu Ile Tyr Gln Glu Asp Ala Met
        210                 215                 220

Arg Asn Asn Val Ile Leu Glu Leu Ala Lys Leu Asn Phe Asn Leu Leu
225                 230                 235                 240

Gln Ser Leu Tyr Gln Glu Glu Leu Lys Lys Ile Ser Ile Trp Trp Asn
                    245                 250                 255

Asp Leu Ala Phe Ala Lys Ser Leu Ser Phe Thr Arg Asp Arg Val Val
                260                 265                 270

Glu Gly Tyr Tyr Trp Val Leu Thr Ile Tyr Phe Glu Pro Gln His Ser
            275                 280                 285

Arg Ala Arg Val Ile Cys Ser Lys Val Phe Ala Phe Leu Ser Ile Met
        290                 295                 300

Asp Asp Ile Tyr Asp Asn Tyr Gly Ile Leu Glu Glu Cys Thr Leu Leu
305                 310                 315                 320

Thr Glu Ala Ile Lys Arg Trp Asn Pro Gln Ala Ile Asp Gly Leu Pro
                    325                 330                 335

Glu Tyr Leu Lys Asp Tyr Tyr Leu Lys Leu Leu Lys Thr Phe Glu Glu
                340                 345                 350

Phe Glu Asp Glu Leu Glu Leu Asn Glu Lys Tyr Arg Met Leu Tyr Leu
            355                 360                 365

Gln Asp Glu Val Lys Ala Leu Ala Ile Ser Tyr Leu Gln Glu Ala Lys
        370                 375                 380

Trp Gly Ile Glu Arg His Val Pro Ser Leu Asp Glu His Leu His Asn
385                 390                 395                 400

Ser Leu Ile Ser Ser Gly Ser Ser Thr Val Ile Cys Ala Ser Phe Val
                    405                 410                 415
```

-continued

```
Gly Met Gly Glu Val Ala Thr Lys Glu Val Phe Asp Trp Leu Ser Ser
            420                 425                 430

Phe Pro Lys Val Val Glu Ala Cys Cys Val Ile Gly Arg Leu Leu Asn
        435                 440                 445

Asp Ile Arg Ser His Glu Leu Glu Gln Gly Arg Asp His Thr Ala Ser
    450                 455                 460

Thr Val Glu Ser Tyr Met Lys Glu His Asp Thr Asn Val Asp Val Ala
465                 470                 475                 480

Cys Glu Lys Leu Arg Glu Ile Val Glu Lys Ala Trp Lys Asp Leu Asn
                485                 490                 495

Asn Glu Ser Leu Asn Pro Thr Lys Val Pro Arg Leu Met Ile Glu Arg
            500                 505                 510

Ile Val Asn Leu Ser Lys Ser Asn Glu Glu Ile Tyr Lys Tyr Asn Asp
        515                 520                 525

Thr Tyr Thr Asn Ser Asp Thr Thr Met Lys Asp Asn Ile Ser Leu Val
    530                 535                 540

Leu Val Glu Ser Cys Asp Tyr Phe Asn Lys
545                 550

<210> SEQ ID NO 10
<211> LENGTH: 556
<212> TYPE: PRT
<213> ORGANISM: Artificial Sequence
<220> FEATURE:
<223> OTHER INFORMATION: Synthetic polypeptide

<400> SEQUENCE: 10

Ala Ser Gln Val Ser Gln Met Pro Ser Ser Pro Leu Ser Ser Asn
1               5                   10                  15

Lys Asp Glu Met Arg Pro Lys Ala Asp Phe Gln Pro Ser Ile Trp Gly
            20                  25                  30

Asp Leu Phe Leu Asn Cys Pro Asp Lys Asn Ile Asp Ala Glu Thr Glu
        35                  40                  45

Lys Arg His Gln Gln Leu Lys Glu Glu Val Arg Lys Met Ile Val Ala
    50                  55                  60

Pro Met Ala Asn Ser Thr Gln Lys Leu Ala Phe Ile Asp Ser Val Gln
65                  70                  75                  80

Arg Leu Gly Val Ser Tyr His Phe Thr Lys Glu Ile Glu Asp Glu Leu
                85                  90                  95

Glu Asn Ile Tyr His Asn Asn Asp Ala Glu Asn Asp Leu Tyr Thr
            100                 105                 110

Thr Ser Leu Arg Phe Arg Leu Leu Arg Glu His Gly Phe Asn Val Ser
        115                 120                 125

Cys Asp Val Phe Asn Lys Phe Lys Asp Glu Gln Gly Asn Phe Lys Ser
    130                 135                 140

Ser Val Thr Ser Asp Val Arg Gly Leu Leu Glu Leu Tyr Gln Ala Ser
145                 150                 155                 160

Tyr Leu Arg Val His Gly Glu Asp Ile Leu Asp Glu Ala Ile Ser Phe
                165                 170                 175

Thr Thr Asn His Leu Ser Leu Ala Val Ala Ser Leu Asp Tyr Pro Leu
            180                 185                 190

Ser Glu Glu Val Ser His Ala Leu Lys Gln Ser Ile Arg Arg Gly Leu
        195                 200                 205

Pro Arg Val Glu Ala Arg His Tyr Leu Ser Val Tyr Gln Asp Ile Glu
    210                 215                 220
```

Ser His Asn Lys Val Leu Leu Glu Phe Ala Lys Ile Asp Phe Asn Met
225                 230                 235                 240

Val Gln Leu Leu His Arg Lys Glu Leu Ser Glu Ile Ser Arg Trp Trp
            245                 250                 255

Lys Asp Leu Asp Phe Gln Arg Lys Leu Pro Tyr Ala Arg Asp Arg Val
        260                 265                 270

Val Glu Gly Tyr Phe Trp Ile Ser Gly Val Tyr Phe Glu Pro Gln Tyr
    275                 280                 285

Ser Leu Gly Arg Lys Met Leu Thr Lys Val Ile Ala Met Ala Ser Ile
290                 295                 300

Val Asp Asp Thr Tyr Asp Ser Tyr Ala Thr Tyr Glu Glu Leu Ile Pro
305                 310                 315                 320

Tyr Thr Lys Ala Ile Glu Arg Trp Asp Ile Lys Cys Ile Asp Glu Leu
                325                 330                 335

Pro Glu Tyr Met Lys Pro Ser Tyr Lys Ala Leu Leu Asp Val Tyr Glu
            340                 345                 350

Glu Met Glu Gln Leu Val Ala Lys His Gly Arg Gln Tyr Arg Val Glu
        355                 360                 365

Tyr Ala Lys Asn Ala Met Ile Arg Leu Ala Gln Ser Tyr Leu Val Glu
370                 375                 380

Ala Arg Trp Thr Leu Gln Asn Tyr Lys Pro Ser Phe Glu Glu Phe Lys
385                 390                 395                 400

Ala Asn Ala Leu Pro Thr Cys Gly Tyr Ala Met Leu Ala Ile Thr Ser
                405                 410                 415

Phe Val Gly Met Gly Asp Ile Val Thr Pro Glu Thr Phe Lys Trp Ala
            420                 425                 430

Ala Asn Asp Pro Lys Ile Ile Gln Ala Ser Thr Ile Ile Cys Arg Phe
        435                 440                 445

Met Asp Asp Val Ala Glu His Lys Phe Glu Gln Glu Arg Gly His Cys
450                 455                 460

Ala Ser Ala Val Glu Cys Tyr Met Arg Glu His Gly Val Ser Glu Glu
465                 470                 475                 480

Glu Ala Cys Ser Glu Leu Lys Lys Gln Val Asp Asn Ala Trp Lys Asp
                485                 490                 495

Ile Asn His Glu Met Ile Phe Ser Glu Thr Ser Lys Ala Val Pro Met
            500                 505                 510

Ser Val Leu Thr Arg Val Leu Asn Leu Thr Arg Val Met Asp Val Leu
        515                 520                 525

Tyr Arg Glu Gly Asp Gly Tyr Thr Tyr Val Gly Lys Ala Ala Lys Gly
530                 535                 540

Gly Ile Thr Ser Leu Leu Ile Glu Pro Val Ala Leu
545                 550                 555

<210> SEQ ID NO 11
<211> LENGTH: 554
<212> TYPE: PRT
<213> ORGANISM: Artificial Sequence
<220> FEATURE:
<223> OTHER INFORMATION: Synthetic polypeptide

<400> SEQUENCE: 11

Ala Ser Gln Val Ser Gln Met Pro Ser Ser Pro Leu Ser Ser Asn
1               5                   10                  15

Lys Asp Glu Met Arg Pro Lys Ala Asp Phe Gln Pro Ser Ile Trp Gly
            20                  25                  30

Asp Leu Phe Leu Asn Cys Pro Asp Lys Asn Ile Asp Ala Glu Thr Glu
            35                  40                  45

Lys Arg His Gln Gln Leu Lys Glu Glu Val Arg Lys Met Ile Val Ala
 50                  55                  60

Pro Met Ala Asn Ser Thr Gln Lys Leu Ala Phe Ile Asp Ser Val Gln
 65                  70                  75                  80

Arg Leu Gly Val Ser Tyr His Phe Thr Lys Glu Ile Glu Asp Glu Leu
                 85                  90                  95

Glu Asn Ile Tyr His Asn Asn Asp Ala Glu Asn Asp Leu Tyr Thr
                100                 105                 110

Thr Ser Ile Arg Phe Arg Leu Leu Arg Glu His Gly Tyr His Val Asp
             115                 120                 125

Gly Glu Glu Ala Phe Asn Met Leu Lys Asp Glu Glu Gly Asn Phe Lys
        130                 135                 140

Ala Ser Leu Thr Ser Asp Val Pro Gly Leu Leu Glu Leu Tyr Gln Ala
145                 150                 155                 160

Ser Tyr Met Arg Ile His Gly Glu Asp Ile Leu Asp Glu Ala Ile Ser
                165                 170                 175

Phe Thr Thr Ala Gln Leu Thr Leu Ala Leu Pro Thr Leu Asp Pro Pro
            180                 185                 190

Leu Ser Glu Glu Val Ser His Ala Leu Lys Gln Ser Ile Arg Arg Gly
        195                 200                 205

Leu Pro Arg Val Glu Ala Arg His Tyr Leu Ser Val Tyr Gln Asp Ile
    210                 215                 220

Glu Ser His Asn Lys Ala Leu Leu Glu Phe Ala Lys Ile Asp Phe Asn
225                 230                 235                 240

Met Leu Gln Phe Leu His Arg Lys Glu Leu Ser Glu Ile Cys Arg Trp
                245                 250                 255

Trp Lys Asp Leu Asp Phe Gln Arg Lys Leu Pro Tyr Ala Arg Asp Arg
            260                 265                 270

Val Val Glu Gly Tyr Phe Trp Ile Ser Gly Val Tyr Phe Glu Pro Gln
        275                 280                 285

Tyr Ser Leu Gly Arg Lys Met Leu Thr Lys Val Ile Ala Met Ala Ser
    290                 295                 300

Ile Val Asp Asp Thr Tyr Asp Ser Tyr Ala Thr Tyr Glu Glu Leu Ile
305                 310                 315                 320

Pro Tyr Thr Asn Ala Ile Glu Arg Trp Asp Ile Lys Cys Ile Asp Glu
                325                 330                 335

Ile Pro Glu Tyr Met Lys Pro Ser Tyr Lys Ala Leu Leu Asp Val Tyr
            340                 345                 350

Glu Glu Met Val Gln Leu Val Ala Glu His Gly Arg Gln Tyr Arg Val
        355                 360                 365

Glu Tyr Ala Lys Asn Ala Met Ile Arg Leu Ala Gln Ser Tyr Leu Val
    370                 375                 380

Glu Ala Lys Trp Thr Leu Gln Asn Tyr Lys Pro Ser Phe Glu Glu Phe
385                 390                 395                 400

Lys Ala Asn Ala Leu Pro Thr Cys Gly Tyr Ala Met Leu Ala Ile Thr
                405                 410                 415

Ser Phe Val Gly Met Gly Asp Ile Val Thr Pro Glu Thr Phe Lys Trp
            420                 425                 430

Ala Ala Ser Asp Pro Lys Ile Ile Gln Ala Ser Thr Ile Ile Cys Arg
        435                 440                 445

Phe Met Asp Asp Val Ala Glu His Lys Phe Lys His Arg Arg Glu Asp
450                 455                 460

Asp Cys Ser Ala Ile Glu Cys Tyr Met Glu Tyr Gly Val Thr Ala
465                 470                 475                 480

Gln Glu Ala Tyr Asp Val Phe Asn Lys His Val Glu Ser Ala Trp Lys
            485                 490                 495

Asp Leu Asn Gln Glu Phe Leu Lys Pro Thr Glu Met Pro Thr Glu Val
            500                 505                 510

Leu Asn Arg Ser Leu Asn Leu Ala Arg Val Met Asp Val Leu Tyr Arg
            515                 520                 525

Glu Gly Asp Gly Tyr Thr Tyr Val Gly Lys Ala Lys Gly Gly Ile
530                 535                 540

Thr Ser Leu Leu Ile Glu Pro Ile Ala Leu
545                 550

<210> SEQ ID NO 12
<211> LENGTH: 557
<212> TYPE: PRT
<213> ORGANISM: Artificial Sequence
<220> FEATURE:
<223> OTHER INFORMATION: Synthetic polypeptide

<400> SEQUENCE: 12

Ala Ser Gln Ala Ser Gln Val Leu Ala Ser Pro His Pro Ala Ile Ser
1               5                   10                  15

Ser Glu Asn Arg Pro Lys Ala Asp Phe His Pro Gly Ile Trp Gly Asp
            20                  25                  30

Met Phe Ile Ile Cys Pro Asp Thr Asp Ile Asp Ala Ala Thr Glu Leu
        35                  40                  45

Gln Tyr Glu Glu Leu Lys Ala Gln Val Arg Lys Met Ile Met Glu Pro
    50                  55                  60

Val Asp Asp Ser Asn Gln Lys Leu Pro Phe Ile Asp Ala Val Gln Arg
65                  70                  75                  80

Leu Gly Val Ser Tyr His Phe Glu Lys Glu Ile Glu Asp Glu Leu Glu
                85                  90                  95

Asn Ile Tyr Arg Asp Thr Asn Asn Asp Ala Asp Thr Asp Leu Tyr
            100                 105                 110

Thr Thr Ala Leu Arg Phe Arg Leu Leu Arg Glu His Gly Phe Asp Ile
        115                 120                 125

Ser Cys Asp Ala Phe Asn Lys Phe Lys Asp Glu Ala Gly Asn Phe Lys
130                 135                 140

Ala Ser Leu Thr Ser Asp Val Gln Gly Leu Leu Glu Leu Tyr Glu Ala
145                 150                 155                 160

Ser Tyr Met Arg Val His Gly Glu Asp Ile Leu Asp Glu Ala Ile Ser
                165                 170                 175

Phe Thr Thr Ala Gln Leu Thr Leu Ala Leu Pro Thr Leu His His Pro
            180                 185                 190

Leu Ser Glu Gln Val Gly His Ala Leu Lys Gln Ser Ile Arg Arg Gly
        195                 200                 205

Leu Pro Arg Val Glu Ala Arg Asn Phe Ile Ser Ile Tyr Gln Asp Leu
210                 215                 220

Glu Ser His Asn Lys Ser Leu Leu Gln Phe Ala Lys Ile Asp Phe Asn
225                 230                 235                 240

Leu Leu Gln Leu Leu His Arg Lys Glu Leu Ser Glu Ile Cys Arg Trp
                245                 250                 255

```
Trp Lys Asp Leu Asp Phe Thr Arg Lys Leu Pro Phe Ala Arg Asp Arg
            260                 265                 270

Val Val Glu Gly Tyr Phe Trp Ile Met Gly Val Tyr Phe Glu Pro Gln
        275                 280                 285

Tyr Ser Leu Gly Arg Lys Met Leu Thr Lys Val Ile Ala Met Ala Ser
    290                 295                 300

Ile Val Asp Asp Thr Tyr Asp Ser Tyr Ala Thr Tyr Asp Glu Leu Ile
305                 310                 315                 320

Pro Tyr Thr Asn Ala Ile Glu Arg Trp Asp Ile Lys Cys Met Asn Gln
                325                 330                 335

Leu Pro Asn Tyr Met Lys Ile Ser Tyr Lys Ala Leu Leu Asn Val Tyr
            340                 345                 350

Glu Glu Met Glu Gln Leu Leu Ala Asn Gln Gly Arg Gln Tyr Arg Val
        355                 360                 365

Glu Tyr Ala Lys Lys Ala Met Ile Arg Leu Val Gln Ala Tyr Leu Leu
    370                 375                 380

Glu Ala Lys Trp Thr His Gln Asn Tyr Lys Pro Thr Phe Glu Glu Phe
385                 390                 395                 400

Arg Asp Asn Ala Leu Pro Thr Ser Gly Tyr Ala Met Leu Ala Ile Thr
                405                 410                 415

Ala Phe Val Gly Met Gly Glu Val Ile Thr Pro Glu Thr Phe Lys Trp
            420                 425                 430

Ala Ala Ser Asp Pro Lys Ile Ile Lys Ala Ser Thr Ile Ile Cys Arg
        435                 440                 445

Phe Met Asp Asp Ile Ala Glu His Lys Phe Gln Glu Arg Gly His
    450                 455                 460

Cys Ala Ser Ala Val Glu Cys Tyr Met Arg Glu His Gly Val Ser Glu
465                 470                 475                 480

Glu Glu Ala Cys Ser Glu Leu Lys Lys Gln Val Asp Asn Ala Trp Lys
                485                 490                 495

Asp Ile Asn His Glu Met Ile Phe Ser Glu Thr Ser Lys Ala Val Pro
            500                 505                 510

Met Ser Val Leu Thr Arg Val Leu Asn Leu Thr Arg Val Met Asp Val
        515                 520                 525

Leu Tyr Arg Glu Gly Asp Gly Tyr Thr His Val Gly Lys Ala Ala Lys
    530                 535                 540

Gly Gly Ile Thr Ser Leu Leu Ile Asp Pro Ile Gln Ile
545                 550                 555

<210> SEQ ID NO 13
<211> LENGTH: 548
<212> TYPE: PRT
<213> ORGANISM: Artificial Sequence
<220> FEATURE:
<223> OTHER INFORMATION: Synthetic polypeptide

<400> SEQUENCE: 13

Ala Ala Ser Phe Ala Asn Lys Cys Arg Pro Leu Ala Asn Phe His Pro
1               5                   10                  15

Thr Val Trp Gly Tyr His Phe Leu Tyr Tyr Asn Pro Glu Ile Thr Asn
            20                  25                  30

Gln Glu Lys Ile Glu Val Asp Glu Tyr Lys Glu Thr Ile Arg Lys Met
        35                  40                  45

Leu Val Glu Ala Pro Gly Ser Glu Gln Lys Leu Val Leu Ile Asp
    50                  55                  60
```

```
Ala Met Gln Arg Leu Gly Val Ala Tyr His Phe His Asn Glu Ile Glu
 65                  70                  75                  80

Thr Ser Ile Gln Asn Ile Phe Asp Ala Pro Lys Gln Asn Asn Asp Asp
                 85                  90                  95

Asn Leu His Ile Val Ser Leu Arg Phe Arg Leu Val Arg Gln Gln Gly
            100                 105                 110

His Tyr Met Ser Ser Asp Val Phe Lys Gln Phe Thr Asn Gln Asp Gly
            115                 120                 125

Lys Phe Lys Glu Thr Leu Thr Asn Asp Val Gln Gly Leu Leu Ser Leu
130                 135                 140

Tyr Glu Ala Ser His Leu Arg Val Arg Asn Glu Glu Ile Leu Glu Glu
145                 150                 155                 160

Ala Leu Thr Phe Thr Thr Thr His Leu Glu Ser Ile Val Ser Asn Leu
                165                 170                 175

Ser Asn Lys Asn Asn Ser Leu Lys Val Glu Val Ser Glu Ala Leu Ser
            180                 185                 190

Gln Pro Ile Arg Met Thr Leu Pro Arg Ile Gly Ala Arg Lys Tyr Ile
            195                 200                 205

Ser Ile Tyr Glu Asn Asn Asp Ala His Asn His Leu Leu Leu Lys Phe
210                 215                 220

Ala Lys Leu Asp Phe Asn Met Leu Gln Lys Phe His Gln Arg Glu Leu
225                 230                 235                 240

Ser Asp Leu Thr Arg Trp Trp Lys Asp Leu Asp Phe Ala Asn Lys Ile
                245                 250                 255

Pro Tyr Ala Arg Asp Arg Leu Val Glu Cys Tyr Phe Trp Ile Leu Gly
            260                 265                 270

Val Tyr Phe Glu Pro Lys Tyr Ser Arg Ala Arg Lys Met Met Thr Lys
            275                 280                 285

Val Leu Lys Met Thr Ser Ile Ile Asp Asp Thr Phe Asp Ala Tyr Ala
290                 295                 300

Asn Phe Asp Glu Leu Val Pro Phe Asn Asp Ala Ile Gln Arg Trp Asp
305                 310                 315                 320

Ala Asn Ala Ile Asp Ser Ile Pro Pro Tyr Met Arg Pro Ile Tyr Gln
                325                 330                 335

Ala Leu Leu Asp Ile Tyr Gly Glu Met Asp Gln Val Leu Ser Lys Glu
            340                 345                 350

Gly Lys Leu Asp Arg Val Tyr Ala Lys Tyr Glu Met Lys Lys Leu
            355                 360                 365

Val Arg Ala Tyr Phe Lys Glu Ser Gln Trp Leu Asn Asp Asp Asn His
370                 375                 380

Ile Pro Lys Tyr Glu Glu His Met Glu Asn Ala Ile Val Thr Val Gly
385                 390                 395                 400

Tyr Met Met Gly Ala Thr Asn Cys Leu Val Gly Met Glu Glu Phe Ile
                405                 410                 415

Ser Lys Glu Thr Phe Glu Trp Leu Met Ser Pro Val Ile Val Arg
            420                 425                 430

Ala Ser Ser Leu Ile Gly Arg Ala Met Asp Asp Ile Val Gly His Glu
            435                 440                 445

Val Glu Gln Glu Arg Gly His Cys Ala Ser Ala Val Glu Cys Tyr Met
450                 455                 460

Arg Glu His Gly Val Ser Glu Glu Ala Cys Ser Glu Leu Lys Lys
465                 470                 475                 480

Gln Val Asp Asn Ala Trp Lys Asp Ile Asn His Glu Met Ile Phe Ser
```

485                 490                 495
Glu Thr Ser Lys Ala Val Pro Met Ser Val Leu Thr Arg Val Leu Asn
                500                 505                 510

Leu Thr Arg Val Ile Asp Thr Leu Tyr Gln Glu Glu Asp Glu Tyr Thr
            515                 520                 525

Asn Ala Lys Gly Lys Leu Lys Asn Met Ile His Ser Ile Leu Ile Glu
        530                 535                 540

Ser Val Lys Ile
545

<210> SEQ ID NO 14
<211> LENGTH: 557
<212> TYPE: PRT
<213> ORGANISM: Artificial Sequence
<220> FEATURE:
<223> OTHER INFORMATION: Synthetic polypeptide

<400> SEQUENCE: 14

Glu Lys Gln Ser Leu Thr Phe Asp Gly Asp Glu Glu Ala Lys Ile Asp
1               5                   10                  15

Arg Lys Ser Ser Lys Tyr His Pro Ser Ile Trp Gly Asp Tyr Phe Ile
            20                  25                  30

Gln Asn Ser Ser Leu Thr His Ala Lys Glu Ser Thr Gln Arg Met Ile
        35                  40                  45

Lys Arg Val Glu Glu Leu Lys Val Gln Val Lys Ser Met Phe Lys Asp
    50                  55                  60

Thr Ser Asp Leu Leu Gln Leu Met Asn Leu Ile Asn Ser Ile Gln Met
65                  70                  75                  80

Leu Gly Leu Asp Tyr His Phe Glu Asn Glu Ile Asp Glu Ala Leu Arg
                85                  90                  95

Leu Ile Tyr Glu Val Asp Asp Lys Ser Tyr Gly Leu Tyr Glu Thr Ser
            100                 105                 110

Leu Arg Phe Gln Leu Leu Arg Gln His Gly Tyr His Val Asp Gly Glu
        115                 120                 125

Glu Ala Phe Asn Met Leu Lys Asp Glu Glu Gly Asn Phe Lys Ala Ser
    130                 135                 140

Leu Thr Ser Asp Val Pro Gly Leu Leu Glu Leu Tyr Gln Ala Ser Tyr
145                 150                 155                 160

Met Arg Ile His Gly Glu Asp Ile Leu Asp Glu Ala Ile Ser Phe Thr
                165                 170                 175

Thr Ala Gln Leu Thr Leu Ala Leu Pro Thr Leu Asp Pro Pro Leu Ser
            180                 185                 190

Ala Gln Val Ser Leu Phe Leu Glu Leu Pro Leu Cys Arg Arg Asn Lys
        195                 200                 205

Ile Leu Leu Ala Arg Lys Tyr Ile Leu Ile Tyr Gln Glu Asp Ala Met
    210                 215                 220

Arg Asn Asn Val Ile Leu Glu Leu Ala Lys Leu Asn Phe Asn Leu Leu
225                 230                 235                 240

Gln Ser Leu Tyr Gln Glu Glu Leu Lys Lys Ile Ser Ile Trp Trp Asn
                245                 250                 255

Asp Leu Ala Phe Ala Lys Ser Leu Ser Phe Thr Arg Asp Arg Val Val
            260                 265                 270

Glu Gly Tyr Tyr Trp Val Leu Thr Ile Tyr Phe Glu Pro Gln His Ser
        275                 280                 285

Arg Ala Arg Val Ile Cys Ser Lys Val Phe Ala Phe Leu Ser Ile Met

```
                    290                 295                 300

Asp Asp Ile Tyr Asp Asn Tyr Gly Ile Leu Glu Glu Cys Thr Leu Leu
305                 310                 315                 320

Thr Glu Ala Ile Lys Arg Trp Asn Pro Gln Ala Ile Asp Gly Leu Pro
                325                 330                 335

Glu Tyr Leu Lys Asp Tyr Leu Lys Leu Leu Lys Thr Phe Glu Glu
                340                 345                 350

Phe Glu Asp Glu Leu Glu Leu Asn Glu Lys Tyr Arg Met Leu Tyr Leu
                355                 360                 365

Gln Asp Glu Val Lys Ala Leu Ala Ile Ser Tyr Leu Gln Glu Ala Lys
                370                 375                 380

Trp Gly Ile Glu Arg His Val Pro Ser Leu Asp Glu His Leu His Asn
385                 390                 395                 400

Ser Leu Ile Ser Ser Gly Ser Ser Thr Val Ile Cys Ala Ser Phe Val
                405                 410                 415

Gly Met Gly Glu Val Ala Thr Lys Glu Val Phe Asp Trp Leu Ser Ser
                420                 425                 430

Phe Pro Lys Val Val Glu Ala Cys Cys Val Ile Gly Arg Leu Leu Asn
                435                 440                 445

Asp Ile Arg Ser His Glu Phe Glu Gln Glu Arg Gly His Cys Ala Ser
                450                 455                 460

Ala Val Glu Cys Tyr Met Arg Glu His Gly Val Ser Glu Glu Ala
465                 470                 475                 480

Cys Ser Glu Leu Lys Lys Gln Val Asp Asn Ala Trp Lys Asp Ile Asn
                485                 490                 495

His Glu Met Ile Phe Ser Glu Thr Ser Lys Ala Val Pro Met Ser Val
                500                 505                 510

Leu Thr Arg Val Leu Asn Leu Thr Arg Gly Asn Glu Glu Ile Tyr Lys
                515                 520                 525

Tyr Asn Asp Thr Tyr Thr Asn Ser Asp Thr Thr Met Lys Asp Asn Ile
                530                 535                 540

Ser Leu Val Leu Val Glu Ser Cys Asp Tyr Phe Asn Lys
545                 550                 555

<210> SEQ ID NO 15
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 15

Ser Ile Gln Val Pro Gln Ile Ser Ser Gln Asn Ala Lys Ser Gln Val
1                 5                  10                  15

Met Arg Arg Thr Ala Asn Phe His Pro Ser Val Trp Gly Asp Arg Phe
                20                  25                  30

Ala Asn Tyr Thr Ala Glu Asp Lys Met Asn His Ala Arg Asp Leu Lys
            35                  40                  45

Glu Leu Lys Ala Leu Lys Glu Glu Val Gly Arg Lys Leu Leu Ala Thr
        50                  55                  60

Ala Gly Pro Ile Gln Leu Asn Leu Ile Asp Ala Ile Gln Arg Leu Gly
65                  70                  75                  80

Val Gly Tyr His Phe Glu Arg Glu Leu Glu Gln Ala Leu Gln His Leu
                85                  90                  95

Tyr Asn Glu Lys Tyr Ser Asp Asp Asp Thr Glu Asp Asp Leu Tyr Arg
```

```
            100                 105                 110
Ile Ser Leu Arg Phe Arg Leu Leu Arg Gln His Gly Tyr Asn Val Ser
        115                 120                 125
Cys Asp Ala Phe Asn Arg Phe Lys Asp Thr Lys Gly Ser Phe Lys Glu
    130                 135                 140
Asp Leu Ile Lys Asp Val Asn Ser Met Leu Cys Leu Tyr Glu Ala Thr
145                 150                 155                 160
His Leu Arg Val His Gly Glu Asp Ile Leu Asp Glu Ala Leu Gly Phe
                165                 170                 175
Thr Thr Ser Gln Leu Lys Ser Ile Leu Pro Lys Leu Lys Pro Leu Leu
            180                 185                 190
Ala Ser Gln Val Met His Ala Leu Lys Gln Pro Leu His Arg Gly Leu
        195                 200                 205
Pro Arg Leu Glu His Arg Arg Tyr Ile Ser Ile Tyr Gln Asp Asp Ala
    210                 215                 220
Ser His Tyr Lys Ala Leu Leu Thr Leu Ala Lys Leu Asp Phe Asn Leu
225                 230                 235                 240
Val Gln Ser Leu His Lys Lys Glu Leu Cys Glu Ile Ser Arg Trp Trp
                245                 250                 255
Lys Asp Leu Asp Phe Ala Arg Lys Leu Pro Phe Ala Arg Asp Arg Met
            260                 265                 270
Val Glu Cys Tyr Phe Trp Ile Leu Gly Val Tyr Phe Glu Pro Asn Tyr
        275                 280                 285
Ser Leu Ala Arg Arg Ile Leu Thr Lys Val Ile Ala Met Thr Ser Ile
    290                 295                 300
Ile Asp Asp Ile Tyr Asp Val Tyr Gly Thr Pro Glu Glu Leu Lys Leu
305                 310                 315                 320
Phe Thr Glu Val Ile Glu Arg Trp Asp Glu Ser Ser Met Asp Gln Leu
                325                 330                 335
Pro Glu Tyr Met Gln Thr Phe Phe Gly Ala Leu Leu Asp Leu Tyr Asn
            340                 345                 350
Glu Ile Glu Lys Glu Ile Ala Asn Glu Gly Trp Ser Tyr Arg Val Gln
        355                 360                 365
Tyr Ala Lys Glu Ala Met Lys Ile Leu Val Glu Gly Tyr Tyr Asp Glu
    370                 375                 380
Ser Lys Trp Phe His Glu Asn Tyr Ile Pro Lys Met Glu Glu Tyr Met
385                 390                 395                 400
Arg Val Ala Leu Val Thr Ser Gly Tyr Thr Met Leu Thr Thr Val Ser
                405                 410                 415
Phe Leu Gly Met Asp Asn Ile Val Thr Lys Glu Thr Phe Asp Trp Val
            420                 425                 430
Phe Ser Arg Pro Lys Ile Ile Arg Ala Ser Glu Ile Ile Gly Arg Phe
        435                 440                 445
Met Asp Asp Ile Lys Ser His Lys Phe Glu Gln Glu Arg Gly His Ala
    450                 455                 460
Ala Ser Ala Val Glu Cys Tyr Met Lys Gln His Gly Leu Ser Glu Gln
465                 470                 475                 480
Glu Val Cys Glu Glu Leu Tyr Arg Gln Val Ser Asn Ala Trp Lys Asp
                485                 490                 495
Ile Asn Glu Glu Cys Leu Asn Pro Thr Ala Val Pro Met Pro Leu Leu
            500                 505                 510
Met Arg Ala Leu Asn Leu Ala Arg Val Ile Asp Val Val Tyr Lys Glu
        515                 520                 525
```

```
Gly Asp Gly Tyr Thr His Val Gly Asn Glu Met Lys Gln Asn Val Ala
            530                 535                 540

Ala Leu Leu Ile Asp Gln Val Pro Ile
545                 550

<210> SEQ ID NO 16
<211> LENGTH: 558
<212> TYPE: PRT
<213> ORGANISM: Artificial Sequence
<220> FEATURE:
<223> OTHER INFORMATION: Synthetic polypeptide

<400> SEQUENCE: 16

Ser Ala Ala Gln Val Ser Pro Ala Pro Val Pro Ala His Asn Ala Ala
1               5                   10                  15

Ala Ser Lys Glu Glu Val Arg Arg Ser Ala Gly Tyr His Pro Ser Phe
                20                  25                  30

Trp Gly Glu Phe Phe Leu Thr His Thr Ser Glu Tyr Ala Lys Lys Asp
            35                  40                  45

Asp Lys Ile Gln Lys Gln His Glu Glu Leu Lys Gln Glu Val Lys Gly
        50                  55                  60

Met Leu Val Asp Ala Thr Thr Glu Pro Thr Lys Lys Leu Glu Leu Ile
65                  70                  75                  80

Asp Ala Ile Leu Arg Leu Gly Val Gly Tyr His Phe Glu Asp Glu Ile
                85                  90                  95

Gln Ala Glu Leu Glu Arg Ile His Arg Leu Gly Asp Leu Asp Cys Asp
                100                 105                 110

Leu Tyr Asn Thr Cys Ile Trp Phe Arg Val Leu Arg Gly Gln Gly Phe
            115                 120                 125

Thr Val Ser Ala Glu Glu Phe Asn Lys Phe Lys Asn Ser Asp Gly Asn
        130                 135                 140

Phe Lys Glu Asp Leu Ile Asn Asp Val Ser Gly Met Leu Cys Leu Tyr
145                 150                 155                 160

Glu Ala Thr His Leu Arg Val His Gly Glu Asp Ile Leu Asp Glu Ala
                165                 170                 175

Leu Glu Phe Thr Thr Thr Arg Leu Lys Ser Ile Leu Pro Asp Leu Glu
            180                 185                 190

Pro Pro Leu Ala Thr Gln Val Met His Ala Leu Glu Leu Pro Tyr His
        195                 200                 205

Lys Gly Met Gln Arg Leu Glu Ala Arg Gln Tyr Ile Pro Ile Tyr Glu
    210                 215                 220

Ala Asp Met Thr Lys Asn Ile Ser Leu Leu His Phe Ala Lys Leu Asp
225                 230                 235                 240

Phe Asn Leu Leu Gln Ala Leu His Gln Ser Glu Ile Arg Glu Ile Thr
                245                 250                 255

Arg Trp Trp Lys Asp Leu Asp Phe Lys Thr Arg Leu Pro Tyr Ala Arg
            260                 265                 270

Asp Arg Leu Val Glu Cys Tyr Phe Trp Ile Leu Gly Val Gln Tyr Glu
        275                 280                 285

Pro Gln Tyr Ser Met Ser Arg Leu Phe Leu Thr Lys Val Ile Ser Leu
    290                 295                 300

Ala Ser Val Phe Asp Asp Thr Tyr Asp Ile Tyr Gly Thr Phe Glu Glu
305                 310                 315                 320

Leu Lys Leu Leu Thr Asp Ala Ile Glu Arg Trp Glu Ile Glu Ala Thr
                325                 330                 335
```

```
Asp Ser Leu Pro Ser Tyr Met Gln Ile Leu Tyr Arg Ala Leu Leu Asp
            340                 345                 350

Val Phe Asp Glu Tyr Lys Asp Lys Leu Ile Asn Val Gln Gly Lys Asp
            355                 360                 365

Tyr Cys Leu Tyr Tyr Gly Lys Glu Ala Met Lys Gly Leu Ile Arg Ser
370                 375                 380

Tyr His Thr Glu Ala Val Ser Phe His Thr Gly Tyr Val Gln Asn Phe
385                 390                 395                 400

Glu Glu Tyr Leu Asp Asn Ser Ala Val Ser Ser Gly Tyr Pro Met Leu
            405                 410                 415

Thr Val Glu Ala Leu Ile Gly Met Gly His Pro Tyr Ala Thr Lys Glu
            420                 425                 430

Ala Leu Asp Trp Ala Leu Lys Val Pro Arg Val Ile Lys Ala Ser Ser
            435                 440                 445

Asp Ile Cys Arg Leu Val Asp Asp Leu Arg Thr Tyr Lys Val Glu Glu
            450                 455                 460

Glu Arg Gly Asp Ala Pro Ser Gly Val His Cys Tyr Met Arg Asp Tyr
465                 470                 475                 480

Asn Val Ser Glu Glu Ala Cys Ser Lys Ile Glu Glu Met Ile Asp
            485                 490                 495

Leu Ala Trp Lys Ala Ile Asn Glu Glu Met Gln Lys Pro Gly His Leu
            500                 505                 510

Pro Leu Pro Ile Leu Leu Pro Ala Leu Asn Phe Thr Arg Met Met Glu
            515                 520                 525

Val Leu Tyr Gln Asn Ile Asp Gly Tyr Thr Asn Ser Gly Gly Arg Thr
            530                 535                 540

Lys Asp Arg Ile Thr Ser Leu Leu Val His Pro Ile Thr Ile
545                 550                 555
```

<210> SEQ ID NO 17
<211> LENGTH: 549
<212> TYPE: PRT
<213> ORGANISM: Artificial Sequence
<220> FEATURE:
<223> OTHER INFORMATION: Synthetic polypeptide

<400> SEQUENCE: 17

```
Ser Ser Ala Lys Leu Gly Ser Ser Glu Asp Val Asn Arg Arg Asp
1               5                   10                  15

Ala Asn Tyr His Pro Thr Val Trp Gly Asp Phe Phe Leu Thr His Ser
            20                  25                  30

Ser Asn Phe Leu Glu Asn Asn Asp Ser Ile Leu Glu Lys His Glu Glu
            35                  40                  45

Leu Lys Gln Glu Val Arg Asn Leu Val Val Glu Thr Ser Asp Leu
        50                  55                  60

Pro Ser Lys Ile Gln Leu Thr Asp Glu Ile Ile Arg Leu Gly Val Gly
65                  70                  75                  80

Tyr His Phe Glu Thr Glu Ile Lys Ala Gln Leu Glu Lys Leu His Asp
            85                  90                  95

His Gln Leu His Leu Asn Phe Asp Leu Leu Thr Thr Ser Val Trp Phe
            100                 105                 110

Arg Leu Leu Arg Gly His Gly Phe Ser Ile Ser Ser Asp Ile Phe Asn
            115                 120                 125

Lys Phe Lys Asn Ser Asp Gly Asn Phe Lys Glu Asp Leu Ile Asn Asp
            130                 135                 140
```

```
Val Ser Gly Met Leu Cys Leu Tyr Glu Ala Thr His Leu Arg Val His
145                 150                 155                 160

Gly Glu Asp Ile Leu Asp Glu Ala Leu Glu Phe Thr Thr Thr Arg Leu
            165                 170                 175

Lys Ser Ile Leu Pro Asp Leu Glu Pro Pro Leu Asn Glu Cys Val Arg
            180                 185                 190

Asp Ala Leu His Ile Pro Tyr His Arg Asn Val Gln Arg Leu Ala Ala
            195                 200                 205

Arg Gln Tyr Ile Pro Gln Tyr Asp Ala Glu Pro Thr Lys Ile Glu Ser
            210                 215                 220

Leu Ser Leu Phe Ala Lys Ile Asp Phe Asn Met Leu Gln Ala Leu His
225                 230                 235                 240

Gln Arg Glu Leu Arg Glu Ala Ser Arg Trp Trp Lys Glu Phe Asp Phe
                245                 250                 255

Pro Ser Lys Leu Pro Tyr Ala Arg Asp Arg Ile Ala Glu Gly Tyr Tyr
            260                 265                 270

Trp Met Met Gly Ala His Phe Glu Pro Lys Phe Ser Leu Ser Arg Lys
            275                 280                 285

Phe Leu Asn Arg Ile Ile Gly Ile Thr Ser Leu Ile Asp Asp Thr Tyr
290                 295                 300

Asp Val Tyr Gly Thr Leu Glu Glu Val Thr Leu Phe Thr Glu Ala Val
305                 310                 315                 320

Glu Arg Trp Asp Ile Glu Ala Val Lys Asp Ile Pro Lys Tyr Met Gln
                325                 330                 335

Val Ile Tyr Thr Gly Met Leu Gly Ile Phe Glu Asp Phe Lys Asp Asn
            340                 345                 350

Leu Ile Asn Ala Arg Gly Lys Asp Tyr Cys Ile Asp Tyr Ala Ile Glu
            355                 360                 365

Val Phe Lys Glu Ile Val Arg Ser Tyr Gln Arg Glu Ala Glu Tyr Phe
370                 375                 380

His Thr Gly Tyr Val Pro Ser Tyr Asp Glu Tyr Met Glu Asn Ser Ile
385                 390                 395                 400

Ile Ser Gly Gly Tyr Lys Met Phe Ile Ile Leu Met Leu Ile Gly Arg
                405                 410                 415

Gly Glu Phe Glu Leu Lys Glu Thr Leu Asp Trp Ala Ser Thr Ile Pro
            420                 425                 430

Glu Met Val Glu Ala Ser Ser Leu Ile Ala Arg Tyr Ile Asp Asp Leu
            435                 440                 445

Gln Thr Tyr Lys Ala Glu Glu Arg Gly Glu Thr Val Ser Ala Val
            450                 455                 460

Arg Cys Tyr Met Arg Glu Phe Gly Val Ser Glu Glu Gln Ala Cys Lys
465                 470                 475                 480

Lys Met Arg Glu Met Ile Glu Ile Glu Trp Lys Arg Leu Asn Lys Thr
                485                 490                 495

Thr Leu Glu Ala Asp Glu Ile Ser Ser Val Val Ile Pro Ser Leu
            500                 505                 510

Asn Phe Thr Arg Val Leu Glu Val Met Tyr Asp Lys Gly Asp Gly Tyr
            515                 520                 525

Ser Asp Ser Gln Gly Val Thr Lys Asp Arg Ile Ala Ala Leu Leu Arg
            530                 535                 540

His Ala Ile Glu Ile
545
```

-continued

```
<210> SEQ ID NO 18
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 18
```

| | | | | | | | | | | | | | | |
|---|---|---|---|---|---|---|---|---|---|---|---|---|---|---|
| Ala | Ser | Gln | Val | Ser | Gln | Met | Pro | Ser | Ser | Pro | Leu | Ser | Ser | Asn |
| 1 | | | | 5 | | | | | 10 | | | | | 15 |
| Lys | Asp | Glu | Met | Arg | Pro | Lys | Ala | Asp | Phe | Gln | Pro | Ser | Ile | Trp | Gly |
| | | | 20 | | | | | 25 | | | | | 30 | | |
| Asp | Leu | Phe | Leu | Asn | Cys | Pro | Asp | Lys | Asn | Ile | Asp | Ala | Glu | Thr | Glu |
| | | 35 | | | | | 40 | | | | | 45 | | | |
| Lys | Arg | His | Gln | Gln | Leu | Lys | Glu | Glu | Val | Arg | Lys | Met | Ile | Val | Ala |
| | 50 | | | | | 55 | | | | | 60 | | | | |
| Pro | Met | Ala | Asn | Ser | Thr | Gln | Lys | Leu | Ala | Phe | Ile | Asp | Ser | Val | Gln |
| 65 | | | | | 70 | | | | | 75 | | | | | 80 |
| Arg | Leu | Gly | Val | Ser | Tyr | His | Phe | Thr | Lys | Glu | Ile | Glu | Asp | Glu | Leu |
| | | | | 85 | | | | | 90 | | | | | 95 | |
| Glu | Asn | Ile | Tyr | His | Asn | Asn | Asp | Ala | Glu | Asn | Asp | Leu | Tyr | Thr |
| | | | 100 | | | | | 105 | | | | | 110 | | |
| Thr | Ser | Leu | Arg | Phe | Arg | Leu | Leu | Arg | Glu | His | Gly | Phe | Asn | Val | Ser |
| | 115 | | | | | 120 | | | | | 125 | | | | |
| Cys | Asp | Ala | Phe | Asn | Arg | Phe | Lys | Asp | Thr | Lys | Gly | Ser | Phe | Lys | Glu |
| 130 | | | | | 135 | | | | | 140 | | | | | |
| Asp | Leu | Ile | Lys | Asp | Val | Asn | Ser | Met | Leu | Cys | Leu | Tyr | Glu | Ala | Thr |
| 145 | | | | | 150 | | | | | 155 | | | | | 160 |
| His | Leu | Arg | Val | His | Gly | Glu | Asp | Ile | Leu | Asp | Glu | Ala | Leu | Gly | Phe |
| | | | | 165 | | | | | 170 | | | | | 175 | |
| Thr | Thr | Ser | Gln | Leu | Lys | Ser | Ile | Leu | Pro | Lys | Leu | Lys | Pro | Leu | Leu |
| | | | 180 | | | | | 185 | | | | | 190 | | |
| Ala | Ser | Gln | Val | Met | His | Ala | Leu | Lys | Gln | Pro | Leu | Arg | Arg | Gly | Leu |
| | | 195 | | | | | 200 | | | | | 205 | | | |
| Pro | Arg | Val | Glu | Ala | Arg | His | Tyr | Leu | Ser | Val | Tyr | Gln | Asp | Ile | Glu |
| | 210 | | | | | 215 | | | | | 220 | | | | |
| Ser | His | Asn | Lys | Val | Leu | Leu | Glu | Phe | Ala | Lys | Ile | Asp | Phe | Asn | Met |
| 225 | | | | | 230 | | | | | 235 | | | | | 240 |
| Val | Gln | Leu | Leu | His | Arg | Lys | Glu | Leu | Ser | Glu | Ile | Ser | Arg | Trp | Trp |
| | | | | 245 | | | | | 250 | | | | | 255 | |
| Lys | Asp | Leu | Asp | Phe | Gln | Arg | Lys | Leu | Pro | Tyr | Ala | Arg | Asp | Arg | Val |
| | | | 260 | | | | | 265 | | | | | 270 | | |
| Val | Glu | Gly | Tyr | Phe | Trp | Ile | Ser | Gly | Val | Tyr | Phe | Glu | Pro | Gln | Tyr |
| | | 275 | | | | | 280 | | | | | 285 | | | |
| Ser | Leu | Gly | Arg | Lys | Met | Leu | Thr | Lys | Val | Ile | Ala | Met | Ala | Ser | Ile |
| | 290 | | | | | 295 | | | | | 300 | | | | |
| Val | Asp | Asp | Thr | Tyr | Asp | Ser | Tyr | Ala | Thr | Tyr | Glu | Glu | Leu | Ile | Pro |
| 305 | | | | | 310 | | | | | 315 | | | | | 320 |
| Tyr | Thr | Lys | Ala | Ile | Glu | Arg | Trp | Asp | Ile | Lys | Cys | Ile | Asp | Glu | Leu |
| | | | | 325 | | | | | 330 | | | | | 335 | |
| Pro | Glu | Tyr | Met | Lys | Pro | Ser | Tyr | Lys | Ala | Leu | Leu | Asp | Val | Tyr | Glu |
| | | | 340 | | | | | 345 | | | | | 350 | | |
| Glu | Met | Glu | Gln | Leu | Val | Ala | Lys | His | Gly | Arg | Gln | Tyr | Arg | Val | Glu |
| | | 355 | | | | | 360 | | | | | 365 | | | |

-continued

```
Tyr Ala Lys Asn Ala Met Ile Arg Leu Ala Gln Ser Tyr Leu Val Glu
370                 375                 380

Ala Arg Trp Thr Leu Gln Asn Tyr Lys Pro Ser Phe Glu Glu Phe Lys
385                 390                 395                 400

Ala Asn Ala Leu Pro Thr Cys Gly Tyr Ala Met Leu Ala Ile Thr Ser
                405                 410                 415

Phe Val Gly Met Gly Asp Ile Val Thr Pro Glu Thr Phe Lys Trp Ala
                420                 425                 430

Ala Asn Asp Pro Lys Ile Ile Gln Ala Ser Thr Ile Ile Cys Arg Phe
                435                 440                 445

Met Asp Asp Val Ala Glu His Lys Phe Lys His Arg Arg Glu Asp Asp
450                 455                 460

Cys Ser Ala Ile Glu Cys Tyr Met Glu Glu Tyr Gly Val Thr Ala Gln
465                 470                 475                 480

Glu Ala Tyr Asp Val Phe Asn Lys His Val Glu Ser Ala Trp Lys Asp
                485                 490                 495

Val Asn Lys Glu Phe Leu Lys Pro Thr Glu Met Pro Thr Glu Val Leu
                500                 505                 510

Asn Arg Ser Leu Asn Leu Ala Arg Val Met Asp Val Leu Tyr Arg Glu
                515                 520                 525

Gly Asp Gly Tyr Thr Tyr Val Gly Lys Ala Ala Lys Gly Gly Ile Thr
530                 535                 540

Ser Leu Leu Ile Glu Pro Val Ala Leu
545                 550

<210> SEQ ID NO 19
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 19

Ala Ser Gln Val Ser Gln Met Pro Ser Ser Ser Pro Leu Ser Ser Asn
1               5                   10                  15

Lys Asp Glu Met Arg Pro Lys Ala Asp Phe Gln Pro Ser Ile Trp Gly
                20                  25                  30

Asp Leu Phe Leu Asn Cys Pro Asp Lys Asn Ile Asp Ala Glu Thr Glu
                35                  40                  45

Lys Arg His Gln Gln Leu Lys Glu Glu Val Arg Lys Met Ile Val Ala
                50                  55                  60

Pro Met Ala Asn Ser Thr Gln Lys Leu Ala Phe Ile Asp Ser Val Gln
65                  70                  75                  80

Arg Leu Gly Val Ser Tyr His Phe Thr Lys Glu Ile Glu Asp Glu Leu
                85                  90                  95

Glu Asn Ile Tyr His Asn Asn Asp Ala Glu Asn Asp Leu Tyr Thr
                100                 105                 110

Thr Ser Ile Arg Phe Arg Leu Leu Arg Glu His Gly Tyr Asn Val Ser
                115                 120                 125

Cys Asp Ile Phe Asn Lys Phe Lys Asn Ser Asp Gly Asn Phe Lys Glu
                130                 135                 140

Asp Leu Ile Asn Asp Val Ser Gly Met Leu Cys Leu Tyr Glu Ala Thr
145                 150                 155                 160

His Leu Arg Val His Gly Glu Asp Ile Leu Asp Glu Ala Leu Glu Phe
                165                 170                 175
```

Thr Thr Thr Arg Leu Lys Ser Ile Leu Pro Asp Leu Glu Pro Pro Leu
            180                 185                 190

Ala Thr Gln Val Met His Ala Leu Lys Gln Ser Ile Arg Arg Gly Leu
        195                 200                 205

Pro Arg Val Glu Ala Arg His Tyr Leu Ser Val Tyr Gln Asp Ile Glu
    210                 215                 220

Ser His Asn Lys Ala Leu Leu Glu Phe Ala Lys Ile Asp Phe Asn Met
225                 230                 235                 240

Leu Gln Phe Leu His Arg Lys Glu Leu Ser Glu Ile Cys Arg Trp Trp
                245                 250                 255

Lys Asp Leu Asp Phe Gln Arg Lys Leu Pro Tyr Ala Arg Asp Arg Val
            260                 265                 270

Val Glu Gly Tyr Phe Trp Ile Ser Gly Val Tyr Phe Glu Pro Gln Tyr
        275                 280                 285

Ser Leu Gly Arg Lys Met Leu Thr Lys Val Ile Ala Met Ala Ser Ile
    290                 295                 300

Val Asp Asp Thr Tyr Asp Ser Tyr Ala Thr Tyr Glu Glu Leu Ile Pro
305                 310                 315                 320

Tyr Thr Asn Ala Ile Glu Arg Trp Asp Ile Lys Cys Ile Asp Glu Ile
                325                 330                 335

Pro Glu Tyr Met Lys Pro Ser Tyr Lys Ala Leu Leu Asp Val Tyr Glu
            340                 345                 350

Glu Met Val Gln Leu Val Ala Glu His Gly Arg Gln Tyr Arg Val Glu
        355                 360                 365

Tyr Ala Lys Asn Ala Met Ile Arg Leu Ala Gln Ser Tyr Leu Val Glu
    370                 375                 380

Ala Lys Trp Thr Leu Gln Asn Tyr Lys Pro Ser Phe Glu Glu Phe Lys
385                 390                 395                 400

Ala Asn Ala Leu Pro Thr Cys Gly Tyr Ala Met Leu Ala Ile Thr Ser
                405                 410                 415

Phe Val Gly Met Gly Asp Ile Val Thr Pro Glu Thr Phe Lys Trp Ala
            420                 425                 430

Ala Ser Asp Pro Lys Ile Ile Gln Ala Ser Thr Ile Ile Cys Arg Phe
        435                 440                 445

Met Asp Asp Val Ala Glu His Lys Phe Lys His Arg Arg Glu Asp Asp
    450                 455                 460

Cys Ser Ala Ile Glu Cys Tyr Met Glu Glu Tyr Gly Val Thr Ala Gln
465                 470                 475                 480

Glu Ala Tyr Asp Val Phe Asn Lys His Val Glu Ser Ala Trp Lys Asp
                485                 490                 495

Leu Asn Gln Glu Phe Leu Lys Pro Thr Glu Met Pro Thr Glu Val Leu
            500                 505                 510

Asn Arg Ser Leu Asn Leu Ala Arg Val Met Asp Val Leu Tyr Arg Glu
        515                 520                 525

Gly Asp Gly Tyr Thr Tyr Val Gly Lys Ala Ala Lys Gly Gly Ile Thr
    530                 535                 540

Ser Leu Leu Ile Glu Pro Ile Ala Leu
545                 550

<210> SEQ ID NO 20
<211> LENGTH: 541
<212> TYPE: PRT
<213> ORGANISM: Artificial Sequence
<220> FEATURE:
<223> OTHER INFORMATION: Synthetic polypeptide

<400> SEQUENCE: 20

```
Glu Ser Arg Arg Ser Ala Asn Tyr Gln Ala Ser Ile Trp Glu Thr Asn
1               5                   10                  15

Phe Thr Asn Ser Pro Leu Leu Ser Lys Leu Gln Asn Glu Leu Ser Val
            20                  25                  30

Ala His Leu Glu Glu Leu Lys Leu Glu Val Lys Gln Leu Ile Trp Ser
        35                  40                  45

Thr Lys Asp Pro Leu Phe Leu Lys Phe Ile Asp Ser Ile Gln Arg
50                  55                  60

Leu Gly Val Ala Tyr His Phe Glu Glu Ile Lys Glu Ser Leu His
65                  70                  75                  80

Leu Val Tyr Leu Glu Glu Arg Asn Gly Asp His Gln His Tyr Lys Glu
            85                  90                  95

Lys Gly Leu His Phe Thr Ala Leu Arg Phe Arg Ile Leu Arg Gln Asp
            100                 105                 110

Gly Tyr His Val Pro Gln Asp Val Phe Ser Ser Phe Met Asn Lys Ala
            115                 120                 125

Gly Asp Phe Glu Glu Ser Leu Ser Lys Asp Thr Lys Gly Leu Val Ser
130                 135                 140

Leu Tyr Glu Ala Ser Tyr Leu Ser Met Glu Gly Glu Thr Ile Leu Asp
145                 150                 155                 160

Met Ala Lys Asp Phe Ser Ser His His Leu His Lys Met Val Glu Asp
                165                 170                 175

Ala Thr Asp Lys Arg Val Ala Asn Gln Ile Ile His Ser Leu Glu Met
            180                 185                 190

Pro Leu His Arg Arg Val Gln Lys Leu Glu Ala Ile Trp Phe Ile Gln
            195                 200                 205

Phe Tyr Glu Cys Gly Ser Asp Ala Asn Pro Thr Leu Val Glu Leu Ala
210                 215                 220

Lys Leu Asp Phe Asn Met Val Gln Ala Thr Tyr Gln Glu Glu Leu Lys
225                 230                 235                 240

Arg Leu Ser Arg Trp Tyr Glu Glu Thr Gly Leu Gln Glu Lys Leu Ser
                245                 250                 255

Phe Ala Arg His Arg Leu Ala Glu Ala Phe Leu Trp Ser Met Gly Ile
            260                 265                 270

Ile Pro Glu Gly His Phe Gly Tyr Gly Arg Met His Leu Met Lys Ile
            275                 280                 285

Gly Ala Tyr Ile Thr Leu Leu Asp Asp Ile Tyr Asp Val Tyr Gly Thr
290                 295                 300

Leu Glu Glu Leu Gln Val Leu Thr Glu Ile Ile Glu Arg Trp Asp Ile
305                 310                 315                 320

Asn Leu Leu Asp Gln Leu Pro Glu Tyr Met Gln Ile Phe Phe Leu Tyr
                325                 330                 335

Met Phe Asn Ser Thr Asn Glu Leu Ala Tyr Glu Ile Leu Arg Asp Gln
            340                 345                 350

Gly Ile Asn Val Ile Ser Asn Leu Lys Gly Leu Trp Val Glu Leu Ser
            355                 360                 365

Gln Cys Tyr Phe Lys Glu Ala Thr Trp Phe His Asn Gly Tyr Thr Pro
370                 375                 380

Thr Thr Glu Glu Tyr Leu Asn Val Ala Cys Ile Ser Ala Ser Gly Pro
385                 390                 395                 400

Val Ile Leu Phe Ser Gly Tyr Phe Thr Thr Thr Asn Pro Ile Asn Lys
```

```
                    405                 410                 415

His Glu Leu Gln Ser Leu Glu Arg His Ala His Ser Leu Ser Met Ile
                420                 425                 430

Leu Arg Leu Ala Asp Asp Leu Gly Thr Ser Ser Asp Glu Met Lys Arg
            435                 440                 445

Gly Asp Val Pro Lys Ala Ile Gln Cys Phe Met Asn Asp Thr Gly Cys
        450                 455                 460

Cys Glu Glu Glu Ala Arg Gln His Val Lys Arg Leu Ile Asp Ala Glu
465                 470                 475                 480

Trp Lys Lys Met Asn Lys Asp Ile Leu Met Glu Lys Pro Phe Lys Asn
                485                 490                 495

Phe Cys Pro Thr Ala Met Asn Leu Gly Arg Ile Ser Met Ser Phe Tyr
            500                 505                 510

Glu His Gly Asp Gly Tyr Gly Gly Pro His Ser Asp Thr Lys Lys Lys
        515                 520                 525

Met Val Ser Leu Phe Val Gln Pro Met Asn Ile Thr Ile
    530                 535                 540

<210> SEQ ID NO 21
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 21

Glu Ser Gln Thr Thr Phe Lys Tyr Glu Ser Leu Ala Phe Thr Lys Leu
1               5                   10                  15

Ser His Cys Gln Trp Thr Asp Tyr Phe Leu Ser Val Pro Ile Asp Glu
                20                  25                  30

Ser Glu Leu Asp Val Ile Thr Arg Glu Ile Asp Ile Leu Lys Pro Glu
            35                  40                  45

Val Met Glu Leu Leu Ser Ser Gln Gly Asp Asp Glu Thr Ser Lys Arg
        50                  55                  60

Lys Val Leu Leu Ile Gln Leu Leu Ser Leu Gly Leu Ala Phe His
65                  70                  75                  80

Phe Glu Asn Glu Ile Lys Asn Ile Leu Glu His Ala Phe Arg Lys Ile
                85                  90                  95

Asp Asp Ile Thr Gly Asp Glu Lys Asp Leu Ser Thr Ile Ser Ile Met
            100                 105                 110

Phe Arg Val Phe Arg Thr Tyr Gly His Asn Leu Pro Ser Ser Ile Phe
        115                 120                 125

Asn Lys Phe Lys Asn Ser Asp Gly Asn Phe Lys Glu Asp Leu Ile Asn
130                 135                 140

Asp Val Ser Gly Met Leu Cys Leu Tyr Glu Ala Thr His Leu Arg Val
145                 150                 155                 160

His Gly Glu Asp Ile Leu Asp Glu Ala Leu Glu Phe Thr Thr Thr Arg
                165                 170                 175

Leu Lys Ser Ile Leu Pro Gly Gly Thr Cys Arg Pro His Ile Leu Arg
            180                 185                 190

Leu Ile Arg Asn Thr Leu Tyr Leu Pro Gln Arg Trp Asn Met Glu Ala
        195                 200                 205

Val Ile Ala Arg Glu Tyr Ile Ser Phe Tyr Glu Gln Glu Glu Asp His
    210                 215                 220

Asp Lys Met Leu Leu Arg Leu Ala Lys Leu Asn Phe Lys Leu Leu Gln
```

```
            225                 230                 235                 240
Leu His Tyr Ile Lys Glu Leu Lys Ser Phe Ile Lys Trp Trp Met Glu
                245                 250                 255

Leu Gly Leu Thr Ser Lys Trp Pro Ser Gln Phe Arg Glu Arg Ile Val
                260                 265                 270

Glu Ala Trp Leu Ala Gly Leu Met Met Tyr Phe Glu Pro Gln Phe Ser
                275                 280                 285

Gly Gly Arg Val Ile Ala Ala Lys Phe Asn Tyr Leu Leu Thr Ile Leu
            290                 295                 300

Asp Asp Ala Cys Asp His Tyr Phe Ser Ile His Glu Leu Thr Arg Leu
305                 310                 315                 320

Val Ala Cys Val Glu Arg Trp Ser Pro Asp Gly Ile Asp Thr Leu Glu
                325                 330                 335

Asp Ile Ser Arg Ser Val Phe Lys Leu Met Leu Asp Val Phe Asp Asp
                340                 345                 350

Ile Gly Lys Gly Val Arg Ser Glu Gly Ser Ser Tyr His Leu Lys Glu
                355                 360                 365

Met Leu Glu Glu Leu Asn Thr Leu Val Arg Ala Asn Leu Asp Leu Val
370                 375                 380

Lys Trp Ala Arg Gly Ile Gln Val Pro Ser Phe Glu Glu His Val Glu
385                 390                 395                 400

Val Gly Gly Ile Ala Leu Thr Ser Tyr Ala Thr Leu Met Tyr Ser Phe
                405                 410                 415

Val Gly Met Gly Glu Thr Ala Gly Lys Glu Ala Tyr Glu Trp Val Arg
                420                 425                 430

Ser Arg Pro Arg Leu Ile Lys Ser Leu Ala Ala Lys Gly Arg Leu Met
                435                 440                 445

Asp Asp Ile Thr Asp Phe Asp Ser Asp Met Ser Asn Gly Phe Ala Ala
                450                 455                 460

Asn Ala Ile Asn Tyr Tyr Met Lys Gln Phe Val Val Thr Lys Glu Glu
465                 470                 475                 480

Ala Ile Leu Glu Cys Gln Arg Met Ile Val Asp Ile Asn Lys Thr Ile
                485                 490                 495

Asn Glu Glu Leu Leu Lys Thr Thr Ser Val Pro Gly Arg Val Leu Lys
                500                 505                 510

Gln Ala Leu Asn Phe Gly Arg Leu Leu Glu Leu Leu Tyr Thr Lys Ser
                515                 520                 525

Asp Asp Ile Tyr Asn Cys Ser Glu Gly Lys Leu Lys Glu Tyr Ile Val
                530                 535                 540

Thr Leu Leu Ile Asp Pro Ile Arg Leu
545                 550

<210> SEQ ID NO 22
<211> LENGTH: 546
<212> TYPE: PRT
<213> ORGANISM: Artificial Sequence
<220> FEATURE:
<223> OTHER INFORMATION: Synthetic polypeptide

<400> SEQUENCE: 22

Ser Ser Ala Lys Leu Gly Ser Ala Ser Glu Asp Val Asn Arg Arg Asp
1               5                   10                  15

Ala Asn Tyr His Pro Thr Val Trp Gly Asp Phe Phe Leu Thr His Ser
                20                  25                  30

Ser Asn Phe Leu Glu Asn Asn Asp Ser Ile Leu Glu Lys His Glu Gly
```

```
                35                  40                  45
Leu Glu Gln Lys Ile Arg Thr Met Leu Ile Ser Pro Thr Asp Thr Ile
 50                  55                  60
Ser Lys Lys Leu Ser Leu Ile Asp Ala Val Gln Arg Leu Gly Val Ala
 65                  70                  75                  80
Tyr His Phe Glu Lys Glu Ile Glu Asp Glu Ile Glu Lys Leu Ser Cys
                     85                  90                  95
Lys Glu Tyr Asn Asp Gly Asn Asp Leu Gln Thr Val Ala Leu Arg Phe
                    100                 105                 110
Arg Leu Leu Arg Gln Gln Gly Tyr Phe Val Ser Cys Asp Val Phe Lys
            115                 120                 125
Arg Phe Lys Asn Thr Lys Gly Glu Phe Glu Thr Glu Asp Ala Arg Thr
            130                 135                 140
Leu Trp Cys Leu Tyr Glu Ala Thr His Leu Arg Val Asp Gly Glu Asp
145                 150                 155                 160
Ile Leu Glu Glu Ala Ile Gln Phe Ser Arg Lys Lys Leu Glu Ala Leu
                165                 170                 175
Leu Pro Glu Leu Ser Phe Pro Leu Asn Glu Cys Val Arg Asp Ala Leu
            180                 185                 190
His Ile Pro Tyr His Arg Asn Val Gln Arg Leu Ala Ala Arg Gln Tyr
            195                 200                 205
Ile Pro Gln Tyr Asp Ala Glu Pro Thr Lys Ile Glu Ser Leu Ser Leu
210                 215                 220
Phe Ala Lys Ile Asp Phe Asn Met Leu Gln Ala Leu His Gln Arg Glu
225                 230                 235                 240
Leu Arg Glu Ala Ser Arg Trp Trp Lys Glu Phe Asp Phe Pro Ser Lys
                245                 250                 255
Leu Pro Tyr Ala Arg Asp Arg Ile Ala Glu Gly Tyr Tyr Trp Met Met
            260                 265                 270
Gly Ala His Phe Glu Pro Lys Phe Ser Leu Ser Arg Lys Phe Leu Asn
            275                 280                 285
Arg Ile Ile Gly Ile Thr Ser Leu Ile Asp Asp Thr Tyr Asp Val Tyr
290                 295                 300
Gly Thr Leu Glu Glu Val Thr Leu Phe Thr Glu Ala Val Glu Arg Trp
305                 310                 315                 320
Asp Ile Glu Ala Val Lys Asp Ile Pro Lys Tyr Met Gln Val Ile Tyr
                325                 330                 335
Thr Gly Met Leu Gly Ile Phe Glu Asp Phe Lys Asp Asn Leu Ile Asn
            340                 345                 350
Ala Arg Gly Lys Asp Tyr Cys Ile Asp Tyr Ala Ile Glu Val Phe Lys
            355                 360                 365
Glu Ile Val Arg Ser Tyr Gln Arg Glu Ala Glu Tyr Phe His Thr Gly
            370                 375                 380
Tyr Val Pro Ser Tyr Asp Glu Tyr Met Glu Asn Ser Ile Ile Ser Gly
385                 390                 395                 400
Gly Tyr Lys Met Phe Ile Ile Leu Met Leu Ile Gly Arg Gly Glu Phe
                405                 410                 415
Glu Leu Lys Glu Thr Leu Asp Trp Ala Ser Thr Ile Pro Glu Met Val
            420                 425                 430
Glu Ala Ser Ser Leu Ile Ala Arg Tyr Ile Asp Asp Leu Gln Thr Tyr
            435                 440                 445
Lys Ala Glu Glu Glu Arg Gly Glu Thr Val Ser Ala Val Arg Cys Tyr
            450                 455                 460
```

```
Met Arg Glu Phe Gly Val Ser Glu Glu Gln Ala Cys Lys Lys Met Arg
465                 470                 475                 480

Glu Met Ile Glu Ile Glu Trp Lys Arg Leu Asn Lys Thr Thr Leu Glu
            485                 490                 495

Ala Asp Glu Ile Ser Ser Val Val Ile Pro Ser Leu Asn Phe Thr
                500                 505                 510

Arg Val Leu Glu Val Met Tyr Asp Lys Gly Asp Gly Tyr Ser Asp Ser
            515                 520                 525

Gln Gly Val Thr Lys Asp Arg Ile Ala Ala Leu Leu Arg His Ala Ile
            530                 535                 540

Glu Ile
545
```

<210> SEQ ID NO 23
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 23

```
Arg Asp Leu Lys Ser Val Leu Ser Ser Lys Glu Ser Thr Lys Ala Asp
1               5                   10                  15

Val Asn Arg Arg Ser Ser Asn Tyr His Pro Ser Ile Trp Gly Asp His
            20                  25                  30

Phe Ile Asn Val Ser Ser Asn Glu Lys Tyr Thr Asn Thr Glu Val Glu
        35                  40                  45

Lys Arg Phe Glu Thr Leu Lys Ala Glu Ile Glu Lys Leu Leu Val Ser
50                  55                  60

Asn Asn Thr Ala Trp Lys Thr Leu Glu Glu Ile Val Ala Ile Val Asn
65                  70                  75                  80

Gln Leu Gln Arg Leu Gly Leu Ala Tyr His Phe Glu Asn Gln Ile Lys
                85                  90                  95

Glu Ala Leu Gln Ser Ile Tyr Asp Ser His Val Asn Gly Asn Cys Asp
            100                 105                 110

Val Asn Tyr Asp His Asn Asn Asp Leu Tyr Ile Val Ala Leu Arg Phe
        115                 120                 125

Arg Leu Leu Arg Gln His Gly Tyr Lys Val Ser Ala Asp Ile Phe Lys
130                 135                 140

Lys Phe Arg Asp Glu Lys Gly Glu Phe Lys Ala Met Leu Thr Asn Asp
145                 150                 155                 160

Ala Lys Gly Leu Leu Cys Leu Tyr Glu Ala Ser Tyr Leu Arg Val Gln
                165                 170                 175

Gly Glu Asn Ile Leu Glu Glu Ala Cys Glu Phe Ser Arg Lys His Leu
            180                 185                 190

Lys Ser Leu Leu Ser His Leu Ser Thr Ser Leu Ala Glu Gln Val Lys
        195                 200                 205

His Ser Leu Glu Ile Pro Leu His Arg Gly Met Pro Arg Leu Glu Ala
210                 215                 220

Arg His Tyr Ile Ser Ile Tyr Glu Glu Asp Asn Ser Ser Arg Asn Glu
225                 230                 235                 240

Leu Ile Leu Glu Leu Ala Lys Leu Asp Phe Asn Leu Leu Gln Ala Leu
                245                 250                 255

His Arg Arg Glu Leu Gly Glu Ile Ser Arg Trp Trp Lys Asp Ile Asp
            260                 265                 270
```

```
Phe Ala Thr Lys Leu Pro Phe Ala Arg Asp Arg Leu Val Glu Cys Tyr
            275                 280                 285

Phe Trp Ile Leu Gly Val Tyr Phe Glu Pro Lys Tyr Ser Ile Thr Arg
    290                 295                 300

Lys Phe Met Thr Lys Val Ile Ala Ile Ala Ser Val Ile Asp Asp Ile
305                 310                 315                 320

Tyr Asp Val Tyr Gly Thr Leu Glu Glu Leu Lys Leu Phe Thr His Ala
                325                 330                 335

Ile Glu Arg Trp Glu Thr Val Ala Ala Asn Glu Leu Pro Lys Tyr Met
            340                 345                 350

Gln Val Cys Tyr Phe Ala Leu Leu Asp Val Phe Lys Glu Met Glu Asp
        355                 360                 365

Lys Leu Val Asn Lys Gly Leu Leu Tyr Ser Met Pro Cys Ala Lys Glu
    370                 375                 380

Ala Val Lys Gly Leu Val Arg Ala Tyr Phe Val Glu Ala Glu Trp Phe
385                 390                 395                 400

Asn Ala Asn Tyr Met Pro Thr Phe Glu Glu Tyr Met Glu Asn Ser Thr
                405                 410                 415

Met Ser Ser Gly Tyr Pro Met Leu Ala Val Glu Ala Leu Ile Gly Ile
            420                 425                 430

Glu Asp Ala Thr Ile Ser Lys Glu Ala Phe Asp Trp Ala Ile Ser Val
        435                 440                 445

Pro Lys Ile Ile Arg Ser Cys Ala Leu Ile Ala Arg Leu Val Asp Asp
    450                 455                 460

Ile His Thr Tyr Lys Val Glu Gln Glu Arg Gly Asp Ala Pro Ser Ser
465                 470                 475                 480

Val Glu Cys Tyr Met Gln Gln Tyr Asp Val Ser Glu Glu Ala Cys
                485                 490                 495

Asn Arg Ile Lys Gly Met Val Glu Ile Glu Trp Met Asn Ile Asn Glu
            500                 505                 510

Glu Ile Gln Asp Pro Asn His Pro Leu Gln Trp Leu Leu Pro Ser
        515                 520                 525

Leu Asn Leu Ala Arg Met Met Val Val Leu Tyr Gln Asn Gly Asp Asn
    530                 535                 540

Tyr Thr Asn Ser Ser Gly Lys Thr Lys Asp Arg Ile Ala Ser Leu Leu
545                 550                 555                 560

Val Asp Pro Leu Pro Met
                565

<210> SEQ ID NO 24
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 24

Arg Asp Leu Lys Ser Val Leu Ser Ser Lys Glu Ser Thr Lys Ala Asp
1               5                   10                  15

Val Asn Arg Arg Ser Ser Asn Tyr His Pro Ser Ile Trp Gly Asp His
            20                  25                  30

Phe Ile Asn Val Ser Ser Asn Glu Lys Tyr Thr Asn Thr Glu Val Glu
        35                  40                  45

Lys Arg Phe Glu Thr Leu Lys Ala Glu Ile Glu Lys Leu Leu Val Ser
    50                  55                  60
```

-continued

Asn Asn Thr Ala Trp Lys Thr Leu Glu Glu Ile Val Ala Ile Val Asn
 65                  70                  75                  80

Gln Leu Gln Arg Leu Gly Leu Ala Tyr His Phe Glu Asn Gln Ile Lys
                 85                  90                  95

Glu Ala Leu Gln Ser Ile Tyr Asp Ser His Val Asn Gly Asn Cys Asp
                100                 105                 110

Val Asn Tyr Asp His Asn Asn Asp Leu Tyr Ile Val Ala Leu Arg Phe
                115                 120                 125

Arg Leu Leu Arg Gln His Gly Tyr Lys Val Ser Ala Asp Ile Phe Lys
130                 135                 140

Lys Phe Lys Asp Glu Lys Gly Glu Phe Lys Asp Met Ile Arg Asn Asp
145                 150                 155                 160

Ala Arg Gly Leu Leu Cys Leu Tyr Glu Ala Ser His Leu Arg Val Lys
                165                 170                 175

Gly Glu Asp Ile Leu Glu Glu Ala Thr Glu Phe Ser Arg Lys His Leu
                180                 185                 190

Lys Ser Leu Leu Pro Gln Leu Ser Thr Ser Leu Ala Glu Gln Val Lys
                195                 200                 205

His Ser Leu Glu Ile Pro Leu His Arg Gly Met Pro Arg Leu Glu Ala
210                 215                 220

Arg His Tyr Ile Ser Ile Tyr Glu Glu Asn Asn Ser Ser Arg Asn Glu
225                 230                 235                 240

Leu Leu Leu Glu Leu Ala Lys Leu Asp Phe Asn Leu Leu Gln Ala Leu
                245                 250                 255

His Arg Arg Glu Leu Gly Asp Ile Ser Arg Trp Lys Asp Ile Asp
                260                 265                 270

Phe Ala Thr Lys Leu Pro Phe Ala Arg Asp Arg Leu Val Glu Cys Tyr
                275                 280                 285

Phe Trp Ile Leu Gly Val Tyr Phe Glu Pro Lys Tyr Ser Ile Thr Arg
                290                 295                 300

Lys Phe Met Thr Lys Val Ile Ala Ile Ala Ser Val Ile Asp Asp Ile
305                 310                 315                 320

Tyr Asp Val Tyr Gly Thr Leu Glu Glu Leu Lys Leu Phe Thr His Ala
                325                 330                 335

Ile Glu Arg Trp Glu Thr Val Ala Ala Asn Glu Leu Pro Lys Tyr Met
                340                 345                 350

Gln Val Cys Tyr Phe Ala Leu Leu Asp Val Phe Lys Glu Met Glu Asp
                355                 360                 365

Lys Leu Val Asn Lys Gly Leu Leu Tyr Ser Met Pro Cys Ala Lys Glu
                370                 375                 380

Ala Val Lys Gly Leu Val Arg Ala Tyr Phe Val Glu Ala Glu Trp Phe
385                 390                 395                 400

Asn Ala Asn Tyr Met Pro Thr Phe Glu Glu Tyr Met Glu Asn Ser Thr
                405                 410                 415

Met Ser Ser Gly Tyr Pro Met Leu Ala Val Glu Ala Leu Ile Gly Ile
                420                 425                 430

Glu Asp Ala Thr Ile Ser Lys Glu Ala Phe Asp Trp Ala Ile Ser Val
                435                 440                 445

Pro Lys Ile Ile Arg Ser Cys Ala Leu Ile Ala Arg Leu Val Asp Asp
                450                 455                 460

Ile His Thr Tyr Lys Val Glu Gln Glu Arg Gly Asp Ala Pro Ser Ser
465                 470                 475                 480

Val Gln Cys Tyr Val Gln Gln Tyr Gly Val Ser Glu Glu Ala Cys
                485                 490                 495

Asn Lys Ile Lys Gly Met Val Glu Ile Glu Trp Met Asn Ile Asn Glu
        500                 505                 510

Glu Ile Gln Asp Pro Asn His Pro Pro Leu Gln Trp Leu Leu Pro Ser
            515                 520                 525

Leu Asn Leu Ala Arg Met Met Val Leu Tyr Gln Asn Gly Asp Asn
530                 535                 540

Tyr Thr Asn Ser Ser Gly Lys Thr Lys Asp Arg Ile Ala Ser Leu Leu
545                 550                 555                 560

Val Asp Pro Leu Pro Met
                565

<210> SEQ ID NO 25
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 25

Arg Asp Leu Lys Ser Val Leu Ser Ser Lys Glu Ser Thr Lys Ala Asp
1               5                   10                  15

Val Asn Arg Arg Ser Ser Asn Tyr His Pro Ser Ile Trp Gly Asp His
            20                  25                  30

Phe Ile Asn Val Ser Ser Asn Glu Lys Tyr Thr Asn Thr Glu Val Glu
        35                  40                  45

Lys Arg Phe Glu Thr Leu Lys Ala Glu Ile Glu Lys Leu Leu Val Ser
    50                  55                  60

Asn Asn Thr Ala Trp Lys Thr Leu Glu Glu Ile Val Ala Ile Val Asn
65                  70                  75                  80

Gln Leu Gln Arg Leu Gly Leu Ala Tyr His Phe Glu Asn Gln Ile Lys
                85                  90                  95

Glu Ala Leu Gln Ser Ile Tyr Asp Ser His Val Asn Gly Asn Cys Asp
            100                 105                 110

Val Asn Tyr Asp His Asn Asn Asp Leu Tyr Ile Val Ala Leu Arg Phe
        115                 120                 125

Arg Leu Leu Arg Gln His Gly Tyr Lys Val Ser Ala Asp Ile Phe Lys
    130                 135                 140

Lys Phe Lys Asp Glu Lys Gly Glu Phe Lys Asp Met Ile Arg Asn Asp
145                 150                 155                 160

Ala Arg Gly Leu Leu Cys Leu Tyr Glu Ala Ser His Leu Arg Val Lys
                165                 170                 175

Gly Glu Asp Ile Leu Glu Glu Ala Thr Glu Phe Ser Arg Lys His Leu
            180                 185                 190

Lys Ser Leu Leu Pro Gln Leu Ser Thr Ser Leu Ala Glu Gln Val Lys
        195                 200                 205

His Ser Leu Glu Ile Pro Leu His Arg Gly Met Pro Arg Leu Glu Ala
    210                 215                 220

Arg His Tyr Ile Ser Ile Tyr Glu Glu Asn Asn Ser Ser Arg Asn Glu
225                 230                 235                 240

Leu Leu Leu Glu Leu Ala Lys Leu Asp Phe Asn Leu Leu Gln Ala Leu
                245                 250                 255

His Arg Arg Glu Leu Gly Asp Ile Ser Arg Trp Trp Lys Asp Ile Asp
            260                 265                 270

```
Phe Ala Thr Lys Leu Pro Phe Ala Arg Asp Arg Leu Val Glu Cys Tyr
            275                 280                 285

Phe Trp Ile Leu Gly Val Tyr Phe Glu Pro Lys Tyr Ser Ile Thr Arg
290                 295                 300

Lys Phe Met Thr Lys Val Ile Ala Ile Ala Ser Val Ile Asp Asp Ile
305                 310                 315                 320

Tyr Asp Val Tyr Gly Thr Leu Glu Glu Leu Lys Leu Phe Thr His Ala
                325                 330                 335

Ile Glu Arg Trp Glu Thr Val Ala Ala Asn Glu Leu Pro Lys Tyr Met
            340                 345                 350

Gln Val Cys Tyr Phe Ala Leu Leu Asp Val Phe Lys Glu Met Glu Asp
            355                 360                 365

Lys Leu Val Asn Lys Gly Leu Leu Tyr Ser Met Pro Cys Ala Lys Glu
        370                 375                 380

Ala Val Lys Gly Leu Val Lys Ala Tyr Phe Val Glu Ala Lys Trp Phe
385                 390                 395                 400

His Ala Lys Tyr Val Pro Thr Phe Glu Glu Tyr Met Glu Asn Ser Thr
                405                 410                 415

Met Ser Ser Gly Tyr Pro Met Leu Ala Val Glu Ala Leu Val Gly Leu
            420                 425                 430

Glu Asp Met Ala Ile Thr Lys Arg Ala Leu Asp Trp Ala Ile Ser Val
        435                 440                 445

Pro Lys Ile Ile Arg Ser Cys Ala Leu Ile Ala Arg Leu Asp Asp Asp
        450                 455                 460

Val His Thr Tyr Lys Val Glu Gln Glu Arg Gly Asp Ala Pro Ser Ser
465                 470                 475                 480

Val Gln Cys Tyr Met Gln Gln Tyr Asp Val Ser Glu Glu Glu Ala Cys
                485                 490                 495

Asn Arg Ile Lys Gly Met Val Glu Thr Ala Trp Met Glu Ile Asn Gly
            500                 505                 510

Glu Ile Gln Asp Thr Asn His Leu Pro Leu Gln Trp Leu Leu Pro Ser
        515                 520                 525

Leu Asn Leu Ala Arg Met Met Val Val Leu Tyr Gln Asn Gly Asp Asn
530                 535                 540

Tyr Thr Asn Ser Ser Gly Lys Thr Lys Asp Arg Ile Ala Ser Leu Leu
545                 550                 555                 560

Val Asp Pro Leu Pro Met
                565

<210> SEQ ID NO 26
<211> LENGTH: 566
<212> TYPE: PRT
<213> ORGANISM: Artificial Sequence
<220> FEATURE:
<223> OTHER INFORMATION: Synthetic polypeptide

<400> SEQUENCE: 26

Arg Asp Leu Lys Ser Val Leu Ser Ser Lys Glu Ser Thr Lys Ala Asp
1               5                   10                  15

Val Asn Arg Arg Ser Ser Asn Tyr His Pro Ser Ile Trp Gly Asp His
            20                  25                  30

Phe Ile Asn Val Ser Ser Asn Glu Lys Tyr Thr Asn Thr Glu Val Glu
        35                  40                  45

Lys Arg Phe Glu Thr Leu Lys Ala Glu Ile Glu Lys Leu Leu Val Ser
    50                  55                  60
```

```
Asn Asn Thr Ala Trp Lys Thr Leu Glu Glu Ile Val Ala Ile Val Asn
 65                  70                  75                  80
Gln Leu Gln Arg Leu Gly Leu Ala Tyr His Phe Glu Asn Gln Ile Lys
                 85                  90                  95
Glu Ala Leu Gln Ser Ile Tyr Asp Ser His Val Asn Gly Asn Cys Asp
            100                 105                 110
Val Asn Tyr Asp His Asn Asn Asp Leu Tyr Ile Val Ala Leu Arg Phe
            115                 120                 125
Arg Leu Leu Arg Gln His Gly Tyr Lys Val Ser Ala Asp Ile Phe Lys
        130                 135                 140
Lys Phe Lys Asp Glu Lys Gly Glu Phe Lys Asp Met Ile Arg Asn Asp
145                 150                 155                 160
Ala Arg Gly Leu Leu Cys Leu Tyr Glu Ala Ser His Leu Arg Val Lys
                165                 170                 175
Gly Glu Asp Ile Leu Glu Glu Ala Thr Glu Phe Ser Arg Lys His Leu
            180                 185                 190
Lys Ser Leu Leu Pro Gln Leu Ser Thr Ser Leu Ala Glu Gln Val Lys
        195                 200                 205
His Ser Leu Glu Ile Pro Leu His Arg Gly Met Pro Arg Leu Glu Ala
210                 215                 220
Arg His Tyr Ile Ser Ile Tyr Glu Glu Asn Asn Ser Ser Arg Asn Glu
225                 230                 235                 240
Leu Leu Leu Glu Leu Ala Lys Leu Asp Phe Asn Leu Leu Gln Ala Leu
                245                 250                 255
His Arg Arg Glu Leu Gly Asp Ile Ser Arg Trp Trp Lys Asp Ile Asp
            260                 265                 270
Phe Ala Thr Lys Leu Pro Phe Ala Arg Asp Arg Leu Val Glu Cys Tyr
        275                 280                 285
Phe Trp Ile Leu Gly Val Tyr Phe Glu Pro Lys Tyr Ser Ile Thr Arg
        290                 295                 300
Lys Phe Met Thr Lys Val Ile Ala Ile Ala Ser Val Ile Asp Asp Ile
305                 310                 315                 320
Tyr Asp Val Tyr Gly Thr Leu Glu Glu Leu Lys Leu Phe Thr His Ala
                325                 330                 335
Ile Glu Arg Trp Glu Thr Val Ala Ala Asn Glu Leu Pro Lys Tyr Met
            340                 345                 350
Gln Val Cys Tyr Phe Ala Leu Leu Asp Val Phe Lys Glu Met Glu Asp
        355                 360                 365
Lys Leu Val Asn Lys Gly Leu Leu Tyr Ser Met Pro Cys Ala Lys Glu
370                 375                 380
Ala Val Lys Gly Leu Val Lys Ala Tyr Phe Val Glu Ala Lys Trp Phe
385                 390                 395                 400
His Ala Lys Tyr Val Pro Thr Phe Glu Glu Tyr Met Glu Asn Ser Thr
                405                 410                 415
Met Ser Ser Gly Tyr Pro Met Leu Ala Val Glu Ala Leu Val Gly Leu
            420                 425                 430
Glu Asp Met Ala Ile Thr Lys Arg Ala Leu Asp Trp Ala Ile Ser Val
        435                 440                 445
Pro Lys Ile Ile Arg Ser Cys Ala Leu Ile Ala Arg Leu Asp Asp Asp
        450                 455                 460
Val His Thr Tyr Lys Val Glu Gln Glu Arg Gly Asp Ala Pro Ser Ser
465                 470                 475                 480
Val Glu Cys Tyr Met Gln Gln Tyr Asp Val Ser Glu Glu Glu Ala Cys
```

```
                    485                 490                 495
Asn Arg Ile Lys Gly Met Val Glu Ile Glu Trp Met Asn Ile Asn Glu
            500                 505                 510

Glu Ile Gln Asp Pro Asn His Pro Pro Leu Gln Trp Leu Leu Pro Ser
        515                 520                 525

Leu Asn Leu Ala Arg Met Met Val Val Leu Tyr Gln Asn Gly Asp Asn
    530                 535                 540

Tyr Thr Asn Ser Ser Gly Lys Thr Lys Asp Arg Ile Ala Ser Leu Leu
545                 550                 555                 560

Val Asp Pro Leu Pro Met
                565

<210> SEQ ID NO 27
<211> LENGTH: 562
<212> TYPE: PRT
<213> ORGANISM: Artificial Sequence
<220> FEATURE:
<223> OTHER INFORMATION: Synthetic polypeptide

<400> SEQUENCE: 27

Ser Phe Ala Val Ser Ala Ser Pro Ala Lys Phe Ile Gln Asn Val Glu
1               5                   10                  15

Lys Asp Ser Thr Arg Arg Ser Ala Asn Phe His Pro Ser Ile Trp Gly
            20                  25                  30

Asp His Phe Leu Gln Tyr Thr Cys Asp Ser Gln Glu Pro Asp Asp Asp
        35                  40                  45

Gly Ser Val Lys His Gln Gln Leu Lys Glu Glu Ile Arg Lys Met Leu
    50                  55                  60

Thr Ala Glu Thr Lys Leu Ser Gln Lys Leu Asp Leu Ile Asp Ala Ile
65                  70                  75                  80

Gln Arg Leu Gly Val Ala Tyr His Phe Glu Ser Glu Ile Asp Glu Ile
                85                  90                  95

Leu Gly Arg Val His Gln Ala Tyr Gln Glu Ser Asp Leu Cys Val Asn
            100                 105                 110

Glu Asn Asp Gly Leu Tyr Tyr Ile Ser Leu Gln Phe Arg Leu Leu Arg
        115                 120                 125

Glu Asn Gly Tyr Arg Ile Ser Ala Asp Val Phe Asn Lys Phe Arg Asp
    130                 135                 140

Ile Asp Gly Asn Phe Lys Pro Ser Leu Ala Arg Asn Val Arg Gly Met
145                 150                 155                 160

Leu Ser Leu Tyr Glu Ala Thr His Leu Arg Val His Gly Glu Asn Ile
                165                 170                 175

Leu Asp Glu Ala His Ala Phe Ala Thr Ser His Leu Glu Ser Ile Ala
            180                 185                 190

Thr His Gln Ile Ser Ser Pro Leu Ala Glu Gln Val Lys His Ala Leu
        195                 200                 205

Phe Gln Pro Ile His Lys Gly Val Gln Arg Leu Glu Ala Arg Asn Tyr
    210                 215                 220

Met Pro Phe Tyr Gln Glu Glu Ala Ser His Asn Glu Ala Leu Leu Thr
225                 230                 235                 240

Phe Ala Lys Leu Asp Phe Asn Lys Leu Gln Lys Leu His Gln Lys Glu
                245                 250                 255

Leu Ser Glu Ile Thr Arg Trp Trp Lys Glu Leu Asp Phe Ala His Asn
            260                 265                 270

Leu Pro Phe Thr Ile Arg Asp Arg Ile Ala Glu Cys Tyr Phe Trp Ala
```

```
                275                 280                 285
Val Ala Val Tyr Phe Glu Pro Gln Tyr Ser Leu Gly Arg Arg Met Leu
        290                 295                 300
Ala Lys Val Phe Pro Met Thr Ser Ile Ile Asp Asp Ile Tyr Asp Val
305                 310                 315                 320
Tyr Gly Lys Phe Glu Glu Leu Glu Leu Phe Thr Ser Ala Ile Glu Arg
                325                 330                 335
Trp Asp Ile Ser Ala Ile Asp Glu Leu Pro Glu Tyr Met Lys Leu Cys
            340                 345                 350
Tyr Arg Ala Leu Leu Asp Val Tyr Ser Glu Ala Glu Lys Asp Leu Ala
                355                 360                 365
Ser Gln Gly Lys Leu Tyr His Leu His Tyr Ala Lys Glu Ala Met Lys
    370                 375                 380
Asn Gln Val Lys Asn Tyr Phe Glu Ala Lys Trp Cys His Gln Asn
385                 390                 395                 400
Tyr Ile Pro Ser Val Asp Glu Tyr Met Thr Val Ala Ser Val Thr Ser
                405                 410                 415
Gly Tyr Pro Met Leu Ser Thr Thr Ser Phe Val Gly Met Gly Asp Ile
            420                 425                 430
Val Thr Lys Glu Ser Phe Glu Trp Ser Leu Thr Asn Pro Arg Val Ile
        435                 440                 445
Arg Ala Ser Ser Val Ala Ala Arg Leu Met Asn Asp Met Val Ser His
    450                 455                 460
Lys Phe Glu Gln Ser Arg Glu His Val Ala Ser Ile Glu Cys Tyr
465                 470                 475                 480
Met Lys Gln Tyr Gly Ala Thr Glu Glu Glu Thr Cys Asn Glu Leu Arg
                485                 490                 495
Lys Gln Val Ser Asn Ala Trp Lys Asp Ile Asn Glu Glu Cys Leu Cys
            500                 505                 510
Pro Thr Ala Val Pro Met Pro Leu Ile Val Arg Ile Leu Asn Leu Thr
        515                 520                 525
Arg Phe Leu Asp Val Val Tyr Arg Phe Glu Asp Gly Tyr Thr His Ser
    530                 535                 540
Gly Val Val Leu Lys Asp Phe Val Ala Ser Leu Leu Ile Asn Pro Val
545                 550                 555                 560
Ser Ile

<210> SEQ ID NO 28
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 28

Glu Ser Gln Thr Thr Phe Lys Tyr Glu Ser Leu Ala Phe Thr Lys Leu
1               5                   10                  15
Ser His Cys Gln Trp Thr Asp Tyr Phe Leu Ser Val Pro Ile Asp Glu
            20                  25                  30
Ser Glu Leu Asp Val Ile Thr Arg Glu Ile Asp Ile Leu Lys Pro Glu
        35                  40                  45
Val Met Glu Leu Leu Ser Ser Gln Gly Asp Asp Glu Thr Ser Lys Arg
    50                  55                  60
Lys Val Leu Leu Ile Gln Leu Leu Leu Ser Leu Gly Leu Ala Phe His
65                  70                  75                  80
```

```
Phe Glu Asn Glu Ile Lys Asn Ile Leu Glu His Ala Phe Arg Lys Ile
                85                  90                  95

Asp Asp Ile Thr Gly Asp Glu Lys Asp Leu Ser Thr Ile Ser Ile Met
            100                 105                 110

Phe Arg Val Phe Arg Thr Tyr Gly His Asn Leu Pro Ala Glu Val Phe
            115                 120                 125

Glu Arg Phe Lys Asp Gln His Gly Asn Phe Lys Ala Ser Leu Ser Ser
130                 135                 140

Asp Val Glu Gly Met Leu Ser Leu Tyr Glu Ala Ser Phe Leu Asp Tyr
145                 150                 155                 160

Glu Gly Glu Asp Ile Leu Asp Glu Ala Lys Ala Phe Thr Ser Phe His
                165                 170                 175

Leu Arg Gly Ala Leu Ala Gly Gly Thr Cys Arg Pro His Ile Leu Arg
            180                 185                 190

Leu Ile Arg Asn Thr Leu Tyr Leu Pro Gln Arg Trp Asn Met Glu Ala
            195                 200                 205

Val Ile Ala Arg Glu Tyr Ile Ser Phe Tyr Glu Gln Glu Glu Asp His
        210                 215                 220

Asp Lys Met Leu Leu Arg Leu Ala Lys Leu Asn Phe Lys Leu Leu Gln
225                 230                 235                 240

Leu His Tyr Ile Lys Glu Leu Lys Ser Phe Ile Lys Trp Trp Met Glu
                245                 250                 255

Leu Gly Leu Thr Ser Lys Trp Pro Ser Gln Phe Arg Glu Arg Ile Val
            260                 265                 270

Glu Ala Trp Leu Ala Gly Leu Met Met Tyr Phe Glu Pro Gln Phe Ser
            275                 280                 285

Gly Gly Arg Val Ile Ala Ala Lys Phe Asn Tyr Leu Leu Thr Ile Leu
290                 295                 300

Asp Asp Ala Cys Asp His Tyr Phe Ser Ile His Glu Leu Thr Arg Leu
305                 310                 315                 320

Val Ala Cys Val Glu Arg Trp Ser Pro Asp Gly Ile Asp Thr Leu Glu
                325                 330                 335

Asp Ile Ser Arg Ser Val Phe Lys Leu Met Leu Asp Val Phe Asp Asp
            340                 345                 350

Ile Gly Lys Gly Val Arg Ser Glu Gly Ser Ser Tyr His Leu Lys Glu
            355                 360                 365

Met Leu Glu Glu Leu Asn Thr Leu Val Arg Ala Asn Leu Asp Leu Val
370                 375                 380

Lys Trp Ala Arg Gly Ile Gln Val Pro Ser Phe Glu Glu His Val Glu
385                 390                 395                 400

Val Gly Gly Ile Ala Leu Thr Ser Tyr Ala Thr Leu Met Tyr Ser Phe
                405                 410                 415

Val Gly Met Gly Glu Thr Ala Gly Lys Glu Ala Tyr Glu Trp Val Arg
            420                 425                 430

Ser Arg Pro Arg Leu Ile Lys Ser Leu Ala Ala Lys Gly Arg Leu Met
            435                 440                 445

Asp Asp Ile Thr Asp Phe Asp Ser Asp Met Ser Asn Gly Phe Ala Ala
450                 455                 460

Asn Ala Ile Asn Tyr Tyr Met Lys Gln Phe Val Val Thr Lys Glu Glu
465                 470                 475                 480

Ala Ile Leu Glu Cys Gln Arg Met Ile Val Asp Ile Asn Lys Thr Ile
                485                 490                 495
```

```
Asn Glu Glu Leu Leu Lys Thr Thr Ser Val Pro Gly Arg Val Leu Lys
            500                 505                 510

Gln Ala Leu Asn Phe Gly Arg Leu Leu Glu Leu Leu Tyr Thr Lys Ser
        515                 520                 525

Asp Asp Ile Tyr Asn Cys Ser Glu Gly Lys Leu Lys Glu Tyr Ile Val
    530                 535                 540

Thr Leu Leu Ile Asp Pro Ile Arg Leu
545             550

<210> SEQ ID NO 29
<211> LENGTH: 552
<212> TYPE: PRT
<213> ORGANISM: Artificial Sequence
<220> FEATURE:
<223> OTHER INFORMATION: Synthetic polypeptide

<400> SEQUENCE: 29

Ser Ile Gln Val Pro Gln Ile Ser Ser Gln Asn Ala Lys Ser Gln Val
1               5                   10                  15

Met Arg Arg Thr Ala Asn Phe His Pro Ser Val Trp Gly Asp Arg Phe
            20                  25                  30

Ala Asn Tyr Thr Ala Glu Asp Lys Met Asn His Ala Arg Asp Leu Lys
        35                  40                  45

Glu Leu Lys Ala Leu Lys Glu Val Gly Arg Lys Leu Leu Ala Thr
    50                  55                  60

Ala Gly Pro Ile Val Lys Leu Glu Leu Val Asp Asp Val Lys Arg Leu
65              70                  75                  80

Gly Ile Gly Tyr Arg Phe Glu Lys Glu Ile Val Glu Ala Leu His Arg
                85                  90                  95

Cys Phe Ile Ser Ser Glu Arg Phe Thr His Arg Asn Leu His Gln Thr
            100                 105                 110

Ala Leu Ser Phe Arg Leu Leu Arg Glu Cys Gly Tyr Asp Val Thr Cys
        115                 120                 125

Asp Lys Phe Asn Lys Phe Thr Asn Lys Glu Gly Lys Phe Asn Ser Lys
    130                 135                 140

Leu Gly Glu Asn Ile Lys Gly Met Ile Asp Leu Tyr Glu Ala Ser Gln
145                 150                 155                 160

Leu Gly Ile Ala Gly Glu Tyr Ile Leu Ala Glu Ala Gly Glu Phe Ser
                165                 170                 175

Gly Leu Val Leu Lys Glu Lys Val Ala Cys Ile Asn Asn Asn Pro Leu
            180                 185                 190

Lys Ala Gln Val Arg His Ala Leu Arg Gln Pro Leu His Arg Gly Leu
        195                 200                 205

Pro Arg Leu Glu His Arg Arg Tyr Ile Ser Ile Tyr Gln Asp Asp Ala
    210                 215                 220

Ser His Tyr Lys Ala Leu Leu Thr Leu Ala Lys Leu Asp Phe Asn Leu
225                 230                 235                 240

Val Gln Ser Leu His Lys Lys Glu Leu Cys Glu Ile Ser Arg Trp Trp
                245                 250                 255

Lys Asp Leu Asp Phe Ala Arg Lys Leu Pro Phe Ala Arg Asp Arg Met
            260                 265                 270

Val Glu Cys Tyr Phe Trp Ile Leu Gly Val Tyr Phe Glu Pro Gln Tyr
        275                 280                 285

Ser Val Pro Arg Arg Thr Thr Thr Lys Val Ile Gly Leu Cys Ser Val
    290                 295                 300
```

-continued

```
Ile Asp Asp Met Tyr Asp Ala Tyr Gly Thr Ile Asp Glu Leu Glu Leu
305                 310                 315                 320

Phe Thr Asn Ala Ile Glu Arg Leu Asp Thr Ser Thr Met Asp Gln Leu
            325                 330                 335

Pro Glu Tyr Met Gln Thr Phe Phe Gly Ala Leu Leu Asp Leu Tyr Asn
        340                 345                 350

Glu Ile Glu Lys Glu Ile Ala Asn Glu Gly Trp Ser Tyr Arg Val Gln
    355                 360                 365

Tyr Ala Lys Glu Ala Met Lys Ile Leu Val Gly Tyr Tyr Asp Glu
370                 375                 380

Ser Arg Trp Leu Lys Cys Asn His Ala Pro Thr Met Glu Glu Tyr Met
385                 390                 395                 400

Lys Val Arg Gly Val Ser Ser Gly Tyr Pro Leu Leu Ile Thr Ile Ser
            405                 410                 415

Phe Ile Gly Met Glu Asp Thr Thr Glu Glu Ile Leu Thr Trp Ala Thr
        420                 425                 430

Ser Glu Pro Met Ile Ile Arg Ala Ser Val Ile Val Cys Arg Leu Met
    435                 440                 445

Asp Asp Ile Lys Ser His Lys Phe Gln Glu Arg Gly His Ala Ala
450                 455                 460

Ser Ala Val Glu Cys Tyr Met Lys Gln His Gly Leu Ser Glu Gln Glu
465                 470                 475                 480

Val Cys Glu Glu Leu Tyr Arg Gln Val Ser Asn Ala Trp Lys Asp Ile
            485                 490                 495

Asn Glu Glu Cys Leu Asn Pro Thr Ala Val Pro Met Pro Leu Leu Met
        500                 505                 510

Arg Ala Leu Asn Leu Ala Arg Val Ile Asp Val Val Tyr Lys Glu Gly
    515                 520                 525

Asp Gly Tyr Thr His Val Gly Asn Glu Met Lys Gln Asn Val Ala Ala
530                 535                 540

Leu Leu Ile Asp Gln Val Pro Ile
545                 550
```

<210> SEQ ID NO 30
<211> LENGTH: 561
<212> TYPE: PRT
<213> ORGANISM: Artificial Sequence
<220> FEATURE:
<223> OTHER INFORMATION: Synthetic polypeptide

<400> SEQUENCE: 30

```
Ala Leu Gln Asp Ser Glu Val Pro Ser Ser Ile Leu Asn Ala Thr Ala
1               5                   10                  15

Gly Asn Arg Pro Thr Ala Ser Tyr His Pro Thr Leu Trp Gly Glu Lys
            20                  25                  30

Phe Leu Val Val Ser Thr Gln Ser Thr Ser Gly Ser Met Lys Asn Glu
        35                  40                  45

Pro Thr Thr Gln Gly Glu Tyr Asp Glu Leu Lys Gln Gln Val Thr Lys
    50                  55                  60

Met Leu Thr Asp Ala Thr Thr Asn Asp Pro Ser Lys Lys Leu His Leu
65                  70                  75                  80

Ile Asp Met Val Gln Arg Leu Gly Ile Ala Tyr His Phe Glu Ile Glu
                85                  90                  95

Ile Glu Asn Ala Leu Glu Lys Ile Asn Leu Gly Asp Ala Asn Tyr Phe
            100                 105                 110
```

Glu Tyr Asp Leu Tyr Thr Ile Ala Leu Gly Phe Arg Leu Leu Arg Gln
            115                 120                 125

Gln Gly Ile Lys Val Ser Ser Glu Ile Phe Lys Lys Phe Met Asp Glu
        130                 135                 140

Lys Gly Lys Phe Lys Glu Asp Val Val Asn Asp Val Leu Gly Met Leu
145                 150                 155                 160

Asn Leu Tyr Glu Ala Ala His Leu Arg Leu Arg Gly Glu Asp Ile Leu
                165                 170                 175

Asp Glu Ala Leu Ala Phe Thr Thr Ser His Leu Glu Ser Met Ala Thr
            180                 185                 190

Lys Val Ser Pro Leu Leu Ala Glu Gln Ile Ala His Ala Leu Asn Cys
        195                 200                 205

Pro Ile Gln Lys Gly Leu Pro Arg Ile Glu Ala Arg His Tyr Ile Ser
    210                 215                 220

Leu Tyr Ser Arg Glu Thr His Phe Ala Ser Ser Asn Ala Ala Leu Leu
225                 230                 235                 240

Arg Phe Ala Lys Ile Asp Phe Asn Met Val Gln Ala Leu His Gln Lys
                245                 250                 255

Glu Ile Ser Gly Ile Thr Lys Trp Trp Lys Asn Leu Asp Phe Ser Thr
            260                 265                 270

Lys Leu Pro Tyr Ala Arg Asp Arg Ile Val Glu Cys Tyr Phe Trp Ile
        275                 280                 285

Met Gly Ala Tyr Phe Glu Pro Lys Tyr Ser Leu Ala Arg Thr Phe Leu
    290                 295                 300

Thr Lys Val Ile Ala Met Thr Ser Ile Leu Asp Asp Thr Tyr Asp Asn
305                 310                 315                 320

Tyr Gly Thr Asn Lys Glu Leu Glu Leu Leu Thr Lys Cys Ile Glu Arg
                325                 330                 335

Trp Asp Ile Asp Val Ile Asp Gln Leu Pro Glu Tyr Met Lys Leu Val
            340                 345                 350

Tyr Gln Ala Leu Leu Asn Val Tyr Ser Glu Met Glu Ala Lys Val Ala
        355                 360                 365

Lys Glu Gly Arg Ser Tyr Ala Ile Asp Tyr Ala Lys Glu Ser Met Lys
    370                 375                 380

Lys Thr Met Lys Ala Tyr Leu Asp Glu Ala Lys Trp Arg Gln Glu Asp
385                 390                 395                 400

Tyr Val Pro Pro Ile Glu Glu Tyr Met Gln Val Ala Arg Ile Ser Ser
                405                 410                 415

Ala Tyr Pro Met Leu Ile Thr Asn Ser Phe Val Gly Met Gly Glu Val
            420                 425                 430

Ala Thr Lys Glu Ala Phe Asp Trp Ile Ser Asn Asp Pro Lys Ile Leu
        435                 440                 445

Lys Ala Ser Thr Thr Ile Cys Arg Leu Met Asp Asp Ile Thr Ser His
    450                 455                 460

Glu Phe Glu Gln Thr Arg Asp His Val Ala Ser Gly Val Glu Cys Tyr
465                 470                 475                 480

Met Lys Gln Tyr Gly Val Ser Arg Glu Glu Thr Val Lys Leu Phe Arg
                485                 490                 495

Glu Asp Val Ala Asn Ala Trp Lys Asp Ile Asn Glu Gly Phe Met Lys
            500                 505                 510

Pro Ala Ile Phe Pro Met Pro Ile Leu Thr Val Val Leu Asn Phe Ala
        515                 520                 525

Arg Val Met Asp Phe Leu Tyr Lys Asp Gly Asp Asn Tyr Thr Asn Ser

```
                530             535             540
His Met Leu Lys Asp Tyr Ile Thr Ser Leu Leu Val Asn Pro Leu Leu
545                 550             555             560

Ile
```

```
<210> SEQ ID NO 31
<211> LENGTH: 561
<212> TYPE: PRT
<213> ORGANISM: Artificial Sequence
<220> FEATURE:
<223> OTHER INFORMATION: Synthetic polypeptide

<400> SEQUENCE: 31

Ala Leu Gln Asp Ser Glu Val Pro Ser Ser Ile Leu Asn Ala Thr Ala
1               5                   10                  15

Gly Asn Arg Pro Thr Ala Ser Tyr His Pro Thr Leu Trp Gly Glu Lys
            20                  25                  30

Phe Leu Val Val Ser Thr Gln Ser Thr Ser Gly Ser Met Lys Asn Glu
        35                  40                  45

Pro Thr Thr Gln Gly Glu Tyr Asp Glu Leu Lys Gln Gln Val Thr Lys
    50                  55                  60

Met Leu Thr Asp Ala Thr Asn Asp Pro Ser Lys Lys Leu His Leu
65                  70                  75                  80

Ile Asp Met Val Gln Arg Leu Gly Ile Ala Tyr His Phe Glu Ile Glu
                85                  90                  95

Ile Glu Asn Ala Leu Glu Lys Ile Asn Leu Gly Asp Ala Asn Tyr Phe
            100                 105                 110

Glu Tyr Asp Leu Tyr Thr Ile Ala Leu Gly Phe Arg Leu Leu Arg Gln
        115                 120                 125

Gln Gly Ile Lys Val Ser Ser Glu Ile Phe Lys Lys Phe Met Asp Glu
    130                 135                 140

Lys Gly Lys Phe Lys Glu Asp Val Val Asn Asp Val Leu Gly Met Leu
145                 150                 155                 160

Asn Leu Tyr Glu Ala Ala His Leu Arg Leu Arg Gly Glu Asp Ile Leu
                165                 170                 175

Asp Glu Ala Leu Ala Phe Thr Thr Ser His Leu Glu Ser Met Ala Thr
            180                 185                 190

Lys Val Ser Pro Leu Leu Ala Glu Gln Ile Ala His Ala Leu Asn Cys
        195                 200                 205

Pro Ile Gln Lys Gly Leu Pro Arg Ile Glu Ala Arg His Tyr Ile Ser
    210                 215                 220

Leu Tyr Ser Arg Glu Thr His Phe Ala Ser Ser Asn Ala Ala Leu Leu
225                 230                 235                 240

Arg Phe Ala Lys Ile Asp Phe Asn Met Val Gln Ala Leu His Gln Lys
                245                 250                 255

Glu Ile Ser Gly Ile Thr Lys Trp Trp Lys Asn Leu Asp Phe Ser Thr
            260                 265                 270

Lys Leu Pro Tyr Ala Arg Asp Arg Ile Val Glu Cys Tyr Phe Trp Ile
        275                 280                 285

Met Gly Ala Tyr Phe Glu Pro Lys Tyr Ser Leu Ala Arg Thr Phe Leu
    290                 295                 300

Thr Lys Val Ile Ala Met Thr Ser Ile Leu Asp Asp Thr Tyr Asp Asn
305                 310                 315                 320

Tyr Gly Thr Asn Lys Glu Leu Glu Leu Leu Thr Lys Cys Ile Glu Arg
                325                 330                 335
```

```
Trp Asp Ile Asp Val Ile Asp Gln Leu Pro Glu Tyr Met Lys Leu Val
                340                 345                 350

Tyr Gln Ala Leu Leu Asn Val Tyr Ser Glu Met Glu Ala Lys Val Ala
                355                 360                 365

Lys Glu Gly Arg Ser Tyr Ala Ile Asp Tyr Ala Lys Glu Ser Met Lys
                370                 375                 380

Lys Thr Met Lys Ala Tyr Leu Asp Glu Ala Lys Trp Arg Gln Glu Asp
385                 390                 395                 400

Tyr Val Pro Thr Ile Glu Glu Tyr Met Gln Val Ala Leu Ile Ser Ser
                405                 410                 415

Ala Tyr Pro Met Leu Ile Thr Asn Ser Phe Val Gly Met Gly Glu Val
                420                 425                 430

Ala Thr Lys Glu Ala Phe Asp Trp Ile Ser Asn Asn Pro Lys Met Leu
                435                 440                 445

Lys Ala Ser Thr Ile Ile Cys Arg Leu Met Asp Asp Ile Thr Ser His
                450                 455                 460

Glu Phe Glu Gln Thr Arg Asp His Val Ala Ser Gly Val Glu Cys Tyr
465                 470                 475                 480

Met Lys Gln Tyr Gly Val Ser Arg Glu Glu Thr Val Lys Leu Phe Arg
                485                 490                 495

Glu Asp Val Ala Asn Ala Trp Lys Asp Ile Asn Glu Gly Phe Met Lys
                500                 505                 510

Pro Ala Ile Phe Pro Met Pro Ile Leu Thr Val Val Leu Asn Phe Ala
                515                 520                 525

Arg Val Met Asp Phe Leu Tyr Lys Asp Gly Asp Asn Tyr Thr Asn Ser
                530                 535                 540

His Met Leu Lys Asp Tyr Ile Thr Ser Leu Leu Val Asn Pro Leu Leu
545                 550                 555                 560

Ile

<210> SEQ ID NO 32
<211> LENGTH: 561
<212> TYPE: PRT
<213> ORGANISM: Artificial Sequence
<220> FEATURE:
<223> OTHER INFORMATION: Synthetic polypeptide

<400> SEQUENCE: 32

Ala Leu Gln Asp Ser Glu Val Pro Ser Ser Ile Leu Asn Ala Thr Ala
1               5                   10                  15

Gly Asn Arg Pro Thr Ala Ser Tyr His Pro Thr Leu Trp Gly Glu Lys
                20                  25                  30

Phe Leu Val Val Ser Thr Gln Ser Thr Ser Gly Ser Met Lys Asn Glu
                35                  40                  45

Pro Thr Thr Gln Gly Glu Tyr Asp Glu Leu Lys Gln Gln Val Thr Lys
                50                  55                  60

Met Leu Thr Asp Ala Thr Thr Asn Asp Pro Ser Lys Lys Leu His Leu
65                  70                  75                  80

Ile Asp Met Val Gln Arg Leu Gly Ile Ala Tyr His Phe Glu Ile Glu
                85                  90                  95

Ile Glu Asn Ala Leu Glu Lys Ile Asn Leu Gly Asp Ala Asn Tyr Phe
                100                 105                 110

Glu Tyr Asp Leu Tyr Thr Ile Ala Leu Gly Phe Arg Leu Leu Arg Gln
                115                 120                 125
```

```
Gln Gly Ile Lys Val Ser Ser Glu Ile Phe Lys Lys Phe Met Asp Glu
    130                 135                 140

Lys Gly Lys Phe Lys Glu Asp Val Val Asn Asp Val Leu Gly Met Leu
145                 150                 155                 160

Asn Leu Tyr Glu Ala Ala His Leu Arg Leu Arg Gly Glu Asp Ile Leu
                165                 170                 175

Asp Glu Ala Leu Ala Phe Thr Thr Ser His Leu Glu Ser Met Ala Thr
            180                 185                 190

Lys Val Ser Pro Leu Leu Ala Glu Gln Ile Ala His Ala Leu Asn Cys
        195                 200                 205

Pro Ile Gln Lys Gly Leu Pro Arg Ile Glu Ala Arg His Tyr Ile Ser
210                 215                 220

Leu Tyr Ser Arg Glu Thr His Phe Ala Ser Ser Asn Ala Ala Leu Leu
225                 230                 235                 240

Arg Phe Ala Lys Ile Asp Phe Asn Met Val Gln Ala Leu His Gln Lys
                245                 250                 255

Glu Ile Ser Gly Ile Thr Lys Trp Trp Lys Asn Leu Asp Phe Ser Thr
            260                 265                 270

Lys Leu Pro Tyr Ala Arg Asp Arg Ile Val Glu Cys Tyr Phe Trp Ile
        275                 280                 285

Met Gly Ala Tyr Phe Glu Pro Lys Tyr Ser Leu Ala Arg Thr Phe Leu
290                 295                 300

Thr Lys Val Ile Ala Met Thr Ser Ile Leu Asp Asp Thr Tyr Asp Asn
305                 310                 315                 320

Tyr Gly Thr Asn Lys Glu Leu Glu Leu Leu Thr Lys Cys Ile Glu Arg
                325                 330                 335

Trp Asp Ile Asp Val Ile Asp Gln Leu Pro Glu Tyr Met Lys Leu Val
            340                 345                 350

Tyr Gln Ala Leu Leu Asn Val Tyr Ser Glu Met Glu Ala Lys Val Ala
        355                 360                 365

Lys Glu Gly Arg Ser Tyr Ala Ile Asp Tyr Ala Lys Glu Ser Met Lys
370                 375                 380

Lys Thr Met Lys Ala Tyr Leu Asp Glu Ala Lys Trp Arg Gln Glu Asp
385                 390                 395                 400

Tyr Val Pro Pro Ile Glu Glu Tyr Met Gln Val Ala Arg Ile Ser Ser
                405                 410                 415

Gly Tyr Pro Met Leu Ile Thr Asn Ser Leu Val Gly Met Gly Glu Val
            420                 425                 430

Ala Thr Lys Glu Ala Phe Asp Leu Ile Ser Asn Asp Pro Lys Met Leu
        435                 440                 445

Lys Ala Ser Thr Thr Ile Cys Arg Leu Met Asp Asp Ile Thr Ser His
450                 455                 460

Glu Phe Glu Gln Thr Arg Asp His Val Ala Ser Gly Val Glu Cys Tyr
465                 470                 475                 480

Met Lys Gln Tyr Gly Val Ser Arg Glu Glu Thr Val Lys Leu Phe Arg
                485                 490                 495

Glu Asp Val Ala Asn Ala Trp Lys Asp Ile Asn Glu Gly Phe Met Lys
            500                 505                 510

Pro Ala Ile Phe Pro Met Pro Ile Leu Thr Val Val Leu Asn Phe Ala
        515                 520                 525

Arg Val Met Asp Phe Leu Tyr Lys Asp Gly Asp Asn Tyr Thr Asn Ser
530                 535                 540

His Met Leu Lys Asp Tyr Ile Thr Ser Leu Leu Val Asn Pro Leu Leu
```

545 550 555 560

Ile

<210> SEQ ID NO 33
<211> LENGTH: 561
<212> TYPE: PRT
<213> ORGANISM: Artificial Sequence
<220> FEATURE:
<223> OTHER INFORMATION: Synthetic polypeptide

<400> SEQUENCE: 33

Ala Leu Gln Asp Ser Glu Val Pro Ser Ser Ile Leu Asn Ala Thr Ala
1               5                   10                  15

Gly Asn Arg Pro Thr Ala Ser Tyr His Pro Thr Leu Trp Gly Glu Lys
            20                  25                  30

Phe Leu Val Val Ser Thr Gln Ser Thr Gly Ser Met Lys Asn Glu
        35                  40                  45

Pro Thr Thr Gln Gly Glu Tyr Asp Glu Leu Lys Gln Gln Val Thr Lys
    50                  55                  60

Met Leu Thr Asp Ala Thr Thr Asn Asp Pro Ser Lys Lys Leu His Leu
65                  70                  75                  80

Ile Asp Met Val Gln Arg Leu Gly Ile Ala Tyr His Phe Glu Ile Glu
                85                  90                  95

Ile Glu Asn Ala Leu Glu Lys Ile Asn Leu Gly Asp Ala Asn Tyr Phe
            100                 105                 110

Glu Tyr Asp Leu Tyr Thr Ile Ala Leu Gly Phe Arg Leu Leu Arg Gln
        115                 120                 125

Gln Gly Ile Lys Val Ser Ser Glu Ile Phe Lys Lys Phe Met Asp Glu
    130                 135                 140

Lys Gly Lys Phe Lys Glu Asp Val Val Asn Asp Val Leu Gly Met Leu
145                 150                 155                 160

Asn Leu Tyr Glu Ala Ala His Leu Arg Leu Arg Gly Glu Asp Ile Leu
                165                 170                 175

Asp Glu Ala Leu Ala Phe Thr Thr Ser His Leu Glu Ser Met Ala Thr
            180                 185                 190

Lys Val Ser Pro Leu Leu Ala Glu Gln Ile Ala His Ala Leu Asn Cys
        195                 200                 205

Pro Ile Gln Lys Gly Leu Pro Arg Ile Glu Ala Arg His Tyr Ile Ser
    210                 215                 220

Leu Tyr Ser Arg Glu Thr His Phe Ala Ser Ser Asn Ala Ala Leu Leu
225                 230                 235                 240

Arg Phe Ala Lys Ile Asp Phe Asn Met Val Gln Ala Leu His Gln Lys
                245                 250                 255

Glu Ile Ser Gly Ile Thr Lys Trp Trp Lys Asn Leu Asp Phe Ser Thr
            260                 265                 270

Lys Leu Pro Tyr Ala Arg Asp Arg Ile Val Glu Cys Tyr Phe Trp Ile
        275                 280                 285

Met Gly Ala Tyr Phe Glu Pro Lys Tyr Ser Leu Ala Arg Thr Phe Leu
    290                 295                 300

Thr Lys Val Ile Ala Met Thr Ser Ile Leu Asp Asp Thr Tyr Asp Asn
305                 310                 315                 320

Tyr Gly Thr Asn Lys Glu Leu Glu Leu Leu Thr Lys Cys Ile Glu Arg
                325                 330                 335

Trp Asp Ile Asp Val Ile Asp Gln Leu Pro Glu Tyr Met Lys Leu Val
            340                 345                 350

```
Tyr Gln Ala Leu Leu Asn Val Tyr Ser Glu Met Glu Ala Lys Val Ala
            355                 360                 365

Lys Glu Gly Arg Ser Tyr Ala Ile Asp Tyr Ala Lys Glu Ser Met Lys
    370                 375                 380

Lys Thr Met Lys Ala Tyr Leu Asp Glu Ala Lys Trp Arg Gln Glu Asp
385                 390                 395                 400

Tyr Val Pro Pro Met Asp Glu Tyr Met Gln Val Ala Leu Ile Ser Cys
                405                 410                 415

Gly Tyr Pro Met Leu Ile Thr Asn Ser Phe Val Gly Met Gly Glu Val
                420                 425                 430

Ala Thr Lys Glu Ala Phe Asp Trp Ile Ser Asn Asp Pro Lys Ile Leu
            435                 440                 445

Lys Ala Ser Thr Thr Ile Cys Arg Leu Met Asp Ile Thr Ser His
450                 455                 460

Glu Phe Glu Gln Thr Arg Asp His Val Ala Ser Gly Val Glu Cys Tyr
465                 470                 475                 480

Met Lys Gln Tyr Gly Val Ser Arg Glu Thr Val Lys Leu Phe Arg
                485                 490                 495

Glu Asp Val Ala Asn Ala Trp Lys Asp Ile Glu Gly Phe Met Lys
                500                 505                 510

Pro Ala Ile Phe Pro Met Pro Ile Leu Thr Val Val Leu Asn Phe Ala
                515                 520                 525

Arg Val Met Asp Phe Leu Tyr Lys Asp Gly Asp Asn Tyr Thr Asn Ser
            530                 535                 540

His Met Leu Lys Asp Tyr Ile Thr Ser Leu Leu Val Asn Pro Leu Leu
545                 550                 555                 560

Ile

<210> SEQ ID NO 34
<211> LENGTH: 561
<212> TYPE: PRT
<213> ORGANISM: Artificial Sequence
<220> FEATURE:
<223> OTHER INFORMATION: Synthetic polypeptide

<400> SEQUENCE: 34

Ala Leu Gln Asp Ser Glu Val Pro Ser Ser Ile Leu Asn Ala Thr Ala
1               5                   10                  15

Gly Asn Arg Pro Thr Ala Ser Tyr His Pro Thr Leu Trp Gly Glu Lys
            20                  25                  30

Phe Leu Val Val Ser Thr Gln Ser Thr Ser Gly Ser Met Lys Asn Glu
        35                  40                  45

Pro Thr Thr Gln Gly Glu Tyr Asp Glu Leu Lys Gln Gln Val Thr Lys
    50                  55                  60

Met Leu Thr Asp Ala Thr Thr Asn Asp Pro Ser Lys Lys Leu His Leu
65                  70                  75                  80

Ile Asp Met Val Gln Arg Leu Gly Ile Ala Tyr His Phe Glu Ile Glu
                85                  90                  95

Ile Glu Asn Ala Leu Glu Lys Ile Asn Leu Gly Asp Ala Asn Tyr Phe
            100                 105                 110

Glu Tyr Asp Leu Tyr Thr Ile Ala Leu Gly Phe Arg Leu Leu Arg Gln
        115                 120                 125

Gln Gly Ile Lys Val Ser Ser Glu Ile Phe Lys Lys Phe Met Asp Glu
    130                 135                 140
```

```
Lys Gly Lys Phe Lys Glu Asp Val Val Asn Asp Val Leu Gly Met Leu
145                 150                 155                 160

Asn Leu Tyr Glu Ala Ala His Leu Arg Leu Arg Gly Glu Asp Ile Leu
            165                 170                 175

Asp Glu Ala Leu Ala Phe Thr Thr Ser His Leu Glu Ser Met Ala Thr
        180                 185                 190

Lys Val Ser Pro Leu Leu Ala Glu Gln Ile Ala His Ala Leu Asn Cys
    195                 200                 205

Pro Ile Gln Lys Gly Leu Pro Arg Ile Glu Ala Arg His Tyr Ile Ser
        210                 215                 220

Leu Tyr Ser Arg Glu Thr His Phe Ala Ser Ser Asn Ala Ala Leu Leu
225                 230                 235                 240

Arg Phe Ala Lys Ile Asp Phe Asn Met Val Gln Ala Leu His Gln Lys
                245                 250                 255

Glu Ile Ser Gly Ile Thr Lys Trp Trp Lys Asn Leu Asp Phe Ala Thr
            260                 265                 270

Met Leu Pro Tyr Ala Arg Asp Arg Ile Val Glu Cys Tyr Phe Trp Ile
        275                 280                 285

Met Gly Val Tyr Phe Glu Pro Lys Tyr Ser Leu Ala Arg Thr Phe Leu
    290                 295                 300

Thr Lys Val Ile Ala Met Thr Ser Ile Leu Asp Asp Thr Tyr Asp Asn
305                 310                 315                 320

Tyr Gly Thr Asn Lys Glu Leu Glu Leu Leu Thr Lys Cys Ile Glu Arg
                325                 330                 335

Trp Asp Ile Asp Val Ile Asp Gln Leu Pro Glu Tyr Met Lys Leu Val
            340                 345                 350

Tyr Gln Ala Leu Leu Asn Val Tyr Ser Glu Met Glu Ala Lys Val Ala
        355                 360                 365

Lys Glu Gly Arg Ser Tyr Ala Ile Asp Tyr Ala Lys Glu Ser Met Lys
    370                 375                 380

Lys Thr Met Lys Ala Tyr Leu Asp Glu Ala Lys Trp Arg Gln Glu Asp
385                 390                 395                 400

Tyr Val Pro Thr Ile Glu Glu Tyr Met Gln Val Ala Leu Ile Ser Ser
                405                 410                 415

Ala Tyr Pro Met Leu Ile Thr Asn Ser Phe Val Gly Met Gly Glu Val
            420                 425                 430

Ala Thr Lys Glu Ala Phe Asp Trp Ile Ser Asn Asn Pro Lys Met Leu
        435                 440                 445

Lys Ala Ser Thr Ile Ile Cys Arg Leu Met Asp Asp Ile Thr Ser His
    450                 455                 460

Glu Phe Glu Gln Thr Arg Asp His Val Ala Ser Gly Val Glu Cys Tyr
465                 470                 475                 480

Met Lys Gln Tyr Gly Val Ser Arg Glu Glu Thr Val Lys Leu Phe Arg
                485                 490                 495

Glu Asp Val Ala Asn Ala Trp Lys Asp Ile Asn Glu Gly Phe Met Lys
            500                 505                 510

Pro Ala Ile Phe Pro Met Pro Ile Leu Thr Val Val Leu Asn Phe Ala
        515                 520                 525

Arg Val Met Asp Phe Leu Tyr Lys Asp Gly Asp Asn Tyr Thr Asn Ser
    530                 535                 540

His Met Leu Lys Asp Tyr Ile Thr Ser Leu Leu Val Asn Pro Leu Leu
545                 550                 555                 560

Ile
```

<210> SEQ ID NO 35
<211> LENGTH: 561
<212> TYPE: PRT
<213> ORGANISM: Artificial Sequence
<220> FEATURE:
<223> OTHER INFORMATION: Synthetic polypeptide

<400> SEQUENCE: 35

```
Ala Leu Gln Asp Ser Glu Val Pro Ser Ser Ile Leu Asn Ala Thr Ala
1               5                   10                  15

Gly Asn Arg Pro Thr Ala Ser Tyr His Pro Thr Leu Trp Gly Glu Lys
            20                  25                  30

Phe Leu Val Val Ser Thr Gln Ser Thr Ser Gly Ser Met Lys Asn Glu
        35                  40                  45

Pro Thr Thr Gln Gly Glu Tyr Asp Glu Leu Lys Gln Gln Val Thr Lys
    50                  55                  60

Met Leu Thr Asp Ala Thr Thr Asn Asp Pro Ser Lys Lys Leu His Leu
65                  70                  75                  80

Ile Asp Met Val Gln Arg Leu Gly Ile Ala Tyr His Phe Glu Ile Glu
                85                  90                  95

Ile Glu Asn Ala Leu Glu Lys Ile Asn Leu Gly Asp Ala Asn Tyr Phe
            100                 105                 110

Glu Tyr Asp Leu Tyr Thr Ile Ala Leu Gly Phe Arg Leu Leu Arg Gln
        115                 120                 125

Gln Gly Ile Lys Val Ser Ser Glu Ile Phe Lys Lys Phe Met Asp Glu
    130                 135                 140

Lys Gly Lys Phe Lys Glu Asp Val Val Asn Asp Val Leu Gly Met Leu
145                 150                 155                 160

Asn Leu Tyr Glu Ala Ala His Leu Arg Leu Arg Gly Glu Asp Ile Leu
                165                 170                 175

Asp Glu Ala Leu Ala Phe Thr Thr Ser His Leu Glu Ser Met Ala Thr
            180                 185                 190

Lys Val Ser Pro Leu Leu Ala Glu Gln Ile Ala His Ala Leu Asn Cys
        195                 200                 205

Pro Ile Gln Lys Gly Leu Pro Arg Ile Glu Ala Arg His Tyr Ile Ser
    210                 215                 220

Leu Tyr Ser Arg Glu Thr His Phe Ala Ser Ser Asn Ala Ala Leu Leu
225                 230                 235                 240

Arg Phe Ala Lys Ile Asp Phe Asn Met Val Gln Ala Leu His Gln Lys
                245                 250                 255

Glu Ile Ser Gly Ile Thr Lys Trp Trp Lys Asn Leu Asp Phe Ala Thr
            260                 265                 270

Met Leu Pro Tyr Ala Arg Asp Arg Ile Val Glu Cys Tyr Phe Trp Ile
        275                 280                 285

Met Gly Val Tyr Phe Glu Pro Lys Tyr Ser Leu Ala Arg Thr Phe Leu
    290                 295                 300

Thr Lys Val Ile Ala Met Thr Ser Ile Leu Asp Asp Thr Tyr Asp Asn
305                 310                 315                 320

Tyr Gly Thr Asn Lys Glu Leu Glu Leu Thr Lys Cys Ile Glu Arg
                325                 330                 335

Trp Asp Ile Asp Val Ile Asp Gln Leu Pro Glu Tyr Met Lys Leu Val
            340                 345                 350

Tyr Gln Ala Leu Leu Asn Val Tyr Ser Glu Met Glu Ala Lys Val Ala
        355                 360                 365
```

Lys Glu Gly Arg Ser Tyr Ala Ile Asp Tyr Ala Lys Glu Ser Met Lys
        370                 375                 380

Lys Thr Met Lys Ala Tyr Leu Asp Glu Ala Lys Trp Arg Gln Glu Asp
385                 390                 395                 400

Tyr Val Pro Pro Ile Glu Glu Tyr Met Gln Val Ala Arg Ile Ser Ser
                405                 410                 415

Gly Tyr Pro Met Leu Ile Thr Asn Ser Leu Val Gly Met Gly Glu Val
                420                 425                 430

Ala Thr Lys Glu Ala Phe Asp Leu Ile Ser Asn Asp Pro Lys Met Leu
            435                 440                 445

Lys Ala Ser Thr Thr Ile Cys Arg Leu Met Asp Asp Ile Thr Ser His
        450                 455                 460

Glu Phe Glu Gln Thr Arg Asp His Val Ala Ser Gly Val Glu Cys Tyr
465                 470                 475                 480

Met Lys Gln Tyr Gly Val Ser Arg Glu Glu Thr Val Lys Leu Phe Arg
                485                 490                 495

Glu Asp Val Ala Asn Ala Trp Lys Asp Ile Asn Glu Gly Phe Met Lys
                500                 505                 510

Pro Ala Ile Phe Pro Met Pro Ile Leu Thr Val Val Leu Asn Phe Ala
            515                 520                 525

Arg Val Met Asp Phe Leu Tyr Lys Asp Gly Asp Asn Tyr Thr Asn Ser
        530                 535                 540

His Met Leu Lys Asp Tyr Ile Thr Ser Leu Leu Val Asn Pro Leu Leu
545                 550                 555                 560

Ile

<210> SEQ ID NO 36
<211> LENGTH: 552
<212> TYPE: PRT
<213> ORGANISM: Artificial Sequence
<220> FEATURE:
<223> OTHER INFORMATION: Synthetic polypeptide

<400> SEQUENCE: 36

Ala Ser Ala Gln Ala Ser Leu Pro Ser Asn Asn Arg Gln Glu Thr Val
1               5                   10                  15

Arg Pro Leu Ala Asp Phe Pro Glu Asn Ile Trp Ala Asp Arg Ile Ala
                20                  25                  30

Pro Phe Thr Leu Asp Lys Gln Glu Tyr Glu Met Cys Gln Arg Glu Ile
            35                  40                  45

Glu Met Leu Lys Ala Glu Val Ala Ser Met Leu Leu Ala Thr Gly Lys
50                  55                  60

Thr Met Met Gln Arg Phe Asp Phe Ile Asp Lys Ile Glu Arg Leu Gly
65                  70                  75                  80

Val Ser His His Phe Asp Ile Glu Ile Glu Asn Gln Leu Gln Glu Phe
                85                  90                  95

Phe Asn Val Tyr Thr Asn Leu Gly Glu Tyr Ser Ala Tyr Asp Leu Ser
                100                 105                 110

Ser Ala Ala Leu Gln Phe Arg Leu Phe Arg Gln His Gly Phe Asn Ile
            115                 120                 125

Ser Cys Gly Ile Phe Asp Gln Phe Ile Asp Ala Lys Gly Lys Phe Lys
        130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
            180                 185                 190

Leu Ala Lys Gln Val Lys Tyr Ala Leu Glu Gln Pro Leu His Lys Gly
        195                 200                 205

Ile Leu Arg Tyr Glu Ala Trp Arg Tyr Ile Ser Ile Tyr Glu Glu Asp
    210                 215                 220

Glu Ser Asn Asn Lys Leu Leu Arg Leu Ala Lys Leu Asp Tyr His
225                 230                 235                 240

Leu Leu Gln Met Ser Tyr Lys Gln Glu Leu Cys Glu Ile Thr Arg Trp
                245                 250                 255

Gly Lys Gly Leu Glu Ser Val Ser Asn Phe Pro Tyr Ala Arg Asp Arg
            260                 265                 270

Phe Val Glu Cys Tyr Phe Trp Ala Val Gly Thr Leu Tyr Glu Pro Gln
        275                 280                 285

Tyr Ser Leu Ala Arg Met Thr Phe Ala Lys Val Ala Ala Leu Ile Thr
    290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
                325                 330                 335

Leu Ser Asp Tyr Ile Arg Ala Ser Tyr Asn Thr Leu Leu Lys Phe Asn
            340                 345                 350

Lys Glu Val Gly Glu Asp Leu Ala Lys Lys Gln Arg Thr Tyr Ala Phe
        355                 360                 365

Asp Lys Tyr Ile Glu Asp Trp Lys Gln Tyr Met Arg Thr Asn Phe Ser
    370                 375                 380

Gln Ser Arg Trp Phe Phe Thr Lys Glu Leu Pro Ser Phe Ala Asp Tyr
385                 390                 395                 400

Ile Asn Asn Gly Ala Ile Thr Ile Gly Ala Tyr Leu Val Ala Ser Ala
                405                 410                 415

Ala Phe Leu Tyr Met Asp Ser Ala Lys Glu Asp Val Ile Asn Trp Met
            420                 425                 430

Ser Thr Asn Pro Lys Leu Val Val Ala Tyr Ser Thr His Ser Arg Leu
        435                 440                 445

Ile Asn Asp Phe Gly Gly His Lys Phe Glu Lys Glu Arg Gly Ser Ser
    450                 455                 460

Thr Ala Ile Glu Cys Tyr Met Lys Asp His Asn Val Ser Glu Glu Glu
465                 470                 475                 480

Ala Ala Asn Lys Phe Arg Glu Met Met Glu Asp Ala Trp Lys Val Met
                485                 490                 495

Asn Glu Glu Cys Leu Arg Pro Thr Thr Ile Pro Arg Asp Gly Leu Lys
            500                 505                 510

Met Leu Leu Asn Ile Ala Arg Val Gly Glu Thr Val Tyr Lys His Arg
        515                 520                 525

Ile Asp Gly Phe Thr Gln Pro His Ala Ile Glu Glu His Ile Arg Ala
    530                 535                 540

Met Leu Val Asp Phe Met Ser Ile
545                 550

<210> SEQ ID NO 37
<211> LENGTH: 552
<212> TYPE: PRT

<213> ORGANISM: Artificial Sequence
<220> FEATURE:
<223> OTHER INFORMATION: Synthetic polypeptide

<400> SEQUENCE: 37

```
Ala Ser Ala Gln Ala Ser Leu Pro Ser Asn Asn Arg Gln Glu Thr Val
1               5                   10                  15

Arg Pro Leu Ala Asp Phe Pro Glu Asn Ile Trp Ala Asp Arg Ile Ala
            20                  25                  30

Pro Phe Thr Leu Asp Lys Gln Glu Tyr Glu Met Cys Gln Arg Glu Ile
        35                  40                  45

Glu Met Leu Lys Ala Glu Val Ala Ser Met Leu Leu Ala Thr Gly Lys
    50                  55                  60

Thr Met Met Gln Arg Phe Asp Phe Ile Asp Lys Ile Glu Arg Leu Gly
65                  70                  75                  80

Val Ser His His Phe Asp Ile Glu Ile Glu Asn Gln Leu Gln Glu Phe
                85                  90                  95

Phe Asn Val Tyr Thr Asn Leu Gly Glu Tyr Ser Ala Tyr Asp Leu Ser
                100                 105                 110

Ser Ala Ala Leu Gln Phe Arg Leu Phe Arg Gln His Gly Phe Asn Ile
            115                 120                 125

Ser Cys Gly Ile Phe Asp Gln Phe Ile Asp Ala Lys Gly Lys Phe Lys
        130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
            180                 185                 190

Leu Ala Lys Gln Val Lys Tyr Ala Leu Glu Gln Pro Leu His Lys Gly
        195                 200                 205

Ile Leu Arg Tyr Glu Ala Trp Arg Tyr Ile Ser Ile Tyr Glu Glu Asp
    210                 215                 220

Glu Ser Asn Asn Lys Leu Leu Leu Arg Leu Ala Lys Leu Asp Tyr His
225                 230                 235                 240

Leu Leu Gln Met Ser Tyr Lys Gln Glu Leu Cys Glu Ile Thr Arg Trp
                245                 250                 255

Gly Lys Gly Leu Glu Ser Val Ser Asn Phe Pro Tyr Ala Arg Asp Arg
            260                 265                 270

Phe Val Glu Cys Tyr Phe Trp Ala Val Gly Thr Leu Tyr Glu Pro Gln
        275                 280                 285

Tyr Ser Leu Ala Arg Met Thr Phe Ala Lys Val Ala Ala Leu Ile Thr
    290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
                325                 330                 335

Leu Ser Asp Tyr Ile Arg Ala Ser Tyr Asn Thr Leu Leu Lys Phe Asn
            340                 345                 350

Lys Glu Val Gly Glu Asp Leu Ala Lys Gln Arg Thr Tyr Ala Phe
        355                 360                 365

Asp Lys Tyr Ile Glu Asp Trp Lys Gln Tyr Met Arg Thr Asn Phe Ser
    370                 375                 380

Gln Ser Arg Trp Phe Phe Thr Lys Glu Leu Pro Ser Phe Ala Asp Tyr
```

-continued

```
                385                 390                 395                 400
        Ile Asn Asn Gly Ala Ile Thr Ile Gly Ala Tyr Leu Val Ala Ser Ala
                        405                 410                 415

Ala Phe Leu Tyr Met Asp Ser Ala Lys Glu Asp Val Ile Asn Trp Met
                        420                 425                 430

Ser Thr Asn Pro Lys Leu Val Val Ala Tyr Ser Thr His Ser Arg Leu
                        435                 440                 445

Ile Asn Asp Phe Gly Gly His Lys Phe Asp Lys Glu Arg Gly Thr Gly
                        450                 455                 460

Thr Ala Ile Glu Cys Tyr Met Lys Asp His Asn Ile Ser Glu Glu Glu
        465                 470                 475                 480

Ala Ala Lys Lys Phe Arg Glu Met Ile Glu Asn Thr Trp Lys Val Met
                        485                 490                 495

Asn Glu Glu Cys Leu Arg Pro Ile Pro Ile Pro Arg Asp Thr Leu Lys
                        500                 505                 510

Met Leu Leu Asn Ile Ala Arg Val Gly Glu Thr Val Tyr Lys His Arg
                        515                 520                 525

Ile Asp Gly Phe Thr Gln Pro His Ala Ile Glu Glu His Ile Arg Ala
                        530                 535                 540

Met Leu Val Asp Phe Met Ser Ile
        545                 550

<210> SEQ ID NO 38
<211> LENGTH: 559
<212> TYPE: PRT
<213> ORGANISM: Artificial Sequence
<220> FEATURE:
<223> OTHER INFORMATION: Synthetic polypeptide

<400> SEQUENCE: 38

Ser Leu Leu Glu Gly Asn Val Asn His Glu Asn Gly Ile Phe Arg Pro
        1               5                   10                  15

Glu Ala Asn Phe Ser Pro Ser Met Trp Gly Asn Ile Phe Arg Asp Ser
                        20                  25                  30

Ser Lys Asp Asn Gln Ile Ser Glu Glu Val Val Glu Glu Ile Glu Ala
                        35                  40                  45

Leu Lys Glu Val Val Lys His Met Ile Ile Ser Thr Thr Ser Asn Ala
                        50                  55                  60

Ile Glu Gln Lys Leu Glu Leu Val Asp Asn Leu Glu Arg Leu Gly Leu
        65                  70                  75                  80

Ala Tyr His Phe Glu Gly Gln Ile Asn Arg Leu Leu Ser Ser Ala Tyr
                        85                  90                  95

Asn Ala Asn His Glu Asp Glu Gly Asn His Lys Arg Asn Lys Glu Asp
                        100                 105                 110

Leu Tyr Ala Ala Ala Leu Glu Phe Arg Ile Phe Arg Gln His Gly Phe
                        115                 120                 125

Asn Val Ser Ser Asp Cys Phe Asn Gln Phe Lys Asp Thr Lys Gly Lys
                        130                 135                 140

Phe Lys Lys Thr Leu Leu Ile Asp Val Lys Gly Met Leu Ser Leu Tyr
        145                 150                 155                 160

Glu Ala Ala His Val Arg Glu His Gly Asp Asp Ile Leu Glu Glu Ala
                        165                 170                 175

Leu Ile Phe Ala Thr Phe His Leu Glu Arg Ile Thr Pro Asn Ser Leu
                        180                 185                 190

Asp Ser Thr Leu Glu Lys Gln Val Gly His Ala Leu Met Gln Ser Leu
```

195                 200                 205
His Arg Gly Ile Pro Arg Ala Glu Ala His Phe Asn Ile Ser Ile Tyr
210                 215                 220
Glu Glu Cys Gly Ser Ser Asn Glu Lys Leu Leu Arg Leu Ala Lys Leu
225                 230                 235                 240
Asp Tyr Asn Leu Val Gln Val Leu His Lys Glu Glu Leu Ser Glu Leu
            245                 250                 255
Thr Lys Trp Trp Lys Asp Leu Asp Phe Ala Ser Lys Leu Ser Tyr Val
        260                 265                 270
Arg Asp Arg Met Val Glu Cys Phe Phe Trp Thr Val Gly Val Tyr Phe
            275                 280                 285
Glu Pro Gln Tyr Ser Arg Ala Arg Val Met Leu Ala Lys Cys Ile Ala
        290                 295                 300
Met Ile Ser Val Ile Asp Asp Thr Tyr Asp Ser Tyr Gly Thr Leu Asp
305                 310                 315                 320
Glu Leu Ile Ile Phe Thr Glu Val Val Asp Arg Trp Asp Ile Ser Glu
                325                 330                 335
Val Asp Arg Leu Pro Asn Tyr Met Lys Pro Ile Tyr Ile Ser Leu Leu
            340                 345                 350
Tyr Leu Phe Asn Glu Tyr Glu Arg Glu Ile Asn Glu Gln Asp Arg Phe
        355                 360                 365
Asn Gly Val Asn Tyr Val Lys Glu Ala Met Lys Glu Ile Val Arg Ser
370                 375                 380
Tyr Tyr Ile Glu Ala Glu Trp Phe Ile Glu Gly Lys Ile Pro Ser Phe
385                 390                 395                 400
Glu Glu Tyr Leu Asn Asn Ala Leu Val Thr Gly Thr Tyr Tyr Leu Leu
                405                 410                 415
Ala Pro Ala Ser Leu Leu Gly Met Glu Ser Thr Ser Lys Arg Thr Phe
            420                 425                 430
Asp Trp Met Met Lys Lys Pro Lys Ile Leu Val Ala Ser Ala Ile Ile
        435                 440                 445
Gly Arg Val Ile Asp Asp Ile Ala Thr Tyr Lys Ile Glu Lys Glu Lys
450                 455                 460
Gly Gln Leu Val Thr Gly Ile Glu Cys Tyr Met Gln Glu Asn Asn Leu
465                 470                 475                 480
Ser Val Glu Lys Ala Ser Ala Gln Leu Ser Glu Ile Ala Glu Ser Ala
                485                 490                 495
Trp Lys Asp Leu Asn Lys Glu Cys Ile Lys Thr Thr Ser Asn Ile
            500                 505                 510
Pro Asn Glu Ile Leu Met Arg Val Val Asn Leu Thr Arg Leu Ile Asp
        515                 520                 525
Val Val Tyr Lys Asn Asn Gln Asp Gly Tyr Ser Asn Pro Lys Asn Asn
            530                 535                 540
Val Lys Ser Val Ile Glu Ala Leu Leu Val Asn Pro Ile Asn Met
545                 550                 555

<210> SEQ ID NO 39
<211> LENGTH: 542
<212> TYPE: PRT
<213> ORGANISM: Artificial Sequence
<220> FEATURE:
<223> OTHER INFORMATION: Synthetic polypeptide

<400> SEQUENCE: 39

Glu Ser Arg Arg Ser Ala Asn Tyr Gln Ala Ser Ile Trp Asp Asp Asn

-continued

```
1               5               10              15
Phe Ile Gln Ser Leu Ala Ser Pro Tyr Ala Gly Glu Lys Tyr Val Ser
        20              25              30
Gln Ala Asn Glu Leu Lys Glu Gln Val Lys Met Met Leu Asp Glu Glu
        35              40              45
Asp Met Lys Leu Leu Asp Cys Leu Glu Leu Val Asp Asn Leu Glu Arg
    50              55              60
Leu Gly Leu Ala Tyr His Phe Glu Gly Gln Ile Asn Arg Leu Leu Ser
65              70              75              80
Ser Ala Tyr Asn Ala Asn His Glu Asp Glu Gly Asn His Lys Arg Asn
                85              90              95
Lys Glu Asp Leu Tyr Ala Ala Ala Leu Glu Phe Arg Ile Phe Arg Gln
                100             105             110
His Gly Phe Asn Val Pro Gln Asp Val Phe Ser Ser Phe Met Asn Lys
                115             120             125
Ala Gly Asp Phe Glu Glu Ser Leu Ser Lys Asp Thr Lys Gly Leu Val
        130             135             140
Ser Leu Tyr Glu Ala Ser Tyr Leu Ser Met Glu Gly Glu Thr Ile Leu
145             150             155             160
Asp Met Ala Lys Asp Phe Ser Ser His His Leu His Lys Met Val Glu
                165             170             175
Asp Ala Thr Asp Lys Arg Val Ala Asn Gln Ile Ile His Ser Leu Glu
        180             185             190
Met Pro Leu His Arg Arg Val Gln Lys Leu Glu Ala Ile Trp Phe Ile
        195             200             205
Gln Phe Tyr Glu Cys Gly Ser Asp Ala Asn Pro Thr Leu Val Glu Leu
        210             215             220
Ala Lys Leu Asp Phe Asn Met Val Gln Ala Thr Tyr Gln Glu Glu Leu
225             230             235             240
Lys Arg Leu Ser Arg Trp Tyr Glu Glu Thr Gly Leu Gln Glu Lys Leu
                245             250             255
Ser Phe Ala Arg His Arg Leu Ala Glu Ala Phe Leu Trp Ser Met Gly
            260             265             270
Ile Ile Pro Glu Gly His Phe Gly Tyr Gly Arg Met His Leu Met Lys
            275             280             285
Ile Gly Ala Tyr Ile Thr Leu Leu Asp Asp Ile Tyr Asp Val Tyr Gly
        290             295             300
Thr Leu Glu Glu Leu Gln Val Leu Thr Glu Ile Ile Glu Arg Trp Asp
305             310             315             320
Ile Asn Leu Leu Asp Gln Leu Pro Glu Tyr Met Gln Ile Phe Phe Leu
                325             330             335
Tyr Met Phe Asn Ser Thr Asn Glu Leu Ala Tyr Glu Ile Leu Arg Asp
                340             345             350
Gln Gly Ile Asn Val Ile Ser Asn Leu Lys Gly Leu Trp Val Glu Leu
            355             360             365
Ser Gln Cys Tyr Phe Lys Glu Ala Thr Trp Phe His Asn Gly Tyr Thr
    370             375             380
Pro Thr Thr Glu Glu Tyr Leu Asn Val Ala Cys Ile Ser Ala Ser Gly
385             390             395             400
Pro Val Ile Leu Phe Ser Gly Tyr Phe Thr Thr Thr Asn Pro Ile Asn
                405             410             415
Lys His Glu Leu Gln Ser Leu Glu Arg His Ala His Ser Leu Ser Met
                420             425             430
```

```
Ile Leu Arg Leu Ala Asp Asp Leu Gly Thr Ser Ser Asp Glu Met Lys
        435                 440                 445

Arg Gly Asp Val Pro Lys Ala Ile Gln Cys Phe Met Asn Asp Thr Gly
    450                 455                 460

Cys Cys Glu Glu Glu Ala Arg Gln His Val Lys Arg Leu Ile Asp Ala
465                 470                 475                 480

Glu Trp Lys Lys Met Asn Lys Asp Ile Leu Met Glu Lys Pro Phe Lys
                485                 490                 495

Asn Phe Cys Pro Thr Ala Met Asn Leu Gly Arg Ile Ser Met Ser Phe
            500                 505                 510

Tyr Glu His Gly Asp Gly Tyr Gly Gly Pro His Ser Asp Thr Lys Lys
        515                 520                 525

Lys Met Val Ser Leu Phe Val Gln Pro Met Asn Ile Thr Ile
    530                 535                 540

<210> SEQ ID NO 40
<211> LENGTH: 551
<212> TYPE: PRT
<213> ORGANISM: Artificial Sequence
<220> FEATURE:
<223> OTHER INFORMATION: Synthetic polypeptide

<400> SEQUENCE: 40

Ala Ser Thr Glu Ile Ala Val Pro Leu Asn Asn Gln His Glu Ser Val
1               5                   10                  15

Arg Gln Leu Ala Asp Phe Pro Glu Asn Ile Trp Ala Asp Arg Val Ala
            20                  25                  30

Ser Phe Thr Leu Asp Lys Gln Gly His Asp Met Cys Ala Lys Glu Ile
        35                  40                  45

Glu Met Leu Lys Glu Glu Val Met Ser Met Leu Leu Glu Glu Lys Pro
    50                  55                  60

Met Met Glu Lys Phe Asn Leu Ile Asp Asn Ile Glu Arg Leu Gly Ile
65                  70                  75                  80

Ser Tyr His Phe Gly Asp Lys Ile Glu Asp Gln Leu Gln Glu Tyr Tyr
                85                  90                  95

Asp Ala Cys Thr Asn Phe Glu Lys His Ala Glu Cys Asp Leu Ser Ile
            100                 105                 110

Ala Ala Leu Gln Phe Arg Leu Phe Arg Gln His Gly Phe Asn Ile Ser
        115                 120                 125

Cys Gly Ile Phe Asp Gly Phe Leu Asp Ala Asn Gly Lys Phe Lys Glu
    130                 135                 140

Ser Leu Cys Asn Asp Ile Lys Gly Leu Leu Ser Leu Tyr Glu Ala Ala
145                 150                 155                 160

His Val Arg Thr His Gly Asp Lys Ile Leu Glu Glu Ala Leu Phe Phe
                165                 170                 175

Thr Thr Thr His Leu Thr Arg Leu Ile Pro Asn Val Gly Ser Thr Leu
            180                 185                 190

Ala Lys Gln Val Lys Tyr Ala Leu Glu Gln Pro Leu His Lys Gly Ile
        195                 200                 205

Pro Arg Tyr Glu Ala Trp Arg Tyr Ile Ser Ile Tyr Glu Glu Asp Glu
    210                 215                 220

Ser Ser Asn Lys Leu Leu Leu Arg Leu Ala Lys Leu Asp Tyr His Leu
225                 230                 235                 240

Ser Gln Met Leu Asn Lys Gln Asp Leu Cys Glu Ile Ile Arg Trp Gly
                245                 250                 255
```

```
Lys Glu Leu Asp Ile Ile Ser Lys Val Pro Tyr Ala Arg Asp Arg Ile
            260                 265                 270

Val Glu Cys Tyr Phe Trp Ala Val Ala Thr Tyr Tyr Glu Pro Gln Tyr
        275                 280                 285

Ser Leu Ala Arg Met Thr Leu Thr Lys Ala Thr Val Phe Ala Gly Met
    290                 295                 300

Ile Asp Asp Thr Tyr Asp Ala Tyr Gly Thr Leu Asp Glu Leu Lys Ile
305                 310                 315                 320

Phe Thr Glu Ala Val Glu Arg Trp Asp Ser Gly Ile Asp Gln Leu
            325                 330                 335

Ser Asp Tyr Met Lys Ala Ala Tyr Thr Leu Val Leu Asn Phe Asn Lys
            340                 345                 350

Glu Val Gly Glu Asp Leu Ala Lys Lys Gln Arg Thr Tyr Ala Phe Asp
            355                 360                 365

Lys Tyr Ile Glu Glu Trp Lys Gln Tyr Ala Arg Thr Ser Phe Thr Gln
    370                 375                 380

Ser Lys Trp Phe Leu Thr Asn Glu Leu Pro Ser Phe Ser Asp Tyr Leu
385                 390                 395                 400

Ser Asn Gly Met Val Thr Ser Thr Tyr Tyr Leu Leu Ser Ala Ala Ala
                405                 410                 415

Phe Leu Asp Met Asp Ser Ala Ser Glu Asp Val Ile Asn Trp Met Ser
                420                 425                 430

Thr Asn Pro Lys Leu Phe Val Ala Leu Thr Thr His Ala Arg Leu Ala
            435                 440                 445

Asn Asp Val Gly Ser His Lys Phe Glu Lys Glu Arg Gly Ser Gly Thr
    450                 455                 460

Ala Ile Glu Cys Tyr Met Lys Asp Tyr His Val Ser Glu Glu Glu Ala
465                 470                 475                 480

Met Lys Lys Phe Glu Glu Met Cys Asp Asp Ala Trp Lys Val Met Asn
                485                 490                 495

Glu Glu Cys Leu Arg Ser Thr Thr Ile Pro Arg Glu Ile Leu Lys Val
            500                 505                 510

Ile Leu Asn Leu Ala Arg Thr Cys Glu Val Val Tyr Lys His Arg Gly
            515                 520                 525

Asp Gly Phe Thr Asp Gln Arg Arg Ile Glu Ala His Ile Asn Ala Met
            530                 535                 540

Leu Met Asp Ser Val Ser Ile
545                 550

<210> SEQ ID NO 41
<211> LENGTH: 551
<212> TYPE: PRT
<213> ORGANISM: Artificial Sequence
<220> FEATURE:
<223> OTHER INFORMATION: Synthetic polypeptide

<400> SEQUENCE: 41

Ala Ser Thr Glu Ile Ala Val Pro Leu Asn Asn Gln His Glu Ser Val
1               5                   10                  15

Arg Gln Leu Ala Asp Phe Pro Glu Asn Ile Trp Ala Arg Val Ala
            20                  25                  30

Ser Phe Thr Leu Asp Lys Gln Gly His Asp Met Cys Ala Lys Glu Ile
            35                  40                  45

Glu Met Leu Lys Glu Glu Val Met Ser Met Leu Leu Glu Glu Lys Pro
    50                  55                  60
```

```
Met Met Glu Lys Phe Asn Leu Ile Asp Asn Ile Glu Arg Leu Gly Ile
 65                  70                  75                  80

Ser Tyr His Phe Gly Asp Lys Ile Glu Asp Gln Leu Gln Glu Tyr Tyr
                 85                  90                  95

Asp Ala Cys Thr Asn Phe Glu Lys His Ala Glu Cys Asp Leu Ser Ile
                100                 105                 110

Ala Ala Leu Gln Phe Arg Leu Phe Arg Gln His Gly Phe Asn Ile Ser
            115                 120                 125

Cys Gly Ile Phe Asp Gly Phe Leu Asp Ala Asn Gly Lys Phe Lys Glu
130                 135                 140

Ser Leu Cys Asn Asp Ile Lys Gly Leu Leu Ser Leu Tyr Glu Ala Ala
145                 150                 155                 160

His Val Arg Thr His Gly Asp Lys Ile Leu Glu Glu Ala Leu Phe Phe
                165                 170                 175

Thr Thr Thr His Leu Thr Arg Glu Ile Pro Asn Val Gly Ser Thr Leu
            180                 185                 190

Ala Lys Gln Val Lys His Ala Leu Glu Gln Pro Leu His Arg Gly Ile
        195                 200                 205

Pro Arg Tyr Glu Ala Tyr Cys Phe Ile Ser Ile Tyr Glu Glu Asp Glu
210                 215                 220

Ser Asn Asn Lys Leu Leu Leu Arg Leu Ala Lys Leu Asp Tyr His Leu
225                 230                 235                 240

Leu Gln Met Ser Tyr Lys Arg Glu Leu Ser Glu Ile Ile Arg Trp Gly
                245                 250                 255

Lys Glu Leu Asp Ile Ile Ser Lys Val Pro Tyr Ala Arg Asp Arg Ile
            260                 265                 270

Val Glu Cys Tyr Phe Trp Ala Val Ala Thr Tyr Tyr Glu Pro Gln Tyr
        275                 280                 285

Ser Leu Ala Arg Met Thr Leu Thr Lys Ala Thr Val Phe Ala Gly Met
290                 295                 300

Ile Asp Asp Thr Tyr Asp Ala Tyr Gly Thr Leu Asp Glu Leu Lys Ile
305                 310                 315                 320

Phe Thr Glu Ala Val Glu Arg Trp Asp Ser Ser Gly Ile Asp Gln Leu
                325                 330                 335

Ser Asp Tyr Met Lys Ala Ala Tyr Thr Leu Val Leu Asn Phe Asn Lys
            340                 345                 350

Glu Val Gly Glu Asp Leu Ala Lys Lys Gln Arg Thr Tyr Ala Phe Asp
        355                 360                 365

Lys Tyr Ile Glu Glu Trp Lys Gln Tyr Ala Arg Thr Ser Phe Thr Gln
370                 375                 380

Ser Lys Trp Phe Leu Thr Asn Glu Leu Pro Ser Phe Ser Asp Tyr Leu
385                 390                 395                 400

Ser Asn Gly Met Val Thr Ser Thr Tyr Leu Leu Ser Ala Ala Thr
                405                 410                 415

Phe Leu Gly Met Asp Gly Ala Ser Glu Asp Val Ile Asn Trp Met Ser
            420                 425                 430

Thr Asn Pro Lys Leu Phe Val Ala Leu Thr Thr His Ala Arg Leu Ala
        435                 440                 445

Asn Asp Val Gly Ser His Lys Phe Glu Lys Glu Arg Gly Ser Gly Thr
        450                 455                 460

Ala Ile Glu Cys Tyr Met Lys Asp Tyr His Val Ser Glu Glu Glu Ala
465                 470                 475                 480
```

Met Lys Lys Phe Glu Met Cys Asp Asp Ala Trp Lys Val Met Asn
                485                 490                 495

Glu Glu Cys Leu Arg Ser Thr Thr Ile Pro Arg Glu Ile Leu Lys Val
            500                 505                 510

Ile Leu Asn Leu Ala Arg Thr Cys Glu Val Val Tyr Lys His Arg Gly
            515                 520                 525

Asp Gly Phe Thr Asp Gln Arg Arg Ile Glu Ala His Ile Asn Ala Met
            530                 535                 540

Leu Met Asp Ser Val Ser Ile
545                 550

<210> SEQ ID NO 42
<211> LENGTH: 551
<212> TYPE: PRT
<213> ORGANISM: Artificial Sequence
<220> FEATURE:
<223> OTHER INFORMATION: Synthetic polypeptide

<400> SEQUENCE: 42

Ala Ser Thr Glu Ile Ala Val Pro Leu Asn Asn Gln His Glu Ser Val
1               5                   10                  15

Arg Gln Leu Ala Asp Phe Pro Glu Asn Ile Trp Ala Asp Arg Val Ala
            20                  25                  30

Ser Phe Thr Leu Asp Lys Gln Gly His Asp Met Cys Ala Lys Glu Ile
        35                  40                  45

Glu Met Leu Lys Glu Glu Val Met Ser Met Leu Leu Glu Glu Lys Pro
    50                  55                  60

Met Met Glu Lys Phe Asn Leu Ile Asp Asn Ile Glu Arg Leu Gly Ile
65                  70                  75                  80

Ser Tyr His Phe Gly Asp Lys Ile Glu Asp Gln Leu Gln Glu Tyr Tyr
                85                  90                  95

Asp Ala Cys Thr Asn Phe Glu Lys His Ala Glu Cys Asp Leu Ser Ile
            100                 105                 110

Ala Ala Leu Gln Phe Arg Leu Phe Arg Gln His Gly Phe Asn Ile Ser
        115                 120                 125

Cys Gly Ile Phe Asp Gly Phe Leu Asp Ala Asn Gly Lys Phe Lys Glu
    130                 135                 140

Ser Leu Cys Asn Asp Ile Lys Gly Leu Leu Ser Leu Tyr Glu Ala Ala
145                 150                 155                 160

His Val Arg Thr His Gly Asp Lys Ile Leu Glu Glu Ala Leu Phe Phe
                165                 170                 175

Thr Thr Thr His Leu Thr Arg Glu Ile Pro Asn Val Gly Ser Thr Leu
            180                 185                 190

Ala Lys Gln Val Lys His Ala Leu Glu Gln Pro Leu His Arg Gly Ile
        195                 200                 205

Pro Arg Tyr Glu Ala Tyr Cys Phe Ile Ser Met Tyr Glu Glu Asp Glu
    210                 215                 220

Ser Ser Asn Lys Leu Leu Leu Arg Leu Ala Lys Leu Asp Tyr His Leu
225                 230                 235                 240

Ser Gln Met Leu Asn Lys Gln Asp Leu Cys Glu Ile Ile Arg Trp Gly
                245                 250                 255

Lys Glu Leu Asp Ile Ile Ser Lys Val Pro Tyr Ala Arg Asp Arg Ile
            260                 265                 270

Val Glu Cys Tyr Phe Trp Ala Val Ala Thr Tyr Tyr Glu Pro Gln Tyr
        275                 280                 285

```
Ser Leu Ala Arg Met Thr Leu Thr Lys Ala Thr Val Phe Ala Gly Met
    290                 295                 300

Ile Asp Asp Thr Tyr Asp Ala Tyr Gly Thr Leu Asp Glu Leu Lys Ile
305                 310                 315                 320

Phe Thr Glu Ala Val Glu Arg Trp Asp Ser Ser Gly Ile Asp Gln Leu
                325                 330                 335

Ser Asp Tyr Met Lys Ala Ala Tyr Thr Leu Val Leu Asn Phe Asn Lys
            340                 345                 350

Glu Val Gly Glu Asp Leu Ala Lys Gln Arg Thr Tyr Ala Phe Asp
        355                 360                 365

Lys Tyr Ile Glu Glu Trp Lys Gln Tyr Ala Arg Thr Ser Phe Thr Gln
370                 375                 380

Ser Lys Trp Phe Leu Thr Asn Glu Leu Pro Ser Phe Ser Asp Tyr Leu
385                 390                 395                 400

Ser Asn Gly Met Val Thr Ser Thr Tyr Leu Leu Ser Ala Ala Thr
                405                 410                 415

Phe Leu Gly Met Asp Gly Ala Ser Glu Asp Val Ile Asn Trp Met Ser
                420                 425                 430

Thr Asn Pro Lys Leu Phe Val Ala Leu Thr Thr His Ala Arg Leu Ala
            435                 440                 445

Asn Asp Val Gly Ser His Lys Phe Glu Lys Glu Arg Gly Ser Gly Thr
        450                 455                 460

Ala Ile Glu Cys Tyr Met Lys Asp Tyr His Val Ser Glu Glu Ala
465                 470                 475                 480

Met Lys Lys Phe Glu Glu Met Cys Asp Asp Ala Trp Lys Val Met Asn
                485                 490                 495

Glu Glu Cys Leu Arg Ser Thr Thr Ile Pro Arg Glu Ile Leu Lys Val
            500                 505                 510

Ile Leu Asn Leu Ala Arg Thr Cys Glu Val Val Tyr Lys His Arg Gly
        515                 520                 525

Asp Gly Phe Thr Asp Gln Arg Arg Ile Glu Ala His Ile Asn Ala Met
    530                 535                 540

Leu Met Asp Ser Val Ser Ile
545                 550

<210> SEQ ID NO 43
<211> LENGTH: 552
<212> TYPE: PRT
<213> ORGANISM: Artificial Sequence
<220> FEATURE:
<223> OTHER INFORMATION: Synthetic polypeptide

<400> SEQUENCE: 43

Ala Ser Ala Gln Ala Ser Leu Pro Ser Asn Asn Arg Gln Glu Thr Val
1               5                   10                  15

Arg Pro Leu Ala Asp Phe Pro Glu Asn Ile Trp Ala Asp Arg Ile Ala
            20                  25                  30

Pro Phe Thr Leu Asp Lys Gln Glu Tyr Glu Met Cys Gln Arg Glu Ile
        35                  40                  45

Glu Met Leu Lys Ala Glu Val Ala Ser Met Leu Leu Ala Thr Gly Lys
    50                  55                  60

Thr Met Met Gln Arg Phe Asp Phe Ile Asp Lys Ile Glu Arg Leu Gly
65              70                  75                  80

Val Ser His His Phe Asp Ile Glu Ile Glu Asn Gln Leu Gln Glu Phe
                85                  90                  95
```

```
Phe Asn Val Tyr Thr Asn Leu Gly Glu Tyr Ser Ala Tyr Asp Leu Ser
            100                 105                 110

Ser Ala Ala Leu Gln Phe Arg Leu Phe Arg Gln His Gly Phe Asn Ile
            115                 120                 125

Ser Cys Gly Ile Phe Asp Gln Phe Ile Asp Ala Lys Gly Lys Phe Lys
            130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
                180                 185                 190

Leu Ala Lys Gln Val Lys Tyr Ala Leu Glu Gln Pro Leu His Lys Gly
            195                 200                 205

Ile Leu Arg Tyr Glu Ala Trp Arg Tyr Ile Ser Ile Tyr Glu Glu Asp
            210                 215                 220

Glu Ser Asn Asn Lys Leu Leu Arg Leu Ala Lys Leu Asp Tyr His
225                 230                 235                 240

Leu Leu Gln Met Ser Tyr Lys Gln Glu Leu Cys Glu Ile Thr Arg Trp
                245                 250                 255

Gly Lys Gly Leu Glu Ser Val Ser Asn Phe Pro Tyr Ala Arg Asp Arg
            260                 265                 270

Phe Val Glu Cys Tyr Phe Trp Ala Val Gly Thr Leu Tyr Glu Pro Gln
            275                 280                 285

Tyr Ser Leu Ala Arg Met Thr Phe Ala Lys Val Ala Ala Leu Ile Thr
            290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
                325                 330                 335

Leu Ser Asp Tyr Ile Arg Ala Ser Tyr Asn Thr Leu Leu Lys Phe Asn
            340                 345                 350

Lys Glu Val Gly Glu Asp Leu Ala Lys Lys Gln Arg Thr Tyr Ala Phe
            355                 360                 365

Asp Lys Tyr Ile Glu Asp Trp Lys Gln Tyr Met Arg Thr Ser Phe Thr
370                 375                 380

Gln Ser Lys Trp Phe Leu Thr Asn Glu Leu Pro Ser Phe Ala Asp Tyr
385                 390                 395                 400

Ile Ser Asn Gly Ala Ile Thr Ile Gly Ala Tyr Leu Ile Ala Ser Ala
                405                 410                 415

Gly Phe Leu Asp Met Asp Ser Ala Leu Glu Asp Val Ile Asn Trp Met
            420                 425                 430

Ser Thr Asn Pro Lys Leu Met Val Ala Tyr Ser Thr His Ser Arg Leu
            435                 440                 445

Ile Asn Asp Tyr Gly Gly His Lys Phe Asp Lys Glu Arg Gly Ser Val
            450                 455                 460

Thr Ala Leu Asp Cys Tyr Met Lys Asp Tyr Ser Val Ser Glu Glu Glu
465                 470                 475                 480

Ala Ala Lys Lys Phe Arg Glu Met Cys Glu Asp Asn Trp Lys Val Met
                485                 490                 495

Asn Glu Glu Cys Leu Arg Pro Thr Thr Ile Pro Arg Asp Gly Leu Lys
            500                 505                 510

Met Leu Leu Asn Ile Ala Arg Val Gly Glu Thr Val Tyr Lys His Arg
```

```
                    515                 520                 525
Ile Asp Gly Phe Thr Gln Pro His Ala Ile Glu Glu His Ile Arg Ala
    530                 535                 540

Met Leu Val Asp Phe Met Ser Ile
545             550

<210> SEQ ID NO 44
<211> LENGTH: 551
<212> TYPE: PRT
<213> ORGANISM: Artificial Sequence
<220> FEATURE:
<223> OTHER INFORMATION: Synthetic polypeptide

<400> SEQUENCE: 44

Ala Ser Thr Glu Ile Ala Val Pro Leu Asn Asn Gln His Glu Ser Val
1               5                   10                  15

Arg Gln Leu Ala Asp Phe Pro Glu Asn Ile Trp Ala Asp Arg Val Ala
                20                  25                  30

Ser Phe Thr Leu Asp Lys Gln Gly His Asp Met Cys Ala Lys Glu Ile
            35                  40                  45

Glu Met Leu Lys Glu Val Met Ser Met Leu Leu Glu Glu Lys Pro
50                  55                  60

Met Met Glu Lys Phe Asn Leu Ile Asp Asn Ile Glu Arg Leu Gly Ile
65                  70                  75                  80

Ser Tyr His Phe Gly Asp Lys Ile Glu Asp Gln Leu Gln Glu Tyr Tyr
                85                  90                  95

Asp Ala Cys Thr Asn Phe Glu Lys His Ala Glu Cys Asp Leu Ser Ile
            100                 105                 110

Ala Ala Leu Gln Phe Arg Leu Phe Arg Gln His Gly Phe Asn Ile Ser
        115                 120                 125

Cys Gly Ile Phe Asp Gly Phe Leu Asp Ala Asn Gly Lys Phe Lys Glu
    130                 135                 140

Ser Leu Cys Asn Asp Ile Lys Gly Leu Leu Ser Leu Tyr Glu Ala Ala
145                 150                 155                 160

His Val Arg Thr His Gly Asp Lys Ile Leu Glu Glu Ala Leu Phe Phe
                165                 170                 175

Thr Thr Thr His Leu Thr Arg Glu Ile Pro Asn Val Gly Ser Thr Leu
            180                 185                 190

Ala Lys Gln Val Lys Tyr Ala Leu Glu Gln Pro Leu His Lys Gly Ile
        195                 200                 205

Pro Arg Tyr Glu Ala Trp Arg Tyr Ile Ser Ile Tyr Glu Glu Asp Glu
    210                 215                 220

Ser Asn Asn Lys Leu Leu Leu Arg Leu Ala Lys Leu Asp Tyr His Leu
225                 230                 235                 240

Leu Gln Met Ser Tyr Lys Arg Glu Leu Ser Glu Ile Ile Arg Trp Gly
                245                 250                 255

Lys Glu Leu Asp Ile Ile Ser Lys Val Pro Tyr Ala Arg Asp Arg Ile
            260                 265                 270

Val Glu Cys Tyr Phe Trp Ala Val Ala Thr Tyr Tyr Glu Pro Gln Tyr
        275                 280                 285

Ser Leu Ala Arg Met Thr Leu Thr Lys Ala Thr Val Phe Ala Gly Met
    290                 295                 300

Ile Asp Asp Thr Tyr Asp Ala Tyr Gly Thr Leu Asp Glu Leu Lys Ile
305                 310                 315                 320

Phe Thr Glu Ala Val Glu Arg Trp Asp Ser Ser Gly Ile Asp Gln Leu
```

325                 330                 335
Ser Asp Tyr Met Lys Ala Ala Tyr Thr Leu Val Leu Asn Phe Asn Lys
                340                 345                 350
Glu Val Gly Glu Asp Leu Ala Lys Lys Gln Arg Thr Tyr Ala Phe Asp
            355                 360                 365
Lys Tyr Ile Glu Glu Trp Lys Gln Tyr Ala Arg Thr Ser Phe Thr Gln
        370                 375                 380
Ser Lys Trp Phe Leu Thr Asn Glu Leu Pro Ser Phe Ser Asp Tyr Leu
385                 390                 395                 400
Ser Asn Gly Met Val Thr Ser Thr Tyr Leu Leu Ser Ala Ala Thr
                405                 410                 415
Phe Leu Gly Met Asp Gly Ala Ser Glu Asp Val Ile Asn Trp Met Ser
                420                 425                 430
Thr Asn Pro Lys Leu Phe Val Ala Leu Thr Thr His Ala Arg Leu Ala
                435                 440                 445
Asn Asp Val Gly Ser His Lys Phe Glu Lys Glu Arg Gly Ser Ser Thr
450                 455                 460
Ala Ile Glu Cys Tyr Met Lys Asp Tyr His Val Ser Glu Glu Glu Ala
465                 470                 475                 480
Met Glu Lys Phe Glu Glu Met Cys Asp Asp Ala Trp Lys Val Met Asn
                485                 490                 495
Glu Glu Cys Leu Arg Ser Thr Thr Ile Pro Arg Glu Ile Leu Lys Val
                500                 505                 510
Ile Leu Asn Leu Ala Arg Thr Cys Glu Val Val Tyr Lys His Arg Gly
                515                 520                 525
Asp Gly Phe Thr Asp Gln Arg Arg Ile Glu Ala His Ile Asn Ala Met
                530                 535                 540
Leu Met Asp Ser Val Ser Ile
545                 550

<210> SEQ ID NO 45
<211> LENGTH: 551
<212> TYPE: PRT
<213> ORGANISM: Artificial Sequence
<220> FEATURE:
<223> OTHER INFORMATION: Synthetic polypeptide

<400> SEQUENCE: 45

Ala Ser Thr Glu Ile Ala Val Pro Leu Asn Asn Gln His Glu Ser Val
1               5                   10                  15
Arg Gln Leu Ala Asp Phe Pro Glu Asn Ile Trp Ala Asp Arg Val Ala
                20                  25                  30
Ser Phe Thr Leu Asp Lys Gln Gly His Asp Met Cys Ala Lys Glu Ile
            35                  40                  45
Glu Met Leu Lys Glu Glu Val Met Ser Met Leu Leu Glu Glu Lys Pro
        50                  55                  60
Met Met Glu Lys Phe Asn Leu Ile Asp Asn Ile Glu Arg Leu Gly Ile
65                  70                  75                  80
Ser Tyr His Phe Gly Asp Lys Ile Glu Asp Gln Leu Gln Glu Tyr Tyr
                85                  90                  95
Asp Ala Cys Thr Asn Phe Glu Lys His Ala Glu Cys Asp Leu Ser Ile
                100                 105                 110
Ala Ala Leu Gln Phe Arg Leu Phe Arg Gln His Gly Phe Asn Ile Ser
            115                 120                 125
Cys Gly Ile Phe Asp Gly Phe Leu Asp Ala Asn Gly Lys Phe Lys Glu

```
                130             135             140
Ser Leu Cys Asn Asp Ile Lys Gly Leu Leu Ser Leu Tyr Glu Ala Ala
145                 150                 155                 160

His Val Arg Thr His Gly Asp Lys Ile Leu Glu Glu Ala Leu Phe Phe
                165                 170                 175

Thr Thr Thr His Leu Thr Arg Glu Ile Pro Asn Val Gly Ser Thr Leu
            180                 185                 190

Ala Lys Gln Val Lys Tyr Ala Leu Glu Gln Pro Leu His Lys Gly Ile
        195                 200                 205

Pro Arg Tyr Glu Ala Trp Arg Tyr Ile Ser Ile Tyr Glu Glu Asp Glu
    210                 215                 220

Ser Asn Asn Lys Leu Leu Leu Arg Leu Ala Lys Leu Asp Tyr His Leu
225                 230                 235                 240

Leu Gln Met Ser Tyr Lys Arg Glu Leu Ser Glu Ile Ile Arg Trp Gly
                245                 250                 255

Lys Glu Leu Asp Ile Ile Ser Lys Val Pro Tyr Ala Arg Asp Arg Ile
            260                 265                 270

Val Glu Cys Tyr Phe Trp Ala Val Ala Thr Tyr Tyr Glu Pro Gln Tyr
        275                 280                 285

Ser Leu Ala Arg Met Thr Leu Thr Lys Ala Thr Val Phe Ala Gly Met
    290                 295                 300

Ile Asp Asp Thr Tyr Asp Ala Tyr Gly Thr Leu Asp Glu Leu Lys Ile
305                 310                 315                 320

Phe Thr Glu Ala Val Glu Arg Trp Asp Ser Ser Gly Ile Asp Gln Leu
                325                 330                 335

Ser Asp Tyr Met Lys Ala Ala Tyr Thr Leu Val Leu Asn Phe Asn Lys
            340                 345                 350

Glu Val Gly Glu Asp Leu Ala Lys Lys Gln Arg Thr Tyr Ala Phe Asp
        355                 360                 365

Lys Tyr Ile Glu Glu Trp Lys Gln Tyr Ala Arg Thr Ser Phe Thr Gln
    370                 375                 380

Ser Lys Trp Phe Leu Thr Asn Glu Leu Pro Ser Phe Ala Asp Tyr Leu
385                 390                 395                 400

Ser Asn Gly Met Val Thr Ser Thr Tyr Tyr Leu Leu Ser Ala Ala Ala
                405                 410                 415

Leu Leu Asp Met Asp Ser Ala Leu Glu Asp Val Ile Asn Trp Met Ser
            420                 425                 430

Thr Asn Pro Lys Phe Phe Val Ala Leu Thr Thr His Ala Arg Leu Thr
        435                 440                 445

Asn Asp Val Gly Ser His Lys Phe Glu Lys Glu Arg Gly Ser Gly Thr
    450                 455                 460

Ala Ile Glu Cys Tyr Met Lys Asp Tyr His Val Ser Glu Glu Glu Ala
465                 470                 475                 480

Met Lys Lys Phe Glu Glu Met Cys Asp Asp Ala Trp Lys Val Met Asn
                485                 490                 495

Glu Glu Cys Leu Arg Ser Thr Thr Ile Pro Arg Glu Ile Leu Lys Val
            500                 505                 510

Ile Leu Asn Leu Ala Arg Thr Cys Glu Val Val Tyr Lys His Arg Gly
        515                 520                 525

Asp Gly Phe Thr Asp Gln Arg Arg Ile Glu Ala His Ile Asn Ala Met
    530                 535                 540

Leu Met Asp Ser Val Ser Ile
545                 550
```

<210> SEQ ID NO 46
<211> LENGTH: 552
<212> TYPE: PRT
<213> ORGANISM: Artificial Sequence
<220> FEATURE:
<223> OTHER INFORMATION: Synthetic polypeptide

<400> SEQUENCE: 46

```
Ala Ser Ala Gln Ala Ser Leu Pro Ser Asn Asn Arg Gln Glu Thr Val
1               5                   10                  15

Arg Pro Leu Ala Asp Phe Pro Glu Asn Ile Trp Ala Asp Arg Ile Ala
            20                  25                  30

Pro Phe Thr Leu Asp Lys Gln Glu Tyr Glu Met Cys Gln Arg Glu Ile
        35                  40                  45

Glu Met Leu Lys Ala Glu Val Ala Ser Met Leu Leu Ala Thr Gly Lys
    50                  55                  60

Thr Met Met Gln Arg Phe Asp Phe Ile Asp Lys Ile Glu Arg Leu Gly
65                  70                  75                  80

Val Ser His His Phe Asp Ile Glu Ile Glu Asn Gln Leu Gln Glu Phe
                85                  90                  95

Phe Asn Val Tyr Thr Asn Leu Gly Glu Tyr Ser Ala Tyr Asp Leu Ser
            100                 105                 110

Ser Ala Ala Leu Gln Phe Arg Leu Phe Arg Gln His Gly Phe Asn Ile
        115                 120                 125

Ser Cys Gly Ile Phe Asp Gln Phe Ile Asp Ala Lys Gly Lys Phe Lys
    130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
            180                 185                 190

Leu Ala Lys Gln Val Lys Tyr Ala Leu Glu Gln Pro Leu His Lys Gly
        195                 200                 205

Ile Leu Arg Tyr Glu Ala Trp Arg Tyr Ile Ser Ile Tyr Glu Glu Asp
    210                 215                 220

Glu Ser Asn Asn Lys Leu Leu Arg Leu Ala Lys Leu Asp Tyr His
225                 230                 235                 240

Leu Leu Gln Met Ser Tyr Lys Gln Glu Leu Cys Glu Ile Thr Arg Trp
            245                 250                 255

Gly Lys Gly Leu Glu Ser Val Ser Asn Phe Pro Tyr Ala Arg Asp Arg
        260                 265                 270

Phe Val Glu Cys Tyr Phe Trp Ala Val Gly Thr Leu Tyr Glu Pro Gln
    275                 280                 285

Tyr Ser Leu Ala Arg Met Thr Phe Ala Lys Val Ala Ala Leu Ile Thr
    290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
                325                 330                 335

Leu Ser Asp Tyr Ile Arg Ala Ser Tyr Asn Thr Leu Leu Lys Phe Asn
            340                 345                 350

Lys Glu Val Gly Glu Asp Leu Ala Lys Lys Gln Arg Thr Tyr Ala Phe
        355                 360                 365
```

```
Asp Lys Tyr Ile Glu Asp Trp Lys Gln Tyr Met Arg Thr Ser Phe Thr
            370                 375                 380

Gln Ser Lys Trp Phe Leu Thr Asn Glu Leu Pro Ser Phe Ala Asp Tyr
385                 390                 395                 400

Ile Ser Asn Gly Ala Ile Thr Ile Gly Ala Tyr Leu Ile Ala Ser Ala
                405                 410                 415

Gly Phe Leu Asp Met Asp Ser Ala Leu Glu Asp Val Ile Asn Trp Met
                420                 425                 430

Ser Thr Asn Pro Lys Leu Met Val Ala Tyr Ser Thr His Ser Arg Leu
            435                 440                 445

Ile Asn Asp Tyr Gly Gly His Lys Phe Asp Lys Glu Arg Gly Thr Gly
        450                 455                 460

Thr Ala Ile Glu Cys Tyr Met Lys Asp His Asn Ile Ser Glu Glu
465                 470                 475                 480

Ala Ala Lys Lys Phe Arg Glu Met Ile Glu Asn Thr Trp Lys Val Met
                485                 490                 495

Asn Glu Glu Cys Leu Arg Pro Ile Pro Ile Pro Arg Asp Thr Leu Lys
                500                 505                 510

Met Leu Leu Asn Ile Ala Arg Val Gly Glu Thr Val Tyr Lys His Arg
            515                 520                 525

Ile Asp Gly Phe Thr Gln Pro His Ala Ile Glu Glu His Ile Arg Ala
530                 535                 540

Met Leu Val Asp Phe Met Ser Ile
545                 550

<210> SEQ ID NO 47
<211> LENGTH: 551
<212> TYPE: PRT
<213> ORGANISM: Artificial Sequence
<220> FEATURE:
<223> OTHER INFORMATION: Synthetic polypeptide

<400> SEQUENCE: 47

Ala Ser Thr Glu Ile Ala Val Pro Leu Asn Asn Gln His Glu Ser Val
1               5                   10                  15

Arg Gln Leu Ala Asp Phe Pro Glu Asn Ile Trp Ala Asp Arg Val Ala
            20                  25                  30

Ser Phe Thr Leu Asp Lys Gln Gly His Asp Met Cys Ala Lys Glu Ile
        35                  40                  45

Glu Met Leu Lys Glu Val Met Ser Met Leu Leu Glu Glu Lys Pro
    50                  55                  60

Met Met Glu Lys Phe Asn Leu Ile Asp Asn Ile Glu Arg Leu Gly Ile
65                  70                  75                  80

Ser Tyr His Phe Gly Asp Lys Ile Glu Asp Gln Leu Gln Glu Tyr Tyr
                85                  90                  95

Asp Ala Cys Thr Asn Phe Glu Lys His Ala Glu Cys Asp Leu Ser Ile
            100                 105                 110

Ala Ala Leu Gln Phe Arg Leu Phe Arg Gln His Gly Phe Asn Ile Ser
        115                 120                 125

Cys Gly Ile Phe Asp Gly Phe Leu Asp Ala Asn Gly Lys Phe Lys Glu
    130                 135                 140

Ser Leu Cys Asn Asp Ile Lys Gly Leu Leu Ser Leu Tyr Glu Ala Ala
145                 150                 155                 160

His Val Arg Thr His Gly Asp Lys Ile Leu Glu Glu Ala Leu Phe Phe
                165                 170                 175
```

Thr Thr Thr His Leu Thr Arg Glu Ile Pro Asn Val Gly Ser Thr Leu
            180                 185                 190

Ala Lys Gln Val Lys His Ala Leu Glu Gln Pro Leu His Arg Gly Ile
        195                 200                 205

Pro Arg Tyr Glu Ala Tyr Cys Phe Ile Ser Ile Tyr Glu Glu Asp Glu
    210                 215                 220

Ser Asn Asn Lys Leu Leu Leu Arg Leu Ala Lys Leu Asp Tyr His Leu
225                 230                 235                 240

Leu Gln Met Ser Tyr Lys Arg Glu Leu Ser Glu Ile Ile Arg Trp Gly
                245                 250                 255

Lys Glu Leu Asp Ile Ile Ser Lys Val Pro Tyr Ala Arg Asp Arg Ile
            260                 265                 270

Val Glu Cys Tyr Phe Trp Ala Val Ala Thr Tyr Tyr Glu Pro Gln Tyr
        275                 280                 285

Ser Leu Ala Arg Met Thr Leu Thr Lys Ala Thr Val Phe Ala Gly Met
    290                 295                 300

Ile Asp Asp Thr Tyr Asp Ala Tyr Gly Thr Leu Asp Glu Leu Lys Ile
305                 310                 315                 320

Phe Thr Glu Ala Val Glu Arg Trp Asp Ser Ser Gly Ile Asp Gln Leu
                325                 330                 335

Ser Asp Tyr Met Lys Ala Ala Tyr Thr Leu Val Leu Asn Phe Asn Lys
            340                 345                 350

Glu Val Gly Glu Asp Leu Ala Lys Lys Gln Arg Thr Tyr Ala Phe Asp
        355                 360                 365

Lys Tyr Ile Glu Glu Trp Lys Gln Tyr Ala Arg Thr Ser Phe Thr Gln
    370                 375                 380

Ser Lys Trp Phe Leu Thr Asn Glu Leu Pro Ser Phe Ser Asp Tyr Leu
385                 390                 395                 400

Ser Asn Gly Met Val Thr Ser Thr Tyr Tyr Leu Leu Ser Ala Ala Ala
                405                 410                 415

Phe Leu Asp Met Asp Ser Ala Ser Glu Asp Val Ile Asn Trp Met Ser
            420                 425                 430

Thr Asn Pro Lys Leu Phe Val Ala Leu Thr Thr His Ala Arg Leu Ala
        435                 440                 445

Asn Asp Val Gly Ser His Lys Phe Glu Lys Glu Arg Gly Ser Gly Thr
    450                 455                 460

Ala Ile Glu Cys Tyr Met Lys Asp Tyr Asn Val Ser Glu Glu Glu Ala
465                 470                 475                 480

Leu Lys Lys Phe Glu Glu Met Cys Glu Asp Thr Trp Lys Val Met Asn
                485                 490                 495

Glu Glu Cys Leu Arg Ser Thr Thr Ile Pro Arg Glu Ile Leu Lys Val
            500                 505                 510

Ile Leu Asn Leu Ala Arg Thr Cys Glu Val Val Tyr Lys His Arg Gly
        515                 520                 525

Asp Gly Phe Thr Asp Gln Arg Arg Ile Glu Ala His Ile Asn Ala Met
    530                 535                 540

Leu Met Asp Ser Val Ser Ile
545                 550

<210> SEQ ID NO 48
<211> LENGTH: 553
<212> TYPE: PRT
<213> ORGANISM: Artificial Sequence
<220> FEATURE:

<223> OTHER INFORMATION: Synthetic polypeptide

<400> SEQUENCE: 48

Ala Ser Ala Gln Ala Ser Leu Pro Ser Asn Arg Gln Glu Thr Val
1               5                   10                  15

Arg Pro Leu Ala Asp Phe Pro Glu Asn Ile Trp Ala Asp Arg Ile Ala
            20                  25                  30

Pro Phe Thr Leu Asp Lys Gln Glu Tyr Glu Met Cys Gln Arg Glu Ile
            35                  40                  45

Glu Met Leu Lys Ala Glu Val Ala Ser Met Leu Leu Ala Thr Gly Lys
        50                  55                  60

Thr Met Met Gln Arg Phe Asp Phe Ile Asp Lys Ile Glu Arg Leu Gly
65                  70                  75                  80

Val Ser His His Phe Asp Ile Glu Ile Glu Asn Gln Leu Gln Glu Phe
                85                  90                  95

Phe Asn Val Tyr Thr Asn Leu Gly Glu Tyr Ser Ala Tyr Asp Leu Ser
            100                 105                 110

Ser Ala Ala Leu Gln Phe Arg Leu Phe Arg Gln His Gly Phe Asn Ile
        115                 120                 125

Ser Cys Gly Ile Phe Asp Gln Phe Ile Asp Ala Lys Gly Lys Phe Lys
130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
            180                 185                 190

Leu Ala Lys Gln Val Lys Tyr Ala Leu Glu Gln Pro Leu His Lys Gly
        195                 200                 205

Ile Leu Arg Tyr Glu Ala Trp Arg Tyr Ile Ser Ile Tyr Glu Glu Asp
    210                 215                 220

Glu Ser Asn Asn Lys Leu Leu Arg Leu Ala Lys Leu Asp Tyr His
225                 230                 235                 240

Leu Leu Gln Met Ser Tyr Lys Gln Glu Leu Cys Glu Ile Thr Arg Trp
            245                 250                 255

Gly Lys Gly Leu Glu Ser Val Ser Asn Phe Pro Tyr Ala Arg Asp Arg
            260                 265                 270

Phe Val Glu Cys Tyr Phe Trp Ala Val Gly Thr Leu Tyr Glu Pro Gln
        275                 280                 285

Tyr Ser Leu Ala Arg Met Thr Phe Ala Lys Val Ala Ala Leu Ile Thr
    290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
            325                 330                 335

Leu Ser Asp Tyr Ile Arg Ala Ser Tyr Asn Thr Leu Leu Lys Phe Asn
        340                 345                 350

Lys Glu Val Gly Glu Asp Leu Ala Lys Lys Gln Arg Thr Tyr Ala Phe
    355                 360                 365

Asp Lys Tyr Ile Glu Asp Trp Lys Gln Tyr Met Arg Thr Asn Phe Ser
370                 375                 380

Gln Ser Arg Trp Phe Phe Thr Lys Glu Leu Pro Ser Phe Ala Asp Tyr
385                 390                 395                 400

```
Ile Asn Asn Gly Ala Ile Thr Ile Gly Ala Tyr Leu Val Ala Ser Ala
                405                 410                 415

Ala Phe Leu Tyr Met Asp Ser Ala Lys Glu Asp Val Ile Asn Trp Met
            420                 425                 430

Ser Thr Asn Pro Lys Leu Val Val Ala Tyr Ser Thr His Ser Arg Leu
        435                 440                 445

Ile Asn Asp Phe Gly Gly His Lys Phe Asp Lys Glu Arg Gly Ser Gly
    450                 455                 460

Thr Ala Leu Glu Cys Tyr Met Lys Asp Tyr Asn Val Ser Glu Glu Glu
465                 470                 475                 480

Ala Ala Asn Lys Phe Arg Glu Met Met Glu Asp Ala Trp Lys Val Met
                485                 490                 495

Asn Glu Asp Cys Leu Arg Pro Thr Ser Ile Pro Arg Asp Val Ser Lys
            500                 505                 510

Val Leu Leu Asn Val Ala Arg Ala Gly Glu Ile Val Tyr Lys His Arg
        515                 520                 525

Ile Asp Gly Phe Thr Glu Pro His Ile Ile Lys Asp His Ile Arg Ala
    530                 535                 540

Thr Leu Val Asp Phe Met Ala Ile Asn
545                 550

<210> SEQ ID NO 49
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 49

Ala Ser Ala Gln Ala Ser Leu Pro Ser Asn Asn Arg Gln Glu Thr Val
1               5                   10                  15

Arg Pro Leu Ala Asp Phe Pro Glu Asn Ile Trp Ala Asp Arg Ile Ala
            20                  25                  30

Pro Phe Thr Leu Asp Lys Gln Glu Tyr Glu Met Cys Gln Arg Glu Ile
        35                  40                  45

Glu Met Leu Lys Ala Glu Val Ala Ser Met Leu Leu Ala Thr Gly Lys
    50                  55                  60

Thr Met Met Gln Arg Phe Asp Phe Ile Asp Lys Ile Glu Arg Leu Gly
65                  70                  75                  80

Val Ser His His Phe Asp Ile Glu Ile Glu Asn Gln Leu Gln Glu Phe
                85                  90                  95

Phe Asn Val Tyr Thr Asn Leu Gly Glu Tyr Ser Ala Tyr Asp Leu Ser
            100                 105                 110

Ser Ala Ala Leu Gln Phe Arg Leu Phe Arg Gln His Gly Phe Asn Ile
        115                 120                 125

Ser Cys Gly Ile Phe Asp Gln Phe Ile Asp Ala Lys Gly Lys Phe Lys
    130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
            180                 185                 190

Leu Ala Lys Gln Val Lys Tyr Ala Leu Glu Gln Pro Leu His Lys Gly
        195                 200                 205
```

```
Ile Leu Arg Tyr Glu Ala Trp Arg Tyr Ile Ser Ile Tyr Glu Glu Asp
    210                 215                 220

Glu Ser Asn Asn Lys Leu Leu Arg Leu Ala Lys Leu Asp Tyr His
225                 230                 235                 240

Leu Leu Gln Met Ser Tyr Lys Gln Leu Cys Glu Ile Thr Arg Trp
                245                 250                 255

Gly Lys Gly Leu Glu Ser Val Ser Asn Phe Pro Tyr Ala Arg Asp Arg
                260                 265                 270

Phe Val Glu Cys Tyr Phe Trp Ala Val Gly Thr Leu Tyr Glu Pro Gln
                275                 280                 285

Tyr Ser Leu Ala Arg Met Thr Phe Ala Lys Val Ala Ala Leu Ile Thr
            290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
                325                 330                 335

Leu Ser Asp Tyr Ile Arg Ala Ser Tyr Asn Thr Leu Leu Lys Phe Asn
                340                 345                 350

Lys Glu Val Gly Glu Asp Leu Ala Lys Lys Gln Arg Thr Tyr Ala Phe
            355                 360                 365

Asp Lys Tyr Ile Glu Asp Trp Lys Gln Tyr Met Arg Thr Ser Phe Thr
370                 375                 380

Gln Ser Lys Trp Phe Leu Thr Asn Glu Leu Pro Ser Phe Ala Asp Tyr
385                 390                 395                 400

Ile Ser Asn Gly Ala Ile Thr Ile Gly Ala Tyr Leu Ile Ala Ser Ala
                405                 410                 415

Gly Phe Leu Asp Met Asp Ser Ala Leu Glu Asp Val Ile Asn Trp Met
                420                 425                 430

Ser Thr Asn Pro Lys Leu Met Val Ala Tyr Ser Thr His Ser Arg Leu
            435                 440                 445

Ile Asn Asp Tyr Gly Gly His Lys Phe Asp Lys Glu Arg Gly Ser Val
450                 455                 460

Thr Ala Leu Asp Cys Tyr Met Lys Asp Tyr Ser Val Ser Glu Glu Glu
465                 470                 475                 480

Ala Ala Lys Lys Phe Arg Glu Met Ile Glu Asn Thr Trp Lys Val Met
                485                 490                 495

Asn Glu Glu Cys Leu Arg Pro Ile Pro Ile Pro Arg Asp Thr Leu Lys
                500                 505                 510

Met Leu Leu Asn Ile Ala Arg Val Gly Glu Thr Val Tyr Lys His Arg
            515                 520                 525

Ile Asp Gly Phe Thr Glu Pro His Ile Ile Lys Asp His Ile Arg Ala
530                 535                 540

Met Leu Val Asp Phe Met Ala Ile Asn
545                 550
```

<210> SEQ ID NO 50
<211> LENGTH: 552
<212> TYPE: PRT
<213> ORGANISM: Artificial Sequence
<220> FEATURE:
<223> OTHER INFORMATION: Synthetic polypeptide

<400> SEQUENCE: 50

```
Ala Ser Ala Gln Ala Ser Leu Pro Ser Asn Asn Arg Gln Glu Thr Val
1               5                   10                  15
```

```
Arg Pro Leu Ala Asp Phe Pro Glu Asn Ile Trp Ala Asp Arg Ile Ala
                 20                  25                  30

Pro Phe Thr Leu Asp Lys Gln Glu Tyr Glu Met Cys Gln Arg Glu Ile
             35                  40                  45

Glu Met Leu Lys Ala Glu Val Ala Ser Met Leu Leu Ala Thr Gly Lys
 50                  55                  60

Thr Met Met Gln Arg Phe Asp Phe Ile Asp Lys Ile Glu Arg Leu Gly
65                   70                  75                  80

Val Ser His His Phe Asp Ile Glu Ile Glu Asn Gln Leu Gln Glu Phe
                 85                  90                  95

Phe Asn Val Tyr Thr Asn Leu Gly Glu Tyr Ser Ala Tyr Asp Leu Ser
             100                 105                 110

Ser Ala Ala Leu Gln Phe Arg Leu Phe Arg Gln His Gly Phe Asn Ile
         115                 120                 125

Ser Cys Gly Ile Phe Asp Gln Phe Ile Asp Ala Lys Gly Lys Phe Lys
    130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
            180                 185                 190

Leu Ala Lys Gln Val Lys Tyr Ala Leu Glu Gln Pro Leu His Lys Gly
        195                 200                 205

Ile Leu Arg Tyr Glu Ala Trp Arg Tyr Ile Ser Ile Tyr Glu Glu Asp
    210                 215                 220

Glu Ser Asn Asn Lys Leu Leu Arg Leu Ala Lys Leu Asp Tyr His
225                 230                 235                 240

Leu Leu Gln Met Ser Tyr Lys Gln Glu Leu Cys Glu Ile Thr Arg Trp
                245                 250                 255

Gly Lys Gly Leu Glu Ser Val Ser Asn Phe Pro Tyr Ala Arg Asp Arg
            260                 265                 270

Phe Val Glu Cys Tyr Phe Trp Ala Val Gly Thr Leu Tyr Glu Pro Gln
        275                 280                 285

Tyr Ser Leu Ala Arg Met Thr Phe Ala Lys Val Ala Ala Leu Ile Thr
    290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
                325                 330                 335

Leu Ser Asp Tyr Ile Arg Ala Ser Tyr Asn Thr Leu Leu Lys Phe Asn
            340                 345                 350

Lys Glu Val Gly Glu Asp Leu Ala Lys Lys Gln Arg Thr Tyr Ala Phe
        355                 360                 365

Asp Lys Tyr Ile Glu Asp Trp Lys Gln Tyr Met Arg Thr Asn Phe Ser
    370                 375                 380

Gln Ser Arg Trp Phe Thr Lys Glu Leu Pro Ser Phe Ala Asp Tyr
385                 390                 395                 400

Ile Asn Asn Gly Ala Ile Thr Ile Gly Ala Tyr Leu Val Ala Ser Ala
                405                 410                 415

Ala Phe Leu Tyr Met Asp Ser Ala Lys Glu Asp Val Ile Asn Trp Met
            420                 425                 430

Ser Thr Asn Pro Lys Leu Val Val Ala Tyr Ser Thr His Ser Arg Leu
```

```
              435                 440                 445
Ile Asn Asp Phe Gly Gly His Lys Phe Asp Lys Glu Arg Gly Ser Val
450                 455                 460

Thr Ala Leu Asp Cys Tyr Met Lys Asp Tyr Ser Val Ser Glu Glu Glu
465                 470                 475                 480

Ala Ala Lys Lys Phe Arg Glu Met Cys Glu Asp Asn Trp Lys Val Met
                485                 490                 495

Asn Glu Glu Cys Leu Arg Pro Thr Thr Ile Pro Arg Asp Gly Leu Lys
                500                 505                 510

Met Leu Leu Asn Ile Ala Arg Val Gly Glu Thr Val Tyr Lys His Arg
                515                 520                 525

Ile Asp Gly Phe Thr Gln Pro His Ala Ile Glu His Ile Arg Ala
530                 535                 540

Met Leu Val Asp Phe Met Ser Ile
545                 550

<210> SEQ ID NO 51
<211> LENGTH: 553
<212> TYPE: PRT
<213> ORGANISM: Artificial Sequence
<220> FEATURE:
<223> OTHER INFORMATION: Synthetic polypeptide

<400> SEQUENCE: 51

Ala Ser Ala Gln Ala Ser Leu Pro Ser Asn Asn Arg Gln Glu Thr Val
1               5                   10                  15

Arg Pro Leu Ala Asp Phe Pro Glu Asn Ile Trp Ala Asp Arg Ile Ala
                20                  25                  30

Pro Phe Thr Leu Asp Lys Gln Glu Tyr Glu Met Cys Gln Arg Glu Ile
                35                  40                  45

Glu Met Leu Lys Ala Glu Val Ala Ser Met Leu Leu Ala Thr Gly Lys
50                  55                  60

Thr Met Met Gln Arg Phe Asp Phe Ile Asp Lys Ile Glu Arg Leu Gly
65                  70                  75                  80

Val Ser His His Phe Asp Ile Glu Ile Glu Asn Gln Leu Gln Glu Phe
                85                  90                  95

Phe Asn Val Tyr Thr Asn Leu Gly Glu Tyr Ser Ala Tyr Asp Leu Ser
                100                 105                 110

Ser Ala Ala Leu Gln Phe Arg Leu Phe Arg Gln His Gly Phe Asn Ile
                115                 120                 125

Ser Cys Gly Ile Phe Asp Gln Phe Ile Asp Ala Lys Gly Lys Phe Lys
                130                 135                 140

Glu Ser Leu Cys Asn Asp Ile Arg Gly Leu Leu Ser Leu Tyr Glu Ala
145                 150                 155                 160

Ala His Val Arg Thr His Gly Asp Lys Ile Leu Glu Glu Ala Leu Ala
                165                 170                 175

Phe Thr Thr Thr His Met Thr Ser Gly Gly Pro His Leu Asp Ser Ser
                180                 185                 190

Leu Ala Lys Gln Val Lys Tyr Ala Leu Glu Gln Pro Leu His Lys Gly
                195                 200                 205

Ile Leu Arg Tyr Glu Ala Trp Arg Tyr Ile Ser Ile Tyr Glu Glu Asp
                210                 215                 220

Glu Ser Asn Asn Lys Leu Leu Leu Arg Leu Ala Lys Leu Asp Tyr His
225                 230                 235                 240

Leu Leu Gln Met Ser Tyr Lys Gln Glu Leu Cys Glu Ile Thr Arg Trp
```

```
                        245                 250                 255
Gly Lys Gly Leu Glu Ser Val Ser Asn Phe Pro Tyr Ala Arg Asp Arg
            260                 265                 270

Phe Val Glu Cys Tyr Phe Trp Ala Val Gly Thr Leu Tyr Glu Pro Gln
            275                 280                 285

Tyr Ser Leu Ala Arg Met Thr Phe Ala Lys Val Ala Ala Leu Ile Thr
            290                 295                 300

Met Ile Asp Asp Ile Tyr Asp Ala Tyr Gly Thr Leu Asp Glu Leu Gln
305                 310                 315                 320

Ile Leu Thr Asp Ser Ala Glu Arg Trp Asp Gly Ser Gly Val Asp Gln
            325                 330                 335

Leu Ser Asp Tyr Ile Arg Ala Ser Tyr Asn Thr Leu Leu Lys Phe Asn
            340                 345                 350

Lys Glu Val Gly Glu Asp Leu Ala Lys Lys Gln Arg Thr Tyr Ala Phe
            355                 360                 365

Asp Lys Tyr Ile Glu Asp Trp Lys Gln Tyr Met Arg Thr Asn Phe Ser
            370                 375                 380

Gln Ser Arg Trp Phe Phe Thr Lys Glu Leu Pro Ser Phe Ala Asp Tyr
385                 390                 395                 400

Ile Asn Asn Gly Ala Ile Thr Ile Gly Ala Tyr Leu Val Ala Ser Ala
            405                 410                 415

Ala Phe Leu Tyr Met Asp Ser Ala Lys Glu Asp Val Ile Asn Trp Met
            420                 425                 430

Ser Thr Asn Pro Lys Leu Val Val Ala Tyr Ser Thr His Ser Arg Leu
            435                 440                 445

Ile Asn Asp Phe Gly Gly His Lys Phe Asp Lys Glu Arg Gly Ser Val
            450                 455                 460

Thr Ala Leu Asp Cys Tyr Met Lys Asp Tyr Ser Val Ser Glu Glu Glu
465                 470                 475                 480

Ala Ala Lys Lys Phe Arg Glu Met Ile Glu Asn Thr Trp Lys Val Met
            485                 490                 495

Asn Glu Glu Cys Leu Arg Pro Ile Pro Ile Pro Arg Asp Thr Leu Lys
            500                 505                 510

Met Leu Leu Asn Ile Ala Arg Val Gly Glu Thr Val Tyr Lys His Arg
            515                 520                 525

Ile Asp Gly Phe Thr Glu Pro His Ile Ile Lys Asp His Ile Arg Ala
            530                 535                 540

Met Leu Val Asp Phe Met Ala Ile Asn
545                 550

<210> SEQ ID NO 52
<211> LENGTH: 355
<212> TYPE: PRT
<213> ORGANISM: Artificial Sequence
<220> FEATURE:
<223> OTHER INFORMATION: Synthetic polypeptide

<400> SEQUENCE: 52

Tyr Glu Arg Glu Ile Glu Met Leu Lys Ala Glu Val Glu Ser Met Leu
1               5                   10                  15

Leu Ala Thr Gly Lys Thr Met Met Gln Arg Phe Asp Phe Ile Asp Lys
            20                  25                  30

Ile Glu Arg Leu Gly Val Ser His His Phe Asp Ile Glu Ile Glu Asn
            35                  40                  45

Gln Leu Gln Glu Phe Phe Asn Val Tyr Thr Asn Phe Gly Glu Tyr Ser
```

```
            50                  55                  60
Ala Tyr Asp Leu Ser Ser Ala Ala Leu Gln Phe Lys Gln Trp Cys Asp
65                  70                  75                  80

His Asn Arg Ser Leu Ser Cys Ser Ile Thr Arg Gly Leu Leu Ser Leu
                85                  90                  95

Tyr Glu Ala Ala His Val Arg Thr His Gly Asp Lys Ile Leu Glu Glu
            100                 105                 110

Ala Leu His Leu Thr Ser Gly Glu Ser His Leu Asp Ser Thr Leu Ala
        115                 120                 125

Lys Gln Val Lys Cys Ala Leu Glu Gln Pro Leu His Lys Gly Ile Pro
    130                 135                 140

Arg Tyr Glu Ala Trp Arg Tyr Ile Ser Ile Tyr Glu Glu Asp Glu Ser
145                 150                 155                 160

His Asn Lys Leu Leu Leu Arg Leu Ala Lys Leu Asp Tyr His Phe Leu
                165                 170                 175

Gln Ile Ser Tyr Arg Gln Asp Leu Cys Glu Ile Ile Arg Trp Asp Ser
            180                 185                 190

Ser Gly Val Asp Gln Leu Ser Asp Tyr Ile Arg Ala Val Gly Glu Glu
        195                 200                 205

Leu Ala Lys Lys Gln Arg Thr Tyr Ala Phe Gly Thr Phe Leu Gly Met
    210                 215                 220

Asp Gly Ala Ser Glu Asp Val Ile Asn Trp Met Ser Thr Ile Pro Lys
225                 230                 235                 240

Leu Met Phe Ala Cys Ser Thr His Ala Arg Leu Ile Asn Asp Phe Gly
                245                 250                 255

Gly His Lys Phe Asp Lys Glu Arg Gly Thr Gly Thr Ala Leu Glu Cys
            260                 265                 270

Tyr Met Lys Asp Tyr Asn Val Ser Glu Glu Ala Ala Asn Lys Phe
        275                 280                 285

Arg Glu Met Met Glu Asp Ala Trp Lys Val Met Asn Glu Glu Cys Leu
    290                 295                 300

Arg Pro Thr Thr Ile Pro Arg Glu Ile Leu Lys Met Leu Leu Asn Ile
305                 310                 315                 320

Val Arg Val Gly Glu Thr Thr Asn Lys His Arg Ile Asp Gly Phe Thr
                325                 330                 335

Gln Pro His Ala Ile Glu Glu His Ile Arg Ala Met Leu Val Asp Phe
            340                 345                 350

Met Ser Val
        355

<210> SEQ ID NO 53
<211> LENGTH: 5718
<212> TYPE: DNA
<213> ORGANISM: Artificial Sequence
<220> FEATURE:
<223> OTHER INFORMATION: Synthetic polynucleotide

<400> SEQUENCE: 53
agggttcgca agtcctgttt ctatgccttt ctcttagtaa ttcacgaaat aaacctatgg      60
tttacgaaat gatccacgaa atcatgttta ttatttacat caacatatcg cgaaaattca     120
tgtcatgtcc acattaacat cattgcagag caacaattca ttttcataga gaaatttgct     180
actatcaccc actagtacta ccattggtac tactactttt gaattgtact accgctgggc     240
gttattaggt gtgaaaccac gaaaagttca ccataacttc gaataaagtc gcggaaaaaa     300
```

-continued

```
gtaaacagct attgctactc aaatgaggtt tgcagaagct tgttgaagca tgatgaagcg    360
ttctaaacgc actattcatc attaaatatt taaagctcat aaaattgtat tcaattccta    420
ttctaaatgg cttttatttc tattacaact attagctcga tgcacgagcg caacgctcac    480
aacgctcgtc caacgccggc ggacctacgg attagagccg ccgagcgggt gacagccctc    540
cgaaggaaga ctctcctccg tgcgtcctcg tcttcaccgg tcgcgttcct gaaacgcaga    600
tgtgcctcgc gccgcactgc tccgaacaat aaagattcta caatactagc ttttatggtt    660
atgaagagga aaaattggca gtaacctggc cccacaaacc ttcaaatgaa cgaatcaaat    720
taacaaccat aggatgataa tgcgattagt tttttagcct tatttctggg gtaattaatc    780
agcgaagcga tgattttga tctattaaca gatatataaa tgcaaaaact gcataaccac    840
tttaactaat acttcaaca ttttcggttt gtattacttc ttattcaaat gtaataaaag    900
tatcaacaaa aaattgttaa tatacctcta tactttaacg tcaaggagaa aaaactataa    960
tggctgcaga ccaattggtg aagactgaag tcaccaagaa gtcttttact gctcctgtac   1020
aaaaggcttc tacaccagtt ttaaccaata aaacagtcat ttctggatcg aaagtcaaaa   1080
gtttatcatc tgcgcaatcg agctcatcag gaccttcatc atctagtgag gaagatgatt   1140
cccgcgatat tgaaagcttg gataagaaaa tacgtccttt agaagaatta gaagcattat   1200
taagtagtgg aaatacaaaa caattgaaga acaaagaggt cgctgccttg gttattcacg   1260
gtaagttacc tttgtacgct ttggagaaaa aattaggtga tactacgaga gcggttgcgg   1320
tacgtaggaa ggctctttca attttggcag aagctcctgt attagcatct gatcgtttac   1380
catataaaaa ttatgactac daccgcgtat ttggcgcttg ttgtgaaaat gttataggtt   1440
acatgccttt gcccgttggt gttataggcc ccttggttat cgatggtaca tcttatcata   1500
taccaatggc aactacagag ggttgtttgg tagcttctgc catgcgtggc tgtaaggcaa   1560
tcaatgctgg cggtggtgca acaactgttt taactaagga tggtatgaca agaggcccag   1620
tagtccgttt cccaactttg aaaagatctg gtgcctgtaa gatatggtta gactcagaag   1680
agggacaaaa cgcaattaaa aaagctttta actctacatc aagatttgca cgtctgcaac   1740
atattcaaac ttgtctagca ggagatttac tcttcatgag atttagaaca actactggtg   1800
acgcaatggg tatgaatatg atttctaagg gtgtcgaata ctcattaaag caaatggtag   1860
aagagtatgg ctgggaagat atggaggttg tctccgtttc tggtaactac tgtaccgaca   1920
aaaaaccagc tgccatcaac tggatcgaag gtcgtggtaa gagtgtcgtc gcagaagcta   1980
ctattcctgg tgatgttgtc agaaaagtgt taaaaagtga tgtttccgca ttggttgagt   2040
tgaacattgc taagaatttg gttggatctg caatggctgg gtctgttggt ggatttaacg   2100
cacatgcagc taatttagtg acagctgttt tcttggcatt aggacaagat cctgcacaaa   2160
atgtcgaaag ttccaactgt ataacattga tgaaagaagt ggacggtgat ttgagaattt   2220
ccgtatccat gccatccatc gaagtaggta ccatcggtgg tggtactgtt ctagaaccac   2280
aaggtgccat gttggactta ttaggtgtaa gaggcccaca tgctaccgct cctggtacca   2340
acgcacgtca attagcaaga atagttgcct gtgccgtctt ggcaggtgaa ttatccttat   2400
gtgctgccct agcagccggc catttggttc aaagttatat gacccacaac aggaaacctg   2460
ctgaaccaac aaaacctaac aatttggacg ccactgatat aaatcgtttg aaagatgggt   2520
ccgtcacctg cattaaatcc taagctagct aagatccgct ctaaccgaaa aggaaggagt   2580
tagacaacct gaagtctagg tccctatta ttttttttata gttatgttag tattaagaac   2640
gttatttata tttcaaattt ttctttttt tctgtacaga cgcgtgtacg catgtaacat   2700
```

```
tatactgaaa accttgcttg agaaggtttt gggacgctcg aagatccagc tcggccgtac   2760
gaaaatcgtt attgtcttga aggtgaaatt tctactctta ttaatggtga acgttaagct   2820
gatgctatga tggaagctga ttggtcttaa cttgcttgtc atcttgctaa tggtcatatg   2880
gctcgtgtta ttacttaagt tatttgtact cgttttgaac gtaatgctaa tgatcatctt   2940
atggaataat agtgaacggc cgagctggat cttcgagcgt cccaaaacct tctcaagcaa   3000
ggttttcagt ataatgttac atgcgtacac gcgtctgtac agaaaaaaaa gaaaaatttg   3060
aaatataaat aacgttctta atactaacat aactataaaa aaataaatag ggacctagac   3120
ttcaggttgt ctaactcctt ccttttcggt tagagcggat cttagctagc ttaggattta   3180
atgcaggtga cggacccatc tttcaaacga tttatatcag tggcgtccaa attgttaggt   3240
tttgttggtt cagcaggttt cctgttgtgg gtcatataac tttgaaccaa atggccggct   3300
gctagggcag cacataagga taattcacct gccaagacgg cacaggcaac tattcttgct   3360
aattgacgtg cgttggtacc aggagcggta gcatgtgggc ctcttacacc taataagtcc   3420
aacatggcac cttgtggttc tagaacagta ccaccaccga tggtacctac ttcgatggat   3480
ggcatggata cggaaattct caaatcaccg tccacttctt tcatcaatgt tatacagttg   3540
gaactttcga cattttgtgc aggatcttgt cctaatgcca agaaaacagc tgtcactaaa   3600
ttagctgcat gtgcgttaaa tccaccaaca gacccagcca ttgcagatcc aaccaaattc   3660
ttagcaatgt tcaactcaac caatgcggaa acatcacttt ttaacacttt tctgacaaca   3720
tcaccaggaa tagtagcttc tgcgacgaca ctcttaccac gaccttcgat ccagttgatg   3780
gcagctggtt ttttgtcggt acagtagtta ccagaaacgg agacaacctc catatcttcc   3840
cagccatact cttctaccat ttgctttaat gagtattcga cacccttaga aatcatattc   3900
atacccattg cgtcaccagt agttgttcta aatctcatga agagtaaatc tcctgctaga   3960
caagtttgaa tatgttgcag acgtgcaaat cttgatgtag agttaaaagc ttttttaatt   4020
gcgttttgtc cctcttctga gtctaaccat atcttacagg caccagatct tttcaaagtt   4080
gggaaacgga ctactgggcc tcttgtcata ccatccttag ttaaaacagt tgttgcacca   4140
ccgccagcat tgattgcctt acagccacgc atggcagaag ctaccaaaca accctctgta   4200
gttgccattg gtatatgata agatgtacca tcgataacca aggggcctat aacaccaacg   4260
ggcaaaggca tgtaacctat aacatttcca caacaagcgc caaatacgcg gtcgtagtca   4320 taattttat atggtaaacg atcagatgct aatacaggag cttctgccaa aattgaaaga   4380
gccttcctac gtaccgcaac cgctctcgta gtatcaccta atttttctc caaagcgtac   4440 aaaggtaact taccgtgaat aaccaaggca gcgacctctt tgttcttcaa ttgttttgta   4500
tttccactac ttaataatgc ttctaattct tctaaaggac gtattttctt atccaagctt   4560
tcaatatcgc gggaatcatc ttcctcacta gatgatgaag gtcctgatga gctcgattgc   4620
gcagatgata aacttttgac tttcgatcca gaaatgactg ttttattggt taaaactggt   4680
gtagaagcct tttgtacagg agcagtaaaa gacttcttgg tgacttcagt cttcaccaat   4740
tggtctgcag ccattatagt tttttctcct tgacgttaaa gtatagaggt atattaacaa   4800
ttttttgttg atacttttat tacatttgaa taagaagtaa tacaaaccga aaatgttgaa   4860
agtattagtt aaagtggtta tgcagttttt gcatttatat atctgttaat agatcaaaaa   4920
tcatcgcttc gctgattaat taccccagaa ataaggctaa aaaactaatc gcattatcat   4980
cctatggttg ttaatttgat tcgttcattt gaaggtttgt ggggccaggt tactgccaat   5040
```

-continued

| | |
|---|---|
| ttttcctctt cataaccata aaagctagta ttgtagaatc tttattgttc ggagcagtgc | 5100 |
| ggcgcgaggc acatctgcgt ttcaggaacg cgaccggtga agacgaggac gcacggagga | 5160 |
| gagtcttcct tcggagggct gtcacccgct cggcggcttc taatccgtag gtccgccggc | 5220 |
| gttggacgag cgttgtgagc gttgcgctcg tgcatcaatg tgtatattag tttaaaaagt | 5280 |
| tgtatgtaat aaaagtaaaa tttaatattt tggatgaaaa aaccattttt tagacttttt | 5340 |
| cttaactaga atgctggagt agaaatacgc catctcaaga tacaaaaagc gttaccggca | 5400 |
| ctgatttgtt tcaaccagta tatagattat tattgggtct tgatcaactt tcctcagaca | 5460 |
| tatcagtaac agttatcaag ctaaatattt acgcgaaaga aaacaaata ttttaattgt | 5520 |
| gatacttgtg aattttattt tattaaggat acaaagttaa gagaaaacaa aatttatata | 5580 |
| caatataagt aatattcata tatatgtgat gaatgcagtc ttaacgagaa gacatggcct | 5640 |
| tggtgacaac tctcttcaaa ccaacttcag cctttctcaa ttcatcagca gatgggtctt | 5700 |
| cgatttgcaa agcagcca | 5718 |

<210> SEQ ID NO 54
<211> LENGTH: 2879
<212> TYPE: DNA
<213> ORGANISM: Artificial Sequence
<220> FEATURE:
<223> OTHER INFORMATION: Synthetic polynucleotide

<400> SEQUENCE: 54

| | |
|---|---|
| atgtccggta aatggagact agtgctgact gggataggca atccagagcc tcagtacgct | 60 |
| ggcacccgtc acaatgtagg gctatatatg ctggagctgc tacgaaagcg gcttggtctg | 120 |
| caggggagaa cctattcccc tgtgcctaat acgggcggca aagtgcatta tatagaagac | 180 |
| gaacattgta cgatactaag atcggatggc cagtacatga atctaagtgg agaacaggtg | 240 |
| tgcaaggtct gggcccggta cgccaagtac caagcccgac acgttgttat tcatgacgag | 300 |
| ttaagtgtgg cgtgtggaaa agtgcagctc agagccccca gcaccagtat tagaggtcat | 360 |
| aatgggctgc gaagtctact gaaatgctcc ggaggccgtg tacccttgc caaattggct | 420 |
| attggaatcg gcagagaacc tgggtcccgc tctagagacc ctgcgagcgt ctcccgctgg | 480 |
| gttctgggag ctctaactcc gcaggaacta caaaccttgc ttacacagag tgaacctgct | 540 |
| gcctggcgtg ctctgactca gtacatttca taggtttaac ttgatactac tagatttttt | 600 |
| ctcttcattt ataaaatttt tggttataat tgaagcttta gaagtatgaa aaaatccttt | 660 |
| tttttcattc tttgcaacca aaataagaag cttcttttat tcattgaaat gatgaatata | 720 |
| aacctaacaa agaaaaaga ctcgaatatc aaacattaaa aaaaaataaa agaggttatc | 780 |
| tgttttccca tttagttgga gtttgcattt tctaatagat agaactctca attaatgtgg | 840 |
| atttagtttc tctgttcgtt ttttttttgtt ttgttctcac tgtatttaca tttctattta | 900 |
| gtatttagtt attcatataa tcttaacttc tcgaggagct cgatcttgaa actgagtaag | 960 |
| atgctcagaa tacccgtcaa gataagagta taatgtagag taatatacca agtattcagc | 1020 |
| atattctcct cttcttttgt ataaatcacg gaagggatga tttataagaa aaatgaatac | 1080 |
| tattacactt catttaccac cctctgatct agatttttcca acgatatgta cgtagtggta | 1140 |
| taaggtgagg gggtccacag atataacatc gtttaattta gtactaacag agacttttgt | 1200 |
| cacaactaca tataagtgta caaatatagt acagatatga cacacttgta gcgccaacgc | 1260 |
| gcatcctacg gattgctgac agaaaaaag gtcacgtgac cagaaaagtc acgtgtaatt | 1320 |
| ttgtaactca ccgcattcta gcggtccctg tcgtgcacac tgcactcaac accataaacc | 1380 |

-continued

```
ttagcaacct ccaaaggaaa tcaccgtata acaaagccac agttttacaa cttagtctct    1440
tatgaagtgt ctctctctgt cgtaacagtt gtgatatcgg aagaagagaa aagacgaaga    1500
gcagaagcgg aaaacgtata cacgtcacat atcacacaca cacaatggga aagctattac    1560
aattggcatt gcatccggtc gagatgaagg cagcttgaa gctgaagttt tgcagaacac     1620
cgctattctc catctatgat cagtccacgt ctccatatct cttgcactgt ttcgaactgt    1680
tgaacttgac ctccagatcg tttgctgctg tgatcagaga gctgcatcca gaattgagaa    1740
actgtgttac tctcttttat ttgatttaa gggctttgga taccatcgaa gacgatatgt     1800
ccatcgaaca cgatttgaaa attgacttgt tgcgtcactt ccacgagaaa ttgttgttaa    1860
ctaaatggag tttcgacgga aatgccccg atgtgaagga cagagccgtt ttgacagatt     1920
tcgaatcgat tcttattgaa ttccacaaat tgaaaccaga atatcaagaa gtcatcaagg    1980
agatcaccga gaaatgggt aatggtatgg ccgactacat cttagatgaa aattacaact     2040
tgaatgggtt gcaaaccgtc cacgactacg acgtgtactg tcactacgta gctggtttgg    2100
tcggtgatgg tttgacccgt ttgattgtca ttgccaagtt tgccaacgaa tctttgtatt    2160
ctaatgagca attgtatgaa agcatgggtc ttttcctaca aaaaaccaac atcatcagag    2220
attacaatga agatttggtc gatggtagat ccttctggcc caaggaaatc tggtcacaat    2280
acgctcctca gttgaaggac ttcatgaaac ctgaaaacga acaactgggg ttggactgta    2340
taaaccacct cgtcttaaac gcattgagtc atgttatcga tgtgttgact tatttggccg    2400
gtatccacga gcaatccact ttccaatttt gtgccattcc ccaagttatg gccattgcaa    2460
ccttggcttt ggtattcaac aaccgtgaag tgctacatgg caatgtaaag attcgtaagg    2520
gtactacctg ctatttaatt ttgaaatcaa ggactttgcg tggctgtgtc gagattttg    2580 actattactt acgtgatatc aaatctaaat tggctgtgca agatccaaat ttcttaaaat    2640
tgaacattca aatctccaag atcgaacagt ttatggaaga aatgtaccag gataaattac    2700
ctcctaacgt gaagccaaat gaaactccaa ttttcttgaa agttaaagaa agatccagat    2760
acgatgatga attggttcca acccaacaag aagaagagta caagttcaat atggttttat    2820
ctatcatctt gtccgttctt cttggggtttt attatatata cactttacac agagcgtga    2879
```

```
<210> SEQ ID NO 55
<211> LENGTH: 9
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(4)
<223> OTHER INFORMATION: Xaa may be any amino acid
<220> FEATURE:
<221> NAME/KEY: MISC_FEATURE
<222> LOCATION: (6)..(8)
<223> OTHER INFORMATION: Xaa may be any amino acid
<220> FEATURE:
<221> NAME/KEY: MISC_FEATURE
<222> LOCATION: (9)..(9)
<223> OTHER INFORMATION: Xaa may be Asp or Glu

<400> SEQUENCE: 55

Asn Asp Xaa Xaa Ser Xaa Xaa Xaa Xaa
1               5

<210> SEQ ID NO 56
<211> LENGTH: 458
```

<212> TYPE: DNA
<213> ORGANISM: Artificial Sequence
<220> FEATURE:
<223> OTHER INFORMATION: Synthetic polynucleotide

<400> SEQUENCE: 56

| | | | | | |
|---|---|---|---|---|---|
| agggttcgca | agtcctgttt | ctatgccttt | ctcttagtaa | ttcacgaaat | aaacctatgg | 60 |
| tttacgaaat | gatccacgaa | atcatgtta | ttatttacat | caacatatcg | cgaaaattca | 120 |
| tgtcatgtcc | acattaacat | cattgcagag | caacaattca | ttttcataga | gaaatttgct | 180 |
| actatcaccc | actagtacta | ccattggtac | ctactacttt | gaattgtact | accgctgggc | 240 |
| gttattaggt | gtgaaaccac | gaaaagttca | ccataacttc | gaataaagtc | gcggaaaaaa | 300 |
| gtaaacagct | attgctactc | aaatgaggtt | tgcagaagct | tgttgaagca | tgatgaagcg | 360 |
| ttctaaacgc | actattcatc | attaaatatt | taaagctcat | aaaattgtat | tcaattccta | 420 |
| ttctaaatgg | cttttatttc | tattacaact | attagctc | | | 458 |

<210> SEQ ID NO 57
<211> LENGTH: 450
<212> TYPE: DNA
<213> ORGANISM: Artificial Sequence
<220> FEATURE:
<223> OTHER INFORMATION: Synthetic polynucleotide

<400> SEQUENCE: 57

| | | | | | |
|---|---|---|---|---|---|
| acggattaga | gccgccgagc | gggtgacagc | cctccgaagg | aagactctcc | tccgtgcgtc | 60 |
| ctcgtcttca | ccggtcgcgt | tcctgaaacg | cagatgtgcc | tcgcgccgca | ctgctccgaa | 120 |
| caataaagat | tctacaatac | tagcttttat | ggttatgaag | aggaaaaatt | ggcagtaacc | 180 |
| tggcccaca | aaccttcaaa | tgaacgaatc | aaattaacaa | ccataggatg | ataatgcgat | 240 |
| tagttttta | gccttatttc | tggggtaatt | aatcagcgaa | gcgatgattt | tgatctatt | 300 |
| aacagatata | taaatgcaaa | aactgcataa | ccactttaac | taatactttc | aacattttcg | 360 |
| gtttgtatta | cttcttattc | aaatgtaata | aaagtatcaa | caaaaaattg | ttaatatacc | 420 |
| tctatacttt | aacgtcaagg | agaaaaaact | | | | 450 |

<210> SEQ ID NO 58
<211> LENGTH: 1584
<212> TYPE: DNA
<213> ORGANISM: Artificial Sequence
<220> FEATURE:
<223> OTHER INFORMATION: Synthetic polynucleotide

<400> SEQUENCE: 58

| | | | | | |
|---|---|---|---|---|---|
| atggctgcag | accaattggt | gaagactgaa | gtcaccaaga | agtcttttac | tgctcctgta | 60 |
| caaaaggctt | ctacaccagt | tttaaccaat | aaaacagtca | tttctggatc | gaaagtcaaa | 120 |
| agtttatcat | ctgcgcaatc | gagctcatca | ggaccttcat | catctagtga | ggaagatgat | 180 |
| tcccgcgata | ttgaaagctt | ggataagaaa | atacgtcctt | tagaagaatt | agaagcatta | 240 |
| ttaagtagtg | gaaatacaaa | acaattgaag | aacaaagagg | tcgctgcctt | ggttattcac | 300 |
| ggtaagttac | ctttgtacgc | tttggagaaa | aaattaggtg | atactacgag | agcggttgcg | 360 |
| gtacgtagga | aggctctttc | aatttttggca | gaagctcctg | tattagcatc | tgatcgttta | 420 |
| ccatataaaa | attatgacta | cgaccgcgta | tttggcgctt | gttgtgaaaa | tgttataggt | 480 |
| tacatgcctt | tgcccgttgg | tgttataggc | cccttggtta | tcgatggtac | atcttatcat | 540 |
| ataccaatgg | caactacaga | gggttgtttg | gtagcttctg | ccatgcgtgg | ctgtaaggca | 600 |

```
atcaatgctg gcggtggtgc aacaactgtt ttaactaagg atggtatgac aagaggccca    660
gtagtccgtt tcccaacttt gaaaagatct ggtgcctgta agatatggtt agactcagaa    720
gagggacaaa acgcaattaa aaaagctttt aactctacat caagatttgc acgtctgcaa    780
catattcaaa cttgtctagc aggagattta ctcttcatga gatttagaac aactactggt    840
gacgcaatgg gtatgaatat gatttctaag ggtgtcgaat actcattaaa gcaaatggta    900
gaagagtatg gctgggaaga tatggaggtt gtctccgttt ctggtaacta ctgtaccgac    960
aaaaaaccag ctgccatcaa ctggatcgaa ggtcgtggta agagtgtcgt cgcagaagct   1020
actattcctg gtgatgttgt cagaaaagtg ttaaaaagtg atgtttccgc attggttgag   1080
ttgaacattg ctaagaattt ggttggatct gcaatggctg ggtctgttgg tggatttaac   1140
gcacatgcag ctaatttagt gacagctgtt ttcttggcat taggacaaga tcctgcacaa   1200
aatgtcgaaa gttccaactg tataacattg atgaaagaag tggacggtga tttgagaatt   1260
tccgtatcca tgccatccat cgaagtaggt accatcggtg gtggtactgt tctagaacca   1320
caaggtgcca tgttggactt attaggtgta agaggcccac atgctaccgc tcctggtacc   1380
aacgcacgtc aattagcaag aatagttgcc tgtgccgtct ggcaggtgaa attatcctta   1440
tgtgctgccc tagcagccgg ccatttggtt caaagttata tgacccacaa caggaaacct   1500
gctgaaccaa caaaacctaa caatttggac gccactgata taaatcgttt gaaagatggg   1560
tccgtcacct gcattaaatc ctaa                                           1584

<210> SEQ ID NO 59
<211> LENGTH: 200
<212> TYPE: DNA
<213> ORGANISM: Artificial Sequence
<220> FEATURE:
<223> OTHER INFORMATION: Synthetic polynucleotide

<400> SEQUENCE: 59
agatccgctc taaccgaaaa ggaaggagtt agacaacctg aagtctaggt ccctatttat     60 tttttatag ttatgttagt attaagaacg ttatttatat ttcaaatttt tcttttttt     120 ctgtacagac gcgtgtacgc atgtaacatt atactgaaaa ccttgcttga aaggttttg     180 ggacgctcga agatccagct                                                200

<210> SEQ ID NO 60
<211> LENGTH: 200
<212> TYPE: DNA
<213> ORGANISM: Artificial Sequence
<220> FEATURE:
<223> OTHER INFORMATION: Synthetic polynucleotide

<400> SEQUENCE: 60
agctggatct tcgagcgtcc aaaaccttc tcaagcaagg ttttcagtat aatgttacat     60
gcgtacacgc gtctgtacag aaaaaaaaga aaatttgaa atataaataa cgttcttaat    120
actaacataa ctataaaaaa ataaataggg acctagactt caggttgtct aactccttcc    180
ttttcggtta gagcggatct                                                200

<210> SEQ ID NO 61
<211> LENGTH: 1584
<212> TYPE: DNA
<213> ORGANISM: Artificial Sequence
<220> FEATURE:
<223> OTHER INFORMATION: Synthetic polynucleotide

<400> SEQUENCE: 61
```

```
ttaggattta atgcaggtga cggacccatc tttcaaacga tttatatcag tggcgtccaa      60
attgttaggt tttgttggtt cagcaggttt cctgttgtgg gtcatataac tttgaaccaa     120
atggccggct gctagggcag cacataagga taattcacct gccaagacgg cacaggcaac     180
tattcttgct aattgacgtg cgttggtacc aggagcggta gcatgtgggc ctcttacacc     240
taataagtcc aacatggcac cttgtggttc tagaacagta ccaccaccga tggtacctac     300
ttcgatggat ggcatggata cggaaattct caaatcaccg tccacttctt tcatcaatgt     360
tatacagttg gaactttcga cattttgtgc aggatcttgt cctaatgcca agaaaacagc     420
tgtcactaaa ttagctgcat gtgcgttaaa tccaccaaca gacccagcca ttgcagatcc     480
aaccaaattc ttagcaatgt tcaactcaac caatgcggaa acatcacttt taacacttt      540 tctgacaaca tcaccaggaa tagtagcttc tgcgacgaca ctcttaccac gaccttcgat     600
ccagttgatg gcagctggtt ttttgtcggt acagtagtta ccagaaacgg agacaacctc     660
catatcttcc cagccatact cttctaccat ttgctttaat gagtattcga cacccttaga     720
aatcatattc atacccattg cgtcaccagt agttgttcta aatctcatga agagtaaatc     780
tcctgctaga caagtttgaa tatgttgcag acgtgcaaat cttgatgtag agttaaaagc     840
ttttttaatt gcgttttgtc cctcttctga gtctaaccat atcttacagg caccagatct     900
tttcaaagtt gggaacggga ctactgggcc tcttgtcata ccatccttag ttaaaacagt     960
tgttgcacca ccgccagcat tgattgcctt acagccacgc atggcagaag ctaccaaaca    1020
accctctgta gttgccattg gtatatgata agatgtacca tcgataacca aggggcctat    1080
aacaccaacg ggcaaaggca tgtaacctat aacattttca caacaagcgc caaatacgcg    1140
gtcgtagtca taattttat atggtaaacg atcagatgct aatacaggag cttctgccaa    1200
aattgaaaga gccttcctac gtaccgcaac cgctctcgta gtatcaccta atttttctc     1260 caaagcgtac aaaggtaact taccgtgaat aaccaaggca gcgacctctt tgttcttcaa    1320
ttgttttgta tttccactac ttaataatgc ttctaattct tctaaaggac gtatttctt     1380 atccaagctt tcaatatcgc gggaatcatc ttcctcacta gatgatgaag gtcctgatga    1440
gctcgattgc gcagatgata aacttttgac tttcgatcca gaaatgactg ttttattggt    1500
taaaactggt gtagaagcct tttgtacagg agcagtaaaa gacttcttgg tgacttcagt    1560
cttcaccaat tggtctgcag ccat                                           1584
```

<210> SEQ ID NO 62
<211> LENGTH: 451
<212> TYPE: DNA
<213> ORGANISM: Artificial Sequence
<220> FEATURE:
<223> OTHER INFORMATION: Synthetic polynucleotide

<400> SEQUENCE: 62

```
agttttttct ccttgacgtt aaagtataga ggtatattaa caattttttg ttgatacttt      60
tattacattt gaataagaag taatacaaac cgaaaatgtt gaaagtatta gttaaagtgg     120
ttatgcagtt tttgcattta tatatctgtt aatagatcaa aaatcatcgc ttcgctgatt     180
aattacccca gaaataaggc taaaaaacta atcgcattat catcctatgg ttgttaattt     240
gattcgttca tttgaaggtt tgtggggcca ggttactgcc aattttttcct cttcataacc     300 ataaaagcta gtattgtaga atctttattg ttcggagcag tgcggcgcga ggcacatctg     360
cgtttcagga acgcgaccgg tgaagacgag gacgcacgga ggagagtctt ccttcggagg     420
```

```
gctgtcaccc gctcggcggc ttctaatccg t                              451
```

<210> SEQ ID NO 63
<211> LENGTH: 462
<212> TYPE: DNA
<213> ORGANISM: Artificial Sequence
<220> FEATURE:
<223> OTHER INFORMATION: Synthetic polynucleotide

<400> SEQUENCE: 63

```
aatgtgtata ttagttttaaa aagttgtatg taataaaagt aaaatttaat attttggatg    60
aaaaaaacca tttttagact ttttcttaac tagaatgctg gagtagaaat acgccatctc   120
aagatacaaa aagcgttacc ggcactgatt tgtttcaacc agtatataga ttattattgg   180
gtcttgatca actttcctca gacatatcag taacagttat caagctaaat atttacgcga   240
aagaaaaaca aatattttaa ttgtgatact tgtgaatttt attttattaa ggatacaaag   300
ttaagagaaa acaaaattta tatacaatat aagtaatatt catatatatg tgatgaatgc   360
agtcttaacg agaagacatg gccttggtga caactctctt caaaccaact tcagcctttc   420
tcaattcatc agcagatggg tcttcgattt gcaaagcagc ca                     462
```

<210> SEQ ID NO 64
<211> LENGTH: 573
<212> TYPE: DNA
<213> ORGANISM: Artificial Sequence
<220> FEATURE:
<223> OTHER INFORMATION: Synthetic polynucleotide

<400> SEQUENCE: 64

```
atgtccggta aatggagact agtgctgact gggataggca atccagagcc tcagtacgct    60
ggcacccgtc acaatgtagg gctatatatg ctggagctgc tacgaaagcg gcttggtctg   120
caggggagaa cctattcccc tgtgcctaat acgggcggca aagtgcatta tatagaagac   180
gaacattgta cgatactaag atcggatggc cagtacatga atctaagtgg agaacaggtg   240
tgcaaggtct gggcccggta cgccaagtac caagcccgac acgttgttat tcatgacgag   300
ttaagtgtgg cgtgtggaaa agtgcagctc agagcccca gcaccagtat tagaggtcat   360
aatgggctgc gaagtctact gaaatgctcc ggaggccgtg tacccttttgc caaattggct   420
attggaatcg gcagagaacc tgggtcccgc tctagagacc ctgcgagcgt ctcccgctgg   480
gttctgggag ctctaactcc gcaggaacta caaaccttgc ttacacagag tgaacctgct   540
gcctggcgtg ctctgactca gtacatttca tag                              573
```

<210> SEQ ID NO 65
<211> LENGTH: 511
<212> TYPE: DNA
<213> ORGANISM: Artificial Sequence
<220> FEATURE:
<223> OTHER INFORMATION: Synthetic polynucleotide

<400> SEQUENCE: 65

```
gatcttgaaa ctgagtaaga tgctcagaat acccgtcaag ataagagtat aatgtagagt    60
aatataccaa gtattcagca tattctcctc ttcttttgta taaatcacgg aagggatgat   120
ttataagaaa aatgaatact attacacttc atttaccacc ctctgatcta gattttccaa   180
cgatatgtac gtagtggtat aaggtgaggg ggtccacaga tataacatcg tttaatttag   240
tactaacaga gactttttgtc acaactacat ataagtgtac aaatatagta cagatatgac   300
acacttgtag cgccaacgcg catcctacgg attgctgaca gaaaaaaagg tcacgtgacc   360
```

```
agaaaagtca cgtgtaattt tgtaactcac cgcattctag cggtccctgt cgtgcacact    420
gcactcaaca ccataaacct tagcaacctc caaaggaaat caccgtataa caaagccaca    480
gttttacaac ttagtctctt atgaagtgtc t                                   511
```

<210> SEQ ID NO 66
<211> LENGTH: 1335
<212> TYPE: DNA
<213> ORGANISM: Artificial Sequence
<220> FEATURE:
<223> OTHER INFORMATION: Synthetic polynucleotide

<400> SEQUENCE: 66

```
atgggaaagc tattacaatt ggcattgcat ccggtcgaga tgaaggcagc tttgaagctg     60
aagttttgca gaacaccgct attctccatc tatgatcagt ccacgtctcc atatctcttg    120
cactgtttcg aactgttgaa cttgacctcc agatcgtttg ctgctgtgat cagagagctg    180
catccagaat tgagaaactg tgttactctc ttttatttga ttttaagggc tttggatacc    240
atcgaagacg atatgtccat cgaacacgat ttgaaaattg acttgttgcg tcacttccac    300
gagaaattgt tgttaactaa atggagtttc gacggaaatg cccccgatgt gaaggacaga    360
gccgttttga cagatttcga atcgattctt attgaattcc acaaattgaa accagaatat    420
caagaagtca tcaaggagat caccgagaaa atgggtaatg gtatggccga ctacatctta    480
gatgaaaatt acaacttgaa tgggttgcaa accgtccacg actacgacgt gtactgtcac    540
tacgtagctg gtttggtcgg tgatggtttg acccgtttga ttgtcattgc aagtttgcc     600 aacgaatctt tgtattctaa tgagcaattg tatgaaagca tgggtctttt cctacaaaaa    660
accaacatca tcagagatta caatgaagat ttggtcgatg gtagatccct ctggcccaag    720
gaaatctggt cacaatacgc tcctcagttg aaggacttca tgaaacctga aaacgaacaa    780
ctggggttgg actgtataaa ccacctcgtc ttaaacgcat tgagtcatgt tatcgatgtg    840
ttgacttatt tggccggtat ccacgagcaa tccactttcc aattttgtgc cattccccaa    900
gttatggcca ttgcaacctt ggctttggta ttcaacaacc gtgaagtgct acatggcaat    960
gtaaagattc gtaagggtac tacctgctat ttaattttga aatcaaggac tttgcgtggc   1020
tgtgtcgaga tttttgacta ttacttacgt gatatcaaat ctaaattggc tgtgcaagat   1080
ccaaatttct taaaattgaa cattcaaatc tccaagatcg aacagtttat ggaagaaatg   1140
taccaggata aattacctcc taacgtgaag ccaaatgaaa ctccaatttt cttgaaagtt   1200
aaagaaagat ccagatacga tgatgaattg gttccaaccc aacaagaaga agagtacaag   1260
ttcaatatgg ttttatctat catcttgtcc gttcttcttg ggttttatta tatatacact   1320
ttacacagag cgtga                                                    1335
```

<210> SEQ ID NO 67
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 67

```
atggccagtc aggcttcaca agttttagca tctccccacc cagctatatc ctctgaaaac     60
cggccaaagg ctgatttcca tcctggtatc tggggcgaca tgtttattat ctgtccagat    120
acggacattg atgccgctac agagctgcaa tatgaagaat tgaaagcgca agtccgcaag    180
```

```
atgatcatgg aaccagtaga cgattctaat caaaagctac cattcattga cgctgttcaa    240
aggctcggag tgagctacca ctttgaaaaa gaaattgaag acgaacttga aaacatctac    300
cgtgatacca ataacaacga cgcagacact gatctataca ctaccgcctt gagattcaga    360
ttattgagag agcatggttt tgatatttcc tgcgatgctt tcaacaagtt gaaagacgaa    420
gaaggtaatt tcaaggcttc gttgacttct gacgttcctg gtttgttaga actctatgag    480
gcttcctact tgagagtcca cggtgaagat atcctagatg aagccatatc tttcgctact    540
gctcagttaa ccttggcttt gccaactttg catcacccgc tttcagagca agttggtcac    600
gcattgaagc aaagtatcag aagaggcctg ccaagagttg aagccagaaa ctttatctct    660
atttaccaag atttagaatc ccacaataag gctttgttgc aattcgccaa aattgacttt    720
aacatgttac aattgctaca taggaaggag ctcagcgaaa tttgtagatg gtggaaagat    780
cttgatttta ccagaaagtt accttcgct cgtgaccgtg tcgtcgaagg ttatttctgg     840
attatgggag tttacttcga accacaatat agcttgggta gaaagatgtt gaccaaggtt    900
attgctatgg cttctatcgt cgatgataca tacgattcct tcgctactta cgacgaattg    960
ataccatata ctgacgccat cgaaagatgg gacatcaagt gtatgaatca gctgccaaac   1020
tatatgcaaa tttcgtacaa agcgttattg gatgtatacg aggaaatgga acaattgctt   1080
gcagataaag gtcgacagta cagagtggaa tacgctaaga agctatgat tcggttggtg    1140
caagcatatt tgttagaagc gaagtggacc catttaaact acaagccaac tttcgaagaa   1200
tttagagaca atgctttgcc gacatctggg tatgccatgc tagctataac cgcgttcgtt   1260
ggtatgggtg aagttatcac gccagaaacc tttgatgggc tgcttctga cccaaagatt    1320
attaaggcct ccactatcat ctgccgcttt atggatgata tcgctgagca taagttcaac   1380
cacagaaggg aggatgactg ttccgctatt gaatgttaca tggagcaata caaagtcaca   1440
gctcaagaag catacgacga atttaacaag cacatagaat cgtcttggaa ggacgttaat   1500
gaagagttct tgaaaccaac tgaaatgcct actccggtac tgtgtagaag tttgaaccta   1560
gccagagtca tggatgtttt gtacagagaa ggtgacggtt atactcatgt tggaaaagcc   1620
gctaagggtg gtataacatc acttcttatc gatcccattc aaatctaa               1668
```

<210> SEQ ID NO 68
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 68

```
atggccagtc aggcttcaca agttttagca tctccccacc cagctatatc ctctgaaaac     60
cggccaaagg ctgatttcca tcctggtatc tggggcgaca tgtttattat ctgtccagat    120
acggacattg atgccgctac agagctgcaa tatgaagaat tgaaagcgca agtccgcaag    180
atgatcatgg aaccagtaga cgattctaat caaaagctac cattcattga cgctgttcaa    240
aggctcggag tgagctacca ctttgaaaaa gaaattgaag acgaacttga aaacatctac    300
cgtgatacca ataacaacga cgcagacact gatctataca ctaccgcctt gagattcaga    360
ttattgagag agcatggttt tgatatttcc tgcgaagctt tcaacaagtt gaaagacgaa    420
gagggtaatt tcaaggcttc gttgacttct gatgttagag gtttgttaga actctatcag    480
gcttcctaca tgagaatcca cggtgaagat attcttgatg aagccatatc tttcaccact    540
gctcaattaa ccttggcttt gcctactttg gatccccat tgtcagagca agtcggtcat     600
```

| | |
|---|---|
| gccctaaagc agagtataag aagaggccta ccaagagttg aagccagaaa ctttatctct | 660 |
| atttaccaag acttggaatc ccacaataag gctttattgc aattcgctaa aattgacttt | 720 |
| aacatgttac aattgctaca taggaaggag ctcagcgaaa tctgtcgttg gtggaaagat | 780 |
| cttgatttta ctagaaagtt gcctttcgca cgggaccgtg tcgttgaagg ttatttctgg | 840 |
| attatgggag tttacttcga accacaatat agcttgggta gaaagatgtt gaccaaggtt | 900 |
| attgctatgg cttctatcgt cgatgataca tacgattcct tcgctacata cgacgaattg | 960 |
| atcccatata ctgacgccat tgaaagatgg gacatcaagt gtatgaatca actgccaaac | 1020 |
| tatatgcaaa tttcgtacaa agcattattg gatgtatacg aggaaatgga acaattgctt | 1080 |
| gcggataaag gtcggcagta cagagtggaa tacgctaaga agctatgat tcgattggta | 1140 |
| caagcatatt tattgaagc gaagtggact cacttgaact acaagccaac cttcgaagaa | 1200 |
| tttagagaca atgctttacc gacatctggg tatgctatgc ttgctataac cgcgttcgtt | 1260 |
| ggtatgggtg aagtcatcac gccagaaact tttgaatggg ccgcttctga cccgaagatt | 1320 |
| atcaaggctt ccactatcat ctgccgcttt atggatgata tcgctgagca taagttcaac | 1380 |
| cacagaaggg aggatgactg ttccgctatt gaatgttaca tgaagcaata cggtgcaacc | 1440 |
| gcccaagagg catacgacga atttaacaaa cacatagaat cgtcttggaa ggacgttaat | 1500 |
| gaagagttct tgaaaccaac tgaaatgcct actccagtgc tgtgtagaag tttgaacctt | 1560 |
| gctagagtca tggatgtttt gtacagagaa ggtgacggtt atactcatgt cgggaaagcc | 1620 |
| gctaagggtg gtataacctc attgctaatt gatcccattc aaatctaa | 1668 |

<210> SEQ ID NO 69
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 69

| | |
|---|---|
| atggccagtc aggcttcaca agtttttagca tctccccacc cagctatatc ctctgaaaac | 60 |
| cggccaaagg ctgatttcca tcctggtatc tggggcgaca tgtttattat ctgtccagat | 120 |
| acggacattg atgccgctac agagctgcaa tatgaagaat tgaaagcgca agtccgcaag | 180 |
| atgatcatgg aaccagtaga cgattctaat caaaagctac cattcattga cgctgttcaa | 240 |
| aggctcggag tgagctacca ctttgaaaaa gaattgaag acgaacttga aaacatctac | 300 |
| cgtgatacca ataacaacga cgcagacact gatctataca ctaccgcctt gagattcaga | 360 |
| ttattgagag agcatggttt tgatatttcc tgcgatgctt caacaagtt gaaagacgaa | 420 |
| gaaggtaatt tcaaggcttc gttgacttct gacgttcctg gtttgttaga actctatgag | 480 |
| gcttcctact tgagagtcca cggtgaagat atcctagatg aagccatatc tttcgctact | 540 |
| gctcagttaa ccttggcttt gccaactttg catcacccgc tttcagagca agttggtcac | 600 |
| gcattgaagc aaagtatcag aagaggcctg ccaagagttg aagccagaaa ctttatctct | 660 |
| atttaccaag atttagaatc ccacaataag gctttgttgc aattcgccaa aattgacttt | 720 |
| aacatgttac aattgctaca taggaaggag ctcagcgaaa tttgtagatg gtggaaagat | 780 |
| cttgatttta ccagaaagtt accttttcgct cgtgaccgtg tcgtcgaagg ttatttctgg | 840 |
| attatgggag tttacttcga accacaatat agcttgggta gaaagatgtt gaccaaggtt | 900 |
| attgctatgg cttctatcgt cgatgataca tacgattcct tcgctactta cgacgaattg | 960 |

| | |
|---|---|
| ataccatata ctgacgccat cgaaagatgg gacatcaagt gtatgaatca gctgccaaac | 1020 |
| tatatgcaaa tttcgtacaa agcgttattg gatgtatacg aggaaatgga acaattgctt | 1080 |
| gcagataaag gtcgacagta cagagtggaa tacgctaaga aagctatgat tcggttggtg | 1140 |
| caagcatatt tgttagaagc gaagtggacc catttaaact acaagccaac tttcgaagaa | 1200 |
| tttagagaca atgctttgcc gacatctggg tatgccatgc tagctataac cgcgttcgtt | 1260 |
| ggtatgggtg aagttatcac gccagaaacc tttgaatggg ctgcttctga cccaaagatt | 1320 |
| attaaggcct ccactatcat ctgccgcttt atggatgata tcgctgagca taagttcaac | 1380 |
| cacagaaggg aggatgactg ttccgctatt gaatgttaca tgaagcaata cggtgcaaca | 1440 |
| gctcaagagg catacgacga atttaacaaa cacatagaat cgtcttggaa ggacgtcaat | 1500 |
| gaagagttct tgaaaccaac tgaaatgcct actccggtac tgtgtagaag tttgaaccta | 1560 |
| gccagagtca tggatgtttt gtacagagaa ggtgacggtt atactcatgt tgggaaagcc | 1620 |
| gctaagggtg gtataacatc acttcttatc gatcccattc aaatctaa | 1668 |

<210> SEQ ID NO 70
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 70

| | |
|---|---|
| atggcctcac aggcttccca agttttagca tctcctcacc cagctatatc ttccgaaaac | 60 |
| cgtccaaagg ctgatttcca tccaggtatc tggggcgaca tgtttattat ctgtccagat | 120 |
| acagacattg atgccgctac cgagttgcaa tatgaagaat tgaaagccca agtcagaaag | 180 |
| atgatcatga aaccgttga cgattctaat caaaagttgc ctttcattga cgctgtccaa | 240 |
| agattgggtg tttcatacca ctttgaaaaa gaaattgaag acgaattaga aaacatctac | 300 |
| agagatacta ataacaacga cgcagacact gatttgtaca ccactgcctt gagattcaga | 360 |
| ttattgcgtg agcatggttt tgatatttct tgcgaagctt tcaacaagtt gaaagacgaa | 420 |
| gagggtaatt tcaaggcttc cttaacctct gatgtcagag gtttgttgga attgtatcag | 480 |
| gcttcctaca tgagaatcca cggtgaagat atttttggatg aagctatatc tttcacaact | 540 |
| gctcaattaa ctttagcttt accaactttg gatcctccat tgtctgagca agttggtcat | 600 |
| gccttgaagc agtcaatacg tagaggtttg ccaagagttg aagccagaaa ctttatctct | 660 |
| atttaccaag acttggaatc ccacaataag tctttattag aatttgctaa aattgatttc | 720 |
| aacttattgc aattgttaca cagaaaggag ttgtccgaaa tctgtagatg gtggaaagac | 780 |
| ttggatttta ccagaaagtt accttttcgct agagatcgtg tcgttgaagg ttatttctgg | 840 |
| atcatgggtg tctacttcga accacaatac tccttgggta gaaagatgtt gaccaaagtt | 900 |
| attgctatgg cctctattgt tgacgatact tatgactcat ttgcaaccta cgacgaattg | 960 |
| ataccatata cagacgctat tgaaagatgg gatatcaagt gtatgaacca attgccaaat | 1020 |
| tatatgcaaa tatcttacaa ggctttgtta gacgtttacg aggaaatgga acaattgttg | 1080 |
| gctgataagg gtagacaata tagagtcgag tacgcaaaaa aagccatgat cagattggtt | 1140 |
| caggcctact tattagaggc taagtggacc catttgaact acaagcctac ttttgaagag | 1200 |
| ttcagagaca atgctttacc aacctccggt tatgccatgt tggctatcac tgcattcgtt | 1260 |
| ggtatgggtg aagtcattac accagaaact tttgaatggg ctgcctctga tccaaagatt | 1320 |
| attaaggctt ctactatcat ctgccgtttc atggatgata ttgctgaaca caattcaac | 1380 |

```
cacagaagag aggacgattg ttccgctatt gaatgttaca tggaacaata caaggttaca    1440
gcccaagaag catacgacga atttaacaag catatcgaat catcttggaa ggacgttaat    1500
gaagaatttt taaagcctac cgaaatgcca acaccagtct tgtgtagatc tttgaacttg    1560
gccagagtta tggatgtctt gtaccgtgaa ggtgatggtt atactcatgt cggtaaggct    1620
gctaaaggtg gtatcaccctc cttgttgatc gaccctattc aaatttaa    1668
```

<210> SEQ ID NO 71
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 71

```
atggcctcac aggcttccca agttttagca tctcctcacc cagctatatc ttccgaaaac     60
cgtccaaagg ctgatttcca tccaggtatc tggggcgaca tgtttattat ctgtccagat    120
acagacattg atgccgctac cgagttgcaa tatgaagaat gaaagcccca agtcagaaag    180
atgatcatgg aaccagttga cgattctaat caaaagttgc ctttcattga cgctgtccaa    240
agattgggtg tttcatacca ctttgaaaaa gaaattgaag acgaattaga aaacatctac    300
agagatacta ataacaacga cgcagacact gatttgtaca ccactgcctt gagattcaga    360
ttattgcgtg agcatggttt tgatatttct tgcgatgctt tcaacaagtt gaaagacgaa    420
gaaggtaatt tcaaggcttc cttaacctct gacgtcccag gtttgttgga attgtatgag    480
gcttcctact taagagttca cggtgaagat atcttggatg aagctatatc tttcgccact    540
gctcagttaa ccttggcttt accaactttg catcacccat tgtctgagca agttggtcac    600
gcattgaagc aatcaatcag aagaggtttg ccaagagttg aagctagaaa ctttatctct    660
atttaccaag atttagaatc ccacaataag tctttattag aatttgccaa aattgatttc    720
aacttgttgc aattgttaca ccgtaaggag ttgtccgaaa tatgtagatg gtggaaagac    780
ttagatttta caagaaagtt acctttcgct agagatagag tcgttgaagg ttatttctgg    840
attatgggtg tctacttcga accacaatac tccttgggta gaaagatgtt gaccaaagtt    900
attgctatgg cttctatcgt tgacgatact tatgactcat ttgccactta cgacgaattg    960
atcccttata cagacgctat tgaacgttgg gatatcaagt gtatgaacca gttgccaaat    1020
tatatgcaaa tatcttacaa ggctttgtta gacgtttacg aggaaatgga acaattgttg    1080
gctgataagg tagacaaata tagagtcgag tacgccaaaa aagcaatgat tagattggtt    1140
caggcctact tattagaggc taagtggacc catttgaact acaagcctac atttgaagag    1200
ttcagagaca atgctttacc aacttccggt tatgccatgt tggctataac cgcattcgtt    1260
ggtatgggtg aagtcattac cccagaaact tttgaatggg ccgcttctga tccaaagatt    1320
atcaaggctt ctactatcat ctgccgtttc atggatgata ttgccgaaca taaattcaac    1380
cacagaagag aggacgattg ttccgctatt gaatgttaca tggaacaata caaggttaca    1440
gcccaagaag cttacgacga atttaacaag cacatcgaat catcttggaa ggacgtcaat    1500
gaagaatttt tgaagcctac cgaaatgcca actccagtct tgtgtagatc tttgaacttg    1560
gcaagagtta tggatgtctt gtacagagaa ggtgatggtt atactcatgt cggtaaggct    1620
gctaaaggtg gtatcaccctc cttgttgatc gaccctattc aaatttaa    1668
```

<210> SEQ ID NO 72

<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 72

| | |
|---|---|
| atggcctcac aggcttccca agttttagca tctcctcacc cagctatatc ttccgaaaac | 60 |
| cgtccaaagg ctgatttcca tccaggtatc tggggcgaca tgtttattat ctgtccagat | 120 |
| acagacattg atgccgctac cgagttgcaa tatgaagaat tgaaagccca agtcagaaag | 180 |
| atgatcatgg aaccagttga cgattctaat caaaagttgc ctttcattga cgctgtccaa | 240 |
| agattgggtg tttcatacca ctttgaaaaa gaaattgaag acgaattaga aaacatctac | 300 |
| agagatacta ataacaacga cgcagacact gatttgtaca ccactgcctt gagattcaga | 360 |
| ttattgcgtg agcatggttt tgatatttct tgcgaagctt tcaacaagtt gaaagacgaa | 420 |
| gagggtaatt tcaaggcttc cttaacctct gatgtcagag gtttgttgga attgtatcag | 480 |
| gcttcctaca tgagaatcca cggtgaagat attttggatg aagctatatc tttcacaact | 540 |
| gctcaattaa cttagctt accaactttg atcctccat tgtctgagca agttggtcat | 600 |
| gccttgaagc agtcaatacg tagaggtttg ccaagagttg aagccagaaa ctttatctct | 660 |
| atttaccaag acttggaatc ccacaataag tctttattag aatttgctaa aattgatttc | 720 |
| aacttattgc aattgttaca cagaaaggag ttgtccgaaa tctgtagatg gtggaaagac | 780 |
| ttggatttta ccagaaagtt acctttcgct agagatcgtg tcgttgaagg ttatttctgg | 840 |
| atcatgggtg tctacttcga accacaatac tccttgggta gaaagatgtt gaccaaagtt | 900 |
| attgctatgg cctctattgt tgacgatact tatgactcat ttgcaaccta cgacgaattg | 960 |
| ataccatata cagacgctat tgaaagatgg gatatcaagt gtatgaacca attgccaaat | 1020 |
| tatatgcaaa tatcttacaa ggctttgtta gacgtttacg aggaaatgga caattgttg | 1080 |
| gctgataagg gtagacaata tagagtcgag tacgcaaaaa aagccatgat cagattggtt | 1140 |
| caggcctact tattagaggc taagtggacc catttgaact acaagcctac ttttgaagag | 1200 |
| ttcagagaca tgctttacc aacctccggt tatgccatgt tggctatcac tgcattcgtt | 1260 |
| ggtatgggtg aagtcattac accagaaact tttgaatggg ctgcctctga tccaaagatt | 1320 |
| attaaggctt ctactatcat ctgccgtttc atggatgata ttgctgaaca caaattcaac | 1380 |
| cacagaagag aggacgattg ttccgctatt gaatgttaca tgaaacaata cggtgctaca | 1440 |
| gcccaagaag catacgacga atttaacaag catatcgaat catcttggaa ggacgttaat | 1500 |
| gaagaatttt taaagcctac cgaaatgcca acaccagtct tgtgtagatc tttgaacttg | 1560 |
| gcaagagtta tggatgtctt gtaccgtgaa ggtgatggtt atactcatgt cggtaaggct | 1620 |
| gctaaaggtg gcatcacctc cttgttgatc gaccctattc aaatttaa | 1668 |

<210> SEQ ID NO 73
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 73

| | |
|---|---|
| atggcctcac aggcttccca agttttagca tctcctcacc cagctatatc ttccgaaaac | 60 |
| cgtccaaagg ctgatttcca tccaggtatc tggggcgaca tgtttattat ctgtccagat | 120 |
| acagacattg atgccgctac cgagttgcaa tatgaagaat tgaaagccca agtcagaaag | 180 |

```
atgatcatgg aaccagttga cgattctaat caaaagttgc ctttcattga cgctgtccaa    240
agattgggtg tttcatacca ctttgaaaaa gaaattgaag acgaattaga aaacatctac    300
agagatacta ataacaacga cgcagacact gatttgtaca ccactgcctt gagattcaga    360
ttattgcgtg agcatggttt tgatatttct tgcgatgctt tcaacaagtt gaaagacgaa    420
gaaggtaatt tcaaggcttc cttaacctct gacgtcccag gtttgttgga attgtatgag    480
gcttcctact taagagttca cggtgaagat atcttggatg aagctatatc tttcgccact    540
gctcagttaa ccttggcttt accaactttg catcacccat gtctgagca agttggtcac     600 gcattgaagc aatcaatcag aagaggtttg ccaagagttg aagctagaaa ctttatctct    660
atttaccaag atttagaatc ccacaataag tctttattag aatttgccaa aattgatttc    720
aacttgttgc aattgttaca ccgtaaggag ttgtccgaaa tatgtagatg gtggaaagac    780
ttagatttta caagaaagtt acctttcgct agagatagag tcgttgaagg ttatttctgg    840
attatgggtg tctacttcga accacaatac tccttgggta gaaagatgtt gaccaaagtt    900
attgctatgg cttctatcgt tgacgatact tatgactcat ttgccactta cgacgaattg    960
atcccttata cagacgctat tgaacgttgg gatatcaagt gtatgaacca gttgccaaat   1020
tatatgcaaa tatcttacaa ggctttgtta gacgtttacg aggaaatgga acaattgttg   1080
gctgataagg gtagacaata tagagtcgag tacgccaaaa aagcaatgat tagattggtt   1140
caggcctact tattagaggc taagtggacc catttgaact acaagcctac atttgaagag   1200
ttcagagaca atgctttacc aacttccggt tatgccatgt tggctataac cgcattcgtt   1260
ggtatgggtg aagtcattac cccagaaact tttgaatggg ccgcttctga tccaaagatt   1320
atcaaggctt ctactatcat ctgccgtttc atggatgata ttgccgaaca taaattcaac   1380
cacagaagag aggacgattg ttccgctatt gaatgttaca tgaaacaata cggtgctaca   1440
gcccaagaag catacgacga atttaacaag cacatcgaat catcttggaa ggacgttaat   1500 gaagaattt tgaagcctac cgaaatgcca actccagtct tgtgtagatc tttgaacttg   1560
gccagagtta tggatgtctt gtacagagaa ggtgatggtt atactcatgt cggtaaggct   1620
gctaaaggtg gcatcacctc cttgttgatc gaccctattc aaatttaa              1668
```

<210> SEQ ID NO 74
<211> LENGTH: 1674
<212> TYPE: DNA
<213> ORGANISM: Artificial Sequence
<220> FEATURE:
<223> OTHER INFORMATION: Synthetic polynucleotide

<400> SEQUENCE: 74

```
atgtccatac aggttcccca aatttcttcg caaaatgcaa agtcacaagt aatgcgtaga     60
accgccaact ttcatccatc tgtgtgggga gacagattcg ctaactacac ggctgaggat    120
aaaatgaacc acgctcgcga cttgaaggaa cttaaagcgt taaggaaga agttggtaga    180 aagctgttgg ccacagctgg cccaattcaa ctcaatctaa tcgatgctat ccaaagattg    240
ggtgtcggtt atcacttcga acgagaattg aacaagcttt gcaacatttt atacaacgag    300
aagtatagcg atgacgacac tgaagatgat ttgtacagga tttctctgag atttagattg    360
ttaagacagc acggttacaa tgtctcctgc gacaaattca acatgtttaa ggatgacaaa    420
ggtaacttca aggaaagttt ggcttctgat gccttgggta tgctctcctt atacgaagcg    480
gctcatttgg gcgttcacgg tgaagatatc ttagacgaag ctattgcatt taccactact    540
```

```
catctaaagt ccgtcgctac tcacttatct aatcctctaa aggcccaagt tcgtcatgcc    600
ttgagacaac cgcttcacag aggtttgcca agattggaac acagaaggta tatcagcatt    660
taccaggatg acgcttctca ttacaaagct tgttgaccc ttgcgaagtt ggatttcaat     720
ctagttcaat cattgcacaa aaaggagcta tgtgagatct ccagatggtg aaggattta    780 gacttcgctc gtaagttgcc ttttgctaga gatagaatgg tcgaatgtta tttctggatc    840
ttgggtgtgt atttcgaacc aaactactca ctggcccgga gaatattgac caaagttatt    900
gctatgactt ctattattga tgacatctat gacgtttacg ggacaccaga agaattgaag    960
ttgttcactg aagtaatcga acgttgggac gaatcgtcaa tggaccaact accagaatac   1020
atgcaaacgt ttttcggtgc tcttttagat ttatacaatg agatagaaaa ggaaattgcc   1080
aacgaaggtt ggtcttacag agtccaatat gcaaaagaag ctatgaagat tttagttgag   1140
ggttactacg atgaatctaa gtggttccat gaaaactaca taccaaagat ggaggaatat   1200
atgcgggtag cattagttac cagcggatac acaatgttga ctaccgtcag tttctgggg    1260 atggacaaca ttgttactaa ggagacattt gattgggttt tctccagacc taaaatcata   1320
agagcatcag aaattatcgg tagattcatg gacgatatta atctcacaa attcgaacag    1380 gaaagaggtc actgtgcgtc cgctgtcgaa tgttatatga gggaacatgg cgtgtctgaa   1440
gaggaagctt gcagtgagct caagaagcaa gtcgataacg cctggaagga catcaaccac   1500
gaaatgattt tctccgaaac ttctaaggct gttcctatga gcgtgctaac cagagttttg   1560
aacttgacga gagttattga tgtcgtctac aaggaaggtg atggttatac tcatgtgggt   1620
aatgaaatga aacaaaacgt tgctgctctt ttgatcgacc aagtcccaat ttaa          1674

<210> SEQ ID NO 75
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 75
atggaaaagc agtccttgac atttgatggc gacgaggaag caaaaataga tcgtaagtcg     60
tcaaagtacc atcctagtat ttggggtgac tatttcatcc aaaattccag cttaacccac    120
gccaaagaat ctactcaaag gatgatcaag agagttgaag aactaaaggt acaagtcaaa    180
tctatgttca aggacacttc tgatttgttg caactgatga acttaattaa ctctattcaa    240
atgctaggac ttgactacca cttttgaaaat gaaatcgatg aggctctccg cttgatctat    300
gaagttgacg ataagtcata cggtctgtac gaaacgagct tgagattcca gttgttgaga    360
caacatggtt accacgtgga tggtgaagaa gctttcaaca tgcttaaaga cgaagagggt    420
aactttaagg cgtccttgac ctctgatgtt ccaggtttat tggaattata tcaagctagc    480
tacatgagaa tacatggtga agatattttg atgaagcca ttagtttcac taccgctcaa    540
ttgactttag ctcttcccac cttagacccg ccattgtcgg cacaagtctc tttgttcttg    600
gagctaccat tatgcagaag aaacaagatt ttgcttgcca gaaaatacat cttgatatat    660
caagaagatg ctatgcgtaa taatgttatt ctcgagttgg ctaagcttaa ctttaactta    720
ttgcaatcct tgtaccaaga agaactgaag aaaatctcta tctggtggaa tgacttagct    780
tttgcaaagt ctttatcttt cactagagat agagtcgttg aaggttatta ctgggtccta    840
accatctact tcgaaccaca gcactcccga gctagggtca tttgttcaaa agttttgcc     900 ttttgtccca ttatggatga catttatgac aactatggaa tccttgaaga atgtacatta    960
```

| | |
|---|---|
| ttaacagaag ctattaagag atggaaccca caagccatcg acgggttgcc tgaataccta | 1020 |
| aaagactatt acttgaagtt gttgaagact ttcgaggaat ttgaagatga gttggaattg | 1080 |
| aatgagaagt acagaatgct gtatttgcaa gatgaagtta aagctctggc tatctcatac | 1140 |
| ttacaagagg ccaagtgggg tattgaaaga cacgtaccat cgttagatga gcatcttcac | 1200 |
| aattctttga taagttccgg ctcttcgact gtgatttgtg ctagcttcgt tggtatgggt | 1260 |
| gaagttgcca cgaaggaagt cttcgattgg ttgtcctctt tcccaaaggt tgtcgaagct | 1320 |
| tgttgtgtca tcggtaggct cttgaacgat attcgttccc atgaattaga gcagggcaga | 1380 |
| gaccacacgg cttccactgt tgaatcttac atgaaggaac acgacaccaa tgtggacgtt | 1440 |
| gcctgcgaaa agttgagaga aatcgtcgaa aaggcgtgga agatctgaa caacgaatct | 1500 |
| ctaaacccta ctaaggttcc aagattgatg atagaaagaa tagtaaactt gtcaaagtcc | 1560 |
| aacgaagaaa tttacaaata caacgacacc tacactaatt ctgatactac aatgaaggac | 1620 |
| aatattagtc tagtattggt tgagtcctgt gattatttca acaaataa | 1668 |

<210> SEQ ID NO 76
<211> LENGTH: 1674
<212> TYPE: DNA
<213> ORGANISM: Artificial Sequence
<220> FEATURE:
<223> OTHER INFORMATION: Synthetic polynucleotide

<400> SEQUENCE: 76

| | |
|---|---|
| atggccagtc aggtttcaca aatgccttcc tcttctccac tatccagcaa caaagatgag | 60 |
| atgagaccaa aggctgactt tcaaccctcg atatggggcg atttgttcct gaattgccca | 120 |
| gacaagaaca ttgatgctga aaccgaaaag cgtcatcaac aattgaaaga agaagtcaga | 180 |
| aagatgatcg tggcaccaat ggctaattct acacaaaagt tggctttcat tgactctgtt | 240 |
| cagaggcttg gagtatccta ccactttact aaagaaattg aggatgaatt agaaaacatc | 300 |
| tatcacaaca ataacgacgc agaaaacgat ttgtacacga cttccctaag attcagatta | 360 |
| ttgagagaac atggtttcaa tgtctcttgt gacgttttta acaagtttaa ggatgagcaa | 420 |
| ggtaatttca agtcaagtgt tacctctgac gtccgcggtc tcttggaatt ataccaagcg | 480 |
| tcgtatttga gagttcacgg tgaagatatc ttggacgaag ctatttcgtt cacaactaat | 540 |
| catctctctt tggccgttgc ttccttagat taccctctgt ctgaagaggt ctctcacgct | 600 |
| ttgaagcaaa gcataagacg tggtcttcca agagtagaag ccagacacta tttgagcgtt | 660 |
| taccaagata tcgaatctca taacaaagtc ttgttagaat ttgctaagat tgacttcaac | 720 |
| atggttcaat tgctacatag gaaagagcta agtgaaattt caagatggtg gaaagatctc | 780 |
| gattttcaaa gaaagttacc ttatgcacgc gaccgtgtag tcgaaggtta cttctggatc | 840 |
| tccgggtttt acttcgaacc acaatacagc ttgggtagaa agatgttgac taaggttatt | 900 |
| gctatggctt ctatcgttga tgataccaat gactcctacg ccacctacga ggaattgatc | 960 |
| ccatatacta aggccattga agatgggac atcaagtgta tagacgaact gccagaatat | 1020 |
| atgaagccta gttacaaagc tttattggat gtctatgagg aaatggaaca attggtcgcc | 1080 |
| aaacacggtc gacagtacag agtggaatac gctaagaatg ctatgattcg attggcgcaa | 1140 |
| tcctacttgg ttgaagcgag atggactctt caaaactaca agccatcttt cgaagaattt | 1200 |
| aaggccaatg cttaccgac atgtggatat gctatgctag ctataaccag cttcgttggt | 1260 |
| atgggtgata ttgtcacgcc agaaactttt aaatgggctg caaatgaccc gaagattatc | 1320 |

| | |
|---|---|
| caggcttcta ctatcatctg ccgatttatg gatgatgtag ctgagcataa gttcgaacaa | 1380 |
| gaaaggggc actgtgcttc cgctgtcgag tgttacatga gagaacacgg tgtgtcagaa | 1440 |
| gaagaggcat gttctgaatt gaaaaagcaa gtcgacaacg cctggaagga cattaaccat | 1500 |
| gaaatgattt tttcggaaac ctccaaagct gtcccaatgt cggttctcac tagagttctt | 1560 |
| aacttgacta gagttatgga cgtattgtac agagaaggtg atggttatac atatgttggt | 1620 |
| aaggctgcaa agggcggtat cacctctta ttgattgaac cagttgcctt gtaa | 1674 |

<210> SEQ ID NO 77
<211> LENGTH: 1668
<212> TYPE: DNA
<213> ORGANISM: Artificial Sequence
<220> FEATURE:
<223> OTHER INFORMATION: Synthetic polynucleotide

<400> SEQUENCE: 77

| | |
|---|---|
| atggccagtc aggtttcaca aatgccttcc tcttctccac tatccagcaa caaagatgag | 60 |
| atgagaccaa aggctgactt tcaaccctcg atatggggcg atttgttcct gaattgccca | 120 |
| gacaagaaca ttgatgctga aaccgaaaag cgtcatcaac aattgaaaga agaagtcaga | 180 |
| aagatgatcg tggcaccaat ggctaattct acacaaaagt tggctttcat tgactctgtt | 240 |
| cagaggcttg gagtatccta ccactttact aaagaaattg aggatgaatt agaaaacatc | 300 |
| tatcacaaca ataacgacgc agaaaacgat ttgtacacga cttccataag attcagatta | 360 |
| ttgagagaac atggttacca cgtcgatggt gaggaagcct tcaacatgct caaggacgaa | 420 |
| gaaggtaatt ttaaggcttc tttgacctca gacgttcctg gtttgttaga actatatcaa | 480 |
| gcctcataca tgcgaatcca tggtgaagat attttggacg aagcgatctc ttttactact | 540 |
| gctcaattaa ccttggcttt gccaaccctg gatccaccgc tctctgaaga ggtcagtcac | 600 |
| gcgctaaagc aaagtattag aagaggttta ccacgtgtag aagctagaca ttatctgtcc | 660 |
| gtttaccaag acatcgaatc tcacaataaa gctctattgg aatttgccaa gattgatttc | 720 |
| aacatgttgc agttcctcca cagaaaggaa cttcagaaa tatgtcgttg gtggaaagat | 780 |
| ttggacttcc aacgcaagtt accatatgct agagatcgcg ttgtcgaggg ttacttctgg | 840 |
| atcagcggag tttactttga gccacaatac agtttgggtc ggaagatgtt aactaaagtt | 900 |
| attgctatgg cttctattgt cgatgacaca tatgactcct acgccaccta cgaagaatta | 960 |
| atcccttata ctaacgccat cgaaagatgg gacattaagt gtatcgatga aattccggaa | 1020 |
| tacatgaaac catcttacaa agctttgctt gacgtctacg aagaaatggt acaattggtt | 1080 |
| gctgagcatg gtaggcaata cagagttgaa tatgcaaaga atgccatgat tagattggct | 1140 |
| caatcttact tggtggaagc aaagtggacg ttgcaaaatt acaaacctag ctttgaggaa | 1200 |
| tttaaggcga acgtctgcc cacctgtggg tatgccatgc tggcaattac ttccttcgtt | 1260 |
| ggtatgggcg acattgtcac tcctgaaaca ttcaaatggg ctgcatccga tccaaagatc | 1320 |
| attcaagctt cgacgataat ctgtcgattc atggatgatg tcgctgagca aagttcaag | 1380 |
| cacaggagag aagatgactg ttctgccata gaatgttaca tggaagaata cggtgttacc | 1440 |
| gcccaggagg cttacgatgt cttcaacaag cacgttgaat ccgcgtggaa agatttgaac | 1500 |
| caagaatttc tcaagccaac tgaaatgcca acagaggtgt tgaacagatc acttaacctc | 1560 |
| gctcgtgtta tggacgtatt gtatagagaa ggtgatggtt atacttacgt tggtaaggct | 1620 |
| gctaagggcg gtatcacctc tttattgatc gaaccaatcg ctttgtaa | 1668 |

<210> SEQ ID NO 78
<211> LENGTH: 1677
<212> TYPE: DNA
<213> ORGANISM: Artificial Sequence
<220> FEATURE:
<223> OTHER INFORMATION: Synthetic polynucleotide

<400> SEQUENCE: 78

```
atggccagtc aggcttcaca agttttagca tctccccacc cagctatatc ctctgaaaac      60
cggccaaagg ctgatttcca tcctggtatc tggggcgaca tgtttattat ctgtccagat     120
acggacattg atgccgctac agagctgcaa tatgaagaat gaaagcgca agtccgcaag      180
atgatcatgg aaccagtaga cgattctaat caaaagctac cattcattga cgctgttcaa     240
aggctcggag tgagctacca ctttgaaaaa gaaattgaag acgaacttga aaacatctac     300
cgtgatacca ataacaacga cgcagacact gatctataca ctaccgcctt gagattcaga     360
ttattgagag agcatggttt tgatatttcc tgcgatgctt caacaagtt caaagacgaa      420
gctggtaatt tcaaggcttc gttgacttct gacgttcaag gtttgttgga attgtatgag     480
gcctcctaca tgagagtcca cggtgaagat atcctagatg aagctatatc ttttaccact     540
gctcagttaa ccttggcttt acctactttg catcacccgt tgtcagagca agttggtcac     600
gcactcaagc agagtatcag aagaggcctg ccaagagttg aagccagaaa ctttatctct     660
atttaccaag atttggaatc ccacaataag tccttgttac aattcgctaa aattgacttt     720
aaccttttac aattgctcca taggaaggaa ctcagcgaaa tttgtagatg gtggaaagat     780
cttgatttca ctagaaagtt gccttttgca cgtgaccgtg tcgtcgaagg ttatttctgg     840
attatgggag tttacttcga accacaatat agcttgggta gaaagatgtt gaccaaggtt     900
attgctatgg cttctatcgt cgatgataca tacgattctt acgctacata tgacgaattg     960
ataccatata ctaacgccat cgaaagatgg gacatcaagt gtatgaatca actgccaaac    1020
tacatgaaga ttagttacaa agcattattg aatgtatatg aggagatgga acaattgctt    1080
gcgaatcaag gtcgacagta cagagtggaa tacgctaaga aagctatgat tcggttggtg    1140
caagcctact tattagaagc gaagtggact catcaaaaact acaagccaac cttcgaagaa    1200
tttagagaca atgctttgcc gacatcaggg tatgctatgc tagctataac cgcgttcgtt    1260
ggtatgggtg aagttatcac gccagaaact tttaaatggg ccgcttctga cccaaagatt    1320
attaaggctt ccactatcat ctgccgcttt atggatgata tcgctgagca taagttcgag    1380
caagaaaggg ggcactgtgc ttccgctgtc gaatgttaca tgagagaaca cggtgtctca    1440
gaagaagagg cctgttctga attgaaaaag caggtcgaca acgcctggaa ggatattaac    1500
catgagatga ttttagtgaa acatccaaa gctgtcccaa tgagtgttct aaccagagtt    1560
ttgaacctta ctagagttat ggacgtattg tacagaaag gtgatggtta acgcatgtc    1620
ggtaaggctg caaagggtgg tatcacctct ttgttgattg accccattca aatctaa     1677
```

<210> SEQ ID NO 79
<211> LENGTH: 1650
<212> TYPE: DNA
<213> ORGANISM: Artificial Sequence
<220> FEATURE:
<223> OTHER INFORMATION: Synthetic polynucleotide

<400> SEQUENCE: 79

```
atggccgcat catttgctaa caatgtaga cctttagcta atttccaccc aactgtttgg       60
ggttaccatt tcttgtatta caacccagag ataaccaatc aggaaaagat cgaagtcgat     120
```

-continued

```
gaatacaagg aaacaattcg taagatgttg gttgaagccc ctgaagggtc cgagcaaaaa      180
ttggtcttaa tcgacgctat gcaaagattg ggtgttgcat atcactttca taacgaaatt      240
gaaacctcta ttcaaaatat cttcgatgct ccaaagcaaa caacgacga taacttgcac       300 attgtctctt taagattcag attggtccgt caacagggtc attacatgtc ctctgacgtt      360
tttaagcaat tcactaacca agatggtaaa ttcaaggaaa ccttgactaa tgatgtccaa      420
ggtttgttgt cattatatga agcttctcac ttgagagtta gaaatgaaga aatattagag      480
gaagctttga cttttaccac aactcatttg gaatccatcg tttctaactt atcaaacaaa      540
aataactctt taaaggttga agtttctgaa gctttgtccc aaccaatcag aatgactttg      600
ccaagaattg gtgccagaaa gtacatttcc atatacgaaa acaatgacgc ccacaaccat      660
ttgttgttaa agttcgctaa gttggattt aatatgttac aaaagttcca ccaaagagaa       720
ttgtccgact tgaccagatg gtggaaagac ttggactttg ctaacaagat cccatatgct      780
agagatcgtt tagtcgagtg ctattttttgg attttgggtg tttacttcga acctaaatac     840
tctcgtgcta gaaagatgat gaccaaggtc ttgaaaatga catctattat tgatgatact      900
tttgatgctt acgccaattt cgacgaattg gttccattca atgacgccat ccaaagatgg      960
gacgctaacg caatcgattc tattccacca tacatgcgtc caatctacca ggccttgtta     1020
gatatatatg gtgaaatgga ccaagtttta tccaaagagg gtaagttgga tagagtctac     1080
tatgctaagt atgagatgaa aaagttggtc agagcctact ttaaggaatc tcaatggtta     1140
aacgacgata tcatataccc taagtatgaa gaacacatgg aaaacgctat tgttactgtc     1200
ggttacatga tgggtgctac aaactgtttg gttggtatgg aggaatttat ctcaaaagaa     1260
accttcgaat ggttgatgtc agaaccagtt attgttagag catcttcctt gataggtaga     1320
gcaatggatg atatcgtcgg tcacgaggtt gaacaagaac gtggtcattg tgcttcagca     1380
gtcgaatgtt acatgagaga gcatggtgtt tctgaagaag aagcttgctc gaattaaag      1440 aagcaagttg acaacgcttg gaaggacatt aaccacgaga tgatcttctc tgaaacttct     1500
aaagctgtcc caatgtctgt cttaaccaga gttttaaact tgacaagagt tattgatact     1560
ttgtaccagg aagaagatga atacaccaac gctaagggta aattaaaaaa tatgatccac     1620
tccatcttga ttgagtcagt caagatctaa                                      1650
```

<210> SEQ ID NO 80
<211> LENGTH: 1677
<212> TYPE: DNA
<213> ORGANISM: Artificial Sequence
<220> FEATURE:
<223> OTHER INFORMATION: Synthetic polynucleotide

<400> SEQUENCE: 80

```
atggaaaagc agtctttgac atttgatggt gacgaggaag caaaaataga tcgtaagtca       60
tccaagtacc atccttctat ttggggcgac tatttcatcc aaaattcctc tttaacccac      120
gccaaagaat ctactcaaag aatgatcaag agagttgaag aattgaaggt ccaagttaaa      180
tcaatgttca aggacacttc cgatttattg caattgatga acttaattaa ctctatatcaa    240 atgttgggtt tggactacca ctttgaaaat gaaatcgatg aggctttgag attgatctat     300
gaagtcgacg ataagtccta cggtttgtac gaaacatcat taagattcca gttgttaaga     360
caacatggtt accacgttga tggtgaagaa gctttcaaca tgttgaagga tgaggaaggt     420
aactttaaag cttcttttaac ctccgacgtt ccaggtttgt tagagttgta tcaagcctct     480
tacatgcgta ttcatggtga agatatattg gatgaagcta tttcattcac taccgctcaa    540
```

```
ttaactttgg ctttgccaac tttagaccca ccattgtccg cacaagtctc tttgttcttg        600
gagttgccat tatgcagaag aaacaagatt ttgttggcca gaaaatacat cttgatatat        660
caagaagatg ctatgcgtaa taatgttatt ttggagttag ccaagttgaa ctttaactta        720
ttgcaatctt tataccaaga agaattgaag aaaatctcta tctggtggaa tgacttagct        780
tttgctaagt ctttatcttt caccagagat agagtcgttg aaggttatta ctgggtcttg        840
actatctact tcgaacctca gcactccaga gccagagtta tttgttccaa agttttgct         900 tttttgtcta ttatggatga catttatgac aactatggta tcttggaaga atgtacatta        960
ttaaccgaag ctattaagag atggaaccca caagcaatcg acgggtttgcc agaatacttg      1020 aaagactatt acttgaagtt gttaaagact ttcgaggaat ttgaagatga attagaattg       1080
aatgagaagt acagaatgtt gtatttgcaa gatgaagtta aagctttggc tatctcctac       1140
ttacaagagg ccaagtgggg tattgaaaga cacgtccctt cattagatga gcatttgcac       1200
aattctttga tatcctctgg ttcttccact gtcatttgtg cttcattcgt tggtatgggt       1260
gaagttgcta ccaaggaagt cttcgattgg ttgtcctctt tcccaaaggt tgtcgaagcc      1320
tgttgtgtta tcggtagatt gttgaacgat attcgttccc atgaatttga gcaggaaaga      1380
ggtcactgcg cttccgctgt tgaatgttac atgagagaac acggtgtctc tgaagaagaa      1440
gcctgctcag aattgaagaa gcaagttgac aacgcatgga agatataaa ccatgaaatg       1500 atattctctg aaacatctaa ggccgttcct atgtcagtct tgaccagagt tttgaacttg      1560
acccgtggta atgaagaaat ctacaagtac aacgatactt atactaattc agacaccacc      1620
atgaaagaca acatctcctt ggtcttggtt gaatcttgtg actatttcaa caagtaa         1677
```

<210> SEQ ID NO 81
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 81

```
atgtccatac aggttcccca aatttcttcg caaaatgcaa agtcacaagt aatgcgtaga         60
accgccaact ttcatccatc tgtgtgggga gacagattcg ctaactacac ggctgaggat        120
aaaatgaacc acgctcgcga cttgaaggaa cttaaagcgt taaaggaaga agttggtaga       180
aagctgttgg ccacagctgg cccaattcaa ctcaatctaa tcgatgctat ccaaagattg       240
ggtgtcggtt atcacttcga acgagaattg aacaagctt tgcaacattt atacaacgag        300
aagtatagcg atgacgacac tgaagatgat ttgtacagga tttctctgag atttagattg       360
ttaagacagc acggttacaa tgtctcctgc gacgccttca acagatttaa agataccaag       420
ggtagtttca aggaagactt gatcaaagat gttaactcta tgctctgttt atacgaagca       480
actcatttgc gggttcacgg tgaagatatt ttggacgaag ctttgggatt acaacttcc       540 caactaaagt ccatcttacc taagttaaaa ccattgctgg cttctcaagt catgcatgcc       600
ttgaagcaac cgctacaccg tggtttgcca agactcgaac acagaaggta tattagcatt       660
taccaggatg acgcttctca ttacaaagcc ttgttgactc ttgcgaagtt ggatttcaat       720
ctagttcaat cattacacaa aaaggagctc tgtgagatct ccagatggtg aaggattta       780 gacttcgctc gtaagttgcc ttttgctaga gatagaatgg tcgaatgtta tttctggatc      840
ttgggtgtgt atttcgaacc aaactactca ctggctagaa gaatattgac caaagttatt      900
```

| | |
|---|---:|
| gctatgacct ctattatcga tgacatttat gacgtttacg gcactccaga agaattgaag | 960 |
| ctattcactg aagtaatcga acgttgggac gaatcgtcaa tggaccaact gccagaatac | 1020 |
| atgcaaacgt ttttcggtgc tttgttagat ttatacaatg agatagaaaa ggaaattgca | 1080 |
| aacgaaggtt ggtcttacag agtccagtat gcgaaagaag ctatgaagat tttggttgag | 1140 |
| ggttactacg atgaatctaa gtggttccat gaaaattaca tacccaagat ggaggaatat | 1200 |
| atgcgggtag ccttagttac cagcgggtac acaatgttga ctaccgtcag ttttctgggg | 1260 |
| atggacaaca tcgttactaa ggagacattt gattgggttt tctccagacc taagataatc | 1320 |
| cgagccagtg aaattattgg tagattcatg gacgatatca aatctcataa gtttgaacaa | 1380 |
| gagagaggtc acgctgcaag cgctgtcgaa tgttatatga agcaacacgg tctctcagaa | 1440 |
| caagaagtct gtgaagaact ttacagacaa gtctccaacg cttggaagga catcaatgag | 1500 |
| gaatgcttga atccaaccgc tgttccaatg ccattgttga tgagagcact aaacttggca | 1560 |
| cgcgtaatcg acgtagttta taagaaggt gacggttaca ctcacgttgg taacgaaatg | 1620 |
| aagcaaaacg tggctgctct acttattgat caagtaccaa tctaa | 1665 |

<210> SEQ ID NO 82
<211> LENGTH: 1680
<212> TYPE: DNA
<213> ORGANISM: Artificial Sequence
<220> FEATURE:
<223> OTHER INFORMATION: Synthetic polynucleotide

<400> SEQUENCE: 82

| | |
|---|---:|
| atgtccgcag cgcaagtcag tcctgctcca gttccagccc acaatgctgc tgcttctaag | 60 |
| gaagaggtgc gtagatcggc cggatatcat ccatcattct ggggtgaatt tttccttact | 120 |
| cacacaagcg aatacgctaa aaaggacgat aagattcaga acaacatga gaattgaag | 180 |
| caagaggtta agggcatgct agtagatgct acgaccgaac ccactaaaaa gttagaattg | 240 |
| atagacgcca tcctgagatt gggtgtcggt taccactttg aagatgagat tcaagctgaa | 300 |
| ttggaaagga tccacagact cggtgactta gattgcgact tgtataacac ctgtatttgg | 360 |
| ttcagagttc ttagaggtca aggttttact gtctctgctg aagaatttaa caagttcaaa | 420 |
| aattccgacg gaaacttcaa ggaagatttg atcaatgacg tttctggtat gttgtgttta | 480 |
| tacgaagcca cccatttgcg ggttcacggt gaggatattt tggatgaagc gctcgaattt | 540 |
| actaccacac gtttaaagtc tatcttacca gacttggaac cgccattggc tactcaagta | 600 |
| atgcacgcac tagaactacc ttaccataag ggtatgcaga gattggaagc ccgacaatac | 660 |
| attccaatct atgaagccga tatgactaaa aacatcagct tgttgcattt cgctaagctt | 720 |
| gatttcaacc tgttacaggc tctccaccaa tccgaaatca gagagataac ccgctggtgg | 780 |
| aaagatcttg actttaaaac tagattgcca tatgctagag atcgcttagt cgaatgttac | 840 |
| ttctggattc taggcgttca atacgagcca aatacagta tgtctcggtt gttttaacc | 900 |
| aaggttattt cattggcttc tgtcttcgat gacacatatg acatttacgg taccttcgaa | 960 |
| gaattaaagt tgttgactga cgccatagaa agatgggaga tcgaagcaac agattccttg | 1020 |
| ccgtcttaca tgcaaatttt atatcgcgct ttgctggacg tcttcgatga atacaaggat | 1080 |
| aaattgatta acgttcaagg gaaggactat tgtttgtatt acggtaaaga agcgatgaag | 1140 |
| ggtttgattc gtagctacca cactgaagct gtgtcgtttc ataccggcta tgttcagaat | 1200 |
| ttcgaggaat acttagacaa ctccgcagtt tcctctggtt acccaatgct gacggttgaa | 1260 |
| gctttgattg gtatgggaca cccttacgct actaaggaag ctttagattg gcattgaag | 1320 |

```
gtgccaagag ttatcaaggc tagttcagac atctgtagat tagtcgatga cttaaggacg    1380
tacaaggtcg aggaggaaag aggtgatgct ccctcggggg tccattgcta catgagagac    1440
tataatgtct cagaagaaga agcatgttct aagatcgaag aaatgatcga tctggcctgg    1500
aaagctataa acgaagaaat gcaaaagcca ggtcatctac cactaccaat cttgttgcct    1560
gccttgaact tcactagaat gatggaggtc ctttaccaaa atattgatgg ttatacaaat    1620
tccggtggta gaaccaagga cagaatcacc tctttgttgg ttcacccaat tactatttaa    1680
```

<210> SEQ ID NO 83
<211> LENGTH: 1653
<212> TYPE: DNA
<213> ORGANISM: Artificial Sequence
<220> FEATURE:
<223> OTHER INFORMATION: Synthetic polynucleotide

<400> SEQUENCE: 83

```
atgtcctcag caaaattggg ttctgcttct gaagatgtca accgtagaga cgctaattac      60
catccaaccg tttggggaga tttctttta acacactcct ctaacttctt ggagaacaat     120
gactcaatat tggaaaagca cgaagaattg aagcaagagg ttagaaactt attggtcgtt     180
gaaacttctg acttgccttc caagattcag ttgactgatg aaattatcag attaggtgtc     240
ggttatcatt ttgagaccga aatcaaagcc aattagaaaa agttcacgta tcatcaattg     300
cacttgaact tcgacttgtt gaccacatct gtttggttca gattattgag aggtcacggt     360
ttttccattt cttccgacat cttcaataag ttcaaaaatt cagatggtaa ctttaaggaa     420
gatttaatca acgacgtttc tggtatgttg tgcttgtacg aagctactca tttgcgtgtc     480
cacggtgaag atattttaga cgaagccttg gaatttacta ctaccagatt gaagtctatt     540
ttgccagatt tagaaccacc attaaatgaa tgtgtcagag acgctttgca tattccttat     600
cacagaaacg ttcaacgttt ggctgcaaga caatacatac cacagtacga tgccgaacca     660
acaaaaatcg agtctttgtc attattcgct aagattgatt caacatgtt gcaagctttg     720 catcaaagag aattgagaga ggcttccaga tggtggaaag aatttgactt cccttctaag     780
ttaccatatg ccagagatcg tatcgctgaa ggttactact ggatgatggg tgcccacttt     840
gaaccaaagt tctcattgtc tcgtaagttc ttaaacagaa tcattggtat cacttcttta     900
attgatgaca cctatgatgt ttacggtact ttggaggaag ttactttgtt taccgaagct     960
gttgaaagat gggacattga agctgtcaag gacattccaa atacatgca agtcatctat    1020 acaggtatgt taggtatatt tgaagatttc aaagacaact tgataaatgc tagaggtaag    1080
gattactgta tcgactatgc aatcgaggtt ttcaaagaaa tcgttagatc ctaccaaaga    1140
gaagctgaat atttccacac cggttacgtt ccatcctacg atgaatacat ggaaaactct    1200
attatatctg gtggttacaa gatgttcatt atcttaatgt taatcggtag aggagaattt    1260
gagttgaagg aaactttgga ctgggcttcc actattcctg aaatggtcga ggcatcttcc    1320
ttgatcgctc gttatattga cgacttgcaa acctataaag ctgaagaaga gagggagaa    1380 accgtctccg cagtcagatg ttacatgcgt gaatttggtg tttcagaaga caagcctgt    1440 aagaagatga gagagatgat cgaaattgaa tggaagagat tgaataaaac aactttagaa    1500
gctgacgaaa tttcttcatc tgtcgttatt ccatcattga acttcaccag agttttggag    1560
gtcatgtacg ataagggtga tggttactct gattcccaag gtgttactaa agaccgtatc    1620
gccgctttat tgagacacgc catcgaaatc taa                                   1653
```

<210> SEQ ID NO 84
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 84

| | |
|---|---|
| atggccagtc aggtttcaca aatgccttcc tcttctccac tatccagcaa caaagatgag | 60 |
| atgagaccaa aggctgactt tcaaccctcg atatggggcg atttgttcct gaattgccca | 120 |
| gacaagaaca ttgatgctga aaccgaaaag cgtcatcaac aattgaaaga agaagtcaga | 180 |
| aagatgatcg tggcaccaat ggctaattct acacaaaagt tggctttcat tgactctgtt | 240 |
| cagaggcttg gagtatccta ccactttact aaagaaattg aggatgaatt agaaaacatc | 300 |
| tatcacaaca ataacgacgc agaaaacgat ttgtacacga cttccctaag attcagatta | 360 |
| ttgagagaac atggtttcaa tgtctcttgt gacgccttta acagatttaa ggataccaaa | 420 |
| ggttcattca aggaagactt gatcaaggat gttaattcca tgttgtgttt atacgaagcg | 480 |
| actcaccttc gagttcatgg tgaggatatt ttggacgaag ctttgggttt cacaacctct | 540 |
| caactcaaat caatcttacc taagttaaag ccattgctgg cttcgcaagt catgcacgct | 600 |
| ttgaagcaac cgctaagacg tggtttgcca agagttgaag ccagacacta tttgagcgtt | 660 |
| taccaagata ttgaatctca taacaaagtc ttgttggaat ttgctaagat cgacttcaac | 720 |
| atggttcaac ttctccatag gaaggagctc agtgaaatta gtagatggtg aaagatttta | 780 |
| gacttccaac gtaaattgcc atacgctaga gatcgcgttg tcgaaggtta tttttggatt | 840 |
| agtggggtat acttcgaacc gcaatattcc ctgggtagaa agatgttaac taaggttatt | 900 |
| gccatggctt ctatcgtcga cgatacctac gattcttacg caacttatga ggaattaatc | 960 |
| ccatacacca aagctataga aagatgggat ataaagtgta tagacgaatt gcctgagtat | 1020 |
| atgaagccat catacaaggc tttgttggac gtgtacgaag aaatgaaaca gttagttgcc | 1080 |
| aaacacggtc ggcaatacag agttgaatat gctaagaatg ctatgatccg gctagcccaa | 1140 |
| tcttatctgg tcgaggctag atggactcta caaaactaca agccttcctt cgaagaattt | 1200 |
| aaggctaacg cattgccaac ttgtggttac gctatgttgg cgatcacttc tttcgttggt | 1260 |
| atgggcgaca ttgttacccc agaaacattt aagtgggccg cgaacgatcc aaagattatt | 1320 |
| caagcttcaa cgataatctg ccggtttatg gatgacgtcg ccgaacacaa gttcaaacat | 1380 |
| aggagggaag acgattgttc tgctatcgag tgttatatgg aagaatacgg agtaactgcc | 1440 |
| caggaggcct acgacgtctt caataagcac gtggaatcag cttggaagga tgttaataag | 1500 |
| gaattttga agcccaccga gatgcctacg gaagtgctga acagatcttt gaacctcgca | 1560 |
| agagttatgg atgtcttgta cagagaaggt gatggttata cttatgtggg taaggctgct | 1620 |
| aaaggtggga ttacctccct attgatcgaa ccagtcgctt tataa | 1665 |

<210> SEQ ID NO 85
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 85

| | |
|---|---|
| atggccagtc aggtttcaca aatgccttcc tcttctccac tatccagcaa caaagatgag | 60 |
| atgagaccaa aggctgactt tcaaccctcg atatggggcg atttgttcct gaattgccca | 120 |

```
gacaagaaca ttgatgctga aaccgaaaag cgtcatcaac aattgaaaga agaagtcaga      180
aagatgatcg tggcaccaat ggctaattct acacaaaagt tggctttcat tgactctgtt      240
cagaggcttg gagtatccta ccactttact aaagaaattg aggatgaatt agaaaacatc      300
tatcacaaca ataacgacgc agaaaacgat ttgtacacga cttccataag attcagatta      360
ttgagagaac atggttacaa tgtctcttgt gacatcttta acaagttcaa gaatagcgat      420
ggtaacttca aggaagactt gattaatgat gtttcaggta tgctctgttt atatgaagcg      480
acccacttgc gagttcatgg tgaggatatc ttagacgaag ctttggaatt tacaactact      540
cgcctaaaat ctattttgcc tgacttagaa ccaccctgg ccacccaagt catgcacgct      600
ttgaagcaaa gcatcagacg tggtcttcca agagttgaag ccagacacta cttgagtgtt      660
tatcaagata ttgaatctca taacaaagct ttgttggaat ttgctaagat tgatttcaac      720
atgttacaat cctacatag aaggagcta tcggaaatct gtagatggtg aaagatctc       780 gattttcaaa gaaagttacc ttacgcacgg gaccgtgtcg tcgaaggtta tttctggatt      840
tccggggttt acttcgaacc acaatacagt ttgggtagaa agatgttgac taaggttatt      900
gctatggctt ctatcgtcga tgacacctac gattcttacg ccacctatga ggaattgata      960
ccatatacta acgccatcga aagatgggac atcaagtgta tagacgagat cccagaatac     1020
atgaagcctt cgtataaagc tttattggat gtatacgagg aaatggtgca attggttgcc     1080
gaacacggta gacagtacag agtggaatac gctaagaatg ctatgattcg ccttgcgcaa     1140
tcctacttgg ttgaagcgaa atggactctc caaaactaca agccatcttt cgaagaattt     1200
aaggccaatg ctttaccgac atgcggatat gctatgctag ctatcaccag cttcgttggt     1260
atgggtgata ttgtcacgcc agaaactttt aaatgggctg catctgaccc aaagattatt     1320
caggcttcca ctatcatctg taggttcatg gatgatgttg ctgaacataa gtttaagcac     1380
agaagagaag acgactgttc agctattgaa tgttacatgg aagaatacgg cgtcaccgcg     1440
caagaagcct acgacgtatt caacaaacac gtcgagtcgg catggaagga tctgaaccaa     1500
gaatttctaa aacccactga gatgccaaca gaagttctca acagaagttt gaacttggct     1560
agagtaatgg acgttttgta tagagagggt gatggttata cttatgttgg taaagccgct     1620
aagggtggca ttacctcatt gcttatcgag ccaatcgctt tgtaa              1665
```

<210> SEQ ID NO 86
<211> LENGTH: 1629
<212> TYPE: DNA
<213> ORGANISM: Artificial Sequence
<220> FEATURE:
<223> OTHER INFORMATION: Synthetic polynucleotide

<400> SEQUENCE: 86

```
atggaaagta ggcgttcagc aaattatcag gcttccatat gggagacaaa ctttactaac       60
tctccacttt tatctaagtt gcaaaatgaa ctgtcggtcg cccatctcga agaattgaaa      120
ctagaggtga agcaattaat ctggagcacg aaggatccct tattcctttt gaaattcatt      180
gactccattc aaagattggg cgttgcttac cactttgaag aagaaatcaa ggaatctttg      240
cacctggtct acctggaaga gcgaaacggt gatcatcaac actataagga aaaaggattg      300
catttcaccg ctttgagatt cagaatattg agacaggacg gttaccacgt accacaagat      360
gttttttctt cattcatgaa taaggctggt gactttgaag aagtttatc caaagacact      420 aagggtttgg tctctttgta cgaagcctcc tacctctcta tggaaggtga aaccattttg      480
```

```
gatatggcca aggatttctc ctctcaccat ttacacaaga tggttgaaga tgctactgac    540
aaaagagttg ctaaccaaat cattcatagc ttggagatgc cttttgcatag aagagttcaa    600 aagctagagg ctatctggtt catccaattt tatgaatgcg gttccgacgc caacccgacc    660
ttggtcgaat tggcgaaatt agattttaat atggtgcaag ctacttacca agaagaatta    720
aagcgtctat ctaggtggta cgaggaaacc ggtctccaag aaaagttgtc tttcgctcgt    780
cacagattgg ctgaagcttt cttgtggtct atgggcatta ttcctgaagg tcatttcgga    840
tatggcagaa tgcaccttat gaagatcggt gcatacatta ccttattgga tgatatttat    900
gacgtttatg gtactttgga agaattgcaa gtattgacag aaatcatcga agatgggat     960 attaaccttt tggaccagtt gccagaatac atgcaaatat tcttcctcta catgtttaac   1020
tctacaaatg aactagctta cgaaatctta agagaccaag gtattaatgt catatccaac   1080
cttaaaggtc tttgggtcga actgtcacaa tgttatttca aagaagccac gtggttccac   1140
aacggttata ccccaaccac tgaggaatac ctaaacgttg cttgtatttc agcgtccggt   1200
ccagttatct tgttttcggg atactttact actacaaatc caatcaacaa gcatgaattg   1260
caatctttag aaagacacgc tcactcctta gtatgatct taagactagc ggatgaccta    1320
ggtacttctt cggatgagat gaagcggggt gatgttccta aggctattca atgtttcatg   1380
aacgacacgg ggtgttgcga agaagaagcc agacagcacg ttaagagatt gattgacgca   1440
gaatggaaga agatgaataa ggatatcttg atggagaagc catttaaaaa cttctgtcca   1500
actgcaatga atttaggccg tatcagtatg tctttctacg agcacggtga cggttacggc   1560
ggtccacatt ctgataccaa aaagaagatg gtctcgttgt tgttcaacc catgaatatt    1620 accatttaa                                                          1629

<210> SEQ ID NO 87
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 87
atggaatcac agactacatt caaatatgag tctttagcat ttaccaagtt gtcccattgc     60
caatggactg attacttctt gtctgttcca atagacgaat ccgaattgga cgtcatcacc    120
agagaaattg atattttaaa gcctgaggtt atggaattgt tatcttcaca aggtgatgac    180
gaaacatcta agcgtaaagt cttgttgatc caattgttgt tatctttggg attagccttt    240
cacttcgaaa acgagattaa gaatatcttg gaacacgctt tcagaaagat tgatgacatc    300
actggtgacg aaaaggattt gtccaccatt tccataatgt ttagagtttt cagaacttac    360
ggtcataact tgccatcctc tatctttaat aaattcaaaa actcagatgg taatttcaag    420
gaagacttga taaacgatgt ttctggtatg ttgtgtttat acgaagctac tcacttgaga    480
gtccatggtg aagacatttt agatgaagct ttagagttta ccactacccg tttgaagtct    540
atcttgccag gtggtacttg tagacctcac atttaagat tgattagaaa cactttatat    600
ttgccacaaa gatggaacat ggaagccgtc atcgctcgtg aatacatatc cttttacgaa    660
caagaggaag accacgataa gatgttattg agattggcta agttgaattt caaattgtta    720
cagttgcatt atattaagga attgaagtca ttcatcaaat ggtggatgga attgggttta    780
acatctaaat ggccatctca atttagagag cgtatcgttg aagcctggtt agctggtttg    840
atgatgtact ttgaaccaca attctccggt ggtagagtta ttgcagctaa gttcaactat    900
```

| | | | | |
|---|---|---|---|---|
| ttattgacca | ttttggatga | tgcttgtgat | cactacttct caattcatga attgaccaga | 960 |
| ttggtcgctt | gtgttgaaag | atggtctcca | gacggtatcg atacattgga ggacatctcc | 1020 |
| cgttctgtct | ttaagttaat | gttggatgtt | tttgacgata tcggtaaggg tgttagatcc | 1080 |
| gaaggttctt | cctatcactt | gaaagaaatg | ttggaagaat aaatactttt agttagagca | 1140 |
| aatttggact | tggttaaatg | ggccagaggt | atccaagtcc catctttcga gagcatgtt | 1200 |
| gaggttggtg | gtattgcttt | aacatcctac | gccactttga tgtactcttt cgtcggaatg | 1260 |
| ggtgaaaccg | ctggtaagga | agcctacgaa | tgggttcgtt ccagacctcg tttgataaag | 1320 |
| tctttggcag | ctaaaggtag | attgatggac | gacattactg attttgattc agatatgtct | 1380 |
| aacggtttcg | ctgctaacgc | aattaactat | tacatgaagc aattcgtcgt taccaaggaa | 1440 |
| gaagccatct | tagaatgcca | gagaatgatc | gtcgacatca acaagaccat taatgaagag | 1500 |
| ttgttaaaaa | ctacatctgt | tcctggtaga | gtcttgaagc aagctttgaa cttcggtaga | 1560 |
| ttattggaat | tgttgtacac | taaatctgac | gacatctata attgttccga aggtaagtta | 1620 |
| aaggaataca | ttgttacttt | gttgatcgat | ccaataagat tgtaa | 1665 |

<210> SEQ ID NO 88
<211> LENGTH: 1644
<212> TYPE: DNA
<213> ORGANISM: Artificial Sequence
<220> FEATURE:
<223> OTHER INFORMATION: Synthetic polynucleotide

<400> SEQUENCE: 88

| | | | | |
|---|---|---|---|---|
| atgtcctcag | caaaattggg | ttctgcttct | gaagatgtca ccgtagaga cgctaattac | 60 |
| catccaaccg | tttggggaga | tttctttta | acacactcct ctaacttctt ggagaacaat | 120 |
| gactcaatat | tggaaaagca | cgaaggtttg | aacaaaaga ttagaactat gttaatctct | 180 |
| cctaccgata | ctatctccaa | gaaattatct | ttgattgacg ccgttcagag attgggtgtc | 240 |
| gcttatcatt | ttgagaagga | aattgaagat | gaaatcgaaa agttatcatg taaagagtac | 300 |
| aacgacggta | tgacttgca | aaccgtcgcc | ttgagattca gattattgag acaacaaggt | 360 |
| tatttcgttt | cctgcgatgt | ttttaagcgt | ttcaagaaca ctaagggtga atttgagact | 420 |
| gaagatgcta | aacattgtg | gtgtttatac | gaagctactc acttgagagt tgacggtgaa | 480 |
| gatattttgg | aagaagctat | ccaattctct | cgtaagaaat tagaagcatt gttgccagaa | 540 |
| ttatcctttc | cattgaatga | atgtgttaga | gatgccttgc atatcccata ccacagaaac | 600 |
| gtccagagat | tggctgcacg | tcaatatata | ccacaatacg acgctgagcc taccaagatt | 660 |
| gaatccttat | ctttgttcgc | taagattgac | tttaatatgt tgcaggcctt gcaccaaaga | 720 |
| gaattgagag | aagcttccag | atggtggaag | gagttcgatt ttccatctaa attgccttat | 780 |
| gcccgtgata | gaatcgctga | aggttactac | tggatgatgg gtgctcattt cgaaccaaaa | 840 |
| ttttctttgt | ctcgtaagtt | cttaaacaga | atcattggta taacctcctt aattgatgat | 900 |
| acttatgacg | tctacggtac | tttagaagaa | gttaccttgt tcaccgaagc cgttgaaaga | 960 |
| tgggatattg | aggctgtcaa | agacatccca | aagtacatgc aagttatata cacaggtatg | 1020 |
| ttaggtattt | tcgaagattt | caaagacaat | ttgattaacg ccagaggtaa ggattattgc | 1080 |
| atcgattacg | ctatcgaagt | tttcaaggag | attgtcagat cttaccaaag agaagcagaa | 1140 |
| tactttcaca | ctggttacgt | tccatcttat | gacgaataca tggaaaactc aattatctca | 1200 |
| ggtggttaca | aaatgtttat | aatcttgatg | ttaatcggta gaggtgagtt cgaattgaaa | 1260 |

```
gaaaccttag attgggcttc aactattcca gaaatggtcg aagcttcttc cttgatagct      1320
agatacatcg acgatttgca aacatacaag gccgaagaag aacgtggtga aacagtttca      1380
gcagtcagat gttacatgag agagtttggt gtttctgagg aacaagcttg taagaagatg      1440
agagaaatga ttgagatcga atggaagaga ttgaacaaga ctaccttgga agctgacgaa      1500
atttcttctt ccgttgttat tccatctttg aactttacta gagtcttgga agtcatgtat      1560
gacaagggag acggttattc tgattcccaa ggtgttacca aggatcgtat tgctgctttg      1620
ttaagacacg ccattgagat ataa                                            1644

<210> SEQ ID NO 89
<211> LENGTH: 1704
<212> TYPE: DNA
<213> ORGANISM: Artificial Sequence
<220> FEATURE:
<223> OTHER INFORMATION: Synthetic polynucleotide

<400> SEQUENCE: 89
atgcgtgact tgaaatccgt cttatcttca aaggaatcta caaaggcaga tgttaataga       60
agatcctcta actatcaccc ttccatctgg ggtgatcatt tcattaacgt ttcttcaaat      120
gagaagtaca ctaacactga agtcgaaaaa agatttgaaa ccttgaaggc cgaaatagaa      180
aagttgttag tttctaacaa caccgcttgg aagaccttgg aggaaattgt cgctatcgtt      240
aatcagttgc aaagattagg gttggcttac cacttcgaaa accaaatcaa agaagccttg      300
caatccattt atgactctca tgtcaacggt aattgcgacg ttaattacga tcacaacaac      360
gatttgtaca tagtcgcttt aagatttcgt ttgttgagac aacacggtta taaagtctct      420
gctgacattt tcaagaagtt tagagatgaa aagggtgaat ttaaggctat gttaacaaat      480
gacgccaaag gttgttgtg tttatacgaa gcatcctatt tgagagttca aggtgaaaat      540
atcttagaag aggcttgtga atttctcgt aagcatttga agtcattatt gtctcacttg      600
tccacctcat ggctgagca agttaagcac tctttggaaa tcccattaca tagaggtatg      660
ccaagattgg aagctagaca ttacatttct atttacgagg aagataactc ctctcgtaat      720
gaattgatat tagagttggc aaagttggac ttcaacttgt tgcaggcctt acacagaaga      780
gaattgggtg aaatttctcg ttggtggaaa gatattgatt tcgctactaa attgccattc      840
gccagagaca gattagttga atgttacttc tggatcttgg gtgtttattt tgaacctaaa      900
tactccatca ctagaaagtt catgactaag gttatcgcta ttgcttccgt catcgatgat      960
atatacgacg tttatggtac cttggaggaa ttgaagttgt tcactcatgc tattgaaaga     1020
tgggaaactg tcgctgccaa cgaattacca agtacatgc aagtttgtta ctttgctttg     1080
ttagacgtct ttaaggaaat ggaagataaa ttagtcaata aaggtttgtt atactccatg     1140
ccatgtgcaa aggaggctgt taaaggtttg gttagagctt acttcgttga ggctgaatgg     1200
ttcaacgcta actatatgcc aaccttcgaa gaatatatgg aaaactcaac tatgtcctct     1260
ggttatccaa tgttggctgt cgaagctttg atcggtattg aagacgcaac tatttcaaag     1320
gaagccttcg attgggcaat atctgttcct aaaattatcc gttcatgcgc attgatcgcc     1380
agattggtcg atgacattca cacctacaag gtcgaacaag agagaggtga tgccccatct     1440
tccgtcgaat gttacatgca acaatacgac gtttctgagg aagaagcctg taatagaatt     1500
aagggtatgg ttgaaattga atggatgaat ataaacgagg aaatccagga tccaaaccac     1560
ccacccttta caatggttgtt gccatctttg aacttagctc gtatgatggt cgttttgtac     1620
caaaatggtg acaactatac aaactcctcc ggtaaaacca aggatagaat tgcttccttg     1680
```
ttggtcgacc ctttgccaat gtaa                                         1704

<210> SEQ ID NO 90
<211> LENGTH: 1704
<212> TYPE: DNA
<213> ORGANISM: Artificial Sequence
<220> FEATURE:
<223> OTHER INFORMATION: Synthetic polynucleotide

<400> SEQUENCE: 90
atgcgtgact tgaaatccgt cttatcttca aggaatcta caaaggcaga tgttaataga      60
agatcctcta actatcaccc ttccatctgg ggtgatcatt tcattaacgt ttcttcaaat    120
gagaagtaca ctaacactga agtcgaaaaa agatttgaaa ccttgaaggc cgaaatagaa    180
aagttgttag tttctaacaa caccgcttgg aagaccttgg aggaaattgt cgctatcgtt    240
aatcagttgc aaagattagg gttggcttac cacttcgaaa accaaatcaa agaagccttg    300
caatccattt atgactctca tgtcaacggt aattgcgacg ttaattacga tcacaacaac    360
gatttgtaca tagtcgcttt aagatttcgt ttgttgagac aacacggtta taaagtctct    420
gctgacattt tcaagaagtt taaagatgaa aagggtgaat ttaaggatat gatcagaaat    480
gacgccagag gtttattgtg tttatacgaa gcatcccatt tgagagttaa gggtgaagat    540
attttagaag aggctactga attttctcgt aagcacttga agtcattgtt accacaattg    600
tccacatcat tggctgagca agttaagcac tctttggaaa tcccattaca tagaggtatg    660
ccaagattgg aagctagaca ttacatttct atttatgagg aaaacaactc ctctcgtaat    720
gaattgttgt tagagttggc aaagttggac ttcaacttgt tgcaggcttt acacagaaga    780
gaattgggtg atatttctcg ttggtggaaa gacatcgatt tcgccactaa attgccattc    840
gccagagaca gattagttga atgttacttc tggatcttgg gtgtttattt tgaacctaaa    900
tactccatta ctagaaaatt catgaccaag gttatcgcta tagcttctgt catcgatgat    960
atatcgacg tttacggtac cttggaagaa ttgaagttgt tcactcatgc tattgagcgt   1020
tgggaaactg tcgctgctaa tgaattacca agtatatgc aagtttgtta ctttgctttg   1080
ttagacgtct ttaaggaaat ggaagataaa ttagtcaata aaggtttgtt atactccatg   1140
ccatgtgcaa aggaggctgt taagggtttg gttagagcct acttcgttga ggctgaatgg   1200
ttcaacgcta actatatgcc aaccttcgaa gaatatatgc aaaactcaac tatgtcctct   1260
ggttatccta tgttggctgt cgaagctttg atcggtattg aagacgcaac tatttcaaag   1320
gaagccttcg attgggcaat atccgttcca aaaattatca gatcttgtgc attgatcgcc   1380
agattggtcg atgacattca cacctacaag gtcgaacaag agagaggtga tgccccatct   1440
tctgtccaat gctacgttca acaatacggt gtctccgaag aagaagcctg taataaaatt   1500
aagggtatgg ttgagattga atggatgaat ataaacgaag aaatccagga tccaaaccac   1560
ccacctttac aatggttgtt gccatctttg aacttagctc gtatgatggt tgttttgtac   1620
caaaatggtg acaactacac aaactcctcc ggtaaaacca aggatagaat tgcttccttg   1680
ttggtcgacc ctttgccaat gtaa                                         1704

<210> SEQ ID NO 91
<211> LENGTH: 1704
<212> TYPE: DNA
<213> ORGANISM: Artificial Sequence
<220> FEATURE:
<223> OTHER INFORMATION: Synthetic polynucleotide

<400> SEQUENCE: 91

```
atgcgtgact tgaaatccgt cttatcttca aggaatctca caaggcaga tgttaataga     60
agatcctcta actatcaccc ttccatctgg ggtgatcatt tcattaacgt ttcttcaaat    120
gagaagtaca ctaacactga agtcgaaaaa agatttgaaa ccttgaaggc cgaaatagaa    180
aagttgttag tttctaacaa caccgcttgg aagaccttgg aggaaattgt cgctatcgtt    240
aatcagttgc aaagattagg gttggcttac cacttcgaaa accaaatcaa agaagccttg    300
caatccattt atgactctca tgtcaacggt aattgcgacg ttaattacga tcacaacaac    360
gatttgtaca tagtcgcttt aagatttcgt ttgttgagac aacacggtta taaagtctct    420
gctgacattt tcaagaagtt taaagatgaa aagggtgaat taaggatat gatcagaaat     480
gacgccagag gttattgtg tttatacgaa gcatcccatt tgagagttaa gggtgaagat    540
attttagaag aggctactga attttctcgt aagcacttga agtcattgtt accacaattg    600
tccacatcat tggctgagca agttaagcac tctttggaaa tcccattaca tagaggtatg    660
ccaagattgg aagctagaca ttacatttct atttatgagg aaaacaactc ctctcgtaat    720
gaattgttgt tagagttggc aaagttggac ttcaacttgt tgcaggcttt acacagaaga    780
gaattgggtg atatttctcg ttggtggaaa gacatcgatt tcgccactaa attgccattc    840
gccagagaca gattagttga atgttacttc tggatcttgg gtgtttattt tgaacctaaa    900
tactccatta ctagaaaatt catgaccaag gttatcgcta tagcttctgt catcgatgat    960
atatacgacg tttacggtac cttggaagaa ttgaagttgt tcactcatgc tattgagcgt   1020
tgggaaactc tcgctgctaa tgaattacca agtatatgc aagtttgtta ctttgctttg    1080
ttagacgtct ttaaggaaat ggaagataaa ttagtcaata aaggtttgtt atactccatg   1140
ccatgtgcaa aggaggctgt taagggttg gttaaggcct acttcgttga ggctaagtgg    1200
ttccacgcta gtatgtccc aaccttcgaa gaatatatgg aaaactcaac tatgtcctct   1260
ggttatccta tgttggctgt tgaagctttg gttggtttag aagacatggc cattacaaag   1320
agagctttgg attgggcaat atccgttcca aaaattatca gatcatgtgc attgatcgcc   1380
agattgacg atgacgttca cacttacaag gtcgaacaag agagaggtga tgccccatct    1440
tctgtccaat gctacatgca acaatacgac gtctccgaag aagaagcatg taatcgtatt   1500
aagggtatgg ttgaaactgc ttggatgaa atcaacggtg agatccagga taccaaccac   1560
ttgccattac aatggttgtt gccatctttg aacttagcta gaatgatggt cgttttgtac   1620
caaaatggtg acaactacac caactcctcc ggtaaaacca aggatagaat tgcctctttg   1680
ttggtcgacc ctttgcctat gtaa                                          1704
```

<210> SEQ ID NO 92
<211> LENGTH: 1704
<212> TYPE: DNA
<213> ORGANISM: Artificial Sequence
<220> FEATURE:
<223> OTHER INFORMATION: Synthetic polynucleotide

<400> SEQUENCE: 92

```
atgcgtgact tgaaatccgt cttatcttca aggaatctca caaggcaga tgttaataga     60
agatcctcta actatcaccc ttccatctgg ggtgatcatt tcattaacgt ttcttcaaat    120
gagaagtaca ctaacactga agtcgaaaaa agatttgaaa ccttgaaggc cgaaatagaa    180
aagttgttag tttctaacaa caccgcttgg aagaccttgg aggaaattgt cgctatcgtt    240
aatcagttgc aaagattagg gttggcttac cacttcgaaa accaaatcaa agaagccttg    300
```

```
caatccattt atgactctca tgtcaacggt aattgcgacg ttaattacga tcacaacaac      360
gatttgtaca tagtcgcttt aagatttcgt ttgttgagac aacacggtta taaagtctct      420
gctgacattt tcaagaagtt taaagatgaa aagggtgaat ttaaggatat gatcagaaat      480
gacgccagag gtttattgtg tttatacgaa gcatcccatt tgagagttaa gggtgaagat      540
attttagaag aggctactga attttctcgt aagcacttga agtcattgtt accacaattg      600
tccacatcat tggctgagca agttaagcac tctttggaaa tcccattaca tagaggtatg      660
ccaagattgg aagctagaca ttacatttct atttatgagg aaaacaactc ctctcgtaat      720
gaattgttgt tagagttggc aaagttggac ttcaacttgt tgcaggcttt acacagaaga      780
gaattgggtg atatttctcg ttggtggaaa gacatcgatt tcgccactaa attgccattc      840
gccagagaca gattagttga atgttacttc tggatcttgg gtgtttattt tgaacctaaa      900
tactccatta ctagaaaatt catgaccaag gttatcgcta tagcttctgt catcgatgat      960
atatacgacg tttacggtac cttggaagaa ttgaagttgt tcactcatgc tattgagcgt     1020
tgggaaactg tcgctgctaa tgaattacca agtatatgc aagtttgtta ctttgctttg     1080
ttagacgtct ttaaggaaat ggaagataaa ttagtcaata aaggtttgtt atactccatg     1140
ccatgtgcaa aggaggctgt taagggtttg gttaaggcct acttcgttga ggctaagtgg     1200
ttccacgcta gtatgtccc aaccttcgaa gaatatatgg aaaactcaac tatgtcctct     1260
ggttatccta tgttggctgt tgaagctttg gttggtttag aagacatggc cattacaaag     1320
agagctttgg attgggcaat atccgttcca aaaattatca gatcatgtgc attgatcgcc     1380
agattggacg atgacgttca cacttacaag gtcgaacaag agagaggtga tgccccatct     1440
tctgtcgaat gctacatgca acaatacgac gtctccgaag aagaagcatg taatcgtatt     1500
aagggtatgg ttgagattga atggatgaac ataaacgaag aaatccagga tccaaaccac     1560
ccacctttac aatggttgtt gccatctttg aacttagcta gaatgatggt cgttttgtac     1620
caaaatggtg acaactacac caactcctcc ggtaaaacca aggatagaat tgcttctttg     1680
ttggtcgacc ctttgccaat gtaa                                             1704
```

<210> SEQ ID NO 93
<211> LENGTH: 1692
<212> TYPE: DNA
<213> ORGANISM: Artificial Sequence
<220> FEATURE:
<223> OTHER INFORMATION: Synthetic polynucleotide

<400> SEQUENCE: 93

```
atgtccttcg cagtttcagc ctctcctgct aaatttatac agaatgtcga agaggattct       60
accagacgtt ctgctaactt ccacccatcc atctggggtg accattttt gcaatacact      120 tgcgactcac aagaaccaga tgatgacggg tctgttaagc atcaacaatt aaaggaagaa      180
attagaaaaa tgttgacagc tgaaactaag ttgtcccaga agttagattt gattgacgcc      240
atccaaagat tgggtgtcgc ttatcacttc gaatctgaaa tcgatgagat tttaggtaga      300
gttcaccaag cttaccaaga atcagacttg tgtgtcaacg aaaatgacgg tttgtattac      360 atttcttttgc aattcagatt attgcgtgaa acggttaca gaatatctgc cgatgtcttt      420
aacaaattca gagatatcga tggtaatttt aagccatcct ggctagaaa cgttagaggt      480 atgttatcct tgtatgaagc cacccatttg cgtgttcacg gtgaaaacat tttggacgaa      540
gctcacgctt tcgcaacttc tcatttagaa tctattgcca cccaccaaat ctcttcccca      600
```

```
ttggctgagc aggtcaagca tgctttgttc caaccaattc acaaggtgt tcaaagatta      660
gaagcaagaa attacatgcc tttctatcaa gaagaagctt cccacaacga ggctttgtta      720
acatttgcta agttggactt taacaagttg caaaagttgc atcagaaaga attgtctgaa      780
atcactcgtt ggtggaagga attagatttc gctcacaatt tgccatttac tattagagat      840
agaatcgcag aatgttactt ctgggctgtt gcagtttact tcgagccaca atattcctta      900
ggtagacgta tgttggccaa agttttcct atgacctcta taattgacga tatctacgac       960
gtctacggta aattcgaaga attagaattg ttcacctcag ctatcgaaag atgggatatc     1020
tctgctatcg atgagttacc agagtatatg aagttgtgtt acagagcctt gttagatgtc     1080
tactctgaag ccgaaaagga cttagcatcc aaggtaagt tgtatcactt gcattacgcc      1140
aaagaagcta tgaagaatca ggttaagaac tactttttcg aggctaagtg gtgccatcaa     1200
aactatattc catctgttga tgaatacatg accgttgctt ccgtcacttc aggttaccca     1260
atgttgtcca ctacttcttt tgtcggtatg ggtgatattg ttacaaagga atccttcgaa     1320
tggtctttga ccaatcctag agttatcaga gcttcctctg ttgctgctag attaatgaat     1380
gacatggtct cacacaagtt cgaacaatct cgtgaacacg tcgcttcttc aatagaatgt     1440
tacatgaaac aatacggtgc aactgaggaa gaaacctgta acgagttgag aaaacaagtt     1500
tctaacgctt ggaaggatat taacgaagaa tgtttatgtc caacagccgt cccaatgcct     1560
ttgatagtca gaattttaaa tttgactaga ttccttggacg ttgtttatcg ttttgaagac    1620
ggttacaccc attccggtgt cgtcttgaag gactttgttg cctctttgtt gattaaccca    1680
gtttccatct aa                                                         1692

<210> SEQ ID NO 94
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 94
atggaatcac agactacatt caaatatgag tctttagcat ttaccaagtt gtcccattgc       60
caatggactg attacttctt gtctgttcca atagacgaat ccgaattgga cgtcatcacc      120
agagaaattg atatttttaaa gcctgaggtt atggaattgt tatcttcaca aggtgatgac     180
gaaacatcta agcgtaaagt cttgttgatc caattgttgt tatctttggg attagccttt     240
cacttcgaaa acgagattaa gaatatcttg gaacacgctt tcagaaagat tgatgacatc     300
actggtgacg aaaaggattt gtccaccatt tccataatgt ttagagttt cagaacttac      360
ggtcataact tgccagctga agtctttgaa agattcaaag accaacacgg taatttcaaa     420
gcttcttttgt catccgatgt tgaaggtatg ttgtctttat acgaagcctc tttcttggac    480
tatgaaggtg aagatatttt agatgaagct aaggccttta cttcttttca tttgcgtggt    540
gctttggctg gtggtacctg tagacctcac atcttaagat tgatcagaaa cactttatac    600
ttgccacaaa gatggaacat ggaggccgtc atagctcgtg aatatatctc cttttacgaa    660
caagaggaag accacgataa gatgttattg agattagcta agttgaattt caagttgtta    720
cagttgcatt acattaagga attgaaatca ttcatcaagt ggtggatgga attgggttta    780
acatctaaat ggccatctca atttagagag cgtattgttg aagcttggtt agctggtttg    840
atgatgtact tcgaaccaca attctccggt ggtagagtta ttgcagccaa gtttaactat   900
ttgttaacca ttttggatga tgcttgtgat cactatttct caatccatga attgactaga   960
```

```
ttggtcgctt gtgttgaaag atggtctcca gacggtatcg ataccttgga ggacatctcc   1020
cgttctgtct ttaagttaat gttggatgtt tttgacgata ttggtaaagg tgttagatcc   1080
gaaggttctt cctaccactt gaaagaaatg ttggaagaat taaataccct agttagagca   1140
aacttggact tggttaaatg ggccagaggt atccaagtcc catctttcga agagcatgtt   1200
gaggttggtg gtattgcttt aacatcctac gcaactttga tgtactcttt cgtcggaatg   1260
ggtgaaactg ctggtaagga agcatacgaa tgggttcgtt caagacctcg tttgataaag   1320
tctttggccg ctaagggtag attgatggac gacatcactg attttgattc cgatatgtct   1380
aacggtttcg ctgctaacgc aattaactat tacatgaagc agttcgtcgt tacaaaggaa   1440
gaagccatct tagaatgcca agaatgatt gtcgacatca ataagaccat caatgaagag   1500
ttgttaaaaa ctacctctgt tccaggtaga gtcttgaaac aagctttgaa cttcggtaga   1560
ttattggaat tgttgtatac taagtccgac gacatttaca actgttctga aggtaaatta   1620
aaggaataca tagttacttt gttgattgat ccaataagat tgtaa                   1665
```

<210> SEQ ID NO 95
<211> LENGTH: 1662
<212> TYPE: DNA
<213> ORGANISM: Artificial Sequence
<220> FEATURE:
<223> OTHER INFORMATION: Synthetic polynucleotide

<400> SEQUENCE: 95

```
atgtccatac aggttcccca aatttcttcg caaaatgcaa agtcacaagt aatgcgtaga     60
accgccaact ttcatccatc tgtgtgggga gacagattcg ctaactacac ggctgaggat    120
aaaatgaacc acgctcgcga cttgaaggaa cttaaagcgt taaggaaga agttggtaga    180 aagctgttgg ccacagctgg cccaattgtt aagctagagt tggtcgatga tgtcaaaaga    240
ctcgggatcg gttatagatt cgaaaaggaa atcgttgaag ctttacaccg ttgctttatt    300
agttccgaaa gattcactca taggaatttg caccaaaccg ccttgagctt cagattgtta    360
cgggaatgtg gttacgacgt cacttgtgat aagtttaata agttcactaa caaagagggt    420
aagtttaact caaagttggg tgaaaatatc aagggtatga tagacttgta tgaagctagc    480
caacttggta ttgctggtga atacatcttg gctgaagcag gtgaattttc gggcttagtt    540
ctaaaagaaa aggttgcttg tattaacaat aacccattga agcgcaggt cagacatgcc    600 ctaagacaac ctctgcacag aggtctccca agattagaac acaggagata catctctatt    660
taccaagatg acgcttctca ctataaggct ttgttgaccc tggccaagtt ggattcaac    720 ttggttcaat ccctccataa gaaagagctt tgcgaaattt ccagatggtg gaaagatctt    780
gacttcgctc ggaagttacc ttttgcacgt gaccgtatgg tcgaatgtta tttctggatc    840
ttgggagttt acttcgaacc acaatacagt gtaccaagaa gaactaccac taaggttatt    900 ggttgtgtt ctgtcatcga tgatatgtac gatgcttacg gtacaattga cgaattagag    960
ctttttacta acgccatcga aagattggac acctctacta tggatcagct accagaatat   1020
atgcaaactt tctttggtgc tttattggat ttgtataacg agatcgaaaa agaaatcgca   1080
aatgaaggtt ggtcctaccg agtgcaatac gctaaggaag ctatgaaaat tttggtggaa   1140
ggatactatg atgaaagcag atggttgaag tgtaaccacg ccccaaccat ggaagaatac   1200
atgaaggtcc gtggtgttag ttctggttac cctctcttga taaccatatc tttcataggt   1260
atggaggaca ctactgaaga gatcttaaca tgggctacat ctgaacctat gattatcaga   1320
```

| | |
|---|---:|
| gccagtgtca ttgtttgtag attgatggac gacattaaat cccataagtt tgagcaagag | 1380 |
| aggggggcatg ctgcgagcgc tgtagaatgc tatatgaagc aacacggtct atcagaacaa | 1440 |
| gaagtttgtg aagaacttta cagacaggtc tctaatgcat ggaaggacat caatgaagaa | 1500 |
| tgtttgaacc cgaccgctgt tccaatgcca ttgttaatga gagcgctgaa cttggctcgc | 1560 |
| gtcattgacg tagtttataa agaaggtgac ggctacaccc acgttggtaa tgaaatgaag | 1620 |
| caaaacgtag ctgctctcct aatcgatcaa gtaccaatct aa | 1662 |

<210> SEQ ID NO 96
<211> LENGTH: 1689
<212> TYPE: DNA
<213> ORGANISM: Artificial Sequence
<220> FEATURE:
<223> OTHER INFORMATION: Synthetic polynucleotide

<400> SEQUENCE: 96

| | |
|---|---:|
| atggctttgc aggattcaga agtcccttct tccatattaa acgccactgc tggtaatcgt | 60 |
| ccaaccgcat cttaccatcc aacattgtgg ggagagaaat tcttagttgt ttccactcaa | 120 |
| tctacctctg gttccatgaa gaacgaacca actacacaag gtgaatatga cgaattgaag | 180 |
| caacaagtca ccaagatgtt gactgatgct accactaacg acccatccaa aaagttgcac | 240 |
| ttgatcgata tggttcaaag attaggtatt gcctaccact ttgagattga atcgaaaat | 300 |
| gctttggaaa agattaactt aggtgacgct aactacttcg aatatgactt gtacaccatc | 360 |
| gctttgggtt ttagattgtt gagacaacag ggtattaaag tctcatctga aatcttcaag | 420 |
| aagtttatgg atgagaaagg taagttcaaa gaagacgttg ttaatgatgt cttaggtatg | 480 |
| ttgaacttat acgaagcagc ccatttgaga ttaagaggtg aagatatctt ggacgaggct | 540 |
| ttagccttca ctacctccca cttgaatct atggctacaa aggtttctcc tttgttggct | 600 |
| gaacaaatag cccatgcttt aaattgccca attcaaaagg gtttaccaag aattgaagcc | 660 |
| agacactata tctcattgta ctcccgtgaa actcactttg cttcttctaa cgctgcattg | 720 |
| ttgagattcg ctaaaattga cttcaacatg gttcaagctt gcaccagaa ggagatctct | 780 |
| ggtattacaa agtggtggaa aaatttggat ttctcaacta agttgccata cgctagagac | 840 |
| agaatcgtcg aatgttattt ttggatcatg ggtgcttact ttgaacctaa gtattccttg | 900 |
| gctagaactt ttttgaccaa ggttatagca atgacctcta tattagatga tacatacgat | 960 |
| aactacggta ctaataagga attggagttg ttaactaaat gtattgaacg ttgggacatc | 1020 |
| gacgttattg atcaattacc agaatatatg aagttggtct accaagcatt gttgaacgtt | 1080 |
| tactcagaaa tggaagccaa agtcgctaag gagggtcgtt cttacgccat tgactatgct | 1140 |
| aaggaatcca tgaaaagac catgaaggca tacttggatg aagctaaatg gagacaagaa | 1200 |
| gactacgttc ctccaataga agaatatatg caagtcgcta gaatttcctc tgcctaccca | 1260 |
| atgttaatca ctaattcctt cgttggtatg ggtgaagttg ctaccaaaga ggcattcgat | 1320 |
| tggatttcca atgacccaaa gattttgaag gcttctacta ctatatgtag attgatggat | 1380 |
| gatatcactt ctcatgaatt tgaacaaaca agagaccatg ttgcctctgg tgtcgaatgt | 1440 |
| tatatgaaac aatacggtgt ttcacgtgaa gaaccgtta agttattcag agaggatgtc | 1500 |
| gctaacgctt ggaaagacat taacgagggt ttcatgaagc ctgctatatt cccaatgcca | 1560 |
| atcttgactg ttgttttgaa ctttgccaga gtcatggatt tcttatacaa ggatggtgac | 1620 |
| aactatacta attctcatat gttgaaggat tacattacat cattgttggt caatccatta | 1680 |
| ttaatctaa | 1689 |

<210> SEQ ID NO 97
<211> LENGTH: 1689
<212> TYPE: DNA
<213> ORGANISM: Artificial Sequence
<220> FEATURE:
<223> OTHER INFORMATION: Synthetic polynucleotide

<400> SEQUENCE: 97

```
atggcattgc aggattctga agtcccttcc tcaatattaa acgccaccgc tggtaataga      60
ccaactgctt cttatcaccc aacattgtgg ggagagaagt tcttggttgt ttccactcaa     120
tctacctcag gttctatgaa aaacgaacca accactcaag gtgaatacga cgaattaaag     180
caacaagtca caaagatgtt gactgatgcc actactaatg acccatccaa aaagttgcat     240
ttaatcgata tggttcaacg tttgggtatt gcttaccact ttgaaattga gatcgaaaac     300
gctttggaaa aaataaactt aggtgacgct aattatttcg aatacgattt gtacaccatt     360
gctttaggtt ttagattgtt gagacaacaa ggtatcaagg tctcttctga gattttcaag     420
aaatttatgg acgaaaaggg taagttcaaa gaagatgttg tcaacgatgt tttgggtatg     480
ttgaacttgt acgaagcagc tcatttaaga ttaagaggtg aagacatctt ggacgaagcc     540
ttggccttca caacctccca cttagagtca atggctacta aggtctctcc tttgttggct     600
gaacaaattg cccatgcttt gaactgccca atccaaaagg gttaccacg tattgaagca     660
agacactata tttctttata ctccagagaa actcacttcg cttcctctaa tgctgctttg     720
ttgagatttg ctaagatcga tttcaatatg gttcaagcct tgcatcagaa ggaaatatca     780
ggtataacca atggtggaa gaacttggac ttttccacta aattaccata tgctagagat     840
cgtattgttg aatgttactt ctggatcatg ggtgcttact ttgaaccaaa gtattcttta     900
gcaagaacat tcttgaccaa agtcattgca atgacctcta tcttagacga tacttacgac     960
aactacggta ctaacaagga attggagttg ttgactaagt gtatcgaaag atgggatatt    1020
gatgttatcg accagttacc tgagtatatg aagttggttt atcaagcttt gttaaatgtt    1080
tactctgaaa tggaagctaa ggtcgccaaa gaaggtcgtt cctacgccat tgactacgca    1140
aaagaatcta tgaagaaaac catgaaagcc tacttggacg aggctaagtg gagacaagaa    1200
gattacgtcc ctaccattga agaatatatg caagttgcat taatatcatc cgcttatcca    1260
atgttgatta caaactcatt cgtcggtatg ggtgaggtcg ctactaagga gcttttgac     1320
tggatctcca ataacccaaa gatgttgaag gcttctacta ttatatgtag attgatggat    1380
gatatcactt cccatgaatt tgaacagacc agagaccacg ttgcctctgg tgttgaatgt    1440
tacatgaaac aatacggtgt ctccagagaa gaaaccgtta agttgttcag agaagatgtt    1500
gctaacgctt ggaaggacat caatgaaggt ttcatgaagc cagcaatctt cccaatgcct    1560
atcttgactg ttgtcttgaa ttttgccaga gttatggact ttttgtacaa ggatggtgat    1620
aactatacta actctcatat gttaaaagac tacattacct cattattggt taatccatta    1680
ttgatttaa                                                            1689
```

<210> SEQ ID NO 98
<211> LENGTH: 1689
<212> TYPE: DNA
<213> ORGANISM: Artificial Sequence
<220> FEATURE:
<223> OTHER INFORMATION: Synthetic polynucleotide

<400> SEQUENCE: 98

```
atggctttac aggactccga ggttccttca tctatattga acgccaccgc tggtaatcgt      60
ccaactgcat cttatcatcc aacattgtgg ggtgaaaaat tcttggtcgt ttctactcaa     120
tccacctctg ggtccatgaa gaacgaacca actacccaag gtgaatacga tgaattaaag     180
caacaagtca caaagatgtt gactgatgct accactaatg acccatctaa aaagttgcac     240
ttgattgaca tggttcaaag attaggtatc gcctaccact ttgaaattga gatcgaaaac     300
gctttggaaa agattaactt aggtgatgct aattatttcg aatacgattt gtacactata     360
gccttgggtt ttagattatt gagacaacag ggtatcaagg tttcatctga aatcttcaaa     420
aagttcatgg acgagaaagg taagtttaag gaagacgtcg ttaacgatgt cttgggtatg     480
ttaaacttgt atgaagctgc ccatttgaga ttgcgtggtg aagacatttt agatgaggct     540 ttggcttttta ccacatccca cttagaatca atggcaacta aggtttcacc tttgttggct     600
gaacaaatcg cccacgcttt aaattgccca attcaaaaag gtttgccaag aatagaagcc     660
agacattaca tttctttgta ctccagagaa acccacttcg cttcttctaa cgcagcattg     720
ttgcgtttcg ctaagatcga ctttaatatg gttcaagcat tgcatcagaa agagatttcc     780
ggtattacta agtggtggaa gaatttagat ttctctacaa aattgccata tgctagagat     840
agaatcgtcg aatgttactt ctggattatg ggtgcttatt ttgaaccaaa gtactctttg     900
gccagaacct ttttaaccaa agtcattgct atgacttcta tcttagatga cacatacgac     960
aattacggta ctaacaagga attggaattg ttaaccaagt gtattgaaag atgggatata    1020
gatgttatcg atcaattgcc tgaatacatg aagttagttt atcaagcttt gttgaacgtc    1080
tactccgaaa tggaggctaa ggtcgctaag gaaggtcgtt cctatgccat cgattacgct    1140
aaggaatcca tgaaaaagac tatgaaagcc tatttggacg aagctaagtg gagacaagag    1200
gactacgttc cacctatcga gagtacatg caagttgcaa gaatttcttc cggttatcca    1260
atgttaatta ccaactcctt ggttggtatg ggtgaagtcg ccactaaaga agccttcgat    1320
ttgatttcta cgaccccaaa aatgttgaag gcttccacca ctatatgtag attgatggac    1380
gatatcactt ctcacgaatt tgaacaaact agagatcacg tcgcttcagg tgttgaatgt    1440
tatatgaagc aatacggtgt ttctcgtgag gaaaccgtta agttattcag agaagacgtc    1500
gctaacgcat ggaaggacat taatgagggt ttcatgaagc cagcaatctt tccaatgcca    1560
atcttgactg tcgtcttaaa cttcgctaga gttatggact ttttgtacaa agatggtgat    1620
aattacacaa actctctatat gttaaaggat tacatcactt cattgttggt caaccctttg    1680
ttgatttaa                                                             1689

<210> SEQ ID NO 99
<211> LENGTH: 1689
<212> TYPE: DNA
<213> ORGANISM: Artificial Sequence
<220> FEATURE:
<223> OTHER INFORMATION: Synthetic polynucleotide

<400> SEQUENCE: 99
atggccttac aggactccga agttccatca tctatttga acgctactgc tggtaataga      60
cctacagcat cttaccatcc aaccttgtgg ggagagaagt ttttggtcgt ttccactcaa     120
tctacctccg gttctatgaa aaacgaacca actacacaag gtgaatatga tgaattaaag     180
caacaagtca ccaagatgtt gactgatgct actaccaacg acccatctaa aaagttgcac     240
ttaatagata tggttcaacg tttgggtatc gcctaccact tcgagattga atcgaaaat     300 gctttagaaa aaattaactt gggtgacgct aactacttcg aatatgattt gtacactatc     360
```

```
gcattaggtt ttagattgtt gagacaacag ggtattaagg tctcctcaga aattttcaag      420
aagttcatgg atgaaaaagg taagtttaag gaggacgttg tcaatgacgt tttaggtatg      480
ttgaacttgt atgaagctgc tcatttacgt ttgagaggtg aagatatctt ggacgaagcc      540
ttggctttca ctacatcaca cttggaatct atggctacca aggtttcccc attgttggcc      600
gagcaaatag cacatgcctt aaattgtcct attcaaaaag gtttgccaag aatcgaagct      660
agacactaca tctctttata ctctcgtgaa actcactttg cttcctctaa cgctgccttg      720
ttgagattcg ctaagattga ttttaatatg gttcaagcct tgcaccagaa agaaatctct      780
ggtatcacca gtggtggaa gaatttggac ttctccacca agttgccata tgctagagac      840
agaattgtcg aatgctactt ctggataatg ggtgcatatt ttgaacctaa gtactcttta      900
gctagaactt ttttgactaa agttattgct atgacatcaa ttttggatga tacttacgat      960
aactacggta ctaacaaaga attagaatta ttgaccaagt gtatcgagag atgggacatt     1020
gacgtcattg accaattacc agaatacatg aagttggttt atcaagcttt gttgaacgtc     1080
tactccgaga tggaagcaaa ggttgccaag gaaggtcgtt cttatgctat agattatgct     1140
aaagaatcta tgaaaaagac aatgaaggca tacttggacg aagctaagtg gagacaagag     1200
gattatgttc ctccaatgga tgaatacatg caagttgctt tgatatcctg tggttaccca     1260
atgttgatca ccaactcttt cgttggtatg ggtgaagtcg ctaccaaaga agcctttgat     1320
tggatctcta atgacccaaa gattttgaaa gcatctacca ctatctgtag attaatggat     1380
gacattacct cccatgagtt cgaacagaca agagatcacg ttgcttcagg tgtcgaatgt     1440
tatatgaagc aatacggtgt ttctcgtgaa gaaactgtta aattattcag agaggatgtt     1500
gctaacgctt ggaaagacat taatgaaggt ttcatgaagc ctgctatttt cccaatgcca     1560
attttgaccg tcgtcttgaa tttcgctaga gtcatggatt ttttatacaa ggacggtgat     1620
aactacacaa actcacatat gttgaaagat tacatcactt cattattagt taatccattg     1680
ttgatataa                                                            1689
```

<210> SEQ ID NO 100
<211> LENGTH: 1689
<212> TYPE: DNA
<213> ORGANISM: Artificial Sequence
<220> FEATURE:
<223> OTHER INFORMATION: Synthetic polynucleotide

<400> SEQUENCE: 100

```
atggcattac aggattcaga ggtcccatcc tctattttga cgctactgc cggtaatcgt       60 cctaccgctt cttaccaccc aacattgtgg ggtgaaaagt ttttagttgt ttccactcaa      120
tctacctccg gctctatgaa aaacgaacca accactcaag gtgaatatga cgaattgaag      180
caacaagtca ctaagatgtt gacagatgct actaccaatg acccatctaa aaagttgcat      240
ttgatagata tggttcaaag attgggtatt gcctaccact cgaaatcga atcgaaaac      300 gctttagaaa agattaattt aggtgacgct aactatttcg aatacgattt atacacaatc      360 gctttggggtt ttagattgtt gagacagcaa ggtatcaagg tctcttcaga gattttcaaa      420
aagttcatgg atgagaaagg taagtttaag gaagacgttg tcaacgacgt tttgggtatg      480
ttgaatttat atgaagcagc ccatttgaga ttgcgtggtg aagatatatt ggacgaggct      540
ttagctttca ctacctccca cttggaatct atggcaacca agtttccccc attgttagct      600
gaacaaattg cccacgcttt gaactgtcct atccaaaagg gtttgccaag aattgaagcc      660
```

| | |
|---|---|
| agacattaca tatctttgta ttcaagagaa actcacttcg cttcttccaa tgctgcttta | 720 |
| ttaagatttg ctaagatcga ttttaacatg gtccaagctt tgcatcaaaa agagatctct | 780 |
| ggtattacaa agtggtggaa gaacttggac ttcgctacta tgttaccata cgccagagat | 840 |
| cgtattgttg aatgctactt ctggatcatg ggtgtttatt ttgaaccaaa gtactcctta | 900 |
| gctagaaacct tcttgaccaa agttattgca atgacttcta ttttagacga tacatacgac | 960 |
| aactacggta ctaataagga attggaattg ttgactaaat gtattgaaag atgggacatc | 1020 |
| gatgtcattg atcaattgcc tgagtatatg aagttggttt atcaggcatt attgaacgtc | 1080 |
| tactcagaaa tggaagctaa ggttgccaaa gagggtagac cctacgctat tgattacgcc | 1140 |
| aaagaatcta tgaagaagac catgaaggcc tatttggacg aagctaagtg gagacaagaa | 1200 |
| gactacgtcc ctaccatcga agaatatatg caagtcgctt taatatcttc agcctaccca | 1260 |
| atgttaataa ctaattcatt tgtcggtatg ggtgaggttg ccactaagga agcttttgat | 1320 |
| tggatctcta acaacccaaa aatgttaaag gcttccacta ttatttgtag attgatggat | 1380 |
| gacatcacct cccacgaatt tgaacagacc cgtgaccacg ttgcctctgg tgttgaatgt | 1440 |
| tatatgaagc aatacggtgt ttcacgtgag gaaaccgtca agttgttcag agaagatgtt | 1500 |
| gctaatgctt ggaaagacat caatgagggt ttcatgaagc cagcaatctt cccaatgcca | 1560 |
| attttgactg tcgttttgaa cttcgcaaga gttatggatt tcttatataa ggacggcgac | 1620 |
| aattacacta actctcatat gttgaaagac tacatcactt ctttgttggt caacccattg | 1680 |
| ttaatataa | 1689 |

<210> SEQ ID NO 101
<211> LENGTH: 1689
<212> TYPE: DNA
<213> ORGANISM: Artificial Sequence
<220> FEATURE:
<223> OTHER INFORMATION: Synthetic polynucleotide

<400> SEQUENCE: 101

| | |
|---|---|
| atggctttgc aagactctga agtccccttcc tcaattttaa acgcaaccgc tggtaataga | 60 |
| ccaacagcct cttaccatcc aactttgtgg ggtgagaaat ttttggttgt ttccactcag | 120 |
| tctacctcag gttctatgaa gaacgaacca actacccaag gtgaatatga tgaattgaag | 180 |
| caacaagtca ctaagatgtt aacagatgct actaccaatg acccatccaa aaagttgcac | 240 |
| ttgatagata tggttcaacg tttgggtatc gcctaccact tcgaaatcga gattgaaaac | 300 |
| gctttagaga aaatcaactt gggcgacgct aattacttcg aatatgattt atacaccatt | 360 |
| gccttaggtt ttagattgtt gagacaacaa ggtattaagg tttcttccga aattttcaag | 420 |
| aagtttatgg atgaaaaagg taagttcaag gaagacgtcg ttaacgacgt tttaggtatg | 480 |
| ttgaacttgt atgaagctgc ccatttaaga ttgcgtggtg aagatatctt ggatgaagct | 540 |
| ttagcattca caacctctca cttggaatct atggctacta agtctctcc attgttagct | 600 |
| gagcagatcg cccacgcttt gaattgccct atccaaaagg gtttgccaag aatagaagca | 660 |
| agacattaca tttccttgta ctcaagagaa acacacttcg cttcctctaa cgctgctttg | 720 |
| ttaagatttg ctaaaattga cttaatatg gttcaagcct tacatcaaaa ggagatttct | 780 |
| ggtatcacca agtggtggaa gaacttggac ttcgcaacta tgttgccata cgcaagagac | 840 |
| cgtattgttg aatgttattt ctggatcatg ggtgtctact tcgaacctaa gtactcattg | 900 |
| gctagaaactt ttttaactaa agtcatagcc atgacctcca ttttgatga cacctacgat | 960 |
| aactatggta ctaacaagga attagagttg ttaacaaagt gtatagaaag atgggacatt | 1020 |

```
gatgtcatcg atcaattgcc tgaatacatg aagttggttt accaggcttt gttaaatgtc    1080
tactcagaaa tggaagctaa ggttgctaaa gaaggtcgtt cttatgcaat tgattacgca    1140
aaggagtcta tgaagaaaac tatgaaagct tatttggacg aagctaaatg gagacaagaa    1200
gactatgttc caccaatcga agaatatatg caagtcgcta gaatctcttc cggttaccca    1260
atgttgatta ctaactcatt agtcggtatg ggtgaggttg ccactaagga agctttcgac    1320
ttgatttcta atgatccaaa gatgttaaaa gcctccacta caatctgtag attgatggac    1380
gacattactt ctcatgaatt tgaacagaca cgtgatcacg ttgcctctgg tgtcgagtgc    1440
tatatgaagc aatacggtgt tccagagaaa gaaaccgtca agttgtttag agaagacgtt    1500
gctaacgctt ggaaggatat caatgaaggc ttcatgaaac cagcaatctt tccaatgcca    1560
attttgaccg ttgttttgaa cttcgctaga gtcatggact tcttgtataa ggatggcgac    1620
aactacacta attcacatat gttgaaagat tacataactt cattattagt taacccttta    1680
ttgatctaa                                                            1689

<210> SEQ ID NO 102
<211> LENGTH: 1662
<212> TYPE: DNA
<213> ORGANISM: Artificial Sequence
<220> FEATURE:
<223> OTHER INFORMATION: Synthetic polynucleotide

<400> SEQUENCE: 102
atggcctcag cacaagcttc cttaccttct aataacagac aggaaacagt ccgtccattg      60
gctgacttcc cagagaacat ctgggctgat agaattgccc catttacctt ggataagcaa     120
gaatacgaaa tgtgtcaaag agaaatagag atgttaaaag ctgaagttgc ttctatgttg     180
ttggcaactg gtaagactat gatgcaaaga ttcgacttca ttgataagat cgaaagattg     240
ggggtctccc accattttga cattgaaatc gaaaatcaat gcaagagtt tttcaacgtt     300 tataccaact taggtgaata ctctgcctat gatttgtcat ctgctgcctt gcagttccgt     360
ttatttagac aacacggttt caatatttcc tgcggtattt tcgaccaatt tatcgacgct     420
aaaggtaagt tcaaggaatc tttatgtaac gatatcagag gtttgttgtc tttgtacgaa     480
gctgctcatg ttagaactca cggtgataaa attttggaag aagctttagc tttcaccact     540
actcacatga cctccggtgg tccacattta gattcttcat tggccaagca agttaaatac     600
gcattggaac agccattgca taagggtata ttgagatatg aagcttggag atacatatct     660
atctacgaag aggacgaatc caacaataag ttattattgc gtttggctaa gttggactat     720
cacttgttac aaatgtcata caagcaagag ttgtgtgaaa ttacaagatg gggtaaaggt     780
ttggaatctg tctccaactt tccttatgcc cgtgacagat cgttgaatg ttacttttgg     840 gctgtcggta ctttgtacga accacaatac tcattggcta gaatgacctt cgctaaggtt     900
gctgctttaa ttactatgat cgatgatatt tatgatgcct acggtacctt ggacgaattg     960
caaatattaa ctgactctgc cgaaagatgg gatggttccg gtgtcgatca gttgtctgac    1020
tatattagag cttcctataa tacattattg aaatttaata aggaggttgg tgaagatttg    1080
gcaaaaaagc aacgtaccta cgctttcgac aagtacatcg aagattggaa acaatacatg    1140
agaaccaact tctctcaatc aagatggttt ttcactaagg agttgccatc tttcgctgat    1200
tacattaaca acggtgccat cacaatcggt gcatatttgg ttgcctctgc tgctttctta    1260
tatatggact ccgcaaaaga agatgttatc aactggatgt ccacaaaccc taagttggtc    1320
```

```
gttgcttact ccactcactc tcgtttaatt aatgactttg gtggtcacaa gttcgaaaag    1380
gagagaggtt cctctactgc tattgaatgc tacatgaagg accataatgt ctccgaagaa    1440
gaagccgcaa acaagtttag agaaatgatg gaggacgctt ggaaggttat gaatgaagaa    1500
tgtttaagac caactaccat ccctagagac gggttgaaga tgttgttaaa catagccaga    1560
gtcggtgaaa ctgtttacaa gcatagaatc gatggtttta cccaaccaca tgctattgaa    1620
gaacacataa gagccatgtt ggtcgatttc atgtctattt aa                      1662
```

<210> SEQ ID NO 103
<211> LENGTH: 1662
<212> TYPE: DNA
<213> ORGANISM: Artificial Sequence
<220> FEATURE:
<223> OTHER INFORMATION: Synthetic polynucleotide

<400> SEQUENCE: 103

```
atggcctcag cacaagcttc cttaccttct aataacagac aggaaacagt ccgtccattg      60
gctgacttcc cagagaacat ctgggctgat agaattgccc catttacctt ggataagcaa     120
gaatacgaaa tgtgtcaaag agaaatagag atgttaaaag ctgaagttgc ttctatgttg     180
ttggcaactg gtaagactat gatgcaaaga ttcgacttca ttgataagat cgaaagattg     240
ggggtctccc accattttga cattgaaatc gaaaatcaat gcaagagtt tttcaacgtt      300 tataccaact taggtgaata ctctgcctat gatttgtcat ctgctgcctt gcagttccgt     360
ttatttagac aacacggttt caatatttcc tgcggtattt cgaccaatt tatcgacgct      420 aaaggtaagt tcaaggaatc tttatgtaac gatatcagag gtttgttgtc tttgtacgaa     480
gctgctcatg ttagaactca cggtgataaa attttggaag aagctttagc tttcaccact     540
actcacatga cctccggtgg tccacattta gattcttcat ggccaagca agttaaatac      600 gcattggaac agccattgca taagggtata ttgagatatg aagcttggag atacatatct     660
atctacgaag aggacgaatc caacaataag ttattattgc gtttggctaa gttggactat     720
cacttgttac aaatgtcata caagcaagag ttgtgtgaaa ttacaagatg gggtaaaggt     780
ttggaatctg tctccaactt tccttatgcc cgtgacagat tcgttgaatg ttacttttgg     840
gctgtcggta cttttgtacga accacaatac tcattggcta gaatgaccctt cgctaaggtt    900 gctgctttaa ttactatgat cgatgatatt tatgatgcct acggtacctt ggacgaattg     960
caaatattaa ctgactctgc cgaaagatgg gatggttccg gtgtcgatca gttgtctgac    1020
tatattgagg cttcctataa tacattattg aaatttaata aggaggttgg tgaagatttg    1080
gcaaaaaagc aacgtaccta cgctttcgac aagtacatcg aagattggaa acaatacatg    1140
agaaccaact tctctcaatc aagatggttt tcactaagg agttgccatc tttcgctgat    1200
tacattaaca acggtgccat cacaatcggt gcatatttgg ttgcctctgc tgctttctta    1260
tatatgaact ccgcaaaaga agatgttatc aactggatgt ccacaaaccc taagttggtc    1320
gttgcttact ccactcactc tcgtttaatt aatgactttg gtggtcacaa gttcgacaag    1380
gagagaggta ccggtactgc tattgaatgc tacatgaagg accataatat atccgaagaa    1440
gaagccgcaa agaagtttag agaaatgatc gagaacacct ggaaggtcat gaatgaagaa    1500
tgtttaagac caattccaat ccctagagac acattgaaga tgttgttaaa catcgccaga    1560
gttggtgaaa ctgtctacaa gcatagaatc gatggtttta ctcaaccaca tgctattgaa    1620
gaacacataa gagctatgtt ggttgatttc atgtctattt aa                      1662
```

-continued

<210> SEQ ID NO 104
<211> LENGTH: 1683
<212> TYPE: DNA
<213> ORGANISM: Artificial Sequence
<220> FEATURE:
<223> OTHER INFORMATION: Synthetic polynucleotide

<400> SEQUENCE: 104

| | | | | | |
|---|---|---|---|---|---|
| atgtccttgt | tagaaggtaa | cgttaatcac | gagaacggaa | tatttagacc | agaagctaat | 60 |
| ttctcacctt | ctatgtgggg | taacattttc | cgtgattctt | ccaaagacaa | ccaaatctct | 120 |
| gaagaagtcg | ttgaagaaat | cgaggcattg | aaggaagtcg | ttaagcatat | gattatttct | 180 |
| acaacctcca | acgccatcga | acagaaatta | gagttggtcg | ataatttgga | aagattgggt | 240 |
| ttggcttacc | acttcgaagg | tcaaatcaac | agattattat | catctgccta | taatgctaac | 300 |
| catgaagacg | aaggtaacca | aagagaaat | aaggaggact | tgtacgcagc | tgctttggaa | 360 |
| tttagaattt | tcagacaaca | tggttttaac | gtttcctctg | attgctttaa | tcaattcaaa | 420 |
| gatactaagg | gtaagttcaa | aaagactttg | ttgattgatg | tcaagggtat | gttgtccttg | 480 |
| tatgaagctg | cccacgttcg | tgaacatggt | gacgacatct | tagaagaagc | tttgatcttt | 540 |
| gctaccttcc | acttagaaag | aattactcca | aattctttgg | attccacatt | ggaaaaacaa | 600 |
| gttggtcacg | cattgatgca | atcattacac | agaggtattc | caagagccga | agctcatttt | 660 |
| aacatatcta | tttacgaaga | gtgtggttct | tctaatgaaa | agttgttaag | attggctaag | 720 |
| ttggactaca | acttagtcca | agtcttgcac | aaggaggaat | tatcagaatt | gaccaaatgg | 780 |
| tggaaagatt | tagacttcgc | ttctaagttg | tcctacgttc | gtgatagaat | ggttgaatgt | 840 |
| tttttctgga | ctgtcggtgt | ttatttcgaa | ccacagtact | ccagagccag | agttatgtta | 900 |
| gctaagtgta | ttgctatgat | ctctgttatc | gacgatactt | acgattccta | tggtaccttg | 960 |
| gacgagttaa | ttatattcac | tgaagtcgtt | gatagatggg | atatatccga | ggtcgaccgt | 1020 |
| ttgcctaact | atatgaaacc | aatctacatt | tctttgttat | acttgtttaa | cgaatatgaa | 1080 |
| agagaaatta | acgaacaaga | ccgtttcaat | ggtgttaact | acgttaagga | agctatgaag | 1140 |
| gaaatcgtca | gatcttatta | catcgaggcc | gaatggttca | tagaaggtaa | aatcccatct | 1200 |
| ttcgaagagt | acttgaacaa | tgcattggtt | acaggtacct | attacttatt | ggccccagca | 1260 |
| tctttgttgg | gtatggaatc | caccctcaaag | agaacttttg | attggatgat | gaagaagcca | 1320 |
| aaaattttgg | tcgcttctgc | tatcattggt | agagttattg | atgatattgc | tacttacaag | 1380 |
| atagaaaagg | aaaagggaca | gttagtcact | ggtattgaat | gctacatgca | agagaacaac | 1440 |
| ttatcagttg | aaaaggcctc | cgctcaattg | tctgaaatcg | ccgagtccgc | ttggaaagac | 1500 |
| ttgaataaag | aatgtatcaa | aactaccacc | tccaacattc | ctaacgaaat | attgatgaga | 1560 |
| gttgtcaact | tgacaagatt | aattgacgtt | gtctacaaga | ataatcaaga | tggttattct | 1620 |
| aaccctaaga | acaatgttaa | gtcagtcatc | gaagctttgt | tggttaatcc | aatcaatatg | 1680 |
| taa | | | | | | 1683 |

<210> SEQ ID NO 105
<211> LENGTH: 1632
<212> TYPE: DNA
<213> ORGANISM: Artificial Sequence
<220> FEATURE:
<223> OTHER INFORMATION: Synthetic polynucleotide

<400> SEQUENCE: 105
atggaaagta ggcgttcagc aaattatcag gcttccatat gggatgacaa ctttattcaa    60

| | |
|---|---|
| tctcttgcct ctccttacgc tggagagaag tacgtctcgc aagctaacga attgaaagaa | 120 |
| caagtgaaga tgatgttaga cgaagaggat atgaaactgt tagattgctt ggaattggtt | 180 |
| gacaacttgg aaagactagg cttggcttat cacttcgagg gtcaaatcaa tagactcttg | 240 |
| agcagtgcct acaacgctaa ccatgaagat gaaggtaatc acaagagaaa taaggaagac | 300 |
| ttatacgcgg cggctttgga gttcagaatt tttagacaac atggtttcaa cgttccacag | 360 |
| gacgtcttct cttcctttat gaataaggcc ggtgattttg aagaatccct ttctaaggat | 420 |
| acaaaaggtt tggtttcatt gtatgaagct tcttacctat caatggaagg tgaaaccatc | 480 |
| ttagacatgg ctaaggattt ctcctctcac catttacaca aaatggtcga agatgctact | 540 |
| gataagcgag ttgctaacca aatcattcac agccttgaaa tgccattgca cagaagggta | 600 |
| caaaaactcg aagcaatatg gttcattcaa ttctacgaat gtggttctga cgccaacccc | 660 |
| actttggtag aattggctaa gttagacttc aacatggttc aagctacgta tcaagaagaa | 720 |
| ctaaagagat tgtcgagatg gtacgaagag accggactgc aagaaaagtt atcttttgca | 780 |
| cgtcatcgtt tggccgaagc ttttttgtgg tctatgggta tcattccaga aggccatttc | 840 |
| ggttacggta gaatgcactt gatgaagatc ggtgcctata ttactttatt ggatgatatt | 900 |
| tatgatgtct acggtacctt ggaagagttg caagttctaa ctgaaatcat cgaacgttgg | 960 |
| gacattaatt tgttggacca gctgcctgag tacatgcaaa tcttctttt atacatgttc | 1020 |
| aattccacaa acgaattagc ttatgagata cttagagatc aaggaattaa tgttatctct | 1080 |
| aacctcaaag ggttgtgggt cgaattgtcc cagtgttatt ttaaggaagc aacctggttt | 1140 |
| cataacggtt acactccaac tacagaggaa tacttgaacg ttgcttgtat tagtgcatct | 1200 |
| ggtccagtga tccttttctc cggttatttc accacgacta acccgattaa taagcatgaa | 1260 |
| ttacaaagtt tagaaagaca cgctcattca ctaagcatga ttctgagatt ggctgacgac | 1320 |
| cttgggacct catctgatga aatgaaacgg ggcgatgtgc aaaggccat ccagtgcttt | 1380 |
| atgaatgaca ctggttgttg tgaagaagag gcaagacaac acgtcaaaag actcatagac | 1440 |
| gctgaatgga agaagatgaa caaggacatc ttgatggaaa aacccttaa gaacttctgt | 1500 |
| ccaactgcta tgaatttagg taggataagc atgtcctttt acgagcacgg tgatggttac | 1560 |
| ggtggtccac actctgatac caaaaaaaag atggttagct tgttcgttca acctatgaac | 1620 |
| attaccatct aa | 1632 |

<210> SEQ ID NO 106
<211> LENGTH: 1659
<212> TYPE: DNA
<213> ORGANISM: Artificial Sequence
<220> FEATURE:
<223> OTHER INFORMATION: Synthetic polynucleotide
<400> SEQUENCE: 106

| | |
|---|---|
| atggcctcaa cagaaatcgc agttcctttg aataaccagc acgagtccgt ccgtcaatta | 60 |
| gctgacttcc cagaaaacat ttgggctgat agagttgctt cttttacctt ggataagcaa | 120 |
| ggtcatgaca tgtgtgctaa agaaatagaa atgttaaagg aagaagtcat gtctatgttg | 180 |
| ttggaggaaa agccaatgat ggaaaaattc aacttgatcg ataatattga agattaggc | 240 |
| atctcctacc acttcggtga caagattgaa gatcaattac aagaatatta cgacgcctgc | 300 |
| actaactttg agaagcatgc tgaatgtgat ttgtcaatag ctgccttgca attcagattg | 360 |
| tttagacaac acgtttcaa tatttcttgt ggtatctttg acggtttctt ggatgcaaac | 420 |
| ggtaaattca aggaatcttt atgtaatgac attaagggtt tgttgtcctt atacgaagcc | 480 |

```
gctcatgtta gaactcacgg tgataaaatt ttggaggaag ctttgttttt taccactact    540
catttgaccc gtgaaatccc aaacgttggt tctactttgg ctaagcaggt caaatatgct    600
ttagagcaac cattgcacaa gggtatccca agatacgaag cctggagata tatttcaatt    660
tacgaagaag acgaatcttc caacaagttg ttattacgtt tggcaaagtt ggattaccat    720
ttgtcccaaa tgttgaacaa acaggacttg tgcgagatca ttagatgggg taaggaatta    780
gacattattt ctaaggttcc ttatgctaga gatagaatcg tcgaatgtta cttctgggct    840
gttgccacat attacgaacc acaatactcc ttggctagaa tgacattgac caaagctact    900 gttttgctg gtatgatcga tgatacctat gacgcttacg gtactttaga tgagttgaag    960
atattcactg aagcagtcga acgttgggac tcttccggta ttgaccaatt gtcagattac   1020
atgaaagcag cttacacctt agtcttaaat tttaacaagg aagttggtga agatttagcc   1080
aagaaacaaa gaacttacgc cttcgacaag tacatcgaag aatggaagca atatgctaga   1140
acctctttca cccaatctaa gtggttcttg accaatgagt tgccatcctt ttctgattat   1200
ttgtctaacg gtatggttac ttcaacatac tacttattgt ctgccgctgc cttcttggac   1260
atggattccg cttctgaaga cgtcataaat tggatgtcta ccaaccctaa attgttcgtc   1320
gctttgacaa ctcacgctag attggccaac gacgttggtt ctcataaatt tgaaaaggaa   1380
agaggttcag gtaccgcaat agaatgttat atgaaggatt accacgtttc tgaggaagaa   1440
gctatgaaga aattcgagga aatgtgtgac gatgcttgga aggtcatgaa cgaagaatgc   1500
ttgcgttcca ctacaatccc aagagagatt ttgaaggtta ttttgaactt ggcaagaact   1560
tgtgaagtcg tttacaagca tcgtggtgat ggcttcaccg atcaaagaag aattgaagct   1620
cacatcaacg ccatgttaat ggactccgtt tccatctaa                           1659

<210> SEQ ID NO 107
<211> LENGTH: 1659
<212> TYPE: DNA
<213> ORGANISM: Artificial Sequence
<220> FEATURE:
<223> OTHER INFORMATION: Synthetic polynucleotide

<400> SEQUENCE: 107
atggcctcaa cagaaatcgc agttcctttg aataaccagc acgagtccgt ccgtcaatta     60
gctgacttcc cagaaaacat ttgggctgat agagttgctt cttttacctt ggataagcaa    120
ggtcatgaca tgtgtgctaa agaaatagaa atgttaaagg aagaagtcat gtctatgttg    180
ttggaggaaa agccaatgat ggaaaaattc aacttgatcg ataatattga agattaggc    240 atctcctacc acttcggtga caagattgaa gatcaattac aagaatatta cgacgcctgc    300
actaactttg agaagcatgc tgaatgtgat ttgtcaatag ctgccttgca attcagattg    360
tttagacaac acggtttcaa tatttcttgt ggtatctttg acggtttctt ggatgcaaac    420
ggtaaattca aggaatcttt atgtaatgac attaagggtt tgttgtccct tatacgaagcc    480 gctcatgtta gaactcacgg tgataaaatt ttggaggaag ctttgttttt taccactact    540
catttgaccc gtgaaatccc aaacgttggt tctactttgg ctaagcaggt caaacacgct    600
ttagagcaac cattgcacag aggtatccca agatatgaag cctactgctt catttcaatt    660
tatgaagaag acgaatctaa caacaagttg ttattacgtt tggcaaagtt ggattaccat    720
ttgttgcaaa tgtcctacaa aagagaattg tccgagatca ttagatgggg taaggaatta    780
gacattattt ctaaggttcc ttatgctaga gatagaatcg tcgaatgtta cttttgggct    840
```

| | |
|---|---|
| gttgccacat attacgagcc acaatactcc ttggctagaa tgacattgac caaagctact | 900 |
| gttttcgctg gtatgatcga tgataccat gacgcttacg gtactttaga cgaattgaag | 960 |
| atattcactg aagcagtcga acgttgggat tcttccggta ttgaccaatt gtcagattac | 1020 |
| atgaaagcag cttacacctt agtcttaaat tttaacaagg aagttggtga ggatttagcc | 1080 |
| aagaaacaaa gaacttacgc cttcgacaag tacatcgaag aatggaagca atatgctaga | 1140 |
| acctctttca cccaatctaa gtggttcttg accaatgaat tgccatcctt ttctgattat | 1200 |
| ttgtctaacg gtatggttac ttcaacatac tacttattgt ctgccgctac attcttgggt | 1260 |
| atggacggtg cttctgaaga cgtcataaat tggatgtcta ctaaccctaa attgttcgtc | 1320 |
| gctttgacaa cccatgctag attggccaac gacgttggtt ctcacaagtt tgaaaaggaa | 1380 |
| agaggctccg gtactgcaat agaatgttat atgaaagatt accacgtttc tgaggaggaa | 1440 |
| gctatgaaga aattcgaaga aatgtgtgac gatgcctgga aggtcatgaa cgaagaatgc | 1500 |
| ttgcgttcta ctaccatccc aagagagatt ttgaaggtta ttttgaactt ggccagaacc | 1560 |
| tgtgaagtcg tttacaagca tcgtggtgat ggtttcactg atcagagaag aattgaagct | 1620 |
| cacatcaacg ctatgttaat ggactccgtt tccatctaa | 1659 |

<210> SEQ ID NO 108
<211> LENGTH: 1659
<212> TYPE: DNA
<213> ORGANISM: Artificial Sequence
<220> FEATURE:
<223> OTHER INFORMATION: Synthetic polynucleotide

<400> SEQUENCE: 108

| | |
|---|---|
| atggcctcaa cagaaatcgc agttcctttg aataaccagc acgagtccgt ccgtcaatta | 60 |
| gctgacttcc cagaaaacat ttgggctgat agagttgctt cttttacctt ggataagcaa | 120 |
| ggtcatgaca tgtgtgctaa agaaatagaa atgttaaagg aagaagtcat gtctatgttg | 180 |
| ttggaggaaa agccaatgat ggaaaaattc aacttgatcg ataatattga agattaggc | 240 |
| atctcctacc acttcggtga caagattgaa gatcaattac aagaatatta cgacgcctgc | 300 |
| actaactttg agaagcatgc tgaatgtgat ttgtcaatag ctgccttgca attcagattg | 360 |
| tttagacaac acggtttcaa tatttcttgt ggtatctttg acggtttctt ggatgcaaac | 420 |
| ggtaaattca aggaatcttt atgtaatgac attaagggtt tgttgtcctt atacgaagcc | 480 |
| gctcatgtta gaactcacgg tgataaaatt ttggaggaag ctttgttttt taccactact | 540 |
| catttgaccc gtgaaatccc aaacgttggt tctacttttgg ctaagcaggt caaacacgct | 600 |
| ttagagcaac cattgcacag aggtatccca agatatgaag cctactgctt catttcaatg | 660 |
| tatgaagaag acgaatcttc caacaagttg ttattacgtt tggcaaagtt ggattaccat | 720 |
| tgtcccaaa tgttgaacaa acaggacttg tgtgagatca ttagatgggg taaggaatta | 780 |
| gacattattt ctaaggttcc ttatgctaga gatagaattg tcgaatgtta cttttgggct | 840 |
| gttgccacat actacgaacc acaatattcc ttggctagaa tgacattgac caaagctact | 900 |
| gttttcgctg gtatgatcga tgataccat gacgcttacg gtactttaga tgagttgaag | 960 |
| atattcactg aagcagtcga acgttgggac tcttccggta ttgaccaatt gtcagattac | 1020 |
| atgaaagcag cttacacctt agtcttaaat tttaacaagg aagttggtga agatttagcc | 1080 |
| aagaaacaaa gaacttacgc cttcgacaag tacatcgaag aatggaagca atatgctaga | 1140 |
| acctctttca cccaatctaa gtggttcttg accaatgagt tgccatcctt ttctgattat | 1200 |
| ttgtctaacg gtatggttac ttcaacatac tacttattgt ctgccgctac attcttgggt | 1260 |

```
atggacggtg cttctgaaga tgtcataaat tggatgtcta ctaaccctaa attgttcgtc    1320
gctttgacaa cccatgctag attggccaac gacgttggtt ctcacaagtt tgaaaaggaa    1380
agaggctccg gtactgcaat agaatgctat atgaaagatt accacgtttc tgaggaagaa    1440
gctatgaaga aattcgagga aatgtgtgac gatgcctgga aggtcatgaa cgaagaatgt    1500
ttgcgttcta ctaccatccc aagagagatt ttgaaggtta ttttgaactt ggccagaacc    1560
tgtgaagtcg tttacaagca tcgtggtgat ggtttcactg accaaagaag aatcgaagct    1620
cacattaacg ctatgttaat ggactccgtt tccatctaa                         1659
```

<210> SEQ ID NO 109
<211> LENGTH: 1662
<212> TYPE: DNA
<213> ORGANISM: Artificial Sequence
<220> FEATURE:
<223> OTHER INFORMATION: Synthetic polynucleotide

<400> SEQUENCE: 109

```
atggcctcag cacaagcttc cttaccttct aataacagac aggaaacagt ccgtccattg      60
gctgacttcc cagagaacat ctgggctgat agaattgccc catttacctt ggataagcaa     120
gaatacgaaa tgtgtcaaag agaaatagag atgttaaaag ctgaagttgc ttctatgttg     180
ttggcaactg gtaagactat gatgcaaaga ttcgacttca ttgataagat cgaaagattg     240
ggggtctccc accattttga cattgaaatc gaaaatcaat gcaagagtt tttcaacgtt      300 tataccaact taggtgaata ctctgcctat gatttgtcat ctgctgcctt gcagttccgt     360
ttatttagac aacacggttt caatatttcc tgcggtattt tcgaccaatt tatcgacgct     420
aaaggtaagt tcaaggaatc tttatgtaac gatatcagag gttgttgtc tttgtacgaa      480 gctgctcatg ttagaactca cggtgataaa attttggaag aagctttagc tttcaccact     540
actcacatga cctccggtgg tccacattta gattcttcat tggccaagca agttaaatac     600
gcattggaac agccattgca taagggtata ttgagatatg aagcttggag atacatatct     660
atctacgaag aggacgaatc caacaataag ttattattgc gtttggctaa gttggactat     720
cacttgttac aaatgtcata caagcaagag ttgtgtgaaa ttacaagatg gggtaaaggt     780
ttggaatctg tctccaactt tccttatgcc cgtgacagat tcgttgaatg ttacttttgg     840
gctgtcggta ctttgtacga accacaatac tcattggcta gaatgacctt cgctaaggtt     900
gctgctttaa ttactatgat cgatgatatt tatgatgcct acggtacctt ggacgaattg     960
caaatattaa ctgactctgc cgaaagatgg gatggttccg gtgtcgatca gttgtctgac    1020
tatattagag cttcctataa tacattattg aaatttaata aggaggttgg tgaagatttg    1080
gcaaaaaagc aacgtaccta cgctttcgac aagtacatcg aagattggaa acaatacatg    1140
agaacctctt tcactcaatc aaagtggttt ttgactaacg agttgccatc tttcgctgat    1200 tacattttcca acggtgccat cacaatcggt gcatatttaa ttgcctctgc cggtttttg    1260 gatatggatt ccgccttgga agacgttatt aactggatgt ctaccaaccc aaaattaatg    1320
gtcgcttatt ccacccactc aagattgatc aatgattacg gtggtcacaa gttcgacaag    1380
gaaagagggt cagttactgc tttggattgc tacatgaagg attactccgt ctctgaggaa    1440
gaagctgcaa agaagttcag agaaatgtgt gaagacaact ggaaggttat gaatgaagaa    1500
tgtttgagac ctactacaat tccaagagat ggtttgaaga tgttgttaaa cattgctaga    1560
gtcggtgaaa ctgtttacaa acatagaatc gacggtttta ctcaacctca tgcaatcgag    1620
```
gagcacatta gagccatgtt agttgacttc atgtctattt aa        1662

<210> SEQ ID NO 110
<211> LENGTH: 1659
<212> TYPE: DNA
<213> ORGANISM: Artificial Sequence
<220> FEATURE:
<223> OTHER INFORMATION: Synthetic polynucleotide

<400> SEQUENCE: 110

| | |
|---|---|
| atggcctcaa cagaaatcgc agttcctttg aataaccagc acgagtccgt ccgtcaatta | 60 |
| gctgacttcc cagaaaacat ttgggctgat agagttgctt cttttacctt ggataagcaa | 120 |
| ggtcatgaca tgtgtgctaa agaaatagaa atgttaaagg aagaagtcat gtctatgttg | 180 |
| ttggaggaaa agccaatgat ggaaaaattc aacttgatcg ataatattga aagattaggc | 240 |
| atctcctacc acttcggtga caagattgaa gatcaattac aagaatatta cgacgcctgc | 300 |
| actaactttg agaagcatgc tgaatgtgat ttgtcaatag ctgccttgca attcagattg | 360 |
| tttagacaac acggtttcaa tatttcttgt ggtatctttg acggtttctt ggatgcaaac | 420 |
| ggtaaattca aggaatcttt atgtaatgac attaagggtt tgttgtcctt atacgaagcc | 480 |
| gctcatgtta gaactcacgg tgataaaatt ttggaggaag ctttgttttt taccactact | 540 |
| catttgaccc gtgaaatccc aaacgttggt tctactttgg ctaagcaggt caaatatgct | 600 |
| ttagagcaac cattgcacaa gggtatccca agatacgaag cctggagata tatttcaatt | 660 |
| tacgaagaag acgaatctaa caacaagttg ttattacgtt tggcaaagtt ggattaccat | 720 |
| ttgttgcaaa tgtcctacaa aagagaattg tccgagatca ttagatgggg taaggaatta | 780 |
| gacattattt ctaaggttcc ttatgctaga gatagaatcg tcgaatgtta tttctgggct | 840 |
| gttgccacat actacgagcc acaatactcc ttggctagaa tgacattgac caaagctact | 900 |
| gttttttgctg gtatgatcga tgatacctat gacgcttacg gtactttaga cgaattgaag | 960 |
| atattcactg aagcagtcga acgttgggat tcttccggta ttgaccaatt gtcagattac | 1020 |
| atgaaagcag cttacacctt agtcttaaat tttaacaagg aagttggtga ggatttagcc | 1080 |
| aagaaacaaa gaacttacgc cttcgacaag tacatcgaag aatggaagca atatgctaga | 1140 |
| acctctttca cccaatctaa gtggttcttg accaatgaat tgccatcctt ttctgattat | 1200 |
| ttgtctaacg gtatggttac ttcaacatac tacttattgt ctgccgctac attcttgggt | 1260 |
| atggacggtg cttctgaaga cgtcataaat tggatgtcta ctaaccctaa attgttcgtc | 1320 |
| gctttgacaa cccacgctag attggccaac gacgttggtt ctcataaatt tgaaaaggaa | 1380 |
| agaggctcct ccactgcaat agaatgctat atgaaggatt accacgtttc tgaggaggaa | 1440 |
| gctatggaaa aattcgaaga aatgtgtgac gatgcctgga aggtcatgaa cgaagaatgc | 1500 |
| ttgcgttcca ctaccatccc aagagagatt ttgaaggtta ttttgaactt ggccagaacc | 1560 |
| tgtgaagtcg tttacaagca tcgtggtgat ggtttcactg atcagagaag aattgaagct | 1620 |
| cacatcaacg ctatgttaat ggactcagtt tccatctaa | 1659 |

<210> SEQ ID NO 111
<211> LENGTH: 1659
<212> TYPE: DNA
<213> ORGANISM: Artificial Sequence
<220> FEATURE:
<223> OTHER INFORMATION: Synthetic polynucleotide

<400> SEQUENCE: 111
atggcctcaa cagaaatcgc agttcctttg aataaccagc acgagtccgt ccgtcaatta        60

```
gctgacttcc cagaaaacat ttgggctgat agagttgctt cttttacctt ggataagcaa      120
ggtcatgaca tgtgtgctaa agaaatagaa atgttaaagg aagaagtcat gtctatgttg      180
ttggaggaaa agccaatgat ggaaaaattc aacttgatcg ataatattga aagattaggc      240
atctcctacc acttcggtga caagattgaa gatcaattac aagaatatta cgacgcctgc      300
actaactttg agaagcatgc tgaatgtgat ttgtcaatag ctgccttgca attcagattg      360
tttagacaac acggtttcaa tatttcttgt ggtatctttg acggtttctt ggatgcaaac      420
ggtaaattca aggaatcttt atgtaatgac attaagggtt tgttgtcctt atacgaagcc      480
gctcatgtta gaactcacgg tgataaaatt ttggaggaag ctttgttttt taccactact      540
catttgaccc gtgaaatccc aaacgttggt tctactttgg ctaagcaggt caaatatgct      600
ttagagcaac cattgcacaa gggtatccca agatacgaag cctggagata tatttcaatt      660
tacgaagaag acgaatctaa caacaagttg ttattacgtt tggcaaagtt ggattaccat      720
ttgttgcaaa tgtcctacaa aagagaattg tccgagatca ttagatgggg taaggaatta      780
gacattattt ctaaggttcc ttatgctaga gatagaatcg tcgaatgtta tttctgggct      840
gttgccacat actacgagcc acaatactcc ttggctagaa tgacattgac caaagctact      900 gttttttgctg gtatgatcga tgatacctat gacgcttacg gtactttaga cgaattgaag      960
atattcactg aagcagtcga acgttgggat tcttccggta ttgaccaatt gtcagattac     1020
atgaaagcag cttacacctt agtcttaaat tttaacaagg aagttggtga ggatttagcc     1080
aagaaacaaa gaacttacgc cttcgacaag tacatcgaag aatggaagca atatgctaga     1140
acctctttca cccaatctaa gtggttcttg accaatgaat tgccatcctt tgcagattat     1200 tgtctaacg gtatggttac ttcaacatac tacttattgt ctgctgctgc cttgttggac     1260
atggactccg ctttagaaga tgtcataaat tggatgtcta ccaaccctaa attcttcgtc     1320
gctttgacaa ctcacgctag attgaccaac gacgttggtt ctcataaatt tgaaaaggaa     1380
agaggttccg gtactgcaat agaatgctat atgaaggatt accacgtttc tgaggaggaa     1440
gctatgaaga aattcgaaga aatgtgtgac gatgcctgga aggtcatgaa cgaagaatgc     1500
ttgcgttcta ctacaatccc aagagagatt ttgaaggtta ttttgaactt ggccagaacc     1560
tgtgaagtcg tttacaagca tcgtggtgat ggcttcactg accagagaag aattgaagct     1620
cacatcaacg ccatgttaat ggactccgtt tccatctaa                            1659

<210> SEQ ID NO 112
<211> LENGTH: 1662
<212> TYPE: DNA
<213> ORGANISM: Artificial Sequence
<220> FEATURE:
<223> OTHER INFORMATION: Synthetic polynucleotide

<400> SEQUENCE: 112
atggccagtg cgcaagcatc attaccttcc aataacagac aggaaacagt ccgtccccta       60
gctgacttcc cagagaacat ctgggctgat aggattgctc catttaccct ggataagcaa      120
gaatacgaaa tgtgtcaaag agaaatagag atgttgaaag ctgaagtggc ctctatgttg      180
cttgccactg gaaagactat gatgcaacga ttcgacttca ttgataagat cgaaagattg      240
ggcgtatcgc accattttga cattgaaatc gaaaatcaac tccaagagtt tttcaacgtt      300
tataccaact ggggtgaata cagcgcgtat gatctgtcat ctgctgcatt gcagttcaga      360
ttatttagac aacacggttt caatatttcc tgcggtattt tcgaccaatt tatcgacgct      420
```

| | |
|---|---|
| aaaggtaagt tcaaggaatc tttatgtaac gatatccggg gtttgttgtc tctctacgaa | 480 |
| gctgctcatg ttagaacgca cggtgataaa attttggaag aagcattggc ttttactact | 540 |
| acccatatga cttccggtgg tccacaccta gactctagct tggctaagca agtcaagtac | 600 |
| gcgcttgagc aaccattaca aaggggatt ttgagatacg aagcttggcg ttatatatcc | 660 |
| atctacgaag aagacgaatc taataacaaa cttctgttaa gattggctaa actcgattat | 720 |
| catttgcttc aaatgtccta caagcaggaa ttatgtgaaa tcacgagatg gggcaagggt | 780 |
| ttagagtcag tttctaattt cccttacgct agagatcgtt ttgttgaatg ttatttctgg | 840 |
| gccgtaggaa cattgtacga accgcaatac agtctagcca gaatgacctt tgctaaagtt | 900 |
| gctgccttga ttactatgat tgacgatatc tacgatgcct atggtacctt ggacgagtta | 960 |
| caaatattga ccgattctgc tgaaagatgg gatggttcgg gagtcgacca attgtctgac | 1020 |
| tatatacgcg ctagttataa cactttgttg aagttcaaca aggaagtcgg tgaggattta | 1080 |
| gccaaaaagc aaagaacgta cgcatttgac aaatacatcg aagattggaa gcaatacatg | 1140 |
| agaacttctt tcacccagtc caagtggttc ctgaccaaca aactcccttc cttcgctgac | 1200 |
| tacatttcca atggggctat tacaattggt gcttacttga tcgccagcgc gggttttttg | 1260 |
| gatatggatt ctgccctaga agacgttatt aactggatgt ctactaaccc aaaattgatg | 1320 |
| gtggcttatt caactcacag cagacttatc aatgattatg gtggtcacaa gttcgacaag | 1380 |
| gaaagaggga cgggtacagc tattgaatgc tacatgaagg atcataacat ctctgaggaa | 1440 |
| gaagctgcaa agaagttcag agaaatgatc gagaacactt ggaaggttat gaatgaagaa | 1500 |
| tgtctacggc caattccaat tccaagagat actctcaaga tgctattgaa cattgctagg | 1560 |
| gtcggtgaaa ctgtttacaa acacagaatc gacggtttta cccaaccaca tgcaatcgag | 1620 |
| gaacacatca gggccatgtt ggtcgacttc atgtcaattt aa | 1662 |

<210> SEQ ID NO 113
<211> LENGTH: 1659
<212> TYPE: DNA
<213> ORGANISM: Artificial Sequence
<220> FEATURE:
<223> OTHER INFORMATION: Synthetic polynucleotide

<400> SEQUENCE: 113

| | |
|---|---|
| atggcctcaa cagaaatcgc agttcctttg aataaccagc acgagtccgt ccgtcaatta | 60 |
| gctgacttcc cagaaaacat ttgggctgat agagttgctt cttttacctt ggataagcaa | 120 |
| ggtcatgaca tgtgtgctaa agaaatagaa atgttaaagg aagaagtcat gtctatgttg | 180 |
| ttggaggaaa agccaatgat ggaaaaattc aacttgatcg ataatattga aagattaggc | 240 |
| atctcctacc acttcggtga caagattgaa gatcaattac aagaatatta cgacgcctgc | 300 |
| actaactttg agaagcatgc tgaatgtgat ttgtcaatag ctgccttgca attcagattg | 360 |
| tttagacaac acggtttcaa tatttcttgt ggtatcttg acggtttctt ggatgcaaac | 420 |
| ggtaaattca aggaatcttt atgtaatgac attaaggggt tgttgtcctt atacgaagcc | 480 |
| gctcatgtta gaactcacgg tgataaaatt ttggaggaag cttttgtttt taccactact | 540 |
| catttgaccc gtgaaatccc aaacgttggt tctacttggg ctaagcaggt caaacacgct | 600 |
| ttagagcaac cattgcacag aggtatccca agatatgaag cctactgctt catttcaatt | 660 |
| tatgaagaag acgaatctaa caacaagttg ttattacgtt tggcaaagtt ggattaccat | 720 |
| ttgttgcaaa tgtcctacaa aagagaattg tccgagatca ttagatgggg taaggaatta | 780 |
| gacattattt ctaaggttcc ttatgctaga gatagaatcg tcgaatgtta cttttgggct | 840 |

```
gttgccacat attacgagcc acaatactcc ttggctagaa tgacattgac caaagctact    900
gttttcgctg gtatgatcga tgatacctat gacgcttacg gtactttaga cgaattgaag    960
atattcactg aagcagtcga acgttgggat tcttccggta ttgaccaatt gtcagattac   1020
atgaaagcag cttacacctt agtcttaaat tttaacaagg aagttggtga ggatttagcc   1080
aagaaacaaa gaacttacgc cttcgacaag tacatcgaag aatggaagca atatgctaga   1140
acctctttca cccaatctaa gtggttcttg accaatgaat tgccatcctt ttctgattat   1200
ttgtctaacg gtatggttac ttcaacatac tacttattgt ctgccgctgc cttcttggac   1260
atggactccg cttctgaaga tgtcataaat tggatgtcta ccaaccctaa attgttcgtc   1320
gctttgacaa ctcatgctag attggccaac gacgttggtt ctcacaagtt tgaaaaggaa   1380
agaggttcag gtaccgcaat agaatgttat atgaaagatt acaacgtttc tgaggaggaa   1440
gctttgaaga aattcgaaga aatgtgtgaa gatacttgga aggtcatgaa cgaagaatgc   1500
ttgcgttcca ctacaatccc aagagagatt ttgaaggtta ttttgaactt ggccagaacc   1560
tgtgaagtcg tttacaagca tcgtggtgac ggcttcactg atcagagaag aattgaagct   1620
cacatcaatg ctatgttaat ggactccgtt tccatctaa                          1659
```

<210> SEQ ID NO 114
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 114

```
atggcctcag cacaagcttc cttaccttct aataacagac aggaaacagt ccgtccattg     60
gctgacttcc cagagaacat ctgggctgat agaattgccc catttacctt ggataagcaa    120
gaatacgaaa tgtgtcaaag agaaatagag atgttaaaag ctgaagttgc ttctatgttg    180
ttggcaactg gtaagactat gatgcaagga ttcgacttca ttgataagat cgaaagattg    240
ggggtctccc accattttga cattgaaatc gaaaatcaat tgcaagagtt tttcaacgtt    300
tataccaact taggtgaata ctctgcctat gatttgtcat ctgctgcctt gcagttccgt    360
ttatttagac aacacggttt caatatttcc tgcggtattt tcgaccaatt tatcgacgct    420
aaaggtaagt tcaaggaatc tttatgtaac gatatcagag gtttgttgtc tttgtacgaa    480
gctgctcatg ttagaactca cggtgataaa attttggaag aagctttagc tttcaccact    540
actcacatga cctccggtgg tccacattta gattcttcat tggccaagca agttaaatac    600
gcattggaac agccattgca taagggtata ttgagatatg aagcttggag atacatatct    660
atctacgaag aggacgaatc caacaataag ttattattgc gtttggctaa gttggactat    720
cacttgttac aaatgtcata caagcaagag ttgtgtgaaa ttacaagatg gggtaaaggt    780
ttggaatctg tctccaactt tccttatgcc cgtgacagat cgttgaatg ttacttttgg    840 gctgtcggta cttttgtacga accacaatac tcattggcta gaatgacctt cgctaaggtt    900
gctgctttaa ttactatgat cgatgatatt tatgatgcct acggtacctt ggacgaattg    960
caaatattaa ctgactctgc cgaaagatgg gatggttccg gtgtcgatca gttgtctgac   1020
tatattagag cttcctataa tacattattg aaatttaata aggaggttgg tgaagatttg   1080
gcaaaaaagc aacgtaccta cgctttcgac aagtacatcg aagattggaa acaatacatg   1140
agaaccaact tctctcaatc aagatggttt ttcactaagg agttgccatc tttcgctgat   1200
```

| | |
|---|---|
| tacattaaca acggtgccat cacaatcggt gcatatttgg ttgcctctgc tgctttctta | 1260 |
| tatatggact ccgcaaaaga agatgttatc aactggatgt ccacaaaccc taagttggtc | 1320 |
| gttgcttact ccactcactc tcgtttaatt aatgactttg gtggtcacaa gttcgacaag | 1380 |
| gagagaggtt ccggtactgc tttggaatgc tacatgaagg actacaatgt ctctgaagaa | 1440 |
| gaagccgcaa acaagtttag agaaatgatg gaggacgctt ggaaggttat gaatgaagac | 1500 |
| tgtttaagac caacttccat ccctagagat gtctccaagg ttttgttaaa cgtcgccaga | 1560 |
| gctggtgaaa ttgtttacaa gcatagaatc gatggtttta ccgaaccaca tatcattaaa | 1620 |
| gatcacataa gagccacctt ggttgatttc atggctatta attaa | 1665 |

<210> SEQ ID NO 115
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 115

| | |
|---|---|
| atggccagtg cgcaagcatc attaccttcc aataacagac aggaaacagt ccgtccccta | 60 |
| gctgacttcc cagagaacat ctgggctgat aggattgctc catttaccct ggataagcaa | 120 |
| gaatacgaaa tgtgtcaaag agaaatagag atgttgaaag ctgaagtggc ctctatgttg | 180 |
| cttgccactg gaaagactat gatgcaacga ttcgacttca ttgataagat cgaaagattg | 240 |
| ggcgtatcgc accattttga cattgaaatc gaaaatcaac tccaagagtt tttcaacgtt | 300 |
| tataccaact ggggtgaata cagcgcgtat gatctgtcat ctgctgcatt gcagttcaga | 360 |
| ttatttagac aacacggttt caatatttcc tgcggtattt tcgaccaatt tatcgacgct | 420 |
| aaaggtaagt tcaaggaatc tttatgtaac gatatccggg gtttgttgtc tctctacgaa | 480 |
| gctgctcatg ttagaacgca cggtgataaa attttggaag aagcattggc ttttactact | 540 |
| acccatatga cttccggtgg tccacaccta gactctagct tggctaagca agtcaagtac | 600 |
| gcgcttgagc aaccattaca caaggggatt ttgagatacg aagcttggcg ttatatatcc | 660 |
| atctacgaag aagacgaatc taataacaaa cttctgttaa gattggctaa actcgattat | 720 |
| catttgcttc aaatgtccta caagcaggaa ttatgtgaaa tcacgagatg gggcaagggt | 780 |
| ttagagtcag tttctaattt ccccttacgct agagatcgtt ttgttgaatg ttatttctgg | 840 |
| gccgtaggaa cattgtacga accgcaatac agtctagcca gaatgacctt tgctaaagtt | 900 |
| gctgccttga ttactatgat tgacgatatc tacgatgcct atggtacctt ggacgagtta | 960 |
| caaatattga ccgattctgc tgaaagatgg gatggttcgg gagtcgacca attgtctgac | 1020 |
| tatatacgcg ctagttataa cactttgttg aagttcaaca aggaagtcgg tgaggattta | 1080 |
| gccaaaaagc aaagaacgta cgcatttgac aaatacatcg aagattggaa gcaatacatg | 1140 |
| agaacttctt tcacccagtc caagtggttc ctgaccaacg aactccccttc cttcgctgac | 1200 |
| tacatttcca atggggctat tacaattggt gcttacttga tcgccagcgc gggttttttg | 1260 |
| gatatggatt ctgccctaga agacgttatt aactggatgt ctactaaccc aaaattgatg | 1320 |
| gtggcttatt caactcacag cagacttatc aatgattatg gtggtcacaa gttcgacaag | 1380 |
| gaaagaggga gcgttacagc tttggattgc tacatgaagg attacagtgt ctctgaggaa | 1440 |
| gaagctgcaa agaagttcag agaaatgatc gaaacacct ggaaggttat gaatgaagaa | 1500 |
| tgtctgcggc caattccaat tccaagagat actctaaaga tgctattgaa cattgctagg | 1560 |
| gtaggtgaaa ctgtttacaa acatagaatc gacggtttta ctgaaccaca tataattaag | 1620 | gaccacatca gggcaatgtt ggtcgacttc atggctatta actaa      1665

<210> SEQ ID NO 116
<211> LENGTH: 1662
<212> TYPE: DNA
<213> ORGANISM: Artificial Sequence
<220> FEATURE:
<223> OTHER INFORMATION: Synthetic polynucleotide

<400> SEQUENCE: 116

| | |
|---|---|
| atggcctcag cacaagcttc cttaccttct aataacagac aggaaacagt ccgtccattg | 60 |
| gctgacttcc cagagaacat ctgggctgat agaattgccc catttacctt ggataagcaa | 120 |
| gaatacgaaa tgtgtcaaag agaaatagag atgttaaaag ctgaagttgc ttctatgttg | 180 |
| ttggcaactg gtaagactat gatgcaaaga ttcgacttca ttgataagat cgaaagattg | 240 |
| ggggtctccc accattttga cattgaaatc gaaaatcaat gcaagagtt tttcaacgtt | 300 |
| tataccaact taggtgaata ctctgcctat gatttgtcat ctgctgcctt gcagttccgt | 360 |
| ttatttagac aacacggttt caatatttcc tgcggtattt tcgaccaatt tatcgacgct | 420 |
| aaaggtaagt tcaaggaatc tttatgtaac gatatcagag gtttgttgtc tttgtacgaa | 480 |
| gctgctcatg ttagaactca cggtgataaa attttggaag aagctttagc tttcaccact | 540 |
| actcacatga cctccggtgg tccacattta gattcttcat tggccaagca agttaaatac | 600 |
| gcattggaac agccattgca taagggtata ttgagatatg aagcttggag atacatatct | 660 |
| atctacgaag aggacgaatc caacaataag ttattattgc gtttggctaa gttggactat | 720 |
| cacttgttac aaatgtcata caagcaagag ttgtgtgaaa ttacaagatg gggtaaaggt | 780 |
| ttggaatctg tctccaactt tccttatgcc cgtgacagat tcgttgaatg ttacttttgg | 840 |
| gctgtcggta ctttgtacga accacaatac tcattggcta gaatgacctt cgctaaggtt | 900 |
| gctgctttaa ttactatgat cgatgatatt tatgatgcct acggtacctt ggacgaattg | 960 |
| caaatattaa ctgactctgc cgaaagatgg gatggttccg gtgtcgatca gttgtctgac | 1020 |
| tatattagag cttcctataa tacattattg aaatttaata aggaggttgg tgaagatttg | 1080 |
| gcaaaaaagc aacgtaccta cgctttcgac aagtacatcg aagattggaa acaatacatg | 1140 |
| agaaccaact ctctcaatc aagatggttt ttcactaagg agttgccatc tttcgctgat | 1200 |
| tacattaaca acggtgccat cacaatcggt gcatatttgg ttgcctctgc tgctttctta | 1260 |
| tatatggact ccgcaaaaga agatgttatc aactggatgt ccacaaaccc taagttggtc | 1320 |
| gttgcttact ccactcactc tcgtttaatt aatgactttg gtggtcacaa gttcgacaag | 1380 |
| gagagaggtt ccgttactgc tttggactgc tacatgaagg actactctgt ctccgaagaa | 1440 |
| gaagccgcaa agaagtttag agaaatgtgt gaagacaatt ggaaggtcat gaatgaagag | 1500 |
| tgtttaagac aactaccat ccctagagat gggttgaaga tgttgttaaa catagccaga | 1560 |
| gttggtgaaa ctgtctacaa gcatagaatt gatggtttta cccaaccaca tgctatcgaa | 1620 |
| gaacacatca gagctatgtt ggttgatttc atgtctattt aa | 1662 |

<210> SEQ ID NO 117
<211> LENGTH: 1665
<212> TYPE: DNA
<213> ORGANISM: Artificial Sequence
<220> FEATURE:
<223> OTHER INFORMATION: Synthetic polynucleotide

<400> SEQUENCE: 117

```
atggcctcag cacaagcttc cttaccttct aataacagac aggaaacagt ccgtccattg      60
gctgacttcc cagagaacat ctgggctgat agaattgccc catttacctt ggataagcaa     120
gaatacgaaa tgtgtcaaag agaaatagag atgttaaaag ctgaagttgc ttctatgttg     180
ttggcaactg gtaagactat gatgcaaaga ttcgacttca ttgataagat cgaaagattg     240
ggggtctccc accatttga cattgaaatc gaaaatcaat gcaagagtt tttcaacgtt      300
tataccaact taggtgaata ctctgcctat gatttgtcat ctgctgcctt gcagttccgt     360
ttatttagac aacacggttt caatatttcc tgcggtattt tcgaccaatt tatcgacgct     420
aaaggtaagt tcaaggaatc tttatgtaac gatatcagag gtttgttgtc tttgtacgaa     480
gctgctcatg ttagaactca cggtgataaa attttggaag aagctttagc tttcaccact     540
actcacatga cctccggtgg tccacattta gattcttcat tggccaagca agttaaatac     600
gcattggaac agccattgca taagggtata ttgagatatg aagcttggag atacatatct     660
atctacgaag aggacgaatc caacaataag ttattattgc gtttggctaa gttggactat     720
cacttgttac aaatgtcata caagcaagag ttgtgtgaaa ttacaagatg gggtaaaggt     780
ttggaatctg tctccaactt tccttatgcc cgtgacagat tcgttgaatg ttacttttgg     840
gctgtcggta ctttgtacga accacaatac tcattggcta gaatgacctt cgctaaggtt     900
gctgctttaa ttactatgat cgatgatatt tatgatgcct acggtacctt ggacgaattg     960
caaatattaa ctgactctgc cgaaagatgg gatggttccg tgtcgatca gttgtctgac     1020
tatattagag cttcctataa tacattattg aaatttaata aggaggttgg tgaagatttg     1080
gcaaaaaagc aacgtaccta cgctttcgac aagtacatcg aagattggaa acaatacatg     1140
agaaccaact tctctcaatc aagatggttt ttcactaagg agttgccatc tttcgctgat     1200
tacattaaca acggtgccat cacaatcggt gcatatttgg ttgcctctgc tgctttctta     1260
tatatggact ccgcaaaaga agatgttatc aactggatgt ccacaaaccc taagttggtc     1320
gttgcttact ccactcactc tcgtttaatt aatgactttg gtggtcacaa gttcgacaag     1380
gagagaggtt ccgttactgc tttggactgc tacatgaagg actactctgt ctccgaagaa     1440
gaagccgcaa agaagtttag agaaatgatc gaaaacacct ggaaggtcat gaatgaagag     1500
tgtttaagac aattccaat ccctagagac acattgaaga tgttgttaaa catagccaga     1560
gttggtgaaa ctgtctacaa gcatagaatt gatggtttta ctgaaccaca tatcatcaaa     1620
gatcacatca gagctatgtt ggttgatttc atggctatta attaa                     1665
```

<210> SEQ ID NO 118
<211> LENGTH: 1071
<212> TYPE: DNA
<213> ORGANISM: Artificial Sequence
<220> FEATURE:
<223> OTHER INFORMATION: Synthetic polynucleotide

<400> SEQUENCE: 118

```
atgtatgaga gagaaatcga atgttaaag gctgaagtcg aatctatgtt gttggccacc       60
ggtaaaacaa tgatgcagcg tttcgatttt atagacaaga ttgaaagatt gggcgtttcc     120
caccatttcg atattgaaat cgagaaccaa ttacaagaat ttttcaatgt ttacactaac     180
ttcggtgaat actcagctta cgacttgtct tccgcagcct tgcaatttaa gcaatggtgt     240
gaccacaata tgatcattatc ttgctctatt actagaggtt tgttatcctt gtatgaggct     300
gctcatgtca gaacccacgg tgataagatc ttggaagaag ctttacactt gacttctggt     360
gaatcccatt tggactccac cttggctaaa caagttaaat gtgcattaga acaaccattg     420
```

```
cacaagggta tacctcgtta cgaagcctgg agatatattt ctatctacga agaggatgaa    480
tcacataaca agttgttgtt gagattagct aaattggatt atcacttctt acagatttct    540
tacagacaag atttgtgtga atcattcgt tgggactcat ctggtgtcga ccaattatct    600
gattacatca gagcagttgg tgaggaattg gctaagaagc aaagaacata cgctttcggt    660 actttttag gtatggatgg tgcctctgaa gatgttatta actggatgtc cactatccca    720
aagttgatgt tcgcttgctc tacacatgcc agattgatta tgactttgg tggtcataaa    780 ttcgataagg aaagaggtac tggtaccgct ttagagtgtt atatgaaaga ctataacgtc    840
tccgaagaag aagccgccaa caagtttaga gaaatgatgg aggacgcttg gaaagttatg    900
aatgaagaat gtttgcgtcc aaccactatt ccaagagaaa tattaaagat gttgttgaac    960
atcgtccgtg ttggtgaaac tactaataag cacagaatcg atggtttcac acagcctcac   1020
gctattgagg aacacattag agctatgttg gttgacttta tgtccgtcta a             1071
```

<210> SEQ ID NO 119
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 119

Leu Lys Asp Glu Glu Gly Asn Phe Lys Ala Ser Leu Thr Ser Asp Val
1               5                   10                  15

Pro Gly Leu Leu Glu Leu Tyr Glu Ala Ser Tyr Leu Arg Val His Gly
            20                  25                  30

Glu Asp Ile Leu Asp Glu Ala Ile Ser Phe Ala
        35                  40

<210> SEQ ID NO 120
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 120

Asn Lys Ala Leu Leu Gln Phe Ala Lys Ile Asp Phe Asn Met Leu Gln
1               5                   10                  15

Leu Leu His Arg Lys Glu Leu Ser Glu Ile Cys Arg Trp Trp Lys Asp
            20                  25                  30

Leu Asp Phe Thr Arg Lys Leu Pro
        35                  40

<210> SEQ ID NO 121
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 121

Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
            20                  25                  30

Ala Ser Ile Val Asp Asp Thr Tyr Asp Ser Phe Ala Thr Tyr Asp Glu
        35                  40                  45

Leu Ile Pro Tyr Thr Asp Ala Ile Glu Arg
    50                  55

<210> SEQ ID NO 122
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 122

Tyr Met Gln Ile Ser Tyr Lys Ala Leu Leu Asp Val Tyr Glu Glu Met
1               5                   10                  15

Glu Gln Leu Leu Ala Asp Lys Gly Arg Gln Tyr Arg Val Glu Tyr
            20                  25                  30

<210> SEQ ID NO 123
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 123

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
            20                  25

<210> SEQ ID NO 124
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 124

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
            20                  25

<210> SEQ ID NO 125
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 125

Glu Asp Asp Cys Ser Ala Ile Glu Cys Tyr Met Glu Gln Tyr Lys Val
1               5                   10                  15

Thr Ala Gln Glu Ala Tyr Asp Glu Phe Asn Lys His Ile Glu Ser Ser
            20                  25                  30

Trp Lys Asp Val Asn Glu Glu Phe Leu Lys
        35                  40

<210> SEQ ID NO 126
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 126

Glu Ala Phe Asn Lys Leu Lys Asp Glu Glu Gly Asn Phe Lys Ala Ser
1               5                   10                  15

Leu Thr Ser Asp Val Arg Gly Leu Leu Glu Leu Tyr Gln Ala Ser Tyr
            20                  25                  30

Met Arg Ile His Gly Glu Asp Ile Leu Asp Glu Ala Ile Ser Phe Thr
        35                  40                  45

Thr Ala Gln Leu Thr Leu Ala Leu Pro Thr Leu Asp Pro Pro
    50                  55                  60

<210> SEQ ID NO 127
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 127

Asn Lys Ala Leu Leu Gln Phe Ala Lys Ile Asp Phe Asn Met Leu Gln
1               5                   10                  15

Leu Leu His Arg Lys Glu Leu Ser Glu Ile Cys Arg Trp Trp Lys Asp
            20                  25                  30

Leu Asp Phe Thr Arg Lys Leu Pro
        35                  40

<210> SEQ ID NO 128
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 128

Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
            20                  25                  30

Ala Ser Ile Val Asp Asp Thr Tyr Asp Ser Phe Ala Thr Tyr Asp Glu
        35                  40                  45

Leu Ile Pro Tyr Thr Asp Ala Ile Glu Arg
    50                  55

<210> SEQ ID NO 129
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 129

Tyr Met Gln Ile Ser Tyr Lys Ala Leu Leu Asp Val Tyr Glu Glu Met
1               5                   10                  15

Glu Gln Leu Leu Ala Asp Lys Gly Arg Gln Tyr Arg Val Glu Tyr
            20                  25                  30

<210> SEQ ID NO 130
<211> LENGTH: 29
<212> TYPE: PRT
<213> ORGANISM: Artificial Sequence
<220> FEATURE:
<223> OTHER INFORMATION: Synthetic polypeptide

```
<400> SEQUENCE: 130

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
            20                  25

<210> SEQ ID NO 131
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 131

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
            20                  25

<210> SEQ ID NO 132
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 132

Ser Ala Ile Glu Cys Tyr Met Lys Gln Tyr Gly Ala Thr Ala Gln Glu
1               5                   10                  15

Ala Tyr Asp Glu Phe Asn Lys His Ile Glu Ser Ser Trp Lys
            20                  25                  30

<210> SEQ ID NO 133
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 133

Leu Lys Asp Glu Glu Gly Asn Phe Lys Ala Ser Leu Thr Ser Asp Val
1               5                   10                  15

Pro Gly Leu Leu Glu Leu Tyr Glu Ala Ser Tyr Leu Arg Val His Gly
            20                  25                  30

Glu Asp Ile Leu Asp Glu Ala Ile Ser Phe Ala
        35                  40

<210> SEQ ID NO 134
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 134

Asn Lys Ala Leu Leu Gln Phe Ala Lys Ile Asp Phe Asn Met Leu Gln
1               5                   10                  15

Leu Leu His Arg Lys Glu Leu Ser Glu Ile Cys Arg Trp Trp Lys Asp
            20                  25                  30

Leu Asp Phe Thr Arg Lys Leu Pro
        35                  40
```

```
<210> SEQ ID NO 135
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 135

Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
                20                  25                  30

Ala Ser Ile Val Asp Asp Thr Tyr Asp Ser Phe Ala Thr Tyr Asp Glu
            35                  40                  45

Leu Ile Pro Tyr Thr Asp Ala Ile Glu Arg
        50                  55

<210> SEQ ID NO 136
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 136

Tyr Met Gln Ile Ser Tyr Lys Ala Leu Leu Asp Val Tyr Glu Glu Met
1               5                   10                  15

Glu Gln Leu Leu Ala Asp Lys Gly Arg Gln Tyr Arg Val Glu Tyr
                20                  25                  30

<210> SEQ ID NO 137
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 137

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
                20                  25

<210> SEQ ID NO 138
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 138

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
                20                  25

<210> SEQ ID NO 139
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 139
```

```
Ser Ala Ile Glu Cys Tyr Met Lys Gln Tyr Gly Ala Thr Ala Gln Glu
1               5                   10                  15

Ala Tyr Asp Glu Phe Asn Lys His Ile Glu Ser Ser Trp Lys
            20                  25                  30
```

<210> SEQ ID NO 140
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 140

```
Glu Ala Phe Asn Lys Leu Lys Asp Glu Glu Gly Asn Phe Lys Ala Ser
1               5                   10                  15

Leu Thr Ser Asp Val Arg Gly Leu Leu Glu Leu Tyr Gln Ala Ser Tyr
            20                  25                  30

Met Arg Ile His Gly Glu Asp Ile Leu Asp Glu Ala Ile Ser Phe Thr
        35                  40                  45

Thr Ala Gln Leu Thr Leu Ala Leu Pro Thr Leu Asp Pro Pro
    50                  55                  60
```

<210> SEQ ID NO 141
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 141

```
Leu Leu Glu Phe Ala Lys Ile Asp Phe Asn Leu Leu Gln Leu Leu His
1               5                   10                  15

Arg Lys Glu Leu Ser Glu Ile Cys Arg Trp Trp Lys Asp
            20                  25
```

<210> SEQ ID NO 142
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 142

```
Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
            20                  25                  30

Ala Ser Ile Val Asp Asp Thr Tyr Asp Ser Phe Ala Thr Tyr Asp Glu
        35                  40                  45

Leu Ile Pro Tyr Thr Asp Ala Ile Glu Arg
    50                  55
```

<210> SEQ ID NO 143
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 143

```
Tyr Met Gln Ile Ser Tyr Lys Ala Leu Leu Asp Val Tyr Glu Glu Met
1               5                   10                  15
```

```
Glu Gln Leu Leu Ala Asp Lys Gly Arg Gln Tyr Arg Val Glu Tyr
        20                  25                  30

<210> SEQ ID NO 144
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 144

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
            20                  25

<210> SEQ ID NO 145
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 145

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
            20                  25

<210> SEQ ID NO 146
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 146

Glu Asp Asp Cys Ser Ala Ile Glu Cys Tyr Met Glu Gln Tyr Lys Val
1               5                   10                  15

Thr Ala Gln Glu Ala Tyr Asp Glu Phe Asn Lys His Ile Glu Ser Ser
            20                  25                  30

Trp Lys Asp Val Asn Glu Glu Phe Leu Lys
        35                  40

<210> SEQ ID NO 147
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 147

Leu Lys Asp Glu Glu Gly Asn Phe Lys Ala Ser Leu Thr Ser Asp Val
1               5                   10                  15

Pro Gly Leu Leu Glu Leu Tyr Glu Ala Ser Tyr Leu Arg Val His Gly
            20                  25                  30

Glu Asp Ile Leu Asp Glu Ala Ile Ser Phe Ala
        35                  40

<210> SEQ ID NO 148
<211> LENGTH: 29
<212> TYPE: PRT
<213> ORGANISM: Artificial Sequence
<220> FEATURE:
```

```
<223> OTHER INFORMATION: Synthetic polypeptide

<400> SEQUENCE: 148

Leu Leu Glu Phe Ala Lys Ile Asp Phe Asn Leu Leu Gln Leu Leu His
1               5                   10                  15

Arg Lys Glu Leu Ser Glu Ile Cys Arg Trp Trp Lys Asp
            20                  25

<210> SEQ ID NO 149
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 149

Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
            20                  25                  30

Ala Ser Ile Val Asp Asp Thr Tyr Asp Ser Phe Ala Thr Tyr Asp Glu
        35                  40                  45

Leu Ile Pro Tyr Thr Asp Ala Ile Glu Arg
    50                  55

<210> SEQ ID NO 150
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 150

Tyr Met Gln Ile Ser Tyr Lys Ala Leu Leu Asp Val Tyr Glu Glu Met
1               5                   10                  15

Glu Gln Leu Leu Ala Asp Lys Gly Arg Gln Tyr Arg Val Glu Tyr
            20                  25                  30

<210> SEQ ID NO 151
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 151

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
            20                  25

<210> SEQ ID NO 152
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 152

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
            20                  25
```

```
<210> SEQ ID NO 153
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 153

Glu Asp Asp Cys Ser Ala Ile Glu Cys Tyr Met Glu Gln Tyr Lys Val
1               5                   10                  15

Thr Ala Gln Glu Ala Tyr Asp Glu Phe Asn Lys His Ile Glu Ser Ser
            20                  25                  30

Trp Lys Asp Val Asn Glu Glu Phe Leu Lys
        35                  40

<210> SEQ ID NO 154
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 154

Glu Ala Phe Asn Lys Leu Lys Asp Glu Glu Gly Asn Phe Lys Ala Ser
1               5                   10                  15

Leu Thr Ser Asp Val Arg Gly Leu Leu Glu Leu Tyr Gln Ala Ser Tyr
            20                  25                  30

Met Arg Ile His Gly Glu Asp Ile Leu Asp Glu Ala Ile Ser Phe Thr
        35                  40                  45

Thr Ala Gln Leu Thr Leu Ala Leu Pro Thr Leu Asp Pro Pro
    50                  55                  60

<210> SEQ ID NO 155
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 155

Leu Leu Glu Phe Ala Lys Ile Asp Phe Asn Leu Leu Gln Leu His
1               5                   10                  15

Arg Lys Glu Leu Ser Glu Ile Cys Arg Trp Trp Lys Asp
            20                  25

<210> SEQ ID NO 156
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 156

Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
            20                  25                  30

Ala Ser Ile Val Asp Asp Thr Tyr Asp Ser Phe Ala Thr Tyr Asp Glu
        35                  40                  45

Leu Ile Pro Tyr Thr Asp Ala Ile Glu Arg
    50                  55
```

<210> SEQ ID NO 157
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 157

Tyr Met Gln Ile Ser Tyr Lys Ala Leu Leu Asp Val Tyr Glu Met
1               5                   10                  15

Glu Gln Leu Leu Ala Asp Lys Gly Arg Gln Tyr Arg Val Glu Tyr
            20                  25                  30

<210> SEQ ID NO 158
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 158

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
            20                  25

<210> SEQ ID NO 159
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 159

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
            20                  25

<210> SEQ ID NO 160
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 160

Ser Ala Ile Glu Cys Tyr Met Lys Gln Tyr Gly Ala Thr Ala Gln Glu
1               5                   10                  15

Ala Tyr Asp Glu Phe Asn Lys His Ile Glu Ser Ser Trp Lys
            20                  25                  30

<210> SEQ ID NO 161
<211> LENGTH: 43
<212> TYPE: PRT
<213> ORGANISM: Artificial Sequence
<220> FEATURE:
<223> OTHER INFORMATION: Synthetic polypeptide

<400> SEQUENCE: 161

Leu Lys Asp Glu Glu Gly Asn Phe Lys Ala Ser Leu Thr Ser Asp Val
1               5                   10                  15

Pro Gly Leu Leu Glu Leu Tyr Glu Ala Ser Tyr Leu Arg Val His Gly

```
                    20                  25                  30

Glu Asp Ile Leu Asp Glu Ala Ile Ser Phe Ala
            35                  40

<210> SEQ ID NO 162
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 162

Leu Leu Glu Phe Ala Lys Ile Asp Phe Asn Leu Leu Gln Leu Leu His
1               5                   10                  15

Arg Lys Glu Leu Ser Glu Ile Cys Arg Trp Trp Lys Asp
            20                  25

<210> SEQ ID NO 163
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 163

Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
            20                  25                  30

Ala Ser Ile Val Asp Asp Thr Tyr Asp Ser Phe Ala Thr Tyr Asp Glu
        35                  40                  45

Leu Ile Pro Tyr Thr Asp Ala Ile Glu Arg
    50                  55

<210> SEQ ID NO 164
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 164

Tyr Met Gln Ile Ser Tyr Lys Ala Leu Leu Asp Val Tyr Glu Glu Met
1               5                   10                  15

Glu Gln Leu Leu Ala Asp Lys Gly Arg Gln Tyr Arg Val Glu Tyr
            20                  25                  30

<210> SEQ ID NO 165
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 165

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
            20                  25

<210> SEQ ID NO 166
<211> LENGTH: 27
<212> TYPE: PRT
```

<213> ORGANISM: Artificial Sequence
<220> FEATURE:
<223> OTHER INFORMATION: Synthetic polypeptide

<400> SEQUENCE: 166

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
            20                  25

<210> SEQ ID NO 167
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 167

Ser Ala Ile Glu Cys Tyr Met Lys Gln Tyr Gly Ala Thr Ala Gln Glu
1               5                   10                  15

Ala Tyr Asp Glu Phe Asn Lys His Ile Glu Ser Ser Trp Lys
            20                  25                  30

<210> SEQ ID NO 168
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 168

Phe Glu Gln Glu Arg Gly His Cys Ala Ser Ala Val Glu Cys Tyr Met
1               5                   10                  15

Arg Glu His Gly Val Ser Glu Glu Glu Ala Cys Ser Glu Leu Lys Lys
            20                  25                  30

Gln Val Asp Asn Ala Trp Lys Asp Ile Asn His Glu Met Ile Phe Ser
        35                  40                  45

Glu Thr Ser Lys Ala Val Pro Met Ser Val Leu Thr Arg Val Leu Asn
    50                  55                  60

Leu Thr Arg
65

<210> SEQ ID NO 169
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 169

Gly Tyr His Val Asp Gly Glu Glu Ala Phe Asn Met Leu Lys Asp Glu
1               5                   10                  15

Glu Gly Asn Phe Lys Ala Ser Leu Thr Ser Asp Val Pro Gly Leu Leu
            20                  25                  30

Glu Leu Tyr Gln Ala Ser Tyr Met Arg Ile His Gly Glu Asp Ile Leu
        35                  40                  45

Asp Glu Ala Ile Ser Phe Thr Thr Ala Gln Leu Thr Leu Ala Leu Pro
    50                  55                  60

Thr Leu Asp Pro Pro Leu Ser
65                  70

```
<210> SEQ ID NO 170
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 170

Phe Glu Gln Glu Arg Gly His Cys Ala Ser Ala Val Glu Cys Tyr Met
1               5                   10                  15

Arg Glu His Gly Val Ser Glu Glu Ala Cys Ser Glu Leu Lys Lys
            20                  25                  30

Gln Val Asp Asn Ala Trp Lys Asp Ile Asn His Glu Met Ile Phe Ser
        35                  40                  45

Glu Thr Ser Lys Ala Val Pro Met Ser Val Leu Thr Arg Val Leu Asn
    50                  55                  60

Leu Thr Arg
65

<210> SEQ ID NO 171
<211> LENGTH: 72
<212> TYPE: PRT
<213> ORGANISM: Artificial Sequence
<220> FEATURE:
<223> OTHER INFORMATION: Synthetic polypeptide

<400> SEQUENCE: 171

Gly Tyr His Val Asp Gly Glu Ala Phe Asn Met Leu Lys Asp Glu
1               5                   10                  15

Glu Gly Asn Phe Lys Ala Ser Leu Thr Ser Asp Val Pro Gly Leu Leu
            20                  25                  30

Glu Leu Tyr Gln Ala Ser Tyr Met Arg Ile His Gly Glu Asp Ile Leu
        35                  40                  45

Asp Glu Ala Ile Ser Phe Thr Thr Ala Gln Leu Thr Leu Ala Leu Pro
    50                  55                  60

Thr Leu Asp Pro Pro Leu Ser Glu
65                  70

<210> SEQ ID NO 172
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 172

Phe Glu Gln Glu Arg Gly His Cys Ala Ser Ala Val Glu Cys Tyr Met
1               5                   10                  15

Arg Glu His Gly Val Ser Glu Glu Ala Cys Ser Glu Leu Lys Lys
            20                  25                  30

Gln Val Asp Asn Ala Trp Lys Asp Ile Asn His Glu Met Ile Phe Ser
        35                  40                  45

Glu Thr Ser Lys Ala Val Pro Met Ser Val Leu Thr Arg Val Leu Asn
    50                  55                  60

Leu Thr Arg
65

<210> SEQ ID NO 173
<211> LENGTH: 66
<212> TYPE: PRT
<213> ORGANISM: Artificial Sequence
```

<220> FEATURE:
<223> OTHER INFORMATION: Synthetic polypeptide

<400> SEQUENCE: 173

Glu Gln Glu Arg Gly His Cys Ala Ser Ala Val Glu Cys Tyr Met Arg
1               5                   10                  15

Glu His Gly Val Ser Glu Glu Ala Cys Ser Glu Leu Lys Lys Gln
            20                  25                  30

Val Asp Asn Ala Trp Lys Asp Ile Asn His Glu Met Ile Phe Ser Glu
        35                  40                  45

Thr Ser Lys Ala Val Pro Met Ser Val Leu Thr Arg Val Leu Asn Leu
    50                  55                  60

Thr Arg
65

<210> SEQ ID NO 174
<211> LENGTH: 71
<212> TYPE: PRT
<213> ORGANISM: Artificial Sequence
<220> FEATURE:
<223> OTHER INFORMATION: Synthetic polypeptide

<400> SEQUENCE: 174

Gly Tyr His Val Asp Gly Glu Glu Ala Phe Asn Met Leu Lys Asp Glu
1               5                   10                  15

Glu Gly Asn Phe Lys Ala Ser Leu Thr Ser Asp Val Pro Gly Leu Leu
            20                  25                  30

Glu Leu Tyr Gln Ala Ser Tyr Met Arg Ile His Gly Glu Asp Ile Leu
        35                  40                  45

Asp Glu Ala Ile Ser Phe Thr Thr Ala Gln Leu Thr Leu Ala Leu Pro
    50                  55                  60

Thr Leu Asp Pro Pro Leu Ser
65                  70

<210> SEQ ID NO 175
<211> LENGTH: 68
<212> TYPE: PRT
<213> ORGANISM: Artificial Sequence
<220> FEATURE:
<223> OTHER INFORMATION: Synthetic polypeptide

<400> SEQUENCE: 175

Phe Glu Gln Glu Arg Gly His Cys Ala Ser Ala Val Glu Cys Tyr Met
1               5                   10                  15

Arg Glu His Gly Val Ser Glu Glu Ala Cys Ser Glu Leu Lys Lys
            20                  25                  30

Gln Val Asp Asn Ala Trp Lys Asp Ile Asn His Glu Met Ile Phe Ser
        35                  40                  45

Glu Thr Ser Lys Ala Val Pro Met Ser Val Leu Thr Arg Val Leu Asn
    50                  55                  60

Leu Thr Arg Gly
65

<210> SEQ ID NO 176
<211> LENGTH: 75
<212> TYPE: PRT
<213> ORGANISM: Artificial Sequence
<220> FEATURE:
<223> OTHER INFORMATION: Synthetic polypeptide

<400> SEQUENCE: 176

Asp Ala Phe Asn Arg Phe Lys Asp Thr Lys Gly Ser Phe Lys Glu Asp
1               5                   10                  15

Leu Ile Lys Asp Val Asn Ser Met Leu Cys Leu Tyr Glu Ala Thr His
            20                  25                  30

Leu Arg Val His Gly Glu Asp Ile Leu Asp Glu Ala Leu Gly Phe Thr
        35                  40                  45

Thr Ser Gln Leu Lys Ser Ile Leu Pro Lys Leu Lys Pro Leu Leu Ala
    50                  55                  60

Ser Gln Val Met His Ala Leu Lys Gln Pro Leu
65                  70                  75

<210> SEQ ID NO 177
<211> LENGTH: 68
<212> TYPE: PRT
<213> ORGANISM: Artificial Sequence
<220> FEATURE:
<223> OTHER INFORMATION: Synthetic polypeptide

<400> SEQUENCE: 177

Phe Asn Lys Phe Lys Asn Ser Asp Gly Asn Phe Lys Glu Asp Leu Ile
1               5                   10                  15

Asn Asp Val Ser Gly Met Leu Cys Leu Tyr Glu Ala Thr His Leu Arg
            20                  25                  30

Val His Gly Glu Asp Ile Leu Asp Glu Ala Leu Glu Phe Thr Thr Thr
        35                  40                  45

Arg Leu Lys Ser Ile Leu Pro Asp Leu Glu Pro Pro Leu Ala Thr Gln
    50                  55                  60

Val Met His Ala
65

<210> SEQ ID NO 178
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 178

Ile Phe Asn Lys Phe Lys Asn Ser Asp Gly Asn Phe Lys Glu Asp Leu
1               5                   10                  15

Ile Asn Asp Val Ser Gly Met Leu Cys Leu Tyr Glu Ala Thr His Leu
            20                  25                  30

Arg Val His Gly Glu Asp Ile Leu Asp Glu Ala Leu Glu Phe Thr Thr
        35                  40                  45

Thr Arg Leu Lys Ser Ile Leu Pro Asp Leu Glu Pro Pro Leu
    50                  55                  60

<210> SEQ ID NO 179
<211> LENGTH: 75
<212> TYPE: PRT
<213> ORGANISM: Artificial Sequence
<220> FEATURE:
<223> OTHER INFORMATION: Synthetic polypeptide

<400> SEQUENCE: 179

Asp Ala Phe Asn Arg Phe Lys Asp Thr Lys Gly Ser Phe Lys Glu Asp
1               5                   10                  15

Leu Ile Lys Asp Val Asn Ser Met Leu Cys Leu Tyr Glu Ala Thr His
            20                  25                  30

-continued

Leu Arg Val His Gly Glu Asp Ile Leu Asp Glu Ala Leu Gly Phe Thr
            35                  40                  45

Thr Ser Gln Leu Lys Ser Ile Leu Pro Lys Leu Lys Pro Leu Leu Ala
 50                  55                  60

Ser Gln Val Met His Ala Leu Lys Gln Pro Leu
 65                  70                  75

<210> SEQ ID NO 180
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 180

Ile Phe Asn Lys Phe Lys Asn Ser Asp Gly Asn Phe Lys Glu Asp Leu
 1               5                  10                  15

Ile Asn Asp Val Ser Gly Met Leu Cys Leu Tyr Glu Ala Thr His Leu
                20                  25                  30

Arg Val His Gly Glu Asp Ile Leu Asp Glu Ala Leu Glu Phe Thr Thr
            35                  40                  45

Thr Arg Leu Lys Ser Ile Leu Pro Asp Leu Glu Pro Pro Leu Ala Thr
 50                  55                  60

Gln Val Met His Ala
 65

<210> SEQ ID NO 181
<211> LENGTH: 72
<212> TYPE: PRT
<213> ORGANISM: Artificial Sequence
<220> FEATURE:
<223> OTHER INFORMATION: Synthetic polypeptide

<400> SEQUENCE: 181

Glu Thr Asn Phe Thr Asn Ser Pro Leu Leu Ser Lys Leu Gln Asn Glu
 1               5                  10                  15

Leu Ser Val Ala His Leu Glu Glu Leu Lys Leu Glu Val Lys Gln Leu
                20                  25                  30

Ile Trp Ser Thr Lys Asp Pro Leu Phe Leu Leu Lys Phe Ile Asp Ser
            35                  40                  45

Ile Gln Arg Leu Gly Val Ala Tyr His Phe Glu Glu Ile Lys Glu
 50                  55                  60

Ser Leu His Leu Val Tyr Leu Glu
 65                  70

<210> SEQ ID NO 182
<211> LENGTH: 56
<212> TYPE: PRT
<213> ORGANISM: Artificial Sequence
<220> FEATURE:
<223> OTHER INFORMATION: Synthetic polypeptide

<400> SEQUENCE: 182

Ile Phe Asn Lys Phe Lys Asn Ser Asp Gly Asn Phe Lys Glu Asp Leu
 1               5                  10                  15

Ile Asn Asp Val Ser Gly Met Leu Cys Leu Tyr Glu Ala Thr His Leu
                20                  25                  30

Arg Val His Gly Glu Asp Ile Leu Asp Glu Ala Leu Glu Phe Thr Thr
            35                  40                  45

Thr Arg Leu Lys Ser Ile Leu Pro 50                  55

<210> SEQ ID NO 183
<211> LENGTH: 78
<212> TYPE: PRT
<213> ORGANISM: Artificial Sequence
<220> FEATURE:
<223> OTHER INFORMATION: Synthetic polypeptide

<400> SEQUENCE: 183

Glu Gly Leu Glu Gln Lys Ile Arg Thr Met Leu Ile Ser Pro Thr Asp
1               5                   10                  15

Thr Ile Ser Lys Lys Leu Ser Leu Ile Asp Ala Val Gln Arg Leu Gly
            20                  25                  30

Val Ala Tyr His Phe Glu Lys Glu Ile Glu Asp Glu Ile Glu Lys Leu
        35                  40                  45

Ser Cys Lys Glu Tyr Asn Asp Gly Asn Asp Leu Gln Thr Val Ala Leu
    50                  55                  60

Arg Phe Arg Leu Leu Arg Gln Gln Gly Tyr Phe Val Ser Cys
65                  70                  75

<210> SEQ ID NO 184
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 184

Leu Gln Arg Leu Gly Leu Ala Tyr His Phe Glu Asn Gln Ile Lys Glu
1               5                   10                  15

Ala Leu Gln Ser Ile
            20

<210> SEQ ID NO 185
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 185

Leu Ser His Leu Ser Thr Ser Leu Ala Glu Gln Val Lys His Ser Leu
1               5                   10                  15

Glu Ile Pro Leu His Arg Gly Met Pro Arg Leu Glu Ala Arg His Tyr
            20                  25                  30

Ile Ser Ile Tyr Glu Glu Asp Asn Ser Ser
        35                  40

<210> SEQ ID NO 186
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 186

Glu Leu Ala Lys Leu Asp Phe Asn Leu Leu Gln Ala Leu His Arg Arg
1               5                   10                  15

Glu Leu Gly Glu Ile Ser Arg Trp Trp Lys Asp Ile Asp Phe Ala Thr
            20                  25                  30

Lys Leu Pro Phe Ala Arg Asp Arg Leu Val Glu Cys Tyr Phe Trp Ile

-continued

```
                35                  40                  45
Leu Gly Val Tyr Phe Glu Pro Lys Tyr Ser Ile Thr Arg Lys Phe Met
 50                  55                  60

Thr Lys Val Ile Ala Ile Ala Ser Val Ile Asp Asp Ile Tyr Asp Val
 65                  70                  75                  80

Tyr Gly Thr Leu Glu Glu Leu Lys Leu Phe Thr His Ala Ile Glu Arg
                 85                  90                  95

Trp Glu Thr Val Ala Ala Asn Glu Leu Pro Lys Tyr Met Gln Val Cys
                100                 105                 110

Tyr Phe Ala Leu Leu Asp Val Phe Lys Glu Met Glu Asp Lys Leu Val
                115                 120                 125

Asn Lys Gly Leu Leu Tyr Ser Met Pro Cys Ala Lys Glu Ala Val Lys
130                 135                 140

Gly Leu Val Arg Ala Tyr Phe Val Glu Ala Glu Trp Phe Asn Ala Asn
145                 150                 155                 160

Tyr Met Pro Thr Phe Glu Glu Tyr Met Glu Asn Ser Thr Met Ser Ser
                165                 170                 175

Gly Tyr Pro Met Leu Ala Val Glu Ala Leu Ile Gly Ile Glu Asp Ala
                180                 185                 190

Thr Ile Ser Lys Glu Ala Phe Asp Trp Ala Ile Ser Val Pro Lys Ile
                195                 200                 205

Ile Arg Ser Cys Ala Leu Ile Ala Arg Leu Val Asp Asp Ile His
210                 215                 220

<210> SEQ ID NO 187
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 187

Asp Ala Pro Ser Ser Val Glu Cys Tyr Met Gln Gln Tyr Asp Val Ser
  1               5                  10                  15

Glu Glu Glu Ala Cys Asn Arg Ile Lys Gly Met Val Glu Ile Glu Trp
                 20                  25                  30

<210> SEQ ID NO 188
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 188

Asn Leu Ala Arg Met Met Val Val Leu Tyr Gln Asn Gly Asp Asn Tyr
  1               5                  10                  15

Thr Asn Ser Ser Gly Lys Thr Lys Asp Arg Ile Ala Ser Leu Leu Val
                 20                  25                  30

<210> SEQ ID NO 189
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 189

Leu Gln Arg Leu Gly Leu Ala Tyr His Phe Glu Asn Gln Ile Lys Glu
  1               5                  10                  15
```

Ala Leu Gln Ser Ile
            20

<210> SEQ ID NO 190
<211> LENGTH: 322
<212> TYPE: PRT
<213> ORGANISM: Artificial Sequence
<220> FEATURE:
<223> OTHER INFORMATION: Synthetic polypeptide

<400> SEQUENCE: 190

Lys Phe Lys Asp Glu Lys Gly Glu Phe Lys Asp Met Ile Arg Asn Asp
1               5                   10                  15

Ala Arg Gly Leu Leu Cys Leu Tyr Glu Ala Ser His Leu Arg Val Lys
            20                  25                  30

Gly Glu Asp Ile Leu Glu Glu Ala Thr Glu Phe Ser Arg Lys His Leu
        35                  40                  45

Lys Ser Leu Leu Pro Gln Leu Ser Thr Ser Leu Ala Glu Gln Val Lys
    50                  55                  60

His Ser Leu Glu Ile Pro Leu His Arg Gly Met Pro Arg Leu Glu Ala
65                  70                  75                  80

Arg His Tyr Ile Ser Ile Tyr Glu Glu Asn Ser Ser Arg Asn Glu
                85                  90                  95

Leu Leu Leu Glu Leu Ala Lys Leu Asp Phe Asn Leu Leu Gln Ala Leu
            100                 105                 110

His Arg Arg Glu Leu Gly Asp Ile Ser Arg Trp Trp Lys Asp Ile Asp
        115                 120                 125

Phe Ala Thr Lys Leu Pro Phe Ala Arg Asp Arg Leu Val Glu Cys Tyr
130                 135                 140

Phe Trp Ile Leu Gly Val Tyr Phe Glu Pro Lys Tyr Ser Ile Thr Arg
145                 150                 155                 160

Lys Phe Met Thr Lys Val Ile Ala Ile Ala Ser Val Ile Asp Asp Ile
                165                 170                 175

Tyr Asp Val Tyr Gly Thr Leu Glu Glu Leu Lys Leu Phe Thr His Ala
            180                 185                 190

Ile Glu Arg Trp Glu Thr Val Ala Ala Asn Glu Leu Pro Lys Tyr Met
        195                 200                 205

Gln Val Cys Tyr Phe Ala Leu Leu Asp Val Phe Lys Glu Met Glu Asp
    210                 215                 220

Lys Leu Val Asn Lys Gly Leu Leu Tyr Ser Met Pro Cys Ala Lys Glu
225                 230                 235                 240

Ala Val Lys Gly Leu Val Arg Ala Tyr Phe Val Glu Ala Glu Trp Phe
                245                 250                 255

Asn Ala Asn Tyr Met Pro Thr Phe Glu Glu Tyr Met Glu Asn Ser Thr
            260                 265                 270

Met Ser Ser Gly Tyr Pro Met Leu Ala Val Glu Ala Leu Ile Gly Ile
        275                 280                 285

Glu Asp Ala Thr Ile Ser Lys Glu Ala Phe Asp Trp Ala Ile Ser Val
    290                 295                 300

Pro Lys Ile Ile Arg Ser Cys Ala Leu Ile Ala Arg Leu Val Asp Asp
305                 310                 315                 320

Ile His

<210> SEQ ID NO 191
<211> LENGTH: 19

```
<212> TYPE: PRT
<213> ORGANISM: Artificial Sequence
<220> FEATURE:
<223> OTHER INFORMATION: Synthetic polypeptide

<400> SEQUENCE: 191

Lys Val Glu Gln Glu Arg Gly Asp Ala Pro Ser Ser Val Gln Cys Tyr
1               5                   10                  15

Val Gln Gln

<210> SEQ ID NO 192
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 192

Asn Leu Ala Arg Met Met Val Val Leu Tyr Gln Asn Gly Asp Asn Tyr
1               5                   10                  15

Thr Asn Ser Ser Gly Lys Thr Lys Asp Arg Ile Ala Ser Leu Leu Val
            20                  25                  30

<210> SEQ ID NO 193
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 193

Leu Gln Arg Leu Gly Leu Ala Tyr His Phe Glu Asn Gln Ile Lys Glu
1               5                   10                  15

Ala Leu Gln Ser Ile
            20

<210> SEQ ID NO 194
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 194

Lys Phe Lys Asp Glu Lys Gly Glu Phe Lys Asp Met Ile Arg Asn Asp
1               5                   10                  15

Ala Arg Gly Leu Leu Cys Leu Tyr Glu Ala Ser His Leu Arg Val Lys
            20                  25                  30

Gly Glu Asp Ile Leu Glu Glu Ala Thr Glu Phe Ser Arg Lys His Leu
        35                  40                  45

Lys Ser Leu Leu Pro Gln Leu Ser Thr Ser Leu Ala Glu Gln Val Lys
    50                  55                  60

His Ser Leu Glu Ile Pro Leu His Arg Gly Met Pro Arg Leu Glu Ala
65                  70                  75                  80

Arg His Tyr Ile Ser Ile Tyr Glu Glu Asn Asn Ser Ser Arg Asn Glu
                85                  90                  95

Leu Leu Leu Glu Leu Ala Lys Leu Asp Phe Asn Leu Gln Ala Leu
            100                 105                 110

His Arg Arg Glu Leu Gly Asp Ile Ser Arg Trp Trp Lys Asp Ile Asp
        115                 120                 125

Phe Ala Thr Lys Leu Pro Phe Ala Arg Asp Arg Leu Val Glu Cys Tyr
```

```
                130               135                140
Phe Trp Ile Leu Gly Val Tyr Phe Glu Pro Lys Tyr Ser Ile Thr Arg
145                 150                 155                 160

Lys Phe Met Thr Lys Val Ile Ala Ile Ala Ser Val Ile Asp Asp Ile
                165                 170                 175

Tyr Asp Val Tyr Gly Thr Leu Glu Glu Leu Lys Leu Phe Thr His Ala
                180                 185                 190

Ile Glu Arg Trp Glu Thr Val Ala Ala Asn Glu Leu Pro Lys Tyr Met
            195                 200                 205

Gln Val Cys Tyr Phe Ala Leu Leu Asp Val Phe Lys Glu Met Glu Asp
        210                 215                 220

Lys Leu Val Asn Lys Gly Leu Leu Tyr Ser Met Pro Cys Ala Lys Glu
225                 230                 235                 240

Ala Val

<210> SEQ ID NO 195
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 195

Tyr Val Pro Thr Phe Glu Glu Tyr Met Glu Asn Ser Thr Met Ser Ser
1               5                   10                  15

Gly Tyr Pro Met Leu Ala Val Glu Ala Leu Val
            20                  25

<210> SEQ ID NO 196
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 196

Asp Trp Ala Ile Ser Val Pro Lys Ile Ile Arg Ser Cys Ala Leu Ile
1               5                   10                  15

Ala

<210> SEQ ID NO 197
<211> LENGTH: 52
<212> TYPE: PRT
<213> ORGANISM: Artificial Sequence
<220> FEATURE:
<223> OTHER INFORMATION: Synthetic polypeptide

<400> SEQUENCE: 197

Lys Val Glu Gln Glu Arg Gly Asp Ala Pro Ser Ser Val Gln Cys Tyr
1               5                   10                  15

Met Gln Gln Tyr Asp Val Ser Glu Glu Glu Ala Cys Asn Arg Ile Lys
            20                  25                  30

Gly Met Val Glu Thr Ala Trp Met Glu Ile Asn Gly Glu Ile Gln Asp
        35                  40                  45

Thr Asn His Leu
    50

<210> SEQ ID NO 198
<211> LENGTH: 32
<212> TYPE: PRT
```

<213> ORGANISM: Artificial Sequence
<220> FEATURE:
<223> OTHER INFORMATION: Synthetic polypeptide

<400> SEQUENCE: 198

```
Asn Leu Ala Arg Met Met Val Val Leu Tyr Gln Asn Gly Asp Asn Tyr
1               5                   10                  15

Thr Asn Ser Ser Gly Lys Thr Lys Asp Arg Ile Ala Ser Leu Leu Val
            20                  25                  30
```

<210> SEQ ID NO 199
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 199

```
Leu Gln Arg Leu Gly Leu Ala Tyr His Phe Glu Asn Gln Ile Lys Glu
1               5                   10                  15

Ala Leu Gln Ser Ile
            20
```

<210> SEQ ID NO 200
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 200

```
Lys Phe Lys Asp Glu Lys Gly Glu Phe Lys Asp Met Ile Arg Asn Asp
1               5                   10                  15

Ala Arg Gly Leu Leu Cys Leu Tyr Glu Ala Ser His Leu Arg Val Lys
            20                  25                  30

Gly Glu Asp Ile Leu Glu Glu Ala Thr Glu Phe Ser Arg Lys His Leu
        35                  40                  45

Lys Ser Leu Leu Pro Gln Leu Ser Thr Ser Leu Ala Glu Gln Val Lys
    50                  55                  60

His Ser Leu Glu Ile Pro Leu His Arg Gly Met Pro Arg Leu Glu Ala
65                  70                  75                  80

Arg His Tyr Ile Ser Ile Tyr Glu Glu Asn Asn Ser Ser Arg Asn Glu
                85                  90                  95

Leu Leu Leu Glu Leu Ala Lys Leu Asp Phe Asn Leu Leu Gln Ala Leu
            100                 105                 110

His Arg Arg Glu Leu Gly Asp Ile Ser Arg Trp Trp Lys Asp Ile Asp
        115                 120                 125

Phe Ala Thr Lys Leu Pro Phe Ala Arg Asp Arg Leu Val Glu Cys Tyr
    130                 135                 140

Phe Trp Ile Leu Gly Val Tyr Phe Glu Pro Lys Tyr Ser Ile Thr Arg
145                 150                 155                 160

Lys Phe Met Thr Lys Val Ile Ala Ile Ala Ser Val Ile Asp Asp Ile
                165                 170                 175

Tyr Asp Val Tyr Gly Thr Leu Glu Glu Leu Lys Leu Phe Thr His Ala
            180                 185                 190

Ile Glu Arg Trp Glu Thr Val Ala Ala Asn Glu Leu Pro Lys Tyr Met
        195                 200                 205

Gln Val Cys Tyr Phe Ala Leu Leu Asp Val Phe Lys Glu Met Glu Asp
    210                 215                 220
```

```
Lys Leu Val Asn Lys Gly Leu Leu Tyr Ser Met Pro Cys Ala Lys Glu
225                 230                 235                 240

Ala Val

<210> SEQ ID NO 201
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 201

Tyr Val Pro Thr Phe Glu Glu Tyr Met Glu Asn Ser Thr Met Ser Ser
1               5                   10                  15

Gly Tyr Pro Met Leu Ala Val Glu Ala Leu Val
            20                  25

<210> SEQ ID NO 202
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 202

Asp Trp Ala Ile Ser Val Pro Lys Ile Ile Arg Ser Cys Ala Leu Ile
1               5                   10                  15

Ala

<210> SEQ ID NO 203
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 203

Asp Ala Pro Ser Ser Val Glu Cys Tyr Met Gln Gln Tyr Asp Val Ser
1               5                   10                  15

Glu Glu Glu Ala Cys Asn Arg Ile Lys Gly Met Val Glu Ile Glu Trp
            20                  25                  30

<210> SEQ ID NO 204
<211> LENGTH: 32
<212> TYPE: PRT
<213> ORGANISM: Artificial Sequence
<220> FEATURE:
<223> OTHER INFORMATION: Synthetic polypeptide

<400> SEQUENCE: 204

Asn Leu Ala Arg Met Met Val Val Leu Tyr Gln Asn Gly Asp Asn Tyr
1               5                   10                  15

Thr Asn Ser Ser Gly Lys Thr Lys Asp Arg Ile Ala Ser Leu Leu Val
            20                  25                  30

<210> SEQ ID NO 205
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 205
```

```
Lys Phe Ile Gln Asn Val Glu Lys Asp Ser Thr Arg Arg Ser Ala Asn
1               5                   10                  15

Phe His Pro Ser Ile Trp Gly Asp His
            20                  25

<210> SEQ ID NO 206
<211> LENGTH: 51
<212> TYPE: PRT
<213> ORGANISM: Artificial Sequence
<220> FEATURE:
<223> OTHER INFORMATION: Synthetic polypeptide

<400> SEQUENCE: 206

Asp Asp Gly Ser Val Lys His Gln Gln Leu Lys Glu Glu Ile Arg Lys
1               5                   10                  15

Met Leu Thr Ala Glu Thr Lys Leu Ser Gln Lys Leu Asp Leu Ile Asp
            20                  25                  30

Ala Ile Gln Arg Leu Gly Val Ala Tyr His Phe Glu Ser Glu Ile Asp
        35                  40                  45

Glu Ile Leu
    50

<210> SEQ ID NO 207
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 207

Ser Leu Ala Arg Asn Val Arg Gly Met Leu Ser Leu Tyr Glu Ala Thr
1               5                   10                  15

His Leu Arg Val His Gly Glu Asn Ile Leu Asp Glu Ala
            20                  25

<210> SEQ ID NO 208
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 208

Leu Glu Ala Arg Asn Tyr Met Pro Phe Tyr Gln Glu Ala Ser His
1               5                   10                  15

Asn Glu Ala Leu Leu Thr Phe Ala Lys Leu Asp Phe Asn Lys Leu Gln
            20                  25                  30

Lys Leu His Gln Lys Glu Leu Ser Glu Ile Thr Arg
        35                  40

<210> SEQ ID NO 209
<211> LENGTH: 63
<212> TYPE: PRT
<213> ORGANISM: Artificial Sequence
<220> FEATURE:
<223> OTHER INFORMATION: Synthetic polypeptide

<400> SEQUENCE: 209

Phe Glu Gln Ser Arg Glu His Val Ala Ser Ser Ile Glu Cys Tyr Met
1               5                   10                  15

Lys Gln Tyr Gly Ala Thr Glu Glu Thr Cys Asn Glu Leu Arg Lys
            20                  25                  30
```

Gln Val Ser Asn Ala Trp Lys Asp Ile Asn Glu Cys Leu Cys Pro
    35                  40                  45

Thr Ala Val Pro Met Pro Leu Ile Val Arg Ile Leu Asn Leu Thr
 50                  55                  60

<210> SEQ ID NO 210
<211> LENGTH: 57
<212> TYPE: PRT
<213> ORGANISM: Artificial Sequence
<220> FEATURE:
<223> OTHER INFORMATION: Synthetic polypeptide

<400> SEQUENCE: 210

Ala Glu Val Phe Glu Arg Phe Lys Asp Gln His Gly Asn Phe Lys Ala
 1               5                  10                  15

Ser Leu Ser Ser Asp Val Glu Gly Met Leu Ser Leu Tyr Glu Ala Ser
            20                  25                  30

Phe Leu Asp Tyr Glu Gly Glu Asp Ile Leu Asp Glu Ala Lys Ala Phe
        35                  40                  45

Thr Ser Phe His Leu Arg Gly Ala Leu
 50                  55

<210> SEQ ID NO 211
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 211

Val Lys Leu Glu Leu Val Asp Asp Val Lys Arg Leu Gly Ile Gly Tyr
 1               5                  10                  15

Arg Phe Glu Lys Glu Ile Val Glu Ala Leu His Arg Cys Phe Ile Ser
            20                  25                  30

Ser Glu Arg Phe Thr His Arg Asn Leu His Gln Thr Ala Leu Ser Phe
        35                  40                  45

Arg Leu Leu Arg Glu Cys Gly Tyr Asp Val Thr
 50                  55

<210> SEQ ID NO 212
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 212

Phe Asn Lys Phe Thr Asn Lys Glu Gly Lys Phe Asn Ser Lys Leu Gly
 1               5                  10                  15

Glu Asn Ile Lys Gly Met Ile Asp Leu Tyr Glu Ala Ser Gln Leu Gly
            20                  25                  30

Ile Ala Gly Glu Tyr Ile Leu Ala Glu Ala Gly Glu Phe Ser Gly Leu
        35                  40                  45

Val Leu Lys Glu Lys Val Ala Cys Ile Asn Asn
 50                  55

<210> SEQ ID NO 213
<211> LENGTH: 51
<212> TYPE: PRT
<213> ORGANISM: Artificial Sequence
<220> FEATURE:
<223> OTHER INFORMATION: Synthetic polypeptide

<400> SEQUENCE: 213

Val Tyr Phe Glu Pro Gln Tyr Ser Val Pro Arg Arg Thr Thr Thr Lys
1               5                   10                  15

Val Ile Gly Leu Cys Ser Val Ile Asp Asp Met Tyr Asp Ala Tyr Gly
            20                  25                  30

Thr Ile Asp Glu Leu Glu Leu Phe Thr Asn Ala Ile Glu Arg Leu Asp
        35                  40                  45

Thr Ser Thr
    50

<210> SEQ ID NO 214
<211> LENGTH: 66
<212> TYPE: PRT
<213> ORGANISM: Artificial Sequence
<220> FEATURE:
<223> OTHER INFORMATION: Synthetic polypeptide

<400> SEQUENCE: 214

Arg Trp Leu Lys Cys Asn His Ala Pro Thr Met Glu Glu Tyr Met Lys
1               5                   10                  15

Val Arg Gly Val Ser Ser Gly Tyr Pro Leu Leu Ile Thr Ile Ser Phe
            20                  25                  30

Ile Gly Met Glu Asp Thr Thr Glu Gly Ile Leu Thr Trp Ala Thr Ser
        35                  40                  45

Glu Pro Met Ile Ile Arg Ala Ser Val Ile Val Cys Arg Leu Met Asp
    50                  55                  60

Asp Ile
65

<210> SEQ ID NO 215
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 215

Phe Met Asp Glu Lys Gly Lys Phe Lys Glu Asp Val Val Asn Asp Val
1               5                   10                  15

Leu Gly Met Leu Asn Leu Tyr Glu Ala Ala His Leu Arg Leu Arg Gly
            20                  25                  30

Glu Asp Ile Leu Asp Glu Ala Leu Ala Phe Thr Thr Ser His Leu Glu
        35                  40                  45

<210> SEQ ID NO 216
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 216

Trp Trp Lys Asn Leu Asp Phe Ser Thr Lys Leu Pro Tyr Ala Arg Asp
1               5                   10                  15

Arg Ile Val Glu Cys Tyr Phe Trp Ile Met Gly Ala Tyr Phe Glu
            20                  25                  30

<210> SEQ ID NO 217
<211> LENGTH: 25
<212> TYPE: PRT

<213> ORGANISM: Artificial Sequence
<220> FEATURE:
<223> OTHER INFORMATION: Synthetic polypeptide

<400> SEQUENCE: 217

Ser Leu Ala Arg Thr Phe Leu Thr Lys Val Ile Ala Met Thr Ser Ile
1               5                   10                  15

Leu Asp Asp Thr Tyr Asp Asn Tyr Gly
            20                  25

<210> SEQ ID NO 218
<211> LENGTH: 61
<212> TYPE: PRT
<213> ORGANISM: Artificial Sequence
<220> FEATURE:
<223> OTHER INFORMATION: Synthetic polypeptide

<400> SEQUENCE: 218

Asp Tyr Val Pro Pro Ile Glu Glu Tyr Met Gln Val Ala Arg Ile Ser
1               5                   10                  15

Ser Ala Tyr Pro Met Leu Ile Thr Asn Ser Phe Val Gly Met Gly Glu
            20                  25                  30

Val Ala Thr Lys Glu Ala Phe Asp Trp Ile Ser Asn Asp Pro Lys Ile
        35                  40                  45

Leu Lys Ala Ser Thr Thr Ile Cys Arg Leu Met Asp Asp
    50                  55                  60

<210> SEQ ID NO 219
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 219

Glu Phe Glu Gln Thr Arg Asp His Val Ala Ser Gly Val Glu Cys Tyr
1               5                   10                  15

Met Lys Gln Tyr Gly Val Ser Arg Glu Glu Thr Val Lys
            20                  25

<210> SEQ ID NO 220
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 220

Phe Met Asp Glu Lys Gly Lys Phe Lys Glu Asp Val Val Asn Asp Val
1               5                   10                  15

Leu Gly Met Leu Asn Leu Tyr Glu Ala Ala His Leu Arg Leu Arg Gly
            20                  25                  30

Glu Asp Ile Leu Asp Glu Ala Leu Ala Phe Thr Thr Ser His Leu Glu
        35                  40                  45

<210> SEQ ID NO 221
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 221

```
Trp Trp Lys Asn Leu Asp Phe Ser Thr Lys Leu Pro Tyr Ala Arg Asp
1               5                   10                  15

Arg Ile Val Glu Cys Tyr Phe Trp Ile Met Gly Ala Tyr Phe Glu
            20                  25                  30
```

<210> SEQ ID NO 222
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 222

```
Ser Leu Ala Arg Thr Phe Leu Thr Lys Val Ile Ala Met Thr Ser Ile
1               5                   10                  15

Leu Asp Asp Thr Tyr Asp Asn Tyr Gly
            20                  25
```

<210> SEQ ID NO 223
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 223

```
Tyr Met Gln Val Ala Leu Ile Ser Ser Ala Tyr Pro Met Leu Ile Thr
1               5                   10                  15

Asn Ser Phe Val Gly Met Gly Glu Val Ala Thr Lys Glu Ala Phe Asp
            20                  25                  30

Trp Ile Ser Asn Asn Pro Lys Met Leu Lys Ala Ser Thr Ile Ile
        35                  40                  45
```

<210> SEQ ID NO 224
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 224

```
Glu Phe Glu Gln Thr Arg Asp His Val Ala Ser Gly Val Glu Cys Tyr
1               5                   10                  15

Met Lys Gln Tyr Gly Val Ser Arg Glu Glu Thr Val Lys
            20                  25
```

<210> SEQ ID NO 225
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 225

```
Phe Met Asp Glu Lys Gly Lys Phe Lys Glu Asp Val Val Asn Asp Val
1               5                   10                  15

Leu Gly Met Leu Asn Leu Tyr Glu Ala Ala His Leu Arg Leu Arg Gly
            20                  25                  30

Glu Asp Ile Leu Asp Glu Ala Leu Ala Phe Thr Thr Ser His Leu Glu
        35                  40                  45
```

<210> SEQ ID NO 226
<211> LENGTH: 31

-continued

```
<212> TYPE: PRT
<213> ORGANISM: Artificial Sequence
<220> FEATURE:
<223> OTHER INFORMATION: Synthetic polypeptide

<400> SEQUENCE: 226

Trp Trp Lys Asn Leu Asp Phe Ser Thr Lys Leu Pro Tyr Ala Arg Asp
1               5                   10                  15

Arg Ile Val Glu Cys Tyr Phe Trp Ile Met Gly Ala Tyr Phe Glu
            20                  25                  30

<210> SEQ ID NO 227
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 227

Ser Leu Ala Arg Thr Phe Leu Thr Lys Val Ile Ala Met Thr Ser Ile
1               5                   10                  15

Leu Asp Asp Thr Tyr Asp Asn Tyr Gly
            20                  25

<210> SEQ ID NO 228
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 228

Asp Tyr Val Pro Pro Ile Glu Glu Tyr Met Gln Val Ala Arg Ile Ser
1               5                   10                  15

<210> SEQ ID NO 229
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 229

Gly Tyr Pro Met Leu Ile Thr Asn Ser Leu Val Gly Met Gly Glu Val
1               5                   10                  15

Ala Thr Lys Glu Ala Phe Asp Leu Ile Ser Asn Asp Pro Lys Met Leu
            20                  25                  30

Lys Ala Ser Thr
        35

<210> SEQ ID NO 230
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 230

Glu Phe Glu Gln Thr Arg Asp His Val Ala Ser Gly Val Glu Cys Tyr
1               5                   10                  15

Met Lys Gln Tyr Gly Val Ser Arg Glu Glu Thr Val Lys
            20                  25

<210> SEQ ID NO 231
```

<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 231

Phe Met Asp Glu Lys Gly Lys Phe Lys Glu Asp Val Val Asn Asp Val
1               5                   10                  15

Leu Gly Met Leu Asn Leu Tyr Glu Ala Ala His Leu Arg Leu Arg Gly
            20                  25                  30

Glu Asp Ile Leu Asp Glu Ala Leu Ala Phe Thr Thr Ser His Leu Glu
        35                  40                  45

<210> SEQ ID NO 232
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 232

Trp Trp Lys Asn Leu Asp Phe Ser Thr Lys Leu Pro Tyr Ala Arg Asp
1               5                   10                  15

Arg Ile Val Glu Cys Tyr Phe Trp Ile Met Gly Ala Tyr Phe Glu
            20                  25                  30

<210> SEQ ID NO 233
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 233

Ser Leu Ala Arg Thr Phe Leu Thr Lys Val Ile Ala Met Thr Ser Ile
1               5                   10                  15

Leu Asp Asp Thr Tyr Asp Asn Tyr Gly
            20                  25

<210> SEQ ID NO 234
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 234

Val Pro Pro Met Asp Glu Tyr Met Gln Val Ala Leu Ile Ser Cys Gly
1               5                   10                  15

Tyr Pro Met Leu Ile Thr Asn Ser Phe Val Gly Met Gly Glu Val Ala
            20                  25                  30

Thr Lys Glu Ala Phe Asp Trp Ile Ser Asn Asp Pro Lys Ile Leu Lys
        35                  40                  45

Ala Ser Thr Thr Ile Cys Arg Leu Met Asp Asp
    50                  55

<210> SEQ ID NO 235
<211> LENGTH: 29
<212> TYPE: PRT
<213> ORGANISM: Artificial Sequence
<220> FEATURE:
<223> OTHER INFORMATION: Synthetic polypeptide

```
<400> SEQUENCE: 235

Glu Phe Glu Gln Thr Arg Asp His Val Ala Ser Gly Val Glu Cys Tyr
1               5                   10                  15

Met Lys Gln Tyr Gly Val Ser Arg Glu Glu Thr Val Lys
            20                  25

<210> SEQ ID NO 236
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 236

Phe Met Asp Glu Lys Gly Lys Phe Lys Glu Asp Val Val Asn Asp Val
1               5                   10                  15

Leu Gly Met Leu Asn Leu Tyr Glu Ala Ala His Leu Arg Leu Arg Gly
                20                  25                  30

Glu Asp Ile Leu Asp Gly Ala Leu Ala Phe Thr Thr Ser His Leu Glu
            35                  40                  45

<210> SEQ ID NO 237
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 237

Trp Trp Lys Asn Leu Asp Phe Ala Thr Met Leu Pro Tyr Ala Arg Asp
1               5                   10                  15

Arg Ile Val Glu Cys Tyr Phe Trp Ile Met Gly Val Tyr Phe Glu Pro
                20                  25                  30

Lys Tyr Ser Leu Ala Arg Thr Phe Leu Thr Lys Val Ile Ala Met Thr
            35                  40                  45

Ser Ile Leu Asp Asp Thr Tyr Asp Asn Tyr Gly
        50                  55

<210> SEQ ID NO 238
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 238

Tyr Met Gln Val Ala Leu Ile Ser Ser Ala Tyr Pro Met Leu Ile Thr
1               5                   10                  15

Asn Ser Phe Val Gly Met Gly Glu Val Ala Thr Lys Glu Ala Phe Asp
                20                  25                  30

Trp Ile Ser Asn Asn Pro Lys Met Leu Lys Ala Ser Thr Ile Ile
            35                  40                  45

<210> SEQ ID NO 239
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 239

Glu Phe Glu Gln Thr Arg Asp His Val Ala Ser Gly Val Glu Cys Tyr
```

```
                1               5                  10                  15
Met Lys Gln Tyr Gly Val Ser Arg Glu Glu Thr Val Lys
                20                  25
```

<210> SEQ ID NO 240
<211> LENGTH: 48
<212> TYPE: PRT
<213> ORGANISM: Artificial Sequence
<220> FEATURE:
<223> OTHER INFORMATION: Synthetic polypeptide

<400> SEQUENCE: 240

```
Phe Met Asp Glu Lys Gly Lys Phe Lys Glu Asp Val Val Asn Asp Val
1               5                   10                  15

Leu Gly Met Leu Asn Leu Tyr Glu Ala Ala His Leu Arg Leu Arg Gly
                20                  25                  30

Glu Asp Ile Leu Asp Glu Ala Leu Ala Phe Thr Thr Ser His Leu Glu
            35                  40                  45
```

<210> SEQ ID NO 241
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 241

```
Trp Trp Lys Asn Leu Asp Phe Ala Thr Met Leu Pro Tyr Ala Arg Asp
1               5                   10                  15

Arg Ile Val Glu Cys Tyr Phe Trp Ile Met Gly Val Tyr Phe Glu Pro
                20                  25                  30

Lys Tyr Ser Leu Ala Arg Thr Phe Leu Thr Lys Val Ile Ala Met Thr
            35                  40                  45

Ser Ile Leu Asp Asp Thr Tyr Asp Asn Tyr Gly
        50                  55
```

<210> SEQ ID NO 242
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 242

```
Asp Tyr Val Pro Pro Ile Glu Glu Tyr Met Gln Val Ala Arg Ile Ser
1               5                   10                  15
```

<210> SEQ ID NO 243
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 243

```
Gly Tyr Pro Met Leu Ile Thr Asn Ser Leu Val Gly Met Gly Glu Val
1               5                   10                  15

Ala Thr Lys Glu Ala Phe Asp Leu Ile Ser Asn Asp Pro Lys Met Leu
                20                  25                  30

Lys Ala Ser Thr
        35
```

```
<210> SEQ ID NO 244
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 244

Glu Phe Glu Gln Thr Arg Asp His Val Ala Ser Gly Val Glu Cys Tyr
1               5                   10                  15

Met Lys Gln Tyr Gly Val Ser Arg Glu Glu Thr Val Lys
            20                  25

<210> SEQ ID NO 245
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 245

Ser Asn Asn Arg Gln Glu Thr Val Arg Pro Leu Ala Asp Phe Pro Glu
1               5                   10                  15

Asn Ile Trp Ala Asp Arg Ile Ala Pro Phe Thr
            20                  25

<210> SEQ ID NO 246
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 246

Glu Met Cys Gln Arg Glu Ile Glu Met Leu Lys Ala Glu Val Ala Ser
1               5                   10                  15

Met Leu Leu Ala Thr Gly Lys Thr Met Met Gln Arg Phe Asp Phe Ile
            20                  25                  30

Asp Lys Ile Glu Arg Leu Gly Val Ser His His Phe Asp
        35                  40                  45

<210> SEQ ID NO 247
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 247

Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
            20                  25                  30

Arg Thr His Gly Asp Lys Ile Leu Glu Glu Ala Leu Ala Phe Thr Thr
        35                  40                  45

Thr His Met Thr Ser Gly Gly Pro His Leu Asp Ser Ser Leu Ala Lys
    50                  55                  60

Gln Val Lys Tyr Ala Leu Glu Gln Pro Leu His Lys Gly Ile Leu Arg
65                  70                  75                  80

Tyr Glu Ala Trp Arg Tyr Ile Ser Ile Tyr Glu Glu Asp Glu Ser Asn
                85                  90                  95

Asn Lys Leu Leu Leu Arg Leu Ala Lys Leu Asp Tyr His Leu Leu Gln
```

Met Ser Tyr Lys Gln Glu Leu
            115

<210> SEQ ID NO 248
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 248

Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
                20                  25                  30

Pro Gln Tyr Ser Leu Ala Arg Met Thr Phe Ala Lys Val Ala Ala
            35                  40                  45

<210> SEQ ID NO 249
<211> LENGTH: 179
<212> TYPE: PRT
<213> ORGANISM: Artificial Sequence
<220> FEATURE:
<223> OTHER INFORMATION: Synthetic polypeptide

<400> SEQUENCE: 249

Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
                20                  25                  30

Ala Lys Lys Gln Arg Thr Tyr Ala Phe Asp Lys Tyr Ile Glu Asp Trp
            35                  40                  45

Lys Gln Tyr Met Arg Thr Asn Phe Ser Gln Ser Arg Trp Phe Phe Thr
50                  55                  60

Lys Glu Leu Pro Ser Phe Ala Asp Tyr Ile Asn Asn Gly Ala Ile Thr
65                  70                  75                  80

Ile Gly Ala Tyr Leu Val Ala Ser Ala Ala Phe Leu Tyr Met Asp Ser
                85                  90                  95

Ala Lys Glu Asp Val Ile Asn Trp Met Ser Thr Asn Pro Lys Leu Val
            100                 105                 110

Val Ala Tyr Ser Thr His Ser Arg Leu Ile Asn Asp Phe Gly Gly His
        115                 120                 125

Lys Phe Glu Lys Glu Arg Gly Ser Ser Thr Ala Ile Glu Cys Tyr Met
    130                 135                 140

Lys Asp His Asn Val Ser Glu Glu Ala Ala Asn Lys Phe Arg Glu
145                 150                 155                 160

Met Met Glu Asp Ala Trp Lys Val Met Asn Glu Glu Cys Leu Arg Pro
                165                 170                 175

Thr Thr Ile

<210> SEQ ID NO 250
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 250

```
Glu Thr Val Tyr Lys His Arg Ile Asp Gly Phe Thr Gln Pro His Ala
1               5                   10                  15

Ile Glu Glu His Ile Arg Ala Met Leu Val Asp Phe Met Ser Ile
            20                  25                  30
```

<210> SEQ ID NO 251
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 251

```
Ser Asn Asn Arg Gln Glu Thr Val Arg Pro Leu Ala Asp Phe Pro Glu
1               5                   10                  15

Asn Ile Trp Ala Asp Arg Ile Ala Pro Phe Thr
            20                  25
```

<210> SEQ ID NO 252
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 252

```
Glu Met Cys Gln Arg Glu Ile Glu Met Leu Lys Ala Glu Val Ala Ser
1               5                   10                  15

Met Leu Leu Ala Thr Gly Lys Thr Met Met Gln Arg Phe Asp Phe Ile
            20                  25                  30

Asp Lys Ile Glu Arg Leu Gly Val Ser His His Phe Asp
        35                  40                  45
```

<210> SEQ ID NO 253
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 253

```
Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
            20                  25                  30

Arg Thr His Gly Asp Lys Ile Leu Glu Glu Ala Leu Ala Phe Thr Thr
        35                  40                  45

Thr His Met Thr Ser Gly Gly Pro His Leu Asp Ser Ser Leu Ala Lys
    50                  55                  60

Gln Val Lys Tyr Ala Leu Glu Gln Pro Leu His Lys Gly Ile Leu Arg
65                  70                  75                  80

Tyr Glu Ala Trp Arg Tyr Ile Ser Ile Tyr Glu Glu Asp Glu Ser Asn
                85                  90                  95

Asn Lys Leu Leu Leu Arg Leu Ala Lys Leu Asp Tyr His Leu Leu Gln
            100                 105                 110

Met Ser Tyr Lys Gln Glu Leu
        115
```

<210> SEQ ID NO 254
<211> LENGTH: 47
<212> TYPE: PRT

<213> ORGANISM: Artificial Sequence
<220> FEATURE:
<223> OTHER INFORMATION: Synthetic polypeptide

<400> SEQUENCE: 254

```
Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
            20                  25                  30

Pro Gln Tyr Ser Leu Ala Arg Met Thr Phe Ala Lys Val Ala Ala
        35                  40                  45
```

<210> SEQ ID NO 255
<211> LENGTH: 129
<212> TYPE: PRT
<213> ORGANISM: Artificial Sequence
<220> FEATURE:
<223> OTHER INFORMATION: Synthetic polypeptide

<400> SEQUENCE: 255

```
Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
            20                  25                  30

Ala Lys Lys Gln Arg Thr Tyr Ala Phe Asp Lys Tyr Ile Glu Asp Trp
        35                  40                  45

Lys Gln Tyr Met Arg Thr Asn Phe Ser Gln Ser Arg Trp Phe Phe Thr
50                  55                  60

Lys Glu Leu Pro Ser Phe Ala Asp Tyr Ile Asn Asn Gly Ala Ile Thr
65                  70                  75                  80

Ile Gly Ala Tyr Leu Val Ala Ser Ala Ala Phe Leu Tyr Met Asp Ser
                85                  90                  95

Ala Lys Glu Asp Val Ile Asn Trp Met Ser Thr Asn Pro Lys Leu Val
            100                 105                 110

Val Ala Tyr Ser Thr His Ser Arg Leu Ile Asn Asp Phe Gly Gly His
        115                 120                 125

Lys
```

<210> SEQ ID NO 256
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 256

```
Lys Glu Arg Gly Thr Gly Thr Ala Ile Glu Cys Tyr Met Lys Asp His
1               5                   10                  15

Asn
```

<210> SEQ ID NO 257
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 257

```
Glu Met Ile Glu Asn Thr Trp Lys Val Met Asn Glu Glu Cys Leu Arg
1               5                   10                  15
```

```
Pro Ile Pro Ile Pro Arg Asp Thr Leu Lys Met Leu
            20                  25
```

<210> SEQ ID NO 258
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 258

```
Glu Thr Val Tyr Lys His Arg Ile Asp Gly Phe Thr Gln Pro His Ala
1               5                   10                  15

Ile Glu Glu His Ile Arg Ala Met Leu Val Asp Phe Met Ser Ile
            20                  25                  30
```

<210> SEQ ID NO 259
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 259

```
Leu Glu Leu Val Asp Asn Leu Glu Arg Leu Gly Leu Ala Tyr His Phe
1               5                   10                  15

Glu Gly Gln Ile Asn Arg Leu Leu Ser Ser Ala Tyr Asn Ala Asn His
            20                  25                  30

Glu Asp Glu Gly Asn His Lys Arg Asn Lys Glu Asp Leu Tyr Ala Ala
        35                  40                  45

Ala Leu Glu Phe Arg Ile Phe Arg Gln His Gly Phe Asn Val
    50                  55                  60
```

<210> SEQ ID NO 260
<211> LENGTH: 90
<212> TYPE: PRT
<213> ORGANISM: Artificial Sequence
<220> FEATURE:
<223> OTHER INFORMATION: Synthetic polypeptide

<400> SEQUENCE: 260

```
Tyr Val Ser Gln Ala Asn Glu Leu Lys Glu Gln Val Lys Met Met Leu
1               5                   10                  15

Asp Glu Glu Asp Met Lys Leu Leu Asp Cys Leu Glu Leu Val Asp Asn
            20                  25                  30

Leu Glu Arg Leu Gly Leu Ala Tyr His Phe Glu Gly Gln Ile Asn Arg
        35                  40                  45

Leu Leu Ser Ser Ala Tyr Asn Ala Asn His Glu Asp Glu Gly Asn His
    50                  55                  60

Lys Arg Asn Lys Glu Asp Leu Tyr Ala Ala Ala Leu Glu Phe Arg Ile
65                  70                  75                  80

Phe Arg Gln His Gly Phe Asn Val Pro Gln
                85                  90
```

<210> SEQ ID NO 261
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 261

Asn Asn Gln His Glu Ser Val Arg Gln Leu Ala Asp Phe Pro Glu Asn
1               5                   10                  15

Ile Trp Ala Asp Arg Val
            20

<210> SEQ ID NO 262
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 262

Gln Gly His Asp Met Cys Ala Lys Glu Ile Glu Met Leu Lys Glu Glu
1               5                   10                  15

Val Met Ser Met Leu Leu Glu
            20

<210> SEQ ID NO 263
<211> LENGTH: 34
<212> TYPE: PRT
<213> ORGANISM: Artificial Sequence
<220> FEATURE:
<223> OTHER INFORMATION: Synthetic polypeptide

<400> SEQUENCE: 263

Ser Thr Leu Ala Lys Gln Val Lys Tyr Ala Leu Glu Gln Pro Leu His
1               5                   10                  15

Lys Gly Ile Pro Arg Tyr Glu Ala Trp Arg Tyr Ile Ser Ile Tyr Glu
            20                  25                  30

Glu Asp

<210> SEQ ID NO 264
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 264

Leu Ala Lys Leu Asp Tyr His Leu Ser Gln Met Leu Asn Lys Gln Asp
1               5                   10                  15

Leu Cys Glu Ile
            20

<210> SEQ ID NO 265
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 265

Arg Asp Arg Ile Val Glu Cys Tyr Phe Trp Ala Val Ala Thr Tyr Tyr
1               5                   10                  15

Glu Pro Gln Tyr Ser Leu Ala Arg Met Thr
            20                  25

<210> SEQ ID NO 266
<211> LENGTH: 20
<212> TYPE: PRT
<213> ORGANISM: Artificial Sequence
<220> FEATURE:
<223> OTHER INFORMATION: Synthetic polypeptide -continued

```
<400> SEQUENCE: 266

Glu Val Gly Glu Asp Leu Ala Lys Lys Gln Arg Thr Tyr Ala Phe Asp
1               5                   10                  15

Lys Tyr Ile Glu
            20

<210> SEQ ID NO 267
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 267

Tyr Ala Arg Thr Ser Phe Thr Gln Ser Lys Trp Phe Leu Thr Asn Glu
1               5                   10                  15

Leu Pro Ser Phe Ser Asp Tyr Leu
            20

<210> SEQ ID NO 268
<211> LENGTH: 84
<212> TYPE: PRT
<213> ORGANISM: Artificial Sequence
<220> FEATURE:
<223> OTHER INFORMATION: Synthetic polypeptide

<400> SEQUENCE: 268

Ala Ala Phe Leu Asp Met Asp Ser Ala Ser Glu Asp Val Ile Asn Trp
1               5                   10                  15

Met Ser Thr Asn Pro Lys Leu Phe Val Ala Leu Thr Thr His Ala Arg
            20                  25                  30

Leu Ala Asn Asp Val Gly Ser His Lys Phe Glu Lys Glu Arg Gly Ser
        35                  40                  45

Gly Thr Ala Ile Glu Cys Tyr Met Lys Asp Tyr His Val Ser Glu Glu
    50                  55                  60

Glu Ala Met Lys Lys Phe Glu Glu Met Cys Asp Ala Trp Lys Val
65                  70                  75                  80

Met Asn Glu Glu

<210> SEQ ID NO 269
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 269

Asn Asn Gln His Glu Ser Val Arg Gln Leu Ala Asp Phe Pro Glu Asn
1               5                   10                  15

Ile Trp Ala Asp Arg Val
            20

<210> SEQ ID NO 270
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 270

Gln Gly His Asp Met Cys Ala Lys Glu Ile Glu Met Leu Lys Glu Glu
```

Val Met Ser Met Leu Leu Glu
            20

<210> SEQ ID NO 271
<211> LENGTH: 54
<212> TYPE: PRT
<213> ORGANISM: Artificial Sequence
<220> FEATURE:
<223> OTHER INFORMATION: Synthetic polypeptide

<400> SEQUENCE: 271

Gln Val Lys His Ala Leu Glu Gln Pro Leu His Arg Gly Ile Pro Arg
1               5                   10                  15

Tyr Glu Ala Tyr Cys Phe Ile Ser Ile Tyr Glu Glu Asp Glu Ser Asn
            20                  25                  30

Asn Lys Leu Leu Leu Arg Leu Ala Lys Leu Asp Tyr His Leu Leu Gln
        35                  40                  45

Met Ser Tyr Lys Arg Glu
    50

<210> SEQ ID NO 272
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 272

Arg Asp Arg Ile Val Glu Cys Tyr Phe Trp Ala Val Ala Thr Tyr Tyr
1               5                   10                  15

Glu Pro Gln Tyr Ser Leu Ala Arg Met Thr
            20                  25

<210> SEQ ID NO 273
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 273

Glu Val Gly Glu Asp Leu Ala Lys Lys Gln Arg Thr Tyr Ala Phe Asp
1               5                   10                  15

Lys Tyr Ile Glu
            20

<210> SEQ ID NO 274
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 274

Tyr Ala Arg Thr Ser Phe Thr Gln Ser Lys Trp Phe Leu Thr Asn Glu
1               5                   10                  15

Leu Pro Ser Phe Ser Asp Tyr Leu
            20

<210> SEQ ID NO 275
<211> LENGTH: 25
<212> TYPE: PRT

```
<213> ORGANISM: Artificial Sequence
<220> FEATURE:
<223> OTHER INFORMATION: Synthetic polypeptide

<400> SEQUENCE: 275

Thr Phe Leu Gly Met Asp Gly Ala Ser Glu Asp Val Ile Asn Trp Met
1               5                   10                  15

Ser Thr Asn Pro Lys Leu Phe Val Ala
            20                  25

<210> SEQ ID NO 276
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 276

Lys Phe Glu Lys Glu Arg Gly Ser Gly Thr Ala Ile Glu Cys Tyr Met
1               5                   10                  15

Lys Asp Tyr His Val Ser Glu Glu Ala Met Lys Lys Phe Glu Glu
            20                  25                  30

Met Cys Asp Asp Ala Trp Lys Val Met Asn Glu Glu
        35                  40

<210> SEQ ID NO 277
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 277

Asn Asn Gln His Glu Ser Val Arg Gln Leu Ala Asp Phe Pro Glu Asn
1               5                   10                  15

Ile Trp Ala Asp Arg Val
            20

<210> SEQ ID NO 278
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 278

Gln Gly His Asp Met Cys Ala Lys Glu Ile Glu Met Leu Lys Glu Glu
1               5                   10                  15

Val Met Ser Met Leu Leu Glu
            20

<210> SEQ ID NO 279
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 279

Gln Val Lys His Ala Leu Glu Gln Pro Leu His Arg Gly Ile Pro Arg
1               5                   10                  15

Tyr Glu Ala Tyr Cys Phe
            20
```

<210> SEQ ID NO 280
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 280

Leu Ala Lys Leu Asp Tyr His Leu Ser Gln Met Leu Asn Lys Gln Asp
1               5                   10                  15

Leu Cys Glu Ile
            20

<210> SEQ ID NO 281
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 281

Arg Asp Arg Ile Val Glu Cys Tyr Phe Trp Ala Val Ala Thr Tyr Tyr
1               5                   10                  15

Glu Pro Gln Tyr Ser Leu Ala Arg Met Thr
            20                  25

<210> SEQ ID NO 282
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 282

Glu Val Gly Glu Asp Leu Ala Lys Lys Gln Arg Thr Tyr Ala Phe Asp
1               5                   10                  15

Lys Tyr Ile Glu
            20

<210> SEQ ID NO 283
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 283

Tyr Ala Arg Thr Ser Phe Thr Gln Ser Lys Trp Phe Leu Thr Asn Glu
1               5                   10                  15

Leu Pro Ser Phe Ser Asp Tyr Leu
            20

<210> SEQ ID NO 284
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 284

Thr Phe Leu Gly Met Asp Gly Ala Ser Glu Asp Val Ile Asn Trp Met
1               5                   10                  15

Ser Thr Asn Pro Lys Leu Phe Val Ala
            20                  25

-continued

<210> SEQ ID NO 285
<211> LENGTH: 44
<212> TYPE: PRT
<213> ORGANISM: Artificial Sequence
<220> FEATURE:
<223> OTHER INFORMATION: Synthetic polypeptide

<400> SEQUENCE: 285

Lys Phe Glu Lys Glu Arg Gly Ser Gly Thr Ala Ile Glu Cys Tyr Met
1               5                   10                  15

Lys Asp Tyr His Val Ser Glu Glu Ala Met Lys Lys Phe Glu Glu
            20                  25                  30

Met Cys Asp Asp Ala Trp Lys Val Met Asn Glu Glu
        35                  40

<210> SEQ ID NO 286
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 286

Ser Asn Asn Arg Gln Glu Thr Val Arg Pro Leu Ala Asp Phe Pro Glu
1               5                   10                  15

Asn Ile Trp Ala Asp Arg Ile Ala Pro Phe Thr
            20                  25

<210> SEQ ID NO 287
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 287

Glu Met Cys Gln Arg Glu Ile Glu Met Leu Lys Ala Glu Val Ala Ser
1               5                   10                  15

Met Leu Leu Ala Thr Gly Lys Thr Met Met Gln Arg Phe Asp Phe Ile
            20                  25                  30

Asp Lys Ile Glu Arg Leu Gly Val Ser His His Phe Asp
        35                  40                  45

<210> SEQ ID NO 288
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 288

Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
            20                  25                  30

Arg Thr His Gly Asp Lys Ile Leu Glu Glu Ala Leu Ala Phe Thr Thr
        35                  40                  45

Thr His Met Thr Ser Gly Gly Pro His Leu Asp Ser Ser Leu Ala Lys
    50                  55                  60

Gln Val Lys Tyr Ala Leu Glu Gln Pro Leu His Lys Gly Ile Leu Arg
65                  70                  75                  80

```
Tyr Glu Ala Trp Arg Tyr Ile Ser Ile Tyr Glu Glu Asp Glu Ser Asn
                 85                  90                  95

Asn Lys Leu Leu Leu Arg Leu Ala Lys Leu Asp Tyr His Leu Leu Gln
            100                 105                 110

Met Ser Tyr Lys Gln Glu Leu
        115
```

<210> SEQ ID NO 289
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 289

```
Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
                20                  25                  30

Pro Gln Tyr Ser Leu Ala Arg Met Thr Phe Ala Lys Val Ala Ala
            35                  40                  45
```

<210> SEQ ID NO 290
<211> LENGTH: 73
<212> TYPE: PRT
<213> ORGANISM: Artificial Sequence
<220> FEATURE:
<223> OTHER INFORMATION: Synthetic polypeptide

<400> SEQUENCE: 290

```
Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
                20                  25                  30

Ala Lys Lys Gln Arg Thr Tyr Ala Phe Asp Lys Tyr Ile Glu Asp Trp
            35                  40                  45

Lys Gln Tyr Met Arg Thr Ser Phe Thr Gln Ser Lys Trp Phe Leu Thr
        50                  55                  60

Asn Glu Leu Pro Ser Phe Ala Asp Tyr
65                  70
```

<210> SEQ ID NO 291
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 291

```
Leu Asp Met Asp Ser Ala Leu Glu Asp Val Ile Asn Trp Met Ser Thr
1               5                   10                  15

Asn Pro Lys Leu Met Val Ala Tyr
            20
```

<210> SEQ ID NO 292
<211> LENGTH: 51
<212> TYPE: PRT
<213> ORGANISM: Artificial Sequence
<220> FEATURE:
<223> OTHER INFORMATION: Synthetic polypeptide

<400> SEQUENCE: 292

```
Lys Phe Asp Lys Glu Arg Gly Ser Val Thr Ala Leu Asp Cys Tyr Met
1               5                   10                  15

Lys Asp Tyr Ser Val Ser Glu Glu Ala Ala Lys Lys Phe Arg Glu
            20                  25                  30

Met Cys Glu Asp Asn Trp Lys Val Met Asn Glu Glu Cys Leu Arg Pro
        35                  40                  45

Thr Thr Ile
    50
```

<210> SEQ ID NO 293
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 293

```
Glu Thr Val Tyr Lys His Arg Ile Asp Gly Phe Thr Gln Pro His Ala
1               5                   10                  15

Ile Glu Glu His Ile Arg Ala Met Leu Val Asp Phe Met Ser Ile
            20                  25                  30
```

<210> SEQ ID NO 294
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 294

```
Asn Asn Gln His Glu Ser Val Arg Gln Leu Ala Asp Phe Pro Glu Asn
1               5                   10                  15

Ile Trp Ala Asp Arg Val
            20
```

<210> SEQ ID NO 295
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 295

```
Gln Gly His Asp Met Cys Ala Lys Glu Ile Glu Met Leu Lys Glu Glu
1               5                   10                  15

Val Met Ser Met Leu Leu Glu
            20
```

<210> SEQ ID NO 296
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 296

```
Ser Thr Leu Ala Lys Gln Val Lys Tyr Ala Leu Glu Gln Pro Leu His
1               5                   10                  15

Lys Gly Ile Pro Arg Tyr Glu Ala Trp Arg Tyr Ile Ser Ile Tyr Glu
            20                  25                  30

Glu Asp Glu Ser Asn Asn Lys Leu Leu Leu Arg Leu Ala Lys Leu Asp
        35                  40                  45
```

Tyr His Leu Leu Gln Met Ser Tyr Lys Arg Glu
                50                  55

<210> SEQ ID NO 297
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 297

Arg Asp Arg Ile Val Glu Cys Tyr Phe Trp Ala Val Ala Thr Tyr Tyr
1               5                   10                  15

Glu Pro Gln Tyr Ser Leu Ala Arg Met Thr
            20                  25

<210> SEQ ID NO 298
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 298

Glu Val Gly Glu Asp Leu Ala Lys Lys Gln Arg Thr Tyr Ala Phe Asp
1               5                   10                  15

Lys Tyr Ile Glu
            20

<210> SEQ ID NO 299
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 299

Tyr Ala Arg Thr Ser Phe Thr Gln Ser Lys Trp Phe Leu Thr Asn Glu
1               5                   10                  15

Leu Pro Ser Phe Ser Asp Tyr Leu
            20

<210> SEQ ID NO 300
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 300

Thr Phe Leu Gly Met Asp Gly Ala Ser Glu Asp Val Ile Asn Trp Met
1               5                   10                  15

Ser Thr Asn Pro Lys Leu Phe Val Ala
            20                  25

<210> SEQ ID NO 301
<211> LENGTH: 36
<212> TYPE: PRT
<213> ORGANISM: Artificial Sequence
<220> FEATURE:
<223> OTHER INFORMATION: Synthetic polypeptide

<400> SEQUENCE: 301

Ser Thr Ala Ile Glu Cys Tyr Met Lys Asp Tyr His Val Ser Glu Glu

```
1               5                  10                 15
Glu Ala Met Glu Lys Phe Glu Glu Met Cys Asp Asp Ala Trp Lys Val
                20                 25                 30

Met Asn Glu Glu
        35
```

<210> SEQ ID NO 302
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 302

```
Asn Asn Gln His Glu Ser Val Arg Gln Leu Ala Asp Phe Pro Glu Asn
1               5                  10                 15

Ile Trp Ala Asp Arg Val
            20
```

<210> SEQ ID NO 303
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 303

```
Gln Gly His Asp Met Cys Ala Lys Glu Ile Glu Met Leu Lys Glu Glu
1               5                  10                 15

Val Met Ser Met Leu Leu Glu
            20
```

<210> SEQ ID NO 304
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 304

```
Ser Thr Leu Ala Lys Gln Val Lys Tyr Ala Leu Glu Gln Pro Leu His
1               5                  10                 15

Lys Gly Ile Pro Arg Tyr Glu Ala Trp Arg Tyr Ile Ser Ile Tyr Glu
                20                 25                 30

Glu Asp Glu Ser Asn Asn Lys Leu Leu Arg Leu Ala Lys Leu Asp
            35                 40                 45

Tyr His Leu Leu Gln Met Ser Tyr Lys Arg Glu
        50                 55
```

<210> SEQ ID NO 305
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 305

```
Arg Asp Arg Ile Val Glu Cys Tyr Phe Trp Ala Val Ala Thr Tyr Tyr
1               5                  10                 15

Glu Pro Gln Tyr Ser Leu Ala Arg Met Thr
            20                 25
```

```
<210> SEQ ID NO 306
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 306

Glu Val Gly Glu Asp Leu Ala Lys Lys Gln Arg Thr Tyr Ala Phe Asp
1               5                   10                  15

Lys Tyr Ile Glu
            20

<210> SEQ ID NO 307
<211> LENGTH: 25
<212> TYPE: PRT
<213> ORGANISM: Artificial Sequence
<220> FEATURE:
<223> OTHER INFORMATION: Synthetic polypeptide

<400> SEQUENCE: 307

Tyr Ala Arg Thr Ser Phe Thr Gln Ser Lys Trp Phe Leu Thr Asn Glu
1               5                   10                  15

Leu Pro Ser Phe Ala Asp Tyr Leu Ser
            20                  25

<210> SEQ ID NO 308
<211> LENGTH: 84
<212> TYPE: PRT
<213> ORGANISM: Artificial Sequence
<220> FEATURE:
<223> OTHER INFORMATION: Synthetic polypeptide

<400> SEQUENCE: 308

Ala Ala Leu Leu Asp Met Asp Ser Ala Leu Glu Asp Val Ile Asn Trp
1               5                   10                  15

Met Ser Thr Asn Pro Lys Phe Phe Val Ala Leu Thr Thr His Ala Arg
            20                  25                  30

Leu Thr Asn Asp Val Gly Ser His Lys Phe Glu Lys Glu Arg Gly Ser
        35                  40                  45

Gly Thr Ala Ile Glu Cys Tyr Met Lys Asp Tyr His Val Ser Glu Glu
    50                  55                  60

Glu Ala Met Lys Lys Phe Glu Glu Met Cys Asp Asp Ala Trp Lys Val
65                  70                  75                  80

Met Asn Glu Glu

<210> SEQ ID NO 309
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 309

Ser Asn Asn Arg Gln Glu Thr Val Arg Pro Leu Ala Asp Phe Pro Glu
1               5                   10                  15

Asn Ile Trp Ala Asp Arg Ile Ala Pro Phe Thr
            20                  25

<210> SEQ ID NO 310
<211> LENGTH: 45
<212> TYPE: PRT
<213> ORGANISM: Artificial Sequence
```

<220> FEATURE:
<223> OTHER INFORMATION: Synthetic polypeptide

<400> SEQUENCE: 310

Glu Met Cys Gln Arg Glu Ile Glu Met Leu Lys Ala Glu Val Ala Ser
1               5                   10                  15

Met Leu Leu Ala Thr Gly Lys Thr Met Met Gln Arg Phe Asp Phe Ile
            20                  25                  30

Asp Lys Ile Glu Arg Leu Gly Val Ser His His Phe Asp
        35                  40                  45

<210> SEQ ID NO 311
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 311

Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
            20                  25                  30

Arg Thr His Gly Asp Lys Ile Leu Glu Glu Ala Leu Ala Phe Thr Thr
        35                  40                  45

Thr His Met Thr Ser Gly Gly Pro His Leu Asp Ser Ser Leu Ala Lys
    50                  55                  60

Gln Val Lys Tyr Ala Leu Glu Gln Pro Leu His Lys Gly Ile Leu Arg
65                  70                  75                  80

Tyr Glu Ala Trp Arg Tyr Ile Ser Ile Tyr Glu Glu Asp Glu Ser Asn
                85                  90                  95

Asn Lys Leu Leu Leu Arg Leu Ala Lys Leu Asp Tyr His Leu Leu Gln
            100                 105                 110

Met Ser Tyr Lys Gln Glu Leu
        115

<210> SEQ ID NO 312
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 312

Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
            20                  25                  30

Pro Gln Tyr Ser Leu Ala Arg Met Thr Phe Ala Lys Val Ala Ala
        35                  40                  45

<210> SEQ ID NO 313
<211> LENGTH: 73
<212> TYPE: PRT
<213> ORGANISM: Artificial Sequence
<220> FEATURE:
<223> OTHER INFORMATION: Synthetic polypeptide

<400> SEQUENCE: 313

Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
            20                  25                  30

Ala Lys Lys Gln Arg Thr Tyr Ala Phe Asp Lys Tyr Ile Glu Asp Trp
        35                  40                  45

Lys Gln Tyr Met Arg Thr Ser Phe Thr Gln Ser Lys Trp Phe Leu Thr
    50                  55                  60

Asn Glu Leu Pro Ser Phe Ala Asp Tyr
65                  70

<210> SEQ ID NO 314
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 314

Leu Asp Met Asp Ser Ala Leu Glu Asp Val Ile Asn Trp Met Ser Thr
1               5                   10                  15

Asn Pro Lys Leu Met Val Ala Tyr
            20

<210> SEQ ID NO 315
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 315

Lys Glu Arg Gly Thr Gly Thr Ala Ile Glu Cys Tyr Met Lys Asp His
1               5                   10                  15

Asn

<210> SEQ ID NO 316
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 316

Glu Met Ile Glu Asn Thr Trp Lys Val Met Asn Glu Cys Leu Arg
1               5                   10                  15

Pro Ile Pro Ile Pro Arg Asp Thr Leu Lys Met Leu
            20                  25

<210> SEQ ID NO 317
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 317

Glu Thr Val Tyr Lys His Arg Ile Asp Gly Phe Thr Gln Pro His Ala
1               5                   10                  15

Ile Glu Glu His Ile Arg Ala Met Leu Val Asp Phe Met Ser Ile
            20                  25                  30

<210> SEQ ID NO 318
<211> LENGTH: 22

```
<212> TYPE: PRT
<213> ORGANISM: Artificial Sequence
<220> FEATURE:
<223> OTHER INFORMATION: Synthetic polypeptide

<400> SEQUENCE: 318

Asn Asn Gln His Glu Ser Val Arg Gln Leu Ala Asp Phe Pro Glu Asn
1               5                   10                  15

Ile Trp Ala Asp Arg Val
            20

<210> SEQ ID NO 319
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 319

Gln Gly His Asp Met Cys Ala Lys Glu Ile Glu Met Leu Lys Glu Glu
1               5                   10                  15

Val Met Ser Met Leu Leu Glu
            20

<210> SEQ ID NO 320
<211> LENGTH: 54
<212> TYPE: PRT
<213> ORGANISM: Artificial Sequence
<220> FEATURE:
<223> OTHER INFORMATION: Synthetic polypeptide

<400> SEQUENCE: 320

Gln Val Lys His Ala Leu Glu Gln Pro Leu His Arg Gly Ile Pro Arg
1               5                   10                  15

Tyr Glu Ala Tyr Cys Phe Ile Ser Ile Tyr Glu Glu Asp Glu Ser Asn
            20                  25                  30

Asn Lys Leu Leu Leu Arg Leu Ala Lys Leu Asp Tyr His Leu Leu Gln
        35                  40                  45

Met Ser Tyr Lys Arg Glu
    50

<210> SEQ ID NO 321
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 321

Arg Asp Arg Ile Val Glu Cys Tyr Phe Trp Ala Val Ala Thr Tyr Tyr
1               5                   10                  15

Glu Pro Gln Tyr Ser Leu Ala Arg Met Thr
            20                  25

<210> SEQ ID NO 322
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 322

Glu Val Gly Glu Asp Leu Ala Lys Lys Gln Arg Thr Tyr Ala Phe Asp
1               5                   10                  15
```

Lys Tyr Ile Glu
        20

<210> SEQ ID NO 323
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 323

Tyr Ala Arg Thr Ser Phe Thr Gln Ser Lys Trp Phe Leu Thr Asn Glu
1               5                   10                  15

Leu Pro Ser Phe Ser Asp Tyr Leu
            20

<210> SEQ ID NO 324
<211> LENGTH: 41
<212> TYPE: PRT
<213> ORGANISM: Artificial Sequence
<220> FEATURE:
<223> OTHER INFORMATION: Synthetic polypeptide

<400> SEQUENCE: 324

Ala Ala Phe Leu Asp Met Asp Ser Ala Ser Glu Asp Val Ile Asn Trp
1               5                   10                  15

Met Ser Thr Asn Pro Lys Leu Phe Val Ala Leu Thr Thr His Ala Arg
            20                  25                  30

Leu Ala Asn Asp Val Gly Ser His Lys
        35                  40

<210> SEQ ID NO 325
<211> LENGTH: 39
<212> TYPE: PRT
<213> ORGANISM: Artificial Sequence
<220> FEATURE:
<223> OTHER INFORMATION: Synthetic polypeptide

<400> SEQUENCE: 325

Arg Gly Ser Gly Thr Ala Ile Glu Cys Tyr Met Lys Asp Tyr Asn Val
1               5                   10                  15

Ser Glu Glu Glu Ala Leu Lys Lys Phe Glu Glu Met Cys Glu Asp Thr
            20                  25                  30

Trp Lys Val Met Asn Glu Glu
        35

<210> SEQ ID NO 326
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 326

Ser Asn Asn Arg Gln Glu Thr Val Arg Pro Leu Ala Asp Phe Pro Glu
1               5                   10                  15

Asn Ile Trp Ala Asp Arg Ile Ala Pro Phe Thr
            20                  25

<210> SEQ ID NO 327
<211> LENGTH: 45
<212> TYPE: PRT
<213> ORGANISM: Artificial Sequence

```
<220> FEATURE:
<223> OTHER INFORMATION: Synthetic polypeptide

<400> SEQUENCE: 327

Glu Met Cys Gln Arg Glu Ile Glu Met Leu Lys Ala Glu Val Ala Ser
1               5                   10                  15

Met Leu Leu Ala Thr Gly Lys Thr Met Met Gln Arg Phe Asp Phe Ile
            20                  25                  30

Asp Lys Ile Glu Arg Leu Gly Val Ser His His Phe Asp
        35                  40                  45

<210> SEQ ID NO 328
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 328

Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
            20                  25                  30

Arg Thr His Gly Asp Lys Ile Leu Glu Glu Ala Leu Ala Phe Thr Thr
        35                  40                  45

Thr His Met Thr Ser Gly Gly Pro His Leu Asp Ser Ser Leu Ala Lys
    50                  55                  60

Gln Val Lys Tyr Ala Leu Glu Gln Pro Leu His Lys Gly Ile Leu Arg
65                  70                  75                  80

Tyr Glu Ala Trp Arg Tyr Ile Ser Ile Tyr Glu Glu Asp Glu Ser Asn
                85                  90                  95

Asn Lys Leu Leu Leu Arg Leu Ala Lys Leu Asp Tyr His Leu Leu Gln
            100                 105                 110

Met Ser Tyr Lys Gln Glu Leu
        115

<210> SEQ ID NO 329
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 329

Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
            20                  25                  30

Ala Lys Lys Gln Arg Thr Tyr Ala Phe Asp Lys Tyr Ile Glu Asp Trp
        35                  40                  45

Lys Gln Tyr Met Arg Thr Asn Phe Ser Gln Ser Arg Trp Phe Phe Thr
    50                  55                  60

Lys Glu Leu Pro Ser Phe Ala Asp Tyr Ile Asn Asn Gly Ala Ile Thr
65                  70                  75                  80

Ile Gly Ala Tyr Leu Val Ala Ser Ala Phe Leu Tyr Met Asp Ser
                85                  90                  95

Ala Lys Glu Asp Val Ile Asn Trp Met Ser Thr Asn Pro Lys Leu Val
            100                 105                 110
```

```
Val Ala Tyr Ser Thr His Ser Arg Leu Ile Asn Asp Phe Gly Gly His
            115                 120                 125

Lys Phe Asp Lys Glu Arg Gly Ser Gly Thr Ala Leu Glu Cys Tyr Met
130                 135                 140

Lys Asp Tyr Asn Val Ser Glu Glu Ala Ala Asn Lys Phe Arg Glu
145                 150                 155                 160

Met Met Glu Asp Ala Trp Lys Val Met Asn Glu Asp Cys Leu Arg Pro
                165                 170                 175

Thr Ser Ile Pro Arg Asp Val Ser Lys Val Leu Leu Asn Val Ala Arg
                180                 185                 190

Ala Gly Glu Ile Val Tyr Lys His Arg Ile Asp Gly Phe Thr Glu Pro
            195                 200                 205

His Ile Ile Lys Asp His Ile Arg Ala Thr Leu Val Asp Phe Met Ala
        210                 215                 220

Ile Asn
225

<210> SEQ ID NO 330
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 330

Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
                20                  25                  30

Pro Gln Tyr Ser Leu Ala Arg Met Thr Phe Ala Lys Val Ala Ala
            35                  40                  45

<210> SEQ ID NO 331
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 331

Ser Asn Asn Arg Gln Glu Thr Val Arg Pro Leu Ala Asp Phe Pro Glu
1               5                   10                  15

Asn Ile Trp Ala Asp Arg Ile Ala Pro Phe Thr
                20                  25

<210> SEQ ID NO 332
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 332

Glu Met Cys Gln Arg Glu Ile Glu Met Leu Lys Ala Glu Val Ala Ser
1               5                   10                  15

Met Leu Leu Ala Thr Gly Lys Thr Met Met Gln Arg Phe Asp Phe Ile
                20                  25                  30

Asp Lys Ile Glu Arg Leu Gly Val Ser His His Phe Asp
            35                  40                  45
```

<210> SEQ ID NO 333
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 333

Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
                20                  25                  30

Arg Thr His Gly Asp Lys Ile Leu Glu Glu Ala Leu Ala Phe Thr Thr
            35                  40                  45

Thr His Met Thr Ser Gly Gly Pro His Leu Asp Ser Ser Leu Ala Lys
        50                  55                  60

Gln Val Lys Tyr Ala Leu Glu Gln Pro Leu His Lys Gly Ile Leu Arg
65                  70                  75                  80

Tyr Glu Ala Trp Arg Tyr Ile Ser Ile Tyr Glu Glu Asp Glu Ser Asn
                85                  90                  95

Asn Lys Leu Leu Leu Arg Leu Ala Lys Leu Asp Tyr His Leu Leu Gln
                100                 105                 110

Met Ser Tyr Lys Gln Glu Leu
            115

<210> SEQ ID NO 334
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 334

Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
                20                  25                  30

Pro Gln Tyr Ser Leu Ala Arg Met Thr Phe Ala Lys Val Ala Ala
            35                  40                  45

<210> SEQ ID NO 335
<211> LENGTH: 73
<212> TYPE: PRT
<213> ORGANISM: Artificial Sequence
<220> FEATURE:
<223> OTHER INFORMATION: Synthetic polypeptide

<400> SEQUENCE: 335

Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
                20                  25                  30

Ala Lys Lys Gln Arg Thr Tyr Ala Phe Asp Lys Tyr Ile Glu Asp Trp
            35                  40                  45

Lys Gln Tyr Met Arg Thr Ser Phe Thr Gln Ser Lys Trp Phe Leu Thr
        50                  55                  60

Asn Glu Leu Pro Ser Phe Ala Asp Tyr
65                  70

<210> SEQ ID NO 336

-continued

```
<211> LENGTH: 24
<212> TYPE: PRT
<213> ORGANISM: Artificial Sequence
<220> FEATURE:
<223> OTHER INFORMATION: Synthetic polypeptide

<400> SEQUENCE: 336

Leu Asp Met Asp Ser Ala Leu Glu Asp Val Ile Asn Trp Met Ser Thr
1               5                   10                  15

Asn Pro Lys Leu Met Val Ala Tyr
            20

<210> SEQ ID NO 337
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 337

Lys Phe Asp Lys Glu Arg Gly Ser Val Thr Ala Leu Asp Cys Tyr Met
1               5                   10                  15

Lys Asp Tyr Ser Val Ser Glu Glu Ala Ala Lys Lys Phe Arg Glu
            20                  25                  30

Met Ile Glu Asn Thr Trp Lys Val Met Asn Glu Glu Cys Leu Arg Pro
        35                  40                  45

Ile Pro Ile Pro Arg Asp Thr Leu Lys Met Leu
        50                  55

<210> SEQ ID NO 338
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 338

Glu Pro His Ile Ile Lys Asp His Ile Arg Ala Met Leu Val Asp Phe
1               5                   10                  15

Met Ala Ile

<210> SEQ ID NO 339
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 339

Ser Asn Asn Arg Gln Glu Thr Val Arg Pro Leu Ala Asp Phe Pro Glu
1               5                   10                  15

Asn Ile Trp Ala Asp Arg Ile Ala Pro Phe Thr
            20                  25

<210> SEQ ID NO 340
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 340

Glu Met Cys Gln Arg Glu Ile Glu Met Leu Lys Ala Glu Val Ala Ser
1               5                   10                  15
```

Met Leu Leu Ala Thr Gly Lys Thr Met Met Gln Arg Phe Asp Phe Ile
            20                  25                  30

Asp Lys Ile Glu Arg Leu Gly Val Ser His His Phe Asp
            35                  40                  45

<210> SEQ ID NO 341
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 341

Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
            20                  25                  30

Arg Thr His Gly Asp Lys Ile Leu Glu Glu Ala Leu Ala Phe Thr Thr
            35                  40                  45

Thr His Met Thr Ser Gly Gly Pro His Leu Asp Ser Ser Leu Ala Lys
        50                  55                  60

Gln Val Lys Tyr Ala Leu Glu Gln Pro Leu His Lys Gly Ile Leu Arg
65                  70                  75                  80

Tyr Glu Ala Trp Arg Tyr Ile Ser Ile Tyr Glu Glu Asp Glu Ser Asn
                85                  90                  95

Asn Lys Leu Leu Leu Arg Leu Ala Lys Leu Asp Tyr His Leu Leu Gln
            100                 105                 110

Met Ser Tyr Lys Gln Glu Leu
        115

<210> SEQ ID NO 342
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 342

Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
            20                  25                  30

Pro Gln Tyr Ser Leu Ala Arg Met Thr Phe Ala Lys Val Ala Ala
            35                  40                  45

<210> SEQ ID NO 343
<211> LENGTH: 179
<212> TYPE: PRT
<213> ORGANISM: Artificial Sequence
<220> FEATURE:
<223> OTHER INFORMATION: Synthetic polypeptide

<400> SEQUENCE: 343

Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
            20                  25                  30

Ala Lys Lys Gln Arg Thr Tyr Ala Phe Asp Lys Tyr Ile Glu Asp Trp
            35                  40                  45

```
Lys Gln Tyr Met Arg Thr Asn Phe Ser Gln Ser Arg Trp Phe Phe Thr
 50                  55                  60
Lys Glu Leu Pro Ser Phe Ala Asp Tyr Ile Asn Asn Gly Ala Ile Thr
 65                  70                  75                  80
Ile Gly Ala Tyr Leu Val Ala Ser Ala Ala Phe Leu Tyr Met Asp Ser
                 85                  90                  95
Ala Lys Glu Asp Val Ile Asn Trp Met Ser Thr Asn Pro Lys Leu Val
            100                 105                 110
Val Ala Tyr Ser Thr His Ser Arg Leu Ile Asn Asp Phe Gly Gly His
            115                 120                 125
Lys Phe Asp Lys Glu Arg Gly Ser Val Thr Ala Leu Asp Cys Tyr Met
130                 135                 140
Lys Asp Tyr Ser Val Ser Glu Glu Ala Ala Lys Lys Phe Arg Glu
145                 150                 155                 160
Met Cys Glu Asp Asn Trp Lys Val Met Asn Glu Cys Leu Arg Pro
                165                 170                 175
Thr Thr Ile

<210> SEQ ID NO 344
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 344

Glu Thr Val Tyr Lys His Arg Ile Asp Gly Phe Thr Gln Pro His Ala
 1               5                  10                  15
Ile Glu Glu His Ile Arg Ala Met Leu Val Asp Phe Met Ser Ile
                20                  25                  30

<210> SEQ ID NO 345
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 345

Ser Asn Asn Arg Gln Glu Thr Val Arg Pro Leu Ala Asp Phe Pro Glu
 1               5                  10                  15
Asn Ile Trp Ala Asp Arg Ile Ala Pro Phe Thr
                20                  25

<210> SEQ ID NO 346
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 346

Glu Met Cys Gln Arg Glu Ile Glu Met Leu Lys Ala Glu Val Ala Ser
 1               5                  10                  15
Met Leu Leu Ala Thr Gly Lys Thr Met Met Gln Arg Phe Asp Phe Ile
                20                  25                  30
Asp Lys Ile Glu Arg Leu Gly Val Ser His His Phe Asp
            35                  40                  45

<210> SEQ ID NO 347
```

<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 347

Ile Phe Asp Gln Phe Ile Asp Ala Lys Gly Lys Phe Lys Glu Ser Leu
1               5                   10                  15

Cys Asn Asp Ile Arg Gly Leu Leu Ser Leu Tyr Glu Ala Ala His Val
                20                  25                  30

Arg Thr His Gly Asp Lys Ile Leu Glu Glu Ala Leu Ala Phe Thr Thr
            35                  40                  45

Thr His Met Thr Ser Gly Gly Pro His Leu Asp Ser Ser Leu Ala Lys
        50                  55                  60

Gln Val Lys Tyr Ala Leu Glu Gln Pro Leu His Lys Gly Ile Leu Arg
65                  70                  75                  80

Tyr Glu Ala Trp Arg Tyr Ile Ser Ile Tyr Glu Glu Asp Glu Ser Asn
                85                  90                  95

Asn Lys Leu Leu Leu Arg Leu Ala Lys Leu Asp Tyr His Leu Leu Gln
                100                 105                 110

Met Ser Tyr Lys Gln Glu Leu
        115

<210> SEQ ID NO 348
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 348

Arg Trp Gly Lys Gly Leu Glu Ser Val Ser Asn Phe Pro Tyr Ala Arg
1               5                   10                  15

Asp Arg Phe Val Glu Cys Tyr Phe Trp Ala Val Gly Thr Leu Tyr Glu
                20                  25                  30

Pro Gln Tyr Ser Leu Ala Arg Met Thr Phe Ala Lys Val Ala Ala
            35                  40                  45

<210> SEQ ID NO 349
<211> LENGTH: 187
<212> TYPE: PRT
<213> ORGANISM: Artificial Sequence
<220> FEATURE:
<223> OTHER INFORMATION: Synthetic polypeptide

<400> SEQUENCE: 349

Arg Trp Asp Gly Ser Gly Val Asp Gln Leu Ser Asp Tyr Ile Arg Ala
1               5                   10                  15

Ser Tyr Asn Thr Leu Leu Lys Phe Asn Lys Glu Val Gly Glu Asp Leu
                20                  25                  30

Ala Lys Lys Gln Arg Thr Tyr Ala Phe Asp Lys Tyr Ile Glu Asp Trp
            35                  40                  45

Lys Gln Tyr Met Arg Thr Asn Phe Ser Gln Ser Arg Trp Phe Phe Thr
        50                  55                  60

Lys Glu Leu Pro Ser Phe Ala Asp Tyr Ile Asn Asn Gly Ala Ile Thr
65                  70                  75                  80

Ile Gly Ala Tyr Leu Val Ala Ser Ala Ala Phe Leu Tyr Met Asp Ser
                85                  90                  95

Ala Lys Glu Asp Val Ile Asn Trp Met Ser Thr Asn Pro Lys Leu Val
            100                 105                 110

Val Ala Tyr Ser Thr His Ser Arg Leu Ile Asn Asp Phe Gly Gly His
        115                 120                 125

Lys Phe Asp Lys Glu Arg Gly Ser Val Thr Ala Leu Asp Cys Tyr Met
    130                 135                 140

Lys Asp Tyr Ser Val Ser Glu Glu Ala Lys Lys Phe Arg Glu
145                 150                 155                 160

Met Ile Glu Asn Thr Trp Lys Val Met Asn Glu Cys Leu Arg Pro
                165                 170                 175

Ile Pro Ile Pro Arg Asp Thr Leu Lys Met Leu
            180                 185

<210> SEQ ID NO 350
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 350

Glu Pro His Ile Ile Lys Asp His Ile Arg Ala Met Leu Val Asp Phe
1               5                   10                  15

Met Ala Ile

<210> SEQ ID NO 351
<211> LENGTH: 62
<212> TYPE: PRT
<213> ORGANISM: Artificial Sequence
<220> FEATURE:
<223> OTHER INFORMATION: Synthetic polypeptide

<400> SEQUENCE: 351

Glu Ala Phe Asn Lys Leu Lys Asp Glu Glu Gly Asn Phe Lys Ala Ser
1               5                   10                  15

Leu Thr Ser Asp Val Arg Gly Leu Leu Glu Leu Tyr Gln Ala Ser Tyr
            20                  25                  30

Met Arg Ile His Gly Glu Asp Ile Leu Asp Glu Ala Ile Ser Phe Thr
        35                  40                  45

Thr Ala Gln Leu Thr Leu Ala Leu Pro Thr Leu Asp Pro Pro
    50                  55                  60

<210> SEQ ID NO 352
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 352

Asn Lys Ala Leu Leu Gln Phe Ala Lys Ile Asp Phe Asn Met Leu Gln
1               5                   10                  15

Leu Leu His Arg Lys Glu Leu Ser Glu Ile Cys Arg Trp Trp Lys Asp
            20                  25                  30

Leu Asp Phe Thr Arg Lys Leu Pro
        35                  40

<210> SEQ ID NO 353
<211> LENGTH: 58
<212> TYPE: PRT
<213> ORGANISM: Artificial Sequence

```
<220> FEATURE:
<223> OTHER INFORMATION: Synthetic polypeptide

<400> SEQUENCE: 353

Asp Arg Val Val Glu Gly Tyr Phe Trp Ile Met Gly Val Tyr Phe Glu
1               5                   10                  15

Pro Gln Tyr Ser Leu Gly Arg Lys Met Leu Thr Lys Val Ile Ala Met
            20                  25                  30

Ala Ser Ile Val Asp Asp Thr Tyr Asp Ser Phe Ala Thr Tyr Asp Glu
        35                  40                  45

Leu Ile Pro Tyr Thr Asp Ala Ile Glu Arg
    50                  55

<210> SEQ ID NO 354
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 354

Tyr Met Gln Ile Ser Tyr Lys Ala Leu Leu Asp Val Tyr Glu Glu Met
1               5                   10                  15

Glu Gln Leu Leu Ala Asp Lys Gly Arg Gln Tyr Arg Val Glu Tyr
            20                  25                  30

<210> SEQ ID NO 355
<211> LENGTH: 29
<212> TYPE: PRT
<213> ORGANISM: Artificial Sequence
<220> FEATURE:
<223> OTHER INFORMATION: Synthetic polypeptide

<400> SEQUENCE: 355

Trp Thr His Leu Asn Tyr Lys Pro Thr Phe Glu Glu Phe Arg Asp Asn
1               5                   10                  15

Ala Leu Pro Thr Ser Gly Tyr Ala Met Leu Ala Ile Thr
            20                  25

<210> SEQ ID NO 356
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 356

Thr Phe Glu Trp Ala Ala Ser Asp Pro Lys Ile Ile Lys Ala Ser Thr
1               5                   10                  15

Ile Ile Cys Arg Phe Met Asp Asp Ile Ala Glu
            20                  25

<210> SEQ ID NO 357
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 357

Glu Asp Asp Cys Ser Ala Ile Glu Cys Tyr Met Glu Gln Tyr Lys Val
1               5                   10                  15

Thr Ala Gln Glu Ala Tyr Asp Glu Phe Asn Lys His Ile Glu Ser Ser
```

```
                    20                  25                  30
Trp Lys Asp Val Asn Glu Glu Phe Leu Lys
                35                  40
```

CHIMERIC TERPENE SYNTHASES

RELATED APPLICATIONS

This application is a national stage filing under 35 U.S.C § 371 of international application PCT/US2019/018122, entitled "CHIMERIC TERPENE SYNTHASES," filed Feb. 14, 2019, which was published under PCT Article 21(2) in English and which claims the benefit under 35 U.S.C. § 119(e) of U.S. Provisional Application Ser. No. 62/630,640, entitled "CHIMERIC TERPENE SYNTHASES" filed on Feb. 14, 2018, the entire disclosures of each of which are herein incorporated by reference in their entireties.

FIELD OF THE INVENTION

The disclosure relates to chimeric terpene synthases, methods for making chimeric terpene synthases, and methods for making terpenes using the same.

BACKGROUND

Terpenes are a diverse class of organic compounds built from five carbon building blocks and encompass at least 400 distinct structural families. Given their structural diversity, terpenes have numerous roles including acting as pheromones, anti-oxidants, and anti-microbial agents. Although terpene synthases produce terpenes in both prokaryotes and eukaryotes, the wide array of terpene isomers often hinder high yield extractions from naturally occurring sources. Furthermore, the structural complexity of terpenes often limits de novo chemical synthesis.

SUMMARY

Aspects of the disclosure relate to chimeric terpene synthases comprising an amino acid sequence at least 90% identical to an amino acid selected from the group consisting of: SEQ ID NOs: 1-52. In some embodiments, the chimeric terpene synthase comprises an amino acid sequence at least 91%, at least 92%, at least 93%, at least 94%, at least 95%, at least 96%, at least 97%, at least 98%, or at least 99% identical to an amino acid selected from the group consisting of: SEQ ID NOs: 1-52. In some embodiments, the chimeric terpene synthase comprises an amino acid sequence identical to an amino acid selected from the group consisting of: SEQ ID NOs: 1-52.

Further aspects of the disclosure relate to nucleic acid molecules encoding a chimeric terpene synthase described herein. In some embodiments, a nucleic acid molecule comprises a sequence that is at least 90% identical to a nucleotide sequence selected from the group consisting of SEQ ID NOs: 67-118. In some embodiments, a nucleic acid molecule comprises a sequence selected from the group consisting of SEQ ID NOs: 67-118.

Further aspects of the disclosure relate to vectors comprising a nucleic acid molecule described herein. In some embodiments, the vector is a viral vector, a vector for transient expression, or a vector for inducible expression. In some embodiments, the vector is a lentiviral vector, a retroviral vector, an adenoviral vector, an adeno-associated vector, a galactose-inducible vector, or a doxycycline-inducible vector.

Further aspects of the disclosure relate to host cells comprising a nucleic acid described herein, or a vector described herein.

In some embodiments, the host cell is a fungal cell. In some embodiments, the cell is a yeast cell. In some embodiments, the cell is a *Saccharomyces, Pichia, Kluyveromyces, Hansenula*, or *Yarrowia* cell. In some embodiments, the cell is a *Saccharomyces cerevisiae* cell.

In some embodiments, the host cell is a plant cell.

In some embodiments, the host cell is a bacteria cell.

Further aspects of the disclosure relate to nucleic acid molecules encoding a chimeric terpene synthase, wherein at least 10% of the nucleic acid molecule sequence, or the amino acid sequence, is derived from a rare or extinct plant. In some embodiments, at least 40% of the nucleic acid molecule sequence, or the amino acid sequence, is derived from a rare or extinct plant.

In some embodiments, at least 20%, at least 30%, at least 40%, at least 50%, at least 60%, at least 70%, at least 80%, or at least 90% of the nucleic acid molecule sequence, or the amino acid sequence, is derived from a rare or extinct plant. In some embodiments, at least 90%, at least 91%, at least 92%, at least 93%, at least 94%, or at least 95% of the nucleic acid molecule sequence, or the amino acid sequence, is derived from a rare or extinct plant.

In some embodiments, the chimeric terpene synthase is a chimeric sesquiterpene synthase. In some embodiments, the rare or extinct plant is selected from the group consisting of: *Hibiscadelphus wilderianus, Leucadendron grandiflorum, Macrostylis villosa, Orbexilum stipulatum, Shorea cuspidate*, and *Wendlandia angustifolia*.

Further aspects of the disclosure relate to nucleic acid molecules encoding a chimeric terpene synthase. In some embodiments, at least 10% of the nucleic acid molecule sequence, or the amino acid sequence is derived from a rare or extinct plant. In some embodiments, at least 20%, at least 30%, at least 40%, at least 50%, at least 60%, at least 70%, at least 80%, or at least 90% of the nucleic acid molecule sequence is derived from a rare or extinct plant. In some embodiments, at least 90%, at least 91%, at least 92%, at least 93%, at least 94%, or at least 95% of the nucleic acid molecule sequence is derived from a rare or extinct plant.

In some embodiments, the nucleic acid molecule further comprises a TATA box sequence.

Further aspects of the disclosure relate to methods of producing one or more sesquiterpenes, wherein the method comprises culturing a host cell described herein under conditions suitable for producing the one or more sesquiterpenes.

Further aspects of the disclosure relate to compositions comprising one or more sesquiterpenes produced by the methods described herein.

In one embodiment, at least one of the one or more sesquiterpenes is an aroma compound.

Further aspects of the disclosure relate to methods of producing a perfume, wherein the method comprises: culturing a host cell described herein under conditions suitable for producing the one or more sesquiterpenes; and extracting the one or more sesquiterpenes.

Each of the limitations of the compositions and methods described herein may encompass various described embodiments. It is, therefore, anticipated that each of the limitations of the invention involving any one element or combinations of elements can be included in each aspect of the invention. This present disclosure is not limited in its application to the details of construction and the arrangement of components set forth in the following description or illustrated in the drawings.

BRIEF DESCRIPTION OF DRAWINGS

The accompanying drawings are not intended to be drawn to scale. The drawings are illustrative only and are not required for enablement of the disclosure. For purposes of clarity, not every component may be labeled in every drawing. In the drawings:

FIG. 8A depicts *Hibiscadelphus wilderianus* (from Radlkofer et al., New and Noteworthy Hawaiian Plants. Hawaiian Board of Agriculture and Forestry Botanical Bulletin. 1911; (1):1-15). FIG. 8B depicts *Leucadendron grandiflorum* (from Salisbury et al., The Paradisus Londinensis or Coloured Figures of Plants Cultivated in the Vicinity of the Metropolis. 1805; (Volume 1, part 2): 105). FIG. 8C depicts *Macrostylis villosa* subsp. *Villosa* (from "Red List of South African Plants: *Macrostylis villosa* subsp. *villosa*," 2007). FIG. 8D depicts *Orbexilum stipulatum* (from Short, "*Orbexilum stipulatum* collected at Falls of the Ohio," 1840 from The Philadelphia Herbarium at the Academy of Natural Sciences). FIG. 8E depicts *Shorea cuspidata* (from "Kew Royal Botanical Gardens: *Shorea cuspidata* specimen K000700460," 1962). FIG. 8F depicts *Wendlandia angustifolia* (from "Kew Royal Botanical Gardens: *Wendlandia angustifolia* K000030921," collection date not recorded).

DETAILED DESCRIPTION

Figure 1:
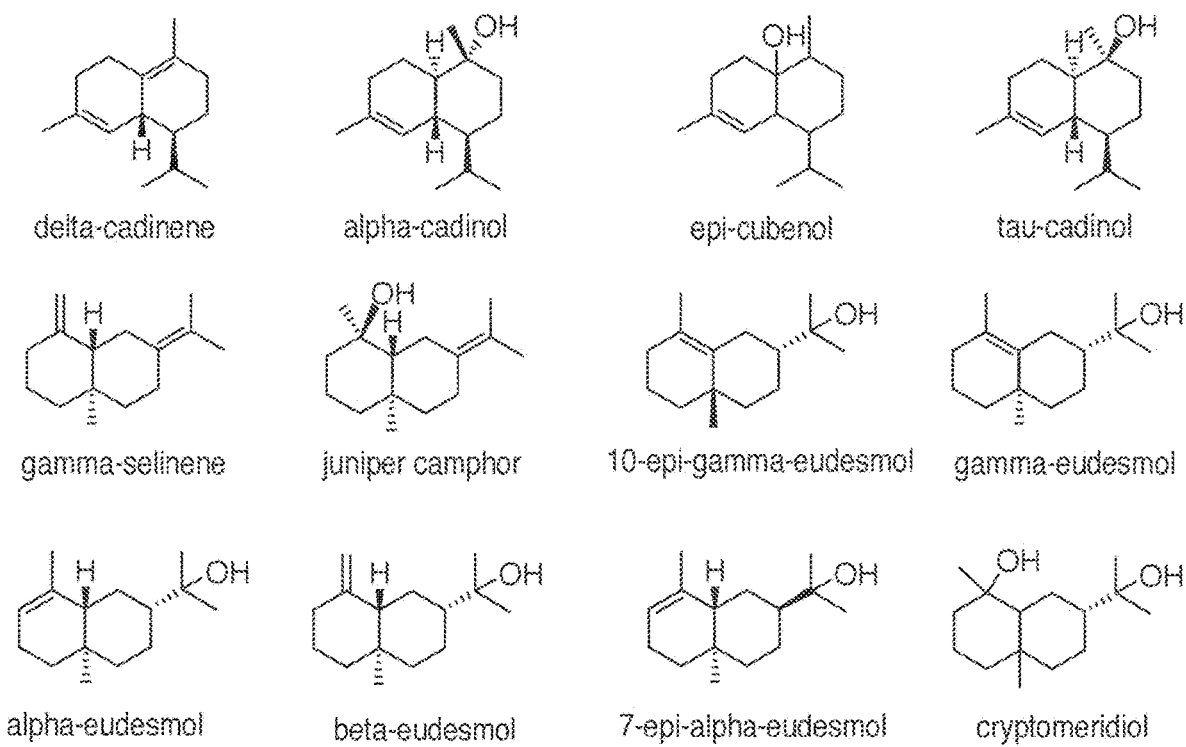
FIG. 1 is a series of pictures depicting structures of identified sesquiterpenes produced using sesquiterpene synthases (SQTSs) containing rare sequences from *H. wilderianus*.

Although terpenes are widely used in the fragrance industry, purification of terpenes from natural sources and de novo chemical synthesis often have high production costs and low yield. This disclosure is premised, in part, on the unexpected finding that chimeric terpene synthases comprising a portion of a terpene synthase sequence from at least one rare or extinct plant can be leveraged to produce a diversity of sesquiterpenes. Accordingly, provided herein are chimeric terpene synthases, methods for making chimeric terpene synthases, and methods for making terpenes using the described chimeric terpene synthases. In some embodiments, the chimeric terpene synthases are chimeric sesquiterpene synthases.

This invention is not limited in its application to the details of construction and the arrangement of components set forth in the description. The invention is capable of other embodiments and of being practiced or of being carried out in various ways. Additionally, the phraseology and terminology used herein is for the purpose of description and should not be regarded as limiting. The use of terms such as "including," "comprising," "having," "containing," "involving," and/or variations thereof herein, is meant to encompass the items listed thereafter and equivalents thereof as well as additional items.

Chimeric Terpene Synthases

Aspects of the present disclosure relate to chimeric terpene synthases comprising fragments (e.g., sequences) from at least two terpene synthases, wherein at least one of the two or more terpene synthases is from a rare or extinct plant. For example, the sequence of a chimeric terpene synthase may comprise one or more fragments (e.g., one or more portions of the total sequence) from at least two, at least three, at least four, at least five, at least six, at least seven, at least eight, at least nine or at least ten terpene synthases. It should be appreciated that chimeric terpene synthases described herein can be synthetic. Accordingly, chimeric terpene synthases, including synthetic chimeric terpene synthases, described herein comprise sequences derived from more than one terpene synthase, wherein at least one of the terpene synthases is from a rare or extinct plant. In some embodiments, the chimeric terpene synthases are chimeric sesquiterpene synthases.

Terpene synthases are enzymes that catalyze the formation of terpenes from isoprenoid diphosphate substrates. At least two types of terpene synthases have been characterized: classic terpene synthases and isoprenyl diphosphate synthase-type terpene synthases. Classic terpene synthases are found in prokaryotes (e.g., bacteria) and in eukaryotes (e.g., plants, fungi and amoebae), while isoprenyl diphosphate synthase-type terpene synthases have been found in insects (see, e.g., Chen et al., Terpene synthase genes in eukaryotes beyond plants and fungi: Occurrence in social amoebae. *Proc Natl Acad Sci USA*. 2016; 113(43):12132-12137, which is hereby incorporated by reference in its entirety for this purpose). Several highly conserved structural motifs have been reported in classic terpene synthases, including an aspartate-rich "DDxx(x)D/E" motif and a "NDxxSxxxD/E" (SEQ ID NO: 55) motif, which have both been implicated in coordinating substrate binding (see, e.g., Starks et al., Structural basis for cyclic terpene biosynthesis by tobacco 5-epi-aristolochene synthase. *Science*. 1997 Sep. 19; 277(5333):1815-20; and Christianson et al., Unearthing the roots of the terpenome. *Curr Opin Chem Biol*. 2008 April; 12(2):141-50, each of which is hereby incorporated by reference in its entirety for this purpose).

Terpene synthases may be classified by the type of terpenes they produce. As used herein, unless otherwise indicated, terpenes are organic compounds comprising isoprene (i.e., $C_5H_8$) units and derivatives thereof. For example, terpenes include pure hydrocarbons with the molecular formula $(C_5H_8)_n$, in which n represents the number of isoprene subunits. Terpenes also include oxygenated compounds (often referred to as terpenoids). Terpenes are structurally diverse compounds and, for example, may be cyclic (e.g., monocyclic, multi-cyclic, homocyclic and heterocyclic compounds) or acyclic (e.g., linear and branched compounds). In some embodiments, a terpene may have an odor. As used herein, an aroma compound refers to a compound that has an odor. Any methods known in the art, including mass spectrometry (e.g., gas chromatography-mass spectrometry (GC/MS, shown in Example 2 below), may be used to identify a terpene of interest.

Terpene synthases may include, for example, monoterpene synthases, diterpene synthases, and sesquiterpene synthases. Certain non-limiting examples of monoterpene synthases and sesquiterpene synthases may be found, for example, in Degenhardt et al., Monoterpene and sesquiterpene synthases and the origin of terpene skeletal diversity in plants. *Phytochemistry.* 2009 October-November; 70(15-16):1621-37, which is hereby incorporated by reference in its entirety for this purpose.

Monoterpene synthases catalyze the formation of 10-carbon monoterpenes. Generally, monoterpene synthases use geranyl diphosphate (GPP) as a substrate. Non-limiting examples of monoterpene synthases include Myrcene synthase (UniProtKb Identifier: O24474), (R)-limonene synthase (UniprotKB Identifier: Q2XSC6), (E)-beta-ocimene synthase (UniProtKB Identifier: Q5CD81) and Limonene synthase (UniProtKB Identifier: Q9FV72). Non-limiting examples of monoterpenes include, but are not limited to, limonene, sabinene, thujene, carene, borneol, eucalyptol and camphene.

Diterpene synthases promote the formation of 20-carbon diterpenes. Generally, diterpene synthases use geranylgeranyl diphosphate as a substrate. Non-limiting examples of diterpene synthases include cis-abienol synthase (UniProtKB identifier: H8ZM73), sclareol synthase (UniProtKB identifier: K4HYB0) and abietadiene synthase (Q38710). See, e.g., Gong et al., Diterpene synthases and their responsible cyclic natural products. *Nat Prod Bioprospect.* 2014; 4(2):59-72, which is hereby incorporated by reference in its entirety for this purpose. Non-limiting examples of diterpenes include, but are not limited to, cembrene and sclareol.

Sesquiterpene synthases catalyze the formation of 15-carbon sesquiterpenes. Generally, sesquiterpene synthases convert farnesyl diphosphate (FDP) into sesquiterpenes. Non-limiting examples of sesquiterpene synthases include (+)-delta-cadinene synthase (UniProtKB Identifier: Q9SAN0), UniProtKB Identifier: A0A067FTE8, Beta-eudesmol synthase (UniProtKB Identifier: B1B1U4), (+)-delta-cadinene synthase isozyme XC14 (UniProtKB Identifier: Q39760), (+)-delta-cadinene synthase isozyme XC1 (UniProtKB Identifier: Q39761), (+)-delta-cadinene synthase isozyme A (UniProtKB Identifier: Q43714), Sesquiterpene synthase 2 (UniProtKB Identifier: Q9FQ26), Putative delta-guaiene synthase (UniProtKB Identifier: A0A0A0QUT9), Delta-guaiene synthase 1 (UniProtKB Identifier: D0VMR6), Alpha-zingiberene synthase (UniProtKB Identifier: Q5SBP4), (Z)-gamma-bisabolene synthase 1 (UniProtKB Identifier: Q9T0J9), A0A067D5M4, Delta-elemene synthase (UniProtKB Identifier: A0A097ZIE0), ShoBecSQTS1, A0A068UHT0, terpene synthase (UniProtKB Identifier: G5CV47), A0A068VE40 and A0A068VI46.

In some embodiments, a sesquiterpene synthase is an alpha-guaiene synthase. As used herein, an alpha-guaiene synthase is capable of catalyzing the formation of alpha-guaiene. In some embodiments, an alpha-guaiene synthase uses (2E,6E)-farnesyl diphosphate as a substrate. Non-limiting examples of alpha-guaiene synthases include UniProtKB Identifier: D0VMR6, UniProtKB Identifier: D0VMR7, UniProtKB Identifier: D0VMR8, UniProtKB Identifier: Q49SP3. As disclosed herein, an alpha-guaiene synthase may comprise a sequence that is at least 50% (e.g., at least 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more than 99%, including all values in between) identical to SEQ ID NO: 17, 22, or 29. In certain embodiments, an alpha-guaiene synthase comprises SEQ ID NO: 17, 22, or 29. In certain embodiments an alpha-guaiene synthase consists of SEQ ID NO: 17, 22, or 29.

As used herein, unless otherwise indicated, sesquiterpenes include sesquiterpene hydrocarbons and sesquiterpene alcohols (sesquiterpenols). Non-limiting examples of sesquiterpenes include but are not limited to, delta-cadinene, epi-cubenol, tau-cadinol, alpha-cadinol, gamma-selinene, 10-epi-gamma-eudesmol, gamma-eudesmol, alpha/beta-eudesmol, juniper camphor, 7-epi-alpha-eudesmol, cryptomeridiol isomer 1, cryptomeridiol isomer 2, cryptomeridiol isomer 3, humulene, alpha-guaiene, delta-guaiene, zingiberene, beta-bisabolene, beta-farnesene, beta-sesquiphellandrene, cubenol, alpha-bisabolol, alpha-curcumene, trans-nerolidol, gamma, bisabolene, beta-caryophyllene, trans-Sesquisabinene hydrate, delta-elemene, cis-eudesm-6-en-11-ol, daucene, isodaucene, trans-bergamotene, alpha-zingiberene, sesquisabinene hydrate, and 8-Isopropenyl-1,5-dimethyl-1,5-cyclodecadiene.

The present disclosure also encompasses chimeric terpene synthases that are multi-functional (e.g., capable of producing more than one sesquiterpene). In some embodiments, a chimeric terpene synthase is capable of producing delta-cadinene and alpha-cadinol. In some embodiments, a chimeric terpene synthase is capable of producing delta-cadinene, tau-cadinol, and alpha-cadinol. In some embodiments, a chimeric terpene synthase is capable of producing alpha-guaiene and delta-guaiene. In some embodiments, the chimeric terpene synthase is capable of producing beta-caryophyllene and humulene.

In some embodiments, a chimeric terpene synthase (e.g., a chimeric sesquiterpene synthase) of the present disclosure comprises an amino sequence at least 50% (e.g., at least 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more than 99%, including all values in between) identical to a sequence selected from the group consisting of SEQ ID NOs: 1-52. In some embodiments, the chimeric terpene synthase comprises an amino acid sequence provided in SEQ ID NOs: 1-52.

In some embodiments, a chimeric terpene synthase comprises one or more sequences provided in SEQ ID NOs: 119-357.

The term "sequence identity," as known in the art, refers to a relationship between the sequences of two polypeptides or polynucleotides, as determined by sequence comparison (alignment). In the art, identity also means the degree of sequence relatedness between two sequences as determined by the number of matches between strings of two or more residues (e.g., nucleic acid or amino acid residues). Identity measures the percent of identical matches between the smaller of two or more sequences with gap alignments (if any) addressed by a particular mathematical model or computer program (e.g., "algorithms").

Identity of related polypeptides can be readily calculated by any of the methods known to one of ordinary skill in the art. The "percent identity" of two sequences (e.g., nucleic acid or amino acid sequences) may, for example, be determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST® and XBLAST® programs (version 2.0) of Altschul et al., *J. Mol. Biol.* 215:403-10, 1990. BLAST® protein searches can be performed, for example, with the XBLAST program, score=50, wordlength=3 to obtain amino acid sequences homologous to the protein molecules of the invention. Where gaps exist between two sequences, Gapped BLAST® can be utilized, for example, as described in Altschul et al., *Nucleic Acids Res.* 25(17):3389-3402, 1997. When utilizing BLAST® and Gapped BLAST® programs, the default parameters of the respective programs (e.g., XBLAST® and NBLAST®) can be used, or the parameters can be adjusted appropriately as would be understood by one of ordinary skill in the art.

Another local alignment technique which may be used, for example, is based on the Smith-Waterman algorithm (Smith, T. F. & Waterman, M. S. (1981) "Identification of common molecular subsequences." *J. Mol. Biol.* 147:195-197). A general global alignment technique which may be used, for example, is the Needleman-Wunsch algorithm (Needleman, S. B. & Wunsch, C. D. (1970) "A general method applicable to the search for similarities in the amino acid sequences of two proteins." *J. Mol. Biol.* 48:443-453), which is based on dynamic programming. More recently, a Fast Optimal Global Sequence Alignment Algorithm (FOGSAA) was developed that purportedly produces global alignment of nucleic acid and amino acid sequences faster than other optimal global alignment methods, including the Needleman—Wunsch algorithm.

The present disclosure also encompasses compositions comprising one or more terpenes (e.g., sesquiterpenes) produced by any one of the chimeric terpene synthases (e.g., sesquiterpene synthases) described herein. In some embodiments, the composition comprises at least one terpene (e.g., sesquiterpene) that is an aroma compound. In some embodiments, the composition is a perfume (e.g., comprising a single fragrance or a mixture of fragrances). In some embodiments, the composition further comprises a fixative (i.e., stabilizer) to reduce volatility of the composition. Non-limiting examples include fixatives include resinoids (e.g., benzoin, olibanum, storax, labdanum, myrrh and tolu balsam) and benzyl benzoate. In some embodiments, the composition further comprises ethyl alcohol. In some embodiments, the composition further comprises distilled water.

In certain embodiments, a terpene synthase (e.g., sesquiterpene synthase) of the present disclosure produces a terpene (e.g., sesquiterpene) composition that comprises at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, at least 90%, at least 95%, or 100% including any values in between of a particular terpene, such as a sesquiterpene. Non-limiting examples of sesquiterpenes include delta-cadinene, epi-cubenol, tau-cadinol, alpha-cadinol, gamma-selinene, 10-epi-gamma-eudesmol, gamma-eudesmol, alpha/beta-eudesmol, juniper camphor, 7-epi-alpha-eudesmol, cryptomeridiol isomer 1, cryptomeridiol isomer 2, cryptomeridiol isomer 3, humulene, alpha-guaiene, delta-guaiene, zingiberene, beta-bisabolene, beta-farnesene, beta-sesquiphellandrene, cubenol, alpha-bisabolol, alpha-curcumene, trans-nerolidol, gamma, bisabolene, beta-caryophyllene, trans-Sesquisabinene hydrate, delta-elemene, cis-eudesm-6-en-11-ol, daucene, isodaucene, trans-bergamotene, alpha-zingiberene, sesquisabinene hydrate, and 8-Isopropenyl-1,5-dimethyl-1,5-cyclodecadiene. As a non-limiting example, a terpene synthase may be heterologously expressed in a host cell, the sesquiterpenes produced by the recombinant host cell may be extracted, and the types of sesquiterpenes in the composition may be determined using gas chromatography-mass spectrometry. In some embodiments, a terpene synthase may be recombinantly expressed and is purified. In some embodiments, the sesquiterpenes produced by a purified terpene synthase may be extracted and the types of sesquiterpenes in the composition may be determined using gas chromatography-mass spectrometry.

In certain embodiments, an alpha-guaiene synthase is capable of producing a sesquiterpene composition that comprises at least 1%, at least 2%, at least 3%, at least 4%, at least 5%, at least 6%, at least 7%, at least 8%, at least 9%, at least 10%, at least 15%, at least 20%, at least 30%, at least 40%, at least 50%, at least 60%, at least 70%, at least 80%, at least 90%, at least 95%, or 100% including any values in between of alpha-guaiene. In some embodiments, an alpha-guaiene synthase is capable of producing a sesquiterpene composition that comprises between 1% to 10%, between 5% to 20%, between 15% to 20%, between 16% and 20%, between 17% and 20%, between 18% and 20%, between 19% and 20%, between 20% and 25%, between 20% and 24%, between 20% and 23%, between 20% and 22%, between 20% and 21%, between 20% and 30%, between 30% and 40%, between 40% and 50%, between 50% and 60%, between 60% and 70%, between 70% and 80%, between 80% and 90%, or between 90% and 100%, including any values in between alpha-guaiene.

Rare and Extinct Plants

At least one portion of the sequence of the chimeric terpene synthases disclosed herein is derived from a rare or extinct plant. As used herein, the term "rare plant" or "rare plants" encompasses plants that are uncommon, scarce, infrequently encountered, endangered (e.g., threatened), vulnerable, only available in private collections, not found in the endemic location, only available in cultivation, and/or extinct. In some embodiments, a rare plant is a plant that is infrequently encountered (e.g., only encountered in a few locations such as 1, 2, 3, 4, or 5 locations). In some embodiments, a rare plant is an extinct plant. As used herein, an extinct plant refers to a species of plant: having no living members; classified as having no living members; or predicted by one of ordinary skill in the art to have no living members. As a non-limiting example, the International Union for Conservation of Nature (IUCN) Red list of Threatened Species may be used to determine the conservation status of a plant and identify rare plants. For example, plants classified as extinct, extinct in the wild, critically endangered, endangered, vulnerable, and near threatened on the IUCN Red List may be considered rare plants.

Non-limiting examples of rare plants include *Leucadendron grandiflorum, Shorea cuspidata, Macrostylis villosa, Orbexilum stipulatum, Myrcia skeldingii, Nesiota Elliptica, Macrostylis villosa, Wendlandia angustofola, Erica Pyramidalis, Stenocarpus dumbeenis, Pradosia glaziovii, Crassula subulata, Hibiscadelphus wilderianus,* and *Erica foliacea.*

In some embodiments, the rare plant may be *Hibiscadelphus wilderianus*. The *Hibiscadelphus* genus belongs to the tribe Hibisceae (Malvaceae) and members of the genus often have petals that form a tubular structure in which the lower petals are often shorter than the upper three petals (see, e.g., Oppenheimer et al., A new species of *Hibiscadelphus* Rock (Malvaceae, Hibisceae) from Maui, Hawaiian Islands; *PhytoKeys*, 2014; (39):65-75, which is hereby incorporated by reference in its entirety). The *Hibiscadelphus* genus is endemic to Hawaii and at least eight species have been described. Four of these species are extinct (including *Hibiscadelphus bombycinus*, *Hibiscadelphus crucibracteatus*, *Hibiscadelphus wilderianus*, and *Hibiscadelphus woodii*), two of these species only persist in cultivation (*Hibiscadelphus giffardianus* and *Hibiscadelphus hualalaiensis*), and two are extant in the wild (*Hibiscadelphus distans* and *Hibiscadelphus stellatus*).

Figure 8A:
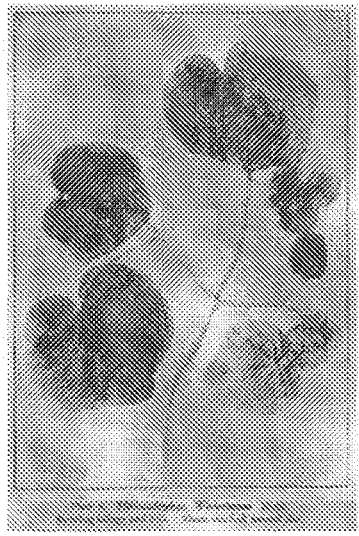
FIGS. 8A-8F include a series of pictures depicting species of rare plants.

*Hibiscadelphus wilderianus* is an extinct tree species last observed at an elevation of 2,600 feet in 1910 on the lava fields of Auwahi on the island of Maui in Hawaii (see, e.g., Radlkofer et al., New and Noteworthy Hawaiian Plants; Hawaiian Board of Agriculture and Forestry Botanical Bulletin, 1911; (1):1-15; "The IUCN Red List of Threatened Species: *Hibiscadelphus wilderianus*," World Conservation Monitoring Centre, 1998, each of which is hereby incorporated by reference in its entirety). A description in Latin of *Hibiscadelphus wilderianus* can be found in the Radlkofer et al. original report. A photo of a tree branch with leaves and fruit was included in the original Radlkofer et al. report and is reproduced in FIG. 8A.

In some embodiments, the rare plant may be *Leucadendron grandiflorum*. *Leucadendron* is a dioecious genus that belongs to the Proteaceae family and is endemic to South Africa. Species in the *Leucadendron* genus include evergreen shrubs and often have cone-shaped infructescences (seed heads). There are at least 80 species in the *Leucadendron* genus including *L. album*, *L. arcuatum*, *L. argenteum*, *L. barkerae*, *L. bonum*, *L. brunioides*, *L. burchellii*, *L. cadens*, *L. chamelaea*, *L. cinereum*, *L. comosum*, *L. concavum*, *L. conicum*, *L. coniferum*, *L. cordatum*, *L. coriaceum*, *L. corymbosum*, *L. cryptocephalum*, *L. daphnoides*, *L. diemontianum*, *L. discolor*, *L. dregei*, *L. dubium*, *L. elimense*, *L. ericifolium*, *L. eucalyptifolium*, *L. flexuosum*, *L. floridum*, *L. foedum*, *L. galpinii*, *L. gandogeri*, *L. glaberrimum*, *L. globosum*, *L. grandiflorum*, *L. gydoense*, *L. immoderatum*, *L. lanigerum*, *L. laureolum*, *L. laxum*, *L. levisanus*, *L. linifolium*, *L. loeriense*, *L. loranthifolium*, *L. macowanii*, *L. meridianum*, *L. meyerianum*, *L. microcephalum*, *L. modestum*, *L. muirii*, *L. nervosum*, *L. nitidum*, *L. nobile*, *L. olens*, *L. orientale*, *L. osbornei*, *L. platyspermum*, *L. pondoense*, *L. procerum*, *L. pubescens*, *L. pubibracteolatum*, *L. radiatum*, *L. remotum*, *L. roodii*, *L. rourkei*, *L. rubrum*, *L. salicifolium*, *L. salignum*, *L. sericeum*, *L. sessile*, *L. sheilae*, *L. singular*, *L. sorocephalodes*, *L. spirale*, *L. spissifolium*, *L. stellare*, *L. stelligerum*, *L. strobilinum*, *L. teretifolium*, *L. thymifolium*, *L. tinctura*, *L. tradouwense*, *L. uliginosum*, *L. verticillatum*, and *L. xanthoconus*.

Figure 8B:

*Leucadendron grandiflorum* is also known commonly as Wynberg Conebush and was last observed in 1806 in Clapham, South Africa. Recorded sightings of *Leucadendron grandiflorum* have occurred on Wynberg Mountain and this species may have existed on the south slopes of Wynberg hill on moister granite soils (see, e.g., T. Rebelo, "Wynberg Conebush—extinct for 200 years," iSpot, 25 Jul. 2015, which is hereby incorporated by reference in its entirety). *Leucadendron grandiflorum* has been described and depicted in Salisbury et al., The Paradisus Londinensis or Coloured Figures of Plants Cultivated in the Vicinity of the Metropolis. 1805; (Volume 1, part 2): 105; see www-dot-biodiversitylibrary.org-backslash-ia/mo-bot31753000575172 #page/248/mode/1up, the contents of each of which is hereby incorporated by reference in its entirety. No modern collections of *Leucadendron grandiflorum* have been recorded, and it is considered that this species was likely scarce or extinct by the early 1800s (see, e.g., T. Rebelo, "Wynberg Conebush—extinct for 200 years," iSpot, 25 Jul. 2015; Catalogue of Life: *Leucadendron grandiflorum* (Salisb.) R. Br., 20 Dec. 2017). Sister species include *L. globosum* and *L. elimense*. FIG. 8B depicts *Leucadendron grandiflorum*.

In some embodiments, the rare plant may be *Macrostylis villosa*. The *Macrostylis* genus belongs to the Rutaceae family and includes at least ten species (e.g., *Macrostylis barbigera*, *Macrostylis cassiopoides*, *Macrostylis cauliflora*, *Macrostylis crassifolia*, *Macrostylis decipiens*, *Macrostylis hirta*, *Macrostylis ramulosa*, *Macrostylis squarrosa*, *Macrostylis tenuis*, and *Macrostylis villosa*).

Figure 8C:

There are two recognized subspecies of *Macrostylis villosa*, *M. villosa* (Thunb.) Sond. subsp. minor and *M. villosa* (Thunb.) Sond. subsp. *villosa*. *M. villosa* (Thunb.) Sond. subsp. minor is classified as extinct as its habitat was converted to agriculture and extensive searches have failed to relocate surviving plants. It was previously found on the Western Cape in South Africa and inhabited gravel and clay soil on slopes (see, e.g., "Red List of South African Plants: *Macrostylis villosa* subsp. minor," 2005, which is hereby incorporated by reference in its entirety). *M. villosa* (Thunb.) Sond. subsp. *villosa* is considered endangered due to population loss from urban expansion, foreign plant invasions and conversion of habitat to agriculture. A picture of *M. villosa* (Thunb.) Sond. subsp. *villosa* is reproduced in FIG. 8C (see, e.g., "Red List of South African Plants: *Macrostylis villosa* subsp. *villosa*," 2007, which is hereby incorporated by reference in its entirety).

In some embodiments, the rare plant may be *Orbexilum stipulatum* (*Psoralea stipulata*). *Orbexilum* belongs to the Fabaceae family and members of this genus often have characteristic pod walls that are rugose and free from hair. *Orbexilum* also may be distinguished by its "scarcely accrescent calyx" (see, e.g., Turner, Revision of the genus *Orbexilum* (Fabaceae: Psoraleeae). Lundellia. 2008; (11):1-7, which is hereby incorporated by reference in its entirety). *Orbexilum* species include *O. chiapasanum*, *O. gracile*, *O. lupinellum*, *O. macrophyllum*, *O. melanocarpum*, *O. oliganthum*, *O. onobrychis*, *O. pedunculatum*, *O. simplex*, *O. stipulatum*, and *O. virgatum*.

*O. stipulatum*, also known as the "Largestipule Leatherroot" or as the "Falls-of-the-Ohio Scurfpea" was only found on Rock Island in Kentucky. The last recorded observation of *O. stipulatum* was in 1881, prior to resurfacing and flooding of this island. Despite many searches of similar habitats, including intensive searches in 1998, on both the Kentucky and Indiana shores of the Ohio River, this species has not been relocated. Therefore, this species has been classified as extinct (see, e.g., NatureServe Explorer: *Orbexilum stipulatum*—(Torr. & Gray) Rydb., 2016 and Baskin et al. described above, which is each hereby incorporated by reference in its entirety).

Figure 8D:

*O. stipulatum* was a perennial herb and had leaves that were divided into 3 leaflets, each about 2 cm in length. The species had a persistent appendage at the base of the leaves and was also described as having a corolla tube that did not extend beyond the calyx. It is likely that this plant bloomed in late May to mid-June, but seeds have not been observed in nature (see e.g., "NatureServe Explorer: *Orbexilum stipulatum*—(Torr. & Gray) Rydb.," 2016; and Baskin et al., Geographical origin of the specimens of *Orbexilum stipulatum* (T. & G.) Rydb. (*Psoralea stipulata* T. & G.). Castanea. 1986; (51): 207-210, each of which is hereby incorporated by reference in its entirety). A picture of *O. stipulatum* may be found in Short, "*Orbexilum stipulatum* collected at Falls of the Ohio," 1840 from The Philadelphia Herbarium at the Academy of Natural Sciences is reproduced in FIG. 8D.

In some embodiments, the rare plant may be *Shorea cuspidata*. *Shorea* is a genus in the Dipterocarpaceae family and includes many rainforest trees endemic to southeast Asia. Many *Shorea* species are angiosperms (flowering plants). Non-limiting examples of *Shorea* species may include *Shorea affinis*, *Shorea congestiflora*, *Shorea cordifolia*, *Shorea disticha*, *Shorea megistophylla*, *Shorea trapezifolia*, *Shorea zeylanica*, *Shorea acuminatissima*, *Shorea alutacea*, *Shorea angustifolia*, *Shorea bakoensis*, *Shorea balanocarpoides*, *Shorea chaiana*, *Shorea collaris*, *Shorea cuspidata*, *Shorea faguetiana*, *Shorea faguetioides*, *Shorea gibbosa*, *Shorea hopeifolia*, *Shorea iliasii*, *Shorea induplicata*, *Shorea kudatensis*, *Shorea laxa*, *Shorea longiflora*, *Shorea longisperma*, *Shorea macrobalanos*, *Shorea mujongensis*, *Shorea multiflora*, *Shorea obovoidea*, *Shorea patoiensis*, *Shorea peltata*, *Shorea polyandra*, *Shorea richetia*, *Shorea subcylindrica*, *Shorea tenuiramulosa*, and *Shorea xanthophylla*.

Figure 8E:
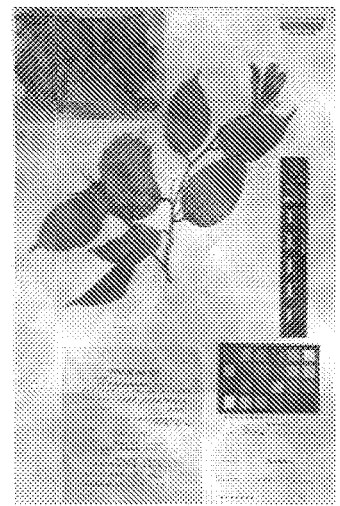

*S. cuspidata* is a tree endemic to Malaysia that is currently classified as extinct on the IUCN Red List ("The IUCN Red List: *Shorea cuspidata*," 1998, which is incorporated in its entirety by reference), although there have been a few recorded sightings of *S. cuspidata* subsequent to this classification in Bako National Park, Lambir National Park, and the Semenggoh Arboretum (Ashton, *Shorea cuspidata*. Tree Flora of Sabah and Sarawek. 2004; (5):246-247; Ling et al., Diversity of the tree flora in Semenggoh Arboretum, Sarawak, Borneo. Gardens' Bulletin Singapore. 2012; (64):139-169, which is each incorporated by reference in its entirety). *Shorea cuspidata* may be considered a rare plant. *Shorea cuspidata* has been characterized as a medium-sized tree with flowers second and pale lime-yellow petals (see, e.g., Ashton, Man. Dipt. Brun. 1968: f. 10, pl. 14 (stem-base)). A picture of a *Shorea cuspidata* specimen is reproduced in FIG. 8E ("Kew Royal Botanical Gardens: *Shorea cuspidata* specimen K000700460," 1962, which is hereby incorporated by reference in its entirety).

In some embodiments, the rare plant may be *Wendlandia angustifolia*. *Wendlandia* is a genus of flowering plants that belongs to the Rubiaceae family. Non-limiting examples of *Wendlandia* species may include *Wendlandia aberrans*, *Wendlandia acuminata*, *Wendlandia amocana*, *Wendlandia andamanica*, *Wendlandia angustifolia*, *Wendlandia appendiculata*, *Wendlandia arabica*, *Wendlandia arborescens*, *Wendlandia augustini*, *Wendlandia basistaminea*, *Wendlandia bicuspidata*, *Wendlandia bouvardioides*, *Wendlandia brachyantha*, *Wendlandia brevipaniculata*, *Wendlandia brevituba*, and *Wendlandia buddleacea*.

Figure 8F:
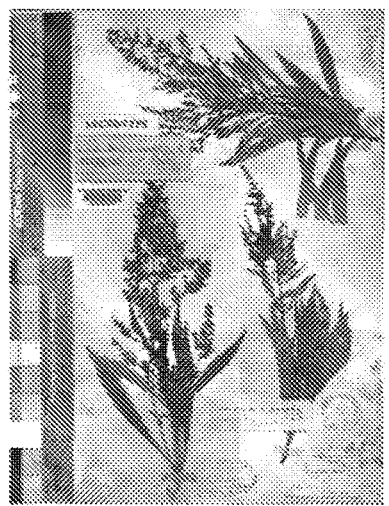

*W. angustifolia* is a plant native to India that is currently classified as extinct in the IUCN Red List (see "The IUCN Red List: *Wendlandia angustifolia*," 1998, which is hereby incorporated by reference in its entirety). Subsequent to this classification, *W. angustifolia* was reportedly observed in Kalakkad Mundantharai Tiger Reserve in India (Viswanathan et al., Rediscovery of *Wendlandia Angustifolia* Wight Ex Hook.f. (Rubiaceae), from Tamil Nadu, a Species Presumed Extinct. Journal of The Bombay Natural History Society. 2000 97(2):311-313, which is hereby incorporated by reference in its entirety). *W. angustifolia* may be considered a rare plant. *W. angustifolia* has been described as a shrub or tree with ternately whorled and linear-lanceolate leaves (see, e.g., Viswanathan et al., Rediscovery of *Wendlandia Angustifolia* Wight Ex Hook.f. (Rubiaceae), from Tamil Nadu, a Species Presumed Extinct, Journal of The Bombay Natural History Society. 2000; 97(2):311-313, which is hereby incorporated by reference in its entirety). A picture of a specimen is reproduced in FIG. 8F ("Kew Royal Botanical Gardens: *Wendlandia angustifolia* K000030921," collection date not recorded), which is hereby incorporated by reference in its entirety.

Methods of Producing Chimeric Terpene Synthases and Terpenes

Also described herein are nucleic acid molecules encoding chimeric terpene synthases. In some embodiments, at least 10% (e.g., at least 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more than 99%, including all values in between) of the nucleic acid molecule encoding such a chimeric terpene synthase may be derived from a rare or extinct plant.

In some instances, a nucleic acid molecule encoding a chimeric terpene synthase comprises a nucleotide sequence that is at least 50% (e.g., at least 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more than 99%, including all values in between) identical to a sequence selected from the group consisting of SEQ ID NOs: 67-118. In some instances, a nucleic acid molecule encoding a chimeric terpene synthase comprises a nucleotide sequence that is identical to a sequence selected from the group consisting of SEQ ID NOs: 67-118. In some instances, a nucleic acid molecule encoding a chimeric terpene synthase further comprises the nucleotide sequence TATA (TATA box sequence). In some instances, a nucleic acid molecule encoding a chimeric terpene synthase comprises the nucleotide sequence TATA (TATA box sequence) that is located N-terminal to a sequence selected from the group consisting of SEQ ID NOs: 67-118. In some instances, a nucleic acid molecule encoding a chimeric terpene synthase comprises a nucleotide sequence that encodes for a sequence set forth in SEQ ID NOs:119-357.

In some embodiments, at least 10% (e.g., at least 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more than 99%, including all values in between) of the amino acid sequence of the chimeric terpene synthase (e.g., a chimeric sesquiterpene synthase) may be derived from a rare or extinct plant. In some instances, a chimeric terpene synthase comprises one or more sequences set forth in SEQ ID NOs:119-357.

Also described herein are chimeric terpene synthases that are capable of producing alpha-guaiene. In some embodiments, at least 10% (e.g., at least 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more than 99%, including all values in between) of the nucleic acid molecule encoding such a chimeric terpene synthase may be derived from a rare or extinct plant.

In some embodiments, at least 10% (e.g., at least 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more than 99%, including all values in between) of the amino acid sequence of the chimeric terpene synthase that is capable of producing alpha-guaiene may be derived from a rare or extinct plant.

In some instances, construction of the chimeras may include sequence (e.g., nucleic acid sequence and/or amino acid sequence) alignments between at least two terpene synthases of interest. For example, sequence alignment analysis may be used to identify fragments (e.g., domains) of a particular terpene synthase to include in a chimeric terpene synthase. In some embodiments, the chimeric terpene synthase is a chimeric sesquiterpene synthase. Non-limiting examples of analyses may include the types described in the blastn-mapdamage and tblastn pipelines described in Example 2.

In some embodiments, a chimeric terpene synthase coding sequence comprises a mutation at 1, 2, 3, 4, 5, or more positions corresponding to a reference chimeric terpene synthase coding sequence. In some embodiments, the chimeric terpene synthase coding sequence comprises a mutation in 1, 2, 3, 4, 5, or more codons of the coding sequence relative to a reference chimeric terpene synthase coding sequence. As will be understood by one of ordinary skill in the art, a mutation within a codon may or may not change the amino acid that is encoded by the codon due to degeneracy of the genetic code. In some embodiments, the one or more mutations in the coding sequence do not alter the amino acid sequence of the chimeric terpene synthase relative to the amino acid sequence of a reference chimeric terpene synthase.

In some embodiments, the one or more mutations in a chimeric terpene synthase sequence alter the amino acid sequence of the chimeric terpene synthase relative to the amino acid sequence of a reference chimeric terpene synthase. In some embodiments, the one or more mutations alter the amino acid sequence of the chimeric terpene synthase relative to the amino acid sequence of a reference chimeric terpene synthase and alter (enhance or reduce) an activity of the chimeric terpene synthase relative to the reference chimeric terpene synthase.

The skilled artisan will also realize that mutations in a chimeric terpene synthase coding sequence may result in conservative amino acid substitutions to provide functionally equivalent variants of the foregoing polypeptides, e.g., variants that retain the activities of the polypeptides. As used herein, a "conservative amino acid substitution" refers to an amino acid substitution that does not alter the relative charge or size characteristics or functional activity of the protein in which the amino acid substitution is made.

In some instances, an amino acid is characterized by its R group (see, e.g., Table 1). For example, an amino acid may comprise a nonpolar aliphatic R group, a positively charged R group, a negatively charged R group, a nonpolar aromatic R group, or a polar uncharged R group. Non-limiting examples of an amino acid comprising a nonpolar aliphatic R group include alanine, glycine, valine, leucine, methionine, and isoleucine. Non-limiting examples of an amino acid comprising a positively charged R group includes lysine, arginine, and histidine. Non-limiting examples of an amino acid comprising a negatively charged R group include aspartic acid and glutamic acid. Non-limiting examples of an amino acid comprising a nonpolar, aromatic R group include phenylalanine, tyrosine, and tryptophan. Non-limiting examples of an amino acid comprising a polar uncharged R group include serine, threonine, cysteine, proline, asparagine, and glutamine.

Variants can be prepared according to methods for altering polypeptide sequence known to one of ordinary skill in the art such as are found in references which compile such methods, e.g., Molecular Cloning: A Laboratory Manual, J. Sambrook, et al., eds., Fourth Edition, Cold Spring Harbor Laboratory Press, Cold Spring Harbor, New York, 2012, or Current Protocols in Molecular Biology, F. M. Ausubel, et al., eds., John Wiley & Sons, Inc., New York, 2010.

Non-limiting examples of functionally equivalent variants of polypeptides may include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. In some embodiments, 1, 2, 3, 4, 5, 6, 7, 8, 9, 10, 11, 12, 13, 14, 15, 16, 17, 18, 19, 20 or more than 20 residues can be changed when preparing variant polypeptides. In some embodiments, amino acids are replaced by conservative amino acid substitutions.

TABLE 1

Non-limiting Examples of Conservative Amino Acid Substitutions

| Original Residue | R Group Type | Conservative Amino Acid Substitutions |
|---|---|---|
| Ala | nonpolar aliphatic R group | Cys, Gly, Ser |
| Arg | positively charged R group | His, Lys |
| Asn | polar uncharged R group | Asp, Gln, Glu |
| Asp | negatively charged R group | Asn, Gln, Glu |
| Cys | polar uncharged R group | Ala, Ser |
| Gln | polar uncharged R group | Asn, Asp, Glu |
| Glu | negatively charged R group | Asn, Asp, Gln |
| Gly | nonpolar aliphatic R group | Ala, Ser |
| His | positively charged R group | Arg, Tyr, Trp |
| Ile | nonpolar aliphatic R group | Leu, Met, Val |
| Leu | nonpolar aliphatic R group | Be, Met, Val |
| Lys | positively charged R group | Arg, His |
| Met | nonpolar aliphatic R group | Ile, Leu, Phe, Val |
| Pro | polar uncharged R group | |
| Phe | nonpolar aromatic R group | Met, Trp, Tyr |
| Ser | polar uncharged R group | Ala, Gly, Thr |

TABLE 1-continued

Non-limiting Examples of Conservative
Amino Acid Substitutions

| Original Residue | R Group Type | Conservative Amino Acid Substitutions |
|---|---|---|
| Thr | polar uncharged R group | Ala, Asn, Ser |
| Trp | nonpolar aromatic R group | His, Phe, Tyr, Met |
| Tyr | nonpolar aromatic R group | His, Phe, Trp |
| Val | nonpolar aliphatic R group | Ile, Leu, Met, Thr |

Amino acid substitutions in the amino acid sequence of a polypeptide to produce a chimeric terpene synthase (e.g., chimeric sesquiterpene synthase) variant having a desired property and/or activity can be made by alteration of the coding sequence of the chimeric terpene synthase (e.g., chimeric sesquiterpene synthase). Similarly, conservative amino acid substitutions in the amino acid sequence of a polypeptide to produce functionally equivalent variants of the polypeptide typically are made by alteration of the coding sequence of the chimeric terpene synthase (e.g., chimeric sesquiterpene synthase).

Mutations (e.g., substitutions) can be made in a nucleotide sequence by a variety of methods known to one of ordinary skill in the art. For example, mutations can be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

Any suitable method, including circular permutation (Yu and Lutz, *Trends Biotechnol.* 2011 January; 29(1):18-25), may be used to produce variants. In circular permutation, the linear primary sequence of a polypeptide can be circularized (e.g., by joining the N-terminal and C-terminal ends of the sequence) and the polypeptide can be severed ("broken") at a different location. Thus, the linear primary sequence of the new polypeptide may have low sequence identity (e.g., less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less or less than 5%, including all values in between) as determined by linear sequence alignment methods (e.g., Clustal Omega or BLAST). Topological analysis of the two proteins, however, may reveal that the tertiary structure of the two polypeptides is similar or dissimilar. Without being bound by a particular theory, a variant polypeptide created through circular permutation of a reference polypeptide and with a similar tertiary structure as the reference polypeptide can share similar functional characteristics (e.g., enzymatic activity, enzyme kinetics, substrate specificity or product specificity). In some instances, circular permutation may alter the secondary structure, tertiary structure or quaternary structure and produce an enzyme with different functional characteristics (e.g., increased or decreased enzymatic activity, different substrate specificity, or different product specificity). See, e.g., Yu and Lutz, *Trends Biotechnol.* 2011 January; 29(1):18-25.

It should be appreciated that in a protein that has undergone circular permutation, the linear amino acid sequence of the protein would differ from a reference protein that has not undergone circular permutation. However, one of ordinary skill in the art would be able to readily determine which residues in the protein that has undergone circular permutation correspond to residues in the reference protein that has not undergone circular permutation by, for example, aligning the sequences and detecting conserved motifs, and/or by comparing the structures or predicted structures of the proteins, e.g., by homology modeling.

Aspects of the present disclosure relate to the recombinant expression of genes encoding enzymes, functional modifications and variants thereof, as well as uses relating thereto.

A nucleic acid encoding any of the chimeric terpene synthases described herein may be incorporated into any appropriate vector through any method known in the art. For example, the vector may be an expression vector, including but not limited to a viral vector (e.g., a lentiviral, retroviral, adenoviral, or adeno-associated viral vector), any vector suitable for transient expression, or any vector for inducible expression (e.g., a galactose-inducible or doxycycline-inducible vector). A non-limiting example of a vector for expression of a chimeric terpene synthase (e.g., a chimeric sesquiterpene synthase) is described in Example 2 below.

In some embodiments, a vector replicates autonomously in the cell. A vector can contain one or more endonuclease restriction sites that are cut by a restriction endonuclease to insert and ligate a nucleic acid containing a gene described herein to produce a recombinant vector that is able to replicate in a cell. Vectors are typically composed of DNA, although RNA vectors are also available. Cloning vectors include, but are not limited to: plasmids, fosmids, phagemids, virus genomes and artificial chromosomes. As used herein, the terms "expression vector" or "expression construct" refer to a nucleic acid construct, generated recombinantly or synthetically, with a series of specified nucleic acid elements that permit transcription of a particular nucleic acid in a host cell (e.g., microbe), such as a yeast cell. In some embodiments, the nucleic acid sequence of a gene described herein is inserted into a cloning vector such that it is operably joined to regulatory sequences and, in some embodiments, expressed as an RNA transcript. In some embodiments, the vector contains one or more markers, such as a selectable marker as described herein, to identify cells transformed or transfected with the recombinant vector.

In some embodiments, a vector is capable of integrating into the genome of a host cell.

A coding sequence and a regulatory sequence are said to be "operably joined" or "operably linked" when the coding sequence and the regulatory sequence are covalently linked and the expression or transcription of the coding sequence is under the influence or control of the regulatory sequence. If the coding sequence is to be translated into a functional protein, the coding sequence and the regulatory sequence are said to be operably joined or linked if induction of a promoter in the 5' regulatory sequence transcribes the coding sequence and if the nature of the linkage between the coding sequence and the regulatory sequence does not (1) result in the introduction of a frame-shift mutation, (2) interfere with the ability of the promoter region to direct the transcription of the coding sequence, or (3) interfere with the ability of the corresponding RNA transcript to be translated into a protein. Thus, a promoter region is operably joined or linked to a coding sequence if the promoter region transcribes the coding sequence and the transcript can be translated into the protein or polypeptide of interest.

In some embodiments, the nucleic acid encoding any of the proteins described herein is under the control of regulatory sequences (e.g., enhancer sequences). In some embodiments, a nucleic acid is expressed under the control of a promoter. The promoter can be a native promoter, e.g., the promoter of the gene in its endogenous context, which provides normal regulation of expression of the gene. Alternatively, a promoter can be a promoter that is different from the native promoter of the gene, e.g., the promoter is different from the promoter of the gene in its endogenous context. As used herein, a "heterologous promoter" or "recombinant promoter" is a promoter that is not naturally or normally associated with or that does not naturally or normally control transcription of a DNA sequence to which it is operably joined or linked. In some embodiments, a nucleotide sequence is under the control of a heterologous promoter.

In some embodiments, the promoter is a eukaryotic promoter. Non-limiting examples of eukaryotic promoters include TDH3, PGK1, PKC1, TDH2, PYK1, TPI1, AT1, CMV, EF1a, SV40, PGK1 (human or mouse), Ubc, human beta actin, CAG, TRE, UAS, Ac5, Polyhedrin, CaMKIIa, GAL1, GAL10, TEF1, GDS, ADH1, CaMV35S, Ubi, H1, U6, as would be known to one of ordinary skill in the art (see, e.g., Addgene website: blog.addgene.org/plasmids-101-the-promoter-region). In some embodiments, the promoter is a prokaryotic promoter (e.g., bacteriophage or bacterial promoter). Non-limiting examples of bacteriophage promoters include Pls1con, T3, T7, SP6, and PL. Non-limiting examples of bacterial promoters include Pbad, PmgrB, Ptrc2, Plac/ara, Ptac, Pm.

In some embodiments, the promoter is an inducible promoter. As used herein, an "inducible promoter" is a promoter controlled by the presence or absence of a molecule. Non-limiting examples of inducible promoters include chemically-regulated promoters and physically-regulated promoters. For chemically-regulated promoters, the transcriptional activity can be regulated by one or more compounds, such as alcohol, tetracycline, galactose, a steroid, a metal, or other compounds. For physically-regulated promoters, transcriptional activity can be regulated by a phenomenon such as light or temperature. Non-limiting examples of tetracycline-regulated promoters include anhydrotetracycline (aTc)-responsive promoters and other tetracycline-responsive promoter systems (e.g., a tetracycline repressor protein (tetR), a tetracycline operator sequence (tetO) and a tetracycline transactivator fusion protein (tTA)). Non-limiting examples of steroid-regulated promoters include promoters based on the rat glucocorticoid receptor, human estrogen receptor, moth ecdysone receptors, and promoters from the steroid/retinoid/thyroid receptor superfamily. Non-limiting examples of metal-regulated promoters include promoters derived from metallothionein (proteins that bind and sequester metal ions) genes. Non-limiting examples of pathogenesis-regulated promoters include promoters induced by salicylic acid, ethylene or benzothiadiazole (BTH). Non-limiting examples of temperature/heat-inducible promoters include heat shock promoters. Non-limiting examples of light-regulated promoters include light responsive promoters from plant cells. In certain embodiments, the inducible promoter is a galactose-inducible promoter. In some embodiments, the inducible promoter is induced by one or more physiological conditions (e.g., pH, temperature, radiation, osmotic pressure, saline gradients, cell surface binding, or concentration of one or more extrinsic or intrinsic inducing agents). Non-limiting examples of an extrinsic inducer or inducing agent include amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or any combination thereof.

In some embodiments, the promoter is a constitutive promoter. As used herein, a "constitutive promoter" refers to an unregulated promoter that allows continuous transcription of a gene. Non-limiting examples of a constitutive promoter includes CP1, CMV, EF1a, SV40, PGK1, Ubc, human beta actin, CAG, Ac5, polyhedrin, TEF1, GDS, CaM35S, Ubi, H1, and U6.

Other inducible promoters or constitutive promoters known to one of ordinary skill in the art are also contemplated herein.

The precise nature of the regulatory sequences needed for gene expression may vary between species or cell types, but generally include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined or linked gene. Regulatory sequences may also include enhancer sequences or upstream activator sequences. The vectors disclosed herein may include 5' leader or signal sequences. The regulatory sequence may also include a terminator sequence. In some embodiments, a terminator sequence marks the end of a gene in DNA during transcription. The choice and design of one or more appropriate vectors suitable for inducing expression of one or more genes described herein in a heterologous organism is within the ability and discretion of one of ordinary skill in the art.

Expression vectors containing the necessary elements for expression are commercially available and known to one of ordinary skill in the art (see, e.g., Sambrook et al., Molecular Cloning: A Laboratory Manual, Fourth Edition, Cold Spring Harbor Laboratory Press, 2012).

Any suitable host cell may be used to produce any of the chimeric terpene synthases disclosed herein, including eukaryotic cells or prokaryotic cells. Suitable host cells include fungal cells (e.g., yeast cells) and bacteria cells (e.g., *E. coli* cells). Non-limiting examples of genera of yeast for expression include *Saccharomyces* (e.g., *S. cerevisiae*), *Pichia*, *Kluyveromyces* (e.g., *K. lactis*), *Hansenula* and *Yarrowia*. In some embodiments, the yeast strain is an industrial polyploid yeast strain. Other non-limiting examples of fungal cells include cells obtained from *Aspergillus* spp., *Penicillium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp.

The term "cell," as used herein, may refer to a single cell or a population of cells, such as a population of cells belonging to the same cell line or strain. Use of the singular term "cell" should not be construed to refer explicitly to a single cell rather than a population of cells.

A vector encoding any of the chimeric terpene synthases (e.g., chimeric sesquiterpene synthases) described herein may be introduced into a suitable host cell using any method known in the art. Non-limiting examples of yeast transformation protocols are described in Example 2 below and in Gietz et al., Yeast transformation by the LiAc/SS Carrier DNA/PEG method. *Methods Mol Biol.* 2006; 313:107-20, which is hereby incorporated by reference in its entirety for this purpose. Host cells may be cultured under any conditions suitable as would be understood by one of ordinary skill in the art. For example, any media, temperature, and incubation conditions known in the art may be used. For host cells carrying an inducible vector, cells may be cultured with an appropriate inducible agent to promote expression.

Any of the cells disclosed herein can be cultured in media of any type (rich or minimal) and any composition prior to, during, and/or after contact and/or integration of a nucleic acid. The conditions of the culture or culturing process can be optimized through routine experimentation as understood by one of ordinary skill in the art. In some embodiments, the selected media is supplemented with various components. In some embodiments, the concentration and amount of a supplemental component is optimized. In some embodiments, other aspects of the media and growth conditions (e.g., pH, temperature, etc.) are optimized through routine experimentation. In some embodiments, the frequency that the media is supplemented with one or more supplemental components, and the amount of time that the cell is cultured is optimized.

Culturing of the cells described herein can be performed in culture vessels known and used in the art. In some embodiments, an aerated reaction vessel (e.g., a stirred tank reactor) is used to culture the cells. In some embodiments, a bioreactor or fermentor is used to culture the cell. Thus, in some embodiments, the cells are used in fermentation. As used herein, the terms "bioreactor" and "fermentor" are interchangeably used and refer to an enclosure, or partial enclosure, in which a biological, biochemical and/or chemical reaction takes place, involving a living organism or part of a living organism. A "large-scale bioreactor" or "industrial-scale bioreactor" is a bioreactor that is used to generate a product on a commercial or quasi-commercial scale. Large scale bioreactors typically have volumes in the range of liters, hundreds of liters, thousands of liters, or more.

In some embodiments, a bioreactor comprises a cell (e.g., a yeast cell) or a cell culture (e.g., a yeast cell culture), such as a cell or cell culture described herein. In some embodiments, a bioreactor comprises a spore and/or a dormant cell type of an isolated microbe (e.g., a dormant cell in a dry state).

Non-limiting examples of bioreactors include: stirred tank fermentors, bioreactors agitated by rotating mixing devices, chemostats, bioreactors agitated by shaking devices, airlift fermentors, packed-bed reactors, fixed-bed reactors, fluidized bed bioreactors, bioreactors employing wave induced agitation, centrifugal bioreactors, roller bottles, and hollow fiber bioreactors, roller apparatuses (for example benchtop, cart-mounted, and/or automated varieties), vertically-stacked plates, spinner flasks, stirring or rocking flasks, shaken multi-well plates, MD bottles, T-flasks, Roux bottles, multiple-surface tissue culture propagators, modified fermentors, and coated beads (e.g., beads coated with serum proteins, nitrocellulose, or carboxymethyl cellulose to prevent cell attachment).

In some embodiments, the bioreactor includes a cell culture system where the cell (e.g., yeast cell) is in contact with moving liquids and/or gas bubbles. In some embodiments, the cell or cell culture is grown in suspension. In other embodiments, the cell or cell culture is attached to a solid phase carrier. Non-limiting examples of a carrier system includes microcarriers (e.g., polymer spheres, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multicartridge reactors, and semi-permeable membranes that can comprising porous fibers), microcarriers having reduced ion exchange capacity, encapsulation cells, capillaries, and aggregates. In some embodiments, carriers are fabricated from materials such as dextran, gelatin, glass, or cellulose.

In some embodiments, industrial-scale processes are operated in continuous, semi-continuous or non-continuous modes. Non-limiting examples of operation modes are batch, fed batch, extended batch, repetitive batch, draw/fill, rotating-wall, spinning flask, and/or perfusion mode of operation. In some embodiments, a bioreactor allows continuous or semi-continuous replenishment of the substrate stock, for example a carbohydrate source and/or continuous or semi-continuous separation of the product, from the bioreactor.

In some embodiments, the bioreactor or fermentor includes a sensor and/or a control system to measure and/or adjust reaction parameters. Non-limiting examples of reaction parameters include biological parameters (e.g., growth rate, cell size, cell number, cell density, cell type, or cell state, etc.), chemical parameters (e.g., pH, redox-potential, concentration of reaction substrate and/or product, concentration of dissolved gases, such as oxygen concentration and $CO_2$ concentration, nutrient concentrations, metabolite concentrations, concentration of an oligopeptide, concentration of an amino acid, concentration of a vitamin, concentration of a hormone, concentration of an additive, serum concentration, ionic strength, concentration of an ion, relative humidity, molarity, osmolarity, concentration of other chemicals, for example buffering agents, adjuvants, or reaction by-products), physical/mechanical parameters (e.g., density, conductivity, degree of agitation, pressure, and flow rate, shear stress, shear rate, viscosity, color, turbidity, light absorption, mixing rate, conversion rate, as well as thermodynamic parameters, such as temperature, light intensity/quality, etc.). Sensors to measure the parameters described herein are well known to one of ordinary skill in the relevant mechanical and electronic arts. Control systems to adjust the parameters in a bioreactor based on the inputs from a sensor described herein are well known to one of ordinary skill in the art in bioreactor engineering.

Terpenes produced by any of the host cells disclosed herein may be extracted using any method known in the art. A non-limiting example of a method for sesquiterpene extraction is provided in Example 2. Any of the terpenes produced from the methods, compositions, or host cells described herein may be used in a suitable composition for topical application to, for example, skin, hair, clothing, or articles in a home (e.g., a perfume). As used herein, the term "perfume" is any fragrance formulation suitable for application to the hair, skin, or clothing of a person or an article in a home. This term includes, but is not limited to: an eau de cologne, eau de toilette, eau de parfum, perfume extract or extrait. In addition to comprising one or more terpenes of the application, such a perfume may include, for example, one or more natural oils, fixatives, emollients, or solvents.

Examples of natural oils which may be used in perfume formulations include, but are not limited to: amyris oil; *Angelica* seed oil; *Angelica* root oil; aniseed oil; valerian oil; basil oil; bay oil; mugwort oil; benzoin resin; bergamot oil; birch tar oil; bitter almond oil; savory oil; bucco-leaf oil; *Cabreuva* oil; cade oil; *Calamus* oil; camphor oil; *Cananga* oil; cardamom oil; *Cascarilla* oil; *Cassia* oil; *Castoreum* absolute; cedar-leaf oil; cedarwood oil; cistus oil; citronella oil; lemon oil; copaiba balsam oil; coriander oil; *Costus* root oil; cumin oil; cypress oil; *Davana* oil; dill oil; dillseed oil; elemi oil; tarragon oil; *eucalyptus citriodora* oil; *eucalyptus* oil; fennel oil; fir oil; *galbanum* oil; *Geranium* oil; grapefruit oil; guaiac wood oil; gurjun balsam oil; *Helichrysum* oil; ginger oil; iris root oil; *Calamus* oil; blue chamomile oil; Roman chamomile oil; carrot-seed oil; *Cascarilla* oil; pine-needle oil; spearmint oil; caraway oil; labdanum oil; lavandin oil; lavender oil; lemongrass oil; lovage oil; lime oil (e.g., distilled or pressed lime oil); linaloe oil: *Litsea cubeba* oil; bay leaf oil; mace oil; marjoram oil; mandarin oil;

massoi bark oil; ambrette oil; clary sage oil; *Myristica* oil; myrrh oil; myrtle oil; clove leaf oil; clove flower oil; neroli oil; olibanum oil; *Opopanax* oil; orange oil; *Origanum* oil; palmar osa oil; patchouli oil; *Perilla* oil; Peru balsam oil; parsley leaf oil; parsley seed oil; petitgrain oil; peppermint oil; pepper oil; pimento oil; pine oil; pennyroyal oil; rosewood oil; rose oil; rosemary oil; Dalmatian sage oil; Spanish sage oil; sandalwood oil; celery seed oil; spike lavender oil; Japanese aniseed oil; *Styrax* oil; *Tagetes* oil; fir-needle oil; tea-tree oil; turpentine oil; thyme oil; tuberose absolute; vanilla extract; violet leaf absolute; *Verbena* oil; vetiver oil; juniper oil; wine-lees oil; wormwood oil; wintergreen oil; ylang oil; hyssop oil; civet absolute; cinnamon leaf oil; cinnamon bark oil; as well as fractions thereof or constituents isolated therefrom; and combinations thereof.

Other examples of compounds which may be used in perfume formulations may include: wood moss absolute; beeswax absolute; *Cassia* absolute; eau de brouts absolute; oakmoss absolute; *Galbanum* resin; *Helichrysum* absolute; iris root absolute; jasmine absolute; labdanum absolute; labdanum resin; lavandin absolute; lavender absolute; *Mimosa* absolute; tincture of musk; myrrh absolute; olibanum absolute; orange blossom absolute; rose absolute; Tolu balsam; Tonka absolute; as well as fractions thereof or constituents isolated therefrom; and combinations thereof.

As used herein, the term "emollient" means a fatty or oleaginous substance which increases tissue moisture content (and may, for example, render skin softer and more pliable). Emollients for use with the instant compounds and methods may include any appropriate animal fats/oils, vegetable oils, and/or waxes. As a non-limiting set of examples, an emollient for use with the instant compositions and methods may be of natural or synthetic origin and may include: cold-pressed almond oil, jojoba oil, sunflower oil, olive oil, hazelnut oil, avocado oil, safflower oil, grapeseed oil, coconut oil, wheat germ oil, apricot kernel oil, natural waxes and "butters" (e.g., unrefined beeswax, shea butter, jojoba butter, and/or cocoa butter), Schercemol™ LL Ester, Schercemol™ 1818 Ester, butylene glycol, capric/caprylic triglyceride, ceteareth-20, one or more fatty alcohols (e.g., cetearyl alcohol, cetyl alcohol, and/or coconut fatty acids), one or more silicones (e.g., cyclomethicone, dimethicone, and/or cyclopentasiloxane), emulsifying wax, petroleum jelly, fatty acids, glyceryl stearate, hydrogenated oils, isopropyl myristate, mineral oil, octyl palmitate, paraffin, squalene, stearic acid, palmitoyl proline, or magnesium palmitoyl glutamate.

As used herein, the term "fixative" means a compound used to equalize the vapor pressures (and thus the volatilities) of one or more compounds in the perfume. As a non-limiting set of examples, a fixative for use with the compounds and perfumes described herein may be: dipropylene glycol, diethyl phthalate, Hedione®, Abalyn™ D-E Methyl Ester of Rosin, Jojoba (such as Floraesters K-100 Jojoba or Floraesters K-20W Jojoba), Sepicide LD, and/or Foralyn™ 5020-F CG Hydrogenated Rosinate.

As used herein, the term "solvent" is the diluent used to create a perfume. As a non-limiting example, the solvent may be an alcohol (e.g., an ethyl alcohol), 1,2-hexanediol, 1,2-heptanediol, a neutral smelling oil (e.g., fractionated coconut oil or jojoba oil), or one or more volatile silicones. As a non-limiting example, Perfumers' Alcohol (a type of ethyl alcohol) may be used. Perfumers' Alcohol is prepared from 200 proof ethyl alcohol which may contain very small amounts of butyl alcohol, denatonium benzoate (Britex), and/or hexylene glycol. Various grades of Perfumers' Alcohol are available including SDA 40B 200 Proof and SDA-B 200 proof.

Additional compounds or fragrance materials for use in the perfume composition according to the disclosure may include any compounds which are customarily used in the field.

The present invention is further illustrated by the following Examples, which in no way should be construed as limiting. The entire contents of all of the references (including literature references, issued patents, published patent applications, and co-pending patent applications) cited throughout this application are hereby expressly incorporated by reference.

EXAMPLES

Example 1. Functional Characterization of Chimeric Terpene Synthases

Genomic DNA from 12 extinct plant samples were sequenced (Table 2). Sesquiterpene synthase (SQTS) fragments were recovered from seven plants (Table 11), but gaps in the sequencing prevented reconstruction of full-length genes. A library comprising 2,738 terpene synthase chimeras (containing sequence from sesquiterpene synthases from extant plants to fill the sequence gaps) was screened. The expression of 52 SQTS chimeras (sequences provided in Table 10) from six rare plants (Table 2) led to the production of sesquiterpenes in the screening strain. Methods and materials for each of the procedures described in this Example may be found in Example 2.

TABLE 2

Rare Plants that were Sequenced (The plants from which functional sesquiterpene chimeras were reconstructed are shown bold face and underlined.)

| Family | Genus | Species | Continent | Location | Year Extinct |
|---|---|---|---|---|---|
| Crassulaceae | *Crassula* | *subulata* | AFRICA | South Africa | 1900 |
| Ericaceae | *Erica* | *pyramidalis* | AFRICA | South Africa | 1910 |
| Malvaceae | *Hibiscadelphus* | *wilderianus* | OCEANIA | Hawaii | 1910 |
| Proteaceae | *Leucadendron* | *grandiflorum* | AFRICA | South Africa | 1806 |
| Rutaceae | *Macrostylis* | *villosa* | AFRICA | South Africa | 1980 |
| Myrtaceae | *Myrcia* | *skeldingii* | AMERICA | Jamaica | 1972 |
| Rhamnaceae | *Nesiota* | *elliptica* | AFRICA | St. Helena | 2003 |

TABLE 2-continued

Rare Plants that were Sequenced (The plants from which functional sesquiterpene chimeras were reconstructed are shown bold face and underlined.)

| Family | Genus | Species | Continent | Location | Year Extinct |
|---|---|---|---|---|---|
| Fabaceae | *Orbexilum* | *stipulatum* | AMERICA | Kentucky | 1881 |
| Sapotaceae | *Pradosia* | *glaziovii* | AMERICA | Brazil | 1997 |
| Dipterocarpaceae | *Shorea* | *cuspidata* | ASIA | Malaysia | 1996 |
| Proteaceae | *Stenocarpus* | *dumbeensis* | OCEANIA | New Caledonia | 1905 |
| Rubiaceae | *Wendlandia* | *angustifolia* | ASIA | India | 1997 |

The terpenes produced by the functional SQTS chimeras were identified initially based on gas chromatography-mass spectrometry (GC/MS) data. In some cases, authentic standards or essential oils containing characterized sesquiterpenes were available to confirm mass spectrum- and retention time-based identifications. In other cases, standards were not available and structural identifications were made based on mass spectral analysis alone. The different methods used to identify the structures are detailed in Table 3, and the specific methods used to identify each sesquiterpene are indicated in Tables 4-9. In some cases, products were identified only as "sesquiterpene" or "sesquiterpenol." In one case, a mass spectrum was recovered but did not yield a match in the NIST/internal database. This sesquiterpenol was identified in the product tables as an "unidentified sesquiterpenol" and additional characterization may be used to determine its structure.

Figure 2:
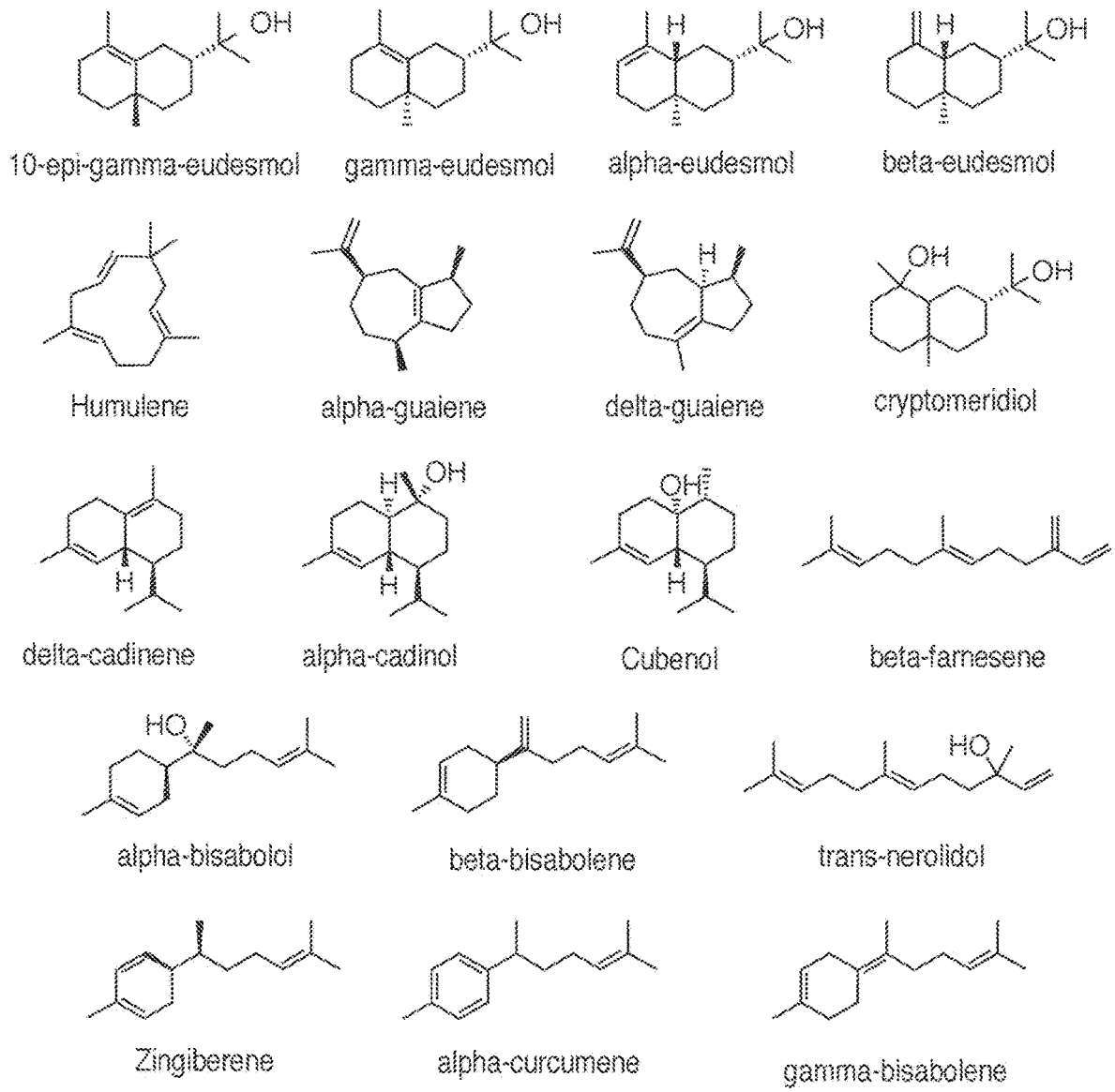
FIG. 2 is a series of pictures depicting structures of identified sesquiterpenes produced using SQTSs containing rare sequences from *L. grandiflorum*.
Figure 3:
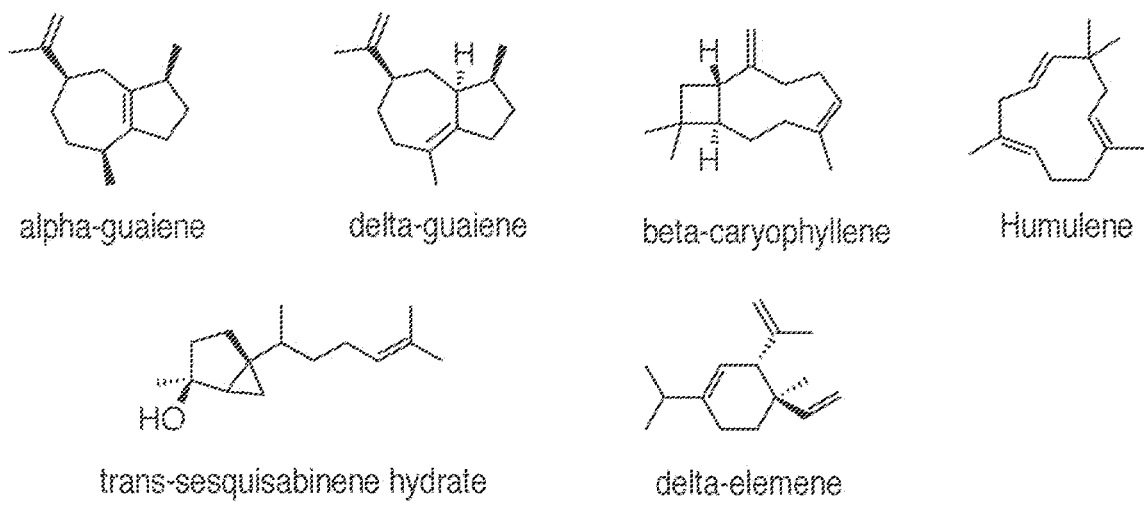
FIG. 3 is a series of pictures depicting structures of sesquiterpenes produced using SQTSs containing rare sequences from *M. villosa*.
Figure 4:
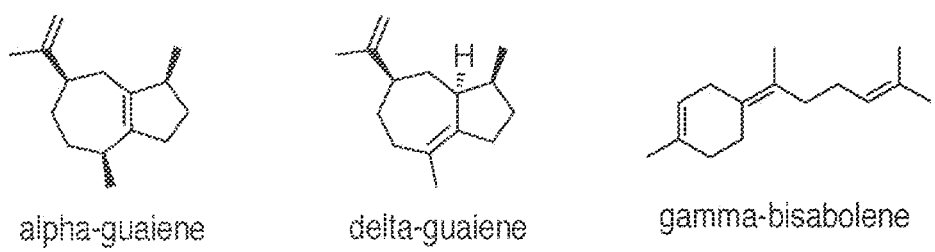
FIG. 4 is a series of pictures depicting structures of sesquiterpenes produced using SQTSs containing rare sequences from *O. stipulatum*.
Figure 5:
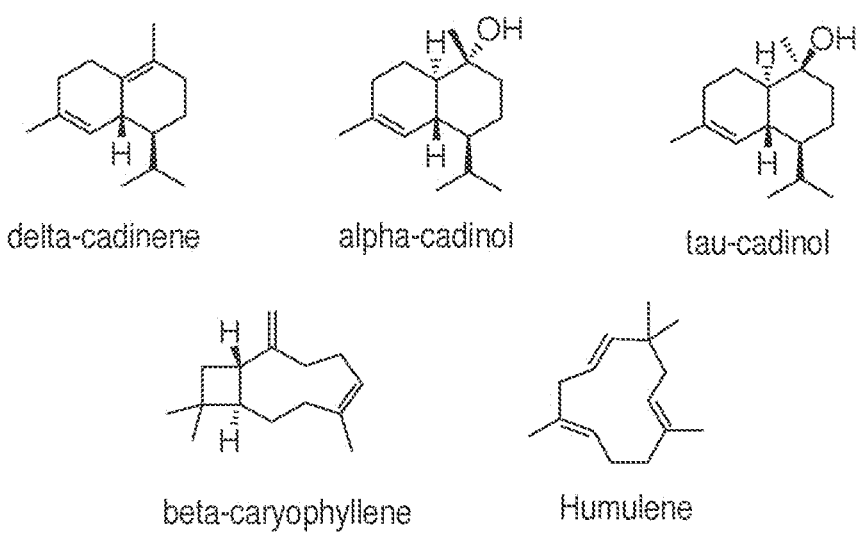
FIG. 5 is a series of pictures depicting structures of identified sesquiterpenes produced using SQTSs containing rare sequences from *S. cuspidata*.
Figure 6:
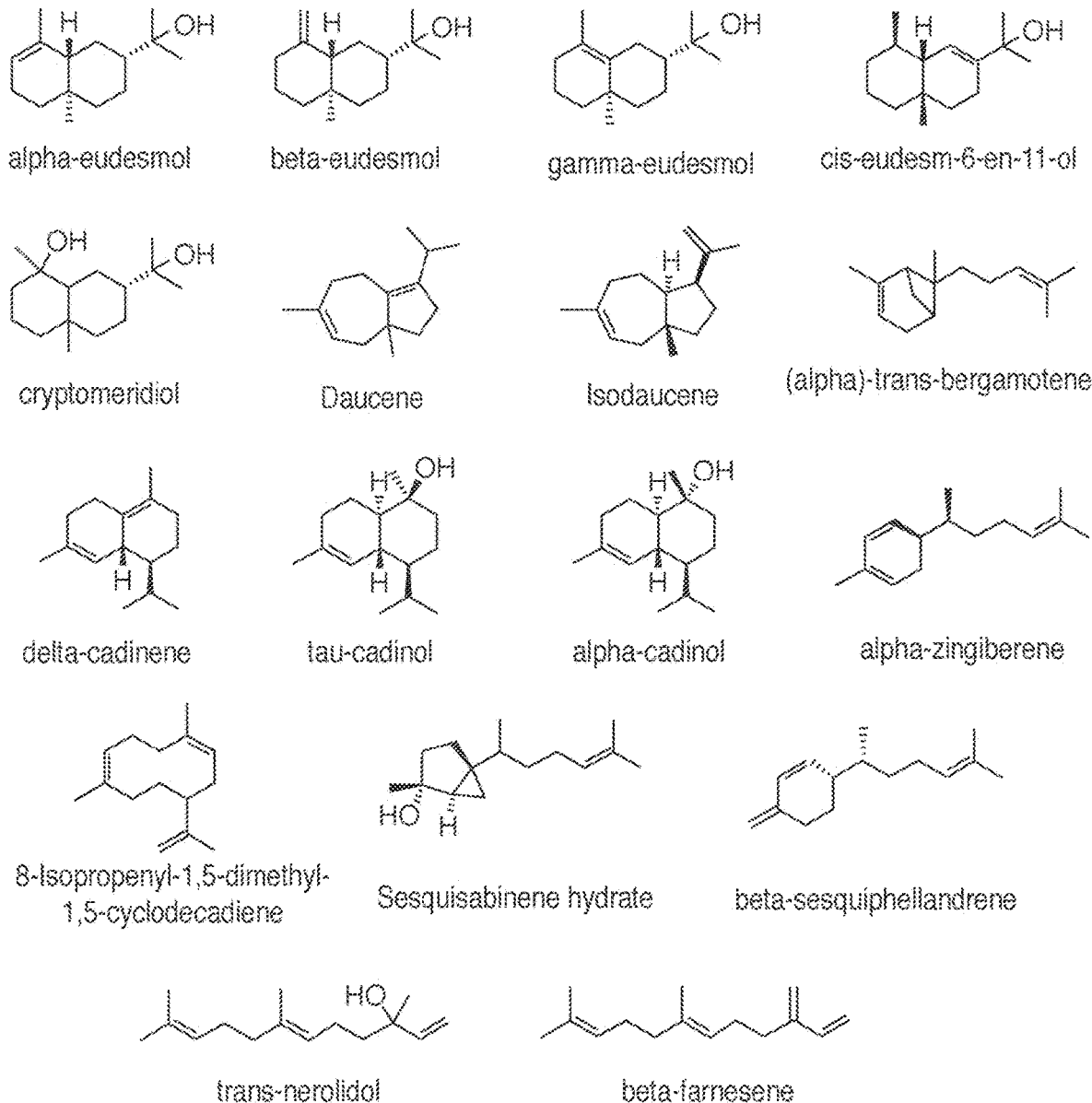
FIG. 6 is a series of pictures depicting structures of identified sesquiterpenes produced using SQTSs containing rare sequences from *W. angustifolia*.
Figure 7:
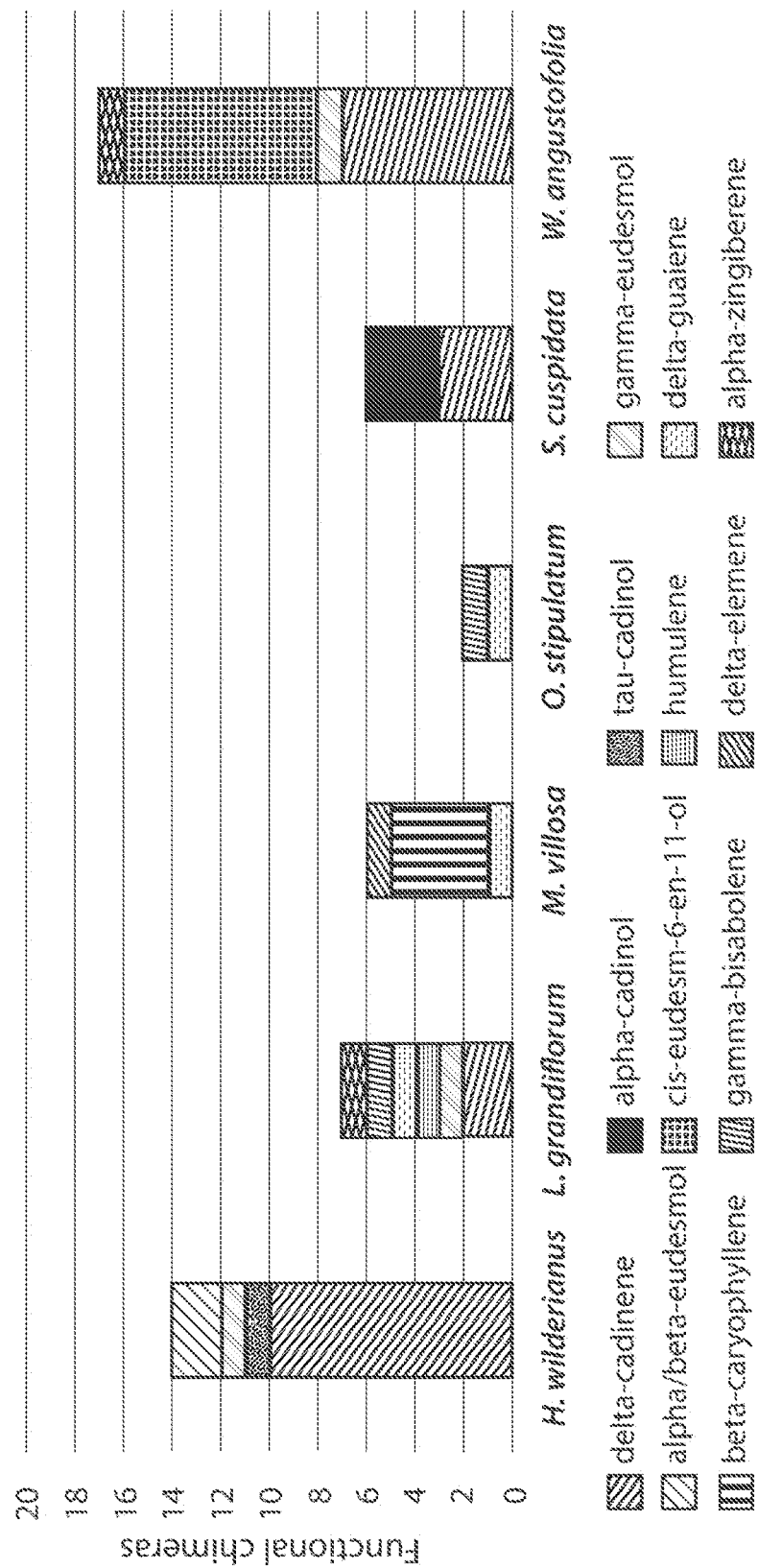
FIG. 7 is a graph showing chimera product distribution versus plant species. The chimeras are categorized based on the sesquiterpene produced in highest yield.
Figure 13:
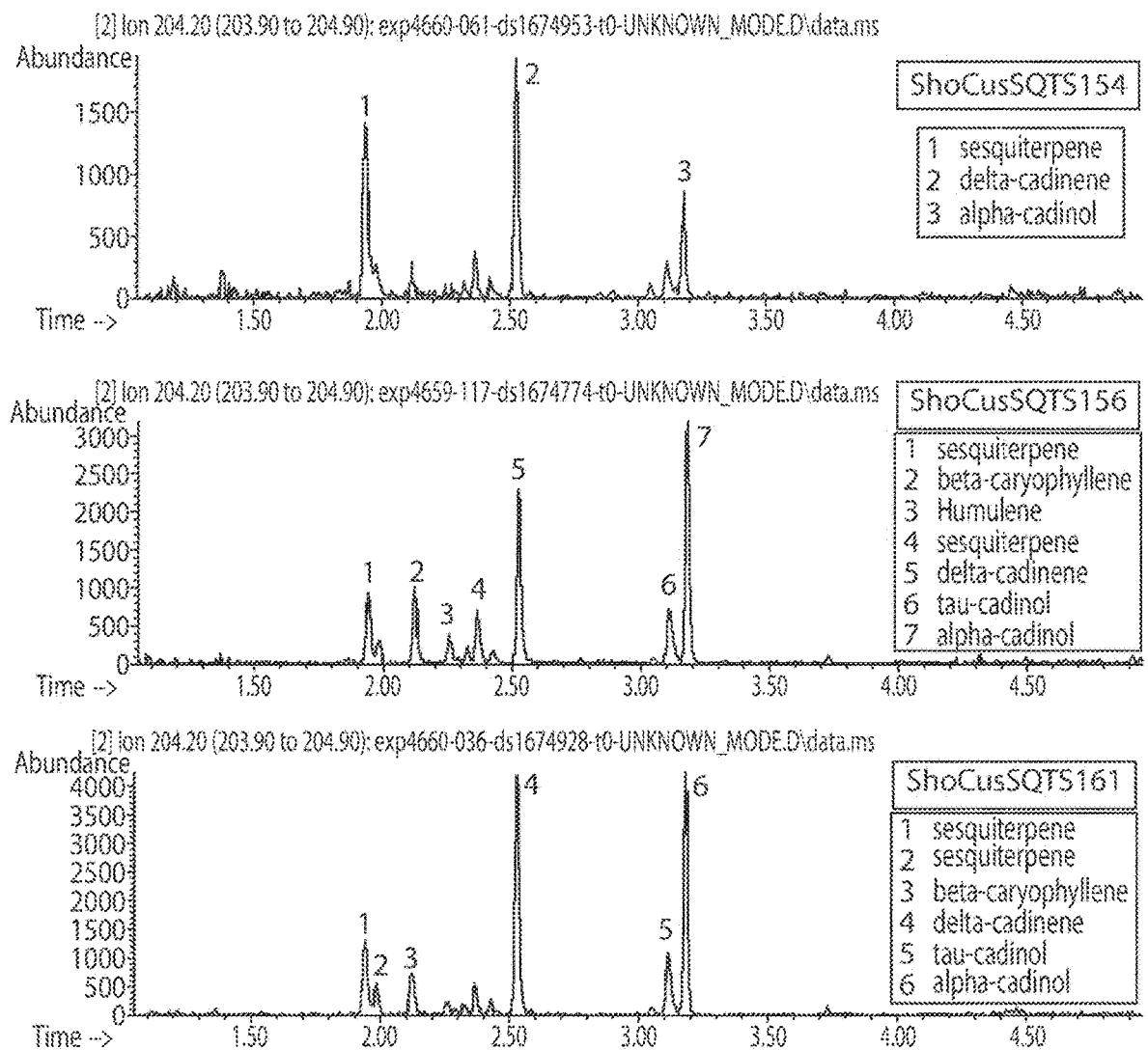
FIG. 13 is a series of pictures depicting selected GC/MS chromatograms from *S. cuspidata* chimera screening data (Table 8).

Fourteen SQTS chimeras derived from *Hibiscadelphus wilderianus* produced 1 or more sesquiterpenes (FIG. 1, Table 3). Seven SQTS chimeras derived from *Leucadendron grandiflorum* also produced sesquiterpenes (FIG. 2, Table 5), as did six SQTS chimeras from *Macrostylis villosa* (FIG. 3, Table 6), two from *O. stipulatum* (FIG. 4, Table 7), six from *Shorea cuspidata* (FIG. 5, Table 8), and seventeen from *Wendlandia angustifolia* (FIG. 6, Table 9). The SQTSs were found to produce one to nine different terpenes. The product profiles of the plant SQTS chimeras were different when the functional SQTS chimeras were grouped by the terpenes produced in highest yield (FIG. 7). Delta-cadinene synthases were the most numerous group of functional chimeras at a total of 22 and were derived from four of the plants. 10 of the 14 of the synthases from *H. wilderianus* were of this variety. Alpha-cadinol was frequently detected as a minor product of the delta-cadinene synthases; however, three SQTS chimeras from *S. cuspidata* yielded more alpha-cadinol than delta-cadinene. These six SQTS chimeras derived *S. cuspidata* produced a very similar product mixture (Table 8, FIG. 13).

The screening of the 2,738-member chimeric sesquiterpene synthase library resulted in the successful expression of 52 functional chimeric sesquiterpene synthases (SQTSs). Fourteen synthases were derived from *H. wilderianus*, a tree which went extinct in Hawaii over 100 years ago. Cadinene, cadinol, and eudesmol-type sesquiterpenes were produced by these chimeras. A few active chimeras were also generated from *O. stipulatum*, a plant that went extinct in Kentucky in the 1800s. Two guaienes and gamma-bisabolene were produced by these synthases. Seven functional SQTS chimeras were constructed from *L. grandiflorum*, a plant that went extinct over 200 years ago. Diverse sesquiterpene and sesquiterpenol structures were produced by these chimeras, along with those derived from three other plants.

TABLE 3

The six methods used to identify the sesquiterpenes produced by the sesquiterpene synthases.

| Method # | Description | Notes |
|---|---|---|
| 1 | Mass spectrum and retention time matched to authentic standard | High confidence in structure and stereochemistry. |
| 2 | Mass spectrum and retention time matched to previously characterized compounds in essential oils from plants. | High confidence in structure and stereochemistry. |
| 3 | Poor mass spectrum obtained due to low titer; retention time and chimera product profile were consistent with authentic standards or components in essential oils | Fairly high confidence in structure and stereochemistry. |
| 4 | Strong mass spectrum match to compound in NIST/internal database | Fairly high confidence in structure, could be an isomer. |
| 5 | Poor mass spectrum obtained due to low titer; retention time and chimera product profiles matched to terpenes identified using method # 4 | Fairly high confidence in structure, could be an isomer. |
| 6 | Poor mass spectrum obtained due to low yields, best (closest) identification possible with NIST/internal database | Lower confidence based on the mass spectral data available. |

TABLE 4

Functional sesquiterpene synthase chimeras derived from *H. wilderianus* sequences and their associated products.

| Chimera name | % rare sequence | Terpene identification | Identification Method[1] | % composition[2] |
|---|---|---|---|---|
| HibWilSQTS117 | 49% | delta-cadinene | 3 | 100% |
| HibWilSQTS118 | 50% | delta-cadinene | 3 | 100% |
| HibWilSQTS120 | 46% | delta-cadinene | 3 | 13% |
| | | epi-cubenol | 5 | 3% |
| | | sesquiterpenol | 6 | 2% |
| | | tau-cadinol | 2 | 82% |
| HibWilSQTS121 | 50% | delta-cadinene | 2 | 99% |
| | | alpha-cadinol | 3 | 1% |
| HibWilSQTS123 | 47% | delta-cadinene | 2 | 99% |
| | | alpha-cadinol | 3 | 1% |
| HibWilSQTS124 | 48% | delta-cadinene | 2 | 98% |
| | | alpha-cadinol | 3 | 2% |
| HibWilSQTS126 | 44% | delta-cadinene | 2 | 97% |
| | | alpha-cadinol | 3 | 3% |

TABLE 4-continued

Functional sesquiterpene synthase chimeras derived from *H. wilderianus* sequences and their associated products.

| Chimera name | % rare sequence | Terpene identification | Identification Method[1] | % composition[2] |
|---|---|---|---|---|
| HibWilSQTS19 | 12% | gamma-selinene | 4 | 1% |
| | | 10-epi-gamma-eudesmol | 2 | 2% |
| | | gamma-eudesmol | 2 | 49% |
| | | alpha/beta-eudesmol[3] | 4 | 22% |
| | | juniper camphor | 6 | 1% |
| | | 7-epi-alpha-eudesmol | 4 | 1% |
| | | cryptomeridiol isomer 1 | 4 | 1% |
| | | cryptomeridiol isomer 2 | 4 | 2% |
| | | cryptomeridiol isomer 3 | 4 | 21% |
| HibWilSQTS34 | 13% | sesquiterpene | 6 | 6% |
| | | 10-epi-gamma-eudesmol | 3 | 15% |
| | | gamma-eudesmol | 3 | 27% |
| | | alpha/beta-eudesmol[3] | 5 | 52% |
| HibWilSQTS52 | 12% | delta-cadinene | 2 | 60% |
| | | tau-cadinol | 3 | 9% |
| | | alpha/beta-eudesmol[3] | 4 | 31% |
| HibWilSQTS54 | 13% | delta-cadinene | 2 | 99% |
| | | alpha-cadinol | 2 | 1% |
| HibWilSQTS55 | 12% | delta-cadinene | 3 | 71% |
| | | tau-cadinol | 3 | 6% |
| | | alpha-cadinol | 3 | 23% |
| HibWilSQTS63 | 12% | sesquiterpene | 6 | 11% |
| | | delta-cadinene | 2 | 29% |
| | | sesquiterpenol | 6 | 15% |
| | | sesquiterpenol | 6 | 5% |
| | | tau-cadinol | 3 | 10% |
| | | alpha-cadinol | 3 | 30% |
| HibWilSQTS90 | 25% | sesquiterpene | 6 | 40% |
| | | alpha/beta-eudesmol[3] | 5 | 60% |

Figure 9:
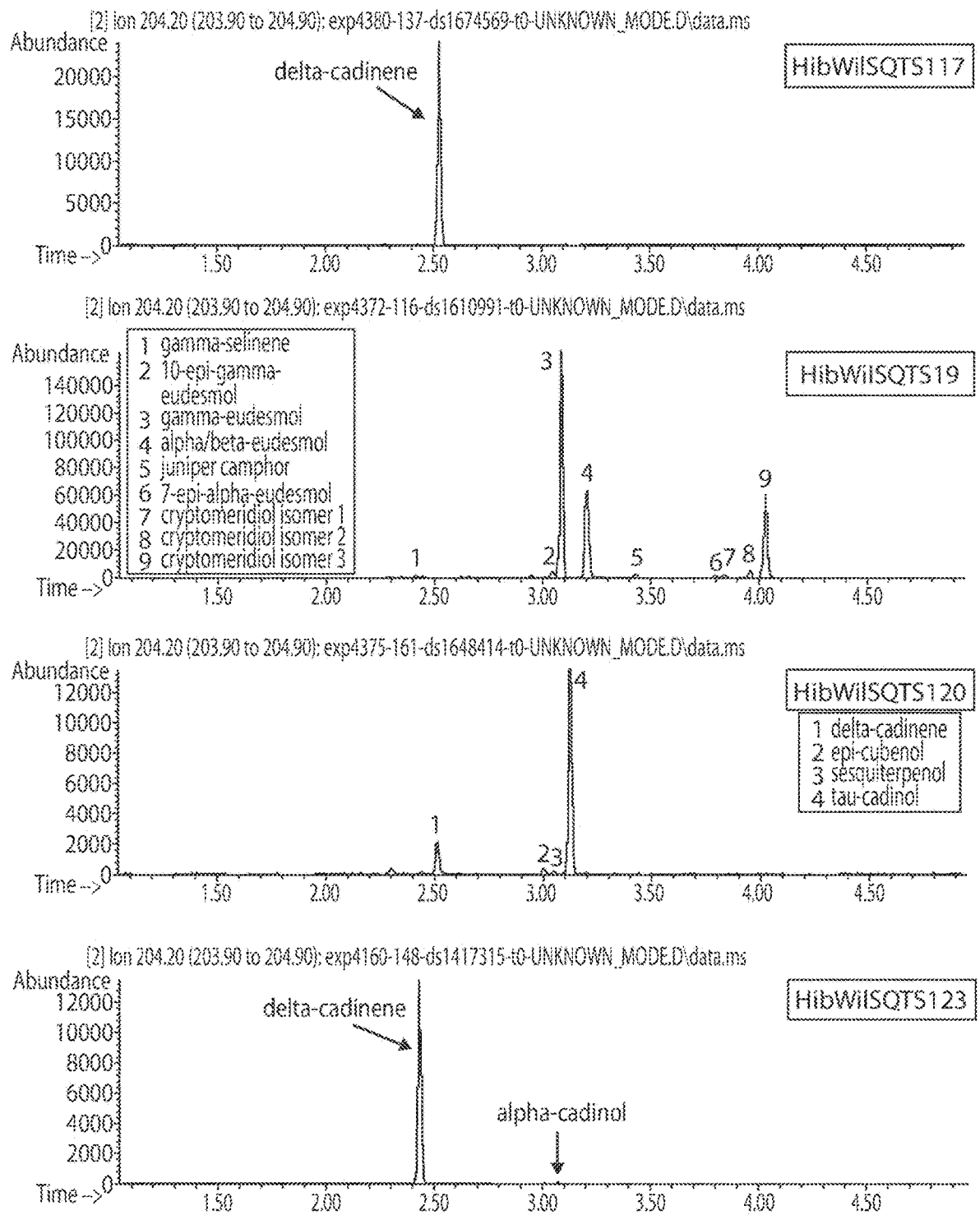
FIG. 9 is a series of pictures depicting selected gas chromatography—mass spectrometry (GC/MS) chromatograms from *H. wilderianus* chimera screening data (Table 4).

[1]The structure identification ranking key is defined in Table 3, with lower numbers indicating a higher degree of confidence.
[2]The composition of total sesquiterpenes from each chimera was a rough estimate based on a common ion count (m/z 204.2). The ratio of metabolites may have been different in the production strains and it is possible other minor metabolites were detected when samples were prepared. Representative GC/MS chromatograms for the chimeras with bold font can be found in FIG. 9.
[3]Co-eluted under these run conditions. The peak was partially resolved under longer run conditions, about 6/4 alpha/beta-eudesmol.

TABLE 5

Functional sesquiterpene synthase chimeras derived from *L. grandiflorum* sequences and their associated products.

| Chimera name | % rare sequence | Terpene identification | Identification Method[1] | % composition[2] |
|---|---|---|---|---|
| LeuGraSQTS335 | 14% | sesquiterpene | 6 | 1% |
| | | 10-epi-gamma-eudesmol | 3 | 1% |
| | | gamma-eudesmol | 3 | 49% |
| | | alpha/beta-eudesmol[3] | 5 | 23% |
| | | cryptomeridiol isomer 2 | 5 | 1% |
| | | cryptomeridiol isomer 3 | 5 | 25% |
| LeuGraSQTS345 | 12% | Humulene | 3 | 100% |
| LeuGraSQTS365 | 11% | alpha-guaiene | 3 | 20% |
| | | delta-guaiene | 3 | 80% |
| LeuGraSQTS377 | 14% | delta-cadinene | 3 | 98% |
| | | alpha-cadinol | 3 | 2% |
| LeuGraSQTS379 | 12% | delta-cadinene | 3 | 98% |
| | | alpha-cadinol | 3 | 2% |
| LeuGraSQTS385 | 13% | Zingiberene | 4 | 55% |
| | | beta-bisabolene | 2 | 19% |
| | | beta-farnesene | 1 | 6% |
| | | beta-sesquiphellandrene | 2 | 6% |
| | | Cubenol | 5 | 5% |
| | | alpha-bisabolol | 1 | 4% |
| | | alpha-curcumene | 5 | 3% |
| | | trans-nerolidol | 1 | 2% |
| LeuGraSQTS393 | 10% | gamma-bisabolene | 4 | 100% |

Figure 10:
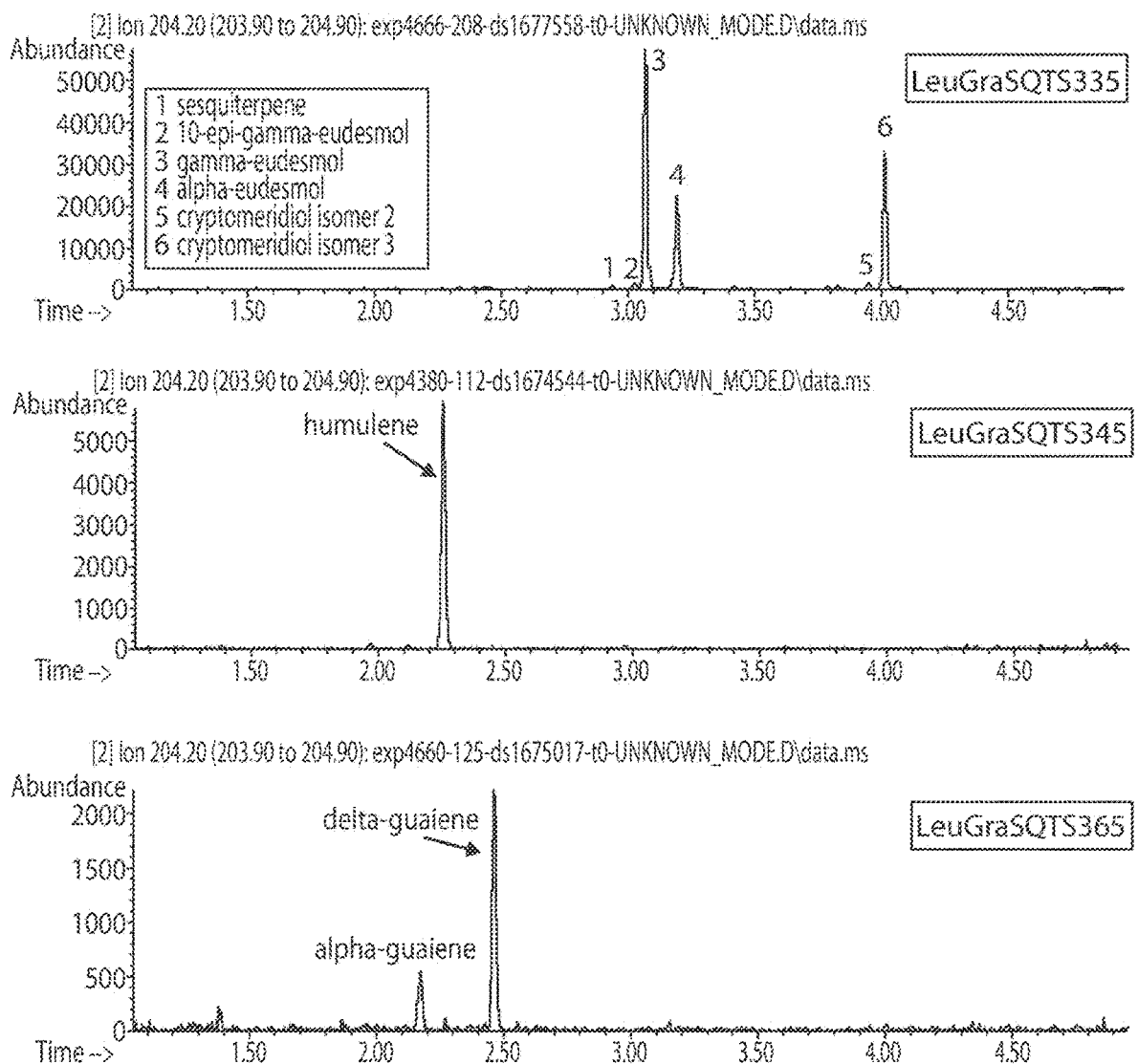
FIG. 10 is a series of pictures depicting selected GC/MS chromatograms from *L. grandiflorum* chimera screening data (Table 5).
Figure 11:
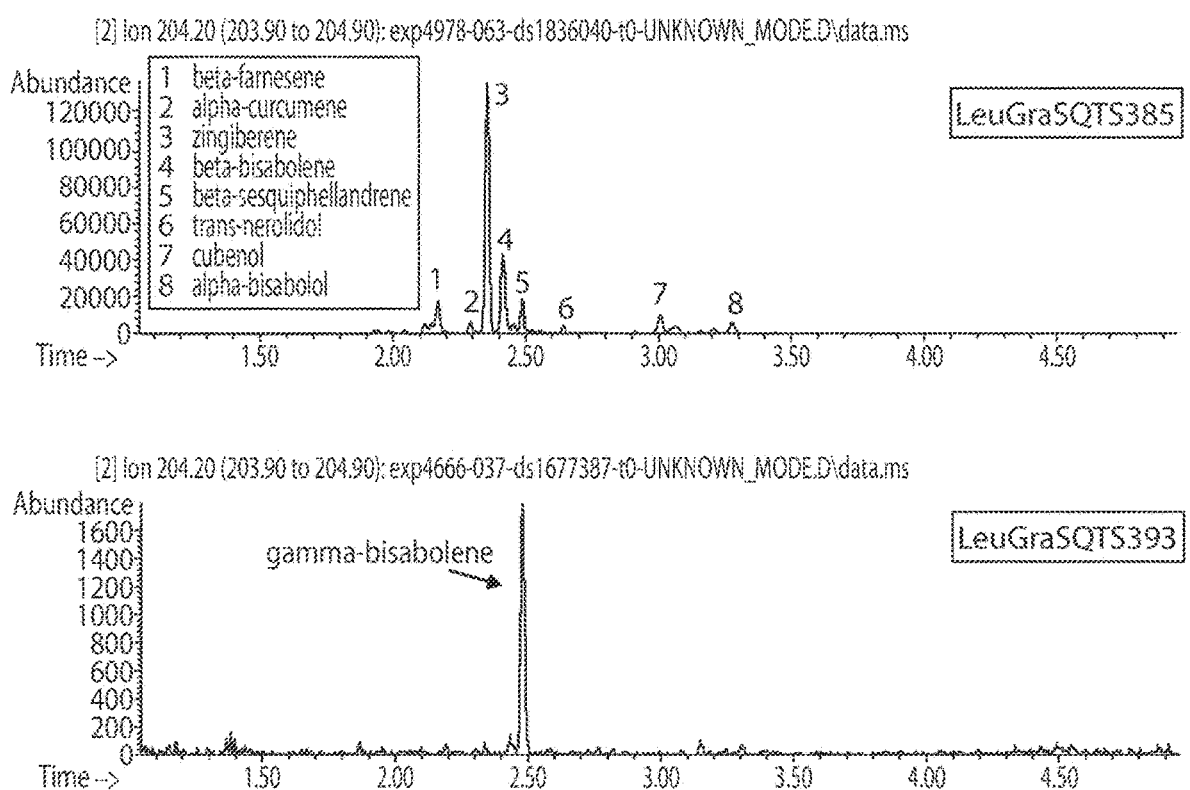
FIG. 11 is a series of pictures depicting selected GC/MS chromatograms from *L. grandiflorum* chimera screening data (Table 5).

[1]The structure identification ranking key is defined in Table 3, with lower numbers indicating a higher degree of confidence.
[2]The composition of total sesquiterpenes from each chimera was a rough estimate based on a common ion count (m/z 204.2). The ratio of metabolites may have been different in the production strains and other minor metabolites may have been detected when samples were prepared. Representative GC/MS chromatograms for the chimeras with bold font can be found in FIG. 10 and FIG. 11.
[3]Co-eluted under these run conditions. The peak was partially resolved under longer run conditions, about 6/4 alpha/beta-eudesmol.

TABLE 6

Functional sesquiterpene synthase chimeras derived from *M. villosa* sequences and their associated products.

| Chimera name | % rare sequence | Terpene identification | Identification Method[1] | % composition[2] |
|---|---|---|---|---|
| MacVolSQTS1139 | 14% | alpha-guaiene | 3 | 19% |
| | | delta-guaiene | 3 | 81% |
| MacVolSQTS2198 | 62% | beta-caryophyllene | 1 | 85% |
| | | Humulene | 1 | 15% |
| MacVolSQTS2202 | 69% | beta-caryophyllene | 1 | 86% |
| | | Humulene | 1 | 14% |
| MacVolSQTS2222 | 69% | beta-caryophyllene | 1 | 86% |
| | | Humulene | 1 | 14% |
| MacVolSQTS2251 | 65% | beta-caryophyllene | 1 | 87% |
| | | Humulene | 1 | 13% |
| MacVolSQTS2274 | 38% | unknown sesquiterpene | 6 | 16% |
| | | trans-Sesquisabinene hydrate | 5 | 14% |
| | | delta-elemene | 6 | 34% |
| | | unknown sesquiterpene | 6 | 16% |

Figure 12:
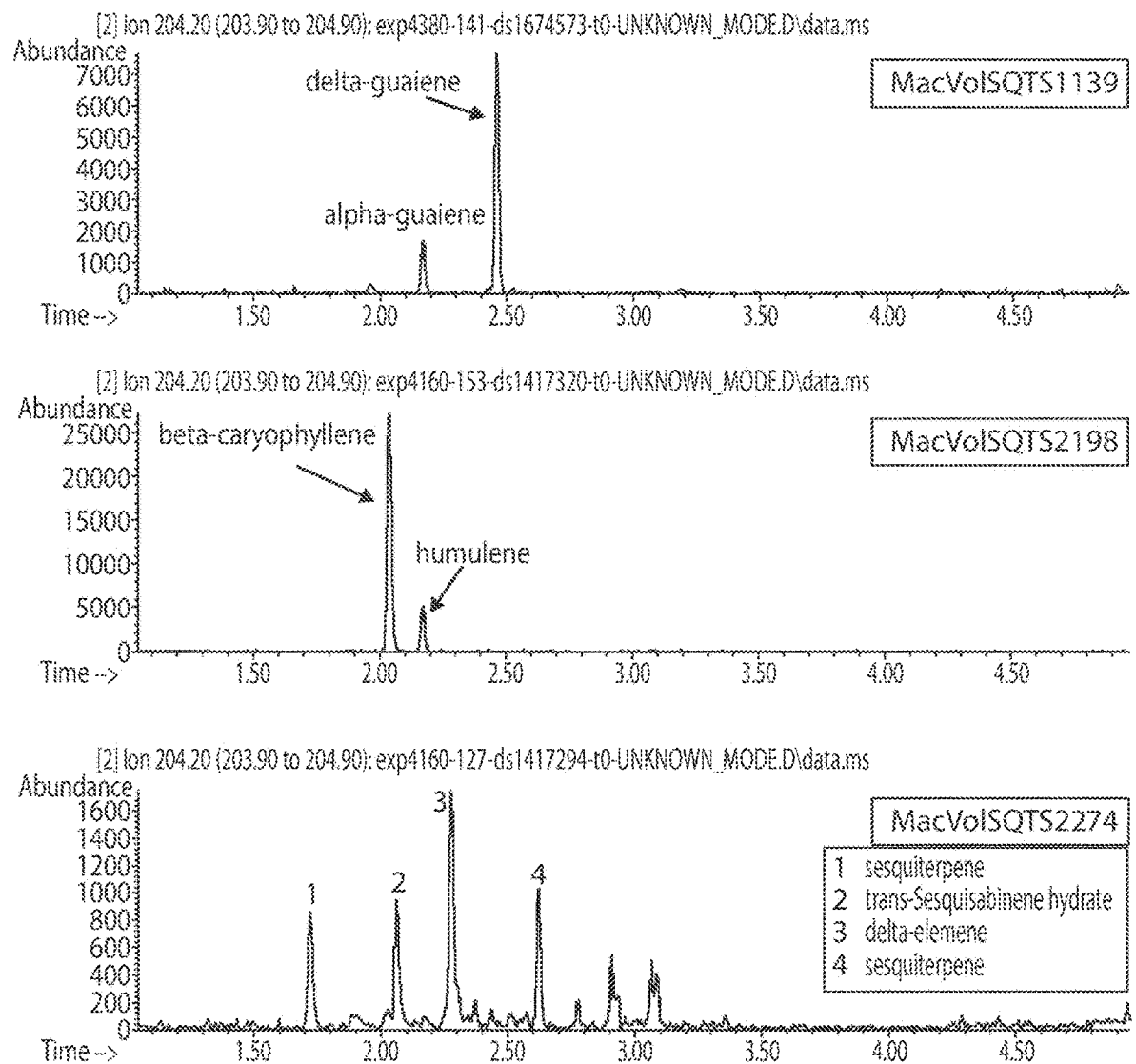
FIG. 12 is a series of pictures depicting selected GC/MS chromatograms from *M. villosa* chimera screening data (Table 6).

[1]The structure identification ranking key is defined in Table 3, with lower numbers indicating a higher degree of confidence.
[2]The composition of total sesquiterpenes from each chimera was a rough estimate based on a common ion count (m/z 204.2). The ratio of metabolites may have been different in the production strains and other minor metabolites may have been detected when samples were prepared. Representative GC/MS chromatograms for the chimeras with bold font can be found in FIG. 12.

TABLE 7

Functional sesquiterpene synthase chimeras derived from *O. stipulatum* sequences and their associated products.

| Chimera name | % rare sequence | Terpene identification | Identification Method[1] | % composition[2] |
|---|---|---|---|---|
| OrbStiSQTS1368 | 10% | gamma-bisabolene | 5 | 100% |
| OrbStiSQTS1414 | 42% | alpha-guaiene | 3 | 21% |
| | | delta-guaiene | 3 | 79% |

[1]The structure identification ranking key is defined in Table 3, with lower numbers indicating a higher degree of confidence.
[2]The composition of total sesquiterpenes from each chimera was a rough estimate based on a common ion count (m/z 204.2). The ratio of metabolites may have been different in the production strains and other minor metabolites may have been detected when samples were prepared.

TABLE 8

Functional sesquiterpene synthase chimeras derived from S. cuspidata sequences and their associated products.

| Chimera name | % rare sequence | Terpene identification | Identification Method[1] | % composition[2] |
|---|---|---|---|---|
| ShoCusSQTS154 | 38% | delta-cadinene | 3 | 41% |
| | | Sesquiterpene | 6 | 41% |
| | | alpha-cadinol | 3 | 18% |
| ShoCusSQTS155 | 35% | delta-cadinene | 3 | 41% |
| | | Sesquiterpene | 6 | 41% |
| | | alpha-cadinol | 3 | 18% |
| ShoCusSQTS156 | 36% | alpha-cadinol | 2 | 34% |
| | | delta-cadinene | 2 | 25% |
| | | beta-caryophyllene | 1 | 10% |
| | | tau-cadinol | 2 | 10% |
| | | Sesquiterpene | 6 | 10% |
| | | Sesquiterpene | 6 | 7% |
| | | Humulene | 1 | 4% |
| ShoCusSQTS157 | 38% | alpha-cadinol | 3 | 59% |
| | | Sesquiterpene | 6 | 25% |
| | | tau-cadinol | 3 | 16% |
| ShoCusSQTS160 | 36% | alpha-cadinol | 3 | 33% |
| | | Sesquiterpene | 6 | 32% |
| | | delta-cadinene | 3 | 5% |
| ShoCusSQTS161 | 37% | delta-cadinene | 3 | 36% |
| | | alpha-cadinol | 3 | 34% |
| | | Sesquiterpene | 6 | 12% |
| | | tau-cadinol | 3 | 10% |
| | | beta-caryophyllene | 3 | 5% |
| | | Sesquiterpene | 6 | 3% |

[1]The structure identification ranking key is defined in Table 3, with lower numbers indicating a higher degree of confidence.
[2]The composition of total sesquiterpenes from each chimera was a rough estimate based on a common ion count (m/z 204.2). The ratio of metabolites may have been different in the production strains and it is possible other minor metabolites were detected when samples were prepared. Representative GC/MS chromatograms for the chimeras with bold font can be found in FIG. 13.

TABLE 9

Functional sesquiterpene synthase chimeras derived from W. angustifolia sequences and their associated products.

| Chimera name | % rare sequence | Terpene identification | Identification Method[1] | % composition[2] |
|---|---|---|---|---|
| WenAngSQTS1007 | 81% | cis-eudesm-6-en-11-ol | 4 | 100% |
| WenAngSQTS1086 | 80% | Daucene | 5 | 5% |
| | | isodaucene | 5 | 6% |
| | | sesquiterpene | 6 | 4% |
| | | cis-eudesm-6-en-11-ol | 4 | 85% |
| WenAngSQTS267 | 11% | gamma-eudesmol | 3 | 66% |
| | | alpha/beta-eudesmol[3] | 5 | 15% |
| | | cryptomeridiol isomer 3 | 5 | 19% |
| WenAngSQTS302 | 17% | sesquiterpene | 6 | 2% |
| | | trans-bergamotene | 4 | 5% |
| | | alpha-zingiberene | 4 | 56% |
| | | sesquisabinene hydrate | 4 | 20% |
| | | beta-sesquiphellandrene | 2 | 7% |
| | | trans-nerolidol | 1 | 2% |
| | | sesquiterpenol | 6 | 4% |
| | | sesquiterpenol | 6 | 4% |
| WenAngSQTS738 | 46% | Sesquiterpene | 6 | 6% |
| | | sesquiterpene | 6 | 7% |
| | | delta-cadinene | 2 | 36% |
| | | unidentified sesquiterpenol | 4 | 27% |
| | | tau-cadinol | 3 | 15% |
| | | alpha-cadinol | 3 | 9% |
| WenAngSQTS760 | 43% | Sesquiterpene | 6 | 9% |
| | | Sesquiterpene | 6 | 4% |
| | | Sesquiterpene | 6 | 6% |
| | | delta-cadinene | 2 | 41% |
| | | sesquiterpenol | 6 | 22% |
| | | tau-cadinol | 3 | 11% |
| | | alpha/beta-eudesmol[3] | 5 | 7% |
| WenAngSQTS780 | 41% | sesquiterpene | 6 | 9% |
| | | sesquiterpene | 6 | 3% |
| | | sesquiterpene | 6 | 6% |
| | | delta-cadinene | 2 | 40% |
| | | sesquiterpenol | 6 | 24% |
| | | tau-cadinol | 3 | 11% |
| | | alpha/beta-eudesmol[3] | 5 | 7% |
| WenAngSQTS793 | 75% | Daucene | 5 | 3% |
| | | beta-farnesene | 1 | 2% |
| | | 8-Isopropenyl-1,5-dimethyl-1,5-cyclodecadiene | 4 | 5% |
| | | sesquiterpene | 6 | 3% |
| | | cis-eudesm-6-en-11-ol | 4 | 87% |
| WenAngSQTS805 | 42% | sesquiterpene | 6 | 5% |
| | | sesquiterpene | 6 | 6% |
| | | delta-cadinene | 2 | 39% |
| | | unidentified sesquiterpenol | 4 | 27% |
| | | tau-cadinol | 3 | 15% |
| | | alpha-cadinol | 3 | 8% |
| WenAngSQTS826 | 47% | delta-cadinene | 3 | 42% |
| | | sesquiterpenol | 6 | 36% |
| | | tau-cadinol | 3 | 22% |
| WenAngSQTS829 | 74% | cis-eudesm-6-en-11-ol | 5 | 100% |
| WenAngSQTS843 | 45% | delta-cadinene | 3 | 53% |
| | | sesquiterpenol | 6 | 47% |
| WenAngSQTS848 | 84% | cis-eudesm-6-en-11-ol | 5 | 100% |
| WenAngSQTS849 | 75% | Daucene | 4 | 3% |
| | | beta-farnesene | 1 | 1% |
| | | isodaucene | 4 | 8% |
| | | sesquiterpene | 6 | 2% |
| | | cis-eudesm-6-en-11-ol | 4 | 86% |
| WenAngSQTS864 | 81% | Daucene | 5 | 2% |
| | | 8-Isopropenyl-1,5-dimethyl-1,5-cyclodecadiene | 4 | 5% |
| | | sesquiterpene | 6 | 3% |
| | | cis-eudesm-6-en-11-ol | 4 | 90% |
| WenAngSQTS925 | 80% | sesquiterpene | 6 | 3% |
| | | sesquiterpene | 6 | 8% |
| | | sesquiterpene | 6 | 3% |
| | | cis-eudesm-6-en-11-ol | 5 | 86% |
| WenAngSQTS960 | 81% | delta-cadinene | 2 | 99% |
| | | alpha-cadinol | 3 | 1% |

Figure 14:
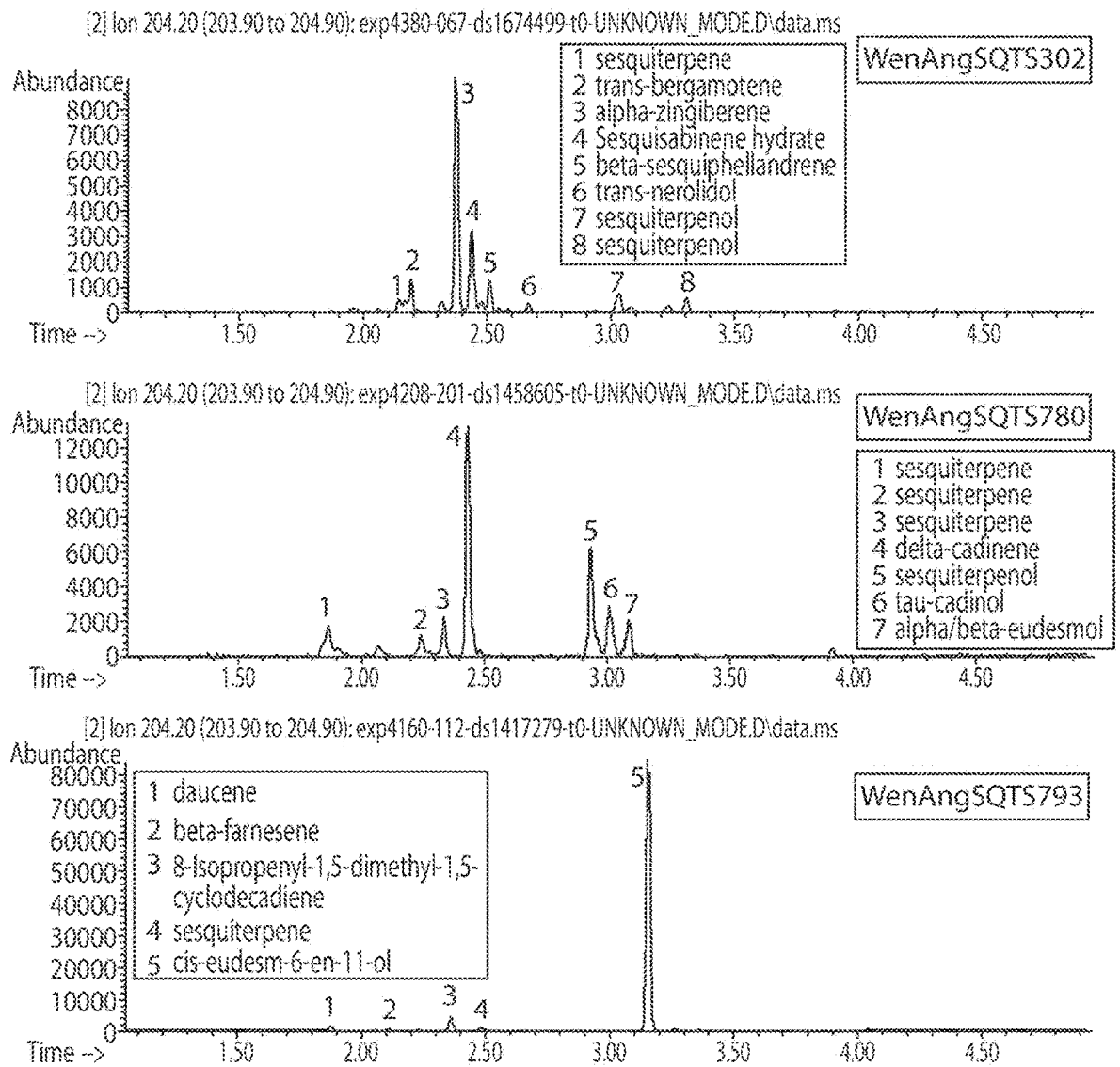
FIG. 14 is a series of pictures depicting selected GC/MS chromatograms from *W. angustifolia* chimera screening data (Table 9).
Figure 15:
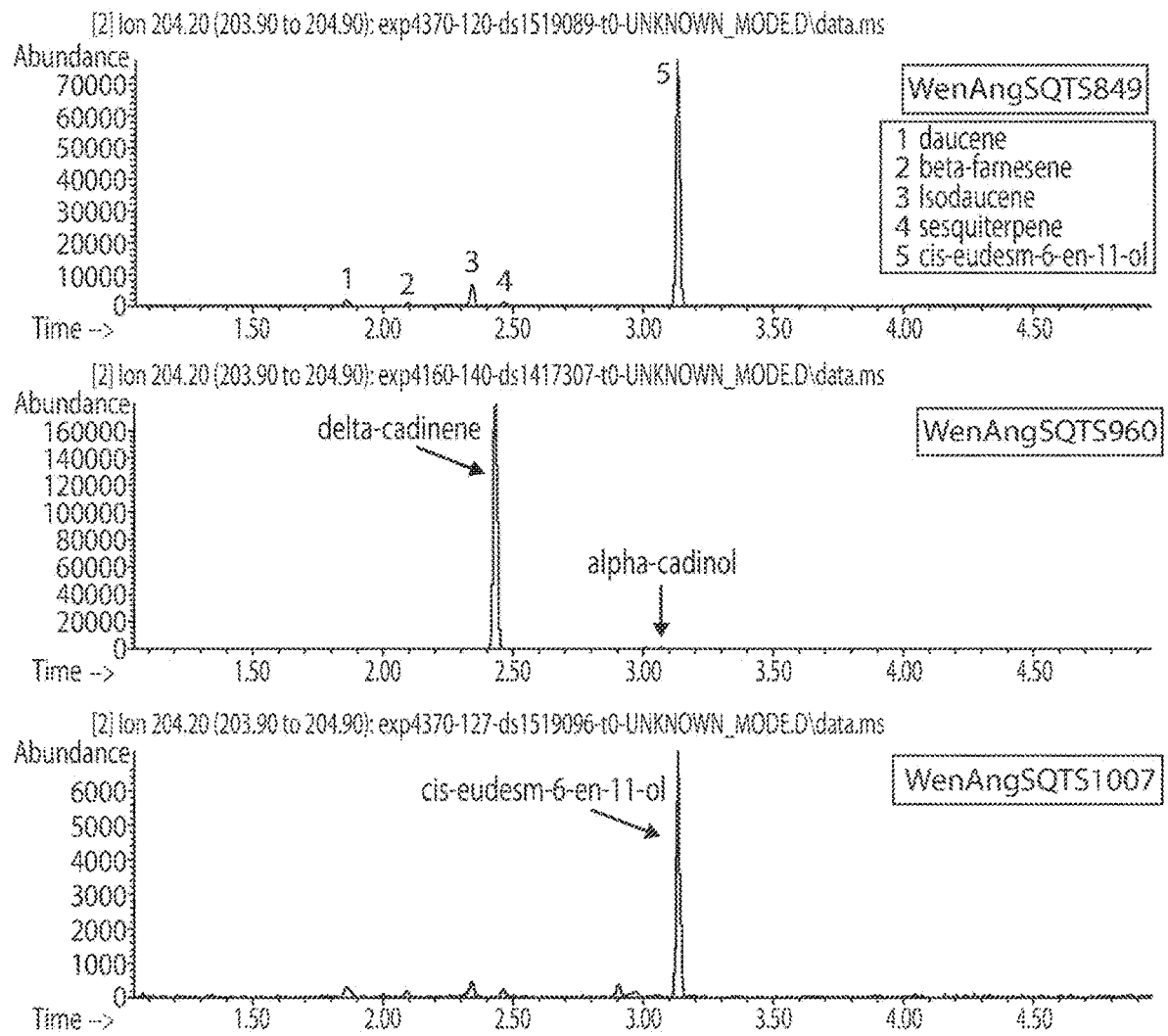
FIG. 15 is a series of pictures depicting selected GC/MS chromatograms from *W. angustifolia* chimera screening data (Table 9).

[1]The structure identification ranking key is defined in Table 3, with lower numbers indicating a higher degree of confidence.
[2]The composition of total sesquiterpenes from each chimera was a rough estimate based on a common ion count (m/z 204.2). The ratio of metabolites may have been different in the production strains and it is possible other minor metabolites were detected when samples were prepared. Representative GC/MS chromatograms for the chimeras with bold font can be found in Appendix FIG. 14 and FIG. 15.
[3]Co-eluted under these run conditions. The peak was partially resolved under longer run conditions, about ⁶⁄₄ alpha/beta-eudesmol.

TABLE 10

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
| --- | --- | --- | --- | --- | --- |
| HibWilS QTS117 | *Hibiscadelphus wilderianus* | Q9SAN0 | 49% | ASQASQVLASPHPAISS ENRPKADFHPGIWGDM FIICPDTDIDAATELQYE ELKAQVRKMIMEPVDD SNQKLPFIDAVQRLGVS YHFEKEIEDELENIYRD TNNNDADTDLYTTALR FRLLREHGFDISCDAFN KLKDEEGNFKASLTSD VPGLLELYEASYLRVH GEDILDEAISFATAQLT LALPTLHHPLSEQVGH ALKQSIRRGLPRVEARN FISIYQDLESHNKALLQ FAKIDFNMLQLLHRKE LSEICRWWKDLDFTRK LPFARDRVVEGYFWIM GVYFEPQYSLGRKMLT KVIAMASIVDDTYDSFA TYDELIPYTDAIERWDI KCMNQLPNYMQISYKA LLDVYEEMEQLLADKG RQYRVEYAKKAMIRLV QAYLLEAKWTHLNYKP TFEEFRDNALPTSGYA MLAITAFVGMGEVITPE TFEWAASDPKIIKASTII CRFMDDIAEHKFNHRR EDDCSAIECYMEQYKV TAQEAYDEFNKHIESS WKDVNEEFLKPTEMPT PVLCRSLNLARVMDVL YREGDGYTHVGKAAK GGITSLLIDPIQI (SEQ ID NO: 1) | atggccagtcaggcttcacaagttttagcatctcc ccacccagctatatcctctgaaaaccggccaaag gctgatttccatcctggtatctggggcgacatgttt attatctgtccagatacggacattgatgccgctac agagctgcaatatgaagaattgaaagcgcaagtc cgcaagatgatcatggaaccagtagacgattcta atcaaaagctaccattcattgacgctgttcaaagg ctcggagtgagctaccactttgaaaaagaattga agacgaacttgaaaacatctaccgtgataccaata acaacgacgcagacactgatctatacactaccgc cttgagattcagattattgagagagcatggttttgat atttcctgcgatgctttcaacaagttgaaagacga agaaggtaatttcaaggcttcgttgacttctgacgt tcctggtttgttagaactctatgaggcttcctacttg agagtccacggtgaagatatcctagatgaagcca tatctttcgctactgctcagttaaccttggctttgcc aactttgcatcacccgcttttcagacgcaagttggtc acgcattgaagcaaagtatcagaagaggcctgc caagagttgaagccagaaactttatctctatttacc aagatttagaatcccacaataaggctttgttgcaat tcgccaaaattgactttaacatgttacaattgctaca taggaaggagctcagcgaaatttgtagatggtgg aaagatcttgattttaccagaaagttacctttcgctc gtgaccgtgtcgtcgaaggttatttctggattatgg gagtttacttcgaaccacaatatagcttgggtaga aagatgttgaccaaggttattgctatggcttctatc gtcgatgatacatacgattccttcgctacttacgac gaattgataccatatactgacgccatcgaagatg ggacatcaagtgtatgaatcagctgccaaactata tgcaaatttcgtacaaagcgttattggatgtatacg aggaaatggaacaattgcttgcagataaaggtcg acagtacagagtggaatacgctaagaaagctatg attcggttggtgcaagcatatttgttagaagcgaa gtggacccatttaaactacaagccaactttcgaag aatttagagacaatgctttgccgacatctgggtatg ccatgctagctataaccgcgttcgttggtatgggt gaagttatcacgccagaaacctttgaatgggctg cttctgacccaaagattattaaggcctccactatca tctgccgctttatggatgatatcgctgagcataagt tcaaccacagaagggaggatgactgttccgctat tgaatgttacatggagcaatacaaagtcacagctc aagaagcatacgacgaatttaacaagcacataga atcgtcttggaaggacgttaatgaagagttcttga aaccaactgaaatgcctactccggtactgtgtaga agtttgaacctagccagagtcatggatgttttgtac agagaaggtgacggttatactcatgttggaaaag ccgctaagggtggtataacatcacttcttatcgatc ccattcaaatctaa (SEQ ID NO: 67) |
| HibWilS QTS118 | *Hibiscadelphus wilderianus* | Q9SAN0 | 50% | ASQASQVLASPHPAISS ENRPKADFHPGIWGDM FIICPDTDIDAATELQYE ELKAQVRKMIMEPVDD SNQKLPFIDAVQRLGVS YHFEKEIEDELENIYRD TNNNDADTDLYTTALR FRLLREHGFDISCEAFN KLKDEEGNFKASLTSD VRGLLELYQASYMRIH GEDILDEAISFTTAQLTL ALPTLDPPLSEQVGHAL KQSIRRGLPRVEARNFI SIYQDLESHNKALLQFA KIDFNMLQLLHRKELSE ICRWWKDLDFTRKLPF ARDRVVEGYFWIMGV YFEPQYSLGRKMLTKVI AMASIVDDTYDSFATY DELIPYTDAIERWDIKC MNQLPNYMQISYKALL DVYEEMEQLLADKGR QYRVEYAKKAMIRLVQ | atggccagtcaggcttcacaagttttagcatctcc ccacccagctatatcctctgaaaaccggccaaag gctgatttccatcctggtatctggggcgacatgttt attatctgtccagatacggacattgatgccgctac agagctgcaatatgaagaattgaaagcgcaagtc cgcaagatgatcatggaaccagtagacgattcta atcaaaagctaccattcattgacgctgttcaaagg ctcggagtgagctaccactttgaaaaagaattga agacgaacttgaaaacatctaccgtgataccaata acaacgacgcagacactgatctatacactaccgc cttgagattcagattattgagagagcatggttttgat atttcctgcgaagctttcaacaagttgaaagacga agagggtaatttcaaggcttcgttgacttctgatgtt agaggtttgttagaactctatcaggcttcctacatg agaatccacggtgaagatatcttgatgaagccat atctttcaccactgctcaattaaccttggctttgcct actttggatcccccattgtcagagcaagtcggtca tgccctaaagcagagtataagaagaggcctacc aagagttgaagccagaaactttatctctatttacca agatttggaatcccacaataaggctttattgcaatt cgctaaaattgactttaacatgttacaattgctacat aggaaggagctcagcgaaatctgtcgttggtgga aagatcttgattttactagaaagttgcctttcgcacg |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | AYLLEAKWTHLNYKPT FEEFRDNALPTSGYAM LAITAFVGMGEVITPET FEWAASDPKIIKASTIIC RFMDDIAEHKFNHRRE DDCSAIECYMKQYGAT AQEAYDEFNKHIESSW KDVNEEFLKPTEMPTP VLCRSLNLARVMDVLY REGDGYTHVGKAAKG GITSLLIDPIQI (SEQ ID NO: 2) | ggaccgtgtcgttgaaggttatttctggattatggg agtttacttcgaaccacaatatagcttgggtagaa agatgttgaccaaggttattgctatggcttctatcgt cgatgatacatacgattccttcgctacatacgacg aattgatcccatatactgacgccattgaaagatgg gacatcaagtgtatgaatcaactgccaaactatat gcaaatttcgtacaaagcattattggatgtatacga ggaaatggaacaattgcttgcggataaaggtcgg cagtacagagtggaatacgctaagaaagctatga ttcgattggtacaagcatatttattagaagcgaagt ggactcacttgaactacaagccaaccttcgaaga atttagagacaatgctttaccgacatctgggtatgc tatgcttgctataaccgcgttcgttggtatgggtga agtcatcacgccagaaacttttgaatgggccgctt ctgacccgaagattatcaaggcttccactatcatct gccgctttatggatgatatcgctgagcataagttca accacagaagggaggatgactgttccgctattga atgttacatgaagcaatacggtgcaaccgcccaa gaggcatacgacgaatttaacaaacacatagaat cgtcttggaaggacgttaatgaagagttcttgaaa ccaactgaaatgcctactccagtgctgtgtagaag tttgaaccttgctagagtcatggatgttttgtacaga gaaggtgacggttatactcatgtcgggaaagccg ctaagggtggtataaccctcattgctaattgatccca ttcaaatctaa (SEQ ID NO: 68) |
| HibWilS QTS120 | Hibiscadelphus wilderianus | Q9SAN0 | 46% | ASQASQVLASPHPAISS ENRPKADFHPGIWGDM FIICPDTDIDAATELQYE ELKAQVRKMIMEPVDD SNQKLPFIDAVQRLGVS YHFEKEIEDELENIYRD TNNNDADTDLYTTALR FRLLREHGFDISCDAFN KLKDEEGNFKASLTSD VPGLLELYEASYLRVH GEDILDEAISFATAQLT LALPTLHHPLSEQVGH ALKQSIRRGLPRVEARN FISIYQDLESHNKALLQ FAKIDFNMLQLLHRKE LSEICRWWKDLDFTRK LPFARDRVVEGYFWIM GVYFEPQYSLGRKMLT KVIAMASIVDDTYDSFA TYDELIPYTDAIERWDI KCMNQLPNYMQISYKA LLDVYEEMEQLLADKG RQYRVEYAKKAMIRLV QAYLLEAKWTHLNYKP TFEEFRDNALPTSGYA MLAITAFVGMGEVITPE TFEWAASDPKIIKASTII CRFMDDIAEHKFNHRR EDDCSAIECYMKQYGA TAQEAYDEFNKHIESS WKDVNEEFLKPTEMPT PVLCRSLNLARVMDVL YREGDGYTHVGKAAK GGITSLLIDPIQI (SEQ ID NO: 3) | atggccagtcaggcttcacaagtttagcatctcc ccacccagctatatcctctgaaaaccggccaaag gctgatttccatcctggtatctgggtggcgacatgttt attatctgtccagatacggacattgatgccgctac agagctgcaatatgaagaattgaaagcgcaagtc cgcaagatgatcatggaaccagtagacgattcta atcaaaagctaccattcattgacgctgttcaaagg ctcggagtgagctaccactttgaaaaagaaattga agacgaacttgaaaacatctaccgtgataccaata acaacgacgcagacactgatctatacactaccgc cttgagattcagattgatgagagagcatggttttgat atttcctgcgatgcttttcaacaagttgaaagacga agaaggtaatttcaaggcttcgttgacttctgacgt tcctggtttgttagaactctatgaggcttcctacttg agagtccacggtgaagatatcctagatgaagcca tatctttcgctactgctcagttaacccttggctttgcc aactttgcatcacccgcttctcagagcaagttggtc acgcattgaagcaaagtatcagaagaggcctgc caagagttgaagccagaaaactttatctctatttacc aagattttaaatcccacaataaggcttgttgcaat tcgccaaaattgactttaacatgttacaattgctaca taggaaggagctcagcgaaatttgtagatggtgg aaagatcttgatttttaccagaaagttaccttctgctc gtgaccgtgtcgtcgaaggttatttctggattatgg gagtttacttcgaaccacaatatagcttgggtaga aagatgttgaccaaggttattgctatggcttctatc gtcgatgatacatacgattccttcgctacttacgac gaattgataccatatactgacgccatctgaaagatg ggacatcaagtgtatgaatcagctgccaaactata tgcaaatttcgtacaaagcgttattggatgtatacg aggaaatggaacaattgcttgcagataaaggtcg acagtacagagtggaatacgctaagaaagctatg attcggttggtgcaagcatatttgttagaagcgaa gtggacccatttaaactacaagccaactttcgaag aatttagagacaatgctttgccgacatctgggtatg ccatgctagctataaccgcgttcgttggtatgggt gaagttatcacgccagaaacttttgaatgggctg cttctgacccaaagattattaaggcctccactatca tctgccgctttatggatgatatcgctgagcataagt tcaaccacagaagggaggatgactgttccgctat tgaatgttacatgaagcaatacggtgcaacagctc aagaggcatacgacgaatttaacaaacacataga atcgtcttggaaggacgtcaatgaagagttcttga aaccaactgaaatgcctactccggtactgtgtaga agtttgaacctagccagagtcatggatgttttgtac |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | agagaaggtgacggttatactcatgttgggaaag ccgctaagggtggtataacatcacttcttatcgatc ccattcaaatct TABLE 10-continued Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | AMASIVDDTYDSFATY DELIPYTDAIERWDIKC MNQLPNYMQISYKALL DVYEEMEQLLADKGR QYRVEYAKKAMIRLVQ AYLLEAKWTHLNYKPT FEEFRDNALPTSGYAM LAITAFVGMGEVITPET FEWAASDPKIIKASTIIC RFMDDIAEHKFNHRRE DDCSAIECYMEQYKVT AQEAYDEFNKHIESSW KDVNEEFLKPTEMPTP VLCRSLNLARVMDVLY REGDGYTHVGKAAKG GITSLLIDPIQI (SEQ ID NO: 5) | ttgaagctagaaacttatctctatttaccaagatttta gaatcccacaataagtctttattagaatttgccaaa attgatttcaacttgttgcaattgttacaccgtaagg agttgtccgaaatatgtagatggtggaaagactta gattttacaagaaagttacctttcgctagagatga gtcgttgaaggttatttctggattatgggtgtctactt cgaaccacaatactccttgggtagaaagatgttga ccaaagttattgctatggcttctatcgttgacgatac ttatgactcatttgccacttacgacgaattgatccct tatacagacgctattgaacgttgggatatcaagtgt atgaaccagttgccaaattatatgcaaatatcttac aaggctttgttagacgtttacgaggaaatggaaca attgttggctgataagggtagacaatatagagtcg agtacgccaaaaaagcaatgattagattggttcag gcctacttattagaggctaagtggacccatttgaa ctacaagcctacatttgaagagttcagagacaatg ctttaccaacttccggttatgccatgttggctataac cgcattcgttggtatgggtgaagtcattaccccag aaacttttgaatgggccgcttctgatccaaagatta tcaaggcttctactatcatctgccgtttcatggatga tattgccgaacataaattcaaccacagaagagag gacgattgttccgctattgaatgttacatggaacaa tacaaggttacagcccaagaagcttacgacgaat ttaacaagcacatcgaatcatcttggaaggacgtc aatgaagaatttttgaagcctaccgaaatgccaac tccagtcttgtgtagatcttttgaacttggcaagagtt atggatgtcttgtacagagaaggtgatggttatact catgtcggtaaggctgctaaaggtggtatcacctc cttgttgatcgaccctattcaaatttaa (SEQ ID NO: 71) |
| HibWilS QTS124 | Hibiscadelphus wilderianus | Q9SAN0 | 48% | ASQASQVLASPHPAISS ENRPKADFHPGIWGDM FIICPDTDIDAATELQYE ELKAQVRKMIMEPVDD SNQKLPFIDAVQRLGVS YHFEKEIEDELENIYRD TNNNDADTDLYTTALR FRLLREHGFDISCEAFN KLKDEEGNFKASLTSD VRGLLELYQASYMRIH GEDILDEAISFTTAQLTL ALPTLDPPLSEQVGHAL KQSIRRGLPRVEARNFI SIYQDLESHNKSLLEFA KIDFNLLQLLHRKELSEI CRWWKDLDFTRKLPFA RDRVVEGYFWIMGVYF EPQYSLGRKMLTKVIA MASIVDDTYDSFATYD ELIPYTDAIERWDIKCM NQLPNYMQISYKALLD VYEEMEQLLADKGRQ YRVEYAKKAMIRLVQA YLLEAKWTHLNYKPTF EEFRDNALPTSGYAML AITAFVGMGEVITPETF EWAASDPKIIKASTIICR FMDDIAEHKFNHRRED DCSAIECYMKQYGATA QEAYDEFNKHIESSWK DVNEEFLKPTEMPTPVL CRSLNLARVMDVLYRE GDGYTHVGKAAKGGIT SLLIDPIQI (SEQ ID NO: 6) | atggcctcacaggcttcccaagttttagcatctcct cacccagctatatcttccgaaaaccgtccaaagg ctgatttccatccaggtatctggggcgacatgttta ttatctgtccagatacagacattgatgccgctacc gagttgcaatatgaagaattgaaagcccaagtca gaaagatgatcatggaaccagttgacgattctaat caaaagttgccttcattgacgctgtccaaagattg ggtgtttcataccactttgaaaaagaaattgaaga cgaattagaaaacatctacagagatactaataaca acgacgcagacactgatttgtacaccactgccttg agattcagattattgcgtgagcatggttttgatattt cttgcgaagcttttcaacaagttgaaagacgaaga gggtaatttcaaggcttccttaacctctgatgtcag aggtttgttggaattgtatcaggcttcctacatgag aatccacggtgaagatattttggatgaagctatatc tttcacaactgctcaattaactttagctttaccaactt tggatcctccattgtctgagcaagttggtcatgcct tgaagcagtcaatacgtagaggtttgccaagagtt gaagccagaaactttatctctatttaccaagacttg gaatcccacaataagtctttattagaatttgctaaa ttgatttcaacttattgcaattgttacacagaaagga gttgtccgaaatctgtagatggtgaaagacttgg attttaccagaaagttacctttcgctagagatcgtgt cgttgaaggttatttctggatcatgggtgtctacttc gaaccacaatactccttgggtagaaagatgttgac caaagttattgctatggcctctattgttgacgatact tatgactcatttgcaacctacgacgaattgatacca tatagacgctattgaaagatggatatcaagtg tatgaaccaattgccaaattatatgcaaatatcttac aaggctttgttagacgtttacgaggaaatggaaca attgttggctgataagggtagacaatatagagtcg agtacgcaaaaaaagccatgatcagattggtca ggcctacttattagaggctaagtggacccatttga actacaagcctactttgaagagttcagagacaat gctttaccaacctccggttatgccatgttggctatc actgcattcgttggtatgggtgaagtcattacacca gaaacttttgaatgggccgcctctgatccaaagatt attaaggcttctactatcatctgccgtttcatggatg atattgctgaacacaaattcaaccacagaagaga ggacgattgttccgctattgaatgttacatgaaaca atacggtgctacagcccaagaagcatacgacga |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | atttaacaagcatatcgaatcatcttggaaggacg ttaatgaagaattttttaaagcctaccgaaatgccaa caccagtcttgtgtagatctttgaacttggcaagag ttatggatgtcttgtaccgtgaaggtgatggttata ctcatgtcggtaaggctgctaaaggtggcatcac ctccttgttgatcgaccctattcaaatttaa (SEQ ID NO: 72) |
| HibWilS QTS126 | Hibiscadelphus wilderianus | Q9SAN0 | 44% | ASQASQVLASPHPAISS ENRPKADFHPGIWGDM FIICPDTDIDAATELQYE ELKAQVRKMIMEPVDD SNQKLPFIDAVQRLGVS YHFEKEIEDELENIYRD TNNNDADTDLYTTALR FRLLREHGFDISCDAFN KLKDEEGNFKASLTSD VPGLLELYEASYLRVH GEDILDEAISFATAQLT LALPTLHHPLSEQVGH ALKQSIRRGLPRVEARN FISIYQDLESHNKSLLEF AKIDFNLLQLLHRKELS EICRWWKDLDFTRKLP FARDRVVEGYFWIMGV YFEPQYSLGRKMLTKVI AMASIVDDTYDSFATY DELIPYTDAIERWDIKC MNQLPNYMQISYKALL DVYEEMEQLLADKGR QYRVEYAKKAMIRLVQ AYLLEAKWTHLNYKPT FEEFRDNALPTSGYAM LAITAFVGMGEVITPET FEWAASDPKIIKASTIIC RFMDDIAEHKFNHRRE DDCSAIECYMKQYGAT AQEAYDEFNKHIESSW KDVNEEFLKPTEMPTP VLCRSLNLARVMDVLY REGDGYTHVGKAAKG GITSLLIDPIQI (SEQ ID NO: 7) | atggcctcacaggcttcccaagttttagcatctcct cacccagctatatcttccgaaaaccgtccaaagg ctgatttccatccaggtatctggggcgacatgttta ttatctgtccagatacagacattgatgccgctacc gagttgcaatatgaagaattgaaagcccaagtca gaaagatgatcatggaaccagttgacgattctaat caaaagttgcctttcattgacgctgtccaaagattg ggtgtttcataccactttgaaaaagaaattgaaga cgaattagaaaacatctacagagatactaataaca acgacgcagacactgatttgtacaccactgccttg agattcagattattgcgtgagcatggttttgatattt cttgcgatgctttcaacaagttgaaagacgaagaa ggtaatttcaaggctttccttaacctctgacgtccca ggtttgttggaattgtatgaggcttcctacttaaga gttcacggtgaagatatcttggatgaagctatatct ttcgccactgctcagttaaccttggctttaccaactt tgcatcacccattgtctgagcaagttggtcacgca ttgaagcaatcaatcagaagaggtttgccaagag ttgaagctagaaactttatctctatttaccaagattta gaatcccacaataagtctttattagaatttgccaaa attgatttcaacttgttgcaattgttacaccgtaagg agttgtccgaaatatgtagatggtggaaagactta gattttacaagaaagttaccttcgctagagataga gtcgttgaaggttatttctggattatgggtgtctactt cgaaccacaatactccttgggtagaaagatgttga ccaaagttattgctatggcttctatcgttgacgatac ttatgactcatttgccacttacgacgaattgatccct tatacagacgctattgaacgttgggatatcaagtgt atgaaccagttgccaaattatatgcaaatatcttac aaggctttgttagacgtttacgaggaaatggaaca attgttggctgataagggtagacaatatagagtcg agtacgccaaaaaagcaatgattagattggttcag gcctacttattagaggctaagtggaccccatttgaa ctacaagcctacattttgaagagttcagagacaatg ctttaccaacttccggttatgccatgttggctataac cgcattcgttggtatgggtgaagtcattaccccag aaacttttgaatgggccgcttctgatccaaagatta tcaaggcttctactatcatctgccgtttcatggatga tattgccgaacataaattcaaccacagaagagag gacgattgttccgctattgaatgttacatgaaacaa tacggtgctacagcccaagaagcatacgacgaa tttaacaagcacatcgaatcatcttggaaggacgt taatgaagaattttgaagcctaccgaaatgccaa ctccagtcttgtgtagatctttgaacttggcagag ttatggatgtcttgtacagagaaggtgatggttata ctcatgtcggtaaggctgctaaaggtggcatcac ctccttgttgatcgaccctattcaaatttaa (SEQ ID NO: 73) |
| HibWilS QTS19 | Hibiscadelphus wilderianus | A0A067 FTE8 | 12% | SIQVPQISSQNAKSQVM RRTANFHPSVWGDRFA NYTAEDKMNHARDLK ELKALKEEVGRKLLAT AGPIQLNLIDAIQRLGV GYHFERELEQALQHLY NEKYSDDDTEDDLYRIS LRFRLLRQHGYNVSCD KFNMFKDDKGNFKESL ASDALGMLSLYEAAHL GVHGEDILDEAIAFTTT HLKSVATHLSNPLKAQ VRHALRQPLHRGLPRL EHRRYISIYQDDASHYK ALLTLAKLDFNLVQSL | atgtccatacaggttccccaaatttcttcgcaaaat gcaaagtcacaagtaatgcgtagaaccgccaact ttcatccatctgtgtggggagacagattcgctaact acacggctgaggataaaatgaaccacgctcgcg acttgaaggaacttaaagcgttaaaggaagaagt tggtagaaagctgttggccacgctggccaatt caactcaatctaatcgatgctatccaaagattgggt gtcggttatcacttcgaacgagaattggaacaag ctttgcaacatttatacaacgagaagtatagcgat gacgacactgaagatgatttgtacaggattctctg agatttagattgttaagacagcacggttacaatgtc tcctgcgacaaattcaacatgtttaaggatgacaa aggtaacttcaaggaaagtttggcttctgatgcctt gggtatgctctccttatacgaagcggctcatttgg gcgttcacggtgaagatatcttagacgaagctatt</td>
</tr>
</tbody>

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | HKKELCEISRWWKDLD FARKLPFARDRMVECY FWILGVYFEPNYSLARR ILTKVIAMTSIIDDIYDV YGTPEELKLFTEVIERW DESSMDQLPEYMQTFF GALLDLYNEIEKEIANE GWSYRVQYAKEAMKI LVEGYYDESKWFHENY IPKMEEYMRVALVTSG YTMLTTVSFLGMDNIV TKETFDWVFSRPKIIRA SEIIGRFMDDIKSHKFEQ ERGHCASAVECYMREH GVSEEEACSELKKQVD NAWKDINHEMIFSETSK AVPMSVLTRVLNLTRVI DVVYKEGDGYTHVGN EMKQNVAALLIDQVPI (SEQ ID NO: 8) | gcatttaccactactcatctaaagtccgtcgctact cacttatctaatcctctaaaggcccaagttcgtcat gccttgagacaaccgcttcacagaggtttgccaa gattggaacacagaaggtatatcagcatttaccag gatgacgcttctcattacaaagctttgttgacccttg cgaagttggatttcaatctagttcaatcattgcaca aaaaggagctatgtgagatctccagatggtggaa ggatttagacttcgctcgtaagttgccttttgctaga gatgaaatggtcgaatgttatttctggatcttgggt gtgtatttcgaaccaaactactcactggcccggag aatattgaccaaagttattgctatgacttctattattg atgacatctatgacgtttacgggacaccagaaga attgaagttgttcactgaagtaatcgaacgttggg acgaatcgtcaatggaccaactaccagaatacat gcaaacgttttcggtgctcttttagatttatacaatg agatagaaaggaaattgccaacgaaggttggtc ttacagagtccaatatgcaaaagaagctatgaag atttagttgaggggttactacgatgaatctaagtggt tccatgaaaactacataccaaagatggaggaata tatgcgggtagcattagttaccagcggatacaca atgttgactaccgtcagttttctcggggatggacaa cattgttactaaggagacatttgattgggttttctcc agacctaaaatcataagagcatcagaaattatcg gtagattcatggacgatattaaatctcacaaattcg aacaggaaagaggtcactgtgcgtccgctgtcg aatgttatatgagggaacatggcgtgtctgaaga ggaagcttgcagtgagctcaagaagcaagtcga taacgcctggaaggacatcaaccacgaaatgatt ttctccgaaacttctaaggctgttcctatgagcgtg ctaaccagagttttgaacttgacgagagttattgat gtcgtctacaaggaaggtgatggttatactcatgt gggtaatgaaatgaaacaaaacgttgctgctctttt gatcgaccaagtcccaatttaa (SEQ ID NO: 74) |
| HibWilS QTS34 | Hibiscadelph TABLE 10-continued Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | gttgtgtcatcggtaggctcttgaacgatattcgttc<br>ccatgaattagagcagggcagagaccacacgg<br>cttccactgttgaatcttacatgaaggaacacgac<br>accaatgtggacgttgcctgcgaaaagttgagag<br>aaatcgtcgaaaaggcgtggaaagatctgaaca<br>acgaatctctaaaccctactaaggttccaagattg<br>atgatagaaagaatagtaaacttgtcaaagtccaa<br>cgaagaaatttacaaatacaacgacacctacact<br>aattctgatactacaatgaaggacaatattagtcta<br>gtattggttgagtcctgtgattatttcaacaaataa<br>(SEQ ID NO: 75) |
| HibWilS QTS52 | Hibiscadelphus wilderianus | Q39760 | 12% | ASQVSQMPSSSPLSSNK DEMRPKADFQPSIWGD LFLNCPDKNIDAETEKR HQQLKEEVRKMIVAPM ANSTQKLAFIDSVQRLG VSYHFTKEIEDELENIY HNNNDAENDLYTTSLR FRLLREHGFNVSCDVF NKFKDEQGNFKSSVTS DVRGLLELYQASYLRV HGEDILDEAISFTTNHLS LAVASLDYPLSEEVSHA LKQSIRRGLPRVEARHY LSVYQDIESHNKVLLEF AKIDFNMVQLLHRKEL SEISRWWKDLDFQRKL PYARDRVVEGYFWISG VYFEPQYSLGRKMLTK VIAMASIVDDTYDSYA TYEELIPYTKAIERWDI KCIDELPEYMKPSYKAL LDVYEEMEQLVAKHG RQYRVEYAKNAMIRLA QSYLVEARWTLQNYKP SFEEFKANALPTCGYA MLAITSFVGMGDIVTPE TFKWAANDPKIIQASTII CRFMDDVAEHKFEQER GHCASAVECYMREHG VSEEEACSELKKQVDN AWKDINHEMIFSETSKA VPMSVLTRVLNLTRVM DVLYREGDGYTYVGK AAKGGITSLLIEPVAL (SEQ ID NO: 10) | atggccagtcaggtttcacaaatgccttcctcttct<br>ccactatccagcaacaaagatgagatgagacca<br>aaggctgactttcaaccctcgatatggggcgattt<br>gttcctgaattgcccagacaagaacattgatgctg<br>aaaccgaaaagcgtcatcaacaattgaaagaag<br>aagtcagaaagatgatcgtggcaccaatggctaa<br>ttctacacaaaagttggctttcattgactctgttcag<br>aggcttggagtatcctaccactttactaaagaaatt<br>gaggatgaattagaaaacatctatcacaacaataa<br>cgacgcagaaaacgatttgtacacgacttcccta<br>agattcagattattgagagaacatggtttcaatgtc<br>tcttgtgacgttttaacaagtttaaggatgagcaa<br>ggtaatttcaagtcaagtgttacctctgacgtccgc<br>ggtctcttggaattataccaagcgtcgtatttgaga<br>gttcacggtgaagatatcttggacgaagctatttc<br>gttcacaactaatcatctctctttggccgttgcttcct<br>tagattaccctctgtctgaagaggtctctcacgcttt<br>gaagcaaagcataagacgtggtcttccaagagta<br>gaagccagacactatttgagcgttaccaagatat<br>cgaatctcataacaaagtcttgttagaatttgctaa<br>gattgacttcaacatggttcaattgctacataggaa<br>agagctaagtgaaatttcaagatggtggaaagt<br>ctcgattttcaaagaaagttaccttatgcacgcgac<br>cgtgagtcgaaggttacttctggatctccggggtt<br>tacttcgaaccacaatacagctggtagaaagat<br>gttgactaaggttattgctatggcttctatcgttgat<br>gataccatgactcctacgccacctacgaggaatt<br>gatcccatatactaaggccattgaaagatgggac<br>atcaagtgtatagacgaactgccagaatatatgaa<br>gcctagtacaaagctttattggatgtctatgagga<br>aatggaacaattggtcgccaaacacggtcgaca<br>gtacagagtggaatacgctaagaatgctatgattc<br>gattggcgcaatcctacttggttgaagcgagatg<br>gactcttcaaaactacaagccatctttcgaagaatt<br>taaggccaatgctttaccgacatgtggatatgctat<br>gctagctataaccagcttcgttggtatgggtgatat<br>tgtcacgccagaaactttaaatgggctgcaaatg<br>acccgaagattatccaggcttctactatcatctgcc<br>gatttatggatgatgtagctgagcataagttcgaa<br>caagaaaggggggcactgtgcttccgctgtcgagt<br>gttacatgagagaacacggtgtgtcagaagaag<br>aggcatgttctgaattgaaaaagcaagtcgacaa<br>cgcctggaaggacattaaccatgaaatgatttttc<br>ggaaaccctccaaagctgtcccaatgtcggttctca<br>ctagagttcttaacttgactagagttatgacgtatt<br>gtacagaaggtgatggttatacatatgttggta<br>aggctgcaaagggcggtatcacctctcttattgatt<br>gaaccagttgccttgtaa<br>(SEQ ID NO: 76) |
| HibWilS QTS54 | Hibiscadelphus wilderianus | Q39761 | 13% | ASQVSQMPSSSPLSSNK DEMRPKADFQPSIWGD LFLNCPDKNIDAETEKR HQQLKEEVRKMIVAPM ANSTQKLAFIDSVQRLG VSYHFTKEIEDELENIY HNNNDAENDLYTTSIRF RLLREHGYHVDGEEAF NMLKDEEGNFKASLTS DVPGLLELYQASYMRI | atggccagtcaggtttcacaaatgccttcctcttct<br>ccactatccagcaacaaagatgagatgagacca<br>aaggctgactttcaaccctcgatatggggcgattt<br>gttcctgaattgcccagacaagaacattgatgctg<br>aaaccgaaaagcgtcatcaacaattgaaagaag<br>aagtcagaaagatgatcgtggcaccaatggctaa<br>ttctacacaaaagttggctttcattgactctgttcag<br>aggcttggagtatcctaccactttactaaagaaatt<br>gaggatgaattagaaaacatctatcacaacaataa<br>cgacgcagaaaacgatttgtacacgacttccata |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | HGEDILDEAISFTTAQL TLALPTLDPPLSEEVSH ALKQSIRRGLPRVEARH YLSVYQDIESHNKALLE FAKIDFNMLQFLHRKEL SEICRWWKDLDFQRKL PYARDRVVEGYFWISG VYFEPQYSLGRKMLTK VIAMASIVDDTYDSYA TYEELIPYTNAIERWDI KCIDEIPEYMKPSYKAL LDVYEEMVQLVAEHG RQYRVEYAKNAMIRLA QSYLVEAKWTLQNYKP SFEEFKANALPTCGYA MLAITSFVGMGDIVTPE TFKWAASDPKIIQASTII CRFMDDVAEHKFKHRR EDDCSAIECYMEEYGV TAQEAYDVFNKHVESA WKDLNQEFLKPTEMPT EVLNRSLNLARVMDVL YREGDGYTYVGKAAK GGITSLLIEPIAL (SEQ ID NO: 11) | agattcagattattgagagaacatggttaccacgt cgatggtgaggaagccttcaacatgctcaaggac gaagaaggtaatttaaggcttctttgacctcagac gttcctggtttgttagaactatatcaagcctcataca tgcgaatccatggtgaagatattttggacgaagcg atctcttttactactgctcaattaaccttggctttgcc aaccctggatccaccgctctctgaagaggtcagt cacgcgctaaagcaaagtattagaagaggtttac cacgtgtagaagctagacattatctgtccgtttacc aagacatcgaatctcacaataaagctctattggaa tttgccaagattgatttcaacatgttgcagttcctcc acagaaaggaactttcagaaatatgtcgttggtgg aaagatttggacttccaacgcaagttaccatatgct agagatcgcgttgtcgagggttacttctggatcag cggagtttactttgagccacaatacagtttgggtc ggaagatgttaactaaagttattgctatggcttctat tgtcgatgacacatatgactcctacgccacctacg aagaattaatcccttatactaacgccatcgaaaga tgggacattaagtgtatcgatgaaattccggaata catgaaaccatcttacaaagctttgcttgacgtcta cgaagaaatggtacaattggttgctgagcatggta ggcaatacagagttgaatatgcaaagaatgccat gattagattggctcaatcttacttggtggaagcaaa gtggacgttgcaaaattacaaacctagctttgagg aatttaaggcgaacgctctgcccacctgtgggtat gccatgctggcaattacttccttcgttggtatgggc gacattgtcactcctgaaacattcaaatgggctgc atccgatccaaagatcattcaagcttcgacgataa tctgtcgattcatggatgatgtcgctgagcacaag ttcaagcacaggagaagatgactgttctgcca tagaatgttacatggaagaatacggtgttaccgcc caggaggcttacgatgtcttcaacaagcacgttg aatccgcgtggaaagatttgaaccaagaatttctc aagccaactgaaatgccaacagaggtgttgaac agatcacttaacctcgtcgtgttatggacgtattg tatagagaaggtgatggttatacttacgttggtaag gctgctaagggcggtatcacctcttttattgatcgaa ccaatcgctttgtaa (SEQ ID NO: 77) |
| HibWilS QTS55 | *Hibiscadelphus wilderianus* | Q43714 | 12% | ASQASQVLASPHPAISS ENRPKADFHPGIWGDM FIICPDTDIDAATELQYE ELKAQVRKMIMEPVDD SNQKLPFIDAVQRLGVS YHFEKEIEDELENIYRD TNNNDADTDLYTTALR FRLLREHGFDISCDAFN KFKDEAGNFKASLTSD VQGLLELYEASYMRVH GEDILDEAISFTTAQLTL ALPTLHHPLSEQVGHA LKQSIRRGLPRVEARNF ISIYQDLESHNKSLLQF AKIDFNLLQLLHRKELS EICRWWKDLDFTRKLP FARDRVVEGYFWIMGV YFEPQYSLGRKMLTKVI AMASIVDDTYDSYATY DELIPYTNAIERWDIKC MNQLPNYMKISYKALL NVYEEMEQLLANQGR QYRVEYAKKAMIRLVQ AYLLEAKWTHQNYKPT FEEFRDNALPTSGYAM LAITAFVGMGEVITPET PKWAASDPKIIKASTIIC RFMDDIAEHKFEQERG HCASAVECYMREHGVS EEEACSELKKQVDNAW KDINHEMIFSETSKAVP MSVLTRVLNLTRVMDV | atggccagtcaggcttcacaagttttagcatctcc ccacccagctatatcctctgaaaaccggccaaag gctgatttccatcctggtatctggggcgacatgttt attatctgtccagatacggacattgatgccgctac agagctgcaatatgaagaattgaaagcgcaagtc cgcaagatgatcatggaaccagtagacgattcta atcaaaagctaccattcattgacgctgttcaaagg ctcggagtgagctaccactttgaaaaagaaatta gacgaacttgaaaacatctaccgtgataccaata acaacgacgcagacactgatctatacactaccgc cttgagattcagattattgagagagcatggttttgat atttcctgcgatgctttcaacaagttcaaagacgaa gctggtaatttcaaggcttcgttgacttctgacgttc aaggtttgttggaattgtatgaggcctcctacatga gagtccacgtgaagatatcctagatgaagctat atcttttaccactgctcagttaaccttggctttaccta ctttgcatcaccgttgtcagagcaagttggtcac gcactcaagcagagtatcagaagaggcctgcca agagttgaagccagaaactttatctctatttaccaa gatttggaatcccacaataagtccttgttacaattc gctaaaattgactttaacctttacaattgctccata ggaaggaactcagcgaaatttgtagatggtggaa agatcttgatttcactagaaagttgccttttgcacgt gaccgtgtcgtcgaaggttatttctggattatggga gtttacttcgaaccacaatatagctgggtagaaa gatgttgaccaaggttattgctatggcttctatcgtc gatgatacatacgattcttacgctacatatgacgaa ttgataccatatactaacgccatcgaaagatgacgga catcaagtgtatgaatcaactgccaaactacatga agaattagttacaaagcattattgaatgtatatgagg agtggaacaattgcttgcgaatcaaggtcgaca gtacagagtggaatacgctaagaaagctatgatt |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | LYREGDGYTHVGKAA KGGITSLLIDPIQI (SEQ ID NO: 12) | cggttggtgcaagcctacttattagaagcgaagtg gactcatcaaaactacaagccaaccttcgaagaa tttagagacaatgctttgccgacatcagggtatgct atgctagctataaccgcgttcgttggtatgggtga agttatcacgccagaaaacttttaaatgggccgctt ctgacccaaagattattaaggcttccactatcatct gccgctttatggatgatatcgctgagcataagttc gagcaagaaaggggggcactgtgcttccgctgtc gaatgttacatgagagaacacggtgtctcagaag aagaggcctgttctgaattgaaaaagcaggtcga caacgcctggaaggatattaaccatgagatgattt ttagtgaaacatccaaagctgtcccaatgagtgtt ctaaccagagttttgaaccttactagagttatggac gtattgtacagagaaggtgatggttatacgcatgt cggtaaggctgcaaaggggtggtatcacctcttttgt tgattgaccccattcaaatctaa (SEQ ID NO: 78) |
| HibWilS QTS63 | Hibis- cadel- phus wilder- ianus | Q9FQ26 | 12% | AASFANKCRPLANFHP TVWGYHFLYYNPEITN QEKIEVDEYKETIRKML VEAPEGSEQKLVLIDA MQRLGVAYHFHNEIET SIQNIFDAPKQNNDDNL HIVSLRFRLVRQQGHY MSSDVFKQFTNQDGKF KETLTNDVQGLLSLYE ASHLRVRNEEILEEALT FTTTHLESIVSNLSNKN NSLKVEVSEALSQPIRM TLPRIGARKYISIYENND AHNHLLLKFAKLDFNM LQKFHQRELSDLTRWW KDLDFANKIPYARDRL VECYFWILGVYFEPKYS RARKMMTKVLKMTSII DDTFDAYANFDELVPF NDAIQRWDANAIDSIPP YMRPIYQALLDIYGEM DQVLSKEGKLDRVYYA KYEMKKLVRAYFKESQ WLNDDNHIPKYEEHME NAIVTVGYMMGATNC LVGMEEFISKETFEWL MSEPVIVRASSLIGRAM DDIVGHEVEQERGHCA SAVECYMREHGVSEEE ACSELKKQVDNAWKDI NHEMIFSETSKAVPMSV LTRVLNLTRVIDTLYQE EDEYTNAKGKLKNMIH SILIESVKI (SEQ ID NO: 13) | atggccgcatcatttgctaacaaatgtagacccttta gctaatttccacccaactgtttgggggttaccatttct tgtattacaacccagagataaccaatcaggaaaa gatcgaagtcgatgaatacaaggaaacaattcgt aagatgttggttgaagcccctgaagggtccgagc aaaaattggtcttaatcgacgctatgcaaagattg ggtgttgcatatcactttcataacgaaattgaaacc tctattcaaaatatcttcgatgctccaaagcaaac aacgacgataacttgcacattgtctctttaagattc agattggtccgtcaacagggtcattacatgtcctct gacgttttaagcaattcactaaccaagatggtaaa ttcaaggaaaccttgactaatgatgtccaaggtttg ttgtcattatatgaagcttctcacttgagagttagaa atgaagaaatattgaggaagctttgacttttacca caactcatttggaatccatcgtttctaacttatcaaa caaaaataactcttttaaaggttgaagtttctgaagc tttgtcccaaccaatcagaatgactttgccaagaat tggtgccagaaagtacatttccatatacgaaaaca atgacgcccacaaccatttgttgttaaagttcgcta agttggattttaatatgttacaaaagttccaccaaa gagaattgtccgacttgaccagatggtggaaaga cttggactttgctaacaagatcccatatgctagag atcgtttagtcgagtgctatttttggattttgggtgttt acttcgaacctaaatactctcgtgctagaaagatg atgaccaagtcttgaaaatgacatctattattgat gatactttgatgcttacgccaatttcgacgaattg ttccattcaatgacgccatccaaagatgggacg ctaacgcaatcgattctattccaccatacatgcgtc caatctaccaggccttgttagatatatatggtgaaa tggaccaagtttatccaaagagggtaagttggat agagtctactatgctaagtatgagatgaaaaagtt ggtcagagcctactttaaggaatctcaatggttaa acgacgataatcatatacctaagtatgaagaacac atggaaacgctattgttactgtcggttacatgatg ggtgctacaaactgtttggttggtatggaggaattt atctcaaagaaaccttcgaatggttgatgtcaga accagttattgttagagcatcttccttgataggtag agcaatggatgatatcgtcggtcacgaggttgaa caagaacgtggtcattgtgcttcagcagtcgaatg ttacatgagagagcatggtgtttctgaagaagaag cttgctccgaattaaagaagcaagttgacaacgct tggaaggacattaaccacgagatgatcttctctga aacttctaaagctgtcccaatgtctgtcttaaccag agttttaaacttgacaagagttattgatactttgtac caggaagaagatgaatacaccaacgctaagggt aaattaaaaaatatgatccactccatcttgattgagt cagtcaagatctaa (SEQ ID NO: 79) |
| HibWilS QTS90 | Hibis- cadel- phus wilder- ianus | B1B1U4 | 25% | EKQSLTFDGDEEAKIDR KSSKYHPSIWGDYFIQN SSLTHAKESTQRMIKRV EELKVQVKSMFKDTSD LLQLMNLINSIQMLGLD | atggaaaagcagtctttgacatttgatggtgacga ggaagcaaaaatagatcgtaagtcatccaagtac catccttctatttggggcgactatttcatccaaaatt cctctttaacccacgccaaagaatctactcaagat gatcaagagagttgaagaattgaaggtccaag |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | YHFENEIDEALRLIYEV DDKSYGLYETSLRFQLL RQHGYHVDGEEAFNM LKDEEGNFKASLTSDVP GLLELYQASYMRIHGE DILDEAISFTTAQLTLAL PTLDPPLSAQVSLFLELP LCRRNKILLARKYILIY QEDAMRNNVILELAKL NFNLLQSLYQEELKKISI WWNDLAFAKSLSFTRD RVVEGYYWVLTIYFEP QHSRARVICSKVFAFLS IMDDIYDNYGILEECTL LTEAIKRWNPQAIDGLP EYLKDYYLKLLKTFEEF EDELELNEKYRMLYLQ DEVKALAISYLQEAKW GIERHVPSLDEHLHNSL ISSGSSTVICASFVGMG EVATKEVFDWLSSFPK VVEACCVIGRLLNDIRS HEFEQERGHCASAVEC YMREHGVSEEEACSEL KKQVDNAWKDINHEMI FSETSKAVPMSVLTRVL NLTRGNEEIYKYNDTY TNSDTTMKDNISLVLVE SCDYFNK (SEQ ID NO: 14) | ttaaatcaatgttcaaggacacttccgatttattgca attgatgaacttaattaactctattcaaatgttgggtt tggactaccactttgaaaatgaaatcgatgaggct ttgagattgatctatgaagtcgacgataagtcctac ggtttgtacgaaacatcattaagattccagttgttaa gacaacatggttaccacgttgatggtgaagaagc tttcaacatgttgaaggatgaggaagtaactttaa agcttctttaacctccgacgttccaggtttgttaga gttgtatcaagcctcttacatgcgtattcatggtga agatatattggatgaagctatttcattcactaccgct caattaactttggctttgccaacttttagacccaccat tgtccgcacaagtctctttgttcttggagttgccatt atgcagaagaaacaagattttgttggccagaaaat acatcttgatatatcaagaagatgctatgcgtaata atgttatttttggagttagccaagttgaactttaactta ttgcaatctttataccaagaagaattgaagaaaatc tctatctggtggaatgacttagcttttgctaagtcttt atctttcaccagagatagagtcgttgaaggttatta ctgggtcttgactatctacttcgaacctcagcactc cagagccagagttatttgttccaaagttttgctttt tgtctattatggatgacattatgacaactatggtat cttggaagaatgtacattattaaccgaagctattaa gagatggaacccacaagcaatcgacggtttgcc agaatacttgaaagactattacttgaagttgttaaa gactttcgaggaatttgaagatgaattagaattgaa tgagaagtacagaatgttgtatttgcaagatgaag ttaaagctttggctatctcctacttacaagaggcca agtggggtattgaaagacacgtcccttcattagat gagcatttgcacaattctttgatatcctctggttcttc cactgtcatttgtgcttcattcgttggtatgggtgaa gttgctaccaaggaagtcttcgattggttgtcctctt tcccaaaggttgtcgaagcctgttgtgttatcggta gattgttgaacgatattcgttcccatgaatttgagc aggaaaagaggtcactgcgcttccgctgttgaatgt tacatgagagaaacacggtgtctctgaagaagaag cctgctcagaattgaagaagcaagttgacaacgc atggaaagatataaaccatgaaatgatattctctga aacatctaaggccgttcctatgtcagtcttgacca gagttttgaacttgacccgtggtaatgaagaaatct acaagtacaacgatacttatactaattcagacacc accatgaaagacaacatctccttggtcttggttga atcttgtgactatttcaacaagtaa (SEQ ID NO: 80) |
| LeuGraS QTS335 | Leucadendron grandiflorum | A0A067 FTE8 | 14% | SIQVPQISSQNAKSQVM RRTANFHPSVWGDRFA NYTAEDKMNHARDLK ELKALKEEVGRKLLAT AGPIQLNLIDAIQRLGV GYHFERELEQALQHLY NEKYSDDDTEDDLYRIS LRFRLLRQHGYNVSCD AFNRFKDTKGSFKEDLI KDVNSMLCLYEATHLR VHGEDILDEALGFTTSQ LKSILPKLKPLLASQVM HALKQPLHRGLPRLEH RRYISIYQDDASHYKAL LTLAKLDFNLVQSLHK KELCEISRWWKDLDFA RKLPFARDRMVECYFW ILGVYFEPNYSLARRILT KVIAMTSIIDDIYDVYG TPEELKLFTEVIERWDE SSMDQLPEYMQTFFGA LLDLYNEIEKEIANEGW SYRVQYAKEAMKILVE GYYDESKWFHENYIPK MEEYMRVALVTSGYT MLTTVSFLGMDNIVTK ETFDWVFSRPKIIRASEI IGRFMDDIKSHKFEQER | atgtccatacaggttccccaaatttcttcgcaaaat gcaaagtcacaagtaatgcgtagaaccgccaact ttcatccatctgtgtggggagacagattcgctaact acacggctgaggataaaatgaaccacgctcgcg acttgaaggaacttaaagcgttaaaggaagaagt tggtagaaagctgttggccacagctggcccaatt caactcaatctaatcgatgctatccaaagattgggt gtcggttatcacttcgaacgagaattggaacaag ctttgcaacatttatacaacgagaagtatagcgat gacgacactgaagatgatttgtacaggatttctctg agatttagattgttaagacagcacggttacaatgtc tcctgcgacgccttcaacagatttaaagataccaa gggtagtttcaaggaagacttgatcaaagatgtta actctatgctctgtttatacgaagcaactcatttgcg ggtcacggtgaagatatttggacgaagctttggt gatttacaacttcccaactaaagtccatcttaccta agtaaaaccattgctggcttctcaagtcatgcatg ccttgaagcaaccgctacaccgtggtttgccaag actcgaacacagaaggtatattagcatttaccagg atgacgcttctcattacaaagccttgttgactcttgc gaagttggatttcaatctagttcaatcattacacaa aaaggagctctgtgagatccagatggtggaag gatttagacttcgctcgtaagttgcctttgctagag atagaatggtcgaatgttatttctggatcttgggtgt gtatttcgaaccaaactactcactggctagaagaa tattgaccaaagttattgctatgacctctattatcgat gacatttatgacgtttacggcactccagaagaatt gaagctattcactgaagtaatcgaacgttgggac |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
| --- | --- | --- | --- | --- | --- |
| | | | | GHAASAVECYMKQHG LSEQEVCEELYRQVSN AWKDINEECLNPTAVP MPLLMRALNLARVIDV VYKEGDGYTHVGNEM KQNVAALLIDQVPI (SEQ ID NO: 15) | gaatcgtcaatggaccaactgccagaatacatgc aaacgttttcggtgctttgttagatttatacaatgag atagaaaaggaaattgcaaacgaaggttggtctt acagagtccagtatgcgaaagaagctatgaagat tttggttgagggttactacgatgaatctaagtggtt ccatgaaaattacatacccaagatggaggaatat atgcgggtagccttagttaccagcgggtacacaa tgttgactaccgtcagttttctggggatggacaac atcgttactaaggagacatttgattgggttttctcca gacctaagataatccgagccagtgaaattattggt agattcatggacgatatcaaatctcataagtttgaa caagagagaggtcacgctgcaagcgctgtcgaa tgttatatgaagcaacacggtctctcagaacaaga agtctgtgaagaactttacagacaagtctccaacg cttggaaggacatcaatgaggaatgcttgaatcc aaccgctgttccaatgccattgttgatgagagcac taaacttggcacgcgtaatcgacgtagtttataaa gaaggtgacggttacactcacgttggtaacgaaa tgaagcaaaacgtggctgctctacttattgatcaa gtaccaatctaa (SEQ ID NO: 81) |
| LeuGraS QTS345 | Leucadendron grandiflorum | A0A0A0 QUT9 | 12% | SAAQVSPAPVPAHNAA ASKEEVRRSAGYHPSF WGEFFLTHTSEYAKKD DKIQKQHEELKQEVKG MLVDATTEPTKKLELID AILRLGVGYHFEDEIQA ELERIHRLGDLDCDLYN TCIWFRVLRGQGFTVS AEEFNKFKNSDGNFKE DLINDVSGMLCLYEAT HLRVHGEDILDEALEFT TTRLKSILPDLEPPLATQ VMHALELPYHKGMQR LEARQYIPIYEADMTKN ISLLHFAKLDFNLLQAL HQSEIREITRWWKDLDF KTRLPYARDRLVECYF WILGVQYEPQYSMSRL FLTKVISLASVFDDTYD IYGTFEELKLLTDAIER WEIEATDSLPSYMQILY RALLDVFDEYKDKLIN VQGKDYCLYYGKEAM KGLIRSYHTEAVSFHTG YVQNFEEYLDNSAVSS GYPMLTVEALIGMGHP YATKEALDWALKVPR VIKASSDICRLVDDLRT YKVEEERGDAPSGVHC YMRDYNVSEEEACSKI EEMIDLAWKAINEEMQ KPGHLPLPILLPALNFTR MMEVLYQNIDGYTNSG GRTKDRITSLLVHPITI (SEQ ID NO: 16) | atgtccgcagcgcaagtcagtcctgctccagttcc agcccacaatgctgctgcttctaaggaagaggtg cgtagatcggccggatatcatccatcattctgggg tgaattttccttactcacacaagcgaatacgctaa aaaggacgataagattcagaaacaacatgaaga attgaagcaagaggttaagggcatgctagtagat gctacgaccgaacccactaaaaagttagaattga tagacgccatcctgagattgggtgtcggttaccac tttgaagatgagattcaagctgaattggaaaggat ccacagactcggtgacttagattgcgacttgtata acacctgtatttggttcagagttcttagaggtcaag gttttactgtctctgctgaagaatttaacaagttcaa aaattccgacggaaacttcaaggaagatttgatca atgacgtttctggtatgttgtgtttatacgaagccac ccatttgcgggtccacggtgaggatattttggatga agcgctcgaatttactaccacacgtttaaagtctat cttaccagacttggaaccgccattggctactcaag taatgcacgcactagaactaccttaccataagggt atgcagagattggaagcccgacaatacattccaa tctatgaagccgatatgactaaaaaacatcagcttgt tgcatttcgctaagcttgatttcaacctgttacaggc tctccaccaatccgaaatcagagagataacccgc tggtggaaagatcttgactttaaaactagattgcca tatgctagagatcgcttagtcgaatgttacttctgg attctaggcgttcaatacgagccacaatacagtat gtctcggttgttttaaccaaggttatttcattggctt ctgtcttcgatgacacatatgacatttacggtacctt cgaagaattaaagttgttgactgacgccatagaaa gatgggagatcgaagcaacagattccttgccgtc ttacatgcaaattttatatcgcgctttgctggacgtc ttcgatgaatacaaggataaattgattaacgttcaa gggaaggactattgtttgtattacggtaaagaagc gatgaaggggttgattcgtagctaccacactgaag ctgtgtcgtttcataccggctatgttcagaatttcga ggaatacttagacaactccgcagtttcctctggtta cccaatgctgacggttgaagctttgattggtatgg gacaccttacgctactaaggaagctttagattgg gcattgaaggtgccaagagttatcaaggctagttc agacatctgtagattagtcgatgacttaaggacgt acaaggtcgaggaggaaagaggtgatgctccct cggggtgccattgctacatgagagactataatgtc tcagaagaagaagcatgttctaagatcgaagaaa tgatcgatctggcctggaaagctataaacgaaga aatgcaaaagccaggtcatctaccactaccaatct tgttgcctgccttgaacttcactagaatgatggag gtcctttaccaaaatattgatggttatacaaattccg gtggtagaaccaaggacagaatcacctctttgttg gttcacccaattactatttaa (SEQ ID NO: 82) |

TABLE 10-continued

Amino acid (AA) and nucleic acid sequences of sesquiterpene chimeras.

| Chimera Name | Rare DNA source | Extant scaffold Uni-prot # | % Rare DNA | Chimera AA sequence (beginning after the first encoded amino acid M) | Chimera Nucleic Acid Sequence |
|---|---|---|---|---|---|
| LeuGraS QTS365 | *Leuca-dendron grandi-florum* | D0VMR6 | 11% | SSAKLGSASEDVNRRD ANYHPTVWGDFFLTHS SNFLENNDSILEKHEEL KQEVRNLLVVETSDLPS KIQLTDEIIRLGVGYHFE TEIKAQLEKLHDHQLH LNFDLLTTSVWFRLLR GHGFSISSDIFNKFKNSD GNFKEDLINDVSGMLC LYEATHLRVHGEDILDE ALEFTTTRLKSILPDLEP PLNECVRDALHIPYHRN VQRLAARQYIPQYDAE PTKIESLSLFAKIDFNML QALHQRELREASRWW KEFDFPSKLPYARDRIA EGYYWMMGAHFEPKF SLSRKFLNRIIGITSLIDD TYDVYGTLEEVTLFTE AVERWDIEAVKDIPKY MQVIYTGMLGIFEDFK DNLINARGKDYCIDYAI EVFKEIVRSYQREAEYF HTGYVPSYDEYMENSII SGGYKMFIILMLIGRGE FELKETLDWASTIPEMV EASSLIARYIDDLQTYK AEEERGETVSAVRCYM REFGVSEEQACKKMRE MIEIEWKRLNKTTLEAD EISSSVVIPSLNFTRVLE VMYDKGDGYSDSQGV TKDRIAALLRHAIEI (SEQ ID NO: 17) | atgtcctcagcaaaattgggttctgcttctgaagat gtcaaccgtagagacgctaattaccatccaaccg tttgggagatttcttttaacacactcctctaacttc ttggagaacaatgactcaatattggaaaagcacg aagaattgaagcaagaggttagaaacttattggtc gttgaaacttctgacttgccttccaagattcagttga ctgatgaaattatcagattaggtgtcggttatcatttt gagaccgaaatcaaagcccaattagaaaagttgc acgatcatcaattgcacttgaacttcgacttgttga ccacatctgtttggttcagattattgagaggtcacg gttttccattcttccgacatcttcaataagttcaaa aattcagatggtaactttaaggaagatttaatcaac gacgtttctggtatgttgtgcttgtacgaacgtactc atttgcgtgtccacggtgaagatattttagacgaa gccttggaatttactactaccagattgaagtctattt tgccagatttagaaccaccattaaatgaatgtgtca gagacgctttgcatattccttatcacagaaacgttc aacgtttggctgcaagacaatacataccacagta cgatgccgaaccaacaaaaatcgagtcttttgtcat tattcgctaagattgatttcaacatgttgcaagcttt gcatcaaagagaattgagagaggcttccagatg gtggaaagaatttgacttcccttctaagttaccatat gccagagatcgtatcgctgaaggttactactggat gatgggtgcccactttgaaccaaagttctcattgtc tcgtaagttcttaaacagaatcattggtatcacttctt taattgatgacacctatgatgtttacggtactttgga ggaagttactttgttaccgaagctgttgaaagatg ggacattgaagctgtcaaggacattccaaaatac atgcaagtcatctataccaggtatgttaggtatatg aagatttcaaagacaacttgataaatgctagaggt aaggattactgtatcgactatgcaatcgaggtttc aaagaaatcgttagatcctaccaaagagaagctg aatatttccacaccggttacgttccatcctacgatg aatacatggaaaactctattatatctggtggttaca agatgttcattatcttaatgttaatcggtagaggag aatttgagttgaaggaaactttggactgggcttcc actattcctgaaatggtcgaggcatcttccttgatc gctcgttatattgacgacttgcaaacctataaagct gaagaagagagaggagaaaccgtctccgcagt cagatgttacatgcgtgaatttggtgtttcagaaga acaagcctgtaagaagatgagagagatgatcga aattgaatggaagagattgaataaaacaacttag aagctgacgaaattctcatcgtcgttatcattccatc attgaacttcaccagagttttggaggtcatgtacga taagggtgatggttactctgattcccaaggtgttac taaagaccgtatcgccgctttattgagacacgcca tcgaaatctaa (SEQ ID NO: 83) |
| LeuGraS QTS377 | *Leuca-dendron grandi-florum* | Q39760 | 14% | ASQVSQMPSSSPLSSNK DEMRPKADFQPSIWGD LFLNCPDKNIDAETEKR HQQLKEEVRKMIVAPM ANSTQKLAFIDSVQRLG VSYHFTKEIEDELENIY HNNNDAENDLYTTSLR FRLLREHGFNVSCDAF NRFKDTKGSFKEDLIKD VNSMLCLYEATHLRVH GEDILDEALGFTTSQLK SILPKLKPLLASQVMHA LKQPLRRGLPRVEARH YLSVYQDIESHNKVLLE FAKIDFNMVQLLHRKE LSEISRWWKDLDFQRK LPYARDRVVEGYFWIS GVYFEPQYSLGRKMLT KVIAMASIVDDTYDSY ATYEELIPYTKAIERWD IKCIDELPEYMKPSYKA LLDVYEEMEQLVAKHG RQYRVEYAKNAMIRLA | atggccagtcaggtttcacaaatgccttcctcttct ccactatccagcaacaaagatgagatgagacca aaggctgactttcaaccctcgatatgggggcgattt gttcctgaattgcccagacaagaacattgatgctg aaaccgaaaagcgtcatcaacaattgaaagaag aagtcagaaagatgatcgtggcaccaatggctaa ttctacacaaaagttggctttcattgactctgttcag aggcttggagtatcctaccactttactaaagaaatt gaggatgaattagaaaacatctatcacaacaataa cgacgcagaaaacgatttgtacacgactcccta agattcagattattgagagacatggtttcaatgtc tcttgtgacgcctttaacagatttaaggataccaaa ggttcattcaaggaagacttgatcaaggatgttaat tccatgtttgtgttatacgaagcgactcaccttcga gttcatggtgaggatattttggacgaagctttgggt ttcacaacctctcaactcaaatcaatcttacctaagt taaagccattgctggcttcgcaagtcatgcacgct tgaagcaaccgctaagacggtggttgccagag ttgaagccagacactatttggcgtttaccaagat attgaatctcataacaaagtcttgttggaatttgcta agatcgacttcaacatggttcaacttctccatagga aggagctcagtgaaattagtagatggtggaaaga tttagacttccaacgtaaattgccatacgctagaga |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | QSYLVEARWTLQNYKP SFEEFKANALPTCGYA MLAITSFVGMGDIVTPE TFKWAANDPKIIQASTII CRFMDDVAEHKFKHRR EDDCSAIECYMEEYGV TAQEAYDVFNKHVESA WKDVNKEFLKPTEMPT EVLNRSLNLARVMDVL YREGDGYTYVGKAAK GGITSLLIEPVAL (SEQ ID NO: 18) | tcgcgttgtcgaaggttatttttggattagtggggta tacttcgaaccgcaatattccctgggtagaaagat gttaactaaggttattgccatggcttctatcgtcga cgatacctacgattcttacgcaacttatgaggaatt aatcccatacaccaaagctatagaaagatgggat ataaagtgtatagacgaattgcctgagtatatgaa gccatcatacaaggctttgttggacgtgtacgaag aaatggaacagttagttgccaaacacggtcggca atacagagttgaatatgctaagaatgctatgatcc ggctagcccaatcttatctggtcgaggctagatgg actctacaaaactacaagccttccttcgaagaattt aaggctaacgcattgccaacttgtggttacgctat gttggcgatcacttctttcgttggtatgggcgacat tgttaccccagaaacatttaagtgggccgcgaac gatccaaagattattcaagcttcaacgataatctgc cggtttatggatgacgtcgccgaacacaagttca aacataggagggaagacgattgttctgctatcga gtgttatatggaagaatacggagtaactgcccag gaggcctacgacgtcttcaataagcacgtggaat cagcttggaaggatgttaataaggaatttttgaag cccaccgagatgcctacggaagtgctgaacaga tctttgaacctcgcaagagttatggatgtcttgtac agagaaggtgatggttatacttatgtgggtaaggc tgctaaaggtgggattacctcccctattgatcgaac cagtcgctttataa (SEQ ID NO: 84) |
| LeuGraS QTS379 | Leucadendron grandiflorum | Q39761 | 12% | ASQVSQMPSSSPLSSNK DEMRPKADFQPSIWGD LFLNCPDKNIDAETEKR HQQLKEEVRKMIVAPM ANSTQKLAFIDSVQRLG VSYHFTKEIEDELENIY HNNNDAENDLYTTSIRF RLLREHGYNVSCDIFNK FKNSDGNFKEDLINDVS GMLCLYEATHLRVHGE DILDEALEFTTTRLKSIL PDLEPPLATQVMHALK QSIRRGLPRVEARHYLS VYQDIESHNKALLEFA KIDFNMLQFLHRKELSE ICRWWKDLDFQRKLPY ARDRVVEGYFWISGVY FEPQYSLGRKMLTKVIA MASIVDDTYDSYATYE ELIPYTNAIERWDIKCID EIPEYMKPSYKALLDV YEEMVQLVAEHGRQY RVEYAKNAMIRLAQSY LVEAKWTLQNYKPSFE EFKANALPTCGYAMLA ITSFVGMGDIVTPETFK WAASDPKIIQASTIICRF MDDVAEHKFKHRRED DCSAIECYMEEYGVTA QEAYDVFNKHVESAW KDLNQEFLKPTEMPTE VLNRSLNLARVMDVLY REGDGYTYVGKAAKG GITSLLIEPIAL (SEQ ID NO: 19) | atggccagtcaggtttcacaaatgccttcctcttct ccactatccagcaacaaagatgagatgagacca aaggctgactttcaaccctcgatatggggcgattt gttcctgaattgcccagacaagaacattgatgctg aaaccgaaaagcgtcatcaacaattgaaagaag aagtcagaaagatgatcgtggcaccaatggctaa ttctacacaaaagttggctttcattgactctgttcag aggcttggagtatcctaccactttactaaagaaatt gaggatgaattagaaaacatctatcacaacaataa cgacgcagaaaacgatttgtacacgacttccata agattcagattattgagagaacatggttacaatgtc tcttgtgacatctttaacaagttcaagaatagcgat ggtaacttcaaggaagacttgattaatgatgtttca ggtatgctctgtttatatgaagcgacccacttgcga gttcatggtgaggatatcttagacgaagctttggga atttacaactactcgcctaaaatctattttgcctgac ttagaaccaccccctggccacccaagtcatgcacg ctttgaagcaaagcatcagacgtggtcttccaaga gttgaagccagacactacttgagtgtttatcaagat attgaatctcataacaaagctttgttggaatttgcta agattgatttcaacatgttacaattcctacataggga aggagctatcggaaatctgtagatggtggaaaga tctcgattttcaaagaaagttaccttacgcacggg accgtgtcgtcgaaggttatttctggatttccgggg tttacttcgaaccacaatacagtttgggtagaaag atgttgactaaggttattgctatggcttctatcgtcg atgacacctacgattcttacgccacctatgaggaa ttgataccatatactaacgccatcgaaagatggga catcaagtgtatagacgagatcccagaatacatg aagcttcgtataaagctttattggatgtatacgag gaaatggtgcaattggttgccgaacacggtagac agtacagagtggaatacgctaagaatgctatgatt cgccttgcgcaatcctacttggttgaagcgaaatg gactctccaaaactacaagccatcttttcgaagaat ttaaggccaatgctttaccgacatgcggatatgct atgctagctatcaccagcttcgttggtatgggtgat attgtcacgccagaaacttttaaatgggctgcatct gacccaaagattattcaggcttccactatcatctgt aggttcatggatgatgttgctgaacataagtttaag cacagaagaagacgactgttcagctattgaat gttacatggaagaatacggcgtcaccgcgcaag aagcctacgacgtattcaacaaacacgtcgagtc ggcatggaaggatctgaaccaagaatttctaaaa cccactgagatgccaacagaagttctcaacagaa gtttgaacttggctagagtaatggacgttttgtata |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | gagagggtgatggttatacttatgttggtaaagcc gctaagggtggcattacctcattgcttatcgagcc aatcgctttgtaa (SEQ ID NO: 85) |
| LeuGraS QTS385 | Leucadendron grandiflorum | Q5SBP4 | 13% | ESRRSANYQASIWETNF TNSPLLSKLQNELSVAH LEELKLEVKQLIWSTKD PLFLLKFIDSIQRLGVAY HFEEEIKESLHLVYLEE RNGDHQHYKEKGLHFT ALRFRILRQDGYHVPQ DVFSSFMNKAGDFEES LSKDTKGLVSLYEASY LSMEGETILDMAKDFSS HHLHKMVEDATDKRV ANQIIHSLEMPLHRRVQ KLEAIWFIQFYECGSDA NPTLVELAKLDFNMVQ ATYQEELKRLSRWYEE TGLQEKLSFARHRLAE AFLWSMGIIPEGHFGYG RMHLMKIGAYITLLDDI YDVYGTLEELQVLTEII ERWDINLLDQLPEYMQ IFFLYMFNSTNELAYEIL RDQGINVISNLKGLWV ELSQCYFKEATWFHNG YTPTTEEYLNVACISAS GPVILFSGYFTTTNPINK HELQSLERHAHSLSMIL RLADDLGTSSDEMKRG DVPKAIQCFMNDTGCC EEEARQHVKRLIDAEW KKKMNKDILMEKPFKNF CPTAMNLGRISMSFYE HGDGYGGPHSDTKKK MVSLFVQPMNITI (SEQ ID NO: 20) | atggaaagtaggcgttcagcaaattatcaggcttc catatgggagacaaactttactaactctccacttta tctaagttgcaaaatgaactgtcggtcgcccatct cgaagaattgaaactagaggtgaagcaattaatct ggagcacgaaggatcccttattccttttgaaattca ttgactccattcaaagattgggcgttgcttaccactt tgaagaagaaatcaaggaatctttgcacctggtct acctggaagagcgaaacggtgatcatcaacact ataaggaaaaaggattgcatttcaccgctttgaga ttcagaatattgagacaggacggttaccacgtacc acaagatgttttttcttcattcatgaataaggctggt gactttgaagaaagtttatccaaagacactaaggg tttggtctctttgtacgaagcctcctacctctctatg gaaggtgaaaccatttggatatggccaaggattt ctcctctcaccatttacacaagatggttgaagatgc tactgacaaaagagttgctaaccaaatcattcata gcttggagatgcctttgcatagaagagttcaaaag ctagaggctatctggttcatccaattttatgaatgc ggttccgacgccaacccgaccttggtcgaattgg cgaaattagattttaatatggtgcaagctacttacc aagaagaattaaagcgtctatctaggtggtacga ggaaaccggtctccaagaaaagttgtctttcgctc gtcacagattggctgaagctttcttgtggtctatgg gcattattcctgaaggtcatttcggatatggcagaa tgcacctatgaagatcggtgcatacattaccttatt ggatgatatttatgacgtttatgtactttggaagaa ttgcaagtattgacagaaatcatcgaaagatggg atattaacctttggaccagttgccagaatacatgc aaatattcttcctctacatgtttaactctacaaatgaa ctagcttacgaaatcttaagagaccaaggtattaat gtcatatccaaccttaaaggtctttgggtcgaactg tcacaatgttatttcaaagaagccacgtggttccac aacggttataccccaaccactgaggaataccta acgttgcttgtatttcagcgtccggtccagttatctt gttttcgggatactttactactacaaatccaatcaac aagcatgaattgcaatcttagaaagacacgctca ctcttaagtatgatcttaagactagcggatgacct aggtacttcttcggatgagatgaagcggggtgat gttcctaaggctattcaatgtttcatgaacgacacg gggtgttgcgaagaagaagccagacagcacgtt aagagattgattgacgcagaatggaagaagatg aataaggatatcttgatggagaagccatttaaaaa cttctgtccaactgcaatgaatttaggccgtatcag tatgtctttctacgagcacggtgacggttacggcg gtccacattctgataccaaaaagaagatggtctcg ttgttttgttcaacccatgaatattaccatttaa (SEQ ID NO: 86) |
| LeuGraS QTS393 | Leucadendron grandiflorum | Q9T0J9 | 10% | ESQTTFKYESLAFTKLS HCQWTDYFLSVPIDESE LDVITREIDILKPEVMEL LSSQGDDETSKRKVLLI QLLLSLGLAFHFENEIK NILEHAFRKIDDITGDE KDLSTISIMFRVFRTYG HNLPSSIFNKFKNSDGN FKEDLINDVSGMLCLY EATHLRVHGEDILDEAL EFTTTRLKSILPGGTCRP HILRLIRNTLYLPQRwN MEAVIAREYISFYEQEE DHDKMLLRLAKLNFKL LQLHYIKELKSFIKWW MELGLTSKWPSQFRERI VEAWLAGLMMYFEPQ FSGGRVIAAKFNYLLTI LDDACDHYFSIHELTRL | atggaatcacagactacattcaaatatgagtcttta gcatttaccaagttgtcccattgccaatggactgat tacttcttgtctgttccaatagacgaatccgaattgg acgtcatcaccagagaaattgatatttaaagcctg aggttatggaattgttatcttcacaaggtgatgacg aaacatctaagcgtaaagtcttgttgatccaattgtt gttatctttgggattagcctttcacttcgaaaacga gattaagaatatcttggaacacgctttcagaaaga aagatgacattactggtgacgaaaaggatttgtcc accatttccataatgtttagagttttcagaacttacg gtcataacttgccatcctctatctttaataaaattcaaa aactcagatggtaatttcaaggaagacttgataaa cgatgtttctggtatgttgtgtttatacgaagctact cacttggagtccatggtgaagacattttagatga agctttagagtttaccactacccgtttgaagtctatc ttgccaggtggtacttgtagacctcacattttaaga ttgattagaaacactttatatttgccacaaagatgg aacatggaagccgtcatcgctcgtgaatacatatc cttttacgaacaagaggaagaccacgataagatg |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
| --- | --- | --- | --- | --- | --- |
| | | | | VACVERWSPDGIDTLE DISRSVFKLMLDVFDDI GKGVRSEGSSYHLKEM LEELNTLVRANLDLVK WARGIQVPSFEEHVEV GGIALTSYATLMYSFV GMGETAGKEAYEWVR SRPRLIKSLAAKGRLMD DITDFDSDMSNGFAAN AINYYMKQFVVTKEEA ILECQRMIVDINKTINEE LLKTTSVPGRVLKQAL NFGRLLELLYTKSDDIY NCSEGKLKEYIVTLLID PIRL (SEQ ID NO: 21) | ttattgagattggctaagttgaatttcaaattgttaca gttgcattatattaaggaattgaagtcattcatcaaa tggtggatggaatttgggtttaacatctaaatggcc atctcaatttagagagcgtatcgttgaagcctggtt agctggtttgatgatgtactttgaaccacaattctcc ggtggtagagttattgcagctaagttcaactatttat tgaccatttggatgatgcttgtgatcactacttctc aattcatgaattgaccagattggtcgcttgtgttga aagatggtctccagacggtatcgatacattggag gacatctcccgttctgtctttaagttaatgttggatgt ttttgacgatatcggtaagggtgttagatccgaag gttcttcctatcacttgaaagaaatgttggaagaatt aaatactttagttagagcaaatttggacttggttaaa tgggccagaggtatccaagtcccatctttcgaag agcatgttgaggttggtggtattgctttaacatcta cgccactttgatgtactctttcgtcggaatgggtga aacgctggtaaggaagcctacgaatgggttcgt tccagacctcgtttgataaagtctttggcagctaaa ggtagattgatggacgacattactgattttgattca gatatgtctaacggtttcgctgctaacgcaattaac tattacatgaagcaattcgtcgttaccaaggaaga agccatcttagaatgccagagaatgatcgtcgac atcaacaagaccattaatgaagagttgttaaaaac tacatctgttcctggtagagtcttgaagcaagcttt gaacttcggtagattattggaattgttgtacactaa atctgacgacatctataattgttccgaaggtaagtt aaaggaatacattgttactttgttgatcgatccaata agattgtaa (SEQ ID NO: 87) |
| MacVolS QTS113 9 | Macro- stylis villosa | D0VMR 6 | 14% | SSAKLGSASEDVNRRD ANYHPTVWGDFFLTHS SNFLENNDSILEKHEGL EQKIRTMLISPTDTISKK LSLIDAVQRLGVAYHFE KEIEDEIEKLSCKEYND GNDLQTVALRFLLRQ QGYFVSCDVFKRFKNT KGEFETEDARTLWCLY EATHLRVDGEDILEEAI QFSRKKLEALLPELSFP LNECVRDALHIPYHRN VQRLAARQYIPQYDAE PTKIESLSLFAKIDFNML QALHQRELREASRWW KEFDFPSKLPYARDRIA EGYYWMMGAHFEPKF SLSRKFLNRIIGITSLIDD TYDVYGTLEEVTLFTE AVERWDIEAVKDIPKY MQVIYTGMLGIFEDFK DNLINARGKDYCIDYAI EVFKEIVRSYQREAEYF HTGYVPSYDEYMENSII SGGYKMFIILMLIGRGE FELKETLDWASTIPEMV EASSLIARYIDDLQTYK AEEERGETVSAVRCYM REFGVSEEQACKKMRE MIEIEWKRLNKTTLEAD EISSSVVIPSLNFTRVLE VMYDKGDGYSDSQGV TKDRIAALLRHAIEI (SEQ ID NO: 22) | atgtcctcagcaaaattgggttctgcttctgaagat gtcaaccgtagagacgctaattaccatccaaccg tttgggagatttctttttaacacactcctctaacttc ttggagaacaatgactcaatattggaaaagcacg aaggtttggaacaaaagattagaactatgttaatct ctcctaccgatactatctccaagaaattatctttgat tgacgccgttcagagattgggtgtcgcttatcattt gagaaggaaattgaagtgaaatcgaaaagttat catgtaaagagtacaacgacggtaatgacttgca aaccgtcgccttgagattcagattattgagacaac aaggttatttcgtttcctgcgatgtttttaagcgtttc aagaacactaagggtgaatttgagactgaagatg ctagaacattgtggtgtttatacgaagctactcactt gagagttgacggtgaagatattttggaagaagct atccaattctctcgtaagaaattagaagcattgttg ccagaattatcctttccattgaatgaatgtgttagag atgccttgcatatcccataccacagaaacgtccag agattggctgcacgtcaatatataccacaatacga cgctgagcctaccaagattgaatcctatctttgttc gctaagattgactttaatatgttgcaggccttgcac caaagagaattgagagaagcttccagatggtgg aaggagttcgattttccatctaaattgccttatgccc gtgatagaatcgctgaaggttactactggatgatg ggtgctcatttcgaaccaaaattttctttgtctcgta agttcttaaacagaatcattggtataacctccttaat tgatgatacttatgacgtctacggtactttagaaga agttaccttgttcaccgaagccgttgaaagatggg atattgaggctgtcaaagacatcccaaagtacatg caagttatatacacaggtatgttaggtattttcgaa gatttcaaagacaatttgattaacgccagaggtaa ggattattgcatcgattacgctatcgaagttttcaa ggagattgtcagatcttaccaaagagaagcagaa tactttcacactggttacgttccatcttatgacgaat acatgaaaactcaattatctcaggtggttacaaa atgtttataatcttgatgttaatcggtagaggtgagt tcgaattgaaagaaaccttagattgggcttcaact attccagaaatggtcgaagcttcttccttgatagct agatacatcgacgatttgcaaacatacaaggccg aagaagaacgtggtgaaacagtttcagcagtcag atgttacatgagagagtttggtgtttctgaggaaca agcttgtaagaagatgagagaaatgattgagatc gaatggaagagattgaacaagactaccttggaag TABLE 10-continued Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | ctgacgaaatttcttcttccgttgttattccatctttga actttactagagtcttggaagtcatgtatgacaagg gagacggttattctgattcccaaggtgttaccaag gatcgtattgctgctttgttaagcacacgccattgag atataa<br>(SEQ ID NO: 88) |
| MacVolS QTS219 8 | Macrostylis villosa | A0A067 D5M4 | 62% | RDLKSVLSSKESTKAD VNRRSSNYHPSIWGDH FINVSSNEKYTNTEVEK RFETLKAEIEKLLVSNN TAWKTLEEIVAIVNQLQ RLGLAYHFENQIKEAL QSIYDSHVGNCDVNY DHNNDLYIVALRFRLL RQHGYKVSADIFKKFR DEKGEFKAMLTNDAK GLLCLYEASYLRVQGE NILEEACEFSRKHLKSL LSHLSTSLAEQVKHSLE IPLHRGMPRLEARHYISI YEEDNSSRNELILELAK LDFNLLQALHRRELGEI SRWWKDIDFATKLPFA RDRLVECYFWILGVYF EPKYSITRKFMTKVIAI ASVIDDIYDVYGTLEEL KLFTHAIERWETVAAN ELPKYMQVCYFALLDV FKEMEDKLVNKGLLYS MPCAKEAVKGLVRAYF VEAEWFNANYMPTFEE YMENSTMSSGYPMLAV EALIGIEDATISKEAFD WAISVPKIIRSCALIARL VDDIHTYKVEQERGDA PSSVECYMQQYDVSEE EACNRIKGMVEIEWMN INEEIQDPNHPPLQWLL PSLNLARMMVVLYQN GDNYTNSSGKTKDRIA SLLVDPLPM<br>(SEQ ID NO: 23) | atgcgtgacttgaaatccgtcttatcttcaaaggaa tctacaaaggcagatgttaatagaagatcctctaa ctatcaccctctccatctgggggtgatcatttcattaac gtttcttcaaatgagaagtacactaacactgaagtc gaaaaaagatttgaaaccttgaaggccgaaatag aaaagttgttagtttctaacaacaccgcttggaag accttggaggaaattgtcgctatcgttaatcagttg caaagattagggttggcttaccacttcgaaaaacca aatcaaagaagccttgcaatccatttatgactctca tgtcaacggtaattgcgacgttaattacgatcaca acaacgatttgtacatagtcgctttaagatttcgttt gttgagacaacacggttataaagtctctgctgaca ttttcaagaagtttagagatgaaaagggtgaattta aggctatgttaacaaatgacgccaaaggtttgttgt gttatacgaagcatcctatttgagagttcaaggtg aaaatatcttagaagaggcttgtgaattttctcgtaa gcatttgaagtcattattgtctcacttgtccacctcat tggctgagcaagttaagcactctttggaaaatccca ttacatagaggtatgccaagattggaagctagac attacatttctatttacgaggaagataactcctctcg taatgaattgatattagagttggcaaagttggactt caacttgttgcaggccttacacagaagagaattg ggtgaaattcctcgttggtggaaagatattgatttc gctactaaattgccattcgccagagacagattagt tgaatgtacttctggatcttgggtgttatttgaac ctaaatactccatcactagaaagttcatgactaag gttatcgctattgcttccgtcatcgatgatatatacg acgtttatggtaccttggaggaattgaagttgttca ctcatgctattgaaagatgggaaactgtcgctgcc aacgaattaccaaagtacatgcaagtttgttacttt gctttgttagacgtctttaaggaaatggaagataaa ttagtcaataaaaggttgtttatactccatgccatgtg caaaggaggctgttaaaggttggttagagcttac ttcgttgaggctgaatggttcaacgctaactatatg ccaacccttcgaagaatatatggaaaactcaactat gtcctctggttatccaatgttggctgtcgaagctttg atcggtattgaagacgcaactattcaaaggaagc cttcgattgggcaatatctgttcctaaaattatccgt tcatgcgcattgatcgccagattggtcgatgacatt cacacctacaaggtcgaacaagagagaggtgat gccccatcttccgtcgaatgttacatgcaacaata cgacgtttctgaggaagaagcctgtaatagaatta agggtatggttgaaattgaatggatgaatataaac gaggaaatccaggatccaaaccacccaccttac aatggttgttgccatctttgaacttagctcgtatgat ggtcgttttgtaccaaaatggtgacaactatacaa actcctccggtaaaaccaaggatagaattgcttcc ttgttggtcgaccctttgccaatgtaa<br>(SEQ ID NO: 89) |
| MacVolS QTS220 2 | Macrostylis villosa | A0A067 D5M4 | 69% | RDLKSVLSSKESTKAD VNRRSSNYHPSIWGDH FINVSSNEKYTNTEVEK RFETLKAEIEKLLVSNN TAWKTLEEIVAIVNQLQ RLGLAYHFENQIKEAL QSIYDSHVGNCDVNY DHNNDLYIVALRFRLL RQHGYKVSADIFKKFK DEKGEFKDMIRNDARG LLCLYEASHLRVKGEDI LEEATEFSRKHLKSLLP QLSTSLAEQVKHSLEIP LHRGMPRLEARHYISIY EENNSSRNELLLELAKL | atgcgtgacttgaaatccgtcttatcttcaaaggaa tctacaaaggcagatgttaatagaagatcctctaa ctatcaccctctccatctgggggtgatcatttcattaac gtttcttcaaatgagaagtacactaacactgaagtc gaaaaaagatttgaaaccttgaaggccgaaatag aaaagttgttagtttctaacaacaccgcttggaag accttggaggaaattgtcgctatcgttaatcagttg caaagattagggttggcttaccacttcgaaaaacca aatcaaagaagccttgcaatccatttatgactctca tgtcaacggtaattgcgacgttaattacgatcaca acaacgatttgtacatagtcgctttaagatttcgttt gttgagacaacacggttataaagtctctgctgaca ttttcaagaagtttaaagatgaaaagggtgaattta aggatatgatcagaaatgacgccagaggtttattg tgttatacgaagcatcccatttgagagttaagggt |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | DFNLLQALHRRELGDIS RWWKDIDFATKLPFAR DRLVECYFWILGVYFEP KYSITRKFMTKVIAIAS VIDDIYDVYGTLEELKL FTHAIERWETVAANELP KYMQVCYFALLDVFKE MEDKLVNKGLLYSMPC AKEAVKGLVRAYFVEA EWFNANYMPTFEEYME NSTMSSGYPMLAVEAL IGIEDATISKEAFDWAIS VPKIIRSCALIARLVDDI HTYKVEQERGDAPSSV QCYVQQYGVSEEEACN KIKGMVEIEWMNINEEI QDPNHPPLQWLLPSLN LARMMVVLYQNGDNY TNSSGKTKDRIASLLVD PLPM (SEQ ID NO: 24) | gaagatattttagaagaggctactgaattttctcgt aagcacttgaagtcattgttaccacaattgtccaca tcattggctgagcaagttaagcactctttggaaatc ccattacatagaggtatgccaagattggaagcta gacattacatttctatttatgaggaaaacaactcctc tcgtaatgaattgttgttagagttggcaaagttgga cttcaacttgttgcaggctttacacagaagagaatt gggtgatatttctcgttggtggaaagacatcgattt cgccactaaattgccattcgccagagacagatta gttgaatgttacttctggatcttgggtgtttattttga acctaaatactccattactagaaaattcatgaccaa ggttatcgctatagcttctgtcatcgatgatatatac gacgtttacggtacctggaagaattgaagttgttc actcatgctattgagcgttgggaaactgtcgctgc taatgaattaccaaagtatatgcaagtttgttacttt gctttgttagacgtcttaaggaaatggaagataaa ttagtcaataaaggtttgttatactccatgccatgtg caaggaggctgttaagggtttggttagagcta cttcgttgaggctgaatggttcaacgctaactatat gccaaccttcgaagaatatatggaaaactcaacta tgtcctctggttatcctatgttggctgtcgaagctttg atcggtattgaagacgcaactattcaaaggaa gccttcgattgggcaatatccgttccaaaaattatc agatcttgtcattgatcgccagattggtcgatga cattcacacctacaaggtcgaacaagagagagg tgatgccccatcttctgtccaatgctacgttcaaca atacggtgtctccgaagaagaagcctgtaataaa attaagggtatggttgagattgaatggatgaatata aacgaagaaatccaggatccaaaccacccacctt tacaatggttgttgccatcttttgaacttagctcgtat gatggttgttttgtaccaaaatggtgacaactacac aaactcctccggtaaaaccaaggatagaattgctt ccttgttggtcgaccctttgccaatgtaa (SEQ ID NO: 90) |
| MacVolS QTS222 2 | Macro- stylis villosa | A0A067 D5M4 | 69% | RDLKSVLSSKESTKAD VNRRSSNYHPSIWGDH FINVSSNEKYTNTEVEK RFETLKAEIEKLLVSNN TAWKTLEEIVAIVNQLQ RLGLAYHFENQIKEAL QSIYDSHVNGNCDVNY DHNNDLYIVALRFRLL RQHGYKVSADIFKKFK DEKGEFKDMIRNDARG LLCLYEASHLRVKGEDI LEEATEFSRKHLKSLLP QLSTSLAEQVKHSLEIP LHRGMPRLEARHYISIY EENNSSRNELLLELAKL DFNLLQALHRRELGDIS RWWKDIDFATKLPFAR DRLVECYFWILGVYFEP KYSITRKFMTKVIAIAS VIDDIYDVYGTLEELKL FTHAIERWETVAANELP KYMQVCYFALLDVFKE MEDKLVNKGLLYSMPC AKEAVKGLVKAYFVEA KWFHAKYVPTFEEYME NSTMSSGYPMLAVEAL VGLEDMAITKRALDWA ISVPKIIRSCALIARLDD DVHTYKVEQERGDAPS SVQCYMQQYDVSEEEA CNRIKGMVETAWMEIN GEIQDTNHLPLQWLLPS LNLARMMVVLYQNGD NYTNSSGKTKDRIASLL VDPLPM (SEQ ID NO: 25) | atgcgtgacttgaaatccgtcttatcttcaaaggaa tctacaaaggcagatgttaatagaagatcctctaa ctatcaccccttccatctggggtgatcatttcattaac gtttcttcaaatgagaagtacactaacactgaagtc gaaaaaagatttgaaaccttgaaggccgaaatag aaaagttgttagtttctaacaacaccgcttggaag accttggaggaaattgtcgctatcgttaatcagttg caaagattagggttggcttaccacttcgaaaacca aatcaaagaagccttgcaatccatttatgactctca tgtcaacggtaattgcgacgttaattacgatcaca caacgatttgtacatagtcgcttaaggatttcgttt gttgagacaacacggttataagtctctgctgaca ttttcaagaagtttaaagatgaaaagggtgaattta aggatatgatcagaaatgacgccagaggtttattg tgtttatacgaagcatcccatttgagagttaagggt gaagatattttagaagaggctactgaattttctcgt aagcacttgaagtcattgttaccacaattgtccaca tcattggctgagcaagttaagcactctttggaaatc ccattacatagaggtatgccaagattggaagcta gacattacatttctatttatgaggaaaacaactcctc tcgtaatgaattgttgttagagttggcaaagttgga cttcaacttgttgcaggctttacacagaagagaatt gggtgatatttctcgttggtggaaagacatcgattt cgccactaaattgccattcgccagagacagatta gttgaatgttacttctggatcttgggtgtttattttga acctaaatactccattactagaaaattcatgaccaa ggttatcgctatagcttctgtcatcgatgatatatac gacgtttacggtacctggaagaattgaagttgttc actcatgctattgagcgttgggaaactgtcgctgc taatgaattaccaaagtatatgcaagtttgttacttt gctttgttagacgtcttaaggaaatggaagataaa ttagtcaataaaggtttgttatactccatgccatgtg caaggaggctgttaagggtttggttaaggctta cttcgttgaggctaagtggttccacgctaagtatgt cccaaccttcgaagaatatatggaaaactcaacta tgtcctctggttatcctatgttggctgttgaagctttg gttggtttagaagacatggccattacaaagagag |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | ctttggattgggcaatatccgttccaaaaattatca gatcatgtgcattgatcgccagattggacgatgac gttcacacttacaaggtcgaacaagagagaggtg atgccccatcttctgtccaatgctacatgcaacaat acgacgtctcccgaagaagaagcatgtaatcgtatt aagggtatggttgaaactgcttggatggaaatcaa cggtgagatccaggataccaaccacttgccatta caatggttgttgccatctttgaacttagctagaatg atggtcgttttgtaccaaaatggtgacaactacac caactcctccggtaaaaccaaggatagaattgcc tctttgttggtcgaccctttgcctatgtaa (SEQ ID NO: 91) |
| MacVolS QTS225 1 | Macro- stylis villosa | A0A067 D5M4 | 65% | RDLKSVLSSKESTKAD VNRRSSNYHPSIWGDH FINVSSNEKYTNTEVEK RFETLKAEIEKLLVSNN TAWKTLEEIVAIVNQLQ RLGLAYHFENQIKEAL QSIYDSHVNGNCDVNY DHNNDLYIVALRFRLL RQHGYKVSADIFKKFK DEKGEFKDMIRNDARG LLCLYEASHLRVKGEDI LEEATEFSRKHLKSLLP QLSTSLAEQVKHSLEIP LHRGMPRLEARHYISIY EENNSSRNELLLELAKL DFNLLQALHRRELGDIS RWWKDIDFATKLPFAR DRLVECYFWILGVYFEP KYSITRKFMTKVIAIAS VIDDIYDVYGTLEELKL FTHAIERWETVAANELP KYMQVCYFALLDVFKE MEDKLVNKGLLYSMPC AKEAVKGLVKAYFVEA KWFHAKYVPTFEEYME NSTMSSGYPMLAVEAL VGLEDMAITKRALDWA ISVPKIIRSCALIARLDD DVHTYKVEQERGDAPS SVECYMQQYDVSEEEA CNRIKGMVEIEWMNIN EEIQDPNHPPLQWLLPS LNLARMMVVLYQNGD NYTNSSGKTKDRIASLL VDPLPM (SEQ ID NO: 26) | atgcgtgacttgaaatccgtcttatcttcaaaggaa tctacaaaggcagatgttaatagaagatcctctaa ctatcacccttccatctggggtgatcatttcattaac gttcttcaaatgagaagtacactaacactgaagtc gaaaaaagatttgaaaccttgaaggccgaaatg aaagttgttagtttctaacaacaccgcttggaag accttggaggaaattgtcgctatcgttaatcagttg caaagattaggggttggcttaccacttcgaaaacca aatcaaagaagccttgcaatccatttatgactctca tgtcaacggtaattgcgacgttaattacgatcaca acaacgatttgtacatagtcgctttaagatttcgttt gttgagacaacacggttataaagtctctgctgaca ttttcaagaagtttaaagatgaaaagggtgaattta aggatatgatcagaaatgacgccagaggtttattg tgtttatacgaagcatcccatttgagagttaagggt gaagatattttagaagaggctactgaattttctcgt aagcacttgaagtcattgttaccacaattgtccaca tcattggctgagcaagttaagcactctttggaaatc ccattacatagaggtatgccaagattggaagcta gacattacatttctatttatgaggaaaacaactcctc tcgtaatgaattgtttgttagagttggcaaagttgga cttcaacttgttgcaggcttttacacagaagagaatt gggtgatatttctcgttggtggaaagacatcgattt cgccactaaattgccattcgccagagacagtta gttgaatgttacttctggatcttgggtgttttattttga acctaaatactccattactagaaaattcatgaccaa ggttatcgctatagcttctgtcatcgatgatatatac gacgtttacggtaccttggaagaattgaagttgttc actcatgctattgagcgttgggaaactgtcgctgc taatgaattaccaaagtatatgcaagtttgttacttt gctttgttagacgtcttttaaggaaatggaagataaa ttagtcaataaaggtttgttatactccatgccatgtg caaaggaggctgttaagggtttaggttaaggccta cttcgttgaggctaagtggttccacgctaagtatgt cccaaccttcgaagaatatatggaaaactcaacta tgtcctctggttatccatgttggctgttgaagctttg gttggtttagaagacatggccattacaaagagag ctttggattgggcaatatccgttccaaaaattatca gatcatgtgcattgatcgccagattggacgatgac gttcacacttacaaggtcgaacaagagagaggtg atgccccatcttctgtcgaatgctacatgcaacaat acgacgtctcccgaagaagaagcatgtaatcgtatt aagggtatggttgagattaatggatgaacataaa cgaagaaatccaggatccaaaccacccaccttta caatggttgttgccatctttgaacttagctagaatg atggtcgttttgtaccaaaatggtgacaactacac caactcctccggtaaaaccaaggatagaattgctt ctttgttggtcgaccctttgccaatgtaa (SEQ ID NO: 92) |
| MacVolS QTS227 4 | Macro- stylis villosa | A0A097 ZIE0 | 38% | SFAVSASPAKFIQNVEK DSTRRSANFHPSIWGDH FLQYTCDSQEPDDDGS VKHQQLKEEIRKMLTA ETKLSQKLDLIDAIQRL GVAYHFESEIDEILGRV HQAYQESDLCVNENDG LYYISLQFRLLRENGYR ISADVFNKFRDIDGNFK | atgtccttcgcagtttcagcctctcctgctaaatttat acagaatgtcgagaaggattctaccagacgttct gctaacttccacccatccatctggggtgaccatttt ttgcaatacacttgcgactcacaagaaccagatg atgacgggtctgttaagcatcaacaattaaaggaa gaaattagaaaaatgttgacagctgaaactaagtt gtcccagaagttagatttgattgacgccatccaaa gattgggtgtcgcttatcacttcgaatctgaaatcg atgagatttaggtagagttcaccaagcttaccaa |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | PSLARNVRGMLSLYEA THLRVHGENILDEAHA FATSHLESIATHQISSPL AEQVKHALFQPIHKGV QRLEARNYMPFYQEEA SHNEALLTFAKLDFNK LQKLHQKELSEITRWW KELDFAHNLPFTIRDRI AECYFWAVAVYFEPQY SLGRRMLAKVFPMTSII DDIYDVYGKFEELELFT SAIERWDISAIDELPEY MKLCYRALLDVYSEAE KDLASQGKLYHLHYAK E TABLE 10-continued Amino acid (AA) and nucleic acid sequences of sesquiterpene chimeras.

| Chimera Name | Rare DNA source | Extant scaffold Uni-prot # | % Rare DNA | Chimera AA sequence (beginning after the first encoded amino acid M) | Chimera Nucleic Acid Sequence |
|---|---|---|---|---|---|
| | | | | KQALNFGRLLELLYTK SDDIYNCSEGKLKEYIV TLLIDPIRL (SEQ ID NO: 28) | attaaataccttagttagagcaaacttggacttggtt aaatgggccagaggtatccaagtcccatcttttcga agagcatgttgaggttggtggtattgctttaacatc ctacgcaactttgatgtactctttcgtcggaatggg tgaaactgctggtaaggaagcatacgaatgggtt cgttcaagacctcgtttgataaagtctttggccgct aagggtagattgatggacgacatcactgattttga ttccgatatgtctaacggtttcgctgctaacgcaatt aactattacatgaagcagttcgtcgttacaaagga agaagccatcttagaatgccaaagaatgattgtcg acatcaataagaccatcaatgaagagttgttaaaa actacctctgttccaggtagagtcttgaaacaagc tttgaacttcggtagattattggaattgttgtatacta agtccgacgacatttacaactgttctgaaggtaaa ttaaaggaatacatagttacttttgttgattgatccaa taagattgtaa (SEQ ID NO: 94) |
| OrbStiS QTS141 4 | Orbexi-lum stipu-latum | A0A067 FTE8 | 43% | SIQVPQISSQNAKSQVM RRTANFHPSVWGDRFA NYTAEDKMNHARDLK ELKALKEEVGRKLLAT AGPIVKLELVDDVKRL GIGYRFEKEIVEALHRC FISSERFTHRNLHQTAL SFRLLRECGYDVTCDK FNKFTNKEGKFNSKLG ENIKGMIDLYEASQLGI AGEYILAEAGEFSGLVL KEKVACINNNPLKAQV RHALRQPLHRGLPRLE HRRYISIYQDDASHYKA LLTLAKLDFNLVQSLH KKELCEISRWWKDLDF ARKLPFARDRMVECYF WILGVYFEPQYSVPRRT TTKVIGLCSVIDDMYD AYGTIDELELFTNAIER LDTSTMDQLPEYMQTF FGALLDLYNEIEKEIAN EGWSYRVQYAKEAMK ILVEGYYDESRWLKCN HAPTMEEYMKVRGVSS GYPLLITISFIGMEDTTE EILTWATSEPMIIRASVI VCRLMDDIKSHKFEQE RGHAASAVECYMKQH GLSEQEVCEELYRQVS NAWKDINEECLNPTAV PMPLLMRALNLARVID VVYKEGDGYTHVGNE MKQNVAALLIDQVPI (SEQ ID NO: 29) | atgtccatacaggttccccaaatttcttcgcaaaat gcaaagtcacaagtaatgcgtagaaccgccaact ttcatccatctgtgtggggagacagattcgctaact acacggctgaggataaaatgaaccacgctcgcg acttgaaggaacttaaagcgttaaaggaagaagt tggtagaaagctgttggccacagctggcccaatt gttaagctagagttggtcgatgatgtcaaaagact cgggatcggttatagattcgaaaaggaaatcgttg aagctttacaccgttgctttattagttccgaaagatt cactcataggaatttgcaccaaaccgccttgagct tcagattgttacgggaatgtggttacgacgtcactt gtgataagtttaataagttcactaacaaagagggt aagtttaactcaaagtttgggtgaaaatatcaaggg tatgatagacttgtatgaagctagccaacttggtat tgctggtaatacatcttggctgaagcaggtgaat tttcgggcttagttctaaaagaaaaggttgcttgtat taacaataacccattgaaagcgcaggtcagacat gccctaagacaacctctgcacagaggtctcccaa gattagaacacaggagatacatctctatttaccaa gatgacgcttctcactataaggcttttgttgaccctg gccaagttggatttcaacttggttcaatccctccat aagaaagagctttgcgaaatttccagatggtgga aagatcttgacttcgctcggaagttacctttgcac gtgaccgtatggtcgaatgttatttctggatcttgg gagtttacttcgaaccacaatacagtgtaccaaga agaactaccactaaggttattggtttgtgttctgtca tcgatgatatgtacgatgcttacggtacaattgacg aattagagctttttactaacgccatcgaaagattgg acacctctactatggatcagctaccagaatatatg caaactttctttggtgctttattggatttgtataacga gatcgaaaaagaaatcgcaaatgaaggttggtcc taccgagtgcaatacgctaaggaagctatgaaaa ttttggtggaaggatactatgatgaaagcagatgg ttgaagtgtaaccacgcccaaccatggaagaat acatgaaggtccgtggtgttagttctggttaccctc tcttgataaccatatctttcataggtatggaggaca ctactgaagagatcttaacatgggctacatctgaa cctatgattatcagagccagtgtcattgtttgtagat tgatggacgacattaaatcccataagtttgagcaa gagaggggggcatgctgcgagcgctgtagaatgc tatatgaagcaacacggtctatcagaacaagaag tttgtgaagaactttacagacaggtctctaatgcat ggaaggacatcaatgaagaatgtttgaacccgac cgctgttccaatgccattgttaatgagagcgctga acttggctcgcgtcattgacgtagtttataaagaag gtgacggctacacccacgttggtaatgaaatgaa gcaaaacgtagctgctctcctaatcgatcaagtac caatctaa (SEQ ID NO: 95) |
| ShoCusS QTS154 | Shorea cuspi-data | ShoBecS QTS1 | 38% | ALQDSEVPSSILNATAG NRPTASYHPTLWGEKF LVVSTQSTSGSMKNEPT TQGEYDELKQQVTKML | atggctttgcaggattcagaagtcccttcttccatat taaacgccactgctggtaatcgtccaaccgcatct taccatccaacattgtggggagagaaattcttagtt gtttccactcaatctacctctggttccatgaagaac |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | TDATTNDPSKKLHLID MVQRLGIAYHFEIEIEN ALEKINLGDANYFEYD LYTIALGFRLLRQQGIK VSSEIFKKFMDEKGKFK EDVVNDVLGMLNLYE AAHLRLRGEDILDEAL AFTTSHLESMATKVSPL LAEQIAHALNCPIQKGL PRIEARHYISLYSRETHF ASSNAALLRFAKIDFN MVQALHQKEISGITKW WKNLDFSTKLPYARDR IVECYFWIMGAYFEPK YSLARTFLTKVIAMTSI LDDTYDNYGTNKELEL LTKCIERWDIDVIDQLP EYMKLVYQALLNVYSE MEAKVAKEGRSYAIDY AKESMKKTMKAYLDE AKWRQEDYVPPIEEYM QVARISSAYPMLITNSF VGMGEVATKEAFDWIS NDPKILKASTTICRLMD DITSHEFEQTRDHVASG VECYMKQYGVSREETV KLFREDVANAWKDINE GFMKPAIFPMPILTVVL NPARVMDFLYKDGDN YTNSHMLKDYITSLLV NPLLI (SEQ ID NO: 30) | gaaccaactacacaaggtgaatatgacgaattga agcaacaagtcaccaagatgttgactgatgctac cactaacgacccatccaaaaagttgcacttgatcg atatggttcaaagattaggtattgcctaccactttga gattgaaatcgaaaatgcttttggaaaagattaactt aggtgacgctaactacttcgaatatgacttgtaca ccatcgctttgggttttagattgttgagacaacagg gtattaaagtctcatctgaaatcttcaagaagtttat ggatgagaaaggtaagttcaaagaagacgttgtt aatgatgtcttaggtatgttgaacttatacgaagca gcccatttgagattaagaggtgaagatatcttgga cgaggctttagccttcactacctcccacttggaatc tatggctacaaaggtttctcctttgttggcgtaaga aatagcccatgctttaaattgcccaattcaaaagg gtttaccaagaattgaagccagacactatatctcat tgtactcccgtgaaactcactttgcttcttctaacgc tgcattgttgagattcgctaaaattgacttcaacatg gttcaagctttgcaccagaaggagatctctggtatt acaaagtggtggaaaaatttggatttctcaactaa gttgccatacgctagagacagaatcgtcgaatgtt atttttggatcatgggtgcttactttgaacctaagtat tccttggctagaactttttttgaccaaggttatagcaa tgacctctatattagatgatacatacgataactacg gtactaataaggaattggagttgttaactaaatgta ttgaacgttgggacatcgacgttattgatcaattac cagaatatatgaagttggtctaccaagcattgttga acgtttactcagaaatggaagccaaagtcgctaa ggagggtcgttcttacgccattgactatgctaagg aatccatgaaaaagaccatgaaggcatacttgga tgaagctaaatggagacaagaagactacgttcct ccaatagaagaatatatgcaagtcgctagaattt ctctgcctacccaatgttaatcactaattccttcgtt ggtatgggtgaagttgctaccaaagaggcattcg attggatttccaatgacccaaagatttgaaggctt ctactactatatgtagattgatggatgatatcacttc tcatgaatttgaacaaacaagagaccatgttgcct ctggtgtcgaatgttatatgaaacaatacggtgttt cacgtgaagaaaccgttaagttattcagagagga tgtcgctaacgcttggaaagacattaacgagggtt tcatgaagcctgctatattcccaatgccaatcttga ctgttgttttgaactttgccagagtcatggatttctta tacaaggatggtgacaactatactaattctcatatg ttgaaggattacattacatcattgttggtcaatccat tattaatctaa (SEQ ID NO: 96) |
| ShoCusS QTS155 | *Shorea cuspidata* | ShoBecS QTS1 | 35% | ALQDSEVPSSILNATAG NRPTASYHPTLWGEKF LVVSTQSTSGSMKNEPT TQGEYDELKQQVTKML TDATTNDPSKKLHLID MVQRLGIAYHFEIEIEN ALEKINLGDANYFEYD LYTIALGFRLLRQQGIK VSSEIFKKFMDEKGKFK EDVVNDVLGMLNLYE AAHLRLRGEDILDEAL AFTTSHLESMATKVSPL LAEQIAHALNCPIQKGL PRIEARHYISLYSRETHF ASSNAALLRFAKIDFN MVQALHQKEISGITKW WKNLDFSTKLPYARDR IVECYFWIMGAYFEPK YSLARTFLTKVIAMTSI LDDTYDNYGTNKELEL LTKCIERWDIDVIDQLP EYMKLVYQALLNVYSE MEAKVAKEGRSYAIDY AKESMKKTMKAYLDE AKWRQEDYVPTIEEYM QVALISSAYPMLITNSF | atggcattgcaggattctgaagtcccttcctcaata ttaaacgccaccgctggtaatagaccaactgcttc ttatcacccaacattgtggggagagaagttcttgg ttgtttccactcaatctacctcaggttctatgaaaaa cgaaccaactcaaggtgaatacgacgaatta aagcaacaagtcacaaagatgttgactgatgcca ctactaatgacccatccaaaaagttgcatttaatcg atatggttcaacgtttgggtattgcttaccactttga aattgagatcgaaaatgcttttggaaaaaataaact taggtgacgctaattatttcgaatacgatttgtacac cattgctttaggttttagattgttgagacaacaaggt atcaaggtctcttctgagattttcaagaaatttatgg acgaaaaggtaagttcaaagaagacgttgtcaa cgatgttttgggtatgttgaacttgtacgaagcagc tcatttaagattaagaggtgaagacatcttggacg aagcttggccttcacaacctcccacttagagtca atggctactaaggtctctcctttgttggctgaacaa attgcccatgctttgaactgcccaatccaaaaggg tttaccacgtattgaagcaagacactatatttctttat actccagagaaactcacttcgcttcctctaatgctg ctttgttgagatttgctaagatcgatttcaatatggtt caagccttgcatcagaaggaaatatcaggtataa ccaaatggtggaagaacttggacttttccactaaa ttaccatatgctagagatcgtattgttgaatgttactt ctggatcatgggtgcttactttgaaccaaagtattc ttagcaagaacattcttgaccaaagtcattgcaat |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | VGMGEVATKEAFDWIS NNPKMLKASTIICRLMD DITSHEFEQTRDHVASG VECYMKQYGVSREETV KLFREDVANAWKDINE GFMKPAIFPMPILTVVL NFARVMDFLYKDGDN YTNSHMLKDYITSLLV NPLLI (SEQ ID NO: 31) | gacctctatcttagacgatacttacgacaactacg gtactaacaaggaattggagttgttgactaagtgt atcgaaagatgggatattgatgttatcgaccagtta cctgagtatatgaagttggtttatcaagctttgttaa atgtttactctgaaatggaagctaaggtcgccaaa gaaggtcgttcctacgccattgactacgcaaaag aatctatgaagaaaaccatgaaagcctacttgga cgaggctaagtggagacaagaagattacgtccct accattgaagaatatatgcaagttgcattaatatca tccgcttatccaatgttgattacaaactcattcgtcg gtatgggtgaggtcgctactaaggaagcttttgac tggatctccaataacccaaagatgttgaaggcttc tactattatatgtagattgatggatgatatcacttcc catgaatttgaacagaccagagaccacgttgcct ctggtgttgaatgttacatgaaacaatacggtgtct ccagagaagaaaccgttaagttgttcagagaaga tgttgctaacgcttggaaggacatcaatgaaggtt tcatgaagccagcaatcttcccaatgcctatcttga ctgttgtcttgaatttttgccagagttatggacttttttgt acaaggatggtgataactatactaactctcatatgt taaaagactacattacctcattattggttaatccatt attgatttaa (SEQ ID NO: 97) |
| ShoCusS QTS156 | Shorea cuspidata | ShoBecS QTS1 | 36% | ALQDSEVPSSILNATAG NRPTASYHPTLWGEKF LVVSTQSTSGSMKNEPT TQGEYDELKQQVTKML TDATTNDPSKKLHLID MVQRLGIAYHFEIEIEN ALEKINLGDANYFEYD LYTIALGFRLLRQQGIK VSSEIFKKFMDEKGKFK EDVVNDVLGMLNLYE AAHLRLRGEDILDEAL AFTTSHLESMATKVSPL LAEQIAHALNCPIQKGL PRIEARHYISLYSRETHF ASSNAALLRFAKIDFN MVQALHQKEISGITKW WKNLDFSTKLPYARDR IVECYFWIMGAYFEPK YSLARTFLTKVIAMTSI LDDTYDNYGTNKELEL LTKCIERWDIDVIDQLP EYMKLVYQALLNVYSE MEAKVAKEGRSYAIDY AKESMKKTMKAYLDE AKWRQEDYVPPIEEYM QVARISSGYPMLITNSL VGMGEVATKEAFDLIS NDPKMLKASTTICRLM DDITSHEFEQTRDHVAS GVECYMKQYGVSREET VKLFREDVANAWKDIN EGFMKPAIFPMPILTVV LNFARVMDFLYKDGD NYTNSHMLKDYITSLL VNPLLI (SEQ ID NO: 32) | atggctttacaggactccgaggttccttcatctatat tgaacgccaccgctggtaatcgtccaactgcatct tatcatccaacattgtggggtgaaaaattcttggtc gtttctactcaatccacctctgggtccatgaagaac gaaccaactacccaaggtgaatacgatgaattaa agcaacaagtcacaaagatgttgactgatgctac cactaatgacccatctaaaaagttgcacttgattga catggttcaaagattaggtatcgcctaccactttga aattgagatcgaaaacgctttggaaaagattaact taggtgatgctaattatttcgaatacgatttgtacac tatagccttgggttttagattattgagacaacaggg tatcaaggtttcatctgaaatcttcaaaaagttcatg gacgagaaaggtaagtttaaggaagacgtcgtta acgatgtcttgggtatgttaaacttgtatgaagctg cccatttgagattgcgtggtgaagacattttagatg aggctttggcttttaccacatcccacttagaatcaa tggcaactaaggtttcacctttgttggctgaacaaa tcgcccacgctttaaattgcccaattcaaaaaggtt tgccaagaatagaagccagacattacatttctttgt actccagagaaaccacttcgcttcttctaacgca gcattgttgcgtttcgctaagatcgactttaatatgg ttcaagcattgcatcagaaagagatttccggtatta ctaagtggtggaagaatttagatttctctacaaaatt gccatatgctagagatagaatcgtcgaatgttactt ctggattatgggtgcttattttgaaccaaagtactct ttggccagaaccttttttaaccaaagtcattgctatg acttctatcttagatgacacatacgacaattacggt actaacaaggaattggaagttgttaaccaagtgtatt gaaagatgggatatgatgttatcgatcaattgcct gaatacatgaagttagtttatcaagctttgttgaac gtctactccgaaatggaggctaaggtcgctaagg aaggtcgttcctatgccatcgattacgctaaggaa tccatgaaaaagactatgaaagcctatttggacga agctaagtggagacaagaggactacgttccacct atcgaagagtacatgcaagttgcaagaatttcttc cggttatccaatgttaattaccaactccttggttggt atgggtgaagtcgccactaaagaagccttcgattt gatttctaacgacccaaaaatgttgaaggcttcca ccactatatgtagattgatggacgatatcacttctc acgaatttgaacaaactagagatcacgtcgcttca ggtgttgaatgttatatgaagcaatacggtgtttctc gtgaggaaaccgttaagttattcagagaagacgt cgctaacgcatggaaggacattaatgagggtttc atgaagccagcaatcttcccaatgcctatcttgact |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | gtcgtcttaaacttcgctagagttatggacttttttgta caaagatggtgataattacacaaactctcatatgtt aaaggattacatcacttcattgttggtcaacccttttg ttgatttaa (SEQ ID NO: 98) |
| ShoCusS QTS157 | *Shorea cuspidata* | ShoBecS QTS1 | 38% | ALQDSEVPSSILNATAG NRPTASYHPTLWGEKF LVVSTQSTSGSMKNEPT TQGEYDELKQQVTKML TDATTNDPSKKLHLID MVQRLGIAYHFEIEIEN ALEKINLGDANYFEYD LYTIALGFRLLRQQGIK VSSEIFKKFMDEKGKFK EDVVNDVLGMLNLYE AAHLRLRGEDILDEAL AFTTSHLESMATKVSPL LAEQIAHALNCPIQKGL PRIEARHYISLYSRETHF ASSNAALLRFAKIDFN MVQALHQKEISGITKW WKNLDFSTKLPYARDR IVECYFWIMGAYFEPK YSLARTFLTKVIAMTSI LDDTYDNYGTNKELEL LTKCIERWDIDVIDQLP EYMKLVYQALLNVYSE MEAKVAKEGRSYAIDY AKESMKKTMKAYLDE AKWRQEDYVPPMDEY MQVALISCGYPMLITNS FVGMGEVATKEAFDWI SNDPKILKASTTICRLM DDITSHEFEQTRDHVAS GVECYMKQYGVSREET VKLFREDVANAWKDIN EGFMKPAIFPMPILTVV LNFARVMDFLYKDGD NYTNSHMLKDYITSLL VNPLLI (SEQ ID NO: 33) | atggccttacaggactccgaagttccatcatctatt ttgaacgctactgctggtaatagacctacagcatc ttaccatccaaccttgtggggagagaagttttggt cgtttccactcaatctacctccggttctatgaaaaa cgaaccaactacacaaggtgaatatgatgaatta aagcaacaagtcaccaagatgttgactgatgcta ctaccaacgaccccatctaaaaagttgcacttaata gatatggttcaacgtttgggtatcgcctaccacttc gagattgaaatcgaaatgctttagaaaaaattaa cttgggtgacgctaactacttcgaatatgatttgta cactatcgcattaggttttagattgttgagacaaca gggtattaaggtctcctcagaaattttcaagaagtt catgatgaaaaaggtaagtttaaggaggacgttt gtcaatgacgttttaggtatgttgaacttgtatgaag ctgctcatttacgtttgagaggtgaagatatcttgg acgaagccttggcttttcactacatcacacttggaat ctatggctaccaaggtttccccattgttggccgag caaatagcacatgccttaaattgtcctattcaaaaa ggtttgccaagaatcgaagctagacactacatctc tttatactctcgtgaaactcactttgcttcctctaacg ctgccttgttgagattcgctaagattgattttaatatg gttcaagccttgcaccagaaagaaatctctggtat caccaagtggtggaagaatttggacttctccacca agttgccatatgctagagacagaattgtcgaatgc tacttctggataatgggtgcatattttgaacctaagt actcttagctagaacttttttgactaaagttattgct atgacatcaatttttggatgatacttacgataactac ggtactaacaaagaattagaattagccaagtg tatcgagagatgggacattgacgtcattgaccaat taccagaatacatgaagttggtttatcaagctttgtt gaacgtctactccgagatggaagcaaaggttgcc aaggaaggtcgttcttatgctatagattatgctaaa gaatctatgaaaaagacaatgaaggcatacttgg acgaagctaagtgggagacaagaggattatgttcc tccaatggatgaatacatgcaagttgctttgatatc ctgtggttacccaatgttgatcaccaactcttttcgtt ggtatgggtgaagtcgctaccaaagaagcctttg attggatctctaatgacccaaagattttgaaagcat ctaccactatctgtagattaatggatgacattacct cccatgagttcgaacagacaagagatcacgttgc ttcaggtgtcgaatgttatatgaagcaatacggtgt ttctcgtgaagaaactgttaaattattcagagagga tgttgctaacgcttggaaagacattaatgaaggttt catgaagcctgctattttcccaatgccaatttttgac cgtcgtcttgaattcgctagagtcatggattttttat acaaggacggtgataactacacaaactcacatat gttgaaagattacatcacttcattattagtaatccat tgttgatataa (SEQ ID NO: 99) |
| ShoCusS QTS160 | *Shorea cuspidata* | ShoBecS QTS1 | 36% | ALQDSEVPSSILNATAG NRPTASYHPTLWGEKF LVVSTQSTSGSMKNEPT TQGEYDELKQQVTKML TDATTNDPSKKLHLID MVQRLGIAYHFEIEIEN ALEKINLGDANYFEYD LYTIALGFRLLRQQGIK VSSEIFKKFMDEKGKFK EDVVNDVLGMLNLYE AAHLRLRGEDILDEAL AFTTSHLESMATKVSPL LAEQIAHALNCPIQKGL PRIEARHYISLYSRETHF ASSNAALLRFAKIDFN MVQALHQKEISGITKW | atggcattacaggattcagaggtcccatcctctatt ttgaacgctactgccggtaatcgtcctaccgcttct taccacccaacattgtggggtgaaaagttttttagtt gtttccactcaatctacctccggctctatgaaaaac gaaccaaccactcaaggtgaatatgacgaattga agcaacaagtcactaagatgttgacagatgctact accaatgacccatctaaaaagttgcatttgatagat atggttcaaagattgggtattgcctaccacttcgaa atcgaaatcgaaaacgcttagaaaagattaattta ggtgacgctaactatttcgaatacgatttatacaca atcgctttgggttttagattgttgagacagcaaggt atcaaggtctcttcagagattttcaaaaagttcatg gatgagaaaggtaagtttaaggaagacgttgtca acgacgttttgggtatgttgaatttatatgaagcag cccatttgagattgcgtggtgaagatatattggac gaggctttagcttttcactacctcccacttggaatct |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | WKNLDFATMLPYARD RIVECYFWIMGVYFEPK YSLARTFLTKVIAMTSI LDDTYDNYGTNKELEL LTKCIERWDIDVIDQLP EYMKLVYQALLNVYSE MEAKVAKEGRSYAIDY AKESMKKTMKAYLDE AKWRQEDYVPTIEEYM QVALISSAYPMLITNSF VGMGEVATKEAFDWIS NNPKMLKASTIICRLMD DITSHEFEQTRDHVASG VECYMKQYGVSREETV KLFREDVANAWKDINE GFMKPAIFPMPILTVVL NFARVMDFLYKDGDN YTNSHMLKDYITSLLV NPLLI (SEQ ID NO: 34) | atggcaaccaaagtttccccattgttagctgaaca aattgcccacgctttgaactgtcctatccaaaagg gtttgccaagaattgaagccagacattacatatctt tgtattcaagagaaactcacttcgcttcttccaatg ctgctttattaagatttgctaaggatcgattttaacatg gtccaagctttgcatcaaaaagagatctctggtatt acaaagtggtggaagaacttggacttcgctactat gttaccatacgccagagatcgtattgttgaatgcta cttctggatcatgggtgtttattttgaaccaaagtac tccttagctagaaccttcttgaccaaagttattgca atgacttctattttagacgatacatacgacaactac ggtactaataaggaattggaattgttgactaaatgt attgaaagatgggacatcgatgtcattgatcaattg cctgagtatatgaagttggtttatcaggcattattga acgtctactcagaaatggaagctaaggttgccaa agagggtagatcctacgctattgattacgccaaa gaatctatgaagaagaccatgaaggcctatttgg acgaagctaagtggagacaagaagactacgtcc ctaccatcgaagaatatatgcaagtcgctttaatat cttcagcctacccaatgttaataactaattcatttgt cggtatgggtgaggttgccactaaggaagcttttg attggatctctaacaacccaaaaatgttaaaggctt ccactatttttgtagattgatggatgacatcacctc ccacgaatttgaacagaccgtgaccacgttgcc tctggtgttgaatgttatatgaagcaatacggtgttt cacgtgaggaaaccgtcaagttgttcagagaaga tgttgctaatgcttggaaagacatcaatgagggttt catgaagccagcaatcttcccaatgccaatttga ctgtcgttttgaacttcgcaagagttatggatttctta tataaggacggcgacaattacactaactctcatat gttgaaagactacatcacttctttgttggtcaaccc attgttaatataa (SEQ ID NO: 100) |
| ShoCusS QTS161 | Shorea cuspidata | ShoBecS QTS1 | 37% | ALQDSEVPSSILNATAG NRPTASYHPTLWGEKF LVVSTQSTSGSMKNEPT TQGEYDELKQQVTKML TDATTNDPSKKLHLID MVQRLGIAYHFEIEIEN ALEKINLGDANYFEYD LYTIALGFRLLRQQGIK VSSEIFKKFMDEKGKFK EDVVNDVLGMLNLYE AAHLRLRGEDILDEAL AFTTSHLESMATKVSPL LAEQIAHALNCPIQKGL PRIEARHYISLYSRETHF ASSNAALLRFAKIDFN MVQALHQKEISGITKW WKNLDFATMLPYARD RIVECYFWIMGVYFEPK YSLARTFLTKVIAMTSI LDDTYDNYGTNKELEL LTKCIERWDIDVIDQLP EYMKLVYQALLNVYSE MEAKVAKEGRSYAIDY AKESMKKTMKAYLDE AKWRQEDYVPPIEEYM QVARISSGYPMLITNSL VGMGEVATKEAFDLIS NDPKMLKASTTICRLM DDITSHEFEQTRDHVAS GVECYMKQYGVSREET VKLFREDVANAWKDIN EGFMKPAIFPMPILTVV LNFARVMDFLYKDGD NYTNSHMLKDYITSLL VNPLLI (SEQ ID NO: 35) | atggctttgcaagactctgaagtcccttcctcaattt taaacgcaaccgctggtaatagaccaacagcctc ttaccatccaactttgtggggtgagaaattttttggtt gtttccactcagtctacctcagtctctatgaagaac gaaccaactacccaaggtgaatatgatgaattga agcaacaagtcactaagatgttaacagatgctact accaatgacccatccaaaaagttgcacttgataga tatggttcaacgtttgggtatcgcctaccacttcga aatcgagattgaaaacgctttagagaaaatcaact ggggcgacgctaattacttcgaatatgatttataca ccattgccttaggttttagattgttgagacaacaag gtattaaggtttcttccgaaattttcaagaagtttatg gatgaaaaaggtaagttcaaggaagacgtcgtta acgacgttttaggtatgttgaacttgtatgaagctg cccatttaagattgcgtggtgaagatatcttggatg aagctttagcattcacaacctctcacttggaatctat ggctactaaagtctctccattgttagctgagcagat cgcccacgctttgaattgcccatccaaaagggtt tgccaagaatagaagcaagacattacatttccttgt actcaagagaaacacacttcgcttcctctaacgct gctttgttaagatttgctaaaattgactttaatatggt tcaagccttacatcaaaaggagatttctggtatcac caagtggtgaagaacttggacttcgaactatgt tgccatacgaagagaccgtattgttgaatgttatt tctggatcatgggtgtcacttcgaacctaagtact cattggctagaactttttttaactaaagtcatagccat gacctccattttggatgacacctacgataactatg gtactaacaaggaattagagttgttaacaaagtgt atagaaagatgggacattgatgtcatcgatcaatt gcctgaatacatgaagttggtttaccaggcttgtt aaatgtctactcagaaatggaagctaaggttgcta aagaggtcgttcttatgcaattgattacgcaaag gagtctatgaagaaaactatgaaagcttatttgga cgaagctaaatggagacaagaagactatgttcca ccaatcgaagaatatatgcaagtcgctagaatctc ttccggttacccaatgttgattactaactcattagtc ggtatgggtgaggttgccactaaggaagctttcg acttgatttctaatgatccaaagatgttaaaagcct |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | ccactacaatctgtagattgatggacgacattactt ctcatgaatttgaacagacacgtgatcacgttgcc tctggtgtcgagtgctatatgaagcaatacggtgtt tccagagaagaaaccgtcaagttgtttagagaag acgttgctaacgcttggaaggatatcaatgaagg cttcatgaaaccagcaatcttttccaatgccaattttg accgttgttttgaacttcgctagagtcatggacttct tgtataaggatggcgacaactacactaattcacat atgttgaaagattacataacttcattattagttaacc ctttattgatctaa (SEQ ID NO: 101) |
| WenAng SQTS10 07 | Wend- landia angust- ifolia | A0A068 UHT0 | 81% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGKFKESLCN DIRGLLSLYEAAHVRTH GDKILEEALAFTTTHMT SGGPHLDSSLAKQVKY ALEQPLHKGILRYEAW RYISIYEEDESNNKLLL RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTNFSQSRWFFTKEL PSFADYINNGAITIGAY LVASAAFLYMDSAKED VINWMSTNPKLVVAYS THSRLINDFGGHKFEKE RGSSTAIECYMKDHNV SEEEAANKFREMMEDA WKVMNEECLRPTTIPR DGLKMLLNIARVGETV YKHRIDGFTQPHAIEEH IRAMLVDFMSI (SEQ ID NO: 36) | atggcctcagcacaagcttccttaccttctaataac agacaggaaacagtccgtccattggctgacttcc cagagaacatctgggctgatagaattgccccattt accttggataagcaagaatacgaaatgtgtcaaa gagaaatagagatgttaaaagctgaagttgcttct atgttgttggcaactggtaagactatgatgcaaag attcgacttcattgataagatcgaaagattggggg tctcccaccattttgacattgaaatcgaaaatcaatt gcaagagttttcaacgtttataccaacttaggtga atactctgcctatgatttgtcatctgctgccttgcag ggatcaacatcctggtttcaatatttcctg cggtattttcgaccaatttatcgacgctaaaggtaa gttcaaggaatctttatgtaacgatatcagaggttt gttgtctttgtacgaagctgctcatgttagaactca cggtgataaaatttggaagaagctttagctttcac cactactcacatgacctccggtggtccacatttag attcttcattggccaagcaagttaaatacgcattgg aacagccattgcataagggtatattgagatatgaa gcttggagatacatatctatctacgaagaggacg aatccaacaataagttattattgcgtttggctaagtt ggactatcacttgttacaaatgtcatacaagcaag agttgtgtgaaattacaagatggggtaaaggtttg gaatctgtctccaacttcctttatgcccgtgacaga ttcgttgaatgttacttttgggctgtcggtacttgta cgaaccacaatactcattggctagaatgaccttcg ctaaggttgctgctttaattactatgatcgatgatat tatgatgcctacggtaccttggacgaattgcaaat attaactgactctgccgaaagatgggatggttccg gtgtcgatcagttgtctgactatattagagcttccta taatacattattgaaatttaataaggaggttggtga agatttggcaaaaaagcaacgtacctacgcttcg acaagtacatcgaagattgaaacaatacatgag aaccaacttctctcaatcaagatggttttcactaag gagttgccatctttcgctgttacattaacaacggt gccatcacaatcggtgcatatttggttgcctctgct gctttcttatatatggactccgcaaaagaagatgtt atcaactggatgtccacaaaccctaagttggtcgt tgcttactccactcactctcgtttaattaatgactttg gtggtcacaagttcgaaaaggagagaggttcctc tactgctattgaatgctacatgaaggaccataatgt ctccgaagaagaagccgcaaacaagtttagaga aatgatggaggacgcttggaaggttatgaatgaa gaatgtttaagaccaactaccatccctagagacg ggttgaagatgttgttaaacatagccagagtcggt gaaactgtttacaagcatagaatcgatggttttacc caaccacatgctattgaagaacacataagagcca tgttggtcgatttcatgtctatttaa (SEQ ID NO: 102) |
| WenAng SQTS10 86 | Wend- landia angust- ifolia | A0A068 UHT0 | 80% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGKFKESLCN DIRGLLSLYEAAHVRTH GDKILEEALAFTTTHMT | atggcctcagcacaagcttccttaccttctaataac agacaggaaacagtccgtccattggctgacttcc cagagaacatctgggctgatagaattgccccattt accttggataagcaagaatacgaaatgtgtcaaa gagaaatagagatgttaaaagctgaagttgcttct atgttgttggcaactggtaagactatgatgcaaag attcgacttcattgataagatcgaaagattggggg tctcccaccattttgacattgaaatcgaaaatcaatt gcaagagttttcaacgtttataccaacttaggtga atactctgcctatgatttgtcatctgctgccttgcag ttccgtttatttagacaacacggtttcaatatttcctg |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | SGGPHLDSSLAKQVKY ALEQPLHKGILRYEAW RYISIYEEDESNNKLLL RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTNFSQSRWFFTKEL PSFADYINNGAITIGAY LVASAAFLYMDSAKED VINWMSTNPKLVVAYS THSRLINDFGGHKFDKE RGTGTAIECYMKDHNIS EEEAAKKFREMIENTW KVMNEECLRPIPIPRDT LKMLLNIARVGETVYK HRIDGFTQPHAIEEHIRA MLVDFMSI (SEQ ID NO: 37) | cggtattttcgaccaatttatcgacgctaaaggtaa gttcaaggaatctttatgtaacgatatcagaggttt gttgtctttgtacgaagctgctcatgttagaactca cggtgataaaattttggaagaagctttagctttcac cactactcacatgacctccggtggtccacatttag attcttcattggccaagcaagttaaatacgcattgg aacagccattgcataagggtatattgagatatgaa gcttggagatacatatctatctacgaagaggacg aatccaacaataagttattattgcgtttggctaagtt ggactatcacttgttacaaatgtcatacaagcaag agttgtgtgaaattacaagatggggtaaaggtttg gaatctgtctccaactttccttatgccgtgacaga ttcgttgaatgttactttggtgctgcggtactttgta cgaaccacaatactcattggctagaatgaccttcg ctaaggttgctgctttaattactatgatcgatgatatt tatgatgcctacggtaccttggacgaattgcaaat attaactgactctgccgaaagatgggatggttccg gtgtcgatcagttgtctgactatattagagcttccta taatacattattgaaatttaataaggaggttggtga agatttggcaaaaaagcaacgtacctacgctttcg acaagtacatcgaagattggaaacaatacatgag aaccaacttctctcaatcaagatggttttttcactaag gagttgccatctttcgctgattacattaacaacggt gccatcacaatcggtgcatatttggttgcctctgct gctttcttatatatggactccgcaaaagaagatgtt atcaactggatgtccacaaaccctaagttggtcgt tgcttactccactcactctcgtttaattaatgactttg gtggtcacaagttcgacaaggagagaggtaccg gtactgctattgaatgctacatgaaggaccataat atatccgaagaagaagccgcaaagaagtttaga gaaatgatcgagaacacctggaaggtcatgaatg aagaatgtttaagaccaattccaatccctagagac acattgaagatgttgttaaacatcgccagagttggt gaaactgtctacaagcatagaatcgatggttttact caaccacatgctattgaagaacacataagagctat gttggttgatttcatgtctatttaa (SEQ ID NO: 103) |
| WenAng SQTS26 7 | Wend- landia angust- ifolia | G5CV47 | 11% | SLLEGNVNHENGIFRPE ANFSPSMWGNIFRDSSK DNQISEEVVEEIEALKE VVKHMIISTTSNAIEQK LELVDNLERLGLAYHF EGQINRLLSSAYNANHE DEGNHKRNKEDLYAA ALEFRIFRQHGFNVSSD CFNQFKDTKGKFKKTL LIDVKGMLSLYEAAHV REHGDDILEEALIFATF HLERITPNSLDSTLEKQ VGHALMQSLHRGIPRA EAHFNISIYEECGSSNEK LLRLAKLDYNLVQVLH KEELSELTKWWKDLDF ASKLSYVRDRMVECFF WTVGVYFEPQYSRARV MLAKCIAMISVIDDTYD SYGTLDELIIFTEVVDR WDISEVDRLPNYMKPI YISLLYLFNEYEREINEQ DRFNGVNYVKEAMKEI VRSYYIEAEWFIEGKIPS FEEYLNNALVTGTYYL LAPASLLGMESTSKRTF DWMMKKPKILVASAII GRVIDDIATYKIEKEKG QLVTGIECYMQENNLS VEKASAQLSEIAESAW KDLNKECIKTTTSNIPN | atgtccttgttagaaggtaacgttaatcacgagaa cggaatatttagaccagaagctaatttctcacctc tatgtggggtaacattttccgtgattcttccaaaga caaccaaatctctgaagaagtcgttgaagaaatc gaggcattgaaggaagtcgttaagcatatgattat ttctacaacctccaacgccatcgaacagaaattag agttggtcgataatttggaaagattgggtttggctt accacttcgaaggtcaaatcaacagattattatcat ctgcctataatgctaaccatgaagacgaaggtaa ccacaagagaaataaggaggacttgtacgcagc tgctttggaatttagaattttcagacaacatggttta acgtttcctctgattgctttaatcaattcaaagatact aagggtaagttcaaaaagactttgttgattgatgtc aagggtatgttgtccttgtatgaagctgcccacgtt cgtgaacatggtgacgacatcttagaagaagcttt gatctttgctaccttccacttagaaagaattactcca aattcttggattccacattggaaaaacaagttggt cacgcattgatgcaatcattacacagaggtattcc aagagccgaagctcattttaacatatctatttacga agatgtggttcttctaatgaaaagttgttaagattg gctaagttggactacaacttagtccaagtcttgca caaggaggaattatcagaattgaccaaatggtgg aaagatttagacttcgcttctaagttgtcctacgttc gtgatagaatggttgaatgtttttctggactgtcgg tgtttatttcgaaccacagtactccagagccagag ttatgttagctaagttgtattgctatgatctctgttatc gacgatacttacgattcctatggtaccttggacga gttaattatattcactgaagtcgttgatagatgggat atatccgaggtcgaccgtttgcctaactatatgaa accaatctacatttctttgttatacttgtttaacgaata tgaaagagaaattaacgaacaagaccgtttcaat |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | EILMRVVNLTRLIDVVY KNNQDGYSNPKNNVKS VIEALLVNPINM (SEQ ID NO: 38) | ggtgttaactacgttaaggaagctatgaaggaaat cgtcagatcttattacatcgaggccgaatggttcat agaaggtaaaatcccatctttcgaagagtacttga acaatgcattggttacaggtacctattacttattggc cccagcatctttgttgggtatggaatccacctcaa agagaacttttgattggatgatgaagaagccaaa aattttggtcgcttctgctatcattggtagagttattg atgatattgctacttacaagatagaaaaggaaaag ggacagttagtcactggtattgaatgctacatgca agagaacaacttatcagttgaaaaggcctccgct caattgtctgaaatcgccgagtccgcttggaaag acttgaataaagaatgtatcaaaactaccacctcc aacattcctaacgaaatattgatgagagtttgtcaac ttgacaagattaattgacgttgtctacaagaataat caagatggttattctaaccctaagaacaatgttaag tcagtcatcgaagctttgttggttaatccaatcaata tgtaa (SEQ ID NO: 104) |
| WenAng SQTS30 2 | Wendlandia angustifolia | Q5SBP4 | 17% | ESRRSANYQASIWDDN FIQSLASPYAGEKYVSQ ANELKEQVKMMLDEE DMKLLDCLELVDNLER LGLAYHFEGQINRLLSS AYNANHEDEGNHKRN KEDLYAAALEFRIFRQH GFNVPQDVFSSFMNKA GDFEESLSKDTKGLVSL YEASYLSMEGETILDM AKDFSSHHLHKMVEDA TDKRVANQIIHSLEMPL HRRVQKLEAIWFIQFYE CGSDANPTLVELAKLD FNMVQATYQEELKRLS RWYEETGLQEKLSFAR HRLAEAFLWSMGIIPEG HFGYGRMHLMKIGAYI TLLDDIYDVYGTLEELQ VLTEIIERWDINLLDQLP EYMQIFFLYMFNSTNEL AYEILRDQGINVISNLK GLWVELSQCYFKEATW FHNGYTPTTEEYLNVA CISASGPVILFSGYFTTT NPINKHELQSLERHAHS LSMILRLADDLGTSSDE MKRGDVPKAIQCFMND TGCCEEEARQHVKRLI DAEWKKMNKDILMEK PFKNFCPTAMNLGRISM SFYEHGDGYGGPHSDT KKKMVSLFVQPMNITI (SEQ ID NO: 39) | atggaaagtaggcgttcagcaaattatcaggcttc catatgggatgacaactttattcaatctcttgcctct cctacgctggagagaagtacgtctcgcaagcta acgaattgaaagaacaagtgaagatgatgttaga cgaagaggatatgaaactgttagattgcttggaat tggttgacaacttggaaagactaggcttggcttat cacttcgagggtcaaatcaatagactcttgagcag tgcctacaacgctaaccatgaagatgaaggtaat cacaagagaaataaggaagacttatacgcggcg gctttggagttcagaatttttagacaacatggtttca acgttccacaggacgtcttctcttccttatgaataa ggccggtgattttgaagaatcccttctaaggatac aaaaggtttggtttcattgtatgaagcttcttacctat caatggaaggtgaaaccatcttagacatggctaa ggattttctcctctcaccatttacacaaaatggtcga agatgctactgataagcgagttgctaaccaaatca ttcacagccttgaaatgccattgcacagaagggta caaaaactcgaagcaatatggttcattcaattctac gaatgtggttctgacgccaaccccacttggtaga attggctaagttagacttcaacatggttcaagctac gtatcaagaagaactaaagagattgtcgagatgg tacgaagagaccggactgcaagaaaagttatcttt tgcacgtcatcgtttggccgaagctttttttgtggtct atgggtatcattccagaaggccatttcggttacgg tagaatgcacttgatgaagatcggtgcctatattac tttattggatgatatttatgatgtctacggtaccttgg aagagttgcaagttctaactgaaatcatcgaacgt tgggacattaatttgttggaccagctgcctgagta catgcaaatcttcttttttatacatgttcaattccacaa acgaattagcttatgagatacttagagatcaagga attaatgttatctctaacctcaaagggttgtgggtc gaattgtcccagtgttatttaaggaagcaacctgg tttcataacggttacactccaactacagaggaata cttgaacgttgcttgtattagtgcatctggtccagtg atcctttctccggttatttcaccacgactaacccga ttaataagcatgaattacaaagtttagaaagacac gctcattcactaagcatgattctgagattggctgac gaccttgggacctcatctgatgaaatgaaacggg gcgatgtgccaaaggccatccagtgctttatgaat gacactggttgttgtgaagaagaggcaagacaa cacgtcaaaagactcatagacgctgaatggaag aagatgaacaaggacatcttgatggaaaaacct ttaagaacttctgtccaactgctatgaatttaggtag ataagcatgtcctttacgagcacggtgatggtt acggtggtccacactctgataccaaaaaaaagat ggttagcttgttcgttcaacctatgaacattaccatc taa (SEQ ID NO: 105) |
| WenAng SQTS73 8 | Wendlandia angustifolia | A0A068 VE40 | 46% | ASTEIAVPLNNQHESVR QLADFPENIWADRVAS FTLDKQGHDMCAKEIE MLKEEVMSMLLEEKP | atggcctcaacagaaatcgcagttcctttgaataa ccagcacgagtccgtccgtcaattagctgacttcc cagaaaacatttgggctgatagagttgcttctttta ccttggataagcaaggtcatgacatgtgtgctaaa |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | MMEKFNLIDNIERLGIS YHFGDKIEDQLQEYYD ACTNFEKHAECDLSIAA LQFRLFRQHGFNISCGIF DGFLDANGKFKESLCN DIKGLLSLYEAAHVRT HGDKILEEALFFTTTHL TREIPNVGSTLAKQVKY ALEQPLHKGIPRYEAW RYISIYEEDESSNKLLLR LAKLDYHLSQMLNKQ DLCEIIRWGKELDIISKV PYARDRIVECYFWAVA TYYEPQYSLARMTLTK ATVFAGMIDDTYDAYG TLDELKIFTEAVERWDS SGIDQLSDYMKAAYTL VLNFNKEVGEDLAKKQ RTYAFDKYIEEWKQYA RTSFTQSKWFLTNELPS FSDYLSNGMVTSTYYL LSAAAFLDMDSASEDVI NWMSTNPKLFVALTTH ARLANDVGSHKFEKER GSGTAIECYMKDYHVS EEEAMKKFEEMCDDA WKVMNEECLRSTTIPR EILKVILNLARTCEVVY KHRGDGFTDQRRIEAHI NAMLMDSVSI (SEQ ID NO: 40) | gaaatagaaatgttaaaggaagaagtcatgtctat gttgttggaggaaaagccaatgatggaaaaattc aacttgatcgataatattgaaagattaggcatctcc taccacttcggtgacaagattgaagatcaattaca agaatattacgacgcctgcactaactttgagaagc atgctgaatgtgatttgtcaatagctgccttgcaatt cagattgtttagacaacacggtttcaatatttcttgt ggtatctttgacggtttcttggatgcaaacggtaaa ttcaaggaatctttatgtaatgacattaagggtttgtt gtccttatacgaagccgctcatgttagaactcacg gtgataaaattttggaggaagctttgttttttaccact actcatttgacccgtgaaatcccaaacgttggttct actttggctaagcaggtcaaatatgctttagagca accattgcacaagggtatcccaagatacgaagcc tggagatatattcaatttacgaagaagacgaatct tccaacaagttgttattacgtttggcaaagttggatt accatttgtcccaaatgttgaacaaacaggacttgt gcgagatcattagatggggtaaggaattagacatt atttctaaggttccttatgctagagatagaatcgtc gaatgttacttctgggctgttgccacatattacgaa ccacaatactccttggctagatgacattgaccaa agctactgttttgctggtatgatcgatgataccctat gacgcttacggtactttagatgagttgaagatattc actgaagcagtcgaacgttgggactcttccggtat tgaccaattgtcagattacatgaaagcagcttaca cctagtcttaaattttaacaaggaagttggtgaag atttagccaagaaacaaagaacttacgccttcgac aagtacatcgaagaatggaagcaatatgctagaa cctcttcacccaatctaagtggttcttgaccaatg agttgccatccttttctgattatttgtctaacggtatg gttacttcaacatactacttattgtctgccgctgcctt cttggacatggattccgcttctgaagacgtcataa attggatgtctaccaaccctaaattgttcgtcgcttt gacaactcacgctagattggccaacgacgttggt tctcataaatttgaaaaggaaagaggttcaggtac cgcaatagaatgttatatgaaggattaccacgttc tgaggaagaagctatgaagaaattcgaggaaat gtgtgacgatgcttggaaggtcatgaacgaagaa tgcttgcgttccactacaatcccaagagagattttg aaggttattttgaacttggcaagaacttgtgaagtc gtttacaagcatcgtggtgatggcttcaccgatca aagaagaattgaagctcacatcaacgccatgtta atggactccgtttccatctaa (SEQ ID NO: 106) |
| WenAng SQTS76 0 | Wend- landia angust- ifolia | A0A068 VE40 | 43% | ASTEIAVPLNNQHESVR QLADFPENIWADRVAS FTLDKQGHDMCAKEIE MLKEEVMSMLLEEKP MMEKFNLIDNIERLGIS YHFGDKIEDQLQEYYD ACTNFEKHAECDLSIAA LQFRLFRQHGFNISCGIF DGFLDANGKFKESLCN DIKGLLSLYEAAHVRT HGDKILEEALFFTTTHL TREIPNVGSTLAKQVKH ALEQPLHRGIPRYEAYC FISIYEEDESNNKLLLRL AKLDYHLLQMSYKREL SEIIRWGKELDIISKVPY ARDRIVECYFWAVATY YEPQYSLARMTLTKAT VFAGMIDDTYDAYGTL DELKIFTEAVERWDSSG IDQLSDYMKAAYTLVL NFNKEVGEDLAKKQRT YAFDKYIEEWKQYART SFTQSKWFLTNELPSFS DYLSNGMVTSTYYLLS AATFLGMDGASEDVIN WMSTNPKLFVALTTHA | atggcctcaacagaaatcgcagttcctttgaataa ccagcacgagtccgtccgtcaattagctgacttcc cagaaaacatttgggctgatagagttgcttctttta ccttggataagcaaggtcatgacatgtgtgctaaa gaaatagaaatgttaaaggaagaagtcatgtctat gttgttggaggaaaagccaatgatggaaaaattc aacttgatcgataatattgaaagattaggcatctcc taccacttcggtgacaagattgaagatcaattaca agaatattacgacgcctgcactaactttgagaagc atgctgaatgtgatttgtcaatagctgccttgcaatt cagattgtttagacaacacggtttcaatatttcttgt ggtatctttgacggtttcttggatgcaaacggtaaa ttcaaggaatctttatgtaatgacattaagggtttgtt gtccttatacgaagccgctcatgttagaactcacg gtgataaaattttggaggaagctttgttttttaccact actcatttgacccgtgaaatcccaaacgttggttct actttggctaagcaggtcaaacacgctttagagca accattgcacagaggtatcccaagatatgaagcc tactgcttcatttcaatttatgaagaagacgaatcta acaacaagttgttattacgtttggcaaagttggatt accatttgttgcaaatgtcctacaaaagagaattgt ccgagatcattagatgggtaaggaattagacatt atttctaaggttccttatgctagagatagaatcgtc gaatgttacttctgggctgttgccacatattacgag ccacaatactccttggctagaatgacattgaccaa agctactgttttcgctggtatgatcgatgataccctat gacgcttacggtactttagacgaattgaagatattc |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | RLANDVGSHKFEKERG SGTAIECYMKDYHVSE EEAMKKFEEMCDDAW KVMNEECLRSTTIPREI LKVILNLARTCEVVYK HRGDGFTDQRRIEAHIN AMLMDSVSI (SEQ ID NO: 41) | actgaagcagtcgaacgttgggattcttccggtat tgaccaattgtcagattacatgaaagcagcttaca cctagtcttaaattttaacaaggaagttggtgagg atttagccaagaaacaaagaacttacgccttcgac aagtacatcgaagaatggaagcaatatgctagaa cctcttcacccaatctaagtggttcttgaccaatg aattgccatcctttctgattatttgtctaacggtatg gttacttcaacatactacttattgtctgccgctacatt cttgggtatggacggtgcttctgaagacgtcataa attggatgtctactaaccctaaattgttcgtcgcttt gacaacccatgctagattggccaacgacgttggt tctcacaagtttgaaaaggaaagaggctccggta ctgcaatagaatgttatatgaaagattaccacgttt ctgaggaggaagctatgaagaaattcgaagaaat gtgtgacgatgcctggaaggtcatgaacgaaga atgcttgcgttctactaccatcccaagagagatttt gaaggttattttgaacttggccagaacctgtgaag tcgtttacaagcatcgtggtgatggtttcactgatc agagaagaattgaagctcacatcaacgctatgtta atggactccgtttccatctaa (SEQ ID NO: 107) |
| WenAng SQTS780 | Wendlandia angustifolia | A0A068 VE40 | 41% | ASTEIAVPLNNQHESVR QLADFPENIWADRVAS FTLDKQGHDMCAKEIE MLKEEVMSMLLEEKP MMEKFNLIDNIERLGIS YHFGDKIEDQLQEYYD ACTNFEKHAECDLSIAA LQFRLFRQHGFNISCGIF DGFLDANGKFKESLCN DIKGLLSLYEAAHVRT HGDKILEEALFFTTTHL TREIPNVGSTLAKQVKH ALEQPLHRGIPRYEAYC FISMYEEDESSNKLLLR LAKLDYHLSQMLNKQ DLCEIIRWGKELDIISKV PYARDRIVECYFWAVA TYYEPQYSLARMTLTK ATVFAGMIDDTYDAYG TLDELKIFTEAVERWDS SGIDQLSDYMKAAYTL VLNFNKEVGEDLAKKQ RTYAFDKYIEEWKQYA RTSFTQSKWFLTNELPS FSDYLSNGMVTSTYYL LSAATFLGMDGASEDV INWMSTNPKLFVALTT HARLANDVGSHKFEKE RGSGTAIECYMKDYHV SEEEAMKKFEEMCDDA WKVMNEECLRSTTIPR EILKVILNLARTCEVVY KHRGDGFTDQRRIEAHI NAMLMDSVSI (SEQ ID NO: 42) | atggcctcaacagaaatcgcagttcctttgaataa ccagcacgagtccgtccgtcaattagctgacttcc cagaaaacatttgggctgatagagttgcttctttta ccttggataagcaaggtcatgacatgtgtgctaaa gaaatagaaatgttaaaggaagaagtcatgtctat gttgttggaggaaaagccaatgatggaaaaattc aacttgatcgataatattgaaagattaggcatctcc taccacttcggtgacaagattgaagatcaattaca agaatattacgacgcctgcactaactttgagaagc atgctgaatgtgatttgtcaatagctgcctttgcaatt cagattgtttagacaacacggtttcaatatttcttgt ggtatctttgacggtttcttggatgcaaacggtaaa ttcaaggaatctttatgtaatgacattaagggtttgtt gtccttatacgaagccgctcatgttagaactcacg gtgataaaatttggaggaagctttgttttttaccact actcatttgacccgtgaaatcccaaacgttggttct actttggctaagcaggtcaaacacgctttagagca accattgcacagaggtatcccaagatatgaagcc tactgcttcatttcaatgtatgaagaagacgaatctt ccaacaagttgttattacgtttggcaaagttggatt accatttgtcccaaatgttgaacaaacaggacttgt gtgagatcattagatgggaagaattagacatt atttctaaggttccttatgctagagatagaattgtcg aatgttacttttgggctgttgccacatactacgaac cacaatattccttggctagaatgacattgaccaaa gctactgttttcgctggtatgatcgatgatacctatg acgcttacggtacttagtgagttgaagatattca ctgaagcagtcgaacgttgggactcttccggtatt gaccaattgtcagattacatgaaagcagcttacac cttagtcttaaattttaacaaggaagttggtgaaga tttagccaagaaacaaagaacttacgccttcgaca agtacatcgaagaatggaagcaatatgctagaac ctcttcacccaatctaagtggttcttgaccaatga gttgccatcctttctgattatttgtctaacggtatgg ttacttcaacatactacttattgtctgccgctacattc ttgggtatggacggtgcttctgaagatgtcataaat tggatgtctactaaccctaaattgttcgtcgctttga caacccatgctagattggccaacgacgttggtct cacaagtttgaaaaggaaagaggctccggtactg caatagaatgctatatgaaagattaccacgtttctg aggaagaagctatgaagaaattcgaggaaatgt gtgacgatgcctggaaggtcatgaacgaagaat gttgcgttctactaccatcccaagagagattttga aggttattttgaacttggccagaacctgtgaagtc gtttacaagcatcgtggtgatggtttcactgaccaa agaagaatcgaagctcacattaacgctatgttaat ggactccgtttccatctaa (SEQ ID NO: 108) |

TABLE 10-continued

Amino acid (AA) and nucleic acid sequences of sesquiterpene chimeras.

| Chimera Name | Rare DNA source | Extant scaffold Uni-prot # | % Rare DNA | Chimera AA sequence (beginning after the first encoded amino acid M) | Chimera Nucleic Acid Sequence |
|---|---|---|---|---|---|
| WenAng SQTS79 3 | Wend-landia angust-ifolia | A0A068 UHT0 | 75% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGKFKESLCN DIRGLLSLYEAAHVRTH GDKILEEALAFTTTHMT SGGPHLDSSLAKQVKY ALEQPLHKGILRYEAW RYISIYEEDESNNKLLL RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTSFTQSKWFLTNEL PSFADYISNGAITIGAYL IASAGFLDMDSALEDVI NWMSTNPKLMVAYST HSRLINDYGGHKFDKE RGSVTALDCYMKDYSV SEEEAAKKFREMCEDN WKVMNEECLRPTTIPR DGLKMLLNIARVGETV YKHRIDGFTQPHAIEEH IRAMLVDFMSI (SEQ ID NO: 43) | atggcctcagcacaagcttccttaccttctaataac agacaggaaacagtccgtccattggctgacttcc cagagaacatctgggctgatagaattgccccattt accttggataagcaagaatacgaaatgtgtcaaa gagaaatagagatgttaaaagctgaagttgcttct atgttgttggcaactggtaagactatgatgcaaag attcgacttcattgataagatcgaaagattggggg tctcccaccattttgacattgaaatcgaaaatcaatt gcaagagttttcaacgtttataccaacttaggtga atactctgcctatgatttgtcatctgctgccttgcag ttccgtttatttagacaacacggttttcaatatttcctg cggtattttcgaccaatttatcgacgctaaagtaa gttcaaggaatctttatgtaacgatatcagaggttt gttgtctttgtacgaagctgctcatgttagaactca cggtgataaaattttggaagaagctttagctttcac cactactcacatgacctccggtggtccacatttag attcttcattggccaagcaagttaaatacgcattgg aacagccattgcataagggtatattgagatatgaa gcttggagatacatatctatctacgaagaggacg aatccaacaataagttattattgcgtttggctaagtt ggactatcacttgttacaaatgtcatacaagcaag agttgtgtgaaattacaagatggggtaaaggtttg gaatctgtctccaactttccttatgcccgtgacaga ttcgttaatgttacttttgggctgtcggtactttgta cgaaccacaatactcattggctagaatgaccttcg ctaaggttgctgctttaattactatgatcgatgatatt tatgatgcctacggtaccttggacgaattgcaaat attaactgactctgccgaaagatgggatggttccg gtgtcgatcagttgtctgactatattagagcttccta taatacattattgaaatttaataaggaggttggtga agatttggcaaaaaagcaacgtacctacgctttcg acaagtacatcgaagattggaaacaatacatgag aacctcttcactcaatcaaagtggttttgactaac gagttgccatctttcgctgattacatttccaacggt gccatcacaatcggtgcatatttaattgcctctgcc ggttttttggatatggattccgccttggaagacgtt attaactggatgtctaccaacccaaaattaatggtc gcttattccacccactcaagattgatcaatgattac ggtggtcacaagttcgacaaggaaagagggtca gttactgctttggattgctacatgaaggattactcc gtctctgaggaagaagctgcaaagaagttcaga gaaatgtgtgaagacaactggaaggttatgaatg aagaatgtttgagacctactacaattccaagagat ggtttgaagatgttgttaaacattgctagagtcggt gaaactgtttacaaacatagaatcgacggttttact caacctcatgcaatcgaggagcacattagagcca tgttagttgacttcatgtctatttaa (SEQ ID NO: 109) |
| WenAng SQTS80 5 | Wend-landia angust-ifolia | A0A068 VE40 | 42% | ASTEIAVPLNNQHESVR QLADFPENIWADRVAS FTLDKQGHDMCAKEIE MLKEEVMSMLLEEKP MMEKFNLIDNIERLGIS YHFGDKIEDQLQEYYD ACTNFEKHAECDLSIAA LQFRLFRQHGFNISCGIF DGFLDANGKFKESLCN DIKGLLSLYEAAHVRT HGDKILEEALFFTTTHL TREIPNVGSTLAKQVKY ALEQPLHKGIPRYEAW RYISIYEEDESNNKLLL RLAKLDYHLLQMSYKR ELSEIIRWGKELDIISKV PYARDRIVECYFWAVA TYYEPQYSLARMTLTK ATVFAGMIDDTYDAYG TLDELKIFTEAVERWDS SGIDQLSDYMKAAYTL VLNFNKEVGEDLAKKQ | atggcctcaacagaaatcgcagttcctttgaataa ccagcacgagtccgtccgtcaattagctgacttcc cagaaacatttgggctgatagagttgcttctttta ccttggataagcaaggtcatgacatgtgtgctaaa gaaatagaaatgttaaaggaagaagtcatgtctat gttgttggaggaaaagccaatgatggaaaaattc aacttgatcgataatattgaaagattaggcatctcc taccactcggtgacaagattgaagatcaattaca agaatattacgacgcctgcactaaccttgagaagc atgctgaatgtgatttgtcaatagctgccttgcaatt cagattgtttagacaacacggttttcaatatttcttgt ggtatctttgacggtttcttggatgcaaacggtaaa ttcaaggaatctttgtaatgacattaagggtttgtt gtccttatacgaagccgctcatgttagaactcacg gtgataaaatttggaggaagctttgttttttaccact actcatttgacccgtgaaatcccaaacgttggttct acttttgcctaagcaggtcaaatatgctttagacga accattgcacaagggtatcccaagatacgaagcc tggagatatattcaatttacgaagaagacgaatct aacaacaagttgttattacgtttggcaaagttggat taccattgttgcaaatgtcctacaaaagagaattg tccgagatcattagatggggtaaggaattagacat |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | RTYAFDKYIEEWKQYA RTSFTQSKWFLTNELPS FSDYLSNGMVTSTYYL LSAATFLGMDGASEDV INWMSTNPKLFVALTT HARLANDVGSHKFEKE RGSSTAIECYMKDYHV SEEEAMEKFEEMCDDA WKVMNEECLRSTTIPR EILKVILNLARTCEVVY KHRGDGFTDQRRIEAHI NAMLMDSVSI (SEQ ID NO: 44) | tatttctaaggttccttatgctagagatagaatcgtc gaatgttatttctgggctgttgccacatactacgag ccacaatactccttggctagaatgacattgaccaa agctactgttttgctggtatgatcgatgatacctat gacgcttacggtactttagacgaattgaagatattc actgaagcagtcgaacgttgggattcttccggtat tgaccaattgtcagattacatgaaagcagcttaca ccttagtcttaaattttaacaaggaagttggtgagg atttagccaagaaacaaagaacttacgccttcgac aagtacatcgaagaatggaagcaatatgctagaa cctctttcacccaatctaagtggttcttgaccaatg aattgccatcctttctgattatttgtctaacggtatg gttacttcaacatactacttattgtctgccgctacatt cttgggtatggacggtgcttctgaagacgtcataa attggatgtctactaaccctaaattgttcgtcgcttt gacaacccacgctagattggccaacgacgttggt tctcataaatttgaaaaggaaagaggctcctccac tgcaatagaatgctatatgaaggattaccacgtttc tgaggaggaagctatggaaaaattcgaagaaat gtgtgacgatgcctggaaggtcatgaacgaaga atgcttgcgttccactaccatcccaagagagattt gaaggttattttgaacttggccagaacctgtgaag tcgtttacaagcatcgtggtgatggtttcactgatc agagaagaattgaagctcacatcaacgctatgtta atggactcagtttccatctaa (SEQ ID NO: 110) |
| WenAng SQTS82 6 | Wendlandia angustifolia | A0A068 VE40 | 47% | ASTEIAVPLNNQHESVR QLADFPENIWADRVAS FTLDKQGHDMCAKEIE MLKEEVMSMLLEEKP MMEKFNLIDNIERLGIS YHFGDKIEDQLQEYYD ACTNFEKHAECDLSIAA LQFRLFRQHGFNISCGIF DGFLDANGKFKESLCN DIKGLLSLYEAAHVRT HGDKILEEALFFTTTHL TREIPNVGSTLAKQVKY ALEQPLHKGIPRYEAW RYISIYEEDESNNKLLL RLAKLDYHLLQMSYKR ELSEIIRWGKELDIISKV PYARDRIVECYFWAVA TYYEPQYSLARMTLTK ATVFAGMIDDTYDAYG TLDELKIFTEAVERWDS SGIDQLSDYMKAAYTL VLNFNKEVGEDLAKKQ RTYAFDKYIEEWKQYA RTSFTQSKWFLTNELPS FADYLSNGMVTSTYYL LSAAALLDMDSALEDV INWMSTNPKFFVALTT HARLTNDVGSHKFEKE RGSGTAIECYMKDYHV SEEEAMKKFEEMCDDA WKVMNEECLRSTTIPR EILKVILNLARTCEVVY KHRGDGFTDQRRIEAHI NAMLMDSVSI (SEQ ID NO: 45) | atggcctcaacagaaatcgcagttcctttgaataa ccagcacgagtccgtccgtcaattagctgacttcc cagaaaacatttgggctgatagagttgcttcttta ccttggataagcaaggtcatgacatgtgtgctaaa gaaatagaaatgttaaaggaagaagtcatgtctat gttgttggaggaaaagccaatgatggaaaaattc aacttgatcgataatattgaaagattaggcatctcc taccacttcggtgacaagattgaagatcaattaca agaatattacgacgcctgcactaactttgagaagc atgctgaatgtgatttgtcaatagctgccttgcaatt cagattgtttagacaacacggtttcaatatttcttgt ggtatctttgacggtttcttggatgcaaacggtaaa ttcaaggaatctttatgtaatgacattaagggtttgtt gtccttatacgaagccgctcatgttagaactcacg gtgataaaattttggaggaagctttgttttttaccact actcatttgacccgtgaaatcccaaacgttggttct actttggctaagcaggtcaaatatgctttagagca accattgcacaagggtatcccaagatacgaagcc tggagatatatttcaatttacgaagaagacgaatct aacaacaagttgttattacgtttggcaaagttggat taccatttgttgcaaatgtcctacaaaagagaattg tccgagatcattagatggggtaaggaattagacat tatttctaaggttccttatgctagagatagaatcgtc gaatgttatttctgggctgttgccacatactacgag ccacaatactccttggctagaatgacattgaccaa agctactgttttgctggtatgatcgatgatacctat gacgcttacggtactttagacgaattgaagatattc actgaagcagtcgaacgttgggattcttccggtat tgaccaattgtcagattacatgaaagcagcttaca ccttagtcttaaattttaacaaggaagttggtgagg atttagccaagaaacaaagaacttacgccttcgac aagtacatcgaagaatggaagcaatatgctagaa cctctttcacccaatctaagtggttcttgaccaatg aattgccatcctttgcagattatttgtctaacggtat ggttacttcaacatactacttattgtctgctgctgcc ttgttggacatggactccgctttagaagatgtcata aattggatgtctaccaaccctaaattcttcgtcgctt tgacaactcacgctagattgaccaacgacgttggt tctcataaatttgaaaaggaaagaggttccggtac tgcaatagaatgctatatgaaggattaccacgtttc tgaggaggaagctatgaaaaattcgaagaaat gtgtgacgatgcctggaaggtcatgaacgaaga atgcttgcgttctactacaatcccaagagagatttt gaaggttattttgaacttggccagaacctgtgaag tcgtttacaagcatcgtggtgatggcttcactgacc |

TABLE 10-continued

Amino acid (AA) and nucleic acid sequences of sesquiterpene chimeras.

| Chimera Name | Rare DNA source | Extant scaffold Uni-prot # | % Rare DNA | Chimera AA sequence (beginning after the first encoded amino acid M) | Chimera Nucleic Acid Sequence |
|---|---|---|---|---|---|
| | | | | | agagaagaattgaagctcacatcaacgccatgtt aatggactccgtttccatctaa (SEQ ID NO: 111) |
| WenAng SQTS82 9 | Wend- landia angust- ifolia | A0A068 UHT0 | 74% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGKFKESLCN DIRGLLSLYEAAHVRTH GDKILEEALAFTTTHMT SGGPHLDSSLAKQVKY ALEQPLHKGILRYEAW RYISIYEEDESNNKLLL RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTSFTQSKWFLTNEL PSFADYISNGAITIGAYL IASAGFLDMDSALEDVI NWMSTNPKLMVAYST HSRLINDYGGHKFDKE RGTGTAIECYMKDHNIS EEEAAKKFREMIENTW KVMNEECLRPIPIPRDT LKMLLNIARVGETVYK HRIDGFTQPHAIEEHIRA MLVDFMSI (SEQ ID NO: 46) | atggccagtgcgcaagcatcattaccttccaataa cagacaggaaacagtccgtcccctagctgacttc ccagagaacatctgggctgataggattgctccatt taccctggataagcaagaatacgaaatgtgtcaa agagaaatagagatgttgaaagctgaagtggcct ctatgttgcttgccactggaaagactatgatgcaa cgattcgacttcattgataagatcgaaagattggg cgtatcgcaccattttgacattgaaatcgaaaatca actccaagagtttttcaacgtttataccaacttgggt gaatacagcgcgtatgatctgtcatctgctgcattg cagttcagattatttagacaacacggtttcaatattt cctgcgtatttcgaccaatttatcgacgctaaag gtaagttcaaggaatctttatgtaacgatatccgg gtttgttgtctctctacgaagctgctcatgttagaac gcacggtgataaaattttggaagaagcattggctt ttactactacccatatgacttccggtggtccacacc tagactctagcttggctaacgaagtcaagtacgc gcttgagcaaccattacacaagggggattttgagat acgaagcttggcgttatatatccatctacgaagaa gacgaatctaataacaaacttctgttaagattggct aaactcgattatcatttgcttcaaatgtcctacaagc aggaattatgtgaaatcacgagatggggcaagg gtttagagtcagtttctaatttccttacgctagaga tcgttttgttgaatgttatttctgggccgtaggaaca ttgtacgaaccgcaatacagtctagccagaatga ccctttgctaaagttgctgccttgattactatgattga cgatatctacgatgcctatggtaccttggacgagtt acaaatattgaccgattctgctgaaagatgggatg gttcgggagtcgaccaattgtctgactatatacgc gctagttataacacttttgttgaagttcaacaaggaa gtcggtgaggatttagccaaaaagcaaagaacgt acgcatttgacaaatacatcgaagattggaagca atacatgagaacttctttcacccagtccaagtggtt cctgaccaacgaactccctccttcgctgactaca tttccaatggggctattacaattggtgcttacttgat cgccagcgcgggttttttggatatggattctgccct agaagacgttattaactggatgtctactaacccaa aattgatggtggcttattcaactcacagcagactta tcaatgattatggtggtcacaagttcgacaaggaa agagggacgggtacagctattgaatgctacatga aggatcataacatctctgaggaagaagctgcaaa gaagttcagagaaatgatcgagaacacttggaag gttatgaatgaagaatgtctacggccaattccaatt ccaagagatactctcaagatgctattgaacattgct agggtcggtgaaactgtttacaaacacagaatcg acggttttacccaaccacatgcaatcgaggaaca catcagggccatgttggtcgacttcatgtcaattta a (SEQ ID NO: 112) |
| WenAng SQTS84 3 | Wend- landia angust- ifolia | A0A068 VE40 | 45% | ASTEIAVPLNNQHESVR QLADFPENIWADRVAS FTLDKQGHDMCAKEIE MLKEEVMSMLLEEKP MMEKFNLIDNIERLGIS YHFGDKIEDQLQEYYD ACTNFEKHAECDLSIAA LQFRLFRQHGFNISCGIF DGFLDANGKFKESLCN DIKGLLSLYEAAHVRT HGDKILEEALFFTTTHL TREIPNVGSTLAKQVKH ALEQPLHRGIPRYEAYC FISIYEEDESNNKLLLRL AKLDYHLLQMSYKREL SEIIRWGKELDIISKVPY ARDRIVECYFWAVATY YEPQYSLARMTLTKAT | atggcctcaacagaaatcgcagttcctttgaataa ccagcacgagtccgtccgtcaattagctgacttcc cagaaaacatttgggctgatagagttgcttcttta ccttggataagcaaggtcatgacatgtgtgctaaa gaaatagaaatgttaaaggaagaagtcatgtctat gttgttggaggaaaagccaatgatggaaaaattc aacttgatcgataatattgaaagattaggcatctcc taccacttcggtgacaagattgaagatcaattaca agaatattacgacgcctgcactaactttgagaagc atgctgaatgtgatttgtcaatagctgccttgcaatt cagattgtttagacaacacggtttcaatatttcttgt ggtatctttgacggttttcttggatgcaaacggtaaa ttcaaggaatctttatgtaatgacattaaggtttgtt gtcctatacgaagccgctcatgttagaactcacg gtgataaaattttggaggaagcttgttttttaccact actcattgacccgtgaaatcccaaacgttggttct actttggctaagcaggtcaaacacgctttagagca accattgcacagaggtatcccaagatatgaagcc |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | VFAGMIDDTYDAYGTL DELKIFTEAVERWDSSG IDQLSDYMKAAYTLVL NFNKEVGEDLAKKQRT YAFDKYIEEWKQYART SFTQSKWFLTNELPSFS DYLSNGMVTSTYYLLS AAAFLDMDSASEDVIN WMSTNPKLFVALTTHA RLANDVGSHKFEKERG SGTAIECYMKDYNVSE EEALKKFEEMCEDTWK VMNEECLRSTTIPREIL KVILNLARTCEVVYKH RGDGFTDQRRIEAHINA MLMDSVSI (SEQ ID NO: 47) | tactgcttcatttcaatttatgaagaagacgaatcta acaacaagttgttattacgtttggcaaagttggatt accatttgttgcaaatgtcctacaaaagagaattgt ccgagatcattagatggggtaaggaattagacatt atttctaaggttccttatgctagagatagaatcgtc gaatgttacttttgggctgttgccacatattacgag ccacaatactccttggctagaatgacattgaccaa agctactgttttcgctggtatgatcgatgatacctat gacgcttacggtacttttagacgaattgaagatattc actgaagcagtcgaacgttgggattcttccggtat tgaccaattgtcagattacatgaaagcagcttaca ccttagtcttaaattttaacaaggaagttggtgagg atttagccaagaaacaaagaaacttacgccttcgac aagtacatcgaagaatggaagcaatatgctagaa cctctttcacccaatctaagtggttcttgaccaatg aattgccatcctttctgattatttgtctaacggtatg gttacttcaacatactacttattgtctgccgctgcctt cttggacatggactccgcttctgaagatgtcataa attggatgtctaccaaccctaaattgttcgtcgcttt gacaactcatgctagattggccaacgacgttggtt ctcacaagtttgaaaaggaaagaggttcaggtac cgcaatagaatgttatatgaaagattacaacgtttc tgaggaggaagctttgaagaaattcgaagaaatg tgtgaagatacttggaaggtcatgaacgaagaat gcttgcgttccactacaatcccaagagagattttg aaggttattttgaacttggccagaacctgtgaagtc gtttacaagcatcgtggtgacggcttcactgatca gagaagaattgaagctcacatcaatgctatgttaa tggactccgtttccatctaa (SEQ ID NO: 113) |
| WenAng SQTS848 | Wendlandia angustifolia | A0A068 UHT0 | 84% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGKFKESLCN DIRGLLSLYEAAHVRTH GDKILEEALAFTTTHMT SGGPHLDSSLAKQVKY ALEQPLHKGILRYEAW RYISIYEEDESNNKLLL RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTNFSQSRWFFTKEL PSFADYINNGAITIGAY LVASAAFLYMDSAKED VINWMSTNPKLVVAYS THSRLINDFGGHKFDKE RGSGTALECYMKDYN VSEEEAANKFREMMED AWKVMNEDCLRPTSIP RDVSKVLLNVARAGEI VYKHRIDGFTEPHIIKD HIRATLVDFMAIN (SEQ ID NO: 48) | atggcctcagcacaagcttccttaccttctaataac agacaggaaacagtccgtccattggctgacttcc cagagaacattcgggctgcatagaattgccccatt acctggataagcaagaatacgaaatgtgtcaaa gagaaatagagatgttaaaagctgaagttgcttct atgttgttggcaactggtaagactatgatgcaaag attcgacttcattgataagatcgaaagattggggg tctcccaccattttgacattgaaatcgaaatcaatt gcaagagttttcaacgtttataccaacttaggtga atactctgcctatgatttgtcatctgctgccttgcag ttccgtttatttagacaacaacggttcaatattcctg cggtattttcgaccaatttatcgacgctaaaggtaa gttcaaggaatctttatgtaacgatatcagaggttt gttgtctttgtacgaagctgctcatgttagaactca cggtgataaaattttggaagaagcttttagcttttcac cactactcacatgaccctccggtggtccacatttag attcttcattggccaagcaagttaaatacgcattgg aacagccattgcataagggtatattgagatatgaa gcttggagatacatatctatctacgaagaggacg aatccaacaataagttattattgcgtttggctaagtt ggactatcacttgttacaaatgtcatacaagcaag agttgtgtgaaattacaagatggggtaaaggtttg gaatctgtctccaactttccttatgcccgtgacaga ttcgttgaatgttactttgggcgtgcggtactttgta cgaaccacaatactcattggctagaatgaccttcg ctaaggttgctgctttaattactatgatcgatgatatt tatgatgcctacggtaccttggacgaattgcaaat attaactgactctgccgaacaagttattgcgttccg gtgtcgatcagtgtctgactatattagagcttccta taatacattattgaaatttaataaggaggttggtga agatttggcaaaaaagcaacgtacctacgctttcg acaagtacatcgaagattggaaacaatacatgag aaccaacttctctcaatcaagatggttttcactaag gagttgccatctttcgctgattacattaacaacggt gccatcacaatcggtgcatatttggttgcctctgct gcttttcttatatatggactccgcaaaagaagatgtt atcaactggatgtccacaaaccctaagttggtcgt tgcttactccactcactctcgtttaattaatgactttg gtggtcacaagttcgacaaggagagaggttccg gtactgctttggaatgctacatgaaggactacaat gtctctgaagaagaagccgcaaacaagtttagag |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | aaatgatggaggacgcttggaaggttatgaatga agactgtttaagaccaacttccatccctagagatgt ctccaaggttttgttaaacgtcgccagagctggtg aaattgtttacaagcatagaatcgatggttttaccg aaccacatatcattaaagatcacataagagccac cttggttgatttcatggctattaattaa (SEQ ID NO: 114) |
| WenAng SQTS84 9 | Wend-landia angust-ifolia | A0A068 UHT0 | 75% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGFKFESLCN DIRGLLSLYEAAHVRTH GDKILEEALAFTTTHMT SGGPHLDSSLAKQVKY ALEQPLHKGILRYEAW RYISIYEEDESNNKLLL RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTSFTQSKWFLTNEL PSFADYISNGAITIGAYL IASAGFLDMDSALEDVI NWMSTNPKLMVAYST HSRLINDYGGHKFDKE RGSVTALDCYMKDYSV SEEEAAKKFREMIENT WKVMNEECLRPIPIPRD TLKMLLNIARVGETVY KHRIDGFTEPHIIKDHIR AMLVDFMAIN (SEQ ID NO: 49) | atggccagtgcgcaagcatcattaccttccaataa cagacaggaaacagtccgtcccctagctgacttc ccagagaacatctgggctgataggattgctccatt taccctggataagcaagaatacgaaatgtgtcaa agagaaatagagatgttgaaagctgaagtggcct ctatgttgcttgccactggaaagactatgatgcaa cgattcgacttcattgataagatcgaaagattggg cgtatcgcaccattttgacattgaaatcgaaatca actccaagagttttcaacgtttataccaacttgggt gaatacagcgcgtatgatctgtcatctgctgcattg cagttcagattatttagacaacacggtttcaatattt cctgcgtattttcgaccaatttatcgacgctaaag gtaagttcaaggaatcttatgtaacgatatccggg gtttgttgtctctctacgaagctgctcatgttagaac gcacggtgataaaattttggaagaagcattggctt tactactacccatatgacttccggtggtccacacc tagactctagcttggctaagcaagtcaagtacgc gcttgagcaaccattacacaaggggattttgagat acgaagcttggcgttatatatccatctacgaagaa gacgaatctaataacaaacttctgttaagattggct aaaactcgattatcatttgcttcaaatgtcctacaagc aggaattatgtgaaatcacgagatggggcaagg gtttagagtcagtttctaatttccccttacgctagaga tcgttttgttgaatgttatttctgggccgtaggaaca ttgtacgaaccgcaatacagtctagccagaatga cctttgctaaagttgctgccttggttactatgattga cgatatctacgatgcctatggtaccttggacgagtt acaaatattgaccgattctgctgaaagatgggatg gttcgggagtcgaccaattgtctgactatatacgc gctagttataaacactttgttgaagttcaacaaggaa gtcggtgaggatttagccaaaaagcaaagaacgt acgcatttgacaaatacatcgaagattggaagca atacatgagaacttctttcacccagtccaagtggtt cctgaccaacgaactccctcccttcgctgactaca tttccaatggggctattacaattggtgcttacttgat cgccagcgcgggtttttttggatatggattctgccct agaagacgttattaactggatgtctactaacccaa aattgatggtggcttattcaactcacagcagactta tcaatgattatggtgtcacaagttcgacaaggaa agagggagcgttacagctttggattgctacatgaa ggattacagtgtctctgaggaagaagctgcaaag aagttcagagaaatgatcgaaaacacctggaag gttatgaatgaagaatgtctgcggccaattccaatt ccaagagatactctaaagatgctattgaacattgct agggtaggtgaaactgtttacaaacatagaatcg acggtttactgaaccacatataattaaggaccac atcagggcaatgttggtcgacttcatggctattaac taa (SEQ ID NO: 115) |
| WenAng SQTS86 4 | Wend-landia angust-ifolia | A0A068 UHT0 | 81% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGFKFESLCN DIRGLLSLYEAAHVRTH GDKILEEALAFTTTHMT SGGPHLDSSLAKQVKY ALEQPLHKGILRYEAW RYISIYEEDESNNKLLL | atggcctcagcacaagcttccttaccttctaataac agacaggaaacagtccgtccattggctgacttcc cagagaacatctgggctgatagaattgccccattt accttggataagcaagaatacgaaatgtgtcaaa gagaaatagagatgttaaaagctgaagttgcttct atgttgttggcaactggtaagactatgatgcaaag attcgacttcattgataagatcgaaagattgggg tctcccaccattttgacattgaaatcgaaatcaatt gcaagagttttcaacgtttataccaacttaggtga atactctgcctatgatttgtcatctgctgccttgcag ttccgtttatttagacaacacggtttcaatatttcctg cggtattttcgaccaatttatcgacgctaaaggtaa gttcaaggaatctttatgtaacgatatcagaggttt gttgtctttgtacgaagctgctcatgttagaactca |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTNFSQSRWFFTKEL PSFADYINNGAITIGAY LVASAAFLYMDSAKED VINWMSTNPKLVVAYS THSRLINDFGGHKFDKE RGSVTALDCYMKDYSV SEEEAAKKFREMCEDN WKVMNEECLRPTTIPR DGLKMLLNIARVGETV YKHRIDGFTQPHAIEEH IRAMLVDFMSI (SEQ ID NO: 50) | cggtgataaaattttggaagaagctttagctttcac cactactcacatgacctccggtggtccacatttag attcttcattggccaagcaagttaaatacgcattgg aacagccattgcataagggtatattgagatatgaa gcttggagatacatatctatctacgaagaggacg aatccaacaataagttattattgcgtttggctaagtt ggactatcacttgttacaaatgtcatacaagcaag agttgtgtgaaattacaagatggggtaaaggtttg gaatctgtctccaactttccttatgcccgtgacaga ttcgttgaatgttactttttgggctgtcggtactttgta cgaaccacaatactcattggctagaatgaccttcg ctaaggttgctgctttaattactatgatcgatgatatt tatgatgcctacggtaccttggacgaattgcaaat attaactgactctgccgaaagatgggatggttccg gtgtcgatcagttgtctgactatattagagcttccta taatacattattgaaatttaataaggaggttggtga agatttggcaaaaaagcaacgtacctacgctttcg acaagtacatcgaagattggaaacaatacatgag aaccaacttctctcaatcaagatggttttcactaag gagttgccatctttcgctgattacattaacaacggt gccatcacaatcggtgcatatttggttgcctctgct gctttcttatatatggactccgcaaaagaagatgtt atcaactggatgtccacaaaccctaagttggtcgt tgcttactccactcactctcgtttaattaatgactttg gtggtcacaagttcgacaaggagagaggttccgt tactgctttggactgctacatgaaggactactctgt ctccgaagaagaagccgcaaagaagtttagaga aatgtgtgaagacaattggaaggtcatgaatgaa gagtgtttaagaccaactaccatccctagagatgg gttgaagatgttgttaaacatagccagagttgtg aaactgtctacaagcatagaattgatggttttaccc aaccacatgctatcgaagaacacatcagagctat gttggttgatttcatgtctatttaa (SEQ ID NO: 116) |
| WenAng SQTS92 5 | Wendlandia angustifolia | A0A068 UHT0 | 80% | ASAQASLPSNNRQETV RPLADFPENIWADRIAP FTLDKQEYEMCQREIE MLKAEVASMLLATGKT MMQRFDFIDKIERLGVS HHFDIEIENQLQEFFNV YTNLGEYSAYDLSSAA LQFRLFRQHGFNISCGIF DQFIDAKGKFKESLCN DIRGLLSLYEAAHVRTH GDKILEEALAFTTTHMT SGGPHLDSSLAKQVKY ALEQPLHKGILRYEAW RYISIYEEDESNNKLLL RLAKLDYHLLQMSYKQ ELCEITRWGKGLESVSN FPYARDRFVECYFWAV GTLYEPQYSLARMTFA KVAALITMIDDIYDAYG TLDELQILTDSAERWD GSGVDQLSDYIRASYN TLLKFNKEVGEDLAKK QRTYAFDKYIEDWKQY MRTNFSQSRWFFTKEL PSFADYINNGAITIGAY LVASAAFLYMDSAKED VINWMSTNPKLVVAYS THSRLINDFGGHKFDKE RGSVTALDCYMKDYSV SEEEAAKKFREMIENT WKVMNEECLRPIPIPRD TLKMLLNIARVGETVY KHRIDGFTEPHIIKDHIR AMLVDFMAIN (SEQ ID NO: 51) | atggcctcagcacaagcttccttaccttctaataac agacaggaaacagtccgtccattggctgacttcc cagagaacatctgggctgatgagaattgccccattt accttggataagcaagaatacgaaatgtgtcaaa gagaaatagagatgttaaaagctgaagttgcttct atgttgttggcaactggtaagactatgatgcaaag attcgacttcattgataaagatcgaaagattggggg tctcccaccatttttgacattgaaatcgaaatcaatt gcaagagtattcaacgtttataccaacttaggtga atactctgcctatgatttgtcatctgctgccttgcag ttccgttatttagacaacaccggtttcaatattttcctg cggtattttcgaccaatttatcgacgctaaaggtaa gttcaaggaatctttatgtaacgatatcagaggttt gttgtctttgtacgaagctgctcatgttagaactca cggtgataaaattttggaagaagctttagctttcac cactactcacatgacctccggtggtccacatttag attcttcattggccaagcaagttaaatacgcattgg aacagccattgcataagggtatattgagatatgaa gcttggagatacatatctatctacgaagaggacg aatccaacaataagttattattgcgtttggctaagtt ggactatcacttgttacaaatgtcatacaagcaag agttgtgtgaaattacaagatggggtaaaggtttg gaatctgtctccaactttccttatgcccgtgacaga ttcgttgaatgttactttttgggctgtcggtactttgta cgaaccacaatactcattggctagaatgaccttcg ctaaggttgctgctttaattactatgatcgatgatatt tatgatgcctacggtaccttggacgaattgcaaat attaactgactctgccgaaagatgggatggttccg gtgtcgatcagttgtctgactatattagagcttccta taatacattattgaaatttaataaggaggttggtga agatttggcaaaaaagcaacgtacctacgctttcg acaagtacatcgaagattggaaacaatacatgag aaccaacttctctcaatcaagatggttttcactaag gagttgccatctttcgctgattacattaacaacggt gccatcacaatcggtgcatatttggttgcctctgct gctttcttatatatggactccgcaaaagaagatgtt atcaactggatgtccacaaaccctaagttggtcgt |

TABLE 10-continued

Amino acid (AA) and nucleic acid sequences of sesquiterpene chimeras.

| Chimera Name | Rare DNA source | Extant scaffold Uniprot # | % Rare DNA | Chimera AA sequence (beginning after the first encoded amino acid M) | Chimera Nucleic Acid Sequence |
|---|---|---|---|---|---|
| | | | | | tgcttactccactcactctcgtttaattaatgactttg gtggtcacaagttcgacaaggagagaggttccgt tactgctttggactgctacatgaaggactactctgt ctccgaagaagaagccgcaaagaagtttagaga aatgatcgaaaacacctggaaggtcatgaatgaa gagtgtttaagaccaattccaatccctagagacac attgaagatgttgttaaacatagccagagttggtg aaactgtctacaagcatagaattgatggttttactg aaccacatatcatcaaagatcacatcagagctatg ttggttgatttcatggctattaattaa (SEQ ID NO: 117) |
| WenAng SQTS960 | Wendlandia angustifolia | A0A068 VI46 | 81% | YEREIEMLKAEVESML LATGKTMMQRFDFIDK IERLGVSHHFDIEIENQL QEFFNVYTNFGEYSAY DLSSAALQFKQWCDHN RSLSCSITRGLLSLYEA AHVRTHGDKILEEALH LTSGESHLDSTLAKQV KCALEQPLHKGIPRYEA WRYISIYEEDESHNKLL LRLAKLDYHFLQISYRQ DLCEIIRWDSSGVDQLs DYIRAVGEELAKKQRT YAFGTFLGMDGASEDV INWMSTIPKLMFACSTH ARLINDFGGHKFDKER GTGTALECYMKDYNVS EEEAANKFREMMEDA WKVMNEECLRPTTIPR EILKMLLNIVRVGETTN KHRIDGFTQPHAIEEHIR AMLVDFMSV (SEQ ID NO: 52) | atgtatgagagagaaatcgaaatgttaaaggctg aagtcgaatctatgttgttggccaccggtaaaaca atgatgcagcgtttcgattttatagacaagattgaa agattgggcgtttcccaccatttcgatattgaaatc gagaaccaattacaagaatttttcaatgtttacacta acttcggtgaatactcagcttacgacttgtcttccg cagccttgcaatttaagcaatggtgtgaccacaat agatcattatccttgctctattactagaggtttgttatc cttgtatgaggctgctcatgtcagaacccacggtg ataagatcttggaagaagctttacacttgacttctg gtgaatcccatttggactccaccttggctaaacaa gttaaatgtgcattagaacaaccattgcacaaggg tatacctcgttacgaagcctggagatatatttctatc tacgaagaggatgaatcacataacaagttgttgtt gagattagctaaattggattatcacttcttacagatt tcttacagacaagatttgtgtgaaatcattcgttgg gactcatctggtgtcgaccaattatctgattacatc agagcagttggtgaggaattggctaagaagcaa agaacatacgctttcggtacttttttaggtatggatg gtgcctctgaagatgttattaactggatgtccacta tcccaaagttgatgttcgcttgctctacacatgcca gattgattaatgactttggtggtcataaattcgataa ggaaagaggtactggtaccgctttagagtgttata tgaaagactataacgtctccgaagaagaagccg ccaacaagtttagagaaatgatggaggacgcttg gaaagttatgaatgaagaatgtttgcgtccaacca ctattccaagagaaatattaaagatgttgttgaaca tcgtccgtgttggtgaaactactaataagcacaga atcgatggtttcacacagcctcacgctattgagga acacattagagctatgttggttgactttatgtccgtc taa (SEQ ID NO: 118) |

TABLE 11

Non-limiting examples of sequence fragment(s) derived from rare plants.

| Chimera Name | Ancient DNA Source | Fragments | SEQ ID NO |
|---|---|---|---|
| HibWilSQTS117 | Hibiscadelphus wilderianus | LKDEEGNFKASLTSDVPGLLELYEASYLRVHGEDI LDEAISFA | 119 |
| | | NKALLQFAKIDFNMLQLLHRKELSEICRWWKDLD FTRKLP | 120 |
| | | DRVVEGYFWIMGVYFEPQYSLGRKMLTKVIAMA SIVDDTYDSFATYDELIPYTDAIER | 121 |
| | | YMQISYKALLDVYEEMEQLLADKGRQYRVEY | 122 |
| | | WTHLNYKPTFEEFRDNALPTSGYAMLAIT | 123 |
| | | TFEWAASDPKIIKASTIICRFMDDIAE | 124 |
| | | EDDCSAIECYMEQYKVTAQEAYDEFNKHIESSWK DVNEEFLK | 125 |
| HibWilSQTS118 | Hibiscadelphus wilderianus | EAFNKLKDEEGNFKASLTSDVRGLLELYQASYMR IHGEDILDEAISFTTAQLTLALPTLDPP | 126 |
| | | NKALLQFAKIDFNMLQLLHRKELSEICRWWKDLD FTRKLP | 127 |

TABLE 11-continued

Non-limiting examples of sequence fragment(s) derived from rare plants.

| Chimera Name | Ancient DNA Source | Fragments | SEQ ID NO |
|---|---|---|---|
| | | DRVVEGYFWIMGVYFEPQYSLGRKMLTKVIAMA SIVDDTYDSFATYDELIPYTDAIER | 128 |
| | | YMQISYKALLDVYEEMEQLLADKGRQYRVEY | 129 |
| | | WTHLNYKPTFEEFRDNALPTSGYAMLAIT | 130 |
| | | TFEWAASDPKIIKASTIICRFMDDIAE | 131 |
| | | SAIECYMKQYGATAQEAYDEFNKHIESSWK | 132 |
| HibWilSQTS120 | Hibiscadelphus wilderianus | LKDEEGNFKASLTSDVPGLLELYEASYLRVHGEDI LDEAISFA | 133 |
| | | NKALLQFAKIDFNMLQLLHRKELSEICRWWKDLD FTRKLP | 134 |
| | | DRVVEGYFWIMGVYFEPQYSLGRKMLTKVIAMA SIVDDTYDSFATYDELIPYTDAIER | 135 |
| | | YMQISYKALLDVYEEMEQLLADKGRQYRVEY | 136 |
| | | WTHLNYKPTFEEFRDNALPTSGYAMLAIT | 137 |
| | | TFEWAASDPKIIKASTIICRFMDDIAE | 138 |
| | | SAIECYMKQYGATAQEAYDEFNKHIESSWK | 139 |
| HibWilSQTS121 | Hibiscadelphus wilderianus | EAFNKLKDEEGNFKASLTSDVRGLLELYQASYMR IHGEDILDEAISFTTAQLTLALPTLDPP | 140 |
| | | LLEFAKIDFNLLQLLHRKELSEICRWWKD | 141 |
| | | DRVVEGYFWIMGVYFEPQYSLGRKMLTKVIAMA SIVDDTYDSFATYDELIPYTDAIER | 142 |
| | | YMQISYKALLDVYEEMEQLLADKGRQYRVEY | 143 |
| | | WTHLNYKPTFEEFRDNALPTSGYAMLAIT | 144 |
| | | TFEWAASDPKIIKASTIICRFMDDIAE | 145 |
| | | EDDCSAIECYMEQYKVTAQEAYDEFNKHIESSWK DVNEEFLK | 146 |
| HibWilSQTS123 | Hibiscadelphus wilderianus | LKDEEGNFKASLTSDVPGLLELYEASYLRVHGEDI LDEAISFA | 147 |
| | | LLEFAKIDFNLLQLLHRKELSEICRWWKD | 148 |
| | | DRVVEGYFWIMGVYFEPQYSLGRKMLTKVIAMA SIVDDTYDSFATYDELIPYTDAIER | 149 |
| | | YMQISYKALLDVYEEMEQLLADKGRQYRVEY | 150 |
| | | WTHLNYKPTFEEFRDNALPTSGYAMLAIT | 151 |
| | | TFEWAASDPKIIKASTIICRFMDDIAE | 152 |
| | | EDDCSAIECYMEQYKVTAQEAYDEFNKHIESSWK DVNEEFLK | 153 |
| HibWilSQTS124 | Hibiscadelphus wilderianus | EAFNKLKDEEGNFKASLTSDVRGLLELYQASYMR IHGEDILDEAISFTTAQLTLALPTLDPP | 154 |
| | | LLEFAKIDFNLLQLLHRKELSEICRWWKD | 155 |
| | | DRVVEGYFWIMGVYFEPQYSLGRKMLTKVIAMA SIVDDTYDSFATYDELIPYTDAIER | 156 |
| | | YMQISYKALLDVYEEMEQLLADKGRQYRVEY | 157 |
| | | WTHLNYKPTFEEFRDNALPTSGYAMLAIT | 158 |
| | | TFEWAASDPKIIKASTIICRFMDDIAE | 159 |
| | | SAIECYMKQYGATAQEAYDEFNKHIESSWK | 160 |
| HibWilSQTS126 | Hibiscadelphus wilderianus | LKDEEGNFKASLTSDVPGLLELYEASYLRVHGEDI LDEAISFA | 161 |
| | | LLEFAKIDFNLLQLLHRKELSEICRWWKD | 162 |
| | | DRVVEGYFWIMGVYFEPQYSLGRKMLTKVIAMA SIVDDTYDSFATYDELIPYTDAIER | 163 |
| | | YMQISYKALLDVYEEMEQLLADKGRQYRVEY | 164 |
| | | WTHLNYKPTFEEFRDNALPTSGYAMLAIT | 165 |
| | | TFEWAASDPKIIKASTIICRFMDDIAE | 166 |
| | | SAIECYMKQYGATAQEAYDEFNKHIESSWK | 167 |
| HibWilSQTS19 | Hibiscadelphus wilderianus | FEQERGHCASAVECYMREHGVSEEEACSELKKQV DNAWKDINHEMIFSETSKAVPMSVLTRVLNLTR | 168 |
| HibWilSQTS34 | Hibiscadelphus wilderianus | GYHVDGEEAFNMLKDEEGNFKASLTSDVPGLLEL YQASYMRIHGEDILDEAISFTTAQLTLALPTLDPPL S | 169 |
| HibWilSQTS52 | Hibiscadelphus wilderianus | FEQERGHCASAVECYMREHGVSEEEACSELKKQV DNAWKDINHEMIFSETSKAVPMSVLTRVLNLTR | 170 |
| HibWilSQTS54 | Hibiscadelphus wilderianus | GYHVDGEEAFNMLKDEEGNFKASLTSDVPGLLEL YQASYMRIHGEDILDEAISFTTAQLTLALPTLDPPL SE | 171 |

TABLE 11-continued

Non-limiting examples of sequence fragment(s) derived from rare plants.

| Chimera Name | Ancient DNA Source | Fragments | SEQ ID NO |
|---|---|---|---|
| HibWilSQTS55 | *Hibiscadelphus wilderianus* | FEQERGHCASAVECYMREHGVSEEEACSELKKQV DNAWKDINHEMIFSETSKAVPMSVLTRVLNLTR | 172 |
| HibWilSQTS63 | *Hibiscadelphus wilderianus* | EQERGHCASAVECYMREHGVSEEEACSELKKQV DNAWKDINHEMIFSETSKAVPMSVLTRVLNLTR | 173 |
| HibWilSQTS90 | *Hibiscadelphus wilderianus* | GYHVDGEEAFNMLKDEEGNFKASLTSDVPGLLEL YQASYMRIHGEDILDEAISFTTAQLTLALPTLDPPL S | 174 |
| | | FEQERGHCASAVECYMREHGVSEEEACSELKKQV DNAWKDINHEMIFSETSKAVPMSVLTRVLNLTRG | 175 |
| LeuGraSQTS335 | *Leucadendron grandiflorum* | DAFNRFKDTKGSFKEDLIKDVNSMLCLYEATHLR VHGEDILDEALGFTTSQLKSILPKLKPLLASQVMH ALKQPL | 176 |
| LeuGraSQTS345 | *Leucadendron grandiflorum* | FNKFKNSDGNFKEDLINDVSGMLCLYEATHLRVH GEDILDEALEFTTTRLKSILPDLEPPLATQVMHA | 177 |
| LeuGraSQTS365 | *Leucadendron grandiflorum* | IFNKFKNSDGNFKEDLINDVSGMLCLYEATHLRV HGEDILDEALEFTTTRLKSILPDLEPPL | 178 |
| LeuGraSQTS377 | *Leucadendron grandiflorum* | DAFNRFKDTKGSFKEDLIKDVNSMLCLYEATHLR VHGEDILDEALGFTTSQLKSILPKLKPLLASQVMH ALKQPL | 179 |
| LeuGraSQTS379 | *Leucadendron grandiflorum* | IFNKFKNSDGNFKEDLINDVSGMLCLYEATHLRV HGEDILDEALEFTTTRLKSILPDLEPPLATQVMHA | 180 |
| LeuGraSQTS385 | *Leucadendron grandiflorum* | ETNFTNSPLLSKLQNELSVAHLEELKLEVKQLIWS TKDPLFLLKFIDSIQRLGVAYHFEEEIKESLHLVYL E | 181 |
| LeuGraSQTS393 | *Leucadendron grandiflorum* | IFNKFKNSDGNFKEDLINDVSGMLCLYEATHLRV HGEDILDEALEFTTTRLKSILP | 182 |
| MacVolSQTS1139 | *Macrostylis villosa* | EGLEQKIRTMLISPTDTISKKLSLIDAVQRLGVAYH FEKEIEDEIEKLSCKEYNDGNDLQTVALRFRLLRQ QGYFVSC | 183 |
| MacVolSQTS2198 | *Macrostylis villosa* | LQRLGLAYHFENQIKEALQSI | 184 |
| | | LSHLSTSLAEQVKHSLEIPLHRGMPRLEARHYISIY EEDNSS | 185 |
| | | ELAKLDFNLLQALHRRELGEISRWWKDIDFATKL PFARDRLVECYFWILGVYFEPKYSITRKFMTKVIAI ASVIDDIYDVYGTLEELKLFTHAIERWETVAANEL PKYMQVCYFALLDVFKEMEDKLVNKGLLYSMPC AKEAVKGLVRAYFVEAEWFNANYMPTFEEYMEN STMSSGYPMLAVEALIGIEDATISKEAFDWAISVP KIIRSCALIARLVDDIH | 186 |
| | | DAPSSVECYMQQYDVSEEEACNRIKGMVEIEW | 187 |
| | | NLARMMVVLYQNGDNYTNSSGKTKDRIASLLV | 188 |
| | | LQRLGLAYHFENQIKEALQSI | 189 |
| MacVolSQTS2202 | *Macrostylis villosa* | KFKDEKGEFKDMIRNDARGLLCLYEASHLRVKGE DILEEATEFSRKHLKSLLPQLSTSLAEQVKHSLEIP LHRGMPRLEARHYISIYEENNSSRNELLLELAKLD FNLLQALHRRELGDISRWWKDIDFATKLPFARDR LVECYFWILGVYFEPKYSITRKFMTKVIAIASVIDD IYDVYGTLEELKLFTHAIERWETVAANELPKYMQ VCYFALLDVFKEMEDKLVNKGLLYSMPCAKEAV KGLVRAYFVEAEWFNANYMPTFEEYMENSTMSS GYPMLAVEALIGIEDATISKEAFDWAISVPKIIRSC ALIARLVDDIH | 190 |
| | | KVEQERGDAPSSVQCYVQQ | 191 |
| | | NLARMMVVLYQNGDNYTNSSGKTKDRIASLLV | 192 |
| | | LQRLGLAYHFENQIKEALQSI | 193 |
| MacVolSQTS2222 | *Macrostylis villosa* | KFKDEKGEFKDMIRNDARGLLCLYEASHLRVKGE DILEEATEFSRKHLKSLLPQLSTSLAEQVKHSLEIP LHRGMPRLEARHYISIYEENNSSRNELLLELAKLD FNLLQALHRRELGDISRWWKDIDFATKLPFARDR LVECYFWILGVYFEPKYSITRKFMTKVIAIASVIDD IYDVYGTLEELKLFTHAIERWETVAANELPKYMQ | 194 |

TABLE 11-continued

Non-limiting examples of sequence fragment(s) derived from rare plants.

| Chimera Name | Ancient DNA Source | Fragments | SEQ ID NO |
|---|---|---|---|
| | | VCYFALLDVFKEMEDKLVNKGLLYSMPCAKEAV YVPTFEEYMENSTMSSGYPMLAVEALV | 195 |
| | | DWAISVPKIIRSCALIA | 196 |
| | | KVEQERGDAPSSVQCYMQQYDVSEEEACNRIKG MVETAWMEINGEIQDTNHL | 197 |
| | | NLARMMVVLYQNGDNYTNSSGKTKDRIASLLV | 198 |
| MacVolSQTS2251 | *Macrostylis villosa* | LQRLGLAYHFENQIKEALQSI | 199 |
| | | KFKDEKGEFKDMIRNDARGLLCLYEASHLRVKGE DILEEATEFSRKHLKSLLPQLSTSLAEQVKHSLEIP LHRGMPRLEARHYISIYEENNSSRNELLLELAKLD FNLLQALHRRELGDISRWWKDIDFATKLPFARDR LVECYFWILGVYFEPKYSITRKFMTKVIAIASVIDD IYDVYGTLEELKLFTHAIERWETVAANELPKYMQ VCYFALLDVFKEMEDKLVNKGLLYSMPCAKEAV YVPTFEEYMENSTMSSGYPMLAVEALV | 200 201 |
| | | DWAISVPKIIRSCALIA | 202 |
| | | DAPSSVECYMQQYDVSEEEACNRIKGMVEIEW | 203 |
| | | NLARMMVVLYQNGDNYTNSSGKTKDRIASLLV | 204 |
| MacVolSQTS2274 | *Macrostylis villosa* | KFIQNVEKDSTRRSANFHPSIWGDH | 205 |
| | | DDGSVKHQQLKEEIRKMLTAETKLSQKLDLIDAIQ RLGVAYHFESEIDEIL | 206 |
| | | SLARNVRGMLSLYEATHLRVHGENILDEA | 207 |
| | | LEARNYMPFYQEEASHNEALLTFAKLDFNKLQKL HQKELSEITR | 208 |
| | | FEQSREHVASSIECYMKQYGATEEETCNELRKQV SNAWKDINEECLCPTAVPMPLIVRILNLT | 209 |
| OrbStiSQTS1368 | *Orbexilum stipulatum* | AEVFERFKDQHGNFKASLSSDVEGMLSLYEASFL DYEGEDILDEAKAFTSFHLRGAL | 210 |
| OrbStiSQTS1414 | *Orbexilum stipulatum* | VKLELVDDVKRLGIGYRFEKEIVEALHRCFISSERF THRNLHQTALSFRLLRECGYDVT | 211 |
| | | FNKFTNKEGKFNSKLGENIKGMIDLYEASQLGIAG EYILAEAGEFSGLVLKEKVACINN | 212 |
| | | VYFEPQYSVPRRTTTKVIGLCSVIDDMYDAYGTID ELELFTNAIERLDTST | 213 |
| | | RWLKCNHAPTMEEYMKVRGVSSGYPLLITISFIG MEDTTEEILTWATSEPMIIRASVIVCRLMDDI | 214 |
| ShoCusSQTS154 | *Shorea cuspidata* | FMDEKGKFKEDVVNDVLGMLNLYEAAHLRLRGE DILDEALAFTTSHLE | 215 |
| | | WWKNLDFSTKLPYARDRIVECYFWIMGAYFE | 216 |
| | | SLARTFLTKVIAMTSILDDTYDNYG | 217 |
| | | DYVPPIEEYMQVARISSAYPMLITNSFVGMGEVAT KEAFDWISNDPKILKASTTICRLMDD | 218 |
| | | EFEQTRDHVASGVECYMKQYGVSREETVK | 219 |
| ShoCusSQTS155 | *Shorea cuspidata* | FMDEKGKFKEDVVNDVLGMLNLYEAAHLRLRGE DILDEALAFTTSHLE | 220 |
| | | WWKNLDFSTKLPYARDRIVECYFWIMGAYFE | 221 |
| | | SLARTFLTKVIAMTSILDDTYDNYG | 222 |
| | | YMQVALISSAYPMLITNSFVGMGEVATKEAFDWI SNNPKMLKASTII | 223 |
| | | EFEQTRDHVASGVECYMKQYGVSREETVK | 224 |
| ShoCusSQTS156 | *Shorea cuspidata* | FMDEKGKFKEDVVNDVLGMLNLYEAAHLRLRGE DILDEALAFTTSHLE | 225 |
| | | WWKNLDFSTKLPYARDRIVECYFWIMGAYFE | 226 |
| | | SLARTFLTKVIAMTSILDDTYDNYG | 227 |
| | | DYVPPIEEYMQVARIS | 228 |
| | | GYPMLITNSLVGMGEVATKEAFDLISNDPKMLKA ST | 229 |
| | | EFEQTRDHVASGVECYMKQYGVSREETVK | 230 |
| ShoCusSQTS157 | *Shorea cuspidata* | FMDEKGKFKEDVVNDVLGMLNLYEAAHLRLRGE DILDEALAFTTSHLE | 231 |
| | | WWKNLDFSTKLPYARDRIVECYFWIMGAYFE | 232 |
| | | SLARTFLTKVIAMTSILDDTYDNYG | 233 |
| | | VPPMDEYMQVALISCGYPMLITNSFVGMGEVATK EAFDWISNDPKILKASTTICRLMDD | 234 |
| | | EFEQTRDHVASGVECYMKQYGVSREETVK | 235 |

TABLE 11-continued

Non-limiting examples of sequence fragment(s) derived from rare plants.

| Chimera Name | Ancient DNA Source | Fragments | SEQ ID NO |
|---|---|---|---|
| ShoCusSQTS160 | Shorea cuspidata | FMDEKGKFKEDVVNDVLGMLNLYEAAHLRLRGE DILDEALAFTTSHLE | 236 |
| | | WWKNLDFATMLPYARDRIVECYFWIMGVYFEPK YSLARTFLTKVIAMTSILDDTYDNYG | 237 |
| | | YMQVALISSAYPMLITNSFVGMGEVATKEAFDWI SNNPKMLKASTII | 238 |
| | | EFEQTRDHVASGVECYMKQYGVSREETVK | 239 |
| ShoCusSQTS161 | Shorea cuspidata | FMDEKGKFKEDVVNDVLGMLNLYEAAHLRLRGE DILDEALAFTTSHLE | 240 |
| | | WWKNLDFATMLPYARDRIVECYFWIMGVYFEPK YSLARTFLTKVIAMTSILDDTYDNYG | 241 |
| | | DYVPPIEEYMQVARIS | 242 |
| | | GYPMLITNSLVGMGEVATKEAFDLISNDPKMLKA ST | 243 |
| | | EFEQTRDHVASGVECYMKQYGVSREETVK | 244 |
| WenAngSQTS1007 | Wendlandia angustofolia | SNNRQETVRPLADFPENIWADRIAPFT | 245 |
| | | EMCQREIEMLKAEVASMLLATGKTMMQRFDFID KIERLGVSHHFD | 246 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 247 |
| | | RWGKGLESVSNFPYARDRFVECYFWAVGTLYEP QYSLARMTFAKVAA | 248 |
| | | RWDGSGVDQLSDYIRASYNTLLKFNKEVGEDLAK KQRTYAFDKYIEDWKQYMRTNFSQSRWFFTKELP SFADYINNGAITIGAYLVASAAFLYMDSAKEDVIN WMSTNPKLVVAYSTHSRLINDFGGHKFEKERGSS TAIECYMKDHNVSEEEAANKFREMMEDAWKVM NEECLRPTTI | 249 |
| | | ETVYKHRIDGFTQPHAIEEHIRAMLVDFMSI | 250 |
| WenAngSQTS1086 | Wendlandia angustofolia | SNNRQETVRPLADFPENIWADRIAPFT | 251 |
| | | EMCQREIEMLKAEVASMLLATGKTMMQRFDFID KIERLGVSHHFD | 252 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 253 |
| | | RWGKGLESVSNFPYARDRFVECYFWAVGTLYEP QYSLARMTFAKVAA | 254 |
| | | RWDGSGVDQLSDYIRASYNTLLKFNKEVGEDLAK KQRTYAFDKYIEDWKQYMRTNFSQSRWFFTKELP SFADYINNGAITIGAYLVASAAFLYMDSAKEDVIN WMSTNPKLVVAYSTHSRLINDFGGHK | 255 |
| | | KERGTGTAIECYMKDHN | 256 |
| | | EMIENTWKVMNEECLRPIPIPRDTLKML | 257 |
| | | ETVYKHRIDGFTQPHAIEEHIRAMLVDFMSI | 258 |
| WenAngSQTS267 | Wendlandia angustofolia | LELVDNLERLGLAYHFEGQINRLLSSAYNANHED EGNHKRNKEDLYAAALEFRIFRQHGFNV | 259 |
| WenAngSQTS302 | Wendlandia angustofolia | YVSQANELKEQVKMMLDEEDMKLLDCLELVDNL ERLGLAYHFEGQINRLLSSAYNANHEDEGNHKRN KEDLYAAALEFRIFRQHGFNVPQ | 260 |
| WenAngSQTS738 | Wendlandia angustofolia | NNQHESVRQLADFPENIWADRV | 261 |
| | | QGHDMCAKEIEMLKEEVMSMLLE | 262 |
| | | STLAKQVKYALEQPLHKGIPRYEAWRYISIYEED | 263 |
| | | LAKLDYHLSQMLNKQDLCEI | 264 |
| | | RDRIVECYFWAVATYYEPQYSLARMT | 265 |
| | | EVGEDLAKKQRTYAFDKYIE | 266 |
| | | YARTSFTQSKWFLTNELPSFSDYL | 267 |
| | | AAFLDMDSASEDVINWMSTNPKLFVALTTHARLA NDVGSHKFEKERGSGTAIECYMKDYHVSEEEAM KKFEEMCDDAWKVMNEE | 268 |
| WenAngSQTS760 | Wendlandia angustofolia | NNQHESVRQLADFPENIWADRV | 269 |
| | | QGHDMCAKEIEMLKEEVMSMLLE | 270 |
| | | QVKHALEQPLHRGIPRYEAYCFISIYEEDESNNKLL LRLAKLDYHLLQMSYKRE | 271 |
| | | RDRIVECYFWAVATYYEPQYSLARMT | 272 |

TABLE 11-continued

Non-limiting examples of sequence fragment(s) derived from rare plants.

| Chimera Name | Ancient DNA Source | Fragments | SEQ ID NO |
|---|---|---|---|
| | | EVGEDLAKKQRTYAFDKYIE | 273 |
| | | YARTSFTQSKWFLTNELPSFSDYL | 274 |
| | | TFLGMDGASEDVINWMSTNPKLFVA | 275 |
| | | KFEKERGSGTAIECYMKDYHVSEEEAMKKFEEMC DDAWKVMNEE | 276 |
| WenAngSQTS780 | Wendlandia angustofolia | NNQHESVRQLADFPENIWADRV | 277 |
| | | QGHDMCAKEIEMLKEEVMSMLLE | 278 |
| | | QVKHALEQPLHRGIPRYEAYCF | 279 |
| | | LAKLDYHLSQMLNKQDLCEI | 280 |
| | | RDRIVECYFWAVATYYEPQYSLARMT | 281 |
| | | EVGEDLAKKQRTYAFDKYIE | 282 |
| | | YARTSFTQSKWFLTNELPSFSDYL | 283 |
| | | TFLGMDGASEDVINWMSTNPKLFVA | 284 |
| | | KFEKERGSGTAIECYMKDYHVSEEEAMKKFEEMC DDAWKVMNEE | 285 |
| WenAngSQTS793 | Wendlandia angustofolia | SNNRQETVRPLADFPENIWADRIAPFT | 286 |
| | | EMCQREIEMLKAEVASMLLATGKTMMQRFDFID KIERLGVSHHFD | 287 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 288 |
| | | RWGKGLESVSNFPYARDRFVECYFWAVGTLYEP QYSLARMTFAKVAA | 289 |
| | | RWDGSGVDQLSDYIRASYNTLLKFNKEVGEDLAK KQRTYAFDKYIEDWKQYMRTSFTQSKWFLTNELP SFADY | 290 |
| | | LDMDSALEDVINWMSTNPKLMVAY | 291 |
| | | KFDKERGSVTALDCYMKDYSVSEEEAAKKFREM CEDNWKVMNEECLRPTTI | 292 |
| | | ETVYKHRIDGFTQPHAIEEHIRAMLVDFMSI | 293 |
| WenAngSQTS805 | Wendlandia angustofolia | NNQHESVRQLADFPENIWADRV | 294 |
| | | QGHDMCAKEIEMLKEEVMSMLLE | 295 |
| | | STLAKQVKYALEQPLHKGIPRYEAWRYISIYEEDE SNNKLLLRLAKLDYHLLQMSYKRE | 296 |
| | | RDRIVECYFWAVATYYEPQYSLARMT | 297 |
| | | EVGEDLAKKQRTYAFDKYIE | 298 |
| | | YARTSFTQSKWFLTNELPSFSDYL | 299 |
| | | TFLGMDGASEDVINWMSTNPKLFVA | 300 |
| | | STAIECYMKDYHVSEEEAMEKFEEMCDDAWKVM NEE | 301 |
| WenAngSQTS826 | Wendlandia angustofolia | NNQHESVRQLADFPENIWADRV | 302 |
| | | QGHDMCAKEIEMLKEEVMSMLLE | 303 |
| | | STLAKQVKYALEQPLHKGIPRYEAWRYISIYEEDE SNNKLLLRLAKLDYHLLQMSYKRE | 304 |
| | | RDRIVECYFWAVATYYEPQYSLARMT | 305 |
| | | EVGEDLAKKQRTYAFDKYIE | 306 |
| | | YARTSFTQSKWFLTNELPSFADYLS | 307 |
| | | AALLDMDSALEDVINWMSTNPKFFVALTTHARLT NDVGSHKFEKERGSGTAIECYMKDYHVSEEEAM KKFEEMCDDAWKVMNEE | 308 |
| WenAngSQTS829 | Wendlandia angustofolia | SNNRQETVRPLADFPENIWADRIAPFT | 309 |
| | | EMCQREIEMLKAEVASMLLATGKTMMQRFDFID KIERLGVSHHFD | 310 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 311 |
| | | RWGKGLESVSNFPYARDRFVECYFWAVGTLYEP QYSLARMTFAKVAA | 312 |
| | | RWDGSGVDQLSDYIRASYNTLLKFNKEVGEDLAK KQRTYAFDKYIEDWKQYMRTSFTQSKWFLTNELP SFADY | 313 |
| | | LDMDSALEDVINWMSTNPKLMVAY | 314 |
| | | KERGTGTAIECYMKDHN | 315 |
| | | EMIENTWKVMNEECLRPIPIPRDTLKML | 316 |
| | | ETVYKHRIDGFTQPHAIEEHIRAMLVDFMSI | 317 |

TABLE 11-continued

Non-limiting examples of sequence fragment(s) derived from rare plants.

| Chimera Name | Ancient DNA Source | Fragments | SEQ ID NO |
|---|---|---|---|
| WenAngSQTS843 | *Wendlandia angustofolia* | NNQHESVRQLADFPENIWADRV | 318 |
| | | QGHDMCAKEIEMLKEEVMSMLLE | 319 |
| | | QVKHALEQPLHRGIPRYEAYCFISIYEEDESNNKLL LRLAKLDYHLLQMSYKRE | 320 |
| | | RDRIVECYFWAVATYYEPQYSLARMT | 321 |
| | | EVGEDLAKKQRTYAFDKYIE | 322 |
| | | YARTSFTQSKWFLTNELPSFSDYL | 323 |
| | | AAFLDMDSASEDVINWMSTNPKLFVALTTHARLA NDVGSHK | 324 |
| | | RGSGTAIECYMKDYNVSEEEALKKFEEMCEDTW KVMNEE | 325 |
| WenAngSQTS848 | *Wendlandia angustofolia* | SNNRQETVRPLADFPENIWADRIAPFT | 326 |
| | | EMCQREIEMLKAEVASMLLATGKTMMQRFDFID KIERLGVSHHFD | 327 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 328 |
| | | RWDGSGVDQLSDYIRASYNTLLKFNKEVGEDLAK KQRTYAFDKYIEDWKQYMRTNFSQSRWFFTKELP SFADYINNGAITIGAYLVASAAFLYMDSAKEDVIN WMSTNPKLVVAYSTHSRLINDFGGHKFDKERGSG TALECYMKDYNVSEEEAANKFREMMEDAWKVM NEDCLRPTSIPRDVSKVLLNVARAGEIVYKHRIDG FTEPHIIKDHIRATLVDFMAIN | 329 |
| | | RWGKGLESVSNFPYARDRFVECYFWAVGTLYEP QYSLARMTFAKVAA | 330 |
| WenAngSQTS849 | *Wendlandia angustofolia* | SNNRQETVRPLADFPENIWADRIAPFT | 331 |
| | | EMCQREIEMLKAEVASMLLATGKTMMQRFDFID KIERLGVSHHFD | 332 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 333 |
| | | RWGKGLESVSNFPYARDRFVECYFWAVGTLYEP QYSLARMTFAKVAA | 334 |
| | | RWDGSGVDQLSDYIRASYNTLLKFNKEVGEDLAK KQRTYAFDKYIEDWKQYMRTSFTQSKWFLTNELP SFADY | 335 |
| | | LDMDSALEDVINWMSTNPKLMVAY | 336 |
| | | KFDKERGSVTALDCYMKDYSVSEEEAAKKFREMI ENTWKVMNEECLRPIPIPRDTLKML | 337 |
| | | EPHIIKDHIRAMLVDFMAI | 338 |
| WenAngSQTS864 | *Wendlandia angustofolia* | SNNRQETVRPLADFPENIWADRIAPFT | 339 |
| | | EMCQREIEMLKAEVASMLLATGKTMMQRFDFID KIERLGVSHHFD | 340 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 341 |
| | | RWGKGLESVSNFPYARDRFVECYFWAVGTLYEP QYSLARMTFAKVAA | 342 |
| | | RWDGSGVDQLSDYIRASYNTLLKFNKEVGEDLAK KQRTYAFDKYIEDWKQYMRTNFSQSRWFFTKELP SFADYINNGAITIGAYLVASAAFLYMDSAKEDVIN WMSTNPKLVVAYSTHSRLINDFGGHKFDKERGSV TALDCYMKDYSVSEEEAAKKFREMCEDNWKVM NEECLRPTTI | 343 |
| | | ETVYKHRIDGFTQPHAIEEHIRAMLVDFMSI | 344 |
| WenAngSQTS925 | *Wendlandia angustofolia* | SNNRQETVRPLADFPENIWADRIAPFT | 345 |
| | | EMCQREIEMLKAEVASMLLATGKTMMQRFDFID KIERLGVSHHFD | 346 |
| | | IFDQFIDAKGKFKESLCNDIRGLLSLYEAAHVRTH GDKILEEALAFTTTHMTSGGPHLDSSLAKQVKYA LEQPLHKGILRYEAWRYISIYEEDESNNKLLLRLA KLDYHLLQMSYKQEL | 347 |
| | | RWGKGLESVSNFPYARDRFVECYFWAVGTLYEP QYSLARMTFAKVAA | 348 |
| | | RWDGSGVDQLSDYIRASYNTLLKFNKEVGEDLAK KQRTYAFDKYIEDWKQYMRTNFSQSRWFFTKELP | 349 |

TABLE 11-continued

Non-limiting examples of sequence fragment(s) derived from rare plants.

| Chimera Name | Ancient DNA Source | Fragments | SEQ ID NO |
|---|---|---|---|
| | | SFADYINNGAITIGAYLVASAAFLYMDSAKEDVIN WMSTNPKLVVAYSTHSRLINDFGGHKFDKERGSV TALDCYMKDYSVSEEEAAKKFREMIENTWKVMN EECLRPIPIPRDTLKML EPHIIKDHIRAMLVDFMAI | 350 |
| WenAngSQTS960 | Wendlandia angustofolia | EAFNKLKDEEGNFKASLTSDVRGLLELYQASYMR IHGEDILDEAISFTTAQLTLALPTLDPP | 351 |
| | | NKALLQFAKIDFNMLQLLHRKELSEICRWWKDLD FTRKLP | 352 |
| | | DRVVEGYFWIMGVYFEPQYSLGRKMLTKVIAMA SIVDDTYDSFATYDELIPYTDAIER | 353 |
| | | YMQISYKALLDVYEEMEQLLADKGRQYRVEY | 354 |
| | | WTHLNYKPTFEEFRDNALPTSGYAMLAIT | 355 |
| | | TFEWAASDPKIIKASTIICRFMDDIAE | 356 |
| | | EDDCSAIECYMEQYKVTAQEAYDEFNKHIESSWK DVNEEFLK | 357 |

Example 2. Materials and Methods for Construction of Terpene Synthase Chimeras

Terpene Synthases for Capture-Seq and Chimera Scaffolding

Candidate sesquiterpene synthases (SQTSs) were designed by combining sequence fragments from rare flower genomes (Table 11) with "scaffold" SQTSs from sources including UniProt and GenBank.

For Capture-seq (targeted sequencing of terpene synthases), a subset of 5,171 terpene synthases (TPSs) were compiled from UniProt that had nucleotide sequences in EMBL/Genbank. Oligonucleotide chips were generated for enriching the flower DNA samples for TPS-homologous sequences, and then subjected first to Illumina sequencing. The Capture-seq libraries were also sequenced a second time at higher depth.

For SQTS chimera reconstruction, sequences closer to annotated SQTSs than annotated mono-, di-, or tri-terpene synthases were selected. This set of 1,521 putative SQTSs were used (in both nucleotide and peptide form) as query sequences for blastn and tblastn in the chimera construction pipeline below.

Chimera Reconstruction

Two methods were used for constructing chimeric SQTSs: 1) the blastn-mapDamage pipeline, and 2) the tblastn pipeline.

Blastn-Mapdamage Pipeline

Generally, the blastn-mapdamage pipeline conservatively detects fragments with high nucleotide similarity to the scaffolds resulting in chimeric terpene synthases (e.g., chimeric sesquiterpene synthases) that are likely very close to the original enzyme sequences in the rare flowers. To detect mutations that may be artifacts of stereotypical rare DNA damage, bam-formatted Illumina read alignments were inputted into mapDamage software.

Specifically, the following steps were used to generate alignments of DNA fragments from each flower to various SQTS scaffolds:

1. Illumina reads (fastq files) from genomic capture-seq runs were combined and assembled by SPADES into longer contigs.
2. The 1521-set of SQTS scaffolds were used as queries in a blastn search with default parameters against the SPADES contigs. Relatively few scaffolds had hits, so all of the scaffolds with hits were chosen to serve as references for read alignment in the next step.
3. Combined reads from the sequencing runs were quality-trimmed (using bbduk) and pair-merged (using bbmerge) and aligned to chosen SQTS reference sequences using bwa mem. Results were reformatted to bam, sorted, and indexed.
4. mapDamage was run on the aligned reads. This resulted in a read alignment where SNPs resembling DNA damage were assigned low quality scores.
5. Read alignments were processed as follows: bases with quality <25 were masked (changed to the reference); alignments were reformatted to fasta; SNPs with counts <6 were masked; duplicate reads were removed; SNPs with frequency <0.1 were masked; reads that were exact subsequences of other reads were removed; reads were translated in the frame of the reference; and subsequences were removed again. The quality and SNP frequency thresholds used for masking the alignment were determined empirically by looking at distributions of quality and SNP frequency.
6. Read alignments and SPADE contig alignments (after reference-frame translation) were combined and realigned using Clustal Omega. This was done because some contigs spanned regions of the scaffolds that the reads did not.

The alignments from the above steps were used to construct SQTS chimeras as follows:

1. The alignment was split into "independent subregions" such that each subregion did not contain any fragment (aligned read) overlapping with and differing from a fragment from another subregion (identical overlaps were allowed between subregions).
2. In each subregion, all possible combinations of "compatible fragments" were enumerated. Compatible fragments were defined as fragments that either overlapped identically (and therefore could be merged into a longer fragment) or did not overlap at all (and, e.g., were assumed to come from the same haplotype). Fragment combinations were "max-coverage"—that is, contained as many compatible fragments as possible. Each max-coverage fragment combination was considered to be a possible reconstruction of that region of the alignment, and was merged into a superfragment (which may have contained gaps) and saved.
3. Superfragments from each subregion were downsampled to 90% or 95% identity using a custom, iterative algorithm, and all possible combinations of downsampled superfragments from different subregions were combined. Regions that were shorter than a certain threshold are downsampled to a single sequence. Each combination of superfragments was merged into the scaffold to generate a chimera sequence. The downsampling parameters were varied slightly varied according to the sample and scaffold to allow >1 but <100 chimeras to be constructed in each case.

After running the above pipeline on each sample, a total of 1136 chimeras were generated. A significant fraction of the chimeras were constructed purely from aligned reads.

A total of 652 sesquiterpene synthase chimeras were created using these methods.

tblastn Pipeline

Generally, the tblastn pipeline maximized the sensitivity of detecting fragments homologous to the SQTS scaffolds, and therefore cast a wide net for potentially usable sequences.

Specifically, the following steps were used to generate alignments of DNA fragments from each flower to various SQTS scaffolds:
1. The 1521-set of SQTS scaffolds were used as protein queries to tblastn to search all-frames translations of the SPADES contigs (described above).
2. Hits (aligned contigs) were filtered to a minimum of 40% identity to the scaffold and a minimum length that depends on hit identity by a heuristic function. The filtering criteria were chosen by inspecting plots of hit length versus identity across all samples.
3. Downsampling scaffolds was performed by hierarchically clustering the scaffolds by the number of identical residues to each hit. The scaffold in each cluster with the greatest number of identities across all of its hits was kept for chimera reconstruction. Downsampling reduced the number of scaffolds by 20-fold. This step was skipped for samples in which fewer than 10 scaffolds have hits.
4. Certain scaffolds were always chosen as a cluster representation because they were previously identified as having activity and/or were known in the literature (even if another sequence had more identities to hits). These preferred scaffolds were not downsampled, and tblastn hits were kept for chimera construction.
5. The aligned portions of all contigs hitting a scaffold were realigned to the scaffold using Clustal Omega. Unaligned portions of contigs were discarded as likely representing introns. This alignment was then used for chimera construction.
6. Chimeras were constructed from aligned tblastn hits using the combinatorial compatible fragments method described above without downsampling in subregions. Both "max-coverage" (as many as possible compatible fragments in each set) and "min-coverage" (only one compatible fragment in each set) chimeras were generated. The min-coverage chimeras may avoid combining fragments from unrelated sequences.

The tblastn pipeline yielded 10,114 "max-coverage" chimeras and 2,624 "min-coverage" chimeras. Certain max-coverage chimeras were downsampled to 95% identity by CD-HIT. This resulted in 388 sequences (382 after removing sequences with ambiguous amino acids). Certain max coverage chimeras were filtered to a minimum rare DNA content of 60% and downsampled to 90% identity. This resulted in 1320 sequences. Certain min-coverage chimeras were filtered to a minimum rare DNA content of 10% and downsampled to 95% identity by CD-HIT.

Encoding and Synthesis Order

Each enzyme was codon-optimized twice: once using a yeast expression-weighted codon table, and once using a yeast expression-weighted codon table after removing codons with <10% frequency. A different random number was used as the seed for each encoding. Encodings for different enzymes were completely independent—no specific procedure was used to preserve codons at residues inherited by chimeras from scaffolds.

Sequences encoding the chimeric enzymes were cloned into the pESC-URA3 screening vector, driven by pGAL1 and terminated by tCYC1.

Chimera Reconstruction Aided by Extant Transcriptome

For one of the extinct flower species, *Shorea cuspidata*, transcriptome sequencing data was available on an extant relative *Shorea beccariana*. This made it possible to construct chimeras using SQTS scaffolds from a related flower. This was done in a 2-step process:
1. The *S. beccariana* (Sb) transcriptome data were assembled and mined for SQTS homologs. The data were downloaded from the data set SRR687302 from the NCBI SRA database. Assembly was done using Trinity, and ORFs were predicted via Transdecoder. BLAST was used to identify fragments homologous to a set of 1,500 curated SQTS sequences.
2. The identified Sb SQTSs or SQTS fragments were used as scaffold sequences in either the tblastn or blastn-mapDamage pipelines to reconstruct chimeras. If the scaffold was a fragment itself, it was in turn merged into the closest Uniprot-sourced SQTS sequence to generate a full-length chimera.

Screening Strain and Sesquiterpene Synthase Transformation

The chimeric sesquiterpene synthases were transformed into high copy pESC-URA3-derived expression vectors under the control of the galactose-inducible P(gal1) promoter (Sikorski et al., A system of shuttle vectors and yeast host strains designed for efficient manipulation of DNA in *Saccharomyces cerevisiae*. Genetics. 1989 May; 122(1):19-27, which is hereby incorporated by reference in its entirety for this purpose).

These vectors were transformed into a haploid *Saccharomyces cerevisiae* CEN.PK2 strain (MATa ura3-52 trp1-289 leu2-3_112 his3Δ1 MAL2-8C SUC2) that had been modified to increase sesquiterpene flux via integration of two copies of the catalytic region of HMG-CoA reductase 1 under control of convergent P(gal1) promoters at the homothallic switching endonuclease (YDL227C) locus on chromosome 4 (see SEQ ID NO: 53 shown below). See: Entian et al., Yeast Genetic Strain and Plasmid Collections. *Methods in Microbiology.* 2007; (36): 629-666; tHMG1, Donald et al., Effects of overproduction of the catalytic domain of 3-hydroxy-3-methylglutaryl coenzyme A reductase on squalene synthesis in *Saccharomyces cerevisiae*. Appl Environ Microbiol. 1997 September; 63(9):3341-4; Özaydin et al., Carotenoid-based phenotypic screen of the yeast deletion collection reveals new genes with roles in isoprenoid production. Metab Eng. 2013 January; 15:174-83, each of which is hereby incorporated by reference in its entirety). Competition for fanesyl pyrophosphate was reduced in these cells by replacing the Erg9 (Farnesyl-diphosphate farnesyl transferase) promoter with the methionine-repressible Met3 promoter as shown below in SEQ ID NO: 54 and incubating in media containing methionine (see: Ro et al., Production of the antimalarial drug precursor artemisinic acid in engineered yeast. *Nature*. 2006 Apr. 13; 440(7086):940-3; and Asadollahi et al., Production of plant sesquiterpenes in *Saccharomyces cerevisiae*: effect of ERG9 repression on sesquiterpene biosynthesis. *Biotechnol Bioeng*. 2008 Feb. 15; 99(3):666-77, each of which is hereby incorporated by reference in its entirety for this purpose). This strain with downregulated Erg9 and containing two copies of galactose-inducible tHMG1 on chromosome 4 was designated t119889.

The transformation of the chimeric sesquiterpene vectors into strain t119889 was performed employing the chemical transformation techniques demonstrated in Gietz et al., Yeast transformation by the LiAc/SS Carrier DNA/PEG method. *Methods Mol Biol*. 2006; 313:107-20, which is hereby incorporated by reference in its entirety for this purpose.

Sesquiterpene Production and Extraction

Transformant colonies were inoculated into 300 µl of SC-ura medium (Synthetic Complete with 2% dextrose, no uracil added) in 96 deep well plates. The plates were covered with Excel Scientific AeroSeal membranes (BS-25) and incubated for 48 hours at 30° C. in a shaking incubator. 30 µl of the cultures (1:15 dilution) were mixed into 420 µl of SC-ura induction medium containing 1.8% galactose and 0.2% raffinose as the carbon sources, yielding a starting optical density at 600 nm ($OD_{600}$) of approximately 0.1-0.2. A 0.88% dodecane overlay (4 µl) was added to each well and the plates were covered with AeroSeal membranes and incubated at 30° C. in a shaking incubator for four days. 15 µl of each culture was removed to measure $OD_{600}$ at the end of the four days. 350 µl of ethyl acetate (250 µM tridecane internal) was added to directly to each well and mixed (1:1 Extraction). The 96-well plates were then centrifuged and the ethyl acetate extractions were stored at −80° C. in glass vials until analysis by GC-MS.

Sesquiterpene Structure Identification

Ethyl Acetate samples (1.0 uL) were injected into the Agilent/Gerstel 7890B GC System, where the GC inlet was set to 250 C with a split ratio of 2:1. The capillary column was an Agilent DB-5MS (20m×0.18 mm×0.18 µm) with carrier gas (helium) flow set to 1.5 ml/min. The GC oven temperature was set to 100° C. (hold for 0.10 min) with a ramp of 40° C./min to 155° C., where the ramp was then 15° C./min to 190° C. and then finally the ramp was changed to 75° C./min to 280 C (5-minute method). For a more comprehensive analysis of targets, the GC oven temperature was set to 100° C. (hold for 2.0 min) with a 10° C./min ramp to 250° C. (hold for 2.0 min) was utilized (20-minute method). The MS source and quadruple for both methods were set to 230° C. and 180° C. on the Agilent 5977B MSD (Etune), respectively. The mass scan range was set to 40-250 mz where spectra and linear retention index calculations were matched against the NIST MS database (2008 version), in addition to available standards and essential oils.

Peaks present in the extracted ion chromatogram (204.2 mz parent mass) were identified in one of six ways (see Table 3). The authentic standards utilized in this screen for verification of products were beta-caryophyllene (Sigma-Aldrich catalog #W225207-SAMPLE-K), beta-farnesene (Sigma-Aldrich catalog #73492-1ML-F), trans-nerolidol (Sigma-Aldrich catalog #18143-100MG-F), and alpha-humulene (Sigma-Aldrich catalog #53675-1ML). Sesquiterpene rich essential oils used to aid structure identification were derived from the following plants: Rhodendron, Sweet Basil, Black Pepper, Citronella, Ylang, Balsam copaiba, and Patchouli.

ΔHO(YDL227C)::2xP(gal)-tHMG1 integration on chromosome 4.

(SEQ ID NO: 53)

AGGGTTCGCAAGTCCTGTTTCTATGCCTTTCTCTTAGTAATTCACGAAATAAACCT

ATGGTTTACGAAATGATCCACGAAAATCATGTTATTATTTACATCAACATATCGCG

AAAATTCATGTCATGTCCACATTAACATCATTGCAGAGCAACAATTCATTTTCATAG

AGAAATTTGCTACTATCACCCACTAGTACTACCATTGGTACCTACTACTTTGAATTG

TACTACCGCTGGGCGTTATTAGGTGTGAAACCACGAAAAGTTCACCATAACTTCGA

ATAAAGTCGCGGAAAAAAGTAAACAGCTATTGCTACTCAAATGAGGTTTGCAGAAG

CTTGTTGAAGCATGATGAAGCGTTCTAAACGCACTATTCATCATTAAATATTTAAA

GCTCATAAAATTGTATTCAATTCCTATTCTAAATGGCTTTTATTTCTATTACAACTA

TTAGCTCGATGCACGAGCGCAACGCTCACAACGCTCGTCCAACGCCGGCGGACCT<u>ACG</u>

<u>GATTAGAGCCGCCGAGCGGGTGACAGCCCTCCGAAGGAAGACTCTCCTCCGTGCGTCCTCG</u>

<u>TCTTCACCGGTCGCGTTCCTGAAACGCAGATGTGCCTCGCGCCGCACTGCTCCGAACAATAA</u>

<u>AGATTCTACAATACTAGCTTTTATGGTTATGAAGAGGAAAAATTGGCAGTAACCTGGCCCCACA</u>

<u>AACCTTCAAATGAACGAATCAAATTAACAACCATAGGATGATAATGCGATTAGTTTTTTAGCCTT</u>

<u>ATTTCTGGGGTAATTAATCAGCGAAGCGATGATTTTTGATCTATTAACAGATATATAAATGCAAA</u>

<u>AACTGCATAACCACTTTAACTAATACTTTCAACATTTTCGGTTTGTATTACTTCTTATTCAAATGT</u>

<u>AATAAAAGTATCAACAAAAAATTGTTAATATACCTCTATACTTTAACGTCAAGGAGAAAAAACTA</u>

TA<u>ATGGCTGCAGACCAATTGGTGAAGACTGAAGTCACCAAGAAGTCTTTTACTGCT</u>

<u>CCTGTACAAAAGGCTTCTACACCAGTTTTAACCAATAAAACAGTCATTTCTGGATC</u>

-continued

GAAAGTCAAAAGTTTATCATCTGCGCAATCGAGCTCATCAGGACCTTCATCATCTA
GTGAGGAAGATGATTCCCGCGATATTGAAAGCTTGGATAAGAAAATACGTCCTTTA
GAAGAATTAGAAGCATTATTAAGTAGTGGAAATACAAAACAATTGAAGAACAAAGA
GGTCGCTGCCTTGGTTATTCACGGTAAGTTACCTTTGTACGCTTTGGAGAAAAAAT
TAGGTGATACTACGAGAGCGGTTGCGGTACGTAGGAAGGCTCTTTCAATTTTGGC
AGAAGCTCCTGTATTAGCATCTGATCGTTTACCATATAAAAATTATGACTACGACC
GCGTATTTGGCGCTTGTTGTGAAAATGTTATAGGTTACATGCCTTTGCCCGTTGGT
GTTATAGGCCCCTTGGTTATCGATGGTACATCTTATCATATACCAATGGCAACTAC
AGAGGGTTGTTTGGTAGCTTCTGCCATGCGTGGCTGTAAGGCAATCAATGCTGGC
GGTGGTGCAACAACTGTTTTAACTAAGGATGGTATGACAAGAGGCCCAGTAGTCC
GTTTCCCAACTTTGAAAAGATCTGGTGCCTGTAAGATATGGTTAGACTCAGAAGAG
GGACAAAACGCAATTAAAAAAGCTTTTAACTCTACATCAAGATTTGCACGTCTGCA
ACATATTCAAACTTGTCTAGCAGGAGATTTACTCTTCATGAGATTTAGAACAACTA
CTGGTGACGCAATGGGTATGAATATGATTTCTAAGGGTGTCGAATACTCATTAAAG
CAAATGGTAGAAGAGTATGGCTGGGAAGATATGGAGGTTGTCTCCGTTTCTGGTA
ACTACTGTACCGACAAAAAACCAGCTGCCATCAACTGGATCGAAGGTCGTGGTAA
GAGTGTCGTCGCAGAAGCTACTATTCCTGGTGATGTTGTCAGAAAAGTGTTAAAAA
GTGATGTTTCCGCATTGGTTGAGTTGAACATTGCTAAGAATTTGGTTGGATCTGCA
ATGGCTGGGTCTGTTGGTGGATTTAACGCACATGCAGCTAATTTAGTGACAGCTGT
TTTCTTGGCATTAGGACAAGATCCTGCACAAAATGTCGAAAGTTCCAACTGTATAA
CATTGATGAAAGAAGTGGACGGTGATTTGAGAATTTCCGTATCCATGCCATCCATC
GAAGTAGGTACCATCGGTGGTGGTACTGTTCTAGAACCACAAGGTGCCATGTTGG
ACTTATTAGGTGTAAGAGGCCCACATGCTACCGCTCCTGGTACCAACGCACGTCAA
TTAGCAAGAATAGTTGCCTGTGCCGTCTTGGCAGGTGAATTATCCTTATGTGCTGC
CCTAGCAGCCGGCCATTTGGTTCAAAGTTATATGACCCACAACAGGAAACCTGCTG
AACCAACAAAACCTAACAATTTGGACGCCACTGATATAAATCGTTTGAAAGATGGG
TCCGTCACCTGCATTAAATCCTAAGCTAGCTA*AGATCCGCTCTAACCGAAAAGGAAGG*
*AGTTAGACAACCTGAAGTCTAGGTCCCTATTTATTTTTTTATAGTTATGTTAGTATTAAGAA*
*CGTTATTTATATTTCAAATTTTTCTTTTTTTTCTGTACAGACGCGTGTACGCATGTAACATT*
*ATACTGAAAACCTTGCTTGAGAAGGTTTTGGGACGCTCGAAGATCCAGCT*CGGCCGTACG
AAAATCGTTATTGTCTTGAAGGTGAAATTTCTACTCTTATTAATGGTGAACGTTAAGCTG
ATGCTATGATGGAAGCTGATTGGTCTTAACTTGCTTGTCATCTTGCTAATGGTCATATGG
CTCGTGTTATTACTTAAGTTATTTGTACTCGTTTTGAACGTAATGCTAATGATCATCTTAT
GGAATAATAGTGAACGGCCG*agctggatcttcgagcgtcccaaaaccttctcaagcaaggttttcagtata*
*atgttacatgcgtacacgcgtctgtacagaaaaaaagaaaaatttgaaatataaataacgttcttaa*
*tactaacataactataaaaaaataa*atagggacctagacttcaggttg*t*ctaactccttcctttt
*cggttagagcggatct*TAGCTAGCttaggatttaatgcaggtgacggacccatctttcaaa
cgatttatatcagtggcgtccaaattgttaggttttgttggttcagcaggtttcctgttgtgggtcatataactttgaac
caaatggccggctgctagggcagcacataaggataattcacctgccaagacggcacaggcaactattcttgctaattgac
gtgcgttggtaccaggagcggtagcatgtgggcctcttacacctaataagtccaacatggcaccttgtggttctagaaca
gtaccaccaccgatggtacctacttcgatggatggcatggatacggaaattctcaaatcaccgtccacttctttcatcaa tgttatacagttggaactttcgacatttttgtgcaggatcttgtcctaatgccaagaaaacagctgtcactaaattagctg catgtgcgttaaatccaccaacagacccagccattgcagatccaaccaaattcttagcaatgttcaactcaaccaatttg gaaacatcacttttttaacacttttctgacaacatcaccaggaatagtagcttctgcgacgacactcttaccacgaccttc gatccagttgatggcagctggttttttgtcggtacagtagttaccagaaacggagacaacctccatatcttcccagccat actcttctaccatttgctttaatgagtattcgacacccttagaaatcatattcatacccattgcgtcaccagtagttgtt ctaaatctcatgaagagtaaatctcctgctagacaagtttgaatatgttgcagacgtgcaaatcttgatgtagagttaaa agctttttttaattgcgttttgtccctcttctgagtctaaccatatcttacaggcaccagatcttttcaaagttgggaaac ggactactgggcctcttgtcataccatccttagttaaaacagttgttgcaccaccgccagcattgattgccttacagcca cgcatggcagaagctaccaaacaaccctctgtagttgccattggtatatgataagatgtaccatcgataaccaaggggcc tataacaccaacgggcaaaggcatgtaacctataacattttcacaacaagcgccaaatacgcggtcgtagtcataatttt tatatggtaaacgatcagatgctaatacaggagcttctgccaaaattgaaagagccttcctacgtaccgcaaccgctctc gtagtatcacctaattttttctccaaagcgtacaaaggtaacttaccgtgaataaccaaggcagcgacctctttgttctt caattgttttgtatttccactacttaataatgcttctaattcttctaaaggacgtattttcttatccaagctttcaatat cgcgggaatcatcttcctcactagatgatgaaggtcctgatgagctcgattgcgcagatgataaacttttgactttcgat ccagaaatgactgttttattggttaaaactggtgtagaagccttttgtacaggagcagtaaaagacttcttggtgacttc agtcttcaccaattggtctgcagccat TAT*agtttttttctccttgacgttaaagtatagaggtatattaacaatttttg*

*ttgatacttttattacatttgaataagaagtaatacaaaccgaaaatgttgaaagtattagttaaagtggttatgcagtt*

*tttgcatttatatatctgttaatagatcaaaaatcatcgcttcgctgattaattaccccagaaataaggctaaaaaacta*

*atcgcattatcatcctatggttgttaatttgattcgttcatttgaaggtttgtggggccaggttactgccaatttttcct*

*cttcataaccataaaagctagtattgtagaatctttattgttcggagcagtgcggcgcgaggcacatctgcgtttcagga*

*acgcgaccggtgaagacgaggacgcacggaggagagtcttccttcggagggctgtcacccgctcggcggcttctaatccg*

*t*AGGTCCGCCGGCGTTGGACGAGCGTTGTGAGCGTTGCGCTCGTGCATCaatgtgtatattagtttaaaaagttgtatgt aataaaagtaaaatttaatattttggatgaaaaaaaccattttttagacttttttcttaactagaatgctggagtagaaata cgccatctcaagatacaaaaagcgttaccggcactgatttgtttcaaccagtatatagattattattgggtcttgatcaa ctttcctcagacatatcagtaacagttatcaagctaaatatttacgcgaaagaaaaacaaatattttaattgtgatactt gtgaatttatttttattaaggatacaaagttaagagaaaacaaaatttatatacaatataagtaatattcatatatatgt gatgaatgcagtcttaacgagaagacatggccttggtgacaactctcttcaaaccaacttcagcctttctcaattcatca gcagatgggtcttcgatttgcaaagcagcca

Upper case, bold: HO upstream homology sequence (SEQ ID NO: 56)

Upper case, italicized and underlined: P(gal1) (SEQ ID NO: 57)

Upper case, underlined and bold: tHMG1 (SEQ ID NO: 58)

Upper case, bold and italicized: CYC1 terminator (SEQ ID NO: 59)

Lower case, bold and italicized: CYC1 terminator, reverse complement (SEQ ID NO: 60)

Lower case, underlined and bold: tHMG1, reverse complement (SEQ ID NO: 61)

Lower case, italicized and underlined: P(gal1), reverse complement (SEQ ID NO: 62)

Lower case, bold: HO downstream homology sequence (SEQ ID NO: 63)

P(met3) integration upstream of Erg9 with flanking genes included.
(SEQ ID NO: 54)

ATGTCCGGTAAATGGAGACTAGTGCTGACTGGGATAGGCAATCCAGAGCCTCAGT

ACGCTGGCACCCGTCACAATGTAGGGCTATATATGCTGGAGCTGCTACGAAAGCG

-continued

GCTTGGTCTGCAGGGGAGAACCTATTCCCCTGTGCCTAATACGGGCGGCAAAGTG

CATTATATAGAAGACGAACATTGTACGATACTAAGATCGGATGGCCAGTACATGAA

TCTAAGTGGAGAACAGGTGTGCAAGGTCTGGGCCCGGTACGCCAAGTACCAAGCC

CGACACGTTGTTATTCATGACGAGTTAAGTGTGGCGTGTGGAAAAGTGCAGCTCA

GAGCCCCAGCACCAGTATTAGAGGTCATAATGGGCTGCGAAGTCTACTGAAATG

CTCCGGAGGCCGTGTACCCTTTGCCAAATTGGCTATTGGAATCGGCAGAGAACCT

GGGTCCCGCTCTAGAGACCCTGCGAGCGTCTCCCGCTGGGTTCTGGGAGCTCTAA

CTCCGCAGGAACTACAAACCTTGCTTACACAGAGTGAACCTGCTGCCTGGCGTGCT

CTGACTCAGTACATTTCATAGGTTTAACTTGATACTACTAGATTTTTTCTCTTCATTTAT

AAAATTTTTGGTTATAATTGAAGCTTTAGAAGTATGAAAAAATCCTTTTTTTTCATTCTTT

GCAACCAAAATAAGAAGCTTCTTTTATTCATTGAAATGATGAATATAAACCTAACAAAA

GAAAAGACTCGAATATCAAACATTAAAAAAAAATAAAAGAGGTTATCTGTTTTCCCAT

TTAGTTGGAGTTTGCATTTTCTAATAGATAGAACTCTCAATTAATGTGGATTTAGTTTCT

CTGTTCGTTTTTTTTTGTTTTGTTCTCACTGTATTTACATTTCTATTTAGTATTTAGTTATT

CATATAATCTTAACTTCTCGAGGAGCTCGATCTTGAAACTGAGTAAGATGCTCAGAATA

CCCGTCAAGATAAGAGTATAATGTAGAGTAATATACCAAGTATTCAGCATATTCTCCTC

TTCTTTTGTATAAATCACGGAAGGGATGATTTATAAGAAAAATGAATACTATTCACTT

CATTTACCACCCTCTGATCTAGATTTTCCAACGATATGTACGTAGTGGTATAAGGTGAGG

GGGTCCACAGATATAACATCGTTTAATTTAGTACTAACAGAGACTTTTGTCACAACTAC

ATATAAGTGTACAAATATAGTACAGATATGACACACTTGTAGCGCCAACGCGCATCCTA

CGGATTGCTGACAGAAAAAAGGTCACGTGACCAGAAAAGTCACGTGTAATTTTGTAA

CTCACCGCATTCTAGCGGTCCCTGTCGTGCACACTGCACTCAACACCATAAACCTTAGC

AACCTCCAAAGGAAATCACCGTATAACAAAGCCACAGTTTTACAACTTAGTCTCTTATG

AAGTGTCTCTCTGTCGTAACAGTTGTGATATCGGAAGAAGAGAAAAGACGAAGAGC

AGAAGCGGAAAACGTATACACGTCACATATCACACACACACAatgggaaagctattacaattggcat tgcatccggtcgagatgaaggcagctttgaagctgaagttttgcagaacaccgctattctccatctatgatcagtccacg tctccatatctcttgcactgtttcgaactgttgaacttgacctccagatcgtttgctgctgtgatcagagagctgcatcc agaattgagaaactgtgttactctcttttatttgattttaagggctttggataccatcgaagacgatatgtccatcgaac acgatttgaaaattgacttgttgcgtcacttccacgagaaattgttgttaactaaatggagtttcgacggaaatgccccc gatgtgaaggacagagccgttttgacagatttcgaatcgattcttattgaattccacaaattgaaaccagaatatcaaga agtcatcaaggagatcaccgagaaaatggggtaatggtatggccgactacatcttagatgaaaattacaacttgaatgggt tgcaaaccgtccacgactacgacgtgtactgtcactacgtagctggtttggtcggtgatggtttgacccgtttgattgtc attgccaagtttgccaacgaatctttgtattctaatgagcaattgtatgaaagcatgggtcttttcctacaaaaaaccaa catcatcagagattacaatgaagatttggtcgatggtagatccttctggcccaaggaaatctggtcacaatacgctcctc agttgaaggacttcatgaaacctgaaaacgaacaactggggttggactgtataaaccacctcgtcttaaacgcattgagt catgttatcgatgtgttgacttatttggccggtatccacgagcaatccactttccaattttgtgccattccccaagttat ggccattgcaaccttggctttggtattcaacaaccgtgaagtgctacatggcaatgtaaagattcgtaagggtactacct gctatttaattttgaaatcaaggactttgcgtggctgtgtcgagattttttgactattacttacgtgatatcaaatctaaa ttggctgtgcaagatccaaatttcttaaaattgaacattcaaatctccaagatcgaacagtttatggaagaaatgtacca ggataaattacctcctaacgtgaagccaaatgaaactccaattttcttgaaagttaaagaaagatccagatacgatgatg aattggttccaacccaacaagaagaagagtacaagttcaatatggttttatctatcatcttgtccgttcttcttgggttt -continued tattatatatacactttacacagagcgtga

Uppercase, bold and underlined: Upstream sequence PTH1 (YHR189W) (SEQ ID NO: 64)

Uppercase and underlined: P(met3) (SEQ ID NO: 65)

Lowercase, bold and underlined: Erg9 (YHR190W) (SEQ ID NO: 66)

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety, particularly for the disclosure referenced herein.

What is claimed is:

1. A method for producing one or more terpenes, comprising:
   culturing a fungal cell that comprises a nucleic acid molecule encoding a synthetic terpene synthase, wherein:
   a) the synthetic terpene synthase comprises an amino acid sequence that is at least 95% identical to SEQ ID NO: 17, 22, or 29;
   b) the synthetic terpene synthase comprises a DDxx(x)D/E motif; and
   c) the fungal cell produces alpha-guaiene.

2. The method of claim 1 further comprising extracting alpha-guaiene.

3. The method of claim 1, wherein the synthetic terpene synthase is capable of producing a sesquiterpene composition that comprises at least 15% alpha-guaiene.

4. A method for producing one or more terpenes, comprising:
   culturing a fungal cell that comprises a nucleic acid molecule encoding a synthetic terpene synthase, wherein:
   (a) the synthetic terpene synthase comprises an amino acid sequence that is at least 95% identical to SEQ ID NO: 17;
   (b) the synthetic terpene synthase comprises a DDxx(x)D/E motif; and
   (c) the fungal cell produces alpha-guaiene.

5. A method for producing one or more terpenes, comprising:
   culturing a fungal cell that comprises a nucleic acid molecule encoding a synthetic terpene synthase, wherein:
   (a) the synthetic terpene synthase comprises the amino acid sequence of SEQ ID NO: 17, 22, or 29;
   (b) the synthetic terpene synthase comprises a DDxx(x)D/E motif; and
   (c) the fungal cell produces alpha-guaiene.

6. The method of claim 1, wherein the fungal cell is a yeast cell.

7. The method of claim 6, wherein the yeast cell is a *Pichia, Kluyveromyces, Hansenula, Saccharomyces,* or *Yarrowia* cell.

8. The method of claim 7, wherein the *Saccharomyces* cell is a *Saccharomyces cerevisiae* cell.

9. The method of claim 1, wherein the method is a method of producing a perfume.

10. The method of claim 4, wherein the cell produces alpha-guaiene and wherein the method further comprising extracting alpha-guaiene.

11. The method of claim 4, wherein the synthetic terpene synthase is capable of producing a sesquiterpene composition that comprises at least 15% alpha-guaiene.

12. The method of claim 4, wherein the fungal cell is a yeast cell.

13. The method of claim 12, wherein the yeast cell is a *Pichia, Kluyveromyces, Hansenula, Saccharomyces,* or *Yarrowia* cell.

14. The method of claim 13, wherein the *Saccharomyces* cell is a *Saccharomyces cerevisiae* cell.

15. The method of claim 5, wherein the cell produces alpha-guaiene and wherein the method further comprising extracting alpha-guaiene.

16. The method of claim 5, wherein the synthetic terpene synthase is capable of producing a sesquiterpene composition that comprises at least 15% alpha-guaiene.

17. The method of claim 5, wherein the fungal cell is a yeast cell.

18. The method of claim 17, wherein the yeast cell is a *Pichia, Kluyveromyces, Hansenula, Saccharomyces,* or *Yarrowia* cell.

19. The method of claim 18, wherein the *Saccharomyces* cell is a *Saccharomyces cerevisiae* cell.

20. The method of claim 4, wherein the method is a method of producing a perfume.

\* \* \* \* \*